US012150976B2

(12) United States Patent
Cooney et al.

(10) Patent No.: US 12,150,976 B2
(45) Date of Patent: Nov. 26, 2024

(54) TREATMENT OF IMMUNE DYSREGULATION DISORDERS

(71) Applicant: University Of Limerick, Limerick (IE)

(72) Inventors: Jakki Cooney, County Cork (IE); Todd Kagawa, Kailua, HI (US); Ruth Cullen, County Cavan (IE); Senan Behan, County Limerick (IE); Brian Noonan, Boxford, MA (US)

(73) Assignee: UNIVERSITY OF LIMERICK, Limerick (IE)

( * ) Notice: Subject to any disclaimer, the term of this patent is extended or adjusted under 35 U.S.C. 154(b) by 453 days.

(21) Appl. No.: 17/287,992

(22) PCT Filed: Oct. 23, 2019

(86) PCT No.: PCT/EP2019/078944
§ 371 (c)(1),
(2) Date: Apr. 22, 2021

(87) PCT Pub. No.: WO2020/084014
PCT Pub. Date: Apr. 30, 2020

(65) Prior Publication Data
US 2021/0386836 A1    Dec. 16, 2021

(30) Foreign Application Priority Data
Oct. 23, 2018    (EP) .................................... 18202147

(51) Int. Cl.
*A61K 38/48*    (2006.01)
*C12N 9/52*    (2006.01)

(52) U.S. Cl.
CPC ............... *A61K 38/48* (2013.01); *C12N 9/52* (2013.01)

(58) Field of Classification Search
CPC ..................................................... C12N 9/52
See application file for complete search history.

(56) References Cited

FOREIGN PATENT DOCUMENTS

EP    2886140 A1    6/2015

OTHER PUBLICATIONS

Sun Zhihong, et al., "Expanding the Biotechnology Potential of Lactobacilli through Comparative Genomics of 213 Strains and Associated Genera," Nature Communications, Nature Publishing Group, GB, vol. 6 (2015).

Raftis, E., et al., "Unusual Genome Complexity In Lactobacillus Salivarius JCM1046", BMC Genomics, Biomed Central, vol. 15, No. 1, p. 771 (2014).
International Search Report and Written Opinion of International Application No. PCT/EP2019/078944, entitled Treatment of Immune Dysregulation Disorders. Dated: Jan. 21, 2020.
International Preliminary Report on Patentability of International Application No. PCT/EP2019/078944, entitled Treatment of Immune Dysregulation Disorders. Dated: Apr. 27, 2021.
Uniprot sequence A0A089QKL1& Anonymous: "LPXTG Cell Wall Anchor Domain-Containing Protein Lactobacillus Saliva—Protein—NCBI", (2018), Retrieved from the Internet: URL:https://www.ncbi.nlm.nih.gov/protein/WP 044005706 [retrieved on Mar. 28, 2019].
Fritzer A., et al., "Chemokine Degradation By The Group A Streptococcal Serine Proteinase Sepe Can Be Reconstituted In Vitro And Requires Two Separate Domains", Biochemical Journal, vol. 422, No. 3, pp. 533-542 (2009).
Matheson, N. R., "Interaction Of A Novel Form Of Pseudomonas Aeruginosa Alkaline Protease (Aeruginolysin) With Interleukin-6 And Interleukin-8", pp. 911-915 (2006) Retrieved from the Internet: URL:http://dx.doi.org/10.1515/BC.2006.115 [retrieved on Mar. 27, 2019].
Kagawa, T. F., et al., "Model for Substrate Interactions in C5a Peptidase from *Streptococcus pyogenes*: A 1.9 A Crystal Structure of the Active Form of ScpA", Journal of Molecular Biology, Academic Press, United Kingdom, vol. 386, No. 3, pp. 754-772 (2009).
Luo, X, et a, "The protease-associated domain: a homology domain associated with multiple classes of proteases", Trends in Biochemical Scie, Elsevier, Amsterdam, NL, vol. 26, No. 3, pp. 147-148 (2001).
Børsting, M.W., et al, "Classification of Lactococcus lactis cell envelope proteinase based on gene sequencing, peptides formed after hydrolysis of milk, and computer modeling" Journal of Dairy Science., vol. 98, No. 1, pp. 68-77 (2015).
Fujisawa, et al, "*Lactobacillus intestinalis* (ex Hemme 1974) sp. nov., nom. rev., Isolated from the Intestines of Mice and Rats" International Joulrnal of Systematic Bacteriology, vol. 40, No. 3, p. 302-304 (1990).
Mahon et al, "The PA domain: A protease-associated domain", Protein Science, 9:1930-1934. Cambridge University Press (2000).
Environmental sequence IBEA_CTG_SLARD54TR, whole genome shotgun sequence, GenBank: AACY01233951.1, Retrieved from the Internet: URL:https://www.ncbi.nlm.nih.gov/nuccore/WP,044005706 [retrieved on Jul. 22, 2021].

*Primary Examiner* — Suzanne M Noakes
(74) *Attorney, Agent, or Firm* — HAMILTON, BROOK, SMITH & REYNOLDS, P.C.

(57) ABSTRACT

An isolated protease comprising a polypeptide having the structure is described: P-A-B5 in which P is a protease domain, A is an A-domain, and B is a B-domain, of a Group VII to XIII cell envelope protease (CEP), wherein the protease does not have a PA domain. An isolated protease according to Claim 1, selected from a wild-type Group VII to XIII cell envelope protease. The use of the protease as a medicament is treating immune dysregulation diseases is also described.

10 Claims, 14 Drawing Sheets
Specification includes a Sequence Listing.

SEQUENCE LISTING

<160> NUMBER OF SEQ ID NOS: 58

<210> SEQ ID NO 1
<211> LENGTH: 1530
<212> TYPE: PRT
<213> ORGANISM: Lactobacillus salivarius

<400> SEQUENCE: 1

```
Met Glu Lys Leu Leu Gly Glu Lys Arg Arg Tyr Lys Leu Tyr Lys Ala
1               5                   10                  15

Lys Ser Lys Trp Val Val Ser Ala Ile Ile Thr Ile Ser Gly Val Thr
            20                  25                  30

Phe Leu Val Thr Ser Pro Val Ser Asn Ala Gln Ala Asp Thr Val Asn
        35                  40                  45

Gly Ser Glu Ser Val Lys Thr Glu Ala Thr Gln Ala Ser Gly Ser Ser
    50                  55                  60

Val Gln Asp Asn Ala Thr Ala Lys Thr Thr Val Thr Thr Asn Ser Asn
65                  70                  75                  80

Ser Ser Asn Asn Val Ser Asn Val Gln Thr Asp Thr Val Lys Glu Ala
                85                  90                  95

Ala Thr Ser Asn Val Asp Ser Val Ala Ser Gln Asn Gln Ala Thr Thr
            100                 105                 110

Ala Gln Gln Ala Lys Thr Thr Ala Asp Thr Ala Asp Gln Thr Val Pro
        115                 120                 125

Pro Thr Thr Tyr Lys Asp His Val Lys Gly Asn Val Gln Thr Ala Trp
    130                 135                 140

Asp Asn Gly Tyr Lys Gly Gln Gly Met Val Val Ala Val Ile Asp Ser
145                 150                 155                 160

Gly Ala Asp Thr Asn His Lys Asp Phe Ser Lys Ala Pro Glu Ser Pro
                165                 170                 175

Ala Ile Ser Lys Glu Asp Ala Asp Lys Lys Ile Ser Glu Leu Gly Tyr
            180                 185                 190

Gly Lys Tyr Ala Ser Glu Lys Phe Pro Phe Val Tyr Asn Tyr Ala Ser
        195                 200                 205

Arg Asp Asn Asn Trp Val Lys Asp Asp Gly Pro Asp Ala Ser Glu His
    210                 215                 220
```

```
Gly Gln His Val Ala Gly Ile Ile Gly Ala Asp Gly Gln Pro Asn Gly
225                 230                 235                 240

Asn Glu Arg Tyr Ala Val Gly Val Ala Pro Glu Thr Gln Leu Met Met
            245                 250                 255

Met Arg Val Phe Asn Asp Gln Phe Ala Asp Glu Asn Thr Asp Asp Ile
        260                 265                 270

Ala Gln Ala Ile Tyr Asp Ala Val Lys Leu Gly Ala Asn Val Ile Gln
    275                 280                 285

Met Ser Leu Gly Gln Gly Val Ala Ala Asn Leu Asn Asp Val Glu
        290                 295                 300

Gln Lys Ala Val Glu Tyr Ala Thr Gln His Gly Val Phe Val Ser Ile
305                 310                 315                 320

Ser Ala Ser Asn Asn Gly Asn Ser Ala Ser Val Thr Gly Glu Glu Val
                325                 330                 335

Pro Tyr Lys Pro Gly Gly Ala Asp Gly Asn Phe Glu Pro Phe Ser Ser
            340                 345                 350

Ser Thr Val Ala Asn Pro Gly Ala Ser Arg Asn Ala Met Thr Val Ala
        355                 360                 365

Ala Glu Asn Ser Val Val Gly Ala Gly Asp Asp Met Ala Asp Phe Ser
    370                 375                 380

Ser Trp Gly Pro Leu Gln Asp Phe Thr Leu Lys Pro Asp Val Ser Ala
385                 390                 395                 400

Pro Gly Val Ser Val Thr Ser Thr Gly Asn Asp Asn Arg Tyr Asn Thr
                405                 410                 415

Met Ser Gly Thr Ser Met Ala Gly Pro Phe Asn Ala Gly Val Ala Ala
            420                 425                 430

Leu Val Met Gln Arg Leu Lys Ala Thr Thr Asn Leu Asn Gly Ala Asp
        435                 440                 445

Leu Val Gln Ala Thr Lys Ala Leu Ile Met Asn Thr Ala Lys Pro Met
    450                 455                 460

Thr Gln Gln Gly Tyr Asp Thr Pro Val Ser Pro Arg Arg Gln Gly Ala
465                 470                 475                 480

Gly Glu Ile Asp Ala Gly Ala Ala Thr Glu Ser Pro Val Tyr Val Val
                485                 490                 495

Ala Ala Asp Gly Thr Ser Ser Val Ser Leu Arg Lys Val Gly Asp Ser
            500                 505                 510

Thr Gln Phe Ala Leu Thr Phe Lys Asn Leu Ser Asp Lys Asp Gln Thr
        515                 520                 525

Tyr Thr Phe Asp Asp Phe Gly Gly Gly Leu Thr Glu Val Arg Asp Ala
    530                 535                 540

Asp Thr Gly Thr Phe His Asp Val Tyr Leu Ala Gly Ala His Val Tyr
545                 550                 555                 560

Gly Asn Lys Thr Val Thr Val Lys Ala Gly Gln Ser Ala Thr Tyr Asn
                565                 570                 575

Phe Thr Leu Ser Leu Thr Gly Leu Lys Glu Asn Gln Leu Val Glu Gly
            580                 585                 590

Trp Leu Arg Phe Val Gly Asn Asp Gly Gln Asn Gln Leu Val Val Pro
        595                 600                 605

Tyr Leu Ala Tyr Tyr Gly Asp Met Thr Ser Glu Asp Val Phe Asp Lys
    610                 615                 620

Ala Ala Asn Gln Glu Gly Thr Val Tyr Gly Asn Tyr Phe Val Asn
625                 630                 635                 640

Glu Asp Asn Tyr Pro Arg Gly Val Ala Asp Glu Asp Ser Leu Lys Ala
```

-continued

```
                645                 650                 655
Leu Val Asn Leu Glu Gly Asn Tyr Asn Trp Gln Gln Val Ala Lys Leu
                660                 665                 670

Tyr Gln Asp Gly Lys Val Ala Phe Ser Pro Asn Ala Asp Gly Lys Ser
                675                 680                 685

Asp Leu Leu Lys Pro Tyr Ala Phe Val Lys Gln Asn Leu Lys Asp Leu
                690                 695                 700

Lys Val Glu Val Leu Asp Lys Ser Gly Lys Val Val Arg Val Val Ala
705                 710                 715                 720

Asp Glu Gln Gly Leu Asp Lys Ser Tyr Tyr Glu Ser Gly Val Asn Lys
                725                 730                 735

Asp Val Thr Leu Ser Val Ser Met Arg Asn Asn Pro Asn Thr Leu Ala
                740                 745                 750

Trp Asp Gly Lys Val Tyr Asp Asp Lys Ala Gly Glu Met Val Asn Ala
                755                 760                 765

Ala Asp Gly Glu Tyr Thr Tyr Arg Tyr Val Ala Thr Leu Tyr Asn Asp
                770                 775                 780

Gly Val Asn Lys Val Gln Thr Ala Asp Tyr Pro Val Ile Asp Thr
785                 790                 795                 800

Thr Ala Pro Val Leu Ser Asn Val Lys Tyr Asp Ala Ala Thr His Thr
                805                 810                 815

Leu Ser Phe Asp Tyr Lys Asp Thr Gly Ser Gly Phe Thr Asp Tyr Ser
                820                 825                 830

Tyr Ala Val Val Lys Val Asn Asp Lys Thr Phe Gly Tyr Lys Leu Asn
                835                 840                 845

Asp Gly Lys Asn Ser Lys Phe Leu Asp Ala Ala Lys Thr Ser Gly Thr
850                 855                 860

Phe Lys Ala Val Leu Gly Ser Asp Thr Leu Ala Ala Leu Thr Ala Ala
865                 870                 875                 880

Lys Asn Ala Leu Ser Val Ala Val Ser Asp Val Ala Asp Asn Thr Ser
                885                 890                 895

Thr Val Thr Leu Leu Val Asn Gly Asn Asn Asp Ala Thr Thr Lys Val
                900                 905                 910

Ser Val Trp Asn Ala Thr Asn Gly Leu Glu Leu Asp Gln Ser Ser Pro
                915                 920                 925

Asp Tyr Gln Ala Ala Thr Ser Thr Tyr Asn Leu Arg Gly Asn Ala Thr
                930                 935                 940

Ser Asp Phe Tyr Tyr Asn Gly Ala Leu Val Gln Val Asp Asn Ser Gly
945                 950                 955                 960

Asn Phe Val Val Pro Val Ser Thr Ser Asp Thr Ala Val Val Phe Thr
                965                 970                 975

Ser Asp Ala Ala Gly Lys Asn Val Val Tyr Lys Leu Asn Thr Ala Thr
                980                 985                 990

Pro Lys Ala Val Phe Ala Trp Gln Val Asn Asn Thr Val Lys Glu Asn
                995                 1000                1005

Phe Gly Ile Val Leu Asp Thr Val Val Ser Asn Asn Lys Asp Asp
    1010                1015                1020

Val Val Val Gln Ala Ala Val Thr Lys Gly Asp Asn Val Glu Ala
    1025                1030                1035

Tyr Ala Arg Asp Tyr Phe Thr Gly Ala Val Tyr Lys Ala Asp Val
    1040                1045                1050

Lys Asp Gly Leu Ala Thr Phe His Val Lys Val Thr Asn Asn Ser
    1055                1060                1065
```

```
Gly Arg Thr Val Leu Leu Gly Trp Thr Glu Val Val Gly Pro Thr
    1070                1075                1080

Phe Asn Asp Val Gln Arg Thr Ser Ala Asn Gly Val Tyr Leu Gly
    1085                1090                1095

Val Asp Thr Asp Thr Glu Asn Pro Thr Pro Ala Pro Ala Phe Thr
    1100                1105                1110

Ser Ala Asp Gln Leu Gly Thr Asn Val Val Gln Glu Lys Ala Asp
    1115                1120                1125

Ser Ala Thr Ile Gly Asn Pro Gly Asp Leu Pro Gly His Ser Leu
    1130                1135                1140

Lys Asp Leu Thr Thr Arg Ala Asp Ala Asn Pro Asp Ile His Phe
    1145                1150                1155

Asp Tyr Leu Lys Asp Asn Asp Tyr Asn Trp Val Gly Ala Gln Ala
    1160                1165                1170

Val Lys Asp Gly Val Tyr Asn Pro Ser Thr Gln Val Phe Thr Leu
    1175                1180                1185

Thr Gly Lys Val Asp Pro Asn Val Lys Ser Leu Val Val Leu Gly
    1190                1195                1200

Asp Ser Tyr Asn Glu Asp Asp Pro Val Asn Lys Val Asn Leu Asn
    1205                1210                1215

Ser Asp Gly Thr Phe Ser Phe Gln Phe His Thr Ala Pro Thr Ser
    1220                1225                1230

Gln Arg Pro Val Ala Tyr Ile Tyr Thr Lys Asp Asp Gly Ser Thr
    1235                1240                1245

Thr Arg Gly Thr Met Glu Leu Ile Leu Asp Thr Val Leu Pro Thr
    1250                1255                1260

Leu Ser Leu Asn Asn Val Ala Asn Leu Gln Leu Asp Ser Asn Gly
    1265                1270                1275

Asp Tyr Gln Val Tyr Thr Asn Asn Lys Asp Phe Ser Val Ser Gly
    1280                1285                1290

Glu Ala Thr Asp Asn Leu Asp Gly Tyr Arg Phe Phe Phe Asn Gly
    1295                1300                1305

Asp Asn Asp Tyr Arg Glu Phe His Asn Ser Gly Val Asn Phe Val
    1310                1315                1320

Ala Glu Ala His Gln Asp Gly Ser Thr Val Thr Asn Pro Tyr Pro
    1325                1330                1335

Ala Tyr Lys Phe Ser Lys Thr Phe Asn Leu Ala Asp Ala Thr Gly
    1340                1345                1350

Glu Thr Thr His Val Tyr Thr Leu Ser Val Val Asp Leu Thr Gly
    1355                1360                1365

Asn Thr Val Thr Arg Lys Phe Tyr Val His Tyr Gln Pro Ala Ser
    1370                1375                1380

Asp Thr Val Lys Thr Val Thr Thr Asp Lys Asp Gly Ala Thr Lys
    1385                1390                1395

Val Leu Val Asp Tyr Asn Asn Asn Thr Leu Gln Val Lys Asp Asn
    1400                1405                1410

Thr Gly Asn Trp Val Asn Ala Thr Ala Gly Val Glu Ala Ala Lys
    1415                1420                1425

Asn Tyr Arg Val Val Asn Glu Tyr Gly Asn Val Val Leu Leu Leu
    1430                1435                1440

Asn Val Leu Ala Asp Lys Glu Gln Asp Asn Asn Lys Val Gln Val
    1445                1450                1455
```

```
Asn Glu Val Thr Asn Asn Lys Val Glu Gln Thr Val Val Thr Lys
    1460                1465                1470

Thr Val Ser Asn Lys Ser Val Ala Lys Val Gly Lys Lys Ala Ala
    1475                1480                1485

Glu Pro Val Lys Val Leu Pro Gln Thr Gly Glu Asn Asn Ser Lys
    1490                1495                1500

Ser Thr Ser Val Leu Gly Ala Val Leu Ala Ser Ile Ala Gly Phe
    1505                1510                1515

Leu Gly Ala Leu Gly Leu Arg Arg Val Lys Lys Asp
    1520                1525                1530

<210> SEQ ID NO 2
<211> LENGTH: 4590
<212> TYPE: DNA
<213> ORGANISM: Lactobacillus salivarius

<400> SEQUENCE: 2
```

| | | | | | |
|---|---|---|---|---|---|
| atggaaaagt | tgctaggtga | aaaacgccgc | tacaagcttt | ataaagctaa | atctaagtgg | 60 |
| gtggtgtcag | cgattattac | tatttctgga | gttacatttt | tagtgacaag | tccagtttct | 120 |
| aacgctcaag | ccgataccgt | taatggtagt | gaaagtgtaa | aaacagaagc | tactcaggca | 180 |
| tcaggttcga | gtgtgcagga | taatgcgaca | gctaaaacaa | ctgttacaac | caatagtaat | 240 |
| agttctaaca | tgtttctaa  | tgttcaaact | gataccgtaa | aagaagcagc | aacgagcaat | 300 |
| gttgattcag | tagctagtca | aaatcaagct | acaacagctc | aacaggctaa | aactactgct | 360 |
| gatactgctg | atcagacagt | accaccaaca | acctataaag | atcatgtcaa | aggaaatgtt | 420 |
| caaactgcat | gggataatgg | ctataaagga | caaggtatgg | tggttgctgt | tattgattct | 480 |
| ggtgctgata | caaccataa  | agatttctct | aaagctcctg | aatctccagc | aatttctaag | 540 |
| gaagatgctg | acaagaagat | tagcgagcta | ggctacggga | aatatgcttc | agagaaattc | 600 |
| ccattcgtat | ataattatgc | gagtcgtgac | aacaactggg | ttaaagatga | tggcccagat | 660 |
| gcatcagaac | acggtcaaca | cgttgctggt | atcattggtg | ctgacggcca | accaaatggc | 720 |
| aatgaacgct | atgcagtagg | ggtagcacct | gaaacacagt | taatgatgat | gcgagtattt | 780 |
| aatgatcaat | ttgctgatga | aaatactgat | gatattgctc | aagcaattta | tgacgcagtt | 840 |
| aaattaggtg | ctaatgtaat | tcaaatgtcc | ttaggtcaag | cgtcgcagc  | tgctaatttg | 900 |
| aatgatgtag | agcagaaagc | ggttgaatat | gcaactcaac | atggtgtgtt | cgtctccatt | 960 |
| tcagcttcta | caatggtaa  | ttcggcaagt | gttactggtg | aagaagttcc | ttataaacca | 1020 |
| ggtgagcag  | atgaaaactt | tgaaccattc | tctagtagta | cggtagctaa | tccaggtgca | 1080 |
| tcgcgcaatg | caatgacagt | tgcagctgaa | aactcggttg | taggtgctgg | tgatgacatg | 1140 |
| gcagacttct | cttcttgggg | tccttacaa  | gatttcactt | tgaaaccaga | tgtatcagct | 1200 |
| cctggggtta | gtgtaacttc | aacagggaac | gataatcgtt | acaatactat | gagtggaact | 1260 |
| tctatggctg | gtccatttaa | cgctggggtt | gcagctttag | taatgcaaag | attaaaagct | 1320 |
| actactaact | taaatggagc | agatttagtt | caagctacta | aagctttaat | catgaataca | 1380 |
| gctaaaccaa | tgacgcaaca | aggatatgac | actccagttt | ctcctagacg | tcaaggtgct | 1440 |
| ggtgaaattg | atgcaggtgc | tgcaacagaa | tctccatat  | atgttgtggc | agcagacggc | 1500 |
| acaagttctg | tatctttgag | aaaagttgga | gattcaactc | aattcgcact | aacgtttaag | 1560 |
| aacttatccg | ataagatca  | aacatatact | tttgatgatt | ttggtggtgg | attaactgaa | 1620 |
| gtgcgcgatg | ccgatacagg | aactttccac | gatgtttatc | tggcaggagc | acatgtctat | 1680 |

```
ggaaataaga cagtaaccgt taaagctgga caaagcgcaa cttataattt cacattatct    1740
ttaacaggtt tgaaagaaaa tcaattagtt gaaggttggt tgagatttgt aggaaatgat    1800
ggtcaaaatc aattagtagt tccatatctc gcatattatg gtgatatgac aagtgaagat    1860
gtatttgaca aagctgctaa tcaagaaggc acagtctatg gtggtaacta ctttgttaat    1920
gaagataact atccaagagg ggtagctgat gaagattcct taaaggcttt agtaaatctt    1980
gaaggtaatt ataattggca acaagttgct aaattatacc aagatggaaa agttgcattc    2040
tcaccaaatg ctgacggtaa gagtgactta ttaaaaccat atgcctttgt taaacaaaat    2100
ctaaaggatc ttaaagttga agtattagat aagagtggaa aagttgttcg tgtagttgca    2160
gatgaacaag gtctggataa gtcttactat gaaagtggag ttaataaaga cgtaacttta    2220
tcagtttcaa tgcgtaataa tccaaatact ttggcttggg atggaaaagt atacgatgat    2280
aaggccggtg aaatggtaaa tgcagcagat ggtgaatata catatcgtta tgttgctact    2340
ttgtataatg atggtgtaaa taaggttcaa acagctgatt atccagtagt tatcgacaca    2400
acagctccag tattatcaaa tgttaagtat gatgctgcaa cacatacttt aagctttgat    2460
tataaagata caggatctgg ctttacagat tattcttatg cagtagttaa agttaatgat    2520
aagacatttg gctataagtt aaatgatggc aagaattcga agttcttaga tgcagctaaa    2580
acatcaggaa catttaaagc cgtattaggt agtgatactt tagcagcact tactgcagct    2640
aagaatgctt tatcagttgc agttagcgat gtagctgata atacttcaac agtaaccttta   2700 ctggtaaatg gaaataatga tgcaacaact aaagtatctg tttggaatgc aactaatgga    2760
ttagaactcg atcaaagttc cccagattat caagcagcaa cttcaactta taacttacgt    2820
gggaatgcaa catctgattt ctattacaat ggtgcattag ttcaagttga taacagtggt    2880
aattttgtgg ttcctgtaag tacaagtgat actgcggttg tcttcacatc agatgcagct    2940
ggtaagaatg tagtatataa attgaataca gcaactccaa aggctgtttt tgcatggcaa    3000
gtaaataata ctgttaagga aaactttggt attgttttag atacagtcgt aagcaacaac    3060
aaggatgatg tagtcgtaca agcagcggtt actaaggggg ataatgttga agcttatgca    3120
cgcgactact tcacaggtgc agtatataaa gcagatgtaa aagatggatt agcaactttc    3180
cacgtaaaag taactaataa tagtggtaga actgtattat taggatggac agaagttgta    3240
ggaccaacat ttaatgatgt tcaaagaact tctgcaaatg tgtttatttt gggtgttgat    3300
acagatacag agaatcctac gccagcacca gcctttacaa gtgctgacca attaggaaca    3360
aatgttgttc aagaaaaagc tgattctgct acaattggta atccaggaga tttgccagga    3420
cacagtctaa aggacctaac aacacgtgca gatgctaacc cagatatcca ctttgactac    3480
ttgaaagata atgattacaa ctgggtagga gcgcaagctg ttaaagatgg tgtatataat    3540
ccatcaacac aagtatttac tttaacaggt aaggttgatc caaatgttaa atcattggtg    3600
gtattgggag atagttacaa tgaagatgat cctgtaaata aggttaactt aaatagtgat    3660
ggaacattta gtttccaatt ccatacagca ccaacttcac aaagacctgt tgcttacatc    3720
tatacaaaag atgatggttc aacaactaga ggtacaatgg agttaatctt agatacagtt    3780
cttccaacac ttagcttaaa taatgtggct aatttacaac tggatagtaa tggtgattac    3840
caagtctaca ctaataataa agactttagt gtatctggag aagctactga taatttggac    3900
ggatatcgtt tcttcttcaa tggagataat gattatcgtg aattccacaa ttctggtgtg    3960
aactttgttg ctgaagctca tcaagatgga agtacagtga ctaatccata tccagcatac    4020
aagtttagta agacatttaa cttagctgat gcaactggcg aaacaacaca tgtatataca    4080
```

-continued

```
ttgagtgtag ttgacttgac aggtaatact gtaactagga agttctatgt tcactatcaa    4140
ccagctagtg atacagttaa gactgtaaca actgataaag atggtgcaac caaagttcta    4200
gtagattaca ataacaatac actacaagta aagataata  ctggtaactg ggtaaatgct    4260
actgctggag ttgaagctgc taagaattat cgagtagtta atgaatatgg taatgtggta    4320
ttgttactaa atgttcttgc agataaagaa caagacaata ataaagtaca agttaatgaa    4380
gttacaaata ataagtaga  acaaacagta gtaactaaga ctgtttcaaa taaatctgta    4440
gctaaagtgg gcaaaaaagc tgcagaacca gtaaaagtat taccacaaac tggtgaaaat    4500
aacagtaaat ctacttctgt tctaggtgca gtcttagcct caatcgcagg attcttaggt    4560
gcattaggct taagacgtgt taaaaaagat                                    4590
```

<210> SEQ ID NO 3
<211> LENGTH: 1335
<212> TYPE: PRT
<213> ORGANISM: Artificial Sequence
<220> FEATURE:
<223> OTHER INFORMATION: Fragment of PrtV from Lactobacillus salivarius
      JCM1046

<400> SEQUENCE: 3

```
Asp Thr Val Asn Gly Ser Glu Ser Val Lys Thr Glu Ala Thr Gln Ala
1               5                   10                  15

Ser Gly Ser Ser Val Gln Asp Asn Ala Thr Ala Lys Thr Thr Val Thr
            20                  25                  30

Thr Asn Ser Asn Ser Ser Asn Asn Val Ser Asn Val Gln Thr Asp Thr
        35                  40                  45

Val Lys Glu Ala Ala Thr Ser Asn Val Asp Ser Val Ala Ser Gln Asn
    50                  55                  60

Gln Ala Thr Thr Ala Gln Gln Ala Lys Thr Thr Ala Asp Thr Ala Asp
65                  70                  75                  80

Gln Thr Val Pro Pro Thr Thr Tyr Lys Asp His Val Lys Gly Asn Val
                85                  90                  95

Gln Thr Ala Trp Asp Asn Gly Tyr Lys Gly Gln Gly Met Val Val Ala
            100                 105                 110

Val Ile Asp Ser Gly Ala Asp Thr Asn His Lys Asp Phe Ser Lys Ala
        115                 120                 125

Pro Glu Ser Pro Ala Ile Ser Lys Glu Asp Ala Asp Lys Lys Ile Ser
    130                 135                 140

Glu Leu Gly Tyr Gly Lys Tyr Ala Ser Glu Lys Phe Pro Phe Val Tyr
145                 150                 155                 160

Asn Tyr Ala Ser Arg Asp Asn Asn Trp Val Lys Asp Asp Gly Pro Asp
                165                 170                 175

Ala Ser Glu His Gly Gln His Val Ala Gly Ile Ile Gly Ala Asp Gly
            180                 185                 190

Gln Pro Asn Gly Asn Glu Arg Tyr Ala Val Gly Val Ala Pro Glu Thr
        195                 200                 205

Gln Leu Met Met Met Arg Val Phe Asn Asp Gln Phe Ala Asp Glu Asn
    210                 215                 220

Thr Asp Asp Ile Ala Gln Ala Ile Tyr Asp Ala Val Lys Leu Gly Ala
225                 230                 235                 240

Asn Val Ile Gln Met Ser Leu Gly Gln Gly Val Ala Ala Ala Asn Leu
                245                 250                 255

Asn Asp Val Glu Gln Lys Ala Val Glu Tyr Ala Thr Gln His Gly Val
```

```
                260                 265                 270
Phe Val Ser Ile Ser Ala Ser Asn Asn Gly Asn Ser Ala Ser Val Thr
            275                 280                 285
Gly Glu Glu Val Pro Tyr Lys Pro Gly Gly Ala Asp Gly Asn Phe Glu
        290                 295                 300
Pro Phe Ser Ser Ser Thr Val Ala Asn Pro Gly Ala Ser Arg Asn Ala
305                 310                 315                 320
Met Thr Val Ala Ala Glu Asn Ser Val Val Gly Ala Gly Asp Asp Met
                325                 330                 335
Ala Asp Phe Ser Ser Trp Gly Pro Leu Gln Asp Phe Thr Leu Lys Pro
            340                 345                 350
Asp Val Ser Ala Pro Gly Val Ser Val Thr Ser Thr Gly Asn Asp Asn
        355                 360                 365
Arg Tyr Asn Thr Met Ser Gly Thr Ser Met Ala Gly Pro Phe Asn Ala
    370                 375                 380
Gly Val Ala Ala Leu Val Met Gln Arg Leu Lys Ala Thr Thr Asn Leu
385                 390                 395                 400
Asn Gly Ala Asp Leu Val Gln Ala Thr Lys Ala Leu Ile Met Asn Thr
                405                 410                 415
Ala Lys Pro Met Thr Gln Gln Gly Tyr Asp Thr Pro Val Ser Pro Arg
            420                 425                 430
Arg Gln Gly Ala Gly Glu Ile Asp Ala Gly Ala Ala Thr Glu Ser Pro
        435                 440                 445
Val Tyr Val Ala Ala Asp Gly Thr Ser Ser Val Ser Leu Arg Lys
    450                 455                 460
Val Gly Asp Ser Thr Gln Phe Ala Leu Thr Phe Lys Asn Leu Ser Asp
465                 470                 475                 480
Lys Asp Gln Thr Tyr Thr Phe Asp Phe Gly Gly Gly Leu Thr Glu
                485                 490                 495
Val Arg Asp Ala Asp Thr Gly Thr Phe His Asp Val Tyr Leu Ala Gly
            500                 505                 510
Ala His Val Tyr Gly Asn Lys Thr Val Thr Val Lys Ala Gly Gln Ser
        515                 520                 525
Ala Thr Tyr Asn Phe Thr Leu Ser Leu Thr Gly Leu Lys Glu Asn Gln
    530                 535                 540
Leu Val Glu Gly Trp Leu Arg Phe Val Gly Asn Asp Gly Gln Asn Gln
545                 550                 555                 560
Leu Val Val Pro Tyr Leu Ala Tyr Tyr Gly Asp Met Thr Ser Glu Asp
                565                 570                 575
Val Phe Asp Lys Ala Ala Asn Gln Glu Gly Thr Val Tyr Gly Gly Asn
            580                 585                 590
Tyr Phe Val Asn Glu Asp Asn Tyr Pro Arg Gly Val Ala Asp Glu Asp
        595                 600                 605
Ser Leu Lys Ala Leu Val Asn Leu Glu Gly Asn Tyr Asn Trp Gln Gln
    610                 615                 620
Val Ala Lys Leu Tyr Gln Asp Gly Lys Val Ala Phe Ser Pro Asn Ala
625                 630                 635                 640
Asp Gly Lys Ser Asp Leu Leu Lys Pro Tyr Ala Phe Val Lys Gln Asn
                645                 650                 655
Leu Lys Asp Leu Lys Val Glu Val Leu Asp Lys Ser Gly Lys Val Val
            660                 665                 670
Arg Val Val Ala Asp Glu Gln Gly Leu Asp Lys Ser Tyr Tyr Glu Ser
        675                 680                 685
```

Gly Val Asn Lys Asp Val Thr Leu Ser Val Ser Met Arg Asn Asn Pro
690                     695                 700

Asn Thr Leu Ala Trp Asp Gly Lys Val Tyr Asp Asp Lys Ala Gly Glu
705                 710                 715                 720

Met Val Asn Ala Ala Asp Gly Glu Tyr Thr Tyr Arg Tyr Val Ala Thr
            725                 730                 735

Leu Tyr Asn Asp Gly Val Asn Lys Val Gln Thr Ala Asp Tyr Pro Val
                740                 745                 750

Val Ile Asp Thr Thr Ala Pro Val Leu Ser Asn Val Lys Tyr Asp Ala
            755                 760                 765

Ala Thr His Thr Leu Ser Phe Asp Tyr Lys Asp Thr Gly Ser Gly Phe
770                 775                 780

Thr Asp Tyr Ser Tyr Ala Val Val Lys Val Asn Asp Lys Thr Phe Gly
785                 790                 795                 800

Tyr Lys Leu Asn Asp Gly Lys Asn Ser Lys Phe Leu Asp Ala Ala Lys
                805                 810                 815

Thr Ser Gly Thr Phe Lys Ala Val Leu Gly Ser Asp Thr Leu Ala Ala
            820                 825                 830

Leu Thr Ala Ala Lys Asn Ala Leu Ser Val Ala Val Ser Asp Val Ala
835                 840                 845

Asp Asn Thr Ser Thr Val Thr Leu Leu Val Asn Gly Asn Asn Asp Ala
850                 855                 860

Thr Thr Lys Val Ser Val Trp Asn Ala Thr Asn Gly Leu Glu Leu Asp
865                 870                 875                 880

Gln Ser Ser Pro Asp Tyr Gln Ala Ala Thr Ser Thr Tyr Asn Leu Arg
                885                 890                 895

Gly Asn Ala Thr Ser Asp Phe Tyr Tyr Asn Gly Ala Leu Val Gln Val
            900                 905                 910

Asp Asn Ser Gly Asn Phe Val Val Pro Val Ser Thr Ser Asp Thr Ala
            915                 920                 925

Val Val Phe Thr Ser Asp Ala Ala Gly Lys Asn Val Val Tyr Lys Leu
930                 935                 940

Asn Thr Ala Thr Pro Lys Ala Val Phe Ala Trp Gln Val Asn Asn Thr
945                 950                 955                 960

Val Lys Glu Asn Phe Gly Ile Val Leu Asp Thr Val Val Ser Asn Asn
                965                 970                 975

Lys Asp Asp Val Val Val Gln Ala Ala Val Thr Lys Gly Asp Asn Val
            980                 985                 990

Glu Ala Tyr Ala Arg Asp Tyr Phe Thr Gly Ala Val Tyr Lys Ala Asp
            995                 1000                1005

Val Lys Asp Gly Leu Ala Thr Phe His Val Lys Val Thr Asn Asn
    1010                1015                1020

Ser Gly Arg Thr Val Leu Leu Gly Trp Thr Glu Val Val Gly Pro
    1025                1030                1035

Thr Phe Asn Asp Val Gln Arg Thr Ser Ala Asn Gly Val Tyr Leu
    1040                1045                1050

Gly Val Asp Thr Asp Thr Glu Asn Pro Thr Pro Ala Pro Ala Phe
    1055                1060                1065

Thr Ser Ala Asp Gln Leu Gly Thr Asn Val Val Gln Glu Lys Ala
    1070                1075                1080

Asp Ser Ala Thr Ile Gly Asn Pro Gly Asp Leu Pro Gly His Ser
    1085                1090                1095

Leu Lys Asp Leu Thr Thr Arg Ala Asp Ala Asn Pro Asp Ile His
1100                1105                1110

Phe Asp Tyr Leu Lys Asp Asn Asp Tyr Asn Trp Val Gly Ala Gln
1115                1120                1125

Ala Val Lys Asp Gly Val Tyr Asn Pro Ser Thr Gln Val Phe Thr
1130                1135                1140

Leu Thr Gly Lys Val Asp Pro Asn Val Lys Ser Leu Val Val Leu
1145                1150                1155

Gly Asp Ser Tyr Asn Glu Asp Pro Val Asn Lys Val Asn Leu
1160                1165                1170

Asn Ser Asp Gly Thr Phe Ser Phe Gln Phe His Thr Ala Pro Thr
1175                1180                1185

Ser Gln Arg Pro Val Ala Tyr Ile Tyr Thr Lys Asp Asp Gly Ser
1190                1195                1200

Thr Thr Arg Gly Thr Met Glu Leu Ile Leu Asp Thr Val Leu Pro
1205                1210                1215

Thr Leu Ser Leu Asn Asn Val Ala Asn Leu Gln Leu Asp Ser Asn
1220                1225                1230

Gly Asp Tyr Gln Val Tyr Thr Asn Asn Lys Asp Phe Ser Val Ser
1235                1240                1245

Gly Glu Ala Thr Asp Asn Leu Asp Gly Tyr Arg Phe Phe Asn
1250                1255                1260

Gly Asp Asn Asp Tyr Arg Glu Phe His Asn Ser Gly Val Asn Phe
1265                1270                1275

Val Ala Glu Ala His Gln Asp Gly Ser Thr Val Thr Asn Pro Tyr
1280                1285                1290

Pro Ala Tyr Lys Phe Ser Lys Thr Phe Asn Leu Ala Asp Ala Thr
1295                1300                1305

Gly Glu Thr Thr His Val Tyr Thr Leu Ser Val Val Asp Leu Thr
1310                1315                1320

Gly Asn Thr Val Thr Arg Lys Phe Tyr Val His Tyr
1325                1330                1335

<210> SEQ ID NO 4
<211> LENGTH: 4005
<212> TYPE: DNA
<213> ORGANISM: Artificial Sequence
<220> FEATURE:
<223> OTHER INFORMATION: Nucleic acid encoding fragment of PrtV

<400> SEQUENCE: 4
gataccgtta atggtagtga aagtgtaaaa acagaagcta ctcaggcatc aggttcgagt        60
gtgcaggata atgcgacagc taaaacaact gttacaacca atagtaatag ttctaacaat       120
gtttctaatg ttcaaactga taccgtaaaa gaagcagcaa cgagcaatgt tgattcagta       180
gctagtcaaa atcaagctac aacagctcaa caggctaaaa ctactgctga tactgctgat       240
cagacagtac caccaacaac ctataaagat catgtcaaag gaaatgttca aactgcatgg       300
gataatggct ataaaggaca aggtatggtg gttgctgtta ttgattctgg tgctgataca       360
aaccataaag atttctctaa agctcctgaa tctccagcaa tttctaagga agatgctgac       420
aagaagatta gcgagctagg ctacgggaaa tatgcttcag agaaattccc attcgtatat       480
aattatgcga gtcgtgacaa caactggggt aaagatgatg cccagatgc atcagaacac        540 ggtcaacacg ttgctggtat cattggtgct gacggccaac caaatggcaa tgaacgctat       600
gcagtagggg tagcacctga aacacagtta atgatgatgc gagtatttaa tgatcaattt       660

```
gctgatgaaa atactgatga tattgctcaa gcaatttatg acgcagttaa attaggtgct    720
aatgtaattc aaatgtcctt aggtcaaggc gtcgcagctg ctaatttgaa tgatgtagag    780
cagaaagcgg ttgaatatgc aactcaacat ggtgtgttcg tctccatttc agcttctaac    840
aatggtaatt cggcaagtgt tactggtgaa gaagttcctt ataaaccagg tggagcagat    900
ggaaactttg aaccattctc tagtagtacg gtagctaatc caggtgcatc gcgcaatgca    960
atgacagttg cagctgaaaa ctcggttgta ggtgctggtg atgacatggc agacttctct   1020
tcttggggtc ctttacaaga tttcactttg aaaccagatg tatcagctcc tggggttagt   1080
gtaacttcaa cagggaacga taatcgttac aatactatga gtggaacttc tatggctggt   1140
ccatttaacg ctggggttgc agctttagta atgcaaagat aaaagctac tactaactta   1200 aatggagcag atttagttca agctactaaa gctttaatca tgaatacagc taaaccaatg   1260
acgcaacaag gatatgacac tccagtttct cctagacgtc aaggtgctgg tgaaattgat   1320
gcaggtgctg caacagaatc tccagtatat gttgtggcag cagacggcac aagttctgta   1380
tctttgagaa aagttggaga ttcaactcaa ttcgcactaa cgtttaagaa cttatccgat   1440
aaagatcaaa catatacttt tgatgatttt ggtggtggat taactgaagt gcgcgatgcc   1500
gatacaggaa ctttccacga tgtttatctg gcaggagcac atgtctatgg aaataagaca   1560
gtaaccgtta aagctggaca aagcgcaact tataatttca cattatcttt aacaggtttg   1620
aaagaaaatc aattagttga aggttggttg agatttgtag gaaatgatgg tcaaaatcaa   1680
ttagtagttc catatctcgc atattatggt gatatgacaa gtgaagatgt atttgacaaa   1740
gctgctaatc aagaaggcac agtctatggt ggtaactact tgttaatga agataactat   1800 ccaagagggg tagctgatga agattcctta aaggctttag taaatcttga aggtaattat   1860
aattggcaac aagttgctaa attataccaa gatggaaaag ttgcattctc accaaatgct   1920
gacggtaaga gtgacttatt aaaccatat gcctttgtta aacaaaatct aaaggatctt   1980
aaagttgaag tattagataa gagtggaaaa gttgttcgtg tagttgcaga tgaacaaggt   2040
ctggataagt cttactatga aagtggagtt aataaagacg taactttatc agtttcaatg   2100
cgtaataatc caaatacttt ggcttgggat ggaaaagtat acgatgataa ggccggtgaa   2160
atggtaaatg cagcagatgg tgaatataca tatcgttatg ttgctacttt gtataatgat   2220
ggtgtaaata aggttcaaac agctgattat ccagtagtta tcgacacaac agctccagta   2280
ttatcaaatg ttaagtatga tgctgcaaca catactttaa gctttgatta taaagataca   2340
ggatctggct ttacagatta ttcttatgca gtagttaaag ttaatgataa gacatttggc   2400
tataagttaa atgatggcaa gaattcgaag ttcttagatg cagctaaaac atcaggaaca   2460
tttaaagccg tattaggtag tgatactta gcagcactta ctgcagctaa gaatgcttta   2520
tcagttgcag ttagcgatgt agctgataat acttcaacag taaccttact ggtaaatgga   2580
aataatgatg caacaactaa agtatctgtt tggaatgcaa ctaatggatt agaactcgat   2640
caaagttccc cagattatca agcagcaact tcaacttata acttacgtgg gaatgcaaca   2700
tctgatttct attacaatgg tgcattagtt caagttgata acagtggtaa ttttgtggtt   2760
cctgtaagta caagtgatac tgcggttgtc ttcacatcag atgcagctgg taagaatgta   2820
gtatataaat tgaatacagc aactccaaag gctgttttg catggcaagt aaataatact   2880
gttaaggaaa actttggtat tgttttagat acagtcgtaa gcaacaacaa ggatgatgta   2940
gtcgtacaag cagcggttac taaggggat aatgttgaag cttatgcacg cgactacttc   3000
```

-continued

```
acaggtgcag tatataaagc agatgtaaaa gatggattag caactttcca cgtaaaagta    3060
actaataata gtggtagaac tgtattatta ggatggacag aagttgtagg accaacattt    3120
aatgatgttc aaagaacttc tgcaaatggt gtttatttgg gtgttgatac agatacagag    3180
aatcctacgc cagcaccagc ctttacaagt gctgaccaat taggaacaaa tgttgttcaa    3240
gaaaaagctg attctgctac aattggtaat ccaggagatt tgccaggaca cagtctaaag    3300
gacctaacaa cacgtgcaga tgctaaccca gatatccact ttgactactt gaaagataat    3360
gattacaact gggtaggagc gcaagctgtt aaagatggtg tatataatcc atcaacacaa    3420
gtatttactt taacaggtaa ggttgatcca aatgttaaat cattggtggt attgggagat    3480
agttacaatg aagatgatcc tgtaaataag gttaacttaa atagtgatgg aacatttagt    3540
ttccaattcc atacagcacc aacttcacaa agacctgttg cttacatcta tacaaaagat    3600
gatggttcaa caactagagg tacaatggag ttaatcttag atacagttct tccaacactt    3660
agcttaaata atgtggctaa tttcaactg gatagtaatg gtgattacca agtctcacact   3720 aataataaag actttagtgt atctggagaa gctactgata atttggacgg atatcgtttc    3780
ttcttcaatg gagataatga ttatcgtgaa ttccacaatt ctggtgtgaa ctttgttgct    3840
gaagctcatc aagatggaag tacagtgact aatccatatc cagcatacaa gtttagtaag    3900
acatttaact tagctgatgc aactggcgaa acaacacatg tatatacatt gagtgtagtt    3960
gacttgacag gtaatactgt aactaggaag ttctatgttc actat               4005
```

<210> SEQ ID NO 5
<211> LENGTH: 1698
<212> TYPE: PRT
<213> ORGANISM: Lactobacillus intestinalis

<400> SEQUENCE: 5

```
Met Ser Asp Tyr Ser Trp Pro Lys Ser His Asn Lys Tyr Ser Tyr Val
1               5                   10                  15

Phe Lys Thr Arg Glu Gly Leu Asn Lys Ile Glu Thr Gln Lys Arg Ala
            20                  25                  30

Lys Ser Val Ser Asp Met Arg Lys Lys Trp Val Ala Thr Ala Ile Ile
        35                  40                  45

Ala Leu Ala Ser Gly Ser Thr Val Phe Leu Ser Gln Thr Ser Ser Val
    50                  55                  60

Glu Ala Ala Ile Gly Glu Thr Ser Val Gln Asn Val Lys Val Ser Val
65                  70                  75                  80

Ala Lys Asn Glu Ser Asp Ser Gln Lys Phe Asn Asn Ser Gln Asn Leu
                85                  90                  95

Glu Gln Lys Thr Pro Gln Ala Ala Ala Ala Asn Gln Asn Gly Ser Gln
            100                 105                 110

Val Gln Asn Asp His Thr Glu Thr Gln Leu Gln Asn Gln Thr Thr
        115                 120                 125

Gln Ser Gln Val Thr Gln Ala His Thr Glu Glu Asn Asn Ala Ser Ser
    130                 135                 140

Ile Pro Glu Pro Ala Asn Gln Ala Asp His Val Lys Gly Asn Val Gln
145                 150                 155                 160

Ser Ala Trp Asp Gln Gly Tyr Lys Gly Gln Asn Thr Val Val Ala Val
                165                 170                 175

Ile Asp Ser Gly Ala Asp Thr Ser His Lys Asp Phe Gln Thr Met Pro
            180                 185                 190

Ser Asn Pro Lys Leu Lys Gln Glu Asp Val Gln Ser Lys Ile Asp Gln
```

```
            195                 200                 205
Gln Gly Tyr Gly Lys Tyr Val Asn Glu Lys Phe Pro Tyr Val Tyr Asn
    210                 215                 220

Tyr Ala Asp Arg Asp Asn Asp Tyr Ile Lys Ser Asp Asn Asn Gln
225                 230                 235                 240

Asn Asp Ser Pro His Gly Gln His Val Ser Gly Ile Ile Ala Ala Asp
                245                 250                 255

Gly His Pro Glu Gly Asp Gln Gln Tyr Val Gly Val Ala Pro Glu
            260                 265                 270

Ala Gln Leu Met Gln Leu Arg Val Phe Gly Gln Phe Ser Asp Glu Lys
            275                 280                 285

Thr Asp Asp Val Ala Arg Ala Ile Tyr Asp Ala Thr Asn Leu Gly Ala
        290                 295                 300

Asp Val Ile Gln Met Ser Leu Gly Gln Gly Val Ala Asp Gln Gln Leu
305                 310                 315                 320

Thr Asn Ile Glu Gln Lys Ala Val Gln Tyr Ala Ile Asp His Gly Val
                325                 330                 335

Phe Val Ser Ile Ser Ala Ser Asn Asn Gly Asn Ser Ala Ser Val Asp
                340                 345                 350

Asn Pro Ser Lys Val Thr Ala Lys Gly Tyr Gly Ser Gly Ser Glu Ala
            355                 360                 365

Gly Asn Tyr Glu Pro Leu Asn Ser Gly Thr Val Ala Asn Pro Gly Ala
    370                 375                 380

Ser Lys Asn Ala Leu Thr Val Ala Ala Glu Thr Ser Gly Thr Gly Lys
385                 390                 395                 400

Asp Ser Asp Met Ala Ser Phe Ser Ser Trp Gly Pro Leu Ser Asp Phe
                405                 410                 415

Ser Leu Lys Pro Asp Leu Ser Ala Pro Gly Tyr Gln Val Val Ser Thr
                420                 425                 430

Val Asn Asp Asn Gln Tyr Gln Thr Met Ser Gly Thr Ser Met Ala Gly
                435                 440                 445

Pro Phe Ala Ala Gly Ser Ala Ala Leu Val Ile Gln Arg Leu Lys Gln
    450                 455                 460

Thr Asn Pro Glu Leu Lys Gly Ala Glu Leu Val Ala Ala Thr Lys Ala
465                 470                 475                 480

Leu Leu Met Asn Ser Ala Lys Val Gln Thr Gln Asn Gly Tyr Thr Thr
                485                 490                 495

Pro Val Ser Pro Arg Arg Gln Gly Ala Gly Gln Ile Asp Val Gly Ala
                500                 505                 510

Ala Thr Ala Asn Pro Val Tyr Val Thr Ala Ala Asp Gly Thr Ser Ser
            515                 520                 525

Leu Ser Leu Arg Gln Val Asp Glu Lys Thr Thr Phe Thr Leu Thr Phe
    530                 535                 540

His Asn Leu Thr Asp Gln Glu Gln Ser Tyr Ser Phe Asn Asp Leu Gly
545                 550                 555                 560

Gly Gly Tyr Thr Glu Gln Arg Asp Pro Asp Ser Gly Val Phe His Glu
                565                 570                 575

Val Gln Leu Ala Gly Ala His Val Asn Gly Val Gly Asn Phe Thr Leu
            580                 585                 590

Ala Pro Lys Glu Val Lys Asp Leu Gln Tyr Thr Leu Asp Leu Gln Gly
        595                 600                 605

Leu Asn Lys Asn Gln Pro Val Glu Gly Trp Leu His Phe Thr Asn Asp
            610                 615                 620
```

```
Lys Asp Lys Ser Thr Val Val Pro Tyr Leu Ala Tyr Tyr Gly Asp
625                 630                 635                 640

Leu Thr Ser Glu Asn Val Phe Asp Gln Asn Ala Asn Glu Glu Lys Pro
            645                 650                 655

Asp Ile Gln Gly Asn Arg Phe Val Asn Glu Asn Asn Tyr Pro Leu Gly
                660                 665                 670

Val Thr Asp Gln Glu Ser Leu Lys Gln Leu Val Asn Val Asp Ser Asp
        675                 680                 685

Tyr Asn Trp Gln Glu Val Ala Lys Leu Tyr Glu Ser Gly Lys Val Ala
    690                 695                 700

Phe Ser Pro Asn Asp Asp His Gln Ser Asp Leu Ile Lys Pro Tyr Ala
705                 710                 715                 720

Tyr Leu Lys Gln Asn Val Lys Asp Leu Lys Val Glu Ile Leu Asp Ala
                725                 730                 735

Lys Gly Asn Val Val Arg Val Val Ser Asp Val Gln Gly Val Asp Lys
                740                 745                 750

Ser Tyr Asp Glu Ser Gly Val Thr Lys Asp Ala Ser Leu Ser Val Ser
        755                 760                 765

Met Arg Asp Asn Pro Asp Ala Phe Glu Trp Asp Gly Lys Val Tyr Asp
    770                 775                 780

Thr Lys Thr Gly Gln Met Val Thr Ala Pro Asp Gly Gln Tyr Thr Tyr
785                 790                 795                 800

Arg Phe Val Ala Thr Leu Trp Asn Glu Gly Pro Asn Gln Lys Gln Thr
                805                 810                 815

Ala Asp Phe Pro Val Val Asp Thr Gln Ala Pro Ser Leu Ser Val
        820                 825                 830

Lys Tyr Asp Ser Ala Thr His Thr Leu Ser Gly Asn Tyr Glu Asp Lys
        835                 840                 845

Gly Ala Gly Phe Thr Asp Tyr Ser Tyr Val Thr Val Gln Val Asn Asp
        850                 855                 860

Lys Val Phe Gly Tyr Lys Leu Asn Glu Gly Glu Ser Gly Phe Asp Asn
865                 870                 875                 880

Ser Glu Lys Thr Lys Gly His Phe Asn Phe Thr Leu Ser Ser Asp Ala
                885                 890                 895

Leu Asp Ala Leu Ser Gly Ser Leu Asn Lys Val Ser Val Thr Leu Ser
            900                 905                 910

Asp Val Ala Asn Asn Thr Thr Val Lys Thr Val Asp Val Pro Ala Val
        915                 920                 925

Lys Asp Gln Pro Ala Val Ser Val Trp Asn Ala Thr Glu Gly Val Glu
        930                 935                 940

Phe Asn Lys Asn Ser Lys Asp Tyr Asn Lys Glu Asn Asp Thr Tyr Thr
945                 950                 955                 960

Leu Tyr Gly Ser Ala Ala Gln Asp Phe Tyr Leu Asn Gly Ala Leu Val
                965                 970                 975

Gln Val Arg Asp Gly Lys Tyr Glu Val Pro Val Lys Thr Thr Thr Gln
            980                 985                 990

Asp Leu Val Phe Ser Thr Asp Gln Ala Gly Lys Asn Val Leu Lys Ser
        995                 1000                1005

Phe Thr Thr Phe Thr Pro Lys Ala Phe Phe Asn Trp Gln Asn Val
    1010                1015                1020

Asp Gly Phe Asp Gly Asn Phe Gly Val Asn Ile Tyr Ser Val Lys
    1025                1030                1035
```

-continued

```
Thr Asn Asp Pro Asn Asn Ala Val Val Gln Ala Ala Val Pro Leu
    1040            1045            1050

Gly Lys Asn Val Lys Ala Tyr Ala Gln Asp Tyr Phe Thr Gly Glu
    1055            1060            1065

Val Tyr Lys Gly Gln Val Glu Asn Gly Val Ala Thr Phe His Val
    1070            1075            1080

His Thr Ser Ile Asn Gln Gly Glu Asp Gly Ile Phe Lys Arg Ala
    1085            1090            1095

Leu Leu Thr Gly Trp Ser Glu Val Asp Gly Pro Ala Tyr Asn Asp
    1100            1105            1110

Lys Gln Val Thr Ser Lys Ala Gly Val Ala Ser Ser Asn His Leu
    1115            1120            1125

Gly Val Tyr Tyr Thr Thr Asp Lys Val Asn Arg Lys Val Tyr Thr
    1130            1135            1140

Asp Arg Ala Asp Leu Gly Val Asp Val Gln Asp Glu Ala Ala Asp
    1145            1150            1155

Leu Ser Ser Phe Gly Pro Thr Ala Tyr Pro Gly His Ala Leu Ala
    1160            1165            1170

Asp Leu Thr Thr Arg Thr Asp Pro Asn Pro Ala Ile His Phe Asp
    1175            1180            1185

Tyr Leu Asn Asp Asn Asp Thr Thr Arg Phe Gly Gln Asn Ala Val
    1190            1195            1200

Thr Asp Gly Tyr Tyr Asp Ser Val Thr Lys Lys Phe Thr Val Thr
    1205            1210            1215

Gly His Val Asp Pro Glu Val Lys Ser Leu Thr Val Leu Gly Asp
    1220            1225            1230

Ser Ser Asp Glu Asn Ala Pro Gln Asn Gln Val Lys Leu Gly Lys
    1235            1240            1245

Asp Gly Lys Phe Ser Phe Ser Phe Thr Thr Glu Asn Val Gly Gln
    1250            1255            1260

Arg Pro Val Ala Tyr Ile Tyr Thr Asp Gln Asn Gly Gln Lys Val
    1265            1270            1275

Arg Gly Thr Leu Asn Val Val Leu Asp Thr Val Ala Pro Thr Leu
    1280            1285            1290

Asn Val Asp Gln Val Asn Gly Asn Glu Leu Glu Val Lys Thr Asn
    1295            1300            1305

Asn Pro Leu Phe Lys Leu Ser Gly Val Val Asn Asp Asn Leu Asp
    1310            1315            1320

Gly Tyr Arg Leu Tyr Val Asn Gly Asn Asn Ile Tyr Arg Glu Phe
    1325            1330            1335

Leu Asn Ser Gly Tyr Asn Lys Leu Ala Gly Leu Asn Thr Asp Gly
    1340            1345            1350

Thr Asp Val Asn Pro Tyr Gly Pro His Asn Phe Glu Glu Ser Phe
    1355            1360            1365

Asn Leu Asn Asp Asp Asn Asn Gln Pro Thr Thr His Val Phe Thr
    1370            1375            1380

Ile Tyr Val Val Asp Gln Val Gly Asn Lys Val Glu Lys Lys Ile
    1385            1390            1395

Ala Val Asn Tyr Asp Pro Asp Tyr Val Ala Glu Pro Pro Lys Thr
    1400            1405            1410

Asp Gln Asp Gln Asn Ser Gly Gln Thr Ala Gln Pro Gln Thr Asn
    1415            1420            1425

Pro Ala Val Asn Val Asp Lys Pro Thr Thr Pro Asp Asn Thr Ser
```

1430              1435              1440

Glu Val Pro Ala Val Asp Gln Thr Lys His Ser Asp Ser Glu Gln
    1445              1450              1455

Thr Asn Gln Val Pro Lys Asp Asn Pro Thr Asp Gln Leu Ser Val
    1460              1465              1470

Gln Val Pro Val Ser Arg Glu Thr Ser Val Thr Lys Asp Asn Asn
    1475              1480              1485

Leu Asn Asp Val Val Leu Thr Ala Lys Ser Phe Pro Leu Leu His
    1490              1495              1500

Asp Ala Tyr Leu Tyr Asp Glu Asn Gly Glu Val Val Leu Thr Ser
    1505              1510              1515

Asp Pro Gln Lys Lys Ser Val Leu Lys Lys Gly Lys Thr Ile Ser
    1520              1525              1530

Ala Leu Gln Asn Gly His Val Tyr Val Ile Lys Gly Val Lys Phe
    1535              1540              1545

Tyr Gln Val Gly Lys Asn Gln Tyr Val Lys Val Ala Asn Thr Thr
    1550              1555              1560

Leu Gln Ala Gly Lys Arg Leu Gln Leu Lys His Asn Ala Phe Val
    1565              1570              1575

Tyr Asp Glu Lys Gly Lys Leu Val Lys Lys His Gly Lys Ser Val
    1580              1585              1590

Leu Leu Pro Lys Asn Lys Trp Val Ser Ala Leu Asn Asn Ala Asp
    1595              1600              1605

Lys Phe Lys Val Asn Gly Val Thr Tyr Tyr Lys Leu Thr Asp His
    1610              1615              1620

Gln Tyr Ile Lys Val Ala Asn Thr Val Val Gln Pro Ala Lys Lys
    1625              1630              1635

Leu Lys Leu Thr His Asn Ala Phe Val Tyr Asp Gln Asn Gly Lys
    1640              1645              1650

Arg Val Lys Lys Ser Lys Leu Leu Lys Lys Gly Thr Val Leu Leu
    1655              1660              1665

Ala Leu Asn Gly Ala Glu Lys Phe Lys Leu Lys Asn Lys Thr Tyr
    1670              1675              1680

Tyr Gln Val Gly Lys Asn Gln Tyr Val Lys Val Ala Asn Thr Leu
    1685              1690              1695

<210> SEQ ID NO 6
<211> LENGTH: 5094
<212> TYPE: DNA
<213> ORGANISM: Lactobacillus intestinalis

<400> SEQUENCE: 6
atgagtgatt atagctggcc aaagagccac aataagtatt cttatgtttt caaacaaga       60 gaaggcttaa acaagattga acacaaaaa cgtgcgaaga gcgtttcaga tatgcgaaag      120
aaatgggtgg ctacagctat tattgcttta gcatctggtt cgactgtctt tttgagtcag     180
acatcttctg ttgaagcagc aataggagag acttctgtcc aaaatgttaa agtttctgtg     240
gctaaaaatg aaagtgattc acaaaaattt aataatagtc agaacttgga acaaaaaact     300
ccgcaagcag cagctgctaa tcaaaatggg tcacaagtac aaaatgacca tactgaaact     360
caattacaaa accaacaaac tactcaatct caggtaactc aagctcacac agaagaaaat     420
aatgcttcat caattcctga accagctaat caggccgatc atgtaaaagg aaatgttcaa     480
tctgcatggg accagggtta taaaggtcaa aatacggttg tagccgtaat tgattctggg     540

```
gctgatacca gtcataaaga tttccaaaca atgccatcta atccaaaact taagcaagaa    600
gatgttcaaa gtaagattga tcagcaagga tatggaaaat atgttaatga aaaatttcca    660
tatgtttata attatgccga tagggacaat gattatatta aatcggatga taataatcaa    720
aatgatagtc ctcatgggca acatgtttct ggaattattg cggcagatgg gcaccctgag    780
ggtgatcaac aatatgttgt cggagttgct ccagaagctc agcttatgca acttagagta    840
tttgggcaat tttctgatga aaaaacagat gatgtagcaa gagctatcta tgatgcaact    900
aacttaggtg ccgatgttat ccaaatgtcc ttaggacagg gtgtggcaga tcaacagtta    960
actaatattg aacaaaaagc agttcaatat gcgattgacc atggtgtatt tgtttcaatt   1020
tctgcttcta ataatggaaa ttctgcttca gtagataatc caagtaaagt taccgcaaaa   1080
ggttatgggt ccggatcaga agctggaaat tatgaaccttg gaattctgg aacggtcgcc   1140 aaccccggtg cttctaagaa tgccttaact gttgctgcgg aaacttctgg aactggcaaa   1200
gatagtgaca tggcttcatt ttcatcatgg ggaccattat ctgattttag tttaaagcca   1260
gatctttcag ctcctggtta tcaggtggtt tcaactgtta atgataatca atatcaaaca   1320
atgagtggaa cttcaatggc tggtccattt gcagctggca gtgctgcttt agtaatccaa   1380
cggctaaagc aaactaatcc agagttaaaa ggagcagaac ttgttgctgc aactaaagca   1440
ttattgatga atagcgctaa agtgcaaacg caaaatggat acaccacgcc tgtttctcca   1500
agaagacaag gtgcaggtca aattgatgta ggagctgcta cggccaatcc agtttatgta   1560
actgctgctg atggaacgag ctccttatct ttacgtcaag ttgatgaaaa aactactttt   1620
actcttactt ttcataattt aacagatcaa gaacaaagct acagctttaa tgatttgggg   1680
ggaggttata ctgaacaacg tgatcccgat agtggggtct ttcatgaggt tcaattagca   1740
ggagctcatg tgaatggtgt aggcaatttt actctagcac caaagaggt taagacctt    1800 caatatacat tagatttaca ggggttaaat aaaaatcagc cagtagaagg atggcttcat   1860
tttactaatg ataaagataa atcgactgtg gtagtgccat atttagcata ttatggtgat   1920
ttgactagtg aaaatgtctt cgatcaaaat gcaaatgaag aaaagccaga tattcaaggt   1980
aatcgtttcg ttaatgaaaa caattatcca cttggagtaa ctgatcaaga atctttaaaa   2040
caattagtaa atgttgacag tgattacaat tggcaagaag ttgctaaact ttacgaaagt   2100
ggaaaagttg cttttttcacc aaatgatgat catcaaagtg accttatcaa gccatatgct   2160
tatttaaagc aaaatgtaaa agacttaaag gttgaaattt tagacgctaa gggtaacgta   2220
gtgcgcgtag tatctgatgt tcaagggggtt gataagtctt acgatgaaag tggagtaact   2280
aaagatgcta gtctttcagt ctccatgaga gacaatcccg atgcttttga atgggacggt   2340
aaagtttacg atactaaaac tggtcaaatg gtaacggcgc cgatggaca atatacttat    2400 cgctttgttg ctactctctg gaatgaagga ccaaatcaaa aacagactgc agattttcca   2460
gttgtagtag atacacaagc tcctagttta agcgttaaat atgattcggc tactcatact   2520
ttgtccggta actatgaaga taagggtgca ggttttacgg attattctta tgttactgtc   2580
caagtaaatg ataaagtctt tggttacaag ttgaatgagg gcgaatcagg ttttgacaac   2640
agtgaaaaaa caaaaggtca tttcaatttt actttaagtt cagatgcttt ggatgcttta   2700
agtggtagtt tgaataaagt ttctgtaact ttaagtgatg tagctaacaa cacgacagtt   2760
aaaactgttg atgttcctgc tgttaaagat caaccagcag tttctgtgtg gaatgcaacc   2820
gaaggggtag aatttaataa aaattctaaa gactacaata aagaaaatga tacttacact   2880
ttatatggtt cagcggccca agatttctat ttaaatggtg ccttagtgca agtacgagat   2940
```

```
ggcaaatacg aggttccagt aaaaacgact acccaagatt tggtattttc tactgatcaa    3000
gcaggtaaaa atgttttaaa gtctttcact acttttaccc ctaaggcatt ctttaattgg    3060
caaaatgtcg atggctttga cgggaatttt ggagtaaata tctattctgt gaagactaat    3120
gatccaaata atgcagttgt gcaagcagca gttcctctag gtaaaaatgt caaagcctat    3180
gctcaagact atttcactgg tgaagtatat aaaggccaag tagaaaatgg agtagctact    3240
ttccatgtgc atacttctat taatcaaggc gaagacggta tatttaaacg tgcgctttta    3300
acagggtgga gtgaagtgga cggtccggca tataatgata acaagttac cagtaaagct     3360 ggtgtagcta gttcaaatca tttaggtgtt tattacacca ctgataaggt taatcgaaag    3420
gtttatactg atcgcgctga tttaggtgta gatgttcaag atgaagcagc tgacttaagt    3480
tcatttggcc caaccgcata cccaggacat gctctagcag atttaactac tcgaacggat    3540
cctaatccag caattcattt tgattatttg aatgataatg acactactag atttggacaa    3600
aatgcagtga ctgatggata ttatgattcc gtaactaaaa agtttactgt tacaggacat    3660
gtcgatccag aagttaaatc gcttactgtc ttaggagata gttctgatga aaatgctcct    3720
caaaatcaag tcaagttggg caaagatggc aagttcagtt ttagttttcac tactgaaaat   3780 gtaggccaac gtcccgtagc ttatatttat actgatcaaa atggtcaaaa agttcgcggt    3840
accctaaatg ttgtcttaga tacagttgcg ccaaccttaa atgtagatca agtaaatggt    3900
aacgaacttg aagtcaaaac taacaatcct cttttcaaac tttcaggagt agttaatgat    3960
aatttagatg ctatagact ttatgtaaat ggcaataata tttatcgaga attcttaaat     4020
tctggctaca ataaattagc aggtttaaat actgatggga cagatgtaaa cccatatggt    4080
ccgcataact ttgaagaaag tttcaattta atgatgaca caatcaacc aactactcat      4140 gtctttacga tttacgtagt tgaccaagtt ggtaataaag tagaaaagaa gatcgctgtt    4200
aattatgatc cagactatgt ggctgaacct ccaaaaacgg atcaagatca aaattctggt    4260
cagactgcac aaccgcaaac aaatccagca gtaaatgttg ataagcctac cactccagat    4320
aacacatctg aagttccagc tgttgatcaa accaaacatt cagatagtga gcaaactaat    4380
caagttccaa aggataatcc gacagatcaa ctctctgttc aagttcctgt ttcacgtgaa    4440
actagtgtta caaagataa taatcttaat gatgtagttt taacggctaa atcattcccg     4500
cttcttcatg atgcatattt atatgatgaa atgggggaag tcgttttaac tagtgatcca    4560
cagaagaaat cagttttgaa gaaaggcaag acaatcagtg cgcttcaaaa tggacatgtt    4620
tatgtaatta aaggtgtaaa attctaccaa gttggtaaga atcagtatgt aaaggtcgcc    4680
aacactactt tgcaagctgg taagagattg caattaaagc ataatgcctt tgtttatgat    4740 gaaaaggaa agctggttaa gaagcatggc aagagtgtac ttttaccaaa aaataagtgg     4800
gtttcagctt taaataatgc agacaagttt aaagtaaatg gtgtaactta ttataaactt    4860
acggatcatc aatatatcaa agttgctaat accgtcgttc aaccagctaa gaaacttaag    4920
ttaactcata atgcctttgt ttatgatcaa aatggcaaac gagttaaaaa gagtaagctt    4980
ttaaagaagg gcacagtgct tttggcctta aatggagctg aaaagtttaa gctcaagaat    5040
aagacttact atcaagttgg taagaatcaa tatgtaaaag tcgctaatac ttta          5094
```

<210> SEQ ID NO 7
<211> LENGTH: 1343
<212> TYPE: PRT
<213> ORGANISM: Artificial Sequence
<220> FEATURE:

<220> FEATURE:
<223> OTHER INFORMATION: Fragment of PrtI from Lactobacillus intestinalis DSM6629
<220> FEATURE:
<221> NAME/KEY: misc_feature
<222> LOCATION: (175)..(175)
<223> OTHER INFORMATION: Xaa can be any naturally occurring amino acid

<400> SEQUENCE: 7

```
Ala Ile Gly Glu Thr Ser Val Gln Asn Val Lys Val Ser Val Ala Lys
1               5                   10                  15

Asn Glu Ser Asp Ser Gln Lys Phe Asn Asn Ser Gln Asn Leu Glu Gln
            20                  25                  30

Lys Thr Pro Gln Ala Ala Ala Asn Gln Asn Gly Ser Gln Val Gln
        35                  40                  45

Asn Asp His Thr Glu Thr Gln Leu Gln Asn Gln Gln Thr Thr Gln Ser
50                  55                  60

Gln Val Thr Gln Ala His Thr Glu Glu Asn Asn Ala Ser Ser Ile Pro
65                  70                  75                  80

Glu Pro Ala Asn Gln Ala Asp His Val Lys Gly Asn Val Gln Ser Ala
                85                  90                  95

Trp Asp Gln Gly Tyr Lys Gly Gln Asn Thr Val Val Ala Val Ile Asp
            100                 105                 110

Ser Gly Ala Asp Thr Ser His Lys Asp Phe Gln Thr Met Pro Ser Asn
        115                 120                 125

Pro Lys Leu Lys Gln Glu Asp Val Gln Ser Lys Ile Asp Gln Gln Gly
    130                 135                 140

Tyr Gly Lys Tyr Val Asn Glu Lys Phe Pro Tyr Val Tyr Asn Tyr Ala
145                 150                 155                 160

Asp Arg Asp Asn Asp Tyr Ile Lys Ser Asp Asn Asn Gln Xaa Asn
                165                 170                 175

Asp Ser Pro His Gly Gln His Val Ser Gly Ile Ile Ala Ala Asp Gly
            180                 185                 190

His Pro Glu Gly Asp Gln Gln Tyr Val Val Gly Val Ala Pro Glu Ala
        195                 200                 205

Gln Leu Met Gln Leu Arg Val Phe Gly Gln Phe Ser Asp Glu Lys Thr
    210                 215                 220

Asp Asp Val Ala Arg Ala Ile Tyr Asp Ala Thr Asn Leu Gly Ala Asp
225                 230                 235                 240

Val Ile Gln Met Ser Leu Gly Gln Gly Val Ala Asp Gln Leu Thr
                245                 250                 255

Asn Ile Glu Gln Lys Ala Val Gln Tyr Ala Ile Asp His Gly Val Phe
            260                 265                 270

Val Ser Ile Ser Ala Ser Asn Asn Gly Asn Ser Ala Ser Val Asp Asn
        275                 280                 285

Pro Ser Lys Val Thr Ala Lys Gly Tyr Gly Ser Gly Ser Glu Ala Gly
    290                 295                 300

Asn Tyr Glu Pro Leu Asn Ser Gly Thr Val Ala Asn Pro Gly Ala Ser
305                 310                 315                 320

Lys Asn Ala Leu Thr Val Ala Ala Glu Thr Ser Gly Thr Gly Lys Asp
                325                 330                 335

Ser Asp Met Ala Ser Phe Ser Ser Trp Gly Pro Leu Ser Asp Phe Ser
            340                 345                 350

Leu Lys Pro Asp Leu Ser Ala Pro Gly Tyr Gln Val Val Ser Thr Val
        355                 360                 365

Asn Asp Asn Gln Tyr Gln Thr Met Ser Gly Thr Ser Met Ala Gly Pro
```

```
            370                 375                 380
Phe Ala Gly Ser Ala Ala Leu Val Ile Gln Arg Leu Lys Gln Thr
385                 390                 395                 400

Asn Pro Glu Leu Lys Gly Ala Glu Leu Val Ala Thr Lys Ala Leu
                405                 410                 415

Leu Met Asn Ser Ala Lys Val Gln Thr Gln Asn Gly Tyr Thr Thr Pro
                420                 425                 430

Val Ser Pro Arg Arg Gln Gly Ala Gly Gln Ile Asp Val Gly Ala Ala
                435                 440                 445

Thr Ala Asn Pro Val Tyr Val Thr Ala Ala Asp Gly Thr Ser Ser Leu
450                 455                 460

Ser Leu Arg Gln Val Asp Glu Lys Thr Thr Phe Thr Leu Thr Phe His
465                 470                 475                 480

Asn Leu Thr Asp Gln Glu Gln Ser Tyr Ser Phe Asn Asp Leu Gly Gly
                485                 490                 495

Gly Tyr Thr Glu Gln Arg Asp Pro Asp Ser Gly Val Phe His Glu Val
                500                 505                 510

Gln Leu Ala Gly Ala His Val Asn Gly Val Gly Asn Phe Thr Leu Ala
                515                 520                 525

Pro Lys Glu Val Lys Asp Leu Gln Tyr Thr Leu Asp Leu Gln Gly Leu
                530                 535                 540

Asn Lys Asn Gln Pro Val Glu Gly Trp Leu His Phe Thr Asn Asp Lys
545                 550                 555                 560

Asp Lys Ser Thr Val Val Val Pro Tyr Leu Ala Tyr Tyr Gly Asp Leu
                565                 570                 575

Thr Ser Glu Asn Val Phe Asp Gln Asn Ala Asn Glu Glu Lys Pro Asp
                580                 585                 590

Ile Gln Gly Asn Arg Phe Val Asn Glu Asn Asn Tyr Pro Leu Gly Val
                595                 600                 605

Thr Asp Gln Glu Ser Leu Lys Gln Leu Val Asn Val Asp Ser Asp Tyr
                610                 615                 620

Asn Trp Gln Glu Val Ala Lys Leu Tyr Glu Ser Gly Lys Val Ala Phe
625                 630                 635                 640

Ser Pro Asn Asp Asp His Gln Ser Asp Leu Ile Lys Pro Tyr Ala Tyr
                645                 650                 655

Leu Lys Gln Asn Val Lys Asp Leu Lys Val Glu Ile Leu Asp Ala Lys
                660                 665                 670

Gly Asn Val Val Arg Val Val Ser Asp Val Gln Gly Val Asp Lys Ser
                675                 680                 685

Tyr Asp Glu Ser Gly Val Thr Lys Asp Ala Ser Leu Ser Val Ser Met
690                 695                 700

Arg Asp Asn Pro Asp Ala Phe Glu Trp Asp Lys Val Tyr Asp Thr
705                 710                 715                 720

Lys Thr Gly Gln Met Val Thr Ala Pro Asp Gly Gln Tyr Thr Tyr Arg
                725                 730                 735

Phe Val Ala Thr Leu Trp Asn Glu Gly Pro Asn Gln Lys Gln Thr Ala
                740                 745                 750

Asp Phe Pro Val Val Asp Thr Gln Ala Pro Ser Leu Ser Val Lys
                755                 760                 765

Tyr Asp Ser Ala Thr His Thr Leu Ser Gly Asn Tyr Glu Asp Lys Gly
                770                 775                 780

Ala Gly Phe Thr Asp Tyr Ser Tyr Val Thr Val Gln Val Asn Asp Lys
785                 790                 795                 800
```

-continued

```
Val Phe Gly Tyr Lys Leu Asn Glu Gly Glu Ser Gly Phe Asp Asn Ser
            805                 810                 815
Glu Lys Thr Lys Gly His Phe Asn Phe Thr Leu Ser Ser Asp Ala Leu
            820                 825                 830
Asp Ala Leu Ser Gly Ser Leu Asn Lys Val Ser Val Thr Leu Ser Asp
            835                 840                 845
Val Ala Asn Asn Thr Thr Val Lys Thr Val Asp Val Pro Ala Val Lys
850                 855                 860
Asp Gln Pro Ala Val Ser Val Trp Asn Ala Thr Glu Gly Val Glu Phe
865                 870                 875                 880
Asn Lys Asn Ser Lys Asp Tyr Asn Lys Glu Asn Asp Thr Tyr Thr Leu
            885                 890                 895
Tyr Gly Ser Ala Ala Gln Asp Phe Tyr Leu Asn Gly Ala Leu Val Gln
            900                 905                 910
Val Arg Asp Gly Lys Tyr Glu Val Pro Val Lys Thr Thr Thr Gln Asp
            915                 920                 925
Leu Val Phe Ser Thr Asp Gln Ala Gly Lys Asn Val Leu Lys Ser Phe
            930                 935                 940
Thr Thr Phe Thr Pro Lys Ala Phe Phe Asn Trp Gln Asn Val Asp Gly
945                 950                 955                 960
Phe Asp Gly Asn Phe Gly Val Asn Ile Tyr Ser Val Lys Thr Asn Asp
            965                 970                 975
Pro Asn Asn Ala Val Val Gln Ala Ala Val Pro Leu Gly Lys Asn Val
            980                 985                 990
Lys Ala Tyr Ala Gln Asp Tyr Phe Thr Gly Glu Val Tyr Lys Gly Gln
            995                 1000                1005
Val Glu Asn Gly Val Ala Thr Phe His Val His Thr Ser Ile Asn
    1010                1015                1020
Gln Gly Glu Asp Gly Ile Phe Lys Arg Ala Leu Leu Thr Gly Trp
    1025                1030                1035
Ser Glu Val Asp Gly Pro Ala Tyr Asn Asp Lys Gln Val Thr Ser
    1040                1045                1050
Lys Ala Gly Val Ala Ser Ser Asn His Leu Gly Val Tyr Tyr Thr
    1055                1060                1065
Thr Asp Lys Val Asn Arg Lys Val Tyr Thr Asp Arg Ala Asp Leu
    1070                1075                1080
Gly Val Asp Val Gln Asp Glu Ala Ala Asp Leu Ser Ser Phe Gly
    1085                1090                1095
Pro Thr Ala Tyr Pro Gly His Ala Leu Ala Asp Leu Thr Thr Arg
    1100                1105                1110
Thr Asp Pro Asn Pro Ala Ile His Phe Asp Tyr Leu Asn Asp Asn
    1115                1120                1125
Asp Thr Thr Arg Phe Gly Gln Asn Ala Val Thr Asp Gly Tyr Tyr
    1130                1135                1140
Asp Ser Val Thr Lys Lys Phe Thr Val Thr Gly His Val Asp Pro
    1145                1150                1155
Glu Val Lys Ser Leu Thr Val Leu Gly Asp Ser Ser Asp Glu Asn
    1160                1165                1170
Ala Pro Gln Asn Gln Val Lys Leu Gly Lys Asp Gly Lys Phe Ser
    1175                1180                1185
Phe Ser Phe Thr Thr Glu Asn Val Gly Gln Arg Pro Val Ala Tyr
    1190                1195                1200
```

```
Ile Tyr Thr Asp Gln Asn Gly Gln Lys Val Arg Gly Thr Leu Asn
    1205                1210                1215

Val Val Leu Asp Thr Val Ala Pro Thr Leu Asn Val Asp Gln Val
1220                1225                1230

Asn Gly Asn Glu Leu Glu Val Lys Thr Asn Asn Pro Leu Phe Lys
    1235                1240                1245

Leu Ser Gly Val Val Asn Asp Asn Leu Asp Gly Tyr Arg Leu Tyr
    1250                1255                1260

Val Asn Gly Asn Asn Ile Tyr Arg Glu Phe Leu Asn Ser Gly Tyr
    1265                1270                1275

Asn Lys Leu Ala Gly Leu Asn Thr Asp Gly Thr Asp Val Asn Pro
    1280                1285                1290

Tyr Gly Pro His Asn Phe Glu Glu Ser Phe Asn Leu Asn Asp Asp
    1295                1300                1305

Asn Asn Gln Pro Thr Thr His Val Phe Thr Ile Tyr Val Val Asp
    1310                1315                1320

Gln Val Gly Asn Lys Val Glu Lys Lys Ile Ala Val Asn Tyr Asp
    1325                1330                1335

Pro Asp Tyr Val Ala
    1340
```

<210> SEQ ID NO 8
<211> LENGTH: 4026
<212> TYPE: DNA
<213> ORGANISM: Artificial Sequence
<220> FEATURE:
<223> OTHER INFORMATION: Nucleic acid sequence of fragment of PrtI

<400> SEQUENCE: 8

```
gcaataggag agacttctgt ccaaaatgtt aaagtttctg tggctaaaaa tgaaagtgat      60
tcacaaaaat ttaataatag tcagaacttg aacaaaaaa ctccgcaagc agcagctgct     120
aatcaaaatg ggtcacaagt acaaaatgac catactgaaa ctcaattaca aaaccaacaa     180
actactcaat ctcaggtaac tcaagctcac acagaagaaa ataatgcttc atcaattcct     240
gaaccagcta tcaggccga tcatgtaaaa ggaaatgttc aatctgcatg ggaccagggt     300
tataaaggtc aaaatacggt tgtagccgta attgattctg gggctgatac cagtcataaa     360
gatttccaaa caatgccatc taatccaaaa cttaagcaag aagatgttca agtaagatt      420
gatcagcaag gatatggaaa atatgttaat gaaaaatttc catatgttta taattatgcc     480
gatagggaca tgattatat taaatcggat gataataatc aaaatgatag tcctcatggg     540
caacatgttt ctggaattat tgcggcagat gggcaccctg agggtgatca acaatatgtt     600
gtcggagttg ctccagaagc tcagcttatg caacttagag tatttgggca attttctgat     660
gaaaaaacag atgatgtagc aagagctatc tatgatgcaa ctaacttagg tgccgatgtt     720
atccaaatgt ccttaggaca gggtgtggca gatcaacagt taactaatat tgaacaaaaa     780
gcagttcaat atgcgattga ccatggtgta tttgtttcaa tttctgcttc taataatgga     840
aattctgctt cagtagataa tccaagtaaa gttaccgcaa aaggttatgg gtccggatca     900
gaagctggaa attatgaacc tttgaattct ggaacggtcg ccaaccccgg tgcttctaag     960
aatgccttaa ctgttgctgc ggaaacttct ggaactggca agatagtga catggcttca    1020
tttttcatcat gggaccatt atctgatttt agtttaaagc cagatctttc agctcctggt    1080
tatcaggtgg tttcaactgt taatgataat caatatcaaa caatgagtgg aacttcaatg    1140
gctggtccat tgcagctgg cagtgctgct ttagtaatcc aacggctaaa gcaaactaat    1200
```

```
ccagagttaa aaggagcaga acttgttgct gcaactaaag cattattgat gaatagcgct    1260
aaagtgcaaa cgcaaaatgg atacaccacg cctgtttctc caagaagaca aggtgcaggt    1320
caaattgatg taggagctgc tacggccaat ccagtttatg taactgctgc tgatggaacg    1380
agctccttat ctttacgtca agttgatgaa aaaactactt ttactcttac ttttcataat    1440
ttaacagatc aagaacaaag ctacagcttt aatgatttgg ggggaggtta tactgaacaa    1500
cgtgatcccg atagtggggt cttccatgag gttcaattag caggagctca tgtgaatggt    1560
gtaggcaatt ttactctagc accaaaagag gttaaagacc ttcaatatac attagattta    1620 cagggttaa ataaaaatca gccagtagaa ggatggcttc atttactaa tgataaagat    1680 aaatcgactg tggtagtgcc atatttagca tattatggtg atttgactag tgaaaatgtc    1740
ttcgatcaaa atgcaaatga agaaaagcca gatattcaag gtaatcgttt cgttaatgaa    1800
aacaattatc cacttggagt aactgatcaa gaatctttaa acaattagt aaatgttgac    1860 agtgattaca attggcaaga agttgctaaa ctttacgaaa gtggaaaagt tgcttttca    1920 ccaaatgatg atcatcaaag tgaccttatc aagccatatg cttatttaaa gcaaaatgta    1980
aaagacttaa aggttgaaat tttagacgct aagggtaacg tagtgcgcgt agtatctgat    2040
gttcaagggg ttgataagtc ttacgatgaa agtggagtaa ctaaagatgc tagtctttca    2100
gtctccatga gagacaatcc cgatgctttt gaatgggacg gtaaagttta cgatactaaa    2160
actggtcaaa tggtaacggc gcccgatgga caatatactt atcgctttgt tgctactctc    2220
tggaatgaag gaccaaatca aaaacagact gcagattttc cagttgtagt agatacacaa    2280
gctcctagtt taagcgttaa atatgattcg gctactcata cttgtccgg taactatgaa    2340 gataagggtg caggttttac ggattattct tatgttactg tccaagtaaa tgataaagtc    2400
tttggttaca agttgaatga gggcgaatca ggttttgaca acagtgaaaa aacaaaaggt    2460
catttcaatt ttactttaag ttcagatgct ttggatgctt taagtggtag tttgaataaa    2520
gtttctgtaa ctttaagtga tgtagctaac aacacgacag ttaaaactgt tgatgttcct    2580
gctgttaaag atcaaccagc agtttctgtg tggaatgcaa ccgaagggt agaatttaat    2640 aaaaattcta aagactacaa taagaaaat gatacttaca ctttatatgg ttcagcggcc    2700
caagatttct attaatgg tgccttagtg caagtacgag atggcaaata cgaggttcca    2760 gtaaaacga ctacccaaga tttggtattt tctactgatc aagcaggtaa aaatgtttta    2820
aagtctttca ctactttac ccctaaggca ttctttaatt ggcaaaatgt cgatggcttt    2880
gacgggaatt ttggagtaaa tatctattct gtgaagacta atgatccaaa taatgcagtt    2940
gtgcaagcag cagttcctct aggtaaaaat gtcaaagcct atgctcaaga ctatttcact    3000
ggtgaagtat ataaaggcca agtagaaaat ggagtagcta cttccatgt gcatacttct    3060 attaatcaag gcgaagacgg tatatttaaa cgtgcgcttt taacagggtg gagtgaagtg    3120
gacggtccgg catataatga taacaagtt accagtaaag ctggtgtagc tagttcaaat    3180
catttaggtg tttattacac cactgataag gttaatcgaa aggtttatac tgatcgcgct    3240
gatttaggtg tagatgttca agatgaagca gctgacttaa gttcatttgg cccaaccgca    3300
tacccaggac atgctctagc agatttaact actcgaacgg atcctaatcc agcaattcat    3360
tttgattatt tgaatgataa tgacactact agatttggac aaaatgcagt gactgatgga    3420
tattatgatt ccgtaactaa aaagtttact gttacaggac atgtcgatcc agaagttaaa    3480
tcgcttactg tcttaggaga tagttctgat gaaaatgctc ctcaaaatca agtcaagttg    3540
```

-continued

```
ggcaaagatg gcaagttcag ttttagtttc actactgaaa atgtaggcca acgtcccgta    3600
gcttatattt atactgatca aaatggtcaa aaagttcgcg gtaccctaaa tgttgtctta    3660
gatacagttg cgccaacctt aaatgtagat caagtaaatg gtaacgaact tgaagtcaaa    3720
actaacaatc ctcttttcaa acttcagga gtagttaatg ataatttaga tggctataga    3780
ctttatgtaa atggcaataa tatttatcga gaattcttaa attctggcta caataaatta    3840
gcaggtttaa atactgatgg gacagatgta aacccatatg gtccgcataa ctttgaagaa    3900
agtttcaatt taaatgatga caacaatcaa ccaactactc atgtctttac gatttacgta    3960
gttgaccaag ttggtaataa agtagaaaag aagatcgctg ttaattatga tccagactat    4020
gtggct                                                               4026
```

<210> SEQ ID NO 9
<211> LENGTH: 1380
<212> TYPE: PRT
<213> ORGANISM: Artificial Sequence
<220> FEATURE:
<223> OTHER INFORMATION: Fragment of PrtI from Lactobacillus
      intestinalis DSM6629
<220> FEATURE:
<221> NAME/KEY: misc_feature
<222> LOCATION: (204)..(204)
<223> OTHER INFORMATION: Xaa can be any naturally occurring amino acid

<400> SEQUENCE: 9

```
Met Arg Lys Lys Trp Val Ala Thr Ala Ile Ile Ala Leu Ala Ser Gly
1               5                   10                  15

Ser Thr Val Phe Leu Ser Gln Thr Ser Ser Val Glu Ala Ala Ile Gly
            20                  25                  30

Glu Thr Ser Val Gln Asn Val Lys Val Ser Val Ala Lys Asn Glu Ser
        35                  40                  45

Asp Ser Gln Lys Phe Asn Asn Ser Gln Asn Leu Glu Gln Lys Thr Pro
    50                  55                  60

Gln Ala Ala Ala Ala Asn Gln Asn Gly Ser Gln Val Gln Asn Asp His
65                  70                  75                  80

Thr Glu Thr Gln Leu Gln Asn Gln Gln Thr Thr Gln Ser Gln Val Thr
                85                  90                  95

Gln Ala His Thr Glu Glu Asn Asn Ala Ser Ser Ile Pro Glu Pro Ala
            100                 105                 110

Asn Gln Ala Asp His Val Lys Gly Asn Val Gln Ser Ala Trp Asp Gln
        115                 120                 125

Gly Tyr Lys Gly Gln Asn Thr Val Val Ala Val Ile Asp Ser Gly Ala
    130                 135                 140

Asp Thr Ser His Lys Asp Phe Gln Thr Met Pro Ser Asn Pro Lys Leu
145                 150                 155                 160

Lys Gln Glu Asp Val Gln Ser Lys Ile Asp Gln Gln Gly Tyr Gly Lys
                165                 170                 175

Tyr Val Asn Glu Lys Phe Pro Tyr Val Tyr Asn Tyr Ala Asp Arg Asp
            180                 185                 190

Asn Asp Tyr Ile Lys Ser Asp Asp Asn Gln Xaa Asn Asp Ser Pro
            195                 200                 205

His Gly Gln His Val Ser Gly Ile Ile Ala Ala Asp Gly His Pro Glu
        210                 215                 220

Gly Asp Gln Gln Tyr Val Val Gly Val Ala Pro Glu Ala Gln Leu Met
225                 230                 235                 240

Gln Leu Arg Val Phe Gly Gln Phe Ser Asp Glu Lys Thr Asp Asp Val
```

```
                    245                 250                 255
Ala Arg Ala Ile Tyr Asp Ala Thr Asn Leu Gly Ala Asp Val Ile Gln
            260                 265                 270

Met Ser Leu Gly Gln Gly Val Ala Asp Gln Gln Leu Thr Asn Ile Glu
            275                 280                 285

Gln Lys Ala Val Gln Tyr Ala Ile Asp His Gly Val Phe Val Ser Ile
            290                 295                 300

Ser Ala Ser Asn Asn Gly Asn Ser Ala Ser Val Asp Asn Pro Ser Lys
305                 310                 315                 320

Val Thr Ala Lys Gly Tyr Gly Ser Gly Glu Ala Gly Asn Tyr Glu
            325                 330                 335

Pro Leu Asn Ser Gly Thr Val Ala Asn Pro Gly Ala Ser Lys Asn Ala
            340                 345                 350

Leu Thr Val Ala Ala Glu Thr Ser Gly Thr Gly Lys Asp Ser Asp Met
            355                 360                 365

Ala Ser Phe Ser Ser Trp Gly Pro Leu Ser Asp Phe Ser Leu Lys Pro
            370                 375                 380

Asp Leu Ser Ala Pro Gly Tyr Gln Val Val Ser Thr Val Asn Asp Asn
385                 390                 395                 400

Gln Tyr Gln Thr Met Ser Gly Thr Ser Met Ala Gly Pro Phe Ala Ala
            405                 410                 415

Gly Ser Ala Ala Leu Val Ile Gln Arg Leu Lys Gln Thr Asn Pro Glu
            420                 425                 430

Leu Lys Gly Ala Glu Leu Val Ala Ala Thr Lys Ala Leu Leu Met Asn
            435                 440                 445

Ser Ala Lys Val Gln Thr Gln Asn Gly Tyr Thr Thr Pro Val Ser Pro
            450                 455                 460

Arg Arg Gln Gly Ala Gly Gln Ile Asp Val Gly Ala Ala Thr Ala Asn
465                 470                 475                 480

Pro Val Tyr Val Thr Ala Ala Asp Gly Thr Ser Ser Leu Ser Leu Arg
            485                 490                 495

Gln Val Asp Glu Lys Thr Thr Phe Thr Leu Thr Phe His Asn Leu Thr
            500                 505                 510

Asp Gln Glu Gln Ser Tyr Ser Phe Asn Asp Leu Gly Gly Gly Tyr Thr
            515                 520                 525

Glu Gln Arg Asp Pro Asp Ser Gly Val Phe His Glu Val Gln Leu Ala
            530                 535                 540

Gly Ala His Val Asn Gly Val Gly Asn Phe Thr Leu Ala Pro Lys Glu
545                 550                 555                 560

Val Lys Asp Leu Gln Tyr Thr Leu Asp Leu Gln Gly Leu Asn Lys Asn
            565                 570                 575

Gln Pro Val Glu Gly Trp Leu His Phe Thr Asn Asp Lys Asp Lys Ser
            580                 585                 590

Thr Val Val Val Pro Tyr Leu Ala Tyr Tyr Gly Asp Leu Thr Ser Glu
            595                 600                 605

Asn Val Phe Asp Gln Asn Ala Asn Glu Glu Lys Pro Asp Ile Gln Gly
            610                 615                 620

Asn Arg Phe Val Asn Glu Asn Tyr Pro Leu Gly Val Thr Asp Gln
625                 630                 635                 640

Glu Ser Leu Lys Gln Leu Val Asn Val Asp Ser Asp Tyr Asn Trp Gln
            645                 650                 655

Glu Val Ala Lys Leu Tyr Glu Ser Gly Lys Val Ala Phe Ser Pro Asn
            660                 665                 670
```

```
Asp Asp His Gln Ser Asp Leu Ile Lys Pro Tyr Ala Tyr Leu Lys Gln
        675                 680                 685

Asn Val Lys Asp Leu Lys Val Glu Ile Leu Asp Ala Lys Gly Asn Val
    690                 695                 700

Val Arg Val Val Ser Asp Val Gln Gly Val Asp Lys Ser Tyr Asp Glu
705                 710                 715                 720

Ser Gly Val Thr Lys Asp Ala Ser Leu Ser Val Ser Met Arg Asp Asn
                725                 730                 735

Pro Asp Ala Phe Glu Trp Asp Gly Lys Val Tyr Asp Thr Lys Thr Gly
            740                 745                 750

Gln Met Val Thr Ala Pro Asp Gly Gln Tyr Thr Tyr Arg Phe Val Ala
            755                 760                 765

Thr Leu Trp Asn Glu Gly Pro Asn Gln Lys Gln Thr Ala Asp Phe Pro
    770                 775                 780

Val Val Val Asp Thr Gln Ala Pro Ser Leu Ser Val Lys Tyr Asp Ser
785                 790                 795                 800

Ala Thr His Thr Leu Ser Gly Asn Tyr Glu Asp Lys Gly Ala Gly Phe
                805                 810                 815

Thr Asp Tyr Ser Tyr Val Thr Val Gln Val Asn Asp Lys Val Phe Gly
            820                 825                 830

Tyr Lys Leu Asn Glu Gly Glu Ser Gly Phe Asp Asn Ser Glu Lys Thr
            835                 840                 845

Lys Gly His Phe Asn Phe Thr Leu Ser Ser Asp Ala Leu Asp Ala Leu
850                 855                 860

Ser Gly Ser Leu Asn Lys Val Ser Val Thr Leu Ser Asp Val Ala Asn
865                 870                 875                 880

Asn Thr Thr Val Lys Thr Val Asp Val Pro Ala Val Lys Asp Gln Pro
                885                 890                 895

Ala Val Ser Val Trp Asn Ala Thr Glu Gly Val Glu Phe Asn Lys Asn
            900                 905                 910

Ser Lys Asp Tyr Asn Lys Glu Asn Asp Thr Tyr Thr Leu Tyr Gly Ser
    915                 920                 925

Ala Ala Gln Asp Phe Tyr Leu Asn Gly Ala Leu Val Gln Val Arg Asp
    930                 935                 940

Gly Lys Tyr Glu Val Pro Val Lys Thr Thr Gln Asp Leu Val Phe
945                 950                 955                 960

Ser Thr Asp Gln Ala Gly Lys Asn Val Leu Lys Ser Phe Thr Thr Phe
                965                 970                 975

Thr Pro Lys Ala Phe Phe Asn Trp Gln Asn Val Asp Gly Phe Asp Gly
            980                 985                 990

Asn Phe Gly Val Asn Ile Tyr Ser Val Lys Thr Asn Asp Pro Asn Asn
    995                 1000                1005

Ala Val Val Gln Ala Ala Val Pro Leu Gly Lys Asn Val Lys Ala
    1010                1015                1020

Tyr Ala Gln Asp Tyr Phe Thr Gly Glu Val Tyr Lys Gly Gln Val
    1025                1030                1035

Glu Asn Gly Val Ala Thr Phe His Val His Thr Ser Ile Asn Gln
    1040                1045                1050

Gly Glu Asp Gly Ile Phe Lys Arg Ala Leu Leu Thr Gly Trp Ser
    1055                1060                1065

Glu Val Asp Gly Pro Ala Tyr Asn Asp Lys Gln Val Thr Ser Lys
    1070                1075                1080
```

Ala Gly Val Ala Ser Ser Asn His Leu Gly Val Tyr Tyr Thr Thr
1085                1090                1095

Asp Lys Val Asn Arg Lys Val Tyr Thr Asp Arg Ala Asp Leu Gly
1100                1105                1110

Val Asp Val Gln Asp Glu Ala Ala Asp Leu Ser Ser Phe Gly Pro
1115                1120                1125

Thr Ala Tyr Pro Gly His Ala Leu Ala Asp Leu Thr Thr Arg Thr
1130                1135                1140

Asp Pro Asn Pro Ala Ile His Phe Asp Tyr Leu Asn Asp Asn Asp
1145                1150                1155

Thr Thr Arg Phe Gly Gln Asn Ala Val Thr Asp Gly Tyr Tyr Asp
1160                1165                1170

Ser Val Thr Lys Lys Phe Thr Val Thr Gly His Val Asp Pro Glu
1175                1180                1185

Val Lys Ser Leu Thr Val Leu Gly Asp Ser Ser Asp Glu Asn Ala
1190                1195                1200

Pro Gln Asn Gln Val Lys Leu Gly Lys Asp Gly Lys Phe Ser Phe
1205                1210                1215

Ser Phe Thr Thr Glu Asn Val Gly Gln Arg Pro Val Ala Tyr Ile
1220                1225                1230

Tyr Thr Asp Gln Asn Gly Gln Lys Val Arg Gly Thr Leu Asn Val
1235                1240                1245

Val Leu Asp Thr Val Ala Pro Thr Leu Asn Val Asp Gln Val Asn
1250                1255                1260

Gly Asn Glu Leu Glu Val Lys Thr Asn Asn Pro Leu Phe Lys Leu
1265                1270                1275

Ser Gly Val Val Asn Asp Asn Leu Asp Gly Tyr Arg Leu Tyr Val
1280                1285                1290

Asn Gly Asn Asn Ile Tyr Arg Glu Phe Leu Asn Ser Gly Tyr Asn
1295                1300                1305

Lys Leu Ala Gly Leu Asn Thr Asp Gly Thr Asp Val Asn Pro Tyr
1310                1315                1320

Gly Pro His Asn Phe Glu Glu Ser Phe Asn Leu Asn Asp Asp Asn
1325                1330                1335

Asn Gln Pro Thr Thr His Val Phe Thr Ile Tyr Val Val Asp Gln
1340                1345                1350

Val Gly Asn Lys Val Glu Lys Lys Ile Ala Val Asn Tyr Asp Pro
1355                1360                1365

Asp Tyr Val Ala Pro Arg His His His His His
1370                1375                1380

<210> SEQ ID NO 10
<211> LENGTH: 4137
<212> TYPE: DNA
<213> ORGANISM: Artificial Sequence
<220> FEATURE:
<223> OTHER INFORMATION: Neicleic acid encoding fragment of PrtI

<400> SEQUENCE: 10
atgcgaaaga atgggtggc tacagctatt attgctttag catctggttc gactgtcttt        60
ttgagtcaga catcttctgt tgaagcagca ataggagaga cttctgtcca aaatgttaaa       120
gtttctgtgg ctaaaaatga aagtgattca caaaaattta ataatagtca gaacttggaa       180
caaaaaactc cgcaagcagc agctgctaat caaaatgggt cacaagtaca aaatgaccat       240
actgaaactc aattacaaaa ccaacaaact actcaatctc aggtaactca agctcacaca       300

```
gaagaaaata atgcttcatc aattcctgaa ccagctaatc aggccgatca tgtaaaagga    360
aatgttcaat ctgcatggga ccagggttat aaaggtcaaa atacggttgt agccgtaatt    420
gattctgggg ctgataccag tcataaagat ttccaaacaa tgccatctaa tccaaaactt    480
aagcaagaag atgttcaaag taagattgat cagcaaggat atggaaaata tgttaatgaa    540
aaatttccat atgtttataa ttatgccgat agggacaatg attatattaa atcggatgat    600
aataatcaaa atgatagtcc tcatgggcaa catgtttctg gaattattgc ggcagatggg    660
caccctgagg gtgatcaaca atatgttgtc ggagttgctc cagaagctca gcttatgcaa    720
cttagagtat ttgggcaatt ttctgatgaa aaaacagatg atgtagcaag agctatctat    780
gatgcaacta acttaggtgc cgatgttatc caaatgtcct taggacaggg tgtggcagat    840
caacagttaa ctaatattga acaaaaagca gttcaatatg cgattgacca tggtgtattt    900
gtttcaattt ctgcttctaa taatggaaat tctgcttcag tagataatcc aagtaaagtt    960
accgcaaaag ttatgggtc cggatcagaa gctggaaatt atgaaccttt gaattctgga   1020
acggtcgcca accccggtgc ttctaagaat gccttaactg ttgctgcgga acttctgga   1080 actggcaaaa atagtgacat ggcttcattt tcatcatggg gaccattatc tgattttagt   1140
ttaaagccag atctttcagc tcctggttat caggtggttt caactgttaa tgataatcaa   1200
tatcaaacaa tgagtggaac ttcaatggct ggtccatttg cagctggcag tgctgcttta   1260
gtaatccaac ggctaaagca aactaatcca gagttaaaag gagcagaact tgttgctgca   1320
actaaagcat tattgatgaa tagcgctaaa gtgcaaacgc aaaatggata caccacgcct   1380
gtttctccaa gaagacaagg tgcaggtcaa attgatgtag gagctgctac ggccaatcca   1440
gtttatgtaa ctgctgctga tggaacgagc tccttatctt tacgtcaagt tgatgaaaaa   1500
actactttta ctcttacttt tcataattta acagatcaag aacaaagcta cagctttaat   1560
gatttggggg gaggttatac tgaacaacgt gatcccgata tgggggtctt tcatgaggtt   1620
caattagcag gagctcatgt gaatggtgta ggcaatttta ctctagcacc aaaagaggtt   1680
aaagaccttc aatatacatt agatttacag gggttaaata aaaatcagcc agtagaagga   1740
tggcttcatt ttactaatga taaagataaa tcgactgtgg tagtgccata tttagcatat   1800
tatggtgatt tgactagtga aaatgtcttc gatcaaaatg caaatgaaga aaagccagat   1860
attcaaggta atcgtttcgt taatgaaaac aattatccac ttggagtaac tgatcaagaa   1920 tcttttaaaac aattagtaaa tgttgacagt gattacaatt ggcaagaagt tgctaaactt   1980
tacgaaagtg gaaaagttgc ttttcacca aatgatgatc atcaaagtga ccttatcaag   2040
ccatatgctt atttaaagca aaatgtaaaa gacttaaagg ttgaaatttt agacgctaag   2100
ggtaacgtag tgcgcgtagt atctgatgtt caagggttg ataagtctta cgatgaaagt   2160
ggagtaacta aagatgctag tctttcagtc tccatgagag acaatcccga tgcttttgaa   2220
tgggacggta agtttacga tactaaaact ggtcaaatgg taacggcgcc cgatggacaa   2280
tatacttatc gctttgttgc tactctctgg aatgaaggac caaatcaaaa acagactgca   2340
gattttccag ttgtagtaga tacacaagct cctagtttaa gcgttaaaata tgattcggct   2400 actcatactt tgtccggtaa ctatgaagat aagggtgcag gttttacgga ttattcttat   2460
gttactgtcc aagtaaatga taaagtcttt ggttacaagt tgaatgaggg cgaatcaggt   2520
tttgacaaca gtgaaaaaac aaaaggtcat ttcaatttta ctttaagttc agatgctttg   2580
gatgctttaa gtggtagttt gaataaagtt tctgtaactt taagtgatgt agctaacaac   2640
```

```
acgacagtta aaactgttga tgttcctgct gttaaagatc aaccagcagt ttctgtgtgg    2700
aatgcaaccg aagggGtaga atttaataaa aattctaaag actacaataa agaaaatgat    2760
acttacactt tatatggttc agcggcccaa gatttctatt taaatggtgc cttagtgcaa    2820
gtacgagatg gcaaatacga ggttccagta aaaacgacta cccaagattt ggtattttct    2880
actgatcaag caggtaaaaa tgttttaaag tctttcacta cttttacccc taaggcattc    2940
tttaattggc aaaatgtcga tggctttgac gggaattttg gagtaaatat ctattctgtg    3000
aagactaatg atccaaataa tgcagttgtg caagcagcag ttcctctagg taaaaatgtc    3060
aaagcctatg ctcaagacta tttcactggt gaagtatata aaggccaagt agaaaatgga    3120
gtagctactt tccatgtgca tacttctatt aatcaaggcg aagacggtat atttaaacgt    3180
gcgcttttaa cagggtggag tgaagtggac ggtccggcat ataatgataa acaagttacc    3240
agtaaagctg gtgtagctag ttcaaatcat ttaggtgttt attacaccac tgataaggtt    3300
aatcgaaagg tttatactga tcgcgctgat ttaggtgtag atgttcaaga tgaagcagct    3360
gacttaagtt catttggccc aaccgcatac ccaggacatg ctctagcaga tttaactact    3420
cgaacggatc ctaatccagc aattcatttt gattatttga atgataatga cactactaga    3480
tttggacaaa atgcagtgac tgatggatat tatgattccg taactaaaaa gtttactgtt    3540
acaggacatg tcgatccaga agttaaatcg cttactgtct taggagatag ttctgatgaa    3600
aatgctcctc aaaatcaagt caagttgggc aaagatggca agttcagttt tagtttcact    3660
actgaaaatg taggccaacg tcccgtagct tatatttata ctgatcaaaa tggtcaaaaa    3720
gttcgcggta ccctaaatgt tgtcttagat acagttgcgc caaccttaaa tgtagatcaa    3780
gtaaatggta acgaacttga agtcaaaact aacaatcctc ttttcaaact ttcaggagta    3840
gttaatgata atttagatgg ctatagactt tatgtaaatg gcaataatat ttatcgagaa    3900
ttcttaaatt ctggctacaa taaattagca ggtttaaata ctgatgggac agatgtaaac    3960
ccatatggtc cgcataactt tgaagaaagt ttcaatttaa atgatgacaa caatcaacca    4020
actactcatg tctttacgat ttacgtagtt gaccaagttg gtaataaagt agaaaagaag    4080
atcgctgtta attatgatcc agactatgtg gctcctaggc atcatcacca ccaccat      4137
```

<210> SEQ ID NO 11
<211> LENGTH: 36
<212> TYPE: DNA
<213> ORGANISM: Artificial Sequence
<220> FEATURE:
<223> OTHER INFORMATION: Forward primer for PrtV

<400> SEQUENCE: 11
cagcagggat ccgataccgt taatggtagt gaaagt                              36

<210> SEQ ID NO 12
<211> LENGTH: 46
<212> TYPE: DNA
<213> ORGANISM: Artificial Sequence
<220> FEATURE:
<223> OTHER INFORMATION: Reverse primer for PrtV

<400> SEQUENCE: 12
cagcagctcg agctatactt ttactggttc tgcagctttt ttgccc                   46

<210> SEQ ID NO 13
<211> LENGTH: 42
<212> TYPE: DNA
<213> ORGANISM: Artificial Sequence

```
<220> FEATURE:
<223> OTHER INFORMATION: Reverse primer for PrtV

<400> SEQUENCE: 13
cagcagctcg agctaatagt gaacatagaa cttcctagtt ac                    42

<210> SEQ ID NO 14
<211> LENGTH: 41
<212> TYPE: DNA
<213> ORGANISM: Artificial Sequence
<220> FEATURE:
<223> OTHER INFORMATION: Reverse primer for PrtV

<400> SEQUENCE: 14
cagcagctcg agctaattat ttacttgcca tgcaaaaaca g                     41

<210> SEQ ID NO 15
<211> LENGTH: 37
<212> TYPE: DNA
<213> ORGANISM: Artificial Sequence
<220> FEATURE:
<223> OTHER INFORMATION: Forwward primer for PrtV

<400> SEQUENCE: 15
cagcagggat ccactgttaa ggaaaacttt ggtattg                          37

<210> SEQ ID NO 16
<211> LENGTH: 34
<212> TYPE: DNA
<213> ORGANISM: Artificial Sequence
<220> FEATURE:
<223> OTHER INFORMATION: Forward primer for PrtI

<400> SEQUENCE: 16
cagcaggaat tccgcaatag gagagacttc tgtc                             34

<210> SEQ ID NO 17
<211> LENGTH: 42
<212> TYPE: DNA
<213> ORGANISM: Artificial Sequence
<220> FEATURE:
<223> OTHER INFORMATION: Reverse primer for PrtI

<400> SEQUENCE: 17
cagcagctcg agttaagcca catagtctgg atcataatta ac                    42

<210> SEQ ID NO 18
<211> LENGTH: 60
<212> TYPE: DNA
<213> ORGANISM: Artificial Sequence
<220> FEATURE:
<223> OTHER INFORMATION: Forward primer for PrtI

<400> SEQUENCE: 18
cttcatcaat tcctgaacca gaaaacctgt attttcaggg cgctaatcag gccgatcatg 60

<210> SEQ ID NO 19
<211> LENGTH: 57
<212> TYPE: DNA
<213> ORGANISM: Artificial Sequence
<220> FEATURE:
<223> OTHER INFORMATION: Forward primer for PrtI

<400> SEQUENCE: 19
cagcaggcat gctaactaag gaggtcatga tatgcgaaag aaatgggtgg ctacagc    57
```

<210> SEQ ID NO 20
<211> LENGTH: 76
<212> TYPE: DNA
<213> ORGANISM: Artificial Sequence
<220> FEATURE:
<223> OTHER INFORMATION: Reverse primer for PrtI

<400> SEQUENCE: 20
cagcagctcg agtctagatt aatggtggtg gtgatgatgc ctaggagcca catagtctgg    60
atcataatta acagcg    76

<210> SEQ ID NO 21
<211> LENGTH: 1571
<212> TYPE: PRT
<213> ORGANISM: Lactobacillus crispatus

<400> SEQUENCE: 21

Met Ser Asn Leu Thr Asn Pro Asn Asp His Lys Asp Leu Ser Phe Leu
1               5                   10                  15

Phe Lys Ser Val Asp Arg Leu Ala Ala Leu Glu Thr Gln Lys Lys Ala
                20                  25                  30

Asp Thr Ile Ile Ser Val Arg Lys Lys Trp Val Ala Ala Ala Met Ile
            35                  40                  45

Ala Leu Ala Ser Gly Ser Thr Val Leu Leu Thr Ser Asn Thr Ala Asn
50                  55                  60

Ala Ala Thr Ser Asp Val Asn Ser Glu Val Gln Val Thr Ala Gln Asn
65                  70                  75                  80

Gln Asn Thr Thr Glu Asn Lys Met Gln Ala Gly Asp Thr Ala Asn Ser
                85                  90                  95

His Asp Thr Glu Gln Asn Val Thr Val Gln Ala Asn Ser Ser Gln Gln
            100                 105                 110

Ser Asn Gln Glu Ala Asn Thr Ala Asp Gln Asn Asn Thr Pro Glu Asn
        115                 120                 125

Asp Asn Gln Val Gln Thr Pro Thr Asn Gln Ala Asp His Val Lys Gly
    130                 135                 140

Asn Val Gln Ser Ala Trp Asp Gln Gly Tyr Lys Gly Gln Gly Thr Val
145                 150                 155                 160

Val Ala Val Ile Asp Ser Gly Ala Asp Pro Ser His Lys Asp Phe Gln
                165                 170                 175

Thr Met Pro Glu Asn Pro Lys Leu Ser Lys Asp Ile Gln Lys Lys
            180                 185                 190

Ile Glu Gln Gln Gly Tyr Gly Lys Tyr Val Asn Glu Lys Phe Pro Tyr
        195                 200                 205

Val Tyr Asn Tyr Ala Asp Arg Asp Asn Asp Tyr Ile Thr Ser Asp Asp
    210                 215                 220

Thr Asn Ser Asn Asp Ser Pro His Gly Gln His Val Ser Gly Ile Ile
225                 230                 235                 240

Ala Ala Asp Gly Lys Pro Asp Gly Asn Lys Glu Tyr Val Val Gly Val
                245                 250                 255

Ala Pro Glu Ala Gln Leu Met Gln Leu Arg Val Phe Gly Gln Phe Ser
            260                 265                 270

Asp Glu Lys Thr Asp Asp Val Ala Lys Ala Ile Tyr Asp Ala Thr Asn
        275                 280                 285

Leu Gly Ala Asp Val Ile Gln Met Ser Leu Gly Gln Gly Val Ala Asp
    290                 295                 300

```
Gln Gln Leu Thr Asn Ile Glu Gln Lys Ala Val Gln Tyr Ala Ile Asp
305                 310                 315                 320

His Gly Val Phe Val Ser Ile Ser Ala Ser Asn Asn Gly His Ser Gly
            325                 330                 335

Ser Val Asp Asn Thr Ser Asn Val Thr Ser Val Glu Ser Tyr Glu Ser
        340                 345                 350

Gly Ser Ala Asp Gly Asn Tyr Glu Pro Leu Asn Ser Ser Thr Val Ala
    355                 360                 365

Asn Pro Gly Ala Ser Lys Asn Ala Leu Thr Val Ala Ala Glu Thr Ser
370                 375                 380

Ala Thr Gly Lys Asp Ser Asp Met Ala Gly Phe Ser Ser Trp Gly Pro
385                 390                 395                 400

Val Gln Asp Phe Thr Leu Lys Pro Asp Leu Ala Ala Pro Gly Tyr Gln
            405                 410                 415

Val Val Ser Thr Val Asn Asn Asn Tyr Gln Thr Met Ser Gly Thr
        420                 425                 430

Ser Met Ala Gly Pro Phe Ala Ala Ser Ala Ala Leu Val Met Gln
    435                 440                 445

Arg Leu Lys Lys Thr Asn Pro Glu Leu Lys Gly Ala Gln Leu Val Ala
450                 455                 460

Ala Thr Lys Ala Leu Leu Met Asn Ser Ala Lys Pro Gln Thr Gln Asn
465                 470                 475                 480

Gly Tyr Thr Thr Pro Val Ser Pro Arg Arg Gln Gly Ala Gly Gln Ile
            485                 490                 495

Asp Val Gly Ala Ala Thr Ser Asn Pro Val Tyr Val Ile Ala Asp Asp
        500                 505                 510

Gly Thr Ser Ser Val Ser Leu His Gln Val Lys Glu Asn Thr Pro Phe
    515                 520                 525

Thr Leu Thr Phe His Asn Leu Thr Asp Gln Glu Val Tyr Thr Phe
530                 535                 540

Asp Asp Phe Gly Gly Gly Tyr Thr Glu Gln Arg Asp Ser Asn Thr Gly
545                 550                 555                 560

Val Tyr His Asp Val Gln Leu Ala Gly Ala Arg Val Tyr Gly Glu Asn
            565                 570                 575

Ser Phe Ser Leu Ala Pro Lys Glu Thr Lys Gln Val Thr Tyr Ser Leu
        580                 585                 590

Asn Leu Asn Gly Leu Asn Asn Asn Gln Leu Val Glu Gly Phe Leu Arg
    595                 600                 605

Phe Thr Asn Thr Asn Asp Lys Ser Thr Val Ser Val Pro Tyr Leu Ala
610                 615                 620

Tyr Tyr Gly Asp Leu Thr Ser Glu Asn Val Phe Asp Gln Asn Ala Asn
625                 630                 635                 640

Glu Glu His Pro Asp Ile Gln Gly Asn Arg Phe Val Asn Glu Gln Ser
            645                 650                 655

Tyr Pro Arg Gly Val Ala Asp Gln Glu Ser Leu Lys Gln Leu Val Asn
        660                 665                 670

Val Glu Gly Asp Tyr Asn Trp Gln Glu Val Ala Lys Leu Tyr Glu Ser
    675                 680                 685

Gly Lys Val Ala Phe Ser Pro Asn Asn Asp Asn Lys Ser Asp Leu Leu
690                 695                 700

Lys Pro Tyr Thr Tyr Leu Lys Gln Asn Val Lys Asp Leu Lys Ala Val
705                 710                 715                 720

Val Leu Asp Ala Gln Gly Asn Val Val Arg Val Val Ala Asp Val Gln
```

```
                725                 730                 735
Gly Val Asp Lys Ser Tyr Asp Glu Asn Gly Val Thr Lys Asp Thr Ser
                740                 745                 750

Leu Ser Val Ser Met Arg Asp Asn Pro Asp Ala Phe Glu Trp Asp Gly
                755                 760                 765

Lys Val Tyr Asn Ser Lys Thr Gly Gln Met Glu Val Ala Lys Asp Gly
    770                 775                 780

Asn Tyr Thr Tyr Arg Leu Val Ala Thr Leu Trp Asn Glu Gly Pro His
785                 790                 795                 800

Gln Val Gln Thr Ala Asp Phe Pro Val Ile Asp Thr Val Ala Pro
                805                 810                 815

Thr Leu Ser Asn Val Lys Tyr Asp Glu Ala Thr Asn Thr Leu Ser Gly
                820                 825                 830

Glu Tyr Gln Asp Thr Gly Ala Gly Phe Thr Asn Tyr Ser Tyr Ala Thr
                835                 840                 845

Val Thr Val Asn Asp Lys Val Phe Gly Tyr Lys Leu Ser Asp Gly Gln
850                 855                 860

Ser Ala Phe Asp Asn Ala Glu Lys Thr Lys Gly His Phe Ser Phe Thr
865                 870                 875                 880

Leu Asp Lys Asp Ala Val Ala Leu Ser Gly Ala Lys Asn Lys Val
                885                 890                 895

Ser Val Val Leu Ser Asp Val Ala Asp Asn Pro Val Val Tyr Ser Val
                900                 905                 910

Asn Val Ala Gly Lys Asp Ile Asp Lys Pro Ala Val Ser Val Trp Asn
                915                 920                 925

Ala Thr Asn Gly Leu Ala Phe Asp Gln Ser Ser Thr Ser Tyr Asn Lys
930                 935                 940

Asp Thr Lys Thr Tyr Thr Leu Ile Gly Gly Ala Asn Gln Asp Phe Tyr
945                 950                 955                 960

Leu Asn Gly Lys Leu Val Gln Val Gln Asn Gly Gln Tyr Ser Val Pro
                965                 970                 975

Val Asp Val Asn Ser Thr Asn Leu Val Phe Ser Thr Asp Ala Ala Gly
                980                 985                 990

Lys Asn Val Leu Lys Asn Phe Ser Thr Val Thr Pro Lys Ala Phe Phe
                995                1000                1005

Asn Trp Gln Val Thr Asp Thr Phe Ala Gly Asn Phe Gly Val Ser
                1010                1015                1020

Ile Asn Ser Val Glu Thr Asn Arg Lys Asp Asp Val Val Val Gln
                1025                1030                1035

Ala Ala Val Pro Lys Gly Glu Asn Ile Gln Ala Phe Ala Lys Asp
                1040                1045                1050

Tyr Phe Thr Gly Glu Leu Tyr Thr Gly Glu Val Asn Asp Gly Val
                1055                1060                1065

Ala Thr Phe His Val His Thr Ser Ile Asn Gly Gly Arg Arg Ala
                1070                1075                1080

Leu Leu Thr Gly Trp Thr Val Val Asn Gly Pro Ser Tyr Asn Asp
                1085                1090                1095

Lys Gln Glu Thr Ser Gln Arg Gly Val Ala Ser Ser Asn His Leu
                1100                1105                1110

Gly Val Tyr Tyr Glu Val Asp Ala Ala Asp Arg Pro Val Tyr Thr
                1115                1120                1125

Asn Arg Asn Gln Leu Gly Val Glu Val Lys Asp Glu Ala Ala Asn
                1130                1135                1140
```

```
Val Asp Ala Phe Gly Pro Gly Ala Tyr Pro Gly His Ala Pro Ser
1145                1150                1155

Asp Leu Thr Thr Arg Thr Ala Ser Asn Pro Asn Ile His Phe Asp
    1160                1165                1170

Tyr Met Asn Asp Asn Asp Thr Thr Arg Phe Gly Gln Asn Ala Val
    1175                1180                1185

Leu Lys Gly Tyr Tyr Asp Pro Thr Thr Met Lys Phe Thr Val Thr
    1190                1195                1200

Gly Asn Val Asp Asp Asn Val Thr Ser Leu Thr Val Leu Ser Asp
    1205                1210                1215

Ser Ser Asn Glu Asn Asp Pro Ala Asn Gln Val Lys Leu Asp Gln
    1220                1225                1230

Asn Gly Lys Phe Ser Phe Ala Val Thr Ala Asn Ser Thr Gly Gln
    1235                1240                1245

Arg Pro Ile Ala Tyr Leu Tyr Arg Thr Lys Asp Gly Gln Thr Val
    1250                1255                1260

Arg Gly Thr Leu Asn Leu Ile Leu Asp Thr Val Lys Pro Thr Leu
    1265                1270                1275

Glu Val Asn Gln Val Asn Gly Asn Glu Leu Glu Leu Trp Thr Asn
    1280                1285                1290

Asn Pro Lys Phe Val Leu Ser Gly Lys Val Asn Asp Asn Leu Asp
    1295                1300                1305

Gly Tyr Arg Leu Tyr Val Asn Gly Asn Asn Ile Tyr Arg Glu Phe
    1310                1315                1320

Leu Asn Ser Gly Tyr Asn Arg Leu Glu Gly Leu Asn Thr Asp Thr
    1325                1330                1335

Glu Leu Thr Asn Pro Tyr Gly Asp His Glu Phe Glu Gln Val Glu
    1340                1345                1350

Asn Leu Asn Asp Asn Asn Asp Gln Pro Thr Thr His Ile Phe Thr
    1355                1360                1365

Val Asn Val Val Asp Gln Ala Gly Asn Thr Val Thr Lys Lys Leu
    1370                1375                1380

Thr Val His Phe Asp Pro Asn Tyr Val Pro Thr Asp Asn Thr
    1385                1390                1395

Asp Val Val Val Asp Thr Ser Thr Ser Asp Thr Asp Gly Val Thr
    1400                1405                1410

Glu Thr Lys Pro Ile Asp Pro Leu Val Gly Lys Ser Phe Lys Leu
    1415                1420                1425

Leu His Asn Ala Tyr Leu Tyr Asp Gln Asn Gly Glu Val Val Leu
    1430                1435                1440

Thr Asp Val Glu Asn Ala Lys Ser Leu Leu Lys Lys Gly Gln Thr
    1445                1450                1455

Ile Val Ala Leu Asp Asn Ala Lys Val Thr Phe Ile Asn Gly Val
    1460                1465                1470

Lys Phe Tyr Arg Val Gly Asn Asn Thr Phe Val Lys Thr Ala Asn
    1475                1480                1485

Thr Val Leu Gln Ala Pro Lys Arg Leu Lys Leu Thr His Asn Ala
    1490                1495                1500

Tyr Val Tyr Asp Gln Lys Gly Asn Val Val Lys Lys His Gly Lys
    1505                1510                1515

Lys Val Leu Leu Lys Lys Asn Gln Trp Ile Ser Ala Leu Asn Asn
    1520                1525                1530
```

-continued

```
Ala Asp Lys Tyr Val Ile Lys Gly Arg Leu Tyr Tyr Lys Leu Ala
        1535                1540                1545

Asp Gly Gln Phe Val Lys Val Ala Asn Thr Val Thr Lys Lys Ala
1550                1555                1560

Lys Leu Arg Lys Thr Val Val Ser
1565                1570

<210> SEQ ID NO 22
<211> LENGTH: 1503
<212> TYPE: PRT
<213> ORGANISM: Artificial Sequence
<220> FEATURE:
<223> OTHER INFORMATION: fragment of Lactobacillus crispatus protease

<400> SEQUENCE: 22

Asp Val Asn Ser Glu Val Gln Val Thr Ala Gln Asn Gln Asn Thr Thr
1               5                   10                  15

Glu Asn Lys Met Gln Ala Gly Asp Thr Ala Asn Ser His Asp Thr Glu
            20                  25                  30

Gln Asn Val Thr Val Gln Ala Asn Ser Ser Gln Gln Ser Asn Gln Glu
        35                  40                  45

Ala Asn Thr Ala Asp Gln Asn Asn Thr Pro Glu Asn Asp Asn Gln Val
    50                  55                  60

Gln Thr Pro Thr Asn Gln Ala Asp His Val Lys Gly Asn Val Gln Ser
65                  70                  75                  80

Ala Trp Asp Gln Gly Tyr Lys Gly Gln Gly Thr Val Val Ala Val Ile
                85                  90                  95

Asp Ser Gly Ala Asp Pro Ser His Lys Asp Phe Gln Thr Met Pro Glu
            100                 105                 110

Asn Pro Lys Leu Ser Lys Asp Asp Ile Gln Lys Lys Ile Glu Gln Gln
        115                 120                 125

Gly Tyr Gly Lys Tyr Val Asn Glu Lys Phe Pro Tyr Val Tyr Asn Tyr
    130                 135                 140

Ala Asp Arg Asp Asn Asp Tyr Ile Thr Ser Asp Asp Thr Asn Ser Asn
145                 150                 155                 160

Asp Ser Pro His Gly Gln His Val Ser Gly Ile Ala Ala Asp Gly
                165                 170                 175

Lys Pro Asp Gly Asn Lys Glu Tyr Val Val Gly Val Ala Pro Glu Ala
            180                 185                 190

Gln Leu Met Gln Leu Arg Val Phe Gly Gln Phe Ser Asp Glu Lys Thr
        195                 200                 205

Asp Asp Val Ala Lys Ala Ile Tyr Asp Ala Thr Asn Leu Gly Ala Asp
    210                 215                 220

Val Ile Gln Met Ser Leu Gly Gln Gly Val Ala Asp Gln Gln Leu Thr
225                 230                 235                 240

Asn Ile Glu Gln Lys Ala Val Gln Tyr Ala Ile Asp His Gly Val Phe
                245                 250                 255

Val Ser Ile Ser Ala Ser Asn Asn Gly His Ser Gly Ser Val Asp Asn
            260                 265                 270

Thr Ser Asn Val Thr Ser Val Glu Ser Tyr Glu Ser Gly Ser Ala Asp
        275                 280                 285

Gly Asn Tyr Glu Pro Leu Asn Ser Ser Thr Val Ala Asn Pro Gly Ala
    290                 295                 300

Ser Lys Asn Ala Leu Thr Val Ala Glu Thr Ser Ala Thr Gly Lys
305                 310                 315                 320
```

```
Asp Ser Asp Met Ala Gly Phe Ser Ser Trp Gly Pro Val Gln Asp Phe
                325                 330                 335

Thr Leu Lys Pro Asp Leu Ala Ala Pro Gly Tyr Gln Val Val Ser Thr
            340                 345                 350

Val Asn Asn Asn Tyr Gln Thr Met Ser Gly Thr Ser Met Ala Gly
        355                 360                 365

Pro Phe Ala Ala Ala Ser Ala Ala Leu Val Met Gln Arg Leu Lys Lys
    370                 375                 380

Thr Asn Pro Glu Leu Lys Gly Ala Gln Leu Ala Ala Thr Lys Ala
385                 390                 395                 400

Leu Leu Met Asn Ser Ala Lys Pro Gln Thr Gln Asn Gly Tyr Thr Thr
                405                 410                 415

Pro Val Ser Pro Arg Arg Gln Gly Ala Gly Gln Ile Asp Val Gly Ala
            420                 425                 430

Ala Thr Ser Asn Pro Val Tyr Val Ile Ala Asp Asp Gly Thr Ser Ser
        435                 440                 445

Val Ser Leu His Gln Val Lys Glu Asn Thr Pro Phe Thr Leu Thr Phe
    450                 455                 460

His Asn Leu Thr Asp Gln Glu Gln Val Tyr Thr Phe Asp Asp Phe Gly
465                 470                 475                 480

Gly Gly Tyr Thr Glu Gln Arg Asp Ser Asn Thr Gly Val Tyr His Asp
                485                 490                 495

Val Gln Leu Ala Gly Ala Arg Val Tyr Gly Glu Asn Ser Phe Ser Leu
            500                 505                 510

Ala Pro Lys Glu Thr Lys Gln Val Thr Tyr Ser Leu Asn Leu Asn Gly
        515                 520                 525

Leu Asn Asn Asn Gln Leu Val Glu Gly Phe Leu Arg Phe Thr Asn Thr
    530                 535                 540

Asn Asp Lys Ser Thr Val Ser Val Pro Tyr Leu Ala Tyr Tyr Gly Asp
545                 550                 555                 560

Leu Thr Ser Glu Asn Val Phe Asp Gln Asn Ala Asn Glu Glu His Pro
                565                 570                 575

Asp Ile Gln Gly Asn Arg Phe Val Asn Glu Gln Ser Tyr Pro Arg Gly
            580                 585                 590

Val Ala Asp Gln Glu Ser Leu Lys Gln Leu Val Asn Val Glu Gly Asp
        595                 600                 605

Tyr Asn Trp Gln Glu Val Ala Lys Leu Tyr Glu Ser Gly Lys Val Ala
    610                 615                 620

Phe Ser Pro Asn Asn Asp Asn Lys Ser Asp Leu Leu Lys Pro Tyr Thr
625                 630                 635                 640

Tyr Leu Lys Gln Asn Val Lys Asp Leu Lys Ala Val Val Leu Asp Ala
                645                 650                 655

Gln Gly Asn Val Val Arg Val Ala Asp Val Gln Gly Val Asp Lys
            660                 665                 670

Ser Tyr Asp Glu Asn Gly Val Thr Lys Asp Thr Ser Leu Ser Val Ser
        675                 680                 685

Met Arg Asp Asn Pro Asp Ala Phe Glu Trp Asp Gly Lys Val Tyr Asn
    690                 695                 700

Ser Lys Thr Gly Gln Met Glu Val Ala Lys Asp Gly Asn Tyr Thr Tyr
705                 710                 715                 720

Arg Leu Val Ala Thr Leu Trp Asn Glu Gly Pro His Gln Val Gln Thr
                725                 730                 735

Ala Asp Phe Pro Val Val Ile Asp Thr Val Ala Pro Thr Leu Ser Asn
```

-continued

```
                740                 745                 750
Val Lys Tyr Asp Glu Ala Thr Asn Thr Leu Ser Gly Glu Tyr Gln Asp
            755                 760                 765

Thr Gly Ala Gly Phe Thr Asn Tyr Ser Tyr Ala Thr Val Thr Val Asn
        770                 775                 780

Asp Lys Val Phe Gly Tyr Lys Leu Ser Asp Gly Gln Ser Ala Phe Asp
785                 790                 795                 800

Asn Ala Glu Lys Thr Lys Gly His Phe Ser Phe Thr Leu Asp Lys Asp
                805                 810                 815

Ala Val Ala Ala Leu Ser Gly Ala Lys Asn Lys Val Ser Val Val Leu
            820                 825                 830

Ser Asp Val Ala Asp Asn Pro Val Tyr Ser Val Asn Val Ala Gly
        835                 840                 845

Lys Asp Ile Asp Lys Pro Ala Val Ser Val Trp Asn Ala Thr Asn Gly
        850                 855                 860

Leu Ala Phe Asp Gln Ser Ser Thr Ser Tyr Asn Lys Asp Thr Lys Thr
865                 870                 875                 880

Tyr Thr Leu Ile Gly Gly Ala Asn Gln Asp Phe Tyr Leu Asn Gly Lys
            885                 890                 895

Leu Val Gln Val Gln Asn Gly Gln Tyr Ser Val Pro Val Asp Val Asn
        900                 905                 910

Ser Thr Asn Leu Val Phe Ser Thr Asp Ala Ala Gly Lys Asn Val Leu
        915                 920                 925

Lys Asn Phe Ser Thr Val Thr Pro Lys Ala Phe Phe Asn Trp Gln Val
        930                 935                 940

Thr Asp Thr Phe Ala Gly Asn Phe Gly Val Ser Ile Asn Ser Val Glu
945                 950                 955                 960

Thr Asn Arg Lys Asp Asp Val Val Gln Ala Ala Val Pro Lys Gly
                965                 970                 975

Glu Asn Ile Gln Ala Phe Ala Lys Asp Tyr Phe Thr Gly Glu Leu Tyr
            980                 985                 990

Thr Gly Glu Val Asn Asp Gly Val  Ala Thr Phe His Val  His Thr Ser
        995                 1000                1005

Ile Asn  Gly Gly Arg Arg Ala  Leu Leu Thr Gly Trp  Thr Val Val
    1010                1015                1020

Asn Gly  Pro Ser Tyr Asn Asp  Lys Gln Glu Thr Ser  Gln Arg Gly
    1025                1030                1035

Val Ala  Ser Ser Asn His Leu  Gly Val Tyr Tyr Glu  Val Asp Ala
    1040                1045                1050

Ala Asp  Arg Pro Val Tyr Thr  Asn Arg Asn Gln Leu  Gly Val Glu
    1055                1060                1065

Val Lys  Asp Glu Ala Ala Asn  Val Asp Ala Phe Gly  Pro Gly Ala
    1070                1075                1080

Tyr Pro  Gly His Ala Pro Ser  Asp Leu Thr Thr Arg  Thr Ala Ser
    1085                1090                1095

Asn Pro  Asn Ile His Phe Asp  Tyr Met Asn Asp Asn  Asp Thr Thr
    1100                1105                1110

Arg Phe  Gly Gln Asn Ala Val  Leu Lys Gly Tyr Tyr  Asp Pro Thr
    1115                1120                1125

Thr Met  Lys Phe Thr Val Thr  Gly Asn Val Asp Asp  Asn Val Thr
    1130                1135                1140

Ser Leu  Thr Val Leu Ser Asp  Ser Ser Asn Glu Asn  Asp Pro Ala
    1145                1150                1155
```

Asn Gln Val Lys Leu Asp Gln Asn Gly Lys Phe Ser Phe Ala Val
    1160                1165                1170

Thr Ala Asn Ser Thr Gly Gln Arg Pro Ile Ala Tyr Leu Tyr Arg
    1175                1180                1185

Thr Lys Asp Gly Gln Thr Val Arg Gly Thr Leu Asn Leu Ile Leu
    1190                1195                1200

Asp Thr Val Lys Pro Thr Leu Glu Val Asn Gln Val Asn Gly Asn
    1205                1210                1215

Glu Leu Glu Leu Trp Thr Asn Asn Pro Lys Phe Val Leu Ser Gly
    1220                1225                1230

Lys Val Asn Asp Asn Leu Asp Gly Tyr Arg Leu Tyr Val Asn Gly
    1235                1240                1245

Asn Asn Ile Tyr Arg Glu Phe Leu Asn Ser Gly Tyr Asn Arg Leu
    1250                1255                1260

Glu Gly Leu Asn Thr Asp Thr Glu Leu Thr Asn Pro Tyr Gly Asp
    1265                1270                1275

His Glu Phe Glu Gln Val Glu Asn Leu Asn Asp Asn Asn Asp Gln
    1280                1285                1290

Pro Thr Thr His Ile Phe Thr Val Asn Val Val Asp Gln Ala Gly
    1295                1300                1305

Asn Thr Val Thr Lys Lys Leu Thr Val His Phe Asp Pro Asn Tyr
    1310                1315                1320

Val Val Pro Thr Asp Asn Thr Asp Val Val Val Asp Thr Ser Thr
    1325                1330                1335

Ser Asp Thr Asp Gly Val Thr Glu Thr Lys Pro Ile Asp Pro Leu
    1340                1345                1350

Val Gly Lys Ser Phe Lys Leu Leu His Asn Ala Tyr Leu Tyr Asp
    1355                1360                1365

Gln Asn Gly Glu Val Val Leu Thr Asp Val Glu Asn Ala Lys Ser
    1370                1375                1380

Leu Leu Lys Lys Gly Gln Thr Ile Val Ala Leu Asp Asn Ala Lys
    1385                1390                1395

Val Thr Phe Ile Asn Gly Val Lys Phe Tyr Arg Val Gly Asn Asn
    1400                1405                1410

Thr Phe Val Lys Thr Ala Asn Thr Val Leu Gln Ala Pro Lys Arg
    1415                1420                1425

Leu Lys Leu Thr His Asn Ala Tyr Val Tyr Asp Gln Lys Gly Asn
    1430                1435                1440

Val Val Lys Lys His Gly Lys Lys Val Leu Leu Lys Lys Asn Gln
    1445                1450                1455

Trp Ile Ser Ala Leu Asn Asn Ala Asp Lys Tyr Val Ile Lys Gly
    1460                1465                1470

Arg Leu Tyr Tyr Lys Leu Ala Asp Gly Gln Phe Val Lys Val Ala
    1475                1480                1485

Asn Thr Val Thr Lys Lys Ala Lys Leu Arg Lys Thr Val Val Ser
    1490                1495                1500

<210> SEQ ID NO 23
<211> LENGTH: 1663
<212> TYPE: PRT
<213> ORGANISM: Lactobacillus ultunensis

<400> SEQUENCE: 23

Met Ser Asn Ser Thr Ala Pro Asn Gly Asn Arg Asn Phe Ser Phe Val

-continued

```
1               5                   10                  15
    Phe Lys Ala Lys Arg Arg Leu Glu Asn Ile Glu Thr Gln Lys Arg Ala
                20                  25                  30
    Arg Thr Ile Ile Asn Val Arg Lys Trp Val Ala Ala Ile Ile
                35                  40                  45
    Ala Leu Ala Ser Gly Ser Thr Val Phe Leu Ser Gln Asn Ala Val Glu
                50                  55                  60
    Ala Ala Thr Asn Asp Pro Asp Ala Ser Asp Val Gln Val Lys Val Val
65                          70                  75                  80
    Gln Gln Asp Gln Lys Gln Asn Gln Asn Thr Thr Ala Asn Val Val
                        85                  90                  95
    Ser Asn Ser Asp Ser Thr Lys Thr Gln Val Asn Thr Thr Val Gln Thr
                    100                 105                 110
    Gln Asn Ser Ala Val Val Ser Gly Asp Ser Thr Thr Ala Asn Pro Lys
                    115                 120                 125
    Thr Ser Gln Ala Ser Asn Val Gln Asn Thr Ser Thr Thr Ala Asn Ser
                130                 135                 140
    Val Asp Pro Asn Gln Glu Gln Gln Pro Ala Asn Gln Ala Asp His Val
145                         150                 155                 160
    Lys Gly Asn Val Gln Ser Ala Trp Asp Gln Gly Tyr Arg Gly Gln Gly
                        165                 170                 175
    Thr Val Val Ala Val Ile Asp Ser Gly Ala Asp Pro Thr His Lys Asp
                    180                 185                 190
    Phe Gln Thr Met Pro Glu Asp Pro Lys Leu Ser Lys Asp Asp Met Gln
                    195                 200                 205
    Ala Lys Ile Ser Lys Gln Gly Tyr Gly Lys Tyr Val Asn Glu Lys Phe
                210                 215                 220
    Pro Tyr Val Tyr Asn Tyr Ala Asp Arg Asp Asn Asp Tyr Ile Thr Ser
225                         230                 235                 240
    Asp Asp Thr Asn Ala Asn Asp Ser Pro His Gly Gln His Val Ser Gly
                        245                 250                 255
    Ile Ile Ala Ala Asp Gly Lys Pro Asp Gly Asn Lys Glu Tyr Val Val
                    260                 265                 270
    Gly Val Ala Pro Glu Ala Gln Leu Met Gln Leu Arg Val Phe Gly Gln
                    275                 280                 285
    Phe Ser Asp Glu Lys Thr Asp Asp Val Ala Arg Ala Ile Tyr Asp Ala
                290                 295                 300
    Thr Asn Leu Gly Ala Asp Val Ile Gln Met Ser Leu Gly Gln Gly Val
305                         310                 315                 320
    Ala Asp Gln Gln Leu Thr Asn Ile Glu Gln Lys Ala Val Gln Tyr Ala
                        325                 330                 335
    Ile Asp His Gly Val Phe Val Ser Ile Ser Ala Ser Asn Asn Gly Asn
                    340                 345                 350
    Ser Ala Ser Val Asp Asn Pro Ser Lys Val Gln Asp Ser Gly Tyr Gln
                    355                 360                 365
    Ser Gly Ser Gln Ala Gly Asn Tyr Glu Pro Leu Asn Ser Ser Thr Val
                370                 375                 380
    Ala Asn Pro Gly Ala Ser Lys Asn Ala Leu Thr Val Ala Ala Glu Thr
385                         390                 395                 400
    Ser Asp Thr Gly Asp Leu Ser Asp Met Ala Tyr Phe Ser Ser Trp Gly
                        405                 410                 415
    Pro Ile Gln Asp Phe Thr Leu Lys Pro Asp Leu Ala Ala Pro Gly Tyr
                    420                 425                 430
```

```
Gln Val Val Ser Thr Val Asn His Asp Gln Tyr Gln Thr Met Ser Gly
            435                 440                 445

Thr Ser Met Ala Gly Pro Phe Ala Ala Ala Ser Ala Ala Leu Val Ile
450                 455                 460

Gln Arg Leu Lys Gln Thr Asn Pro Glu Leu Lys Gly Ala Gln Leu Val
465                 470                 475                 480

Thr Ala Ala Lys Ala Met Leu Met Asn Thr Ala Lys Pro Gln Lys Gln
                485                 490                 495

Leu Gly Tyr Thr Thr Pro Val Ser Pro Arg Arg Gln Gly Ala Gly Gln
            500                 505                 510

Ile Asp Val Gly Gly Ala Thr Ala Thr Pro Val Tyr Val Thr Thr Asp
    515                 520                 525

Asp Gly Thr Ser Ser Val Ser Leu His Gln Val Asn Glu Asn Thr Lys
530                 535                 540

Phe Thr Leu Thr Phe His Asn Leu Thr Asp Gln Asn Gln Thr Tyr Thr
545                 550                 555                 560

Phe Asp Asp Tyr Gly Gly Tyr Thr Glu Gln Arg Asp Thr Thr Thr
                565                 570                 575

Gly Val Phe His Asp Val Gln Leu Ala Gly Ala Arg Val Asn Gly Glu
            580                 585                 590

Asn Ser Phe Thr Leu Ala Pro Lys Glu Glu Arg Lys Val Ser Tyr Ser
            595                 600                 605

Leu Asp Leu Thr Gly Leu Asn Lys Asn Gln Leu Val Glu Gly Phe Leu
            610                 615                 620

Arg Phe Thr Asn Ala Asn Val Ser Thr Val Ser Val Pro Tyr Leu
625                 630                 635                 640

Ala Tyr Tyr Gly Asp Leu Thr Ser Glu Asn Val Phe Asp Gln Asn Ala
                645                 650                 655

Asn Glu Glu His Pro Asp Ile Gln Gly Asn Arg Leu Val Asn Glu Gln
                660                 665                 670

Asn Tyr Pro Arg Gly Ile Ala Asp Gln Glu Ser Leu Lys Glu Leu Val
            675                 680                 685

Asn Val Asp Gly Asn Tyr Asn Trp Gln Glu Val Ala Lys Leu Tyr Glu
            690                 695                 700

Ser Gly Lys Val Ala Phe Ser Pro Asn Asp Asn Gln Lys Ser Asp Leu
705                 710                 715                 720

Leu Lys Pro Tyr Val Tyr Leu Lys Gln Asn Val Lys Asp Leu Lys Val
                725                 730                 735

Glu Val Leu Asp Ala Gln Gly Lys Val Val Arg Val Val Ser Asp Val
                740                 745                 750

Gln Gly Val Asp Lys Ser Tyr Asp Glu Asn Asp Val Thr Lys Asp Thr
            755                 760                 765

Ser Leu Ser Val Ser Met Arg Asp Asn Pro Asp Ala Phe Glu Trp Asp
770                 775                 780

Gly Lys Val Tyr Asn Ser Lys Thr Gly Lys Met Glu Thr Ala Lys Asp
785                 790                 795                 800

Gly Asn Tyr Thr Tyr Arg Leu Val Ala Thr Leu Trp Asn Lys Gly Pro
                805                 810                 815

His Gln Val Gln Thr Ala Asp Phe Pro Val Val Asp Thr Val Ala
            820                 825                 830

Pro Thr Leu Ser Asn Ile Lys Tyr Asp Pro Ala Ser His Thr Leu Ser
            835                 840                 845
```

```
Gly Glu Tyr Gln Asp Thr Gly Ala Gly Phe Thr Asn Tyr Ser Tyr Ala
            850                 855                 860

Thr Val Thr Val Asn Asp Lys Val Phe Gly Tyr Lys Leu Ser Asp Asp
865                 870                 875                 880

Glu Ser Gly Phe Asp Asn Thr Glu Lys Thr Lys Gly His Phe Asn Phe
                885                 890                 895

Val Leu Gly Gln Asp Ala Leu Ser Ala Leu Thr Thr Ala Thr Asn Lys
            900                 905                 910

Met Thr Val Ala Leu Ser Asp Val Ala Asp Asn Thr Ser Leu Ala Thr
            915                 920                 925

Val Asp Val Ala Gly Asp His Asp Ser Glu Thr Gly Val Ser Ile Trp
930                 935                 940

Asn Ala Val Asn Gly Leu Ala Phe Asp Gln Lys Ser Pro Asn Tyr Asn
945                 950                 955                 960

Ser Val Thr Lys Thr Tyr Ile Leu Phe Gly Gly Ala Asn His Asp Phe
                965                 970                 975

Tyr Leu Asn Gly Lys Leu Val Gln Val Gln Asn Gly Lys Tyr Gln Ala
            980                 985                 990

Pro Val Ser Val Asp Thr Thr Glu Phe Val Phe Ser Thr Asp Pro Glu
            995                 1000                1005

Gly Arg His Val Leu Asn Ser Leu Ser Thr Val Thr Ala Lys Ala
            1010                1015                1020

Phe Phe Asn Trp Gln Lys Thr Asp Thr Phe Asp Gly Asn Phe Gly
            1025                1030                1035

Val Thr Ile Gly Ser Val Lys Thr Asn Asp Pro Asn Asp Thr Val
            1040                1045                1050

Val Gln Ala Val Val Thr Lys Gly Gln Asn Val Lys Ala Tyr Ala
            1055                1060                1065

Met Asp Tyr Phe Thr Gly Glu Val Tyr Thr Gly Glu Val Lys Asp
            1070                1075                1080

Gly Ile Ala Thr Phe His Val His Thr Ser Val Asn Gln Asp Asn
            1085                1090                1095

Thr Thr Gly Val Tyr Lys Arg Ala Leu Leu Thr Gly Trp Thr Glu
            1100                1105                1110

Val Asp Gly Pro Ser Phe Asn Asp Lys Gln Glu Thr Ser Arg Gly
            1115                1120                1125

Gly Val Ala Ser Ser Asn His Leu Gly Val Tyr Tyr Phe Ala Asp
            1130                1135                1140

Ala Ala Asp Arg Pro Ile Tyr Thr Asp Arg Ser Ala Leu Gly Val
            1145                1150                1155

Glu Ala Lys Asp Glu Val Ala Lys Leu Asp Ser Phe Gly Pro Gly
            1160                1165                1170

Phe Tyr Pro Gly His Ala Pro Ser Asp Leu Thr Thr Arg Thr Asp
            1175                1180                1185

Pro Asn Pro Asp Ile His Phe Asp Tyr Met Asn Asp Asn Asp Thr
            1190                1195                1200

Thr Arg Phe Gly Gln Asn Ala Val Thr Arg Gly Tyr Tyr Asp Pro
            1205                1210                1215

Leu Thr Gln Lys Phe Met Val Thr Gly Lys Val Asp Gly Asn Val
            1220                1225                1230

Ala Ser Leu Thr Val Leu Gly Asp Asn Ser Asn Glu Asn Ala Pro
            1235                1240                1245

Glu Asn Gln Val Lys Leu Gly Asn Asp Gly Lys Phe Ser Phe Thr
```

-continued

```
            1250                1255                1260
Val Thr Ala Asn Arg Thr Gly Gln Arg Pro Ile Ala Tyr Ile Tyr
1265                1270                1275

Gln Thr Lys Asp Gly Gln Arg Val Arg Gly Thr Leu Asn Leu Ile
1280                1285                1290

Leu Asp Thr Val Ala Pro Ser Leu Glu Val Asn Gln Val Asn Gly
1295                1300                1305

Asp Lys Leu Glu Leu Trp Thr Asn Asn Pro Lys Phe Ile Leu Ser
1310                1315                1320

Gly Lys Val Asn Asp Asn Leu Asp Gly Tyr Arg Leu Phe Val Asn
1325                1330                1335

Gly Asn Asn Ile Tyr Arg Glu Phe Leu Asn Ser Gly Tyr Asn Gln
1340                1345                1350

Val Ala Gly Leu Asn Met Asp Thr Glu Phe Thr Asn Pro Tyr Gly
1355                1360                1365

Ala His Asp Phe Glu Glu Val Glu Asn Leu Asn Asp Asn Asn Asp
1370                1375                1380

Gln Pro Thr Thr His Val Phe Thr Val Tyr Val Val Asp Gln Val
1385                1390                1395

Gly Asn Lys Val Lys Lys Lys Leu Thr Val His Phe Asp Pro Asn
1400                1405                1410

Tyr Val Ala Pro Glu Glu Val Ser Asn Thr Asp Thr Ser Asn Asn
1415                1420                1425

Ser Asn Thr Ser Gly Thr Val Glu Asn Leu Ser Ser Thr Thr Ile
1430                1435                1440

Glu Lys Ser Val Thr Asp Val Ser Thr Val Gln Pro Lys Gly Glu
1445                1450                1455

Thr Leu Thr Gly Lys Ser Phe Asn Leu Leu His Asp Ala Tyr Ile
1460                1465                1470

Tyr Asn Lys Asp Gly Gln Val Val Leu Ser Thr Asp Thr Asn Lys
1475                1480                1485

Thr Ser Leu Leu Lys Lys Gly Gln Arg Ile Thr Ala Leu Asp Asn
1490                1495                1500

Gly Lys Thr Val Val Ile Asn Gly Val Gln Tyr Tyr Arg Val Gly
1505                1510                1515

Asp Asn Gln Phe Val Lys Val Ala Asn Thr Val Leu Gln Ala Gly
1520                1525                1530

Lys Arg Leu Gln Leu Lys His Asn Ala His Leu Tyr Asp Lys Asn
1535                1540                1545

Gly Lys Val Val Lys Arg Asn Gly Lys Thr Ile Leu Leu Arg Asn
1550                1555                1560

Gly Arg Trp Ile Ser Ala Leu Asn Asn Ala Asp Lys Tyr Val Ile
1565                1570                1575

Lys Gly Lys Asn Phe Tyr Lys Leu Ala Asn Asp Gln Phe Val Lys
1580                1585                1590

Val Ala Asn Thr Lys Leu Gln Lys Pro Lys Ala Leu Lys Leu Thr
1595                1600                1605

His Asn Ala Phe Val Tyr Asp Lys Asn Gly Lys Arg Val Lys Lys
1610                1615                1620

Ser Lys Val Leu Lys Lys Gly Gln Thr Ile Leu Ala Glu Asn Asn
1625                1630                1635

Ala Glu Lys Phe His Ile Lys Gly Lys Phe Tyr Tyr Arg Val Asn
1640                1645                1650
```

Gly Gln Phe Val Lys Val Ala Asn Thr Leu
        1655                1660

<210> SEQ ID NO 24
<211> LENGTH: 1595
<212> TYPE: PRT
<213> ORGANISM: Artificial Sequence
<220> FEATURE:
<223> OTHER INFORMATION: fragment of Lactobacillus ultunensis protease

<400> SEQUENCE: 24

Asp Pro Asp Ala Ser Asp Val Gln Val Lys Val Gln Gln Asp Gln
1               5                   10                  15

Lys Gln Asn Gln Asn Thr Thr Ala Asn Val Val Ser Asn Ser Asp
            20                  25                  30

Ser Thr Lys Thr Gln Val Asn Thr Thr Val Gln Thr Gln Asn Ser Ala
            35                  40                  45

Val Val Ser Gly Asp Ser Thr Thr Ala Asn Pro Lys Thr Ser Gln Ala
50                  55                  60

Ser Asn Val Gln Asn Thr Ser Thr Thr Ala Asn Ser Val Asp Pro Asn
65                  70                  75                  80

Gln Glu Gln Gln Pro Ala Asn Gln Ala Asp His Val Lys Gly Asn Val
                85                  90                  95

Gln Ser Ala Trp Asp Gln Gly Tyr Arg Gly Gln Gly Thr Val Val Ala
                100                 105                 110

Val Ile Asp Ser Gly Ala Asp Pro Thr His Lys Asp Phe Gln Thr Met
            115                 120                 125

Pro Glu Asp Pro Lys Leu Ser Lys Asp Met Gln Ala Lys Ile Ser
            130                 135                 140

Lys Gln Gly Tyr Gly Lys Tyr Val Asn Glu Lys Phe Pro Tyr Val Tyr
145                 150                 155                 160

Asn Tyr Ala Asp Arg Asp Asn Asp Tyr Ile Thr Ser Asp Asp Thr Asn
                165                 170                 175

Ala Asn Asp Ser Pro His Gly Gln His Val Ser Gly Ile Ile Ala Ala
            180                 185                 190

Asp Gly Lys Pro Asp Gly Asn Lys Glu Tyr Val Val Gly Val Ala Pro
        195                 200                 205

Glu Ala Gln Leu Met Gln Leu Arg Val Phe Gly Gln Phe Ser Asp Glu
    210                 215                 220

Lys Thr Asp Asp Val Ala Arg Ala Ile Tyr Asp Ala Thr Asn Leu Gly
225                 230                 235                 240

Ala Asp Val Ile Gln Met Ser Leu Gly Gln Gly Val Ala Asp Gln Gln
                245                 250                 255

Leu Thr Asn Ile Glu Gln Lys Ala Val Gln Tyr Ala Ile Asp His Gly
            260                 265                 270

Val Phe Val Ser Ile Ser Ala Ser Asn Asn Gly Asn Ser Ala Ser Val
        275                 280                 285

Asp Asn Pro Ser Lys Val Gln Asp Ser Gly Tyr Gln Ser Gly Ser Gln
    290                 295                 300

Ala Gly Asn Tyr Glu Pro Leu Asn Ser Ser Thr Val Ala Asn Pro Gly
305                 310                 315                 320

Ala Ser Lys Asn Ala Leu Thr Val Ala Ala Glu Thr Ser Asp Thr Gly
                325                 330                 335

Asp Leu Ser Asp Met Ala Tyr Phe Ser Ser Trp Gly Pro Ile Gln Asp
            340                 345                 350

```
Phe Thr Leu Lys Pro Asp Leu Ala Ala Pro Gly Tyr Gln Val Val Ser
        355                 360                 365

Thr Val Asn His Asp Gln Tyr Gln Thr Met Ser Gly Thr Ser Met Ala
370                 375                 380

Gly Pro Phe Ala Ala Ser Ala Ala Leu Val Ile Gln Arg Leu Lys
385                 390                 395                 400

Gln Thr Asn Pro Glu Leu Lys Gly Ala Gln Leu Val Thr Ala Ala Lys
                405                 410                 415

Ala Met Leu Met Asn Thr Ala Lys Pro Gln Lys Gln Leu Gly Tyr Thr
            420                 425                 430

Thr Pro Val Ser Pro Arg Arg Gln Gly Ala Gly Gln Ile Asp Val Gly
        435                 440                 445

Gly Ala Thr Ala Thr Pro Val Tyr Val Thr Thr Asp Asp Gly Thr Ser
450                 455                 460

Ser Val Ser Leu His Gln Val Asn Glu Asn Thr Lys Phe Thr Leu Thr
465                 470                 475                 480

Phe His Asn Leu Thr Asp Gln Asn Thr Tyr Thr Phe Asp Asp Tyr
                485                 490                 495

Gly Gly Gly Tyr Thr Glu Gln Arg Asp Thr Thr Thr Gly Val Phe His
            500                 505                 510

Asp Val Gln Leu Ala Gly Ala Arg Val Asn Gly Glu Asn Ser Phe Thr
        515                 520                 525

Leu Ala Pro Lys Glu Glu Arg Lys Val Ser Tyr Ser Leu Asp Leu Thr
530                 535                 540

Gly Leu Asn Lys Asn Gln Leu Val Glu Gly Phe Leu Arg Phe Thr Asn
545                 550                 555                 560

Ala Asn Asn Val Ser Thr Val Ser Val Pro Tyr Leu Ala Tyr Tyr Gly
                565                 570                 575

Asp Leu Thr Ser Glu Asn Val Phe Asp Gln Asn Ala Asn Glu Glu His
            580                 585                 590

Pro Asp Ile Gln Gly Asn Arg Leu Val Asn Glu Gln Asn Tyr Pro Arg
        595                 600                 605

Gly Ile Ala Asp Gln Glu Ser Leu Lys Glu Leu Val Asn Val Asp Gly
610                 615                 620

Asn Tyr Asn Trp Gln Glu Val Ala Lys Leu Tyr Glu Ser Gly Lys Val
625                 630                 635                 640

Ala Phe Ser Pro Asn Asp Asn Gln Lys Ser Asp Leu Leu Lys Pro Tyr
                645                 650                 655

Val Tyr Leu Lys Gln Asn Val Lys Asp Leu Lys Val Glu Val Leu Asp
            660                 665                 670

Ala Gln Gly Lys Val Val Arg Val Ser Asp Val Gln Gly Val Asp
        675                 680                 685

Lys Ser Tyr Asp Glu Asn Asp Val Thr Lys Asp Thr Ser Leu Ser Val
690                 695                 700

Ser Met Arg Asp Asn Pro Asp Ala Phe Glu Trp Asp Gly Lys Val Tyr
705                 710                 715                 720

Asn Ser Lys Thr Gly Lys Met Glu Thr Ala Lys Asp Gly Asn Tyr Thr
                725                 730                 735

Tyr Arg Leu Val Ala Thr Leu Trp Asn Lys Gly Pro His Gln Val Gln
            740                 745                 750

Thr Ala Asp Phe Pro Val Val Asp Thr Val Ala Pro Thr Leu Ser
        755                 760                 765
```

```
Asn Ile Lys Tyr Asp Pro Ala Ser His Thr Leu Ser Gly Glu Tyr Gln
770                 775                 780

Asp Thr Gly Ala Gly Phe Thr Asn Tyr Ser Tyr Ala Thr Val Thr Val
785                 790                 795                 800

Asn Asp Lys Val Phe Gly Tyr Lys Leu Ser Asp Asp Glu Ser Gly Phe
                805                 810                 815

Asp Asn Thr Glu Lys Thr Lys Gly His Phe Asn Phe Val Leu Gly Gln
                820                 825                 830

Asp Ala Leu Ser Ala Leu Thr Thr Ala Thr Asn Lys Met Thr Val Ala
                835                 840                 845

Leu Ser Asp Val Ala Asp Asn Thr Ser Leu Ala Thr Val Asp Val Ala
850                 855                 860

Gly Asp His Asp Ser Glu Thr Gly Val Ser Ile Trp Asn Ala Val Asn
865                 870                 875                 880

Gly Leu Ala Phe Asp Gln Lys Ser Pro Asn Tyr Asn Ser Val Thr Lys
                885                 890                 895

Thr Tyr Ile Leu Phe Gly Gly Ala Asn His Asp Phe Tyr Leu Asn Gly
                900                 905                 910

Lys Leu Val Gln Val Gln Asn Gly Lys Tyr Gln Ala Pro Val Ser Val
                915                 920                 925

Asp Thr Thr Glu Phe Val Phe Ser Thr Asp Pro Glu Gly Arg His Val
930                 935                 940

Leu Asn Ser Leu Ser Thr Val Thr Ala Lys Ala Phe Phe Asn Trp Gln
945                 950                 955                 960

Lys Thr Asp Thr Phe Asp Gly Asn Phe Gly Val Thr Ile Gly Ser Val
                965                 970                 975

Lys Thr Asn Asp Pro Asn Asp Thr Val Val Gln Ala Val Val Thr Lys
                980                 985                 990

Gly Gln Asn Val Lys Ala Tyr Ala Met Asp Tyr Phe Thr Gly Glu Val
            995                 1000                1005

Tyr Thr Gly Glu Val Lys Asp Gly Ile Ala Thr Phe His Val His
1010                1015                1020

Thr Ser Val Asn Gln Asp Asn Thr Thr Gly Val Tyr Lys Arg Ala
1025                1030                1035

Leu Leu Thr Gly Trp Thr Glu Val Asp Gly Pro Ser Phe Asn Asp
1040                1045                1050

Lys Gln Glu Thr Ser Arg Gly Gly Val Ala Ser Ser Asn His Leu
1055                1060                1065

Gly Val Tyr Tyr Phe Ala Asp Ala Ala Asp Arg Pro Ile Tyr Thr
1070                1075                1080

Asp Arg Ser Ala Leu Gly Val Glu Ala Lys Asp Glu Val Ala Lys
1085                1090                1095

Leu Asp Ser Phe Gly Pro Gly Phe Tyr Pro Gly His Ala Pro Ser
1100                1105                1110

Asp Leu Thr Thr Arg Thr Asp Pro Asn Pro Asp Ile His Phe Asp
1115                1120                1125

Tyr Met Asn Asp Asn Asp Thr Thr Arg Phe Gly Gln Asn Ala Val
1130                1135                1140

Thr Arg Gly Tyr Tyr Asp Pro Leu Thr Gln Lys Phe Met Val Thr
1145                1150                1155

Gly Lys Val Asp Gly Asn Val Ala Ser Leu Thr Val Leu Gly Asp
1160                1165                1170

Asn Ser Asn Glu Asn Ala Pro Glu Asn Gln Val Lys Leu Gly Asn
```

```
           1175                1180                1185
Asp Gly Lys Phe Ser Phe Thr Val Thr Ala Asn Arg Thr Gly Gln
           1190                1195                1200

Arg Pro Ile Ala Tyr Ile Tyr Gln Thr Lys Asp Gly Gln Arg Val
           1205                1210                1215

Arg Gly Thr Leu Asn Leu Ile Leu Asp Thr Val Ala Pro Ser Leu
           1220                1225                1230

Glu Val Asn Gln Val Asn Gly Asp Lys Leu Glu Leu Trp Thr Asn
           1235                1240                1245

Asn Pro Lys Phe Ile Leu Ser Gly Lys Val Asn Asp Asn Leu Asp
           1250                1255                1260

Gly Tyr Arg Leu Phe Val Asn Gly Asn Ile Tyr Arg Glu Phe
           1265                1270                1275

Leu Asn Ser Gly Tyr Asn Gln Val Ala Gly Leu Asn Met Asp Thr
           1280                1285                1290

Glu Phe Thr Asn Pro Tyr Gly Ala His Asp Phe Glu Glu Val Glu
           1295                1300                1305

Asn Leu Asn Asp Asn Asn Asp Gln Pro Thr Thr His Val Phe Thr
           1310                1315                1320

Val Tyr Val Val Asp Gln Val Gly Asn Lys Val Lys Lys Lys Leu
           1325                1330                1335

Thr Val His Phe Asp Pro Asn Tyr Val Ala Pro Glu Glu Val Ser
           1340                1345                1350

Asn Thr Asp Thr Ser Asn Asn Ser Asn Thr Ser Gly Thr Val Glu
           1355                1360                1365

Asn Leu Ser Ser Thr Thr Ile Glu Lys Ser Val Thr Asp Val Ser
           1370                1375                1380

Thr Val Gln Pro Lys Gly Glu Thr Leu Thr Gly Lys Ser Phe Asn
           1385                1390                1395

Leu Leu His Asp Ala Tyr Ile Tyr Asn Lys Asp Gly Gln Val Val
           1400                1405                1410

Leu Ser Thr Asp Thr Asn Lys Thr Ser Leu Leu Lys Lys Gly Gln
           1415                1420                1425

Arg Ile Thr Ala Leu Asp Asn Gly Lys Thr Val Val Ile Asn Gly
           1430                1435                1440

Val Gln Tyr Tyr Arg Val Gly Asp Asn Gln Phe Val Lys Val Ala
           1445                1450                1455

Asn Thr Val Leu Gln Ala Gly Lys Arg Leu Gln Leu Lys His Asn
           1460                1465                1470

Ala His Leu Tyr Asp Lys Asn Gly Lys Val Val Lys Arg Asn Gly
           1475                1480                1485

Lys Thr Ile Leu Leu Arg Asn Gly Arg Trp Ile Ser Ala Leu Asn
           1490                1495                1500

Asn Ala Asp Lys Tyr Val Ile Lys Gly Lys Asn Phe Tyr Lys Leu
           1505                1510                1515

Ala Asn Asp Gln Phe Val Lys Val Ala Asn Thr Lys Leu Gln Lys
           1520                1525                1530

Pro Lys Ala Leu Lys Leu Thr His Asn Ala Phe Val Tyr Asp Lys
           1535                1540                1545

Asn Gly Lys Arg Val Lys Lys Ser Lys Val Leu Lys Lys Gly Gln
           1550                1555                1560

Thr Ile Leu Ala Glu Asn Asn Ala Glu Lys Phe His Ile Lys Gly
           1565                1570                1575
```

```
Lys Phe Tyr Tyr Arg Val Asn  Gly Gln Phe Val Lys  Val Ala Asn
    1580               1585                1590

Thr Leu
    1595

<210> SEQ ID NO 25
<211> LENGTH: 927
<212> TYPE: PRT
<213> ORGANISM: Anaerofustis stercorihominis

<400> SEQUENCE: 25

Met Lys Asn Lys Lys Ile Ile Tyr Thr Leu Leu Ser Ile Leu Leu Ile
1               5                   10                  15

Leu Leu Phe Thr Asn Thr Val Tyr Ala Gln Asn Lys Ala Asp Glu Arg
            20                  25                  30

Tyr Asp Pro Asn Ser Val Leu Val Phe Lys Asp Asn Ile Ser Asn
        35                  40                  45

Ser Lys Lys Ser Lys Ile Leu Ser Asn Glu Asn Leu Asn Ile Glu Glu
    50                  55                  60

Thr Val Asp Lys Lys Glu Asn Ile Glu Leu Val Glu Val Pro Lys Asp
65                  70                  75                  80

Ser Thr Val Glu Glu Thr Ile Arg Thr Leu Asn Glu Lys Asn Glu Val
                85                  90                  95

Leu Tyr Ala Gln Pro Asn Phe Lys Tyr Lys Ala Leu Ala Thr Thr Asn
            100                 105                 110

Asp Pro Leu Leu Ser Ala Gln Lys His Leu Thr Trp Thr Asn Ile Ser
        115                 120                 125

Gly Ser Gly Thr Thr Ala Trp Asn Tyr Ser Thr Gly Glu Asn Thr Lys
    130                 135                 140

Ile Ala Ile Phe Asp Thr Gly Ala Tyr Thr Ser Asn Pro Asp Leu Ser
145                 150                 155                 160

Asn Ile Lys Gly Thr Tyr Asn Ala Ser Thr Gly Ser Ser Ala Lys Ser
                165                 170                 175

Ser Val Val Asp Tyr Glu Gly His Gly Thr His Val Ala Gly Ile Ala
            180                 185                 190

Ala Ala Cys Gly Asn Asn Lys Ser Leu Gly Ala Gly Val Ala Tyr Asn
        195                 200                 205

Ser Asp Leu Tyr Ile Ala Lys Val Ala Asp Ser Asn Gly Asp Ile Ser
    210                 215                 220

Ser Ala Tyr Leu Ile Arg Ala Phe Asp Trp Ala Glu Glu Gln Gly Cys
225                 230                 235                 240

Arg Ile Ile Asn Met Ser Leu Gly Gly Tyr Gly Tyr Glu Tyr Asp Ser
                245                 250                 255

Asp Gly Lys Val Asn Leu Asp Leu Leu Leu Lys Ser Arg Ile Asp Asp
            260                 265                 270

Ala Tyr Asn Lys Ser Asn Asn Ser Ile Leu Thr Val Cys Ala Ala Gly
        275                 280                 285

Asn Gly Asp Asp Ile Asn Gly Tyr Pro Tyr Tyr Ser Tyr Pro Ser Asp
    290                 295                 300

Phe Pro Asn Ser Tyr Ser Val Val Ala Leu Gln Tyr Asp Ser Asn Gly
305                 310                 315                 320

Asn Pro Thr Arg Ala Lys Tyr Ser Asp Tyr Asn Glu Tyr Lys Asp Ile
                325                 330                 335

Ala Ala Pro Gly Ser Asn Ile Asn Ser Leu Ser Asn Thr Ser Thr Ser
```

```
                340                 345                 350
Lys Leu Ile Thr Glu Ser Gly Thr Ser Met Ala Ala Pro Phe Val Ser
            355                 360                 365

Gly Val Ala Gly Leu Ile Met Ser Lys Val Pro Asp Leu Thr Ala Lys
        370                 375                 380

Glu Val Val Asp Ile Ile Asn Ser Thr Ala Asn Lys Ile Gly Ser Tyr
385                 390                 395                 400

Ser Tyr Ser Lys Gly Arg Asn Asn Tyr Tyr Gly Tyr Gly Glu Ile Asn
                405                 410                 415

Pro Leu Lys Ala Ile Lys Thr Ala Ile Trp Lys Lys Ser Ser Met Thr
            420                 425                 430

Ile Ser Lys Thr Ser Asp Ile Ile Gly Glu Asn Lys Lys Leu Asp Ile
        435                 440                 445

Thr Leu Asn Met Tyr Thr Glu Val Pro Met Lys Val Glu Val Tyr Asp
    450                 455                 460

Ser Asn Asn Asn Leu Ile Asn Thr Leu Ala Asp Lys Thr Phe Thr Ala
465                 470                 475                 480

Gly Glu Thr Lys Leu Ser Trp Asp Tyr Ser Asn Tyr Lys Gly Asp Lys
                485                 490                 495

Tyr Ser Ile Gln Ala Thr Met Pro Tyr Lys Asn Ser Lys Asp Lys Val
            500                 505                 510

Ile Gln Ser Lys Thr Phe Asn Leu Cys Asp Leu Leu Asp Ile Thr Gly
        515                 520                 525

Leu Ser Ser Ser Tyr Thr Pro Leu Ala Asn Thr Ser Ile Thr Gly Asn
    530                 535                 540

Leu Asn Leu Asn Thr Asp Cys Thr Val Ser Ala Gly Phe Tyr Asp Lys
545                 550                 555                 560

Asp Asn Lys Leu Val Lys Thr Ile Tyr Asn Lys Asn Thr Ser Leu Thr
                565                 570                 575

Lys Glu Asn Lys Ser Phe Ser Trp Asn Tyr Leu Asp Asp Asn Asn Lys
            580                 585                 590

Leu Ile Pro Ser Gly Thr Tyr Glu Phe Lys Val Ser Ala Thr Ser Gly
        595                 600                 605

Asp Ile Thr Lys Glu Tyr Ser Lys Asn Ile Lys Ile Thr Ile Pro Glu
    610                 615                 620

Lys Ala Ser Ile Ser Lys Met Ser Val Thr Ser Ser Ile Lys Arg Asn
625                 630                 635                 640

Asp Phe Asn Lys Ala Ser Ile Lys Tyr Thr Leu Asn Asn Gln Cys Val
                645                 650                 655

Thr Ser Ile Lys Ile Tyr Asn Ser Ser Asn Thr Leu Ile Lys Ser Ile
            660                 665                 670

Ser Arg Asn Arg Lys Gly Ser Asn Thr Glu Tyr Trp Asn Leu Lys Asp
        675                 680                 685

Ser Lys Gly Asn Leu Val Val Ala Gly Thr Tyr Lys Ile Ile Ser
    690                 695                 700

Gly Tyr Asn Ile Ala Gly Lys Phe Glu Thr Thr Lys Tyr Ile Lys Ile
705                 710                 715                 720

Thr Asn Pro Ser Lys Val Ser Ile Ser Lys Phe Lys Asn Lys Ser Lys
                725                 730                 735

Val Ile Arg Ala Ser Gly Tyr Tyr Thr Ser Thr Lys Phe Tyr Leu Asn
            740                 745                 750

Glu Asp Ala Arg Val Lys Val Leu Leu Thr Thr Thr Lys Asn Lys Lys
        755                 760                 765
```

```
Leu Lys Thr Leu Lys Asn Val Met Lys Lys Gly Thr Asn Thr Val
    770             775             780

Lys Trp Asn Leu Lys Ser Thr Lys Gly Asn Val Tyr Lys Ala Gly Lys
785             790             795             800

Tyr Lys Ile Val Val Tyr Ala Thr Asn Ser Arg Asn Thr Tyr Gln Lys
                805             810             815

Ser Ser Tyr Val Thr Leu Val Lys Lys Pro Ser Ile Lys Val Ser
            820             825             830

Lys Val Lys Ser Ser Tyr Lys Ile Arg Gly Ser Lys Asn Asn Pro Thr
            835             840             845

Ile Lys Val Lys Thr Asn Ile Ile Ala Lys Val Thr Val Arg Val Tyr
    850             855             860

Asn Arg Lys Asn Lys Leu Ile Lys Thr Ile Thr Lys Asn Lys Thr Tyr
865             870             875             880

Lys Thr Gly Thr Tyr Lys Phe Lys Trp Asn Gly Lys Ser Gly Lys Asn
            885             890             895

Lys Lys Val Ser Lys Thr Lys Tyr Tyr Phe Lys Val Thr Ile Lys Asn
            900             905             910

Glu Asn Gly Ser Lys Thr Val Lys Thr Lys Gln Phe Lys Tyr Lys
            915             920             925

<210> SEQ ID NO 26
<211> LENGTH: 901
<212> TYPE: PRT
<213> ORGANISM: Artificial Sequence
<220> FEATURE:
<223> OTHER INFORMATION: fragment of Anaerofustis stercorihominis
      protease

<400> SEQUENCE: 26

Asn Lys Ala Asp Glu Arg Tyr Asp Pro Asn Ser Val Leu Val Val Phe
1               5                   10                  15

Lys Asp Asn Ile Ser Asn Ser Lys Lys Ser Lys Ile Leu Ser Asn Glu
            20                  25                  30

Asn Leu Asn Ile Glu Glu Thr Val Asp Lys Lys Glu Asn Ile Glu Leu
        35                  40                  45

Val Glu Val Pro Lys Asp Ser Thr Val Glu Glu Thr Ile Arg Thr Leu
    50                  55                  60

Asn Glu Lys Asn Glu Val Leu Tyr Ala Gln Pro Asn Phe Lys Tyr Lys
65                  70                  75                  80

Ala Leu Ala Thr Thr Asn Asp Pro Leu Leu Ser Ala Gln Lys His Leu
                85                  90                  95

Thr Trp Thr Asn Ile Ser Gly Ser Gly Thr Thr Ala Trp Asn Tyr Ser
            100                 105                 110

Thr Gly Glu Asn Thr Lys Ile Ala Ile Phe Asp Thr Gly Ala Tyr Thr
        115                 120                 125

Ser Asn Pro Asp Leu Ser Asn Ile Lys Gly Thr Tyr Asn Ala Ser Thr
    130                 135                 140

Gly Ser Ser Ala Lys Ser Val Val Asp Tyr Glu Gly His Gly Thr
145                 150                 155                 160

His Val Ala Gly Ile Ala Ala Cys Gly Asn Asn Lys Ser Leu Gly
                165                 170                 175

Ala Gly Val Ala Tyr Asn Ser Asp Leu Tyr Ile Ala Lys Val Ala Asp
            180                 185                 190

Ser Asn Gly Asp Ile Ser Ser Ala Tyr Leu Ile Arg Ala Phe Asp Trp
```

-continued

```
            195                 200                 205
Ala Glu Glu Gln Gly Cys Arg Ile Ile Asn Met Ser Leu Gly Gly Tyr
210                 215                 220
Gly Tyr Glu Tyr Asp Ser Asp Gly Lys Val Asn Leu Asp Leu Leu Leu
225                 230                 235                 240
Lys Ser Arg Ile Asp Asp Ala Tyr Asn Lys Ser Asn Ser Ile Leu
            245                 250                 255
Thr Val Cys Ala Ala Gly Asn Gly Asp Asp Ile Asn Gly Tyr Pro Tyr
            260                 265                 270
Tyr Ser Tyr Pro Ser Asp Phe Pro Asn Ser Tyr Ser Val Val Ala Leu
            275                 280                 285
Gln Tyr Asp Ser Asn Gly Asn Pro Thr Arg Ala Lys Tyr Ser Asp Tyr
290                 295                 300
Asn Glu Tyr Lys Asp Ile Ala Ala Pro Gly Ser Asn Ile Asn Ser Leu
305                 310                 315                 320
Ser Asn Thr Ser Thr Ser Lys Leu Ile Thr Glu Ser Gly Thr Ser Met
                    325                 330                 335
Ala Ala Pro Phe Val Ser Gly Val Ala Gly Leu Ile Met Ser Lys Val
            340                 345                 350
Pro Asp Leu Thr Ala Lys Glu Val Val Asp Ile Ile Asn Ser Thr Ala
            355                 360                 365
Asn Lys Ile Gly Ser Tyr Ser Tyr Ser Lys Gly Arg Asn Asn Tyr Tyr
370                 375                 380
Gly Tyr Gly Glu Ile Asn Pro Leu Lys Ala Ile Lys Thr Ala Ile Trp
385                 390                 395                 400
Lys Lys Ser Ser Met Thr Ile Ser Lys Thr Ser Asp Ile Ile Gly Glu
                    405                 410                 415
Asn Lys Lys Leu Asp Ile Thr Leu Asn Met Tyr Thr Glu Val Pro Met
            420                 425                 430
Lys Val Glu Val Tyr Asp Ser Asn Asn Asn Leu Ile Asn Thr Leu Ala
            435                 440                 445
Asp Lys Thr Phe Thr Ala Gly Glu Thr Lys Leu Ser Trp Asp Tyr Ser
            450                 455                 460
Asn Tyr Lys Gly Asp Lys Tyr Ser Ile Gln Ala Thr Met Pro Tyr Lys
465                 470                 475                 480
Asn Ser Lys Asp Lys Val Ile Gln Ser Lys Thr Phe Asn Leu Cys Asp
                    485                 490                 495
Leu Leu Asp Ile Thr Gly Leu Ser Ser Ser Tyr Thr Pro Leu Ala Asn
            500                 505                 510
Thr Ser Ile Thr Gly Asn Leu Asn Leu Asn Thr Asp Cys Thr Val Ser
            515                 520                 525
Ala Gly Phe Tyr Asp Lys Asp Asn Lys Leu Val Lys Thr Ile Tyr Asn
            530                 535                 540
Lys Asn Thr Ser Leu Thr Lys Glu Asn Lys Ser Phe Ser Trp Asn Tyr
545                 550                 555                 560
Leu Asp Asp Asn Asn Lys Leu Ile Pro Ser Gly Thr Tyr Glu Phe Lys
                    565                 570                 575
Val Ser Ala Thr Ser Gly Asp Ile Thr Lys Glu Tyr Ser Lys Asn Ile
            580                 585                 590
Lys Ile Thr Ile Pro Glu Lys Ala Ser Ile Ser Lys Met Ser Val Thr
            595                 600                 605
Ser Ser Ile Lys Arg Asn Asp Phe Asn Lys Ala Ser Ile Lys Tyr Thr
610                 615                 620
```

Leu Asn Asn Gln Cys Val Thr Ser Ile Lys Ile Tyr Asn Ser Ser Asn
625                 630                 635                 640

Thr Leu Ile Lys Ser Ile Ser Arg Asn Arg Lys Gly Ser Asn Thr Glu
                645                 650                 655

Tyr Trp Asn Leu Lys Asp Ser Lys Gly Asn Leu Val Val Ala Gly Thr
            660                 665                 670

Tyr Lys Ile Ile Ile Ser Gly Tyr Asn Ile Ala Gly Lys Phe Glu Thr
        675                 680                 685

Thr Lys Tyr Ile Lys Ile Thr Asn Pro Ser Lys Val Ser Ile Ser Lys
    690                 695                 700

Phe Lys Asn Lys Ser Lys Val Ile Arg Ala Ser Gly Tyr Tyr Thr Ser
705                 710                 715                 720

Thr Lys Phe Tyr Leu Asn Glu Asp Ala Arg Val Lys Val Leu Leu Thr
                725                 730                 735

Thr Thr Lys Asn Lys Lys Leu Lys Thr Leu Lys Asn Val Val Met Lys
            740                 745                 750

Lys Gly Thr Asn Thr Val Lys Trp Asn Leu Lys Ser Thr Lys Gly Asn
        755                 760                 765

Val Tyr Lys Ala Gly Lys Tyr Lys Ile Val Val Tyr Ala Thr Asn Ser
    770                 775                 780

Arg Asn Thr Tyr Gln Lys Ser Ser Tyr Val Thr Leu Val Lys Lys Lys
785                 790                 795                 800

Pro Ser Ile Lys Val Ser Lys Val Lys Ser Ser Tyr Lys Ile Arg Gly
                805                 810                 815

Ser Lys Asn Asn Pro Thr Ile Lys Val Lys Thr Asn Ile Ile Ala Lys
            820                 825                 830

Val Thr Val Arg Val Tyr Asn Arg Lys Asn Lys Leu Ile Lys Thr Ile
        835                 840                 845

Thr Lys Asn Lys Thr Tyr Lys Thr Gly Thr Tyr Lys Phe Lys Trp Asn
    850                 855                 860

Gly Lys Ser Gly Lys Asn Lys Lys Val Ser Lys Thr Lys Tyr Tyr Phe
865                 870                 875                 880

Lys Val Thr Ile Lys Asn Glu Asn Gly Ser Lys Thr Val Lys Thr Lys
                885                 890                 895

Gln Phe Lys Tyr Lys
            900

<210> SEQ ID NO 27
<211> LENGTH: 1009
<212> TYPE: PRT
<213> ORGANISM: Paenisporosarcina sp. HGH0030

<400> SEQUENCE: 27

Met Asn Ile Lys Lys Gln Leu Lys Ile Phe Leu Phe Ala Tyr Ile Phe
1               5                   10                  15

Phe Trp Leu Pro Ala Gln Phe Ala Gly Ala Glu Glu Ile Lys Val Glu
            20                  25                  30

Pro Lys Ile Ser Lys Phe Asn Ile Glu Ala Leu Phe Asp Asp Ser Lys
        35                  40                  45

Asp Phe Tyr Ser Asn Gln Leu Ile Val Thr Phe Lys Ala Ser Pro Thr
    50                  55                  60

Gly Ser Glu Arg Lys Gln Ile Leu Asp Ser Val Asn Ala Lys Glu Leu
65                  70                  75                  80

Ser Ile Gln Val Asn Gly Lys Phe Ala Leu Val Ser Thr Pro Lys Ser

-continued

```
                85                  90                  95
Ser Asp Leu Ser Ala Val Ala Lys Glu Leu Leu Lys His Lys Gln Val
            100                 105                 110

Glu Phe Val Glu Pro Asn Tyr Gln Leu Glu Asn Thr Phe Arg Pro Lys
            115                 120                 125

Asp Pro Ser Tyr Ser Lys Gln Trp His Leu Lys Lys Ile His Ala Ser
            130                 135                 140

Ser Ala Trp Asp Gln Thr Lys Gly Arg Ser Gly Val Ile Val Ala Val
145                 150                 155                 160

Ile Asp Glu Gly Val Gln Thr Asn His Pro Asp Leu Lys Gly Lys Phe
            165                 170                 175

Val Ser Pro Tyr Asn Ala Val Thr Gly Gly Thr Ser Phe Tyr Ser Gly
            180                 185                 190

Asp His Ala Thr His Val Ala Gly Ile Ile Ala Ala Ser Phe Asn Asn
            195                 200                 205

Ser Gly Gly Ala Gly Val Ala Pro Asn Ile Lys Ile Met Pro Ile Asn
            210                 215                 220

Val Phe Thr Gly Asp Ser Ala Ser Ser Tyr Asp Val Gly Glu Ala Ile
225                 230                 235                 240

Ile Tyr Ala Ala Asp His His Ala Asp Ile Ile Asn Leu Ser Leu Gly
            245                 250                 255

Gly Ser Tyr Thr Tyr Ala Met Asp Tyr Ala Thr Gln Tyr Ala Lys Ala
            260                 265                 270

Lys Asp Val Leu Ile Ile Ala Ala Ala Gly Asn Glu Arg Ser Tyr Glu
            275                 280                 285

Leu Ser Tyr Pro Ala Ala Leu Asp Gly Val Ile Gly Val Ser Ala Thr
            290                 295                 300

Asp Ser Asn Asp Glu Ile Thr Asp Phe Ser Asn Tyr Gly Ser Tyr Ile
305                 310                 315                 320

Asp Leu Ala Ala Pro Gly Glu Gly Ile Phe Ser Ser Leu Ser Gly Ser
            325                 330                 335

Lys Tyr Gly Ala Met Asp Gly Thr Ser Met Ala Ala Pro Val Val Ser
            340                 345                 350

Gly Val Ala Ala Leu Val Leu Ser Lys Asn Pro Leu Leu Thr Ser Asp
            355                 360                 365

Gln Leu Glu Lys Ile Leu Thr Lys Ser Ser Val Asp Leu Tyr His Arg
            370                 375                 380

Gly Trp Asp Asp Phe Tyr Gly Tyr Gly Arg Val Asp Ala Tyr Arg Ala
385                 390                 395                 400

Leu Gln Phe Thr Thr Ser Ala Ile Ser Asn Leu Lys Leu Ser Ser Thr
            405                 410                 415

Lys Phe Thr Met Asn Gly Ser Asn Lys Thr Ala Phe Ser Phe Glu Gly
            420                 425                 430

Val Lys Gly Ser Lys Ile Ser Leu Tyr Leu Gln Asn Ser Lys Gly Thr
            435                 440                 445

Thr Ile Lys Lys Ile Val Ser Tyr Lys Asp Trp Ser Gly Gly Lys Phe
            450                 455                 460

Ser Ala Ser Trp Asp Gly Arg Met Asp Asn Gly Met Tyr Ala Ser Thr
465                 470                 475                 480

Gly Thr Tyr Lys Ile Ile Ala Ala Val Ser Gly Asn Gly Glu Asn Leu
            485                 490                 495

His Leu Ser Ala Thr Leu Lys Val Ile Asp Lys Ile Val Pro Ser Ile
            500                 505                 510
```

```
Asn Leu Ser Gly Ser Val Asn Tyr Ser Pro Thr Val Thr Gly Lys Leu
            515                 520                 525

Thr Val Pro Tyr Glu Leu Asn Lys Asn Ala Lys Val Thr Ala Phe Ile
        530                 535                 540

Lys Asp Lys Asn Asn Lys Ile Ile Lys Ser Ile Leu Asn Asn Ser Ser
545                 550                 555                 560

Val Ser Arg Gly Gln Arg Thr Val Gln Trp Asp Gly Lys Asp Ser Glu
                565                 570                 575

Gly Asn Arg Val Lys Asp Gly Val Tyr Ser Leu Glu Met Ser Leu Val
                580                 585                 590

Asp Ala Asn Lys Ile Lys Gly Thr Ser Arg Lys Phe Ser Ile Thr Val
            595                 600                 605

Asp Thr Ile Ile Pro Thr Ala Lys Ile Ala Leu Ser Ser Glu Leu Met
        610                 615                 620

Lys Leu Asn Gly Ser Leu Leu Asn Met Gly Lys Ile Asp Val Ser Glu
625                 630                 635                 640

Thr Val Phe Leu Thr Thr Tyr Ile Ala Asn Asp Asn Gly Val Lys Val
                645                 650                 655

Arg Lys Ile Asp Thr Glu Lys Ser Ile Lys Lys Gly Ala Tyr Ser Leu
            660                 665                 670

Asn Trp Asp Gly Lys Asn Glu Asn Ser Glu Phe Val Ala Glu Gly Asn
        675                 680                 685

Tyr His Leu Leu Phe Glu Leu Leu Asp Ser Ala Gly Asn Lys Ala Ser
        690                 695                 700

Leu Lys Ser Thr Thr Phe Ala Phe Gln Asp Trp Asn Gln Pro Val Ile
705                 710                 715                 720

Glu Gly Asp Ala Asn Tyr Phe Phe Thr Ser Asp Gly Lys Gln Thr Phe
                725                 730                 735

Ser Tyr Lys Leu Ser Lys Pro Gly Ile Val Thr Ile Gln Leu Phe Lys
                740                 745                 750

Asn Asp Asn Leu Val Ser Thr Ile Glu Gln Asn Val Pro Lys Ser Gln
            755                 760                 765

Gly Asn Gln Ser Phe Val Trp Asp Gly Lys Asp Gln Ser Gly Thr Ile
        770                 775                 780

Leu Pro Asp Gly Gln Tyr Ser Tyr Lys Ile Ser Ile Val Asp Ala Tyr
785                 790                 795                 800

Asn Leu Ser Gln Thr Tyr Lys Gly Ile Met Asn Ile Ala Leu Thr Gln
                805                 810                 815

Ile Glu Ile Gln Tyr Pro Thr Val Val Gln Phe Ile Asp Asp Thr
            820                 825                 830

Ala Glu Ile Phe Tyr Lys Leu Ser Gln Gln Ala Asn Val Thr Ile Glu
        835                 840                 845

Ile Tyr Glu Gly Asn Ala Lys Ile Arg Thr Ile Ser Asp Lys Lys
850                 855                 860

Thr Asp Lys Gly Ile Asn His Phe Ile Trp Asp Gly Tyr Asp Asp Asn
865                 870                 875                 880

Gly Asp Leu Val Tyr Ser Asp Glu Leu Ile Tyr Lys Ile Lys Val Ile
                885                 890                 895

Asn Thr Ser Gly Asn Glu Gln Thr Val Leu Gly Lys Ile Thr Asn Asp
            900                 905                 910

Asp Leu Pro Ile Trp Leu Val Asp His Lys Tyr Thr Phe Ser Ser Ser
        915                 920                 925
```

```
Asp Asn Tyr Ser Thr Tyr Tyr Thr His Leu Lys Leu Thr Leu Val Val
        930                 935                 940

Lys Ala Pro Val Lys Val Glu Leu Phe Val Trp Asp Ser Tyr Asn Asp
945                 950                 955                 960

Leu Ile Asp Glu Lys Glu Tyr Asn Leu Lys Asn Gly Ile Asn Asn Leu
                965                 970                 975

Val Tyr Thr Lys Phe Pro Val Ala Ser Val Asn Thr Tyr Gly Leu Leu
            980                 985                 990

Tyr Thr Asp Ser Leu Gly Asn Gln Tyr Phe Phe Thr Ile Glu Glu Ala
        995                 1000                1005

Tyr
```

<210> SEQ ID NO 28
<211> LENGTH: 983
<212> TYPE: PRT
<213> ORGANISM: Artificial Sequence
<220> FEATURE:
<223> OTHER INFORMATION: fragment of Paenisporosarcina sp. HGH0030
      protease

<400> SEQUENCE: 28

```
Glu Glu Ile Lys Val Glu Pro Lys Ile Ser Lys Phe Asn Ile Glu Ala
1               5                   10                  15

Leu Phe Asp Asp Ser Lys Asp Phe Tyr Ser Asn Gln Leu Ile Val Thr
                20                  25                  30

Phe Lys Ala Ser Pro Thr Gly Ser Glu Arg Lys Gln Ile Leu Asp Ser
            35                  40                  45

Val Asn Ala Lys Glu Leu Ser Ile Gln Val Asn Gly Lys Phe Ala Leu
50                  55                  60

Val Ser Thr Pro Lys Ser Ser Asp Leu Ser Ala Val Ala Lys Glu Leu
65                  70                  75                  80

Leu Lys His Lys Gln Val Glu Phe Val Glu Pro Asn Tyr Gln Leu Glu
                85                  90                  95

Asn Thr Phe Arg Pro Lys Asp Pro Ser Tyr Ser Lys Gln Trp His Leu
                100                 105                 110

Lys Lys Ile His Ala Ser Ser Ala Trp Asp Gln Thr Lys Gly Arg Ser
            115                 120                 125

Gly Val Ile Val Ala Val Ile Asp Glu Gly Val Gln Thr Asn His Pro
130                 135                 140

Asp Leu Lys Gly Lys Phe Val Ser Pro Tyr Asn Ala Val Thr Gly Gly
145                 150                 155                 160

Thr Ser Phe Tyr Ser Gly Asp His Ala Thr His Val Ala Gly Ile Ile
                165                 170                 175

Ala Ala Ser Phe Asn Asn Ser Gly Gly Ala Gly Val Ala Pro Asn Ile
            180                 185                 190

Lys Ile Met Pro Ile Asn Val Phe Thr Gly Asp Ser Ala Ser Ser Tyr
        195                 200                 205

Asp Val Gly Glu Ala Ile Ile Tyr Ala Ala Asp His Ala Asp Ile
    210                 215                 220

Ile Asn Leu Ser Leu Gly Gly Ser Tyr Thr Tyr Ala Met Asp Tyr Ala
225                 230                 235                 240

Thr Gln Tyr Ala Lys Ala Lys Asp Val Leu Ile Ile Ala Ala Ala Gly
                245                 250                 255

Asn Glu Arg Ser Tyr Glu Leu Ser Tyr Pro Ala Ala Leu Asp Gly Val
            260                 265                 270
```

```
Ile Gly Val Ser Ala Thr Asp Ser Asn Asp Glu Ile Thr Asp Phe Ser
            275                 280                 285

Asn Tyr Gly Ser Tyr Ile Asp Leu Ala Ala Pro Gly Glu Gly Ile Phe
        290                 295                 300

Ser Ser Leu Ser Gly Ser Lys Tyr Gly Ala Met Asp Gly Thr Ser Met
305                 310                 315                 320

Ala Ala Pro Val Val Ser Gly Val Ala Ala Leu Val Leu Ser Lys Asn
                325                 330                 335

Pro Leu Leu Thr Ser Asp Gln Leu Glu Lys Ile Leu Thr Lys Ser Ser
            340                 345                 350

Val Asp Leu Tyr His Arg Gly Trp Asp Asp Phe Tyr Gly Tyr Gly Arg
        355                 360                 365

Val Asp Ala Tyr Arg Ala Leu Gln Phe Thr Thr Ser Ala Ile Ser Asn
    370                 375                 380

Leu Lys Leu Ser Ser Thr Lys Phe Thr Met Asn Gly Ser Asn Lys Thr
385                 390                 395                 400

Ala Phe Ser Phe Glu Gly Val Lys Gly Ser Lys Ile Ser Leu Tyr Leu
                405                 410                 415

Gln Asn Ser Lys Gly Thr Thr Ile Lys Lys Ile Val Ser Tyr Lys Asp
            420                 425                 430

Trp Ser Gly Gly Lys Phe Ser Ala Ser Trp Asp Gly Arg Met Asp Asn
        435                 440                 445

Gly Met Tyr Ala Ser Thr Gly Thr Tyr Lys Ile Ile Ala Ala Val Ser
    450                 455                 460

Gly Asn Gly Glu Asn Leu His Leu Ser Ala Thr Leu Lys Val Ile Asp
465                 470                 475                 480

Lys Ile Val Pro Ser Ile Asn Leu Ser Gly Ser Val Asn Tyr Ser Pro
                485                 490                 495

Thr Val Thr Gly Lys Leu Thr Val Pro Tyr Glu Leu Asn Lys Asn Ala
            500                 505                 510

Lys Val Thr Ala Phe Ile Lys Asp Lys Asn Asn Lys Ile Ile Lys Ser
        515                 520                 525

Ile Leu Asn Asn Ser Ser Val Ser Arg Gly Gln Arg Thr Val Gln Trp
    530                 535                 540

Asp Gly Lys Asp Ser Glu Gly Asn Arg Val Lys Asp Gly Val Tyr Ser
545                 550                 555                 560

Leu Glu Met Ser Leu Val Asp Ala Asn Lys Ile Lys Gly Thr Ser Arg
                565                 570                 575

Lys Phe Ser Ile Thr Val Asp Thr Ile Ile Pro Thr Ala Lys Ile Ala
            580                 585                 590

Leu Ser Ser Glu Leu Met Lys Leu Asn Gly Ser Leu Leu Asn Met Gly
        595                 600                 605

Lys Ile Asp Val Ser Glu Thr Val Phe Leu Thr Thr Tyr Ile Ala Asn
    610                 615                 620

Asp Asn Gly Val Lys Val Arg Lys Ile Asp Thr Glu Lys Ser Ile Lys
625                 630                 635                 640

Lys Gly Ala Tyr Ser Leu Asn Trp Asp Gly Lys Asn Glu Asn Ser Glu
                645                 650                 655

Phe Val Ala Glu Gly Asn Tyr His Leu Leu Phe Glu Leu Leu Asp Ser
            660                 665                 670

Ala Gly Asn Lys Ala Ser Leu Lys Ser Thr Thr Phe Ala Phe Gln Asp
        675                 680                 685

Trp Asn Gln Pro Val Ile Glu Gly Asp Ala Asn Tyr Phe Phe Thr Ser
```

```
                690                 695                 700
Asp Gly Lys Gln Thr Phe Ser Tyr Lys Leu Ser Lys Pro Gly Ile Val
705                 710                 715                 720

Thr Ile Gln Leu Phe Lys Asn Asp Asn Leu Val Ser Thr Ile Glu Gln
                725                 730                 735

Asn Val Pro Lys Ser Gln Gly Asn Gln Ser Phe Val Trp Asp Gly Lys
                740                 745                 750

Asp Gln Ser Gly Thr Ile Leu Pro Asp Gly Gln Tyr Ser Tyr Lys Ile
                755                 760                 765

Ser Ile Val Asp Ala Tyr Asn Leu Ser Gln Thr Tyr Lys Gly Ile Met
770                 775                 780

Asn Ile Ala Leu Thr Gln Ile Glu Ile Gln Tyr Pro Thr Val Val Gln
785                 790                 795                 800

Phe Ile Asp Asp Thr Ala Glu Ile Phe Tyr Lys Leu Ser Gln Gln
                805                 810                 815

Ala Asn Val Thr Ile Glu Ile Tyr Glu Gly Asn Ala Lys Ile Arg Thr
                820                 825                 830

Ile Ile Ser Asp Lys Lys Thr Asp Lys Gly Ile Asn His Phe Ile Trp
                835                 840                 845

Asp Gly Tyr Asp Asp Asn Gly Asp Leu Val Tyr Ser Asp Glu Leu Ile
850                 855                 860

Tyr Lys Ile Lys Val Ile Asn Thr Ser Gly Asn Glu Gln Thr Val Leu
865                 870                 875                 880

Gly Lys Ile Thr Asn Asp Asp Leu Pro Ile Trp Leu Val Asp His Lys
                885                 890                 895

Tyr Thr Phe Ser Ser Ser Asp Asn Tyr Ser Thr Tyr Tyr Thr His Leu
                900                 905                 910

Lys Leu Thr Leu Val Val Lys Ala Pro Val Lys Val Glu Leu Phe Val
                915                 920                 925

Trp Asp Ser Tyr Asn Asp Leu Ile Asp Glu Lys Glu Tyr Asn Leu Lys
930                 935                 940

Asn Gly Ile Asn Asn Leu Val Tyr Thr Lys Phe Pro Val Ala Ser Val
945                 950                 955                 960

Asn Thr Tyr Gly Leu Leu Tyr Thr Asp Ser Leu Gly Asn Gln Tyr Phe
                965                 970                 975

Phe Thr Ile Glu Glu Ala Tyr
            980

<210> SEQ ID NO 29
<211> LENGTH: 1133
<212> TYPE: PRT
<213> ORGANISM: Actinomyces sp. ICM47

<400> SEQUENCE: 29

Met Thr Pro Lys Lys Pro Ala Lys Leu Phe Ala Ile Ala Gly Ala Cys
1               5                   10                  15

Ala Val Ala Ile Ala Leu Pro Thr Ser Leu Ala Met Pro Gly Ser Leu
                20                  25                  30

Leu His Gln Ala Gly Ser Asp Ala Asp Ala Ala Gln Ser Ala Gln Ser
            35                  40                  45

Ala Ala Asp Glu Ala Ala Ala Ser Glu Pro Ala Pro Glu Leu Pro Val
        50                  55                  60

Gly Asp Val Asp Asn Ala Leu Thr Ser Ala Asp Gly Glu Ser Leu Leu
65                  70                  75                  80
```

```
Asp Glu Gly Asp Pro Ala Thr Thr Glu Glu Asp Ser Ser Thr Val Val
                85                  90                  95

Asp Met Ile Val Gln Leu Glu Asp Gly Thr Thr Ala Ala Ala Leu
            100                 105                 110

Ala Ser Ile Asn Ser Ala Val Ala Ala Tyr Pro Asp Ala Ser Ala
            115                 120                 125

Glu Val Ser Arg Glu Tyr Thr Asn Ala Phe Thr Gly Phe Ala Leu Ser
            130                 135                 140

Ala Pro Ile Gly Ser Met Asp Ala Ile Arg Gly Val Ser Gly Val Gln
145                 150                 155                 160

Ser Ala Phe Leu Asp His Glu Thr Gln Val Ser Asp Glu Gly Asp Asp
                165                 170                 175

Thr Pro Ala Asp Ala Glu Gly Thr Gly Gly Ala Asp Ala Ser Ala Asp
                180                 185                 190

Ser Gly Ser Ala Ala Asp Ala Glu Ser Asn Pro Met Ala Ala Met Arg
            195                 200                 205

Ala Ala Gln His Gly Asp Val Leu Ser Ala Gln Val Met Met Lys Ala
            210                 215                 220

Asp Lys Ile Ser Gln Thr Gly Ala Gly Lys Val Val Ala Ile Ile Asp
225                 230                 235                 240

Thr Gly Val Asp Met Ser His Pro Ala Phe Ala Gly Gly Leu His Gly
                245                 250                 255

Thr Pro Ala Ile Asp Ser Ser Lys Gly Ala Ser Leu Ala Arg Gln Val
                260                 265                 270

Gly Lys Ser Gly Thr Tyr Val Asn Gln Lys Phe Pro Phe Ala Tyr Asp
            275                 280                 285

Tyr Ala Asp Gly Asp Asn Asp Ala Ser Pro Ala Gly Ser His Gly Thr
            290                 295                 300

His Val Ala Gly Ile Thr Ala Ala Asn Gly Ser Gln Ile Thr Gly Ile
305                 310                 315                 320

Ala Pro Asp Ala Gln Ile Ile Val Gly Lys Val Ala Arg Ser Arg Gly
                325                 330                 335

Gly Ile Pro Asp Ser Ala Leu Leu Ala Ala Leu Asp Asp Met Ala Val
            340                 345                 350

Ile Lys Pro Asp Val Val Asn Leu Ser Leu Gly Arg Thr Ala Gly Met
            355                 360                 365

Asp Ser Ala Ala Asp Thr Leu Phe Ala Gly Val Tyr Glu Lys Leu Gln
            370                 375                 380

Asn Asn Gly Thr Ile Val Asp Val Ala Ala Gly Asn Glu Tyr Ser Ala
385                 390                 395                 400

Ala Tyr Gly Asn Lys Ser Gly Lys Asn Leu Pro Tyr Ala Ser Asp Pro
            405                 410                 415

Asp Ser Ser Thr Leu Gly Glu Pro Ser Thr Phe Ala Pro Val Val Ser
            420                 425                 430

Val Ala Ser Ile Glu Asn Ala Arg Asn Gly Arg Gly Ala Tyr Lys Met
            435                 440                 445

Ser Asp Phe Ser Ser Trp Gly Val Ser Pro Asp Met Arg Leu Lys Pro
450                 455                 460

Glu Val Thr Ala Pro Gly Asn Ile Tyr Ser Ser Val Pro Gly Gly
465                 470                 475                 480

Gly Tyr Gln Tyr Met Ser Gly Thr Ser Met Ala Thr Pro Gln Ile Thr
            485                 490                 495

Gly Val Ser Ala Val Val Leu Glu Arg Val Gln Asn Asp Pro Leu Phe
```

```
              500                 505                 510
Ser Ser Met Ser Ala Arg Gln Lys Ala Asp Val Val Gln Asn Leu Ile
            515                 520                 525
Met Gly Thr Ala Val Pro Val Ala Asp Pro Asn Ala Ser Ser Gly Ala
            530                 535                 540
Tyr Tyr Ser Pro Arg Lys Gln Gly Ala Gly Leu Val Asn Val Gln Ala
545                 550                 555                 560
Ala Thr Thr Ser Ser Val Tyr Pro Thr Val Asn Gly Ala Ala Asp Ser
                565                 570                 575
Ser Arg Pro Lys Ala Glu Leu Gly Asp Gly Thr Lys Gly Trp His Phe
            580                 585                 590
Asp Val Thr Leu His Asn Met Ser Gly Thr Ala Ala Thr Tyr Asp Leu
                595                 600                 605
Ser Ala Gln Ala Leu Ser Glu Asn Ile Ser Gly Gly Leu Phe Thr Gly
            610                 615                 620
Ser Ser Thr Asp Trp Asn Gly Lys Gly Val Ser Val Ser Phe Ser Asn
625                 630                 635                 640
Asn Ser Val Thr Val Pro Ala Lys Gly Glu Ala Thr Val Gly Ile Asp
                645                 650                 655
Val Thr Pro Gly Ser Gln Phe Ala Gln Trp Val Ser Ala Asn Ala Pro
            660                 665                 670
Ser Gly Thr Phe Leu Asp Gly Phe Val Arg Phe Thr Ala Arg Thr Asn
            675                 680                 685
Gly Gln Ser Asp Met Thr Val Pro Tyr Leu Gly Phe Tyr Gly Ser Trp
            690                 695                 700
Gly Thr Pro Ser Ile Phe Asp Gln Met Leu Ser Glu Gly Asp Gly His
705                 710                 715                 720
Ala Ala Ser Ser Ala Ile Tyr Asn Gly Gln Asn Gly Ser Leu Leu Gly
                725                 730                 735
Tyr Asn Pro Leu Val Lys Gly Ser Glu Arg Glu Gly Arg Pro Asn Ala
            740                 745                 750
Asp Arg Tyr Val Ile Ser Arg Ser Thr Ala Ser Gly Ala Pro Thr Ala
            755                 760                 765
Ile Thr Pro Arg Thr Gly Thr Leu Arg Ser Val His Thr Met Thr Thr
            770                 775                 780
Thr Tyr Ala Asn Glu Ala Gly Lys Ser Val Ala Ser Phe Thr Ser Thr
785                 790                 795                 800
Gln Asn Trp Lys Ser Val Tyr Asn Ser Asp Glu Arg Arg Met Thr Trp
                805                 810                 815
Val Glu Glu Asn His Glu Ser Arg Ser Ile Asn Leu Asn Asp Tyr Lys
                820                 825                 830
Tyr Ser Arg Leu Pro Asp Gly Lys Tyr Thr Leu Thr Ile Ser Ala Ser
            835                 840                 845
Asn Asp Gly Pro Ser Pro Thr Lys Gln Ser Leu Thr Tyr Asn Phe Arg
            850                 855                 860
Val Asp Thr Lys Ala Pro Val Val Glu Arg Ala Thr Leu Ser Asn Gly
865                 870                 875                 880
Gly Ser Thr Leu Asn Val Glu Ile Ser Asp Glu Ser Pro Leu Ala Gly
                885                 890                 895
Phe Thr Val Asn Asp Pro Asn Ser Gly Gln Tyr Ile Tyr Arg Asp Val
                900                 905                 910
Ile Arg Asn Asp Ala Asp Gln Thr Tyr Ser Asn Gly Arg Tyr His Tyr
            915                 920                 925
```

Thr Ala Thr Val Asp Met Ser Arg Val Ser Gly Gly Asn Ser Ser Lys
    930                 935                 940

Pro Tyr Val Leu Ala Trp Asp Tyr Gly Leu Asn His Ser Lys Ala Thr
945                 950                 955                 960

Thr Ile Gly Ala Ala Thr Gly Asn Gly Gly Asn Asp Gly Gly Asn
            965                 970                 975

Thr Gly Asp Gln Pro Gly Asn Gly Gly Asp Asn Gly Gly Asn Thr
            980                 985                 990

Gly Asp Gln Pro Gly Asn Gly Gly  Gly Asn Asp Gly Gly  Asn Thr Gly
            995                 1000                1005

Asp Gln  Pro Gly Asn Gly Gly  Gly Asp Gly Gly Gly  Ile Gly Gly
   1010                1015                1020

Asn Val  Cys Ser Pro Ser Met  Gly Gly Arg Trp Val  Thr Asp Gly
   1025                1030                1035

Tyr Arg  Trp Ala Trp Gln Cys  Asn Asn Gly Ala Tyr  Leu Arg Asn
   1040                1045                1050

Gly Trp  Tyr Leu Ile Asp Gly  Arg Tyr Tyr Tyr Phe  Asp Gly Asn
   1055                1060                1065

Gly Tyr  Met Arg Ser Gly Trp  Val Arg Gly Arg Gly  Ser Trp Tyr
   1070                1075                1080

Tyr Leu  Gly Asn Asn Gly Ala  Met Gln Thr Gly Trp  Val Lys Ile
   1085                1090                1095

Gly Gly  Arg Trp Tyr Tyr Leu  Gly Ser Asp Gly Ala  Met Tyr Ser
   1100                1105                1110

Gly Thr  Arg Thr Ile Asp Gly  Asn Ser Tyr Glu Phe  Ser Glu Ser
   1115                1120                1125

Gly Glu  Trp Ile Lys
   1130

<210> SEQ ID NO 30
<211> LENGTH: 1105
<212> TYPE: PRT
<213> ORGANISM: Artificial Sequence
<220> FEATURE:
<223> OTHER INFORMATION: fragment of Actinomyces sp. ICM47 protease

<400> SEQUENCE: 30

Pro Gly Ser Leu Leu His Gln Ala Gly Ser Asp Ala Asp Ala Ala Gln
1               5                   10                  15

Ser Ala Gln Ser Ala Ala Asp Glu Ala Ala Ala Ser Glu Pro Ala Pro
            20                  25                  30

Glu Leu Pro Val Gly Asp Val Asp Asn Ala Leu Thr Ser Ala Asp Gly
        35                  40                  45

Glu Ser Leu Leu Asp Glu Gly Asp Pro Ala Thr Thr Glu Glu Asp Ser
    50                  55                  60

Ser Thr Val Val Asp Met Ile Val Gln Leu Glu Asp Gly Thr Asp Thr
65                  70                  75                  80

Ala Ala Ala Leu Ala Ser Ile Asn Ser Ala Val Ala Ala Ala Tyr Pro
                85                  90                  95

Asp Ala Ser Ala Glu Val Ser Arg Glu Tyr Thr Asn Ala Phe Thr Gly
            100                 105                 110

Phe Ala Leu Ser Ala Pro Ile Gly Ser Met Asp Ala Ile Arg Gly Val
        115                 120                 125

Ser Gly Val Gln Ser Ala Phe Leu Asp His Glu Thr Gln Val Ser Asp
    130                 135                 140

```
Glu Gly Asp Asp Thr Pro Ala Asp Ala Glu Thr Gly Gly Ala Asp
145                 150                 155                 160

Ala Ser Ala Asp Ser Gly Ser Ala Ala Asp Ala Glu Ser Asn Pro Met
            165                 170                 175

Ala Ala Met Arg Ala Ala Gln His Gly Asp Val Leu Ser Ala Gln Val
        180                 185                 190

Met Met Lys Ala Asp Lys Ile Ser Gln Thr Gly Ala Gly Lys Val Val
    195                 200                 205

Ala Ile Ile Asp Thr Gly Val Asp Met Ser His Pro Ala Phe Ala Gly
210                 215                 220

Gly Leu His Gly Thr Pro Ala Ile Asp Ser Ser Lys Gly Ala Ser Leu
225                 230                 235                 240

Ala Arg Gln Val Gly Lys Ser Gly Thr Tyr Val Asn Gln Lys Phe Pro
                245                 250                 255

Phe Ala Tyr Asp Tyr Ala Asp Gly Asp Asn Asp Ala Ser Pro Ala Gly
            260                 265                 270

Ser His Gly Thr His Val Ala Gly Ile Thr Ala Ala Asn Gly Ser Gln
        275                 280                 285

Ile Thr Gly Ile Ala Pro Asp Ala Gln Ile Ile Val Gly Lys Val Ala
290                 295                 300

Arg Ser Arg Gly Gly Ile Pro Asp Ser Ala Leu Leu Ala Ala Leu Asp
305                 310                 315                 320

Asp Met Ala Val Ile Lys Pro Asp Val Val Asn Leu Ser Leu Gly Arg
                325                 330                 335

Thr Ala Gly Met Asp Ser Ala Ala Asp Thr Leu Phe Ala Gly Val Tyr
            340                 345                 350

Glu Lys Leu Gln Asn Asn Gly Thr Ile Val Asp Val Ala Ala Gly Asn
        355                 360                 365

Glu Tyr Ser Ala Ala Tyr Gly Asn Lys Ser Gly Lys Asn Leu Pro Tyr
370                 375                 380

Ala Ser Asp Pro Asp Ser Ser Thr Leu Gly Glu Pro Ser Thr Phe Ala
385                 390                 395                 400

Pro Val Val Ser Val Ala Ser Ile Glu Asn Ala Arg Asn Gly Arg Gly
                405                 410                 415

Ala Tyr Lys Met Ser Asp Phe Ser Ser Trp Gly Val Ser Pro Asp Met
            420                 425                 430

Arg Leu Lys Pro Glu Val Thr Ala Pro Gly Gly Asn Ile Tyr Ser Ser
        435                 440                 445

Val Pro Gly Gly Gly Tyr Gln Tyr Met Ser Gly Thr Ser Met Ala Thr
450                 455                 460

Pro Gln Ile Thr Gly Val Ser Ala Val Val Leu Glu Arg Val Gln Asn
465                 470                 475                 480

Asp Pro Leu Phe Ser Ser Met Ser Ala Arg Gln Lys Ala Asp Val Val
                485                 490                 495

Gln Asn Leu Ile Met Gly Thr Ala Val Pro Val Ala Asp Pro Asn Ala
            500                 505                 510

Ser Ser Gly Ala Tyr Tyr Ser Pro Arg Lys Gln Gly Ala Gly Leu Val
        515                 520                 525

Asn Val Gln Ala Ala Thr Thr Ser Ser Val Tyr Pro Thr Val Asn Gly
530                 535                 540

Ala Ala Asp Ser Ser Arg Pro Lys Ala Glu Leu Gly Asp Gly Thr Lys
545                 550                 555                 560
```

```
Gly Trp His Phe Asp Val Thr Leu His Asn Met Ser Gly Thr Ala Ala
            565                 570                 575

Thr Tyr Asp Leu Ser Ala Gln Ala Leu Ser Glu Asn Ile Ser Gly Gly
            580                 585                 590

Leu Phe Thr Gly Ser Ser Thr Asp Trp Asn Gly Lys Gly Val Ser Val
            595                 600                 605

Ser Phe Ser Asn Asn Ser Val Thr Val Pro Ala Lys Gly Glu Ala Thr
            610                 615                 620

Val Gly Ile Asp Val Thr Pro Gly Ser Gln Phe Ala Gln Trp Val Ser
625                 630                 635                 640

Ala Asn Ala Pro Ser Gly Thr Phe Leu Asp Gly Phe Val Arg Phe Thr
            645                 650                 655

Ala Arg Thr Asn Gly Gln Ser Asp Met Thr Val Pro Tyr Leu Gly Phe
            660                 665                 670

Tyr Gly Ser Trp Gly Thr Pro Ser Ile Phe Asp Gln Met Leu Ser Glu
            675                 680                 685

Gly Asp Gly His Ala Ala Ser Ser Ala Ile Tyr Asn Gly Gln Asn Gly
            690                 695                 700

Ser Leu Leu Gly Tyr Asn Pro Leu Val Lys Gly Ser Glu Arg Glu Gly
705                 710                 715                 720

Arg Pro Asn Ala Asp Arg Tyr Val Ile Ser Arg Ser Thr Ala Ser Gly
            725                 730                 735

Ala Pro Thr Ala Ile Thr Pro Arg Thr Gly Thr Leu Arg Ser Val His
            740                 745                 750

Thr Met Thr Thr Thr Tyr Ala Asn Glu Ala Gly Lys Ser Val Ala Ser
            755                 760                 765

Phe Thr Ser Thr Gln Asn Trp Lys Ser Val Tyr Asn Ser Asp Glu Arg
            770                 775                 780

Arg Met Thr Trp Val Glu Glu Asn His Glu Ser Arg Ser Ile Asn Leu
785                 790                 795                 800

Asn Asp Tyr Lys Tyr Ser Arg Leu Pro Asp Gly Lys Tyr Thr Leu Thr
            805                 810                 815

Ile Ser Ala Ser Asn Asp Gly Pro Ser Pro Thr Lys Gln Ser Leu Thr
            820                 825                 830

Tyr Asn Phe Arg Val Asp Thr Lys Ala Pro Val Val Glu Arg Ala Thr
            835                 840                 845

Leu Ser Asn Gly Gly Ser Thr Leu Asn Val Glu Ile Ser Asp Glu Ser
            850                 855                 860

Pro Leu Ala Gly Phe Thr Val Asn Asp Pro Asn Ser Gly Gln Tyr Ile
865                 870                 875                 880

Tyr Arg Asp Val Ile Arg Asn Asp Ala Asp Gln Thr Tyr Ser Asn Gly
            885                 890                 895

Arg Tyr His Tyr Thr Ala Thr Val Asp Met Ser Arg Val Ser Gly Gly
            900                 905                 910

Asn Ser Ser Lys Pro Tyr Val Leu Ala Trp Asp Tyr Gly Leu Asn His
            915                 920                 925

Ser Lys Ala Thr Thr Ile Gly Ala Ala Thr Gly Asn Gly Gly Asn
            930                 935                 940

Asp Gly Gly Asn Thr Gly Asp Gln Pro Gly Asn Gly Gly Asp Asn
945                 950                 955                 960

Gly Gly Asn Thr Gly Asp Gln Pro Gly Asn Gly Gly Asn Asp Gly
            965                 970                 975

Gly Asn Thr Gly Asp Gln Pro Gly Asn Gly Gly Gly Asp Gly Gly Gly
```

```
                980             985             990
Ile Gly Gly Asn Val Cys Ser Pro Ser Met Gly Gly Arg Trp Val Thr
            995             1000            1005

Asp Gly Tyr Arg Trp Ala Trp Gln Cys Asn Asn Gly Ala Tyr Leu
        1010            1015            1020

Arg Asn Gly Trp Tyr Leu Ile Asp Gly Arg Tyr Tyr Tyr Phe Asp
        1025            1030            1035

Gly Asn Gly Tyr Met Arg Ser Gly Trp Val Arg Gly Arg Gly Ser
        1040            1045            1050

Trp Tyr Tyr Leu Gly Asn Asn Gly Ala Met Gln Thr Gly Trp Val
        1055            1060            1065

Lys Ile Gly Gly Arg Trp Tyr Tyr Leu Gly Ser Asp Gly Ala Met
        1070            1075            1080

Tyr Ser Gly Thr Arg Thr Ile Asp Gly Asn Ser Tyr Glu Phe Ser
        1085            1090            1095

Glu Ser Gly Glu Trp Ile Lys
        1100            1105

<210> SEQ ID NO 31
<211> LENGTH: 1195
<212> TYPE: PRT
<213> ORGANISM: Actinomyces georgiae

<400> SEQUENCE: 31

Met Pro Thr Arg Arg Thr Asn Ala Leu Ala Ser Leu Ile Ala Ser Ser
1               5                   10                  15

Ser Leu Leu Leu Ala Ser Ala Val Ala Leu Pro Ala Gln Ala Phe Ser
                20                  25                  30

Pro Pro Gly Glu Asp Asp Gln Gly Arg Gly Ser Pro Ala Thr Ser Gln
            35                  40                  45

Ala Ala Ala Asp Thr Ala Leu Thr Ser Lys Ala Asp Tyr Glu Asn Gly
        50                  55                  60

Thr Gly Pro Gly Pro Val Asp Asp Thr Gln Ser Asp Ala Ala Glu Pro
65                  70                  75                  80

Asp Gly Thr Gly Gly His Ala Pro Asp Glu Val Arg Ile Ile Val
                85                  90                  95

Gln Phe Glu Asp Gly Val Ser Glu Ser Asp Cys Asp Glu Met Val Asp
            100                 105                 110

Arg Ile Gly Glu Ala Val Ala Ala Ser Val Pro Ser Ala Ala Ala Gly
        115                 120                 125

Gly Pro Ala Val Thr Arg Ala Arg Asp Tyr Arg Asn Val Phe Ile Gly
        130                 135                 140

Val Ala Ile Asp Ala Pro Ala Ala Leu Pro Val Ile Gln Gly Val
145                 150                 155                 160

Asp Gly Met Lys Ser Ala Phe Ile Glu Arg Glu Gly His Ile Glu Thr
                165                 170                 175

Asp Glu Ser Glu Gln Pro Gly Gly Pro Ser Gly Asn Ser Ser Pro Ala
            180                 185                 190

His Glu Ala Gly Ala Ala Gly Ser Gly Ser Ala Ser Ala Ala Gly Ser
        195                 200                 205

Pro Ser Pro Ala Asp Ala Pro Ser Pro Ala Asp Thr Pro Ser Ser Gly
        210                 215                 220

Gly Ala Ala Ser Asn Gly Asp Asp Ala Pro Ser Gly Ala Pro Ala Ser
225                 230                 235                 240
```

```
Gly Ala Ala Pro Ser Gln Asp Pro Ala Ala Asp Ser Gly Asn Val Glu
                245                 250                 255

Gly Thr Ala Gly Ser Leu Ala Ala Glu Gly Ile Asp Pro Ser Asn Arg
            260                 265                 270

Ser Ala His Gln Met Met Arg Met Asp Arg Val Pro His Lys Gly Glu
        275                 280                 285

Gly Arg Val Ile Ala Phe Leu Asp Thr Gly Leu Glu Val Ala His Pro
    290                 295                 300

Ala Phe Ser Gly Ala Val Asp Ala Ser Lys Thr Ala Leu Lys Arg Ala
305                 310                 315                 320

Asp Val Glu Gln Ala Leu Pro Arg Leu Gly Glu Gly Lys Asp Gly Arg
                325                 330                 335

Tyr Val Asn Asp Lys Ile Pro Phe Ala Tyr Asp Tyr Ala Asp Asp Asp
            340                 345                 350

Ala Asp Val Ala Pro Ser Ser Gly Ala Gly Phe His Gly Thr His
        355                 360                 365

Val Ala Gly Ile Ala Ala Ala Asn Ala Asp Arg Ile Arg Gly Thr Ala
    370                 375                 380

Ser Gly Ala Gln Ile Ile Val Ala Lys Val Ala Arg Ser Gly Asn Gly
385                 390                 395                 400

Ser Leu Pro Asp Ser Ala Val Leu Ala Ala Leu Asp Asp Met Ala Val
                405                 410                 415

Leu Arg Pro Asp Val Ile Asn Leu Ser Ile Gly Trp Ser Ala Gly Met
            420                 425                 430

Asp Asn Ala Ala Asp Ser Leu Tyr Ser Thr Val Tyr Ala Arg Leu Gln
        435                 440                 445

Glu Ala Gly Val Thr Val Asp Ala Ala Ala Gly Asn Ala Tyr Ser Ala
    450                 455                 460

Gly Arg Gly Asn Asn Ser Gly Lys Asn Leu Pro Tyr Ala Ser Asp Pro
465                 470                 475                 480

Asp Ser Ser Val Met Asp Glu Pro Ala Thr Tyr Ser Ser Ala Val Ala
                485                 490                 495

Val Ala Ser Val Asp Asn Ala Pro Ala Asn Gly Ala Tyr Lys Ala Ser
            500                 505                 510

Asp Phe Ser Ala Trp Gly Val Ser Pro Asp Leu Arg Leu Lys Pro Glu
        515                 520                 525

Ile Ala Ser Pro Gly Gly Gly Val Ser Ala Val Pro Gly Gly Ala
    530                 535                 540

Tyr Asp Gln Ala Ser Gly Thr Ser Met Ala Thr Pro Gln Met Ala Gly
545                 550                 555                 560

Ile Ser Ala Ile Val Leu Glu Arg Val Asn Thr Asp Pro Leu Phe Ala
                565                 570                 575

Ser Met Ser Ala Ala Glu Arg Met Gly Val Ala Gln Ser Leu Ile Met
            580                 585                 590

Gly Thr Ala His Pro Leu Val Asp Ala Asp Gln Gly Thr Gly Ala Phe
        595                 600                 605

Tyr Ser Pro Arg Lys Gln Gly Ala Gly Leu Val Asp Ala Leu Ala Ala
    610                 615                 620

Thr Thr Ser Pro Val Tyr Pro Thr Val Asp Gly Ala Ala Glu Pro Ser
625                 630                 635                 640

Arg Pro Lys Ala Asp Leu Gly Asp Gly Thr Ala Gly Trp Ser Phe Thr
                645                 650                 655

Ile Thr Val His Asn Leu Ser Asp Ser Ala Lys Ser Tyr Ala Leu Ser
```

-continued

```
                660             665             670
Ser Gln Ala Leu Ser Glu Ala Val Glu Gly Phe Phe Thr Leu Arg
            675             680             685
Ser Lys Asp Trp Arg Gly Arg Gly Ile Ser Val Ser Tyr Ser Gly Ala
        690             695             700
Ala Val Ala Gly Ser Gly Glu Gly Ala Thr Leu Ala Val Pro Ala Ser
705             710             715             720
Gly Gln Ala Ser Val Thr Val Ser Val Ser Pro Gly Ala Asp Phe Ala
            725             730             735
Ser Tyr Ala Ala Ala Asn Ala Pro Lys Gly Thr Phe Ile Asp Gly Phe
            740             745             750
Val Arg Leu Val Ala Gln Gly Gly Ser Gly Pro Asp Leu Ser Val Pro
            755             760             765
Tyr Leu Gly Phe Tyr Gly Ser Trp Gly Ala Ala Asp Val Phe Asp Ala
            770             775             780
Lys Ala Ser Asp Ala Ala Ala Ser Pro Ala His Ile Tyr Pro Ser Ala
785             790             795             800
Phe Val Asp Ser Arg Thr Gly Arg Ser Leu Gly Ala Asn Pro Phe Ala
            805             810             815
Pro Gln Asn Thr Glu Thr Ile Pro Asp Pro Gly Arg Tyr Val Val Ser
            820             825             830
Arg Ala Ala Ser Ser Leu Ala Thr Arg Arg Ala Glu Pro Arg Thr Gly
            835             840             845
Leu Leu Arg Ser Val His Thr Leu Thr Ser Thr Tyr Ala Asn Glu Ala
            850             855             860
Gly Thr Thr Val Leu Glu Tyr Arg Asn Tyr Gln Asn Tyr Lys Ser Val
865             870             875             880
Arg Asn Ala Asn Gly Thr Val Ser Arg Ala Glu Ser Tyr His Leu Ala
            885             890             895
Pro Val Phe Asp Ser Glu Asp Lys Gln Val Ala Gly Leu Pro Asp Gly
            900             905             910
Lys Tyr Thr Leu Thr Ile Ala Ala Thr Thr Ser Gly Pro Ser Pro Thr
            915             920             925
Arg His Ala Ile Ala Tyr Asp Phe Ala Leu Asp Thr Thr Ala Pro Arg
            930             935             940
Val Thr Val Arg Gly Val Ser Gly Glu Gly Ala Gly Ala Lys Val Ala
945             950             955             960
Phe Asp Val Thr Asp Ala Ser Pro Leu Ala Ala Phe Asp Phe His Asp
            965             970             975
Pro Ser Asn Gly Thr Trp Tyr Tyr Arg Glu Leu Val Asn Asp Asp Gly
            980             985             990
Thr Val Asn Pro Asp Gly Ser His Thr Tyr His Phe Glu Val Ser Ala
            995             1000            1005
Ser Ala Leu Gln Ala Ala Trp Glu Ala Gln His Gly Lys Gly Ala
            1010            1015            1020
Ala Pro Ser Glu Pro Tyr Val Leu Ala Trp Asp Trp Gly Ala Asn
            1025            1030            1035
Pro Ser Asp Lys Ala Val Val Arg Phe Pro Gly Thr Thr Ser Gly
            1040            1045            1050
Ala Trp Thr His Asp Ser His Gly Trp Trp Tyr Arg Leu Ser Asp
            1055            1060            1065
Gly Ser Trp Pro Ser Ser Thr Ser Met Val Ile Asp Gly Ala Thr
            1070            1075            1080
```

```
Tyr Arg Phe Asp Ala Ser Gly Tyr Met Arg Thr Gly Trp Val Ser
    1085            1090                1095

Glu Ala Gly Ser Trp Tyr Tyr His Leu Pro Ser Gly Ala Met Ala
    1100            1105                1110

Lys Gly Trp Ala Asn Val Gly Gly Thr Trp Tyr Tyr Leu Ser Ser
    1115            1120                1125

Gly Thr Gly Ala Met Ala Thr Gly Trp Leu Asn Gln Gly Gly Thr
    1130            1135                1140

Trp Tyr Tyr Leu Ala Ala Ser Gly Ala Met Ala Thr Gly Trp Ala
    1145            1150                1155

Asp Val Gly Gly Thr Trp Tyr Tyr Phe Ser Ser Ser Gly Ala Met
    1160            1165                1170

Ala Thr Gly Trp Lys Trp Ile Asp Gly Ala Trp Tyr Gln Phe Ser
    1175            1180                1185

Ser Ser Gly Ala Trp Thr Gly
    1190            1195

<210> SEQ ID NO 32
<211> LENGTH: 1163
<212> TYPE: PRT
<213> ORGANISM: Artificial Sequence
<220> FEATURE:
<223> OTHER INFORMATION: fragment of Actinomyces georgiae F0490 protease

<400> SEQUENCE: 32

Pro Pro Gly Glu Asp Asp Gln Gly Arg Gly Ser Pro Ala Thr Ser Gln
1               5                   10                  15

Ala Ala Ala Asp Thr Ala Leu Thr Ser Lys Ala Asp Tyr Glu Asn Gly
                20                  25                  30

Thr Gly Pro Gly Pro Val Asp Asp Thr Gln Ser Asp Ala Ala Glu Pro
            35                  40                  45

Asp Gly Thr Gly Gly His Ala Pro Asp Glu Gly Val Arg Ile Ile Val
        50                  55                  60

Gln Phe Glu Asp Gly Val Ser Glu Ser Asp Cys Asp Glu Met Val Asp
65                  70                  75                  80

Arg Ile Gly Glu Ala Val Ala Ser Val Pro Ser Ala Ala Gly
                85                  90                  95

Gly Pro Ala Val Thr Arg Ala Arg Asp Tyr Arg Asn Val Phe Ile Gly
            100                 105                 110

Val Ala Ile Asp Ala Pro Ala Ala Leu Pro Val Ile Gln Gly Val
            115                 120                 125

Asp Gly Met Lys Ser Ala Phe Ile Glu Arg Glu Gly His Ile Glu Thr
        130                 135                 140

Asp Glu Ser Glu Gln Pro Gly Gly Pro Ser Gly Asn Ser Ser Pro Ala
145                 150                 155                 160

His Glu Ala Gly Ala Ala Gly Ser Gly Ser Ala Ser Ala Ala Gly Ser
                165                 170                 175

Pro Ser Pro Ala Asp Ala Pro Ser Pro Ala Asp Thr Pro Ser Ser Gly
            180                 185                 190

Gly Ala Ala Ser Asn Gly Asp Asp Ala Pro Ser Gly Ala Pro Ala Ser
        195                 200                 205

Gly Ala Ala Pro Ser Gln Asp Pro Ala Ala Asp Ser Gly Asn Val Glu
    210                 215                 220

Gly Thr Ala Gly Ser Leu Ala Ala Glu Gly Ile Asp Pro Ser Asn Arg
225                 230                 235                 240
```

```
Ser Ala His Gln Met Met Arg Met Asp Arg Val Pro His Lys Gly Glu
                245                 250                 255
Gly Arg Val Ile Ala Phe Leu Asp Thr Gly Leu Glu Val Ala His Pro
                260                 265                 270
Ala Phe Ser Gly Ala Val Asp Ala Ser Lys Thr Ala Leu Lys Arg Ala
                275                 280                 285
Asp Val Glu Gln Ala Leu Pro Arg Leu Gly Glu Gly Lys Asp Gly Arg
                290                 295                 300
Tyr Val Asn Asp Lys Ile Pro Phe Ala Tyr Asp Tyr Ala Asp Asp
305                 310                 315                 320
Ala Asp Val Ala Pro Ser Ser Gly Ala Gly Phe His Gly Thr His
                325                 330                 335
Val Ala Gly Ile Ala Ala Asn Ala Asp Arg Ile Arg Gly Thr Ala
                340                 345                 350
Ser Gly Ala Gln Ile Ile Val Ala Lys Val Ala Arg Ser Gly Asn Gly
                355                 360                 365
Ser Leu Pro Asp Ser Ala Val Leu Ala Ala Leu Asp Asp Met Ala Val
            370                 375                 380
Leu Arg Pro Asp Val Ile Asn Leu Ser Ile Gly Trp Ser Ala Gly Met
385                 390                 395                 400
Asp Asn Ala Ala Asp Ser Leu Tyr Ser Thr Val Tyr Ala Arg Leu Gln
                405                 410                 415
Glu Ala Gly Val Thr Val Asp Ala Ala Ala Gly Asn Ala Tyr Ser Ala
                420                 425                 430
Gly Arg Gly Asn Asn Ser Gly Lys Asn Leu Pro Tyr Ala Ser Asp Pro
                435                 440                 445
Asp Ser Ser Val Met Asp Glu Pro Ala Thr Tyr Ser Ser Ala Val Ala
            450                 455                 460
Val Ala Ser Val Asp Asn Ala Pro Ala Asn Gly Ala Tyr Lys Ala Ser
465                 470                 475                 480
Asp Phe Ser Ala Trp Gly Val Ser Pro Asp Leu Arg Leu Lys Pro Glu
                485                 490                 495
Ile Ala Ser Pro Gly Gly Gly Val Val Ser Ala Val Pro Gly Gly Ala
                500                 505                 510
Tyr Asp Gln Ala Ser Gly Thr Ser Met Ala Thr Pro Gln Met Ala Gly
                515                 520                 525
Ile Ser Ala Ile Val Leu Glu Arg Val Asn Thr Asp Pro Leu Phe Ala
            530                 535                 540
Ser Met Ser Ala Ala Glu Arg Met Gly Val Ala Gln Ser Leu Ile Met
545                 550                 555                 560
Gly Thr Ala His Pro Leu Val Asp Ala Asp Gln Gly Thr Gly Ala Phe
                565                 570                 575
Tyr Ser Pro Arg Lys Gln Gly Ala Gly Leu Val Asp Ala Leu Ala Ala
                580                 585                 590
Thr Thr Ser Pro Val Tyr Pro Thr Val Asp Gly Ala Ala Glu Pro Ser
                595                 600                 605
Arg Pro Lys Ala Asp Leu Gly Asp Gly Thr Ala Gly Trp Ser Phe Thr
                610                 615                 620
Ile Thr Val His Asn Leu Ser Asp Ser Ala Lys Ser Tyr Ala Leu Ser
625                 630                 635                 640
Ser Gln Ala Leu Ser Glu Ala Val Glu Gly Gly Phe Phe Thr Leu Arg
                645                 650                 655
```

-continued

```
Ser Lys Asp Trp Arg Gly Arg Gly Ile Ser Val Ser Tyr Ser Gly Ala
            660                 665                 670

Ala Val Ala Gly Ser Gly Glu Gly Ala Thr Leu Ala Val Pro Ala Ser
        675                 680                 685

Gly Gln Ala Ser Val Thr Val Ser Val Ser Pro Gly Ala Asp Phe Ala
        690                 695                 700

Ser Tyr Ala Ala Ala Asn Ala Pro Lys Gly Thr Phe Ile Asp Gly Phe
705                 710                 715                 720

Val Arg Leu Val Ala Gln Gly Ser Gly Pro Asp Leu Ser Val Pro
                725                 730                 735

Tyr Leu Gly Phe Tyr Gly Ser Trp Gly Ala Ala Asp Val Phe Asp Ala
            740                 745                 750

Lys Ala Ser Asp Ala Ala Ala Ser Pro Ala His Ile Tyr Pro Ser Ala
            755                 760                 765

Phe Val Asp Ser Arg Thr Gly Arg Ser Leu Gly Ala Asn Pro Phe Ala
            770                 775                 780

Pro Gln Asn Thr Glu Thr Ile Pro Asp Pro Gly Arg Tyr Val Val Ser
785                 790                 795                 800

Arg Ala Ala Ser Ser Leu Ala Thr Arg Arg Ala Glu Pro Arg Thr Gly
                805                 810                 815

Leu Leu Arg Ser Val His Thr Leu Thr Ser Thr Tyr Ala Asn Glu Ala
            820                 825                 830

Gly Thr Thr Val Leu Glu Tyr Arg Asn Tyr Gln Asn Tyr Lys Ser Val
            835                 840                 845

Arg Asn Ala Asn Gly Thr Val Ser Arg Ala Glu Ser Tyr His Leu Ala
850                 855                 860

Pro Val Phe Asp Ser Glu Asp Lys Gln Val Ala Gly Leu Pro Asp Gly
865                 870                 875                 880

Lys Tyr Thr Leu Thr Ile Ala Ala Thr Thr Ser Gly Pro Ser Pro Thr
                885                 890                 895

Arg His Ala Ile Ala Tyr Asp Phe Ala Leu Asp Thr Thr Ala Pro Arg
            900                 905                 910

Val Thr Val Arg Gly Val Ser Gly Glu Gly Ala Gly Ala Lys Val Ala
            915                 920                 925

Phe Asp Val Thr Asp Ala Ser Pro Leu Ala Ala Phe Asp Phe His Asp
        930                 935                 940

Pro Ser Asn Gly Thr Trp Tyr Tyr Arg Glu Leu Val Asn Asp Asp Gly
945                 950                 955                 960

Thr Val Asn Pro Asp Gly Ser His Thr Tyr His Phe Glu Val Ser Ala
                965                 970                 975

Ser Ala Leu Gln Ala Ala Trp Glu Ala Gln His Gly Lys Gly Ala Ala
            980                 985                 990

Pro Ser Glu Pro Tyr Val Leu Ala Trp Asp Trp Gly Ala Asn Pro Ser
        995                 1000                1005

Asp Lys Ala Val Val Arg Phe Pro Gly Thr Ser Gly Ala Trp
        1010                1015                1020

Thr His Asp Ser His Gly Trp Trp Tyr Arg Leu Ser Asp Gly Ser
        1025                1030                1035

Trp Pro Ser Ser Thr Ser Met Val Ile Asp Gly Ala Thr Tyr Arg
        1040                1045                1050

Phe Asp Ala Ser Gly Tyr Met Arg Thr Gly Trp Val Ser Glu Ala
        1055                1060                1065

Gly Ser Trp Tyr Tyr His Leu Pro Ser Gly Ala Met Ala Lys Gly
```

```
            1070                1075                1080
Trp Ala Asn Val Gly Gly Thr Trp Tyr Tyr Leu Ser Ser Gly Thr
        1085                1090                1095
Gly Ala Met Ala Thr Gly Trp Leu Asn Gln Gly Gly Thr Trp Tyr
    1100                1105                1110
Tyr Leu Ala Ala Ser Gly Ala Met Ala Thr Gly Trp Ala Asp Val
1115                1120                1125
Gly Gly Thr Trp Tyr Tyr Phe Ser Ser Ser Gly Ala Met Ala Thr
        1130                1135                1140
Gly Trp Lys Trp Ile Asp Gly Ala Trp Tyr Gln Phe Ser Ser Ser
    1145                1150                1155
Gly Ala Trp Thr Gly
        1160
```

<210> SEQ ID NO 33
<211> LENGTH: 1236
<212> TYPE: PRT
<213> ORGANISM: Actinomyces sp. oral taxon 877 str. F0543

<400> SEQUENCE: 33

```
Met Pro Thr Arg Arg Thr Asn Ala Leu Ala Ala Leu Leu Ala Ser Ser
1               5                   10                  15
Ser Leu Leu Leu Ala Ser Ala Val Ala Leu Pro Ala Gln Ser Phe Pro
            20                  25                  30
Pro Pro Gly Gly Asp Asp Gln Gly Gln Gly Ser Pro Ala Thr Ser Gln
        35                  40                  45
Ala Ala Ala Asp Thr Ala Leu Thr Ser Lys Ala Asp Tyr Glu Asn Gly
    50                  55                  60
Ala Gly Pro Gly Pro Ala Asp Glu Ala His Pro Tyr Gly Ala Gln Ser
65                  70                  75                  80
Asp Ala Ser Gln Pro Asp Ala Pro Gln Ser Asp Ala Ser Gln Pro Asp
                85                  90                  95
Gly Ala Glu Gly His Ala Pro Glu Glu Gly Val Arg Ile Ile Val Gln
            100                 105                 110
Phe Ala Asp Glu Ala Ser Glu Ser Asp Cys Asp Glu Leu Val Asp Arg
        115                 120                 125
Ile Gly Glu Ala Val Ala Ser Val Pro Ala Ala Gly Gly Pro
    130                 135                 140
Ala Ile Thr Arg Ala Arg Asp Tyr Arg Asn Val Phe Thr Gly Val Ala
145                 150                 155                 160
Ile Asp Ala Pro Ala Ala Ser Leu Pro Val Val Gln Gly Val Asp Gly
                165                 170                 175
Val Lys Ser Ala Phe Ile Glu Arg Glu Gly His Ile Glu Gly Asp Glu
            180                 185                 190
Ser Glu Gln Pro Gly Gly Pro Ser Gly Asn Gly Gly Pro Ala His Glu
        195                 200                 205
Ala Gly Ala Asp Gly Ser Ser Ala Ser Ala Ala His Ser Pro Ser
    210                 215                 220
Pro Ala His Ser Pro Ser Pro Ala Gly Ile Pro Pro Ser Gly Asp Ala
225                 230                 235                 240
Ala Ser Asn Gly Asp Gly Ala Pro Ser Gly Ala Pro Ala Ser Gly Ala
                245                 250                 255
Ser Pro Ser Pro Ala Ala Thr Pro Ser Gln Asp Ala Ala Ala Gly Ser
            260                 265                 270
```

```
Gly Asn Val Glu Gly Gly Ala Asp Ser Leu Ala Ala Glu Gly Ile Asp
            275                 280                 285

Pro Ser Asn Arg Ser Ala His Leu Met Met Arg Met Asp His Val Ser
            290                 295                 300

His Lys Gly Glu Gly Arg Val Ile Ala Phe Leu Asp Thr Gly Leu Glu
305                 310                 315                 320

Val Ala His Pro Ala Phe Ser Gly Ala Val Asp Ala Ser Lys Thr Ala
            325                 330                 335

Leu Lys Arg Ala Asp Val Glu Gln Val Leu Pro Arg Leu Gly Glu Gly
            340                 345                 350

Lys Asp Gly His Tyr Val Asn Asp Lys Ile Pro Phe Val Tyr Asp Tyr
            355                 360                 365

Ala Asp Asp Asp Ala Asp Val Ala Pro Ser Ser Gly Pro Gly Gly Phe
            370                 375                 380

His Gly Thr His Val Ala Gly Ile Ala Ala Asn Ala Asp Arg Ile
385                 390                 395                 400

Arg Gly Thr Ala Pro Gly Ala Gln Ile Ile Val Ala Lys Val Ala Arg
            405                 410                 415

Ser Gly Asn Gly Ser Leu Pro Asp Ser Ala Val Leu Ala Ala Leu Asp
            420                 425                 430

Asp Met Ala Val Leu Arg Pro Asp Val Val Asn Leu Ser Ile Gly Trp
            435                 440                 445

Ser Ala Gly Met Asp Asn Ala Ala Asp Ser Leu Tyr Ser Thr Val Tyr
            450                 455                 460

Ala Ser Leu Gln Gly Ala Gly Val Thr Val Asn Ala Ala Ala Gly Asn
465                 470                 475                 480

Ser Tyr Ser Ala Gly Arg Gly Asn Arg Ser Gly Lys Asn Leu Pro Tyr
            485                 490                 495

Ala Ser Asp Pro Asp Ser Ser Val Met Asp Glu Pro Ala Thr Tyr Ser
            500                 505                 510

Ser Ala Val Ala Val Ala Ser Val Asp Asn Ala Pro Ala Asn Gly Ala
            515                 520                 525

Tyr Arg Ala Ser Asp Phe Ser Ala Trp Gly Val Ser Pro Asp Leu Arg
            530                 535                 540

Leu Lys Pro Glu Ile Ala Ser Pro Gly Gly Gly Val Val Ser Ala Val
545                 550                 555                 560

Pro Gly Gly Ala Tyr Asp Gln Ala Ser Gly Thr Ser Met Ala Thr Pro
            565                 570                 575

Gln Met Ala Gly Ile Ser Ala Ile Val Leu Glu Arg Val Ser Thr Asp
            580                 585                 590

Pro Leu Phe Ala Gly Met Ser Ala Ala Glu Arg Thr Gly Val Ala Gln
            595                 600                 605

Ser Leu Ile Met Gly Thr Ala His Pro Leu Val Asp Ala Asp Gln Gly
            610                 615                 620

Thr Gly Ala Phe Tyr Ser Pro Arg Lys Gln Gly Ala Gly Leu Val Asp
625                 630                 635                 640

Ala Leu Ala Ala Thr Thr Ser Pro Val Tyr Pro Thr Val Asp Gly Ala
            645                 650                 655

Ala Glu Pro Ser Arg Pro Lys Ala Asp Leu Gly Asp Gly Thr Ala Gly
            660                 665                 670

Trp Ser Phe Thr Ile Thr Val His Asn Leu Ser Asp Ser Ala Lys Ser
            675                 680                 685

Tyr Ala Leu Ser Ser Gln Ala Leu Ser Glu Ala Val Glu Gly Gly Phe
```

```
              690             695             700
Phe Thr Leu His Ser Thr Asp Trp Arg Gly Arg Gly Val Ser Val Ser
705                 710             715                 720

Tyr Ser Gly Ala Ala Val Ala Gly Ser Gly Glu Gly Ala Ala Leu Thr
                725             730             735

Val Pro Ala Ser Gly Arg Ala Ser Val Thr Val Ser Val Ala Pro Gly
            740             745             750

Ala Ala Phe Ala Ser Tyr Ala Asn Ala Asn Ala Pro Lys Gly Thr Phe
        755             760             765

Ile Asp Gly Phe Val Arg Leu Ala Ala Gln Asn Gly Ser Gly Pro Asp
    770             775             780

Leu Ser Val Pro Tyr Leu Gly Phe Tyr Gly Ser Trp Gly Ala Ala Asp
785             790             795             800

Val Phe Asp Ala Lys Ala Ser Asp Ala Ala Val Ser Pro Ala His Ile
                805             810             815

Tyr Pro Ser Ala Phe Val Asp Ser Arg Thr Gly Arg Pro Leu Gly Ala
            820             825             830

Asn Pro Leu Ala Pro Arg Asn Thr Glu Thr Val Pro Asp Pro Gly Arg
        835             840             845

Tyr Val Val Ser Arg Ala Ala Ser Ser Leu Ala Thr Arg Arg Ala Glu
    850             855             860

Pro Arg Thr Gly Leu Leu Arg Ser Val His Thr Leu Thr Ser Thr Tyr
865             870             875             880

Ala Asn Glu Ala Gly Ala Thr Val Arg Glu Tyr Thr Asn Tyr Gln Asn
                885             890             895

Tyr Lys Ser Val Arg Asn Ala Asn Gly Thr Val Ser Arg Ala Glu Ser
            900             905             910

Tyr His Leu Ala Pro Val Phe Asp Ser Glu Asp Gln Val Gly Ala Gly
        915             920             925

Leu Pro Asp Gly Lys Tyr Thr Leu Thr Ile Ala Ala Thr Thr Ser Gly
    930             935             940

Pro Ser Pro Thr Arg His Ala Ile Ser Tyr Asp Phe Ala Leu Asp Thr
945             950             955             960

Thr Ala Pro Arg Val Thr Val Arg Gly Val Ile Gly Glu Gly Ala Gly
                965             970             975

Ala Lys Val Ala Phe Asp Val Asp Ala Ser Pro Leu Ala Ala Phe
            980             985             990

Asp Phe His Asp Pro Ser Asn Gly Thr Trp Tyr Tyr Arg Glu Leu Val
        995             1000            1005

Asn Asp Asp Gly Thr Val Asn Pro Asp Gly Ser His Thr Tyr His
    1010            1015            1020

Phe Glu Val Ser Ala Ser Ala Leu Gln Ala Ala Trp Glu Ala Gln
    1025            1030            1035

Arg Gly Lys Gly Ala Ala Pro Ser Gln Pro Tyr Val Leu Ala Trp
    1040            1045            1050

Asp Trp Gly Val Asn Pro Ser Asp Lys Thr Val Arg Phe Pro
    1055            1060            1065

Gly Thr Thr Ser Gly Ala Trp Thr His Asp Ser His Gly Trp Trp
    1070            1075            1080

Tyr Arg Leu Pro Asp Gly Ser Trp Pro Ser Ser Thr Ser Met Val
    1085            1090            1095

Ile Asp Gly Glu Thr Tyr Arg Phe Asp Ala Ser Gly Tyr Met Arg
    1100            1105            1110
```

```
Thr Gly Trp Val Gly Glu Ala Gly Ser Trp Tyr Tyr His Leu Pro
    1115            1120                1125

Ser Gly Ala Met Ala Lys Gly Trp Ala His Asp Ser Gly Ser Trp
    1130            1135                1140

Tyr Tyr Leu Ser Pro Gly Thr Gly Ala Met Ala Thr Gly Trp Ile
    1145            1150                1155

Glu Gln Gly Gly Thr Trp Tyr Tyr Leu Ser Pro Gly Thr Gly Ala
    1160            1165                1170

Met Ala Thr Gly Trp Thr Asn Val Gly Gly Thr Trp Tyr Tyr Phe
    1175            1180                1185

Ser Ser Ser Gly Ala Met Ala Thr Gly Trp Leu Lys Val Gly Gly
    1190            1195                1200

Thr Trp Tyr Tyr Leu Ala Pro Ser Gly Ala Met Ala Thr Gly Trp
    1205            1210                1215

Thr Asn Ile Asp Gly Thr Trp Tyr Tyr Phe Ser Ser Ser Gly Ala
    1220            1225                1230

Trp Thr Gly
    1235

<210> SEQ ID NO 34
<211> LENGTH: 1204
<212> TYPE: PRT
<213> ORGANISM: Artificial Sequence
<220> FEATURE:
<223> OTHER INFORMATION: fragment of Actinomyces sp. oral taxon 877 str.
      F0543

<400> SEQUENCE: 34

Pro Pro Gly Gly Asp Asp Gln Gly Gln Gly Ser Pro Ala Thr Ser Gln
1               5                   10                  15

Ala Ala Ala Asp Thr Ala Leu Thr Ser Lys Ala Asp Tyr Glu Asn Gly
                20                  25                  30

Ala Gly Pro Gly Pro Ala Asp Glu Ala His Pro Tyr Gly Ala Gln Ser
            35                  40                  45

Asp Ala Ser Gln Pro Asp Ala Pro Gln Ser Asp Ala Ser Gln Pro Asp
    50                  55                  60

Gly Ala Glu Gly His Ala Pro Glu Gly Val Arg Ile Ile Val Gln
65                  70                  75                  80

Phe Ala Asp Glu Ala Ser Glu Ser Asp Cys Asp Glu Leu Val Asp Arg
                85                  90                  95

Ile Gly Glu Ala Val Ala Ser Val Pro Ala Ala Gly Gly Pro
            100                 105                 110

Ala Ile Thr Arg Ala Arg Asp Tyr Arg Asn Val Phe Thr Gly Val Ala
        115                 120                 125

Ile Asp Ala Pro Ala Ala Ser Leu Pro Val Val Gln Gly Val Asp Gly
    130                 135                 140

Val Lys Ser Ala Phe Ile Glu Arg Glu Gly His Ile Glu Gly Asp Glu
145                 150                 155                 160

Ser Glu Gln Pro Gly Gly Pro Ser Gly Asn Gly Gly Pro Ala His Glu
                165                 170                 175

Ala Gly Ala Asp Gly Ser Gly Ser Ala Ser Ala Ala His Ser Pro Ser
            180                 185                 190

Pro Ala His Ser Pro Ser Pro Ala Gly Ile Pro Pro Ser Gly Asp Ala
        195                 200                 205

Ala Ser Asn Gly Asp Gly Ala Pro Ser Gly Ala Pro Ala Ser Gly Ala
```

```
            210                 215                 220
Ser Pro Ser Pro Ala Ala Thr Pro Ser Gln Asp Ala Ala Gly Ser
225                 230                 235                 240

Gly Asn Val Glu Gly Gly Ala Asp Ser Leu Ala Ala Glu Gly Ile Asp
                245                 250                 255

Pro Ser Asn Arg Ser Ala His Leu Met Met Arg Met Asp His Val Ser
                260                 265                 270

His Lys Gly Glu Gly Arg Val Ile Ala Phe Leu Asp Thr Gly Leu Glu
                275                 280                 285

Val Ala His Pro Ala Phe Ser Gly Ala Val Asp Ala Ser Lys Thr Ala
            290                 295                 300

Leu Lys Arg Ala Asp Val Glu Gln Val Leu Pro Arg Leu Gly Glu Gly
305                 310                 315                 320

Lys Asp Gly His Tyr Val Asn Asp Lys Ile Pro Phe Val Tyr Asp Tyr
                325                 330                 335

Ala Asp Asp Ala Asp Val Ala Pro Ser Ser Gly Pro Gly Gly Phe
                340                 345                 350

His Gly Thr His Val Ala Gly Ile Ala Ala Ala Asn Ala Asp Arg Ile
                355                 360                 365

Arg Gly Thr Ala Pro Gly Ala Gln Ile Ile Val Ala Lys Val Ala Arg
            370                 375                 380

Ser Gly Asn Gly Ser Leu Pro Asp Ser Ala Val Leu Ala Ala Leu Asp
385                 390                 395                 400

Asp Met Ala Val Leu Arg Pro Asp Val Val Asn Leu Ser Ile Gly Trp
                405                 410                 415

Ser Ala Gly Met Asp Asn Ala Ala Asp Ser Leu Tyr Ser Thr Val Tyr
                420                 425                 430

Ala Ser Leu Gln Gly Ala Gly Val Thr Val Asn Ala Ala Gly Asn
            435                 440                 445

Ser Tyr Ser Ala Gly Arg Gly Asn Arg Ser Gly Lys Asn Leu Pro Tyr
            450                 455                 460

Ala Ser Asp Pro Asp Ser Ser Val Met Asp Glu Pro Ala Thr Tyr Ser
465                 470                 475                 480

Ser Ala Val Ala Val Ala Ser Val Asp Asn Ala Pro Ala Asn Gly Ala
                485                 490                 495

Tyr Arg Ala Ser Asp Phe Ser Ala Trp Gly Val Ser Pro Asp Leu Arg
            500                 505                 510

Leu Lys Pro Glu Ile Ala Ser Pro Gly Gly Val Val Ser Ala Val
            515                 520                 525

Pro Gly Gly Ala Tyr Asp Gln Ala Ser Gly Thr Ser Met Ala Thr Pro
            530                 535                 540

Gln Met Ala Gly Ile Ser Ala Ile Val Leu Glu Arg Val Ser Thr Asp
545                 550                 555                 560

Pro Leu Phe Ala Gly Met Ser Ala Ala Glu Arg Thr Gly Val Ala Gln
                565                 570                 575

Ser Leu Ile Met Gly Thr Ala His Pro Leu Val Asp Ala Asp Gln Gly
            580                 585                 590

Thr Gly Ala Phe Tyr Ser Pro Arg Lys Gln Gly Ala Gly Leu Val Asp
            595                 600                 605

Ala Leu Ala Ala Thr Thr Ser Pro Val Tyr Pro Thr Val Asp Gly Ala
            610                 615                 620

Ala Glu Pro Ser Arg Pro Lys Ala Asp Leu Gly Asp Gly Thr Ala Gly
625                 630                 635                 640
```

-continued

```
Trp Ser Phe Thr Ile Thr Val His Asn Leu Ser Asp Ser Ala Lys Ser
                645                 650                 655

Tyr Ala Leu Ser Ser Gln Ala Leu Ser Glu Ala Val Glu Gly Gly Phe
                660                 665                 670

Phe Thr Leu His Ser Thr Asp Trp Arg Gly Arg Gly Val Ser Val Ser
                675                 680                 685

Tyr Ser Gly Ala Ala Val Ala Gly Ser Gly Glu Gly Ala Ala Leu Thr
                690                 695                 700

Val Pro Ala Ser Gly Arg Ala Ser Val Thr Val Ser Val Ala Pro Gly
705                 710                 715                 720

Ala Ala Phe Ala Ser Tyr Ala Asn Ala Asn Ala Pro Lys Gly Thr Phe
                725                 730                 735

Ile Asp Gly Phe Val Arg Leu Ala Ala Gln Asn Gly Ser Gly Pro Asp
                740                 745                 750

Leu Ser Val Pro Tyr Leu Gly Phe Tyr Gly Ser Trp Gly Ala Ala Asp
                755                 760                 765

Val Phe Asp Ala Lys Ala Ser Asp Ala Ala Val Ser Pro Ala His Ile
                770                 775                 780

Tyr Pro Ser Ala Phe Val Asp Ser Arg Thr Gly Arg Pro Leu Gly Ala
785                 790                 795                 800

Asn Pro Leu Ala Pro Arg Asn Thr Glu Thr Val Pro Asp Pro Gly Arg
                805                 810                 815

Tyr Val Val Ser Arg Ala Ala Ser Ser Leu Ala Thr Arg Ala Glu
                820                 825                 830

Pro Arg Thr Gly Leu Leu Arg Ser Val His Thr Leu Thr Ser Thr Tyr
                835                 840                 845

Ala Asn Glu Ala Gly Ala Thr Val Arg Glu Tyr Thr Asn Tyr Gln Asn
                850                 855                 860

Tyr Lys Ser Val Arg Asn Ala Asn Gly Thr Val Ser Arg Ala Glu Ser
865                 870                 875                 880

Tyr His Leu Ala Pro Val Phe Asp Ser Glu Asp Gln Val Gly Ala Gly
                885                 890                 895

Leu Pro Asp Gly Lys Tyr Thr Leu Thr Ile Ala Ala Thr Thr Ser Gly
                900                 905                 910

Pro Ser Pro Thr Arg His Ala Ile Ser Tyr Asp Phe Ala Leu Asp Thr
                915                 920                 925

Thr Ala Pro Arg Val Thr Val Arg Gly Val Ile Gly Glu Gly Ala Gly
                930                 935                 940

Ala Lys Val Ala Phe Asp Val Thr Asp Ala Ser Pro Leu Ala Ala Phe
945                 950                 955                 960

Asp Phe His Asp Pro Ser Asn Gly Thr Trp Tyr Tyr Arg Glu Leu Val
                965                 970                 975

Asn Asp Asp Gly Thr Val Asn Pro Asp Gly Ser His Thr Tyr His Phe
                980                 985                 990

Glu Val Ser Ala Ser Ala Leu Gln Ala Ala Trp Glu Ala Gln Arg Gly
                995                 1000                1005

Lys Gly Ala Ala Pro Ser Gln Pro Tyr Val Leu Ala Trp Asp Trp
                1010                1015                1020

Gly Val Asn Pro Ser Asp Lys Thr Val Val Arg Phe Pro Gly Thr
                1025                1030                1035

Thr Ser Gly Ala Trp Thr His Asp Ser His Gly Trp Trp Tyr Arg
                1040                1045                1050
```

```
Leu Pro Asp Gly Ser Trp Pro Ser Ser Thr Ser Met Val Ile Asp
    1055                1060                1065

Gly Glu Thr Tyr Arg Phe Asp Ala Ser Gly Tyr Met Arg Thr Gly
    1070                1075                1080

Trp Val Gly Glu Ala Gly Ser Trp Tyr Tyr His Leu Pro Ser Gly
    1085                1090                1095

Ala Met Ala Lys Gly Trp Ala His Asp Ser Gly Ser Trp Tyr Tyr
    1100                1105                1110

Leu Ser Pro Gly Thr Gly Ala Met Ala Thr Gly Trp Ile Glu Gln
    1115                1120                1125

Gly Gly Thr Trp Tyr Tyr Leu Ser Pro Gly Thr Gly Ala Met Ala
    1130                1135                1140

Thr Gly Trp Thr Asn Val Gly Gly Thr Trp Tyr Tyr Phe Ser Ser
    1145                1150                1155

Ser Gly Ala Met Ala Thr Gly Trp Leu Lys Val Gly Gly Thr Trp
    1160                1165                1170

Tyr Tyr Leu Ala Pro Ser Gly Ala Met Ala Thr Gly Trp Thr Asn
    1175                1180                1185

Ile Asp Gly Thr Trp Tyr Tyr Phe Ser Ser Gly Ala Trp Thr
    1190                1195                1200

Gly

<210> SEQ ID NO 35
<211> LENGTH: 1157
<212> TYPE: PRT
<213> ORGANISM: Actinomyces sp. ICM47

<400> SEQUENCE: 35

Met Thr Leu Lys Lys Pro Ala Lys Leu Ile Ala Ile Ala Gly Ala Cys
1               5                   10                  15

Ala Val Ala Val Ala Leu Pro Thr Ser Leu Ala Leu Pro Gly Ser Phe
                20                  25                  30

Gly Pro Glu Ala Asp Ser Asp Pro Glu Ala Ala Gln Ser Ala Ala Gly
            35                  40                  45

Val Val Ala Gln Pro Glu Pro Glu Pro Glu Leu Pro Val Gly Asn Ala
        50                  55                  60

Glu Asn Ala Leu Thr Ser Glu Glu Gly Glu Gln Val Val Asp Gly Glu
65                  70                  75                  80

Thr Gln Ala Ser Thr Asp Asp Gly Ser Ser Arg Val Val Asp Met Ile
                85                  90                  95

Val Gln Leu Lys Asp Gly Thr Asp Thr Ala Ala Ala Leu Ala Ser Ile
            100                 105                 110

Asn Ser Ala Val Ala Ala Tyr Pro Asp Ala Ser Ala Glu Val Lys
        115                 120                 125

Arg Glu Tyr Ser Asn Thr Phe Thr Gly Phe Ala Leu Ser Ala Pro Ile
130                 135                 140

Gly Ser Met Asp Ala Ile Arg Gly Val Ser Gly Val Gln Ser Ala Phe
145                 150                 155                 160

Leu Asp Arg Glu Thr Gln Val Ser Asp Asp Ala Asn Gly Asp Ser Asp
                165                 170                 175

Asp Ala Gly Ser Gly Ser Ala Thr Thr Ala Ser Arg Ser Gln His Pro
            180                 185                 190

Asp Asn Leu Ser Ala Gln Ile Met Met His Ala Asp Lys Val Thr Gln
        195                 200                 205
```

-continued

| | | | | | | | | | | | | | | |
|---|---|---|---|---|---|---|---|---|---|---|---|---|---|---|
|Lys|Gly|Glu|Gly|Lys|Val|Val|Ala|Ile|Ile|Asp|Thr|Gly|Val|Glu|Met|
| |210| | | |215| | | |220| | | | | | |

Asn His Pro Ala Phe Ser Gly Ala Leu His Gly Thr Pro Ala Ile Asp
225                 230                 235                 240

Ser Ser Lys Gly Ala Ser Leu Ala Gln Gln Val Gly Lys Ser Gly Thr
            245                 250                 255

Tyr Val Ser Glu Lys Phe Pro Phe Ala Tyr Asp Tyr Ala Asp Gly Asp
                260                 265                 270

Asn Asp Ala Ser Pro Ala Gly His Gly Thr His Val Ala Gly Ile
                275                 280                 285

Thr Ala Ala Asn Gly Asp Gln Ile Met Gly Ile Ala Pro Asp Ala Gln
    290                 295                 300

Ile Ile Val Ala Lys Val Ala Arg Ser Arg Gly Gly Ile Pro Asp
305                 310                 315                 320

Ser Ala Leu Leu Ala Ala Leu Asp Asp Met Ala Thr Leu His Pro Asp
                325                 330                 335

Ala Val Asn Met Ser Leu Gly Arg Thr Ala Gly Met Asp Ser Asp Ala
            340                 345                 350

Asp Thr Leu Phe Ala Gly Val Tyr Glu Lys Leu Gln Glu Lys Gly Ile
        355                 360                 365

Thr Leu Asp Val Ala Gly Gly Asn Glu Phe Gln Ala Gly Tyr Gly Asn
    370                 375                 380

Lys Ser Gly Lys Asn Leu Pro Tyr Ala Ser Asp Pro Asp Ser Ser Thr
385                 390                 395                 400

Leu Gly Glu Pro Gly Ser Phe Ala Pro Val Val Thr Val Ala Ser Ile
                405                 410                 415

Glu Asn Ala Arg Asn Gly Ala Asn Gly Asn Tyr Lys Met Ser Asp Phe
                420                 425                 430

Ser Ser Trp Gly Val Ser Pro Asp Met Arg Leu Lys Pro Glu Val Thr
            435                 440                 445

Ala Pro Gly Gly Asn Ile Tyr Ser Ser Val Pro Gly Gly Gly Tyr Gln
    450                 455                 460

Met Met Ser Gly Thr Ser Met Ala Thr Pro Gln Met Thr Gly Ala Ser
465                 470                 475                 480

Ala Val Val Leu Glu Arg Val Gln Asn Asp Pro Leu Phe Ser Ser Leu
                485                 490                 495

Asn Asp Arg Gln Lys Val Asp Val Val Gln Asn Leu Ile Met Gly Thr
                500                 505                 510

Ala Val Pro Val Val Asp Pro Gly Gln Gly Gly Gly Ala Tyr Tyr Ser
            515                 520                 525

Pro Arg Lys Gln Gly Ala Gly Leu Ala Asn Leu Glu Gly Ala Thr Thr
    530                 535                 540

Ser Ser Val Tyr Pro Thr Val Asn Gly Ala Ala Asp Ser Ser Arg Pro
545                 550                 555                 560

Lys Ala Glu Leu Gly Asp Gly Thr Asn Gly Trp His Phe Asp Val Thr
                565                 570                 575

Leu His Asn Val Ser Asp Thr Pro Ala Thr Tyr Glu Leu Ser Ser Gln
                580                 585                 590

Ala Leu Ser Glu Asn Ile Glu Gly Gly Phe Phe Thr Gly His Ser Thr
            595                 600                 605

Asp Trp Asn Gly Lys Gly Val Ser Val Ser Phe Ser Gly Ser Ser Val
    610                 615                 620

Thr Val Pro Ala Lys Gly Glu Thr Val Gly Ile Asp Ile Lys Pro

```
              625                 630                 635                 640
Gly Asn Glu Phe Ala Gln Tyr Val Ser Ala Asn Ala Pro Ala Gly Thr
                    645                 650                 655
Phe Leu Asp Gly Phe Val Arg Phe Thr Ser Arg Thr Asn Gly Gln Pro
                    660                 665                 670
Asp Leu Gly Val Pro Phe Leu Gly Phe Tyr Gly Ser Trp Ala Lys Pro
                    675                 680                 685
Ala Ile Phe Asp Ala Leu Val Ser Glu Gly Asp Ala His Ala Ala Ser
                    690                 695                 700
Ser Gly Ile Tyr Asn Gly Asp Arg Gly Gly Leu Leu Gly Tyr Asn Pro
705                 710                 715                 720
Leu Leu Lys Gly Arg Glu Arg Gln Gly Arg Pro Asn Ala Glu Arg Tyr
                    725                 730                 735
Val Val Ser Arg Ser Thr Val Ser Gly Ala Pro Thr Ala Ile Ser Pro
                    740                 745                 750
Arg Thr Gly Thr Leu Arg Ser Val His Lys Met Thr Thr Thr Tyr Thr
                    755                 760                 765
Asn Glu Ala Gly Lys Ser Val Ala Ser Phe Thr Ser Phe Gln Asn Phe
770                 775                 780
Lys Ser Thr Ile Asp Pro Glu Glu Glu Arg Met Ser Trp Val Glu Glu
785                 790                 795                 800
Gly Gln Glu Pro Arg Ser Ile Asp Leu Lys Glu Gly Lys Tyr Ala Ser
                    805                 810                 815
Leu Pro Asp Gly Asn Tyr Lys Leu Thr Ile Ala Ala Asn Asn Asp Gly
                    820                 825                 830
Pro Ser Ser Thr Glu Gln Ser Ile Thr Tyr Asn Phe Arg Ile Asp Thr
                    835                 840                 845
Lys Ala Pro Val Val Asp Ser Ala Lys Val Asn Gly Ser Thr Leu Ser
                    850                 855                 860
Val Glu Leu Ser Asp Glu Ser Pro Leu Ala Gly Phe Thr Leu Asn Asp
865                 870                 875                 880
Pro Asn Ser Gly Arg Tyr Ile His Leu Glu Val Ala Arg Asp Glu Asn
                    885                 890                 895
Ser Gln Thr Tyr Glu Asn Gly Arg Tyr His Tyr Lys Thr Ser Ile Asp
                    900                 905                 910
Leu Asn Gln Val Gln Gly Gly Ala Ser Asn Pro Tyr Val Val Ala
                    915                 920                 925
Trp Asp Tyr Gly Leu Asn His Ser Glu Pro Val Thr Met Asn Gly Gly
930                 935                 940
Lys Pro Gly Asn Gly Gly Gln Pro Gly Val Gly Asp Asp Gln Pro
945                 950                 955                 960
Gly Asn Gly Gly Gly Gln Pro Gly Val Gly Asp Asp Gln Pro Gly Asn
                    965                 970                 975
Gly Gly Gly Gln Pro Gly Asn Gly Gly Gln Pro Gly Asp Asp Trp
                    980                 985                 990
Gly Asp Asp Gln Pro Gly Asn Gly Gly Gln Pro Gly Asp Asp Trp
                    995                 1000                1005
Gly Asn Gly Gly Gly Gln Pro Gly Asp Asp Trp Gly Asn Gly Gly
                    1010                1015                1020
Gly Gln Pro Gly Asn Gly Gly Gln Pro Gly Asp Gly Trp Asp
                    1025                1030                1035
Asn Gly Gly Gly Gln Pro Gly Gly Gly Trp Asp Asn Gly Gly Gly
                    1040                1045                1050
```

```
Gln Pro Gly Gly Asn Pro Gly Asn Gly Gly Asn Ser Gly Tyr Cys
    1055                1060                1065

Asp Phe Leu Asn Gly Tyr Trp Leu Ser Asp Pro Val Gly Trp Trp
    1070                1075                1080

Gln Lys Cys Val Ser Gly Lys Ser Leu Pro Arg Asn Gln Trp Ser
    1085                1090                1095

Asn Ile Gly Gly Lys Asp Tyr Phe Val Gly Pro Asp Gly Asn Ala
    1100                1105                1110

Gln Thr Gly Trp Leu Asn Gln Gly Asp Thr Trp Tyr Tyr Leu Asp
    1115                1120                1125

Pro Ser Asn Gly Gly Ser Met Cys Thr Gly Thr Arg Asn Ile Asp
    1130                1135                1140

Gly Lys Thr Tyr Thr Phe Asp Asn Ser Gly Ala Leu Val Lys
    1145                1150                1155

<210> SEQ ID NO 36
<211> LENGTH: 1129
<212> TYPE: PRT
<213> ORGANISM: Artificial Sequence
<220> FEATURE:
<223> OTHER INFORMATION: fragment of Actinomyces sp. ICM47 protease

<400> SEQUENCE: 36

Pro Gly Ser Phe Gly Pro Glu Ala Asp Ser Asp Pro Glu Ala Gln
1               5                   10                  15

Ser Ala Ala Gly Val Val Ala Gln Pro Glu Pro Glu Pro Leu Pro
                20                  25                  30

Val Gly Asn Ala Glu Asn Ala Leu Thr Ser Glu Glu Gly Glu Gln Val
                35                  40                  45

Val Asp Gly Glu Thr Gln Ala Ser Thr Asp Asp Gly Ser Ser Arg Val
    50                  55                  60

Val Asp Met Ile Val Gln Leu Lys Asp Gly Thr Asp Thr Ala Ala Ala
65                  70                  75                  80

Leu Ala Ser Ile Asn Ser Ala Val Ala Ala Tyr Pro Asp Ala Ser
                85                  90                  95

Ala Glu Val Lys Arg Glu Tyr Ser Asn Thr Phe Thr Gly Phe Ala Leu
                100                 105                 110

Ser Ala Pro Ile Gly Ser Met Asp Ala Ile Arg Gly Val Ser Gly Val
                115                 120                 125

Gln Ser Ala Phe Leu Asp Arg Glu Thr Gln Val Ser Asp Asp Ala Asn
    130                 135                 140

Gly Asp Ser Asp Ala Gly Ser Gly Ser Ala Thr Thr Ala Ser Arg
145                 150                 155                 160

Ser Gln His Pro Asp Asn Leu Ser Ala Gln Ile Met Met His Ala Asp
                165                 170                 175

Lys Val Thr Gln Lys Gly Glu Gly Lys Val Val Ala Ile Ile Asp Thr
                180                 185                 190

Gly Val Glu Met Asn His Pro Ala Phe Ser Gly Ala Leu His Gly Thr
                195                 200                 205

Pro Ala Ile Asp Ser Ser Lys Gly Ala Ser Leu Ala Gln Gln Val Gly
    210                 215                 220

Lys Ser Gly Thr Tyr Val Ser Glu Lys Phe Pro Phe Ala Tyr Asp Tyr
225                 230                 235                 240

Ala Asp Gly Asp Asn Asp Ala Ser Pro Ala Gly Ala His Gly Thr His
                245                 250                 255
```

```
Val Ala Gly Ile Thr Ala Ala Asn Gly Asp Gln Ile Met Gly Ile Ala
            260                 265                 270

Pro Asp Ala Gln Ile Ile Val Ala Lys Val Ala Arg Ser Arg Gly Gly
            275                 280                 285

Gly Ile Pro Asp Ser Ala Leu Leu Ala Ala Leu Asp Asp Met Ala Thr
290                 295                 300

Leu His Pro Asp Ala Val Asn Met Ser Leu Gly Arg Thr Ala Gly Met
305                 310                 315                 320

Asp Ser Asp Ala Asp Thr Leu Phe Ala Gly Val Tyr Glu Lys Leu Gln
                325                 330                 335

Glu Lys Gly Ile Thr Leu Asp Val Ala Gly Asn Glu Phe Gln Ala
            340                 345                 350

Gly Tyr Gly Asn Lys Ser Gly Lys Asn Leu Pro Tyr Ala Ser Asp Pro
            355                 360                 365

Asp Ser Ser Thr Leu Gly Glu Pro Gly Ser Phe Ala Pro Val Val Thr
370                 375                 380

Val Ala Ser Ile Glu Asn Ala Arg Asn Gly Ala Asn Gly Asn Tyr Lys
385                 390                 395                 400

Met Ser Asp Phe Ser Ser Trp Gly Val Ser Pro Asp Met Arg Leu Lys
                405                 410                 415

Pro Glu Val Thr Ala Pro Gly Gly Asn Ile Tyr Ser Val Pro Gly
            420                 425                 430

Gly Gly Tyr Gln Met Met Ser Gly Thr Ser Met Ala Thr Pro Gln Met
            435                 440                 445

Thr Gly Ala Ser Ala Val Val Leu Glu Arg Val Gln Asn Asp Pro Leu
450                 455                 460

Phe Ser Ser Leu Asn Asp Arg Gln Lys Val Asp Val Val Gln Asn Leu
465                 470                 475                 480

Ile Met Gly Thr Ala Val Pro Val Val Asp Pro Gly Gln Gly Gly Gly
                485                 490                 495

Ala Tyr Tyr Ser Pro Arg Lys Gln Gly Ala Gly Leu Ala Asn Leu Glu
            500                 505                 510

Gly Ala Thr Thr Ser Ser Val Tyr Pro Thr Val Asn Gly Ala Ala Asp
            515                 520                 525

Ser Ser Arg Pro Lys Ala Glu Leu Gly Asp Gly Thr Asn Gly Trp His
530                 535                 540

Phe Asp Val Thr Leu His Asn Val Ser Asp Thr Pro Ala Thr Tyr Glu
545                 550                 555                 560

Leu Ser Ser Gln Ala Leu Ser Glu Asn Ile Glu Gly Gly Phe Phe Thr
                565                 570                 575

Gly His Ser Thr Asp Trp Asn Gly Lys Gly Val Ser Val Ser Phe Ser
            580                 585                 590

Gly Ser Ser Val Thr Val Pro Ala Lys Gly Glu Thr Thr Val Gly Ile
            595                 600                 605

Asp Ile Lys Pro Gly Asn Glu Phe Ala Gln Tyr Val Ser Ala Asn Ala
            610                 615                 620

Pro Ala Gly Thr Phe Leu Asp Gly Phe Val Arg Phe Thr Ser Arg Thr
625                 630                 635                 640

Asn Gly Gln Pro Asp Leu Gly Val Pro Phe Leu Gly Phe Tyr Gly Ser
                645                 650                 655

Trp Ala Lys Pro Ala Ile Phe Asp Ala Leu Val Ser Glu Gly Asp Ala
            660                 665                 670
```

-continued

His Ala Ala Ser Ser Gly Ile Tyr Asn Gly Asp Arg Gly Leu Leu
            675                 680                 685

Gly Tyr Asn Pro Leu Leu Lys Gly Arg Glu Arg Gln Gly Arg Pro Asn
690                 695                 700

Ala Glu Arg Tyr Val Val Ser Arg Ser Thr Val Ser Gly Ala Pro Thr
705                 710                 715                 720

Ala Ile Ser Pro Arg Thr Gly Thr Leu Arg Ser Val His Lys Met Thr
                725                 730                 735

Thr Thr Tyr Thr Asn Glu Ala Gly Lys Ser Val Ala Ser Phe Thr Ser
            740                 745                 750

Phe Gln Asn Phe Lys Ser Thr Ile Asp Pro Glu Glu Arg Met Ser
    755                 760                 765

Trp Val Glu Glu Gly Gln Glu Pro Arg Ser Ile Asp Leu Lys Glu Gly
    770                 775                 780

Lys Tyr Ala Ser Leu Pro Asp Gly Asn Tyr Lys Leu Thr Ile Ala Ala
785                 790                 795                 800

Asn Asn Asp Gly Pro Ser Ser Thr Glu Gln Ser Ile Thr Tyr Asn Phe
                805                 810                 815

Arg Ile Asp Thr Lys Ala Pro Val Val Asp Ser Ala Lys Val Asn Gly
            820                 825                 830

Ser Thr Leu Ser Val Glu Leu Ser Asp Glu Ser Pro Leu Ala Gly Phe
            835                 840                 845

Thr Leu Asn Asp Pro Asn Ser Gly Arg Tyr Ile His Leu Glu Val Ala
            850                 855                 860

Arg Asp Glu Asn Ser Gln Thr Tyr Glu Asn Gly Arg Tyr His Tyr Lys
865                 870                 875                 880

Thr Ser Ile Asp Leu Asn Gln Val Gln Gly Gly Ala Ser Asn Asn Pro
                885                 890                 895

Tyr Val Val Ala Trp Asp Tyr Gly Leu Asn His Ser Glu Pro Val Thr
            900                 905                 910

Met Asn Gly Gly Lys Pro Gly Asn Gly Gly Gln Pro Gly Val Gly
            915                 920                 925

Asp Asp Gln Pro Gly Asn Gly Gly Gln Pro Gly Val Gly Asp Asp
930                 935                 940

Gln Pro Gly Asn Gly Gly Gln Pro Gly Asn Gly Gly Gln Pro
945                 950                 955                 960

Gly Asp Asp Trp Gly Asp Gln Pro Gly Asn Gly Gly Gln Pro
                965                 970                 975

Gly Asp Asp Trp Gly Asn Gly Gly Gln Pro Gly Asp Asp Trp Gly
            980                 985                 990

Asn Gly Gly Gln Pro Gly Asn Gly Gly Gln Pro Gly Asp Gly
            995                 1000                1005

Trp Asp Asn Gly Gly Gly Gln Pro Gly Gly Gly Trp Asp Asn Gly
    1010                1015                1020

Gly Gly Gln Pro Gly Gly Asn Pro Gly Asn Gly Asn Ser Gly
    1025                1030                1035

Tyr Cys Asp Phe Leu Asn Gly Tyr Trp Leu Ser Asp Pro Val Gly
    1040                1045                1050

Trp Trp Gln Lys Cys Val Ser Gly Lys Ser Leu Pro Arg Asn Gln
    1055                1060                1065

Trp Ser Asn Ile Gly Gly Lys Asp Tyr Phe Val Gly Pro Asp Gly
    1070                1075                1080

Asn Ala Gln Thr Gly Trp Leu Asn Gln Gly Asp Thr Trp Tyr Tyr

```
                        1085                1090                1095
Leu Asp Pro Ser Asn Gly Gly Ser Met Cys Thr Gly Thr Arg Asn
        1100                1105                1110

Ile Asp Gly Lys Thr Tyr Thr Phe Asp Asn Ser Gly Ala Leu Val
    1115                1120                1125

Lys

<210> SEQ ID NO 37
<211> LENGTH: 1627
<212> TYPE: PRT
<213> ORGANISM: Lactobacillus acidophilus

<400> SEQUENCE: 37

Met Arg Asn Lys Lys Val Gly Ser Val Thr Thr Asp Tyr Ser Tyr Leu
1               5                   10                  15

Asn Gln Ser Arg Asn His Leu Asn Leu Val Thr Gly Lys Glu Asn Asp
            20                  25                  30

Ser Lys Leu Lys Ile Trp Arg Lys Asn Phe Ala Thr Ala Ala Ile Ile
        35                  40                  45

Ala Leu Ala Ser Gly Thr Thr Met Leu Phe Ser Ala His Ser Val Lys
50                  55                  60

Ala Asp Glu Val Asp Asp Ile Thr Val Gln Asn Asp Lys Gln Val Asn
65                  70                  75                  80

Thr Thr Ile Val Gln Asn Asn Lys Asp Gln Gln Ser Ser Asp Thr Gln
                85                  90                  95

Gln Asn Val Asn Glu Asn Arg Ala Ser Ser Gln Ala Ile Arg Arg
            100                 105                 110

Pro Gly Thr Gly Asn Lys Leu Thr Asp Gln Trp Pro Asp Asn Tyr Gln
        115                 120                 125

Ser Asp Gln Gln Asn Asn Ser Ser Gln Ala Glu Thr Thr Lys Ile Ser
    130                 135                 140

Thr Thr Gly Tyr Ser Asn Gln Thr Glu Gln Gln Ser Asn Asn Thr Val
145                 150                 155                 160

Pro Ser Thr Val Ala Ser Ser Thr Val Tyr Lys Glu Ser Ser Asp Asp
                165                 170                 175

Gln Ala Gly Gln Lys Asp Thr Asn Gly Val Glu Leu Pro Ala Asn Asn
            180                 185                 190

Gln Asp His Ile Lys Gly Asn Val Gln Asp Ala Trp Asp Gln Gly Tyr
        195                 200                 205

Lys Gly Gln His Thr Val Val Ala Val Ile Asp Ser Gly Val Asp Thr
    210                 215                 220

Ser His Lys Asp Phe Gln Thr Met Pro Glu Asn Pro Lys Leu Ser Gln
225                 230                 235                 240

Ala Glu Ile Glu Ala Leu Ile Ala Lys Leu Gly Tyr Gly Thr Tyr Ile
                245                 250                 255

Asn Ser Lys Phe Pro Phe Val Tyr Asn Ala Val Asp His Glu Asn Gln
            260                 265                 270

Ser Met Lys Gly Pro Asp Gly Glu Pro His Gly Gln His Val Ser Gly
        275                 280                 285

Ile Ile Ala Ala Asp Gly Gln Pro Asn Gly Gln Glu Tyr Val Val
    290                 295                 300

Gly Val Ala Pro Glu Ala Gln Leu Met His Phe Lys Val Phe Gly Asp
305                 310                 315                 320

Asn Ala Thr Ser Leu Asp Leu Ala Gln Glu Ile Tyr Asp Ala Thr Asn
```

```
                325                 330                 335
Leu Gly Ala Asp Val Ile Gln Met Ser Leu Gly Gly Val Ala Ala
                340                 345                 350
Ala Asp Leu Asn Val Ala Asp Gln Arg Ala Val Gln Tyr Ala Ile Asp
                355                 360                 365
His Gly Val Ile Val Ser Ile Ser Ala Ser Asn Asn Gly Asn Ala Ala
                370                 375                 380
Ser Ile Gln Asn Pro Ser Asn Val Thr Asp Leu Asp Asn Tyr Glu Ala
385                 390                 395                 400
Gly Thr His Val Gly Asn Tyr Glu Pro Phe Ser Ser Thr Val Ala
                405                 410                 415
Asp Pro Gly Ala Ala Arg Gly Ala Ile Thr Gly Ala Ala Glu Thr Ser
                420                 425                 430
Gly Leu Gly Asp Lys Ser Asp Met Ala Thr Phe Thr Ser Trp Gly Pro
                435                 440                 445
Leu Pro Asp Phe Thr Leu Lys Pro Asp Val Ser Ala Pro Gly Ser Asn
                450                 455                 460
Val Ile Ser Leu Ala Asn Asp Asn Gly Tyr Thr Thr Met Ser Gly Thr
465                 470                 475                 480
Ser Met Ala Gly Pro Phe Ile Ala Gly Ala Ala Leu Val Arg Gln
                485                 490                 495
Arg Leu Gln Gln Thr Asn Pro Glu Leu Lys Gly Ala Asp Leu Val Ala
                500                 505                 510
Ala Val Lys Ala Leu Leu Met Asn Thr Ala Asp Pro Gln Ile Gln Gln
                515                 520                 525
Gly Phe Thr Thr Ile Val Ser Pro Arg Arg Gln Gly Ala Gly Gln Ile
                530                 535                 540
Asn Val Gly Ala Ala Thr Lys Ala Pro Val Tyr Ile Leu Ala Asn Asp
545                 550                 555                 560
Gly Thr Gly Ser Val Ser Leu Arg Asn Ile Lys Glu Thr Thr Asn Phe
                565                 570                 575
Glu Leu Thr Phe His Asn Leu Thr Asp Asn Thr Glu Thr Tyr Thr Phe
                580                 585                 590
Asp Asp Leu Gly Gly Phe Thr Glu Val Arg Asp Thr Asp Thr Gly
                595                 600                 605
Leu Phe His Asp Val Gln Leu Ala Gly Ala Arg Val Thr Gly Pro Asn
                610                 615                 620
Thr Ile Thr Val Asn Pro Lys Glu Thr Lys Ile Val Phe Thr Leu
625                 630                 635                 640
Asn Leu Thr Gly Leu Lys Gln Asn Gln Leu Val Glu Gly Tyr Leu Asn
                645                 650                 655
Phe Thr Asn Ser Lys Asp Lys Leu Ser Leu Ser Val Pro Tyr Leu Gly
                660                 665                 670
Tyr Tyr Gly Asp Met Thr Ser Glu Asp Val Phe Asp Lys Lys Ala Asn
                675                 680                 685
Glu Asp Lys Pro Asp Ile Lys Gly Asn Arg Leu Thr Asn Glu Asp Asn
                690                 695                 700
Tyr Pro Arg Gly Ile Ala Asp Glu Glu Ser Leu Lys Glu Leu Val Asn
705                 710                 715                 720
Ile Glu Gly Asn Tyr Asn Trp Gln Glu Val Ala Lys Leu Tyr Glu Ser
                725                 730                 735
Gly Lys Val Ala Phe Ser Pro Asn Gly Asp Asn Lys Ser Asp Leu Ile
                740                 745                 750
```

```
Met Pro Tyr Val Tyr Leu Lys Gln Asn Leu Gln Asp Leu Lys Val Glu
        755                 760                 765

Ile Leu Asp Ala Lys Gly Asn Val Val Arg Val Leu Ala Asp Ala His
        770                 775                 780

Gly Val Gln Lys Ser Tyr Asn Glu Asp Gly Thr Gly Thr Val Asp Ala
785                 790                 795                 800

Leu Ile Ser Val Asp Ser Gly Lys Phe Asn Trp Asp Gly Lys Val Tyr
            805                 810                 815

Asn Tyr Lys Thr Gly Lys Met Glu Val Ala Pro Asp Gly Gln Tyr Thr
                820                 825                 830

Tyr Arg Phe Val Ala Thr Leu Tyr Asn Asp Gly Pro His Lys Val Gln
            835                 840                 845

Thr Asn Asp Thr Ser Val Ile Ile Asp Thr Thr Ala Pro Ile Leu Lys
        850                 855                 860

Asp Val Glu Tyr Asp Val Thr Thr Lys Thr Ile Thr Gly Thr Tyr Ser
865                 870                 875                 880

Asp Ala Gly Ala Gly Phe Thr Asp Tyr Ser Tyr Ala Thr Val Thr Ile
            885                 890                 895

Asn Asp Arg Val Phe Gly Phe Lys Leu Asn Asp Asn Asp Asn Ser Thr
        900                 905                 910

Phe Asp Asn Thr Asp Lys Thr Ile Gly His Phe Ser Phe Ala Leu Thr
        915                 920                 925

Pro Leu Glu Gln Gln Ala Leu Thr Ala Ala His Asn Lys Val Ser Val
        930                 935                 940

Cys Leu Ser Asp Val Ala Asp Asn Thr Ala Val Lys Thr Leu Asp Val
945                 950                 955                 960

Ala Ser Val Gly Asp Gly Asn Lys Ile Ala Ile Trp Asn Ala Val Asn
            965                 970                 975

Gly Val Pro Phe Asn Ser Asn Ser Gln Asp Tyr Ser Asp Lys Asn Asn
                980                 985                 990

Ser Tyr Leu Leu Arg Gly Ser Ala Thr Glu Asn Phe Tyr Val Asn Gly
        995                 1000                1005

Lys Leu Val Gln Val Ala Pro Asn Gly Glu Phe Val Leu Pro Val
    1010                1015                1020

Ser Leu Asp Glu Gln Asn Leu Val Phe Thr Ser Asp Glu Asn Gly
    1025                1030                1035

Gln Asn Val Leu Arg Gln Phe Thr Thr Tyr Thr Pro Lys Ala Asp
    1040                1045                1050

Phe Ala Trp Gln His Ile Asp Gly Ser Glu Arg Ser Phe Gly Val
    1055                1060                1065

Ser Val Tyr Ser Ile Asp Ala Ala Asp Pro Asn Asp Ala Ile Val
    1070                1075                1080

Gln Ala Ala Val Pro Lys Gly Asn Asn Val Lys Ala Phe Ala Lys
    1085                1090                1095

Asp Tyr Phe Thr Gly Glu Thr Tyr Val Gly Glu Val Lys Asp Gly
    1100                1105                1110

Val Ala Thr Phe His Ile His Thr Ser Ile Asn Pro Asp Pro Gln
    1115                1120                1125

Thr Gly Ile Asn Arg Arg Ala Leu Leu Gln Gly Trp Val Glu Ile
    1130                1135                1140

Asp Gly Pro Thr Tyr Asn Ala Lys Gln Val Thr Asp Pro Thr Ala
    1145                1150                1155
```

```
Ile Ser Asp Arg Asn Tyr Ile Gly Val Tyr Tyr Lys Pro Asp Ala
1160                1165                1170

Ser Ser His Val Tyr Ser Asn Arg Asp Glu Leu Gly Val Asp Asp
1175                1180                1185

Phe Thr Asp Glu Gln Ala Asp Val Ser Asp Phe Gly Pro Ser Lys
1190                1195                1200

Phe Leu Tyr Pro Gly His Asn Ala Pro Ser Asp Gly Asn Ala Asn
1205                1210                1215

Ile Ser Phe Asp Tyr Val Asn Asp Asn Asn Ile Ser Thr Phe Gly
1220                1225                1230

Gln Glu Ala Val Lys Ala Gly Tyr Tyr Asp Pro Ile Ala Lys Val
1235                1240                1245

Phe Thr Ile Thr Gly His Val Asp Lys Asp Val Val Ser Leu Val
1250                1255                1260

Ala Leu Gln Asp Asn Pro Asn Glu Asp Ala Pro Glu Asn Arg Val
1265                1270                1275

Ala Ile Asp Lys Asp Gly Asn Phe Ile Ile Lys Phe His Met Asp
1280                1285                1290

Asp Pro Ser Thr Arg Gln Leu Thr Tyr Ile Tyr Lys Val Lys Asp
1295                1300                1305

Ser Ser Thr Asp Lys Ile Asp Thr Val Lys Gly Ser Ile Thr Leu
1310                1315                1320

Ile Leu Asp Thr Val Leu Pro Thr Leu His Val Asp Gln Leu Asn
1325                1330                1335

Gly Ala Asp Asn Leu Thr Ile Thr Thr Asn Asn Pro Thr Phe Lys
1340                1345                1350

Ile Ser Gly Asn Ala Asn Asp Asp Leu Asp Asp Tyr Ser Val Tyr
1355                1360                1365

Ile Asn Gly Asp Asn Val Phe Thr Gln Phe Asn Gly Ser Ser Phe
1370                1375                1380

Asn Tyr Ile Pro Gly Met Tyr Gly Asp Pro Asn Gln Lys Thr Pro
1385                1390                1395

Asn Leu Tyr Gly Gly Tyr Asp Phe Glu Gln Glu Val Asn Leu Asp
1400                1405                1410

Asp Glu Asn Gly Lys Pro Thr Thr His Ile Phe Asn Ile Glu Leu
1415                1420                1425

Ile Asp Gln Val Gly Asn Lys Val Phe Lys Thr Leu Thr Val Asn
1430                1435                1440

Tyr Asp Pro Asn Ala Thr Asn Ser Glu Asp Pro Ser Asn Gly Thr
1445                1450                1455

Gly Asp Ser Gly Ile Glu Val Val Pro Thr Val Pro Arg Lys Val
1460                1465                1470

Gln Pro Leu Ser Asp Asp Asn Ser Thr Asn Ile Asn Asp Lys Gln
1475                1480                1485

Thr Leu Ser Thr Glu Leu Thr Ile Thr Leu Pro Arg Asn Ile Phe
1490                1495                1500

Ala Phe Asp Tyr Gln Gly Lys Val Ala Arg Lys His Gly Lys Asp
1505                1510                1515

Ile Ile Leu Lys Lys Gly Val Val Leu Tyr Asn Pro Lys Glu Val
1520                1525                1530

Asn Ile Arg Lys His Lys Tyr Tyr Lys Val Ser Lys Asn Val Tyr
1535                1540                1545

Ile Lys Val Thr Ser Thr Arg Val Asn Lys Lys Leu Lys Arg Leu
```

```
                   1550                1555                1560

Ile Leu Ile Lys Asn Ser Tyr Val Tyr Asn Leu Asn Gly Lys Ala
        1565                1570                1575

Asn Lys Val His Asn Lys Arg Val Leu Leu Lys Arg Gly Leu Ala
    1580                1585                1590

Val Asp Val Leu His Gly Gly Lys Ile Thr Lys Val Gly Lys Tyr
    1595                1600                1605

Asp Cys Tyr Gln Ile Gly Ile Asn Gln Tyr Ile Lys Val Ala Asn
    1610                1615                1620

Thr Ala Leu Lys
    1625

<210> SEQ ID NO 38
<211> LENGTH: 1057
<212> TYPE: PRT
<213> ORGANISM: Artificial Sequence
<220> FEATURE:
<223> OTHER INFORMATION: fragment of Lactobacillus acidophilus ATCC
      4796protease

<400> SEQUENCE: 38

Asp Gly Thr Asp Thr Ala Ala Ala Leu Ala Ser Ile Asn Ser Ala Val
1               5                   10                  15

Ala Ala Ala Tyr Pro Asp Ala Ser Ala Glu Val Lys Arg Glu Tyr Ser
            20                  25                  30

Asn Thr Phe Thr Gly Phe Ala Leu Ser Ala Pro Ile Gly Ser Met Asp
        35                  40                  45

Ala Ile Arg Gly Val Ser Gly Val Gln Ser Ala Phe Leu Asp Arg Glu
    50                  55                  60

Thr Gln Val Ser Asp Asp Ala Asn Gly Asp Ser Asp Ala Gly Ser
65                  70                  75                  80

Gly Ser Ala Thr Thr Ala Ser Arg Ser Gln His Pro Asp Asn Leu Ser
                85                  90                  95

Ala Gln Ile Met Met His Ala Asp Lys Val Thr Gln Lys Gly Glu Gly
            100                 105                 110

Lys Val Val Ala Ile Ile Asp Thr Gly Val Glu Met Asn His Pro Ala
        115                 120                 125

Phe Ser Gly Ala Leu His Gly Thr Pro Ala Ile Asp Ser Ser Lys Gly
    130                 135                 140

Ala Ser Leu Ala Gln Gln Val Gly Lys Ser Gly Thr Tyr Val Ser Glu
145                 150                 155                 160

Lys Phe Pro Phe Ala Tyr Asp Tyr Ala Asp Gly Asp Asn Asp Ala Ser
                165                 170                 175

Pro Ala Gly Ala His Gly Thr His Val Ala Gly Ile Thr Ala Ala Asn
            180                 185                 190

Gly Asp Gln Ile Met Gly Ile Ala Pro Asp Ala Gln Ile Ile Val Ala
        195                 200                 205

Lys Val Ala Arg Ser Arg Gly Gly Gly Ile Pro Asp Ser Ala Leu Leu
    210                 215                 220

Ala Ala Leu Asp Asp Met Ala Thr Leu His Pro Asp Ala Val Asn Met
225                 230                 235                 240

Ser Leu Gly Arg Thr Ala Gly Met Asp Ser Asp Ala Asp Thr Leu Phe
                245                 250                 255

Ala Gly Val Tyr Glu Lys Leu Gln Glu Lys Gly Ile Thr Leu Asp Val
            260                 265                 270
```

-continued

```
Ala Gly Gly Asn Glu Phe Gln Ala Gly Tyr Gly Asn Lys Ser Gly Lys
            275                 280                 285
Asn Leu Pro Tyr Ala Ser Asp Pro Asp Ser Ser Thr Leu Gly Glu Pro
        290                 295                 300
Gly Ser Phe Ala Pro Val Val Thr Val Ala Ser Ile Glu Asn Ala Arg
305                 310                 315                 320
Asn Gly Ala Asn Gly Asn Tyr Lys Met Ser Asp Phe Ser Ser Trp Gly
                325                 330                 335
Val Ser Pro Asp Met Arg Leu Lys Pro Glu Val Thr Ala Pro Gly Gly
            340                 345                 350
Asn Ile Tyr Ser Ser Val Pro Gly Gly Gly Tyr Gln Met Met Ser Gly
        355                 360                 365
Thr Ser Met Ala Thr Pro Gln Met Thr Gly Ala Ser Ala Val Val Leu
    370                 375                 380
Glu Arg Val Gln Asn Asp Pro Leu Phe Ser Ser Leu Asn Asp Arg Gln
385                 390                 395                 400
Lys Val Asp Val Val Gln Asn Leu Ile Met Gly Thr Ala Val Pro Val
                405                 410                 415
Val Asp Pro Gly Gln Gly Gly Gly Ala Tyr Tyr Ser Pro Arg Lys Gln
            420                 425                 430
Gly Ala Gly Leu Ala Asn Leu Glu Gly Ala Thr Thr Ser Ser Val Tyr
        435                 440                 445
Pro Thr Val Asn Gly Ala Ala Asp Ser Ser Arg Pro Lys Ala Glu Leu
    450                 455                 460
Gly Asp Gly Thr Asn Gly Trp His Phe Asp Val Thr Leu His Asn Val
465                 470                 475                 480
Ser Asp Thr Pro Ala Thr Tyr Glu Leu Ser Ser Gln Ala Leu Ser Glu
                485                 490                 495
Asn Ile Glu Gly Gly Phe Phe Thr Gly His Ser Thr Asp Trp Asn Gly
            500                 505                 510
Lys Gly Val Ser Val Ser Phe Ser Gly Ser Ser Val Thr Val Pro Ala
        515                 520                 525
Lys Gly Glu Thr Thr Val Gly Ile Asp Ile Lys Pro Gly Asn Glu Phe
    530                 535                 540
Ala Gln Tyr Val Ser Ala Asn Ala Pro Ala Gly Thr Phe Leu Asp Gly
545                 550                 555                 560
Phe Val Arg Phe Thr Ser Arg Thr Asn Gly Gln Pro Asp Leu Gly Val
                565                 570                 575
Pro Phe Leu Gly Phe Tyr Gly Ser Trp Ala Lys Pro Ala Ile Phe Asp
            580                 585                 590
Ala Leu Val Ser Glu Gly Asp Ala His Ala Ala Ser Ser Gly Ile Tyr
        595                 600                 605
Asn Gly Asp Arg Gly Gly Leu Leu Gly Tyr Asn Pro Leu Leu Lys Gly
    610                 615                 620
Arg Glu Arg Gln Gly Arg Pro Asn Ala Glu Arg Tyr Val Val Ser Arg
625                 630                 635                 640
Ser Thr Val Ser Gly Ala Pro Thr Ala Ile Ser Pro Arg Thr Gly Thr
                645                 650                 655
Leu Arg Ser Val His Lys Met Thr Thr Thr Tyr Thr Asn Glu Ala Gly
            660                 665                 670
Lys Ser Val Ala Ser Phe Thr Ser Phe Gln Asn Phe Lys Ser Thr Ile
        675                 680                 685
Asp Pro Glu Glu Glu Arg Met Ser Trp Val Glu Glu Gly Gln Glu Pro
```

```
                    690                 695                 700
Arg Ser Ile Asp Leu Lys Glu Gly Lys Tyr Ala Ser Leu Pro Asp Gly
705                 710                 715                 720

Asn Tyr Lys Leu Thr Ile Ala Ala Asn Asn Asp Gly Pro Ser Ser Thr
                    725                 730                 735

Glu Gln Ser Ile Thr Tyr Asn Phe Arg Ile Asp Thr Lys Ala Pro Val
                740                 745                 750

Val Asp Ser Ala Lys Val Asn Gly Ser Thr Leu Ser Val Glu Leu Ser
                755                 760                 765

Asp Glu Ser Pro Leu Ala Gly Phe Thr Leu Asn Asp Pro Asn Ser Gly
            770                 775                 780

Arg Tyr Ile His Leu Glu Val Ala Arg Asp Glu Asn Ser Gln Thr Tyr
785                 790                 795                 800

Glu Asn Gly Arg Tyr His Tyr Lys Thr Ser Ile Asp Leu Asn Gln Val
                    805                 810                 815

Gln Gly Gly Ala Ser Asn Asn Pro Tyr Val Val Ala Trp Asp Tyr Gly
                820                 825                 830

Leu Asn His Ser Glu Pro Val Thr Met Asn Gly Gly Lys Pro Gly Asn
                    835                 840                 845

Gly Gly Gly Gln Pro Gly Val Gly Asp Asp Gln Pro Gly Asn Gly Gly
            850                 855                 860

Gly Gln Pro Gly Val Gly Asp Asp Gln Pro Gly Asn Gly Gly Gly Gln
865                 870                 875                 880

Pro Gly Asn Gly Gly Gly Gln Pro Gly Asp Asp Trp Gly Asp Gln
                    885                 890                 895

Pro Gly Asn Gly Gly Gly Gln Pro Gly Asp Asp Trp Gly Asn Gly Gly
                900                 905                 910

Gly Gln Pro Gly Asp Asp Trp Gly Asn Gly Gly Gln Pro Gly Asn
            915                 920                 925

Gly Gly Gly Gln Pro Gly Asp Gly Trp Asp Asn Gly Gly Gln Pro
            930                 935                 940

Gly Gly Gly Trp Asp Asn Gly Gly Gln Pro Gly Gly Asn Pro Gly
945                 950                 955                 960

Asn Gly Gly Asn Ser Gly Tyr Cys Asp Phe Leu Asn Gly Tyr Trp Leu
                    965                 970                 975

Ser Asp Pro Val Gly Trp Trp Gln Lys Cys Val Ser Gly Lys Ser Leu
                980                 985                 990

Pro Arg Asn Gln Trp Ser Asn Ile Gly Gly Lys Asp Tyr Phe Val Gly
                995                 1000                1005

Pro Asp Gly Asn Ala Gln Thr Gly Trp Leu Asn Gln Gly Asp Thr
    1010                1015                1020

Trp Tyr Tyr Leu Asp Pro Ser Asn Gly Gly Ser Met Cys Thr Gly
    1025                1030                1035

Thr Arg Asn Ile Asp Gly Lys Thr Tyr Thr Phe Asp Asn Ser Gly
    1040                1045                1050

Ala Leu Val Lys
    1055

<210> SEQ ID NO 39
<211> LENGTH: 1203
<212> TYPE: PRT
<213> ORGANISM: Lactobacillus brevis

<400> SEQUENCE: 39
```

```
Met Lys Arg Leu Cys Ile Lys Lys Gly Phe Ile Val Phe Val Ser
 1               5                  10                  15

Ala Gly Ile Leu Leu Thr Leu Gly Leu Leu Ile Gly Phe Ser Ser Pro
             20                  25                  30

Val Gly Ala Gly Arg Val Ser Ile Asp Leu Pro Val Tyr Ala Lys Gly
             35                  40                  45

Arg Asn Glu Asn Gln Ala Ala Ile Asp Lys Gly Asn Val Pro Lys Leu
 50                  55                  60

Trp Gln Ser Gly Asn Arg Gly Gln Gly Met Val Ala Val Ile Asp
 65                  70                  75                  80

Thr Gly Ile Gln Pro His Lys Asp Phe Arg Leu Thr Ser Pro Gly Thr
                 85                  90                  95

Ala Lys Ile Ser Lys Ala Asp Ala Gln Arg Met Ile Ala Gln Lys Gly
             100                 105                 110

Tyr Gly Arg Tyr Val Asn Ser Lys Ile Pro Phe Ala Tyr Asn Tyr Ala
             115                 120                 125

Ser Asn Ser Asn Gln Ala Thr Glu Pro Asp Asp Val Ser Gly Phe His
             130                 135                 140

Gly Gln His Val Ala Gly Ile Ile Ala Ala Asn Gly Arg Tyr Thr Lys
145                 150                 155                 160

Lys Gln His Glu Tyr Val Val Gly Val Ala Pro Glu Ala Gln Leu Leu
                 165                 170                 175

Asp Leu Arg Val Ser Asp Met Ile Asp Asp Glu Asn Lys Asn Asp Val
             180                 185                 190

Ala Arg Ala Ile His Asp Ala Val Asp Leu Gly Ala Asn Val Ile Ser
             195                 200                 205

Ile Ser Leu Gly Ile Ser Leu Pro Asn Gln Ser Phe Thr Asp Glu Glu
210                 215                 220

Gln Ala Ala Val Gln Tyr Ala Ile Asn His Gly Val Phe Val Ser Leu
225                 230                 235                 240

Ala Gly Gly Asn Tyr Gly Asn Ser Ala Ser Ile Phe Thr Ser Asn Pro
             245                 250                 255

Leu Thr Asn Thr Asn Gly Ile Asn Thr Ala Tyr Gln Glu Ala Asn Ser
             260                 265                 270

Gly Thr Leu Ala Asp Pro Ala Val Ser Ala Asn Ser Met Thr Val Ala
             275                 280                 285

Ala Glu Asn Ser Leu Lys Gly Ser Gln Asn Glu Met Ala Ser Phe Ser
             290                 295                 300

Ser Trp Gly Pro Thr Pro Asp Tyr Thr Leu Lys Pro Asp Ile Ser Val
305                 310                 315                 320

Pro Gly Met Gly Ile Thr Ser Thr Trp Gln Asn Asn Thr Tyr Ala Met
                 325                 330                 335

Leu Glu Gly Thr Ser Met Ala Thr Pro Phe Val Ser Gly Ala Ala Ala
             340                 345                 350

Leu Val Ile Gln Lys Leu Lys Gln Ser Gln Pro Asp Leu Ser Gly Ser
             355                 360                 365

Gln Leu Val Ser Gln Thr Lys Asn Met Leu Met Asn Ser Ala Thr Pro
             370                 375                 380

Met Lys Asp Val Asn Tyr Pro Gly Asn Ile Val Ser Pro Arg Arg Gln
385                 390                 395                 400

Gly Ala Gly Gln Ile Asn Val Thr Ala Ala Asn Leu Lys Ala Thr
             405                 410                 415

Val Gln Asp Pro Ala Thr Gly Ile Gly Ser Val Ser Leu Gly Gln Ile
```

-continued

```
                420             425             430
Gly Gly Ser His Ser Phe Lys Val Glu Leu Ser Asn His Gly Ser Val
            435                 440                 445
Pro Ile Asn Tyr Ala Val Asp Asn Asp Gly Pro Met Thr Gln Ile
        450                 455                 460
Arg Asp Gln Lys Lys Asp Gly Gln Val His Asp Ile Ser Leu Thr Gly
465                 470                 475                 480
Ala Ser Leu Thr Ser Asp Gln Ser Asn Ile Val Ile Asp Pro Gly Gln
            485                 490                 495
Arg Lys Thr Leu Thr Leu Ser Leu Ser Ile Ser Pro Thr Val Lys Pro
        500                 505                 510
Asn Gln Val Val Glu Gly Tyr Leu His Phe Lys Ala Asp Gln Pro Gly
        515                 520                 525
Gln Ser Leu Ser Met Pro Tyr Leu Ala Tyr Tyr Gly Asp Thr Thr Lys
        530                 535                 540
Glu Gln Val Ile Asp Ser Pro Ala Phe Met Pro Asn Ser Ala Phe His
545                 550                 555                 560
Gly Gly Tyr Leu Met Asp Glu Asn Asn Thr Pro Leu Gly Ile Ser Asp
            565                 570                 575
Arg Val Ser Leu Ser Ala Tyr Val Asn Asn His Asp Asn Lys Thr Asn
            580                 585                 590
Trp Arg Lys Val Ala Ser Tyr Ile His Pro Ala Arg Val Ala Phe Ser
            595                 600                 605
Pro Asn Gly Asp His His Gln Asp Ser Val Thr Pro Phe Val Phe Ala
        610                 615                 620
Lys Gln Ser Leu Ala Asn Val Lys Ala Gln Ile Val Asn Asp Gln Gly
625                 630                 635                 640
Asn Val Ile Arg Val Ile Asp Gln Glu Thr Asp Thr Asp Lys Ser Ile
            645                 650                 655
Ala Asn Asp Ser Gly Asn Leu Asp Leu Ser Thr Ser Phe Ser Met Arg
            660                 665                 670
Gln Asn Pro Lys Ala Leu Gln Trp Asn Gly Arg Tyr Ile Asp Gln Ser
        675                 680                 685
Thr Gly Lys Ser Ile Val Val Pro Asn Gly Arg Tyr His Tyr Gln Leu
        690                 695                 700
Val Thr Thr Asn Tyr Asn Asp Gly Ala Asp Gln Gln Gln Leu Ala Ser
705                 710                 715                 720
Tyr Pro Val Glu Val Asp Thr Arg Ala Pro Gln Ala Thr Ala Val Thr
            725                 730                 735
Tyr Asn Arg Lys Thr Gly Arg Leu Thr Gly Gln Phe Asn Asp His Gly
            740                 745                 750
Ala Gly Phe Thr Gly Ile Ser Arg Gly Ile Leu Ser Thr Asn Gly His
            755                 760                 765
Gln Phe Gly Ile Lys Leu Thr Lys Lys Ala Ala Leu Ala Gly Gln Phe
        770                 775                 780
Ser Asp Arg Leu Thr Ser Ile Val Lys Gln Met Leu Met Lys His Gln
785                 790                 795                 800
Ala Asn Leu Thr Leu Thr Asp Ile Ala Gly Asn Ser Thr Lys Val Ala
            805                 810                 815
Val His Arg Lys Leu Ser Gly Leu Val Thr Lys Lys Ala Asn Val Ser
            820                 825                 830
Phe Asp Arg Ala Pro Gln Leu Lys Trp Phe Lys Tyr Gly Thr Gly Lys
            835                 840                 845
```

Asn Ala Ser Ser Ser Tyr Leu Glu Ile Ser Asn Lys Lys Val Phe Thr
850                 855                 860

Leu Tyr Ala Arg Val Pro Lys Gly Val Pro Ala Leu Asn Ala Tyr Ala
865                 870                 875                 880

Lys Asp Thr Gly Thr Asn Lys Val Val Lys Gly Arg Leu Asn Pro Lys
                885                 890                 895

Thr Gly Val Val Ala Phe Thr Cys His Phe Ser Gln Thr Gly Tyr Glu
            900                 905                 910

Thr Ile Gln Gly Trp Ser Gln Val Pro Gln Lys Lys Phe Gly Ala Tyr
        915                 920                 925

Leu Lys Ser Pro Ser Thr Leu Ile Val Val Ser Gln Leu Pro Lys Ala
    930                 935                 940

Pro Leu Ile Ala Lys Leu Lys Lys Thr Thr Pro Lys Leu Ile Ser Asn
945                 950                 955                 960

Ala Gln Ala Gln Lys Lys Thr Lys Ser Ile Phe Gly Ser Pro Ile Pro
                965                 970                 975

Asn Gly His Lys Thr Ser Gln Leu Thr Tyr Arg Arg Ala Pro Ser Lys
            980                 985                 990

Gly Ile Lys Phe Phe Gln Leu His Asp Asn Ala Ser Thr Phe Leu Asn
        995                 1000                1005

Ala Ala Asn Ser Ala Thr Ile Tyr Asp Leu Gln Thr His Gln Leu
    1010                1015                1020

Thr Ile Asn Gly Gln Ile Ser Ser Pro Asn Lys Gln Arg Leu Val
    1025                1030                1035

Ile Leu Ala Thr Pro Asp Glu Thr Asp Pro Ala Asn Arg Val Arg
    1040                1045                1050

Ile Ser Lys Asn Gly Thr Phe Lys Phe Lys Val Pro Phe Asn Pro
    1055                1060                1065

Thr Glu Gln Arg Gly Val Gly Tyr Asn Leu Tyr Thr Lys Thr Ile
    1070                1075                1080

Leu Arg Asn Gly Gln Ser Lys Val Gln Lys Gln Arg Gly Ile Leu
    1085                1090                1095

Glu Ile Tyr Leu Asp Val Val Lys Pro Ser Leu Ala Val Ser Glu
    1100                1105                1110

Asn Val Glu Asn Asn Arg Ile Arg Leu Thr Gly Thr Val Asn Asp
    1115                1120                1125

Asn Val Ser Gly Val Lys Leu Asp Val Asn Gly Asn Asn Leu Phe
    1130                1135                1140

Ser Gln Gln Lys Asp Ala Gly Phe Asn Arg His Asp Gln Asn Gln
    1145                1150                1155

Pro Leu Asn Pro Tyr Pro Asp Tyr Gln Ile Asn Gln Ser Tyr Asp
    1160                1165                1170

Leu Thr Pro Gly Arg Asn Thr Phe Thr Val Lys Ala Ile Asp Gln
    1175                1180                1185

Val Gly Asn Val Thr Thr Lys Arg Phe Val Ala Asn Gly His Gly
    1190                1195                1200

<210> SEQ ID NO 40
<211> LENGTH: 1178
<212> TYPE: PRT
<213> ORGANISM: Artificial Sequence
<220> FEATURE:
<223> OTHER INFORMATION: fragment of Lactobacillus brevis subsp.
      gravesensis ATCC 27305 protease

<400> SEQUENCE: 40

```
Leu Ile Gly Phe Ser Ser Pro Val Gly Ala Arg Val Ser Ile Asp
1               5                   10                  15

Leu Pro Val Tyr Ala Lys Gly Arg Asn Glu Asn Gln Ala Ala Ile Asp
            20                  25                  30

Lys Gly Asn Val Pro Lys Leu Trp Gln Ser Gly Asn Arg Gly Gln Gly
        35                  40                  45

Met Val Val Ala Val Ile Asp Thr Gly Ile Gln Pro His Lys Asp Phe
    50                  55                  60

Arg Leu Thr Ser Pro Gly Thr Ala Lys Ile Ser Lys Ala Asp Ala Gln
65                  70                  75                  80

Arg Met Ile Ala Gln Lys Gly Tyr Gly Arg Tyr Val Asn Ser Lys Ile
                85                  90                  95

Pro Phe Ala Tyr Asn Tyr Ala Ser Asn Ser Gln Ala Thr Glu Pro
            100                 105                 110

Asp Asp Val Ser Gly Phe His Gly Gln His Val Ala Gly Ile Ile Ala
            115                 120                 125

Ala Asn Gly Arg Tyr Thr Lys Lys Gln His Glu Tyr Val Val Gly Val
    130                 135                 140

Ala Pro Glu Ala Gln Leu Leu Asp Leu Arg Val Ser Asp Met Ile Asp
145                 150                 155                 160

Asp Glu Asn Lys Asn Asp Val Ala Arg Ala Ile His Asp Ala Val Asp
                165                 170                 175

Leu Gly Ala Asn Val Ile Ser Ile Ser Leu Gly Ile Ser Leu Pro Asn
            180                 185                 190

Gln Ser Phe Thr Asp Glu Gln Ala Ala Val Gln Tyr Ala Ile Asn
    195                 200                 205

His Gly Val Phe Val Ser Leu Ala Gly Gly Asn Tyr Gly Asn Ser Ala
    210                 215                 220

Ser Ile Phe Thr Ser Asn Pro Leu Thr Asn Thr Asn Gly Ile Asn Thr
225                 230                 235                 240

Ala Tyr Gln Glu Ala Asn Ser Gly Thr Leu Ala Asp Pro Ala Val Ser
                245                 250                 255

Ala Asn Ser Met Thr Val Ala Ala Glu Asn Ser Leu Lys Gly Ser Gln
            260                 265                 270

Asn Glu Met Ala Ser Phe Ser Ser Trp Gly Pro Thr Pro Asp Tyr Thr
    275                 280                 285

Leu Lys Pro Asp Ile Ser Val Pro Gly Met Gly Ile Thr Ser Thr Trp
    290                 295                 300

Gln Asn Asn Thr Tyr Ala Met Leu Glu Gly Thr Ser Met Ala Thr Pro
305                 310                 315                 320

Phe Val Ser Gly Ala Ala Leu Val Ile Gln Lys Leu Lys Gln Ser
                325                 330                 335

Gln Pro Asp Leu Ser Gly Ser Gln Leu Val Ser Gln Thr Lys Asn Met
            340                 345                 350

Leu Met Asn Ser Ala Thr Pro Met Lys Asp Val Asn Tyr Pro Gly Asn
        355                 360                 365

Ile Val Ser Pro Arg Arg Gln Gly Ala Gly Gln Ile Asn Val Thr Ala
    370                 375                 380

Ala Ala Asn Leu Lys Ala Thr Val Gln Asp Pro Ala Thr Gly Ile Gly
385                 390                 395                 400

Ser Val Ser Leu Gly Gln Ile Gly Gly Ser His Ser Phe Lys Val Glu
                405                 410                 415
```

-continued

```
Leu Ser Asn His Gly Ser Val Pro Ile Asn Tyr Ala Val Asp Asn Asp
            420                 425                 430

Gly Gly Pro Met Thr Gln Ile Arg Asp Gln Lys Lys Asp Gly Gln Val
            435                 440                 445

His Asp Ile Ser Leu Thr Gly Ala Ser Leu Thr Ser Asp Gln Ser Asn
            450                 455                 460

Ile Val Ile Asp Pro Gly Gln Arg Lys Thr Leu Thr Leu Ser Leu Ser
465                 470                 475                 480

Ile Ser Pro Thr Val Lys Pro Asn Gln Val Val Glu Gly Tyr Leu His
                485                 490                 495

Phe Lys Ala Asp Gln Pro Gly Gln Ser Leu Ser Met Pro Tyr Leu Ala
            500                 505                 510

Tyr Tyr Gly Asp Thr Thr Lys Glu Gln Val Ile Asp Ser Pro Ala Phe
            515                 520                 525

Met Pro Asn Ser Ala Phe His Gly Gly Tyr Leu Met Asp Glu Asn Asn
            530                 535                 540

Thr Pro Leu Gly Ile Ser Asp Arg Val Ser Leu Ser Ala Tyr Val Asn
545                 550                 555                 560

Asn His Asp Asn Lys Thr Asn Trp Arg Lys Val Ala Ser Tyr Ile His
                565                 570                 575

Pro Ala Arg Val Ala Phe Ser Pro Asn Gly Asp His His Gln Asp Ser
            580                 585                 590

Val Thr Pro Phe Val Phe Ala Lys Gln Ser Leu Ala Asn Val Lys Ala
            595                 600                 605

Gln Ile Val Asn Asp Gln Gly Asn Val Ile Arg Val Ile Asp Gln Glu
            610                 615                 620

Thr Asp Thr Asp Lys Ser Ile Ala Asn Asp Ser Gly Asn Leu Asp Leu
625                 630                 635                 640

Ser Thr Ser Phe Ser Met Arg Gln Asn Pro Lys Ala Leu Gln Trp Asn
                645                 650                 655

Gly Arg Tyr Ile Asp Gln Ser Thr Gly Lys Ser Ile Val Val Pro Asn
            660                 665                 670

Gly Arg Tyr His Tyr Gln Leu Val Thr Thr Asn Tyr Asn Asp Gly Ala
            675                 680                 685

Asp Gln Gln Gln Leu Ala Ser Tyr Pro Val Glu Val Asp Thr Arg Ala
690                 695                 700

Pro Gln Ala Thr Ala Val Thr Tyr Asn Arg Lys Thr Gly Arg Leu Thr
705                 710                 715                 720

Gly Gln Phe Asn Asp His Gly Ala Gly Phe Thr Gly Ile Ser Arg Gly
                725                 730                 735

Ile Leu Ser Thr Asn Gly His Gln Phe Gly Ile Lys Leu Thr Lys Lys
            740                 745                 750

Ala Ala Leu Ala Gly Gln Phe Ser Asp Arg Leu Thr Ser Ile Val Lys
            755                 760                 765

Gln Met Leu Met Lys His Gln Ala Asn Leu Thr Leu Thr Asp Ile Ala
            770                 775                 780

Gly Asn Ser Thr Lys Val Ala Val His Arg Lys Leu Ser Gly Leu Val
785                 790                 795                 800

Thr Lys Lys Ala Asn Val Ser Phe Asp Arg Ala Pro Gln Leu Lys Trp
                805                 810                 815

Phe Lys Tyr Gly Thr Gly Lys Asn Ala Ser Ser Tyr Leu Glu Ile
            820                 825                 830
```

Ser Asn Lys Lys Val Phe Thr Leu Tyr Ala Arg Val Pro Lys Gly Val
            835                 840                 845

Pro Ala Leu Asn Ala Tyr Ala Lys Asp Thr Gly Thr Asn Lys Val Val
        850                 855                 860

Lys Gly Arg Leu Asn Pro Lys Thr Gly Val Val Ala Phe Thr Cys His
865                 870                 875                 880

Phe Ser Gln Thr Gly Tyr Glu Thr Ile Gln Gly Trp Ser Gln Val Pro
                885                 890                 895

Gln Lys Lys Phe Gly Ala Tyr Leu Lys Ser Pro Ser Thr Leu Ile Val
            900                 905                 910

Val Ser Gln Leu Pro Lys Ala Pro Leu Ile Ala Lys Leu Lys Lys Thr
        915                 920                 925

Thr Pro Lys Leu Ile Ser Asn Ala Gln Ala Gln Lys Lys Thr Lys Ser
930                 935                 940

Ile Phe Gly Ser Pro Ile Pro Asn Gly His Lys Thr Ser Gln Leu Thr
945                 950                 955                 960

Tyr Arg Arg Ala Pro Ser Lys Gly Ile Lys Phe Phe Gln Leu His Asp
                965                 970                 975

Asn Ala Ser Thr Phe Leu Asn Ala Ala Asn Ser Ala Thr Ile Tyr Asp
            980                 985                 990

Leu Gln Thr His Gln Leu Thr Ile Asn Gly Gln Ile Ser Ser Pro Asn
        995                 1000                1005

Lys Gln Arg Leu Val Ile Leu Ala Thr Pro Asp Glu Thr Asp Pro
    1010                1015                1020

Ala Asn Arg Val Arg Ile Ser Lys Asn Gly Thr Phe Lys Phe Lys
    1025                1030                1035

Val Pro Phe Asn Pro Thr Glu Gln Arg Gly Val Gly Tyr Asn Leu
    1040                1045                1050

Tyr Thr Lys Thr Ile Leu Arg Asn Gly Gln Ser Lys Val Gln Lys
    1055                1060                1065

Gln Arg Gly Ile Leu Glu Ile Tyr Leu Asp Val Val Lys Pro Ser
    1070                1075                1080

Leu Ala Val Ser Glu Asn Val Glu Asn Asn Arg Ile Arg Leu Thr
    1085                1090                1095

Gly Thr Val Asn Asp Asn Val Ser Gly Val Lys Leu Asp Val Asn
    1100                1105                1110

Gly Asn Asn Leu Phe Ser Gln Gln Lys Asp Ala Gly Phe Asn Arg
    1115                1120                1125

His Asp Gln Asn Gln Pro Leu Asn Pro Tyr Pro Asp Tyr Gln Ile
    1130                1135                1140

Asn Gln Ser Tyr Asp Leu Thr Pro Gly Arg Asn Thr Phe Thr Val
    1145                1150                1155

Lys Ala Ile Asp Gln Val Gly Asn Val Thr Thr Lys Arg Phe Val
    1160                1165                1170

Ala Asn Gly His Gly
    1175

<210> SEQ ID NO 41
<211> LENGTH: 1625
<212> TYPE: PRT
<213> ORGANISM: Lactobacillus helveticus

<400> SEQUENCE: 41

Met Lys Glu Leu Ser Glu His Ser Ser Glu Lys Phe Val Tyr Leu Asn
1               5                   10                  15

```
Arg Ser Lys Lys Arg Leu Asp Asn Leu Glu Ser Tyr Thr His Ser Lys
         20                  25                  30

Phe Leu Lys Thr Leu Arg Lys Lys Trp Ala Lys Ala Ala Ile Val Thr
         35                  40                  45

Leu Ala Ser Gly Ser Ala Ile Leu Phe Ser Ala Asn Lys Val Lys Ala
 50                  55                  60

Asp Glu Val Glu Gln Asn Gln Ala Thr Glu Val Gln Gln Gly Ser Gln
 65                  70                  75                  80

Ala Thr Asp Gln Thr Gln Asn Gln Ser Asp Asn Ser Glu Asn Thr Gly
                 85                  90                  95

Gln Gln Asn Ser Asp Asn Gly Gln Ala Asp Thr Gln Val Asp Glu Val
            100                 105                 110

Gln Thr Ala Asp Lys Ala Gly Gln Lys Asp Ala Asn Gly Val Glu Leu
            115                 120                 125

Pro Ala Asn Asn Gln Asp His Val Lys Gly Asn Val Gln Asp Ala Trp
130                 135                 140

Asn Gln Gly Tyr Ser Gly Glu His Met Ala Val Ala Val Ile Asp Ser
145                 150                 155                 160

Gly Ile Asp Val Asp His Lys Asp Phe Gln Thr Met Pro Lys Asp Pro
                165                 170                 175

Lys Leu Thr Ala Asp Glu Met Lys Lys Lys Leu Lys Glu Leu Gly Tyr
            180                 185                 190

Gly Arg Tyr Val Asn Glu Lys Ile Pro Tyr Ala Tyr Asn Tyr Val Asp
            195                 200                 205

Asn Glu Asn Glu His Leu Lys Gly Pro Asp Asp Glu Pro His Gly Gln
210                 215                 220

His Val Ser Gly Thr Ile Ala Ala Asp Gly His Pro Asp Gly Asp Lys
225                 230                 235                 240

Glu Tyr Val Val Gly Val Ala Pro Gln Ala Gln Leu Leu His Leu Lys
                245                 250                 255

Val Phe Gly Asp Thr Thr Thr Ser Leu Asp Leu Ala Lys Glu Ile Tyr
            260                 265                 270

Asp Ala Val Asn Leu Gly Ala Asp Val Ile Gln Met Ser Leu Gly Gly
            275                 280                 285

Gly Val Ser Ala Ala Asp Leu Asn Asn Ala Asp Gln Arg Ala Val Gln
            290                 295                 300

Tyr Ala Ile Asp His Gly Val Ile Val Ser Ile Ser Ala Ser Asn Asn
305                 310                 315                 320

Gly Asn Ser Ala Ser Val Asp Asn Pro Ser Lys Ile Thr Asp Leu Asp
                325                 330                 335

Asp Tyr Glu Pro Gly Gly Glu Arg Gly Asn Tyr Leu Pro Phe Ser Ser
            340                 345                 350

Ser Thr Val Ala Asn Pro Gly Ala Ala Lys Gly Ala Ile Thr Val Ala
            355                 360                 365

Ala Glu Asn Ser Gly Leu Gly Lys Asp Ser Asp Met Ala Ser Phe Ser
            370                 375                 380

Ser Trp Gly Pro Leu Pro Asp Tyr Thr Leu Lys Pro Asp Ile Ser Ala
385                 390                 395                 400

Pro Gly Val Asp Val Ile Ser Thr Ala Asn Asp Asn Gly Tyr Thr Thr
                405                 410                 415

Met Ser Gly Thr Ser Met Ala Gly Pro Phe Val Ala Gly Ala Ala Thr
            420                 425                 430
```

Leu Val Lys Gln Arg Leu Leu Lys Thr Asn Pro Glu Leu Lys Gly Ala
                435                 440                 445

Ala Leu Val Glu Ala Val Lys Ala Leu Leu Met Asn Thr Ala Val Pro
        450                 455                 460

Gln Thr Gln Lys Gly Phe Asp Thr Pro Val Ser Pro Arg Arg Gln Gly
465                 470                 475                 480

Ser Gly Gln Ile Asp Val Gly Ala Ala Thr Lys Ser Pro Val Tyr Ile
                485                 490                 495

Thr Ala Asp Asp Gly Thr Gly Ser Ser Leu Arg Gln Ile Lys Asp
        500                 505                 510

Gly Ser Glu Phe Ala Leu Thr Phe His Asn Leu Ser Asn Gln Val Gln
        515                 520                 525

Ala Tyr Asp Phe Asp Asp Met Gly Gly Gly Phe Thr Glu Val Arg Asp
        530                 535                 540

Glu Glu Thr Gly Leu Phe His Asp Val Gln Leu Ala Gly Ala Asn Ile
545                 550                 555                 560

Ser Gly Pro Asn Ser Val Glu Leu Ala Pro Asn Glu Thr Lys Thr Val
                565                 570                 575

Asn Phe Val Leu Asn Leu Ala Gly Leu Lys Asn Asn Gln Leu Val Glu
        580                 585                 590

Gly Phe Leu Asn Phe Lys Ser Ser Lys Gly Ala Asn Asp Leu Ser Val
        595                 600                 605

Pro Tyr Leu Gly Tyr Phe Gly Asp Met Thr Ser Glu Asn Val Phe Asp
        610                 615                 620

Gln Asn Ala Asn Asp Ala Ala Pro Asp Ile Gln Gly Asn His Leu Ile
625                 630                 635                 640

Asn Glu Asp Asn Tyr Pro Arg Gly Ile Ala Asp Glu Ser Leu Lys
                645                 650                 655

Ala Leu Val Asn Val Asp Gly Thr Tyr Asn Trp Gln Glu Val Ala Lys
        660                 665                 670

Leu Tyr Glu Ser Gly Lys Val Ala Phe Ser Pro Asn Asn Gln Lys
        675                 680                 685

Ser Asp Leu Leu Lys Pro Val Ala Phe Leu Lys Gln Asn Leu Glu Asp
690                 695                 700

Leu Lys Val Glu Ile Leu Asp Ala Asn Gly Asn Val Val Arg Val Leu
705                 710                 715                 720

Ser Asp Asn His Gly Pro Glu Lys Ser Tyr His Asp His Asn Gly
                725                 730                 735

Met Met Asp Leu Ser Ser Thr Val Asn Asn Ser Asp Thr Leu Glu Trp
        740                 745                 750

Asp Gly Lys Leu Tyr Asp Lys Thr Thr Gly Lys Met Val Val Ala Pro
        755                 760                 765

Asp Gly Gln Tyr Thr Tyr Arg Phe Val Ala Thr Leu Tyr Asn Asn Gly
        770                 775                 780

Glu Asn Lys Val Gln Thr Asn Asp Thr Pro Val Ile Ile Asp Thr Thr
785                 790                 795                 800

Ala Pro Val Leu Asn Asn Val Lys Tyr Asp Thr Ser Ser Phe Thr Leu
                805                 810                 815

Ser Gly Asp Tyr Ala Asp Ala Gly Ala Gly Phe Thr Asp Tyr Ser Tyr
        820                 825                 830

Ala Thr Val Thr Val Asn Asp His Val Phe Gly Phe Lys Leu Asn Glu
        835                 840                 845

Gly Asp Lys Ser Asn Phe Asp Asn Ala Asn Lys Thr Lys Gly His Phe

```
                    850             855             860
Val Phe Val Leu Thr Pro Glu Gln Ala Ala Leu Thr Ser Ala Ala
865                 870             875             880

Asn Lys Val Thr Val Ala Phe Ser Asp Val Ala Asp Asn Thr Ala Thr
                        885             890             895

Gln Thr Phe Asn Val Ala Pro Val Ala Gly His Lys Lys Ile Ala Val
                    900             905             910

Trp Asn Ala Ile Asn Gly Leu Pro Phe Asn Glu Asn Ser Asp Asp Tyr
        915             920             925

Asn Val Gly Arg Lys Val Phe Met Leu Arg Gly Gly Ala Glu His Asp
    930             935             940

Phe Tyr Val Asn Gly Lys Trp Val Gln Val Asp Gln Gly Gln Phe Val
945             950             955             960

Leu Pro Val Ser Val Asp Glu Gln Asn Phe Val Phe Ser Asp Gln
                965             970             975

Ala Gly Lys Asn Ile Leu Gly Lys Phe Thr Thr Phe Thr Pro Lys Ala
                980             985             990

Gln Phe Ala Trp Gln His Val Asp Gly Glu Glu Arg Ser Phe Gly Val
            995             1000            1005

Ser Val Tyr Ser Val Glu Gly Lys Asp Pro Gln Asp Ile Val Val
    1010            1015            1020

Gln Ala Ala Val Pro Lys Gly Asp Asn Val Lys Ala Phe Ala Lys
    1025            1030            1035

Asp Tyr Phe Thr His Glu Val Tyr Thr Gly Glu Val His Asp Gly
    1040            1045            1050

Val Ala Thr Phe His Ile His Thr Ser Val Asn Lys Asp Ala Ala
    1055            1060            1065

Thr Gly Ile Asn Leu Arg Ala Leu Leu Gln Gly Trp Val Glu Ile
    1070            1075            1080

Asp Gly Pro Thr Phe Asn Ala Lys Gln Val Thr Asp Pro Ser Pro
    1085            1090            1095

Ile Asn Asp Ala Asn Tyr Leu Gly Val Tyr Tyr Asn Pro Asn Ala
    1100            1105            1110

Glu Glu Arg Lys Asn Tyr Asp Asn Arg Asp Asp Leu Gly Val Asp
    1115            1120            1125

Phe Glu Asp Glu Ala Ala Asp Thr Asn Thr Phe Gly Pro Gly Asn
    1130            1135            1140

His Ser Ser Ala Lys Asp Asp Ala Lys Ile His Phe Asp Tyr Leu
    1145            1150            1155

Asn Asn Asn Asp Ile Ser Thr Leu Gly Asn Lys Ala Val Glu Lys
    1160            1165            1170

Gly Tyr Tyr Asn Pro Ala Thr His Lys Phe Thr Leu Thr Gly Arg
    1175            1180            1185

Val Asn Pro Glu Val Ile Ser Leu Thr Phe Leu Ala Asp Ser Pro
    1190            1195            1200

Tyr Glu Val Asp Pro Glu Asn Gln Ala Asp Ile His Asp Asn Gly
    1205            1210            1215

Lys Phe Ser Val Thr Phe Thr Ile Asp Asn Pro Ala Thr Arg Gln
    1220            1225            1230

Leu Ser Tyr Phe Phe Lys Thr Asn Asp Gly Lys Thr Thr Arg Gly
    1235            1240            1245

Ser Leu Thr Leu Ile Leu Asp Thr Val Asp Pro Thr Leu Thr Val
    1250            1255            1260
```

Asp Gln Leu Gly Asp Lys Asp Glu Ala Glu Ile Thr Thr Asn Lys
1265                 1270                1275

Pro Thr Phe Lys Leu Ser Gly Glu Ala Asn Asp Asn Ile Asp Gly
1280                 1285                1290

Tyr Asn Val Phe Ile Asn Gly Asp Asn Val Phe Gly Gln Phe Gly
1295                 1300                1305

Asn Ser Gly Tyr Asp Phe Leu Pro Gly Ile Tyr Asn Asp Leu Asn
1310                 1315                1320

Gln Asn Thr Pro Asn Leu Tyr Gly Ser Tyr Lys Phe Asp Gln Glu
1325                 1330                1335

Glu Gln Leu Asp Asp Gln Asn Gly Gln Pro Thr Thr His Val Phe
1340                 1345                1350

Thr Ile Ala Val Glu Asp Gln Ala Gly Asn Arg Val Glu Lys Lys
1355                 1360                1365

Val Thr Val His Tyr Asp Pro Asn Tyr Leu Thr Glu Pro Val Asn
1370                 1375                1380

Thr Gly Lys Lys Asp Asp Gln Ala Asp Val Lys Pro Ala Glu Gly
1385                 1390                1395

Gln Lys Gln Asp Lys Asn Asp Asn Gln Thr Val Asn Asn Ser Lys
1400                 1405                1410

Glu Asp Pro Glu Ser Gly Gln Thr Thr Glu Asn Ala Gln Ser Thr
1415                 1420                1425

Glu Ser Gln Glu Gln Asn Lys Thr Asp Val Thr Lys Pro Ala Ala
1430                 1435                1440

Lys Pro Ser Asn Asp Asp Gln Lys Glu Asn His Gly Ala Gly Glu
1445                 1450                1455

Ser Thr Ile Glu Ser Asn Gln Glu Lys Gln Leu Gly Gln Ser Asn
1460                 1465                1470

Val Gln Ala Gln Asp Thr Lys Pro Asp Lys Thr Val Val Gln Gly
1475                 1480                1485

Asn Val Gln Asn Thr Ala Pro Thr Thr Gly His Leu Thr Asn Ser
1490                 1495                1500

Ser Val Asn Val Gln Gln Phe Lys Thr Lys Glu Thr Leu Gln
1505                 1510                1515

Leu Lys Lys Phe Lys Leu Leu Lys Asn Thr Tyr Gly Tyr Thr Leu
1520                 1525                1530

Asn Gly Lys Ile Ala Lys Lys His Gly Lys Lys Leu Leu Phe Asn
1535                 1540                1545

Lys Gly Lys Thr Val Leu Val Trp Asn Asn Arg Lys Val Val Thr
1550                 1555                1560

Ile Lys Gly Gln Lys Tyr Tyr Arg Val Ala Lys Asn Val Phe Val
1565                 1570                1575

Lys Val Ser Thr Ile Lys Gln Val Lys Asp Leu Lys Leu Val Leu
1580                 1585                1590

Thr Lys Asn Ser Tyr Val Tyr Asn Lys Leu Gly Lys Arg Val Lys
1595                 1600                1605

Tyr Lys Ser Gln Ser Leu Ile Lys Glu Gly Lys His Leu Ser Thr
1610                 1615                1620

His Gln
1625

<210> SEQ ID NO 42
<211> LENGTH: 1558

<212> TYPE: PRT
<213> ORGANISM: Artificial Sequence
<220> FEATURE:
<223> OTHER INFORMATION: fragment of Lactobacillus helveticus DSM
      20075 = CGMCC 1.1877 protease

<400> SEQUENCE: 42

Glu Gln Asn Gln Ala Thr Glu Val Gln Gln Gly Ser Gln Ala Thr Asp
1               5                   10                  15

Gln Thr Gln Asn Gln Ser Asp Asn Ser Glu Asn Thr Gly Gln Gln Asn
            20                  25                  30

Ser Asp Asn Gly Gln Ala Asp Thr Gln Val Asp Glu Val Gln Thr Ala
        35                  40                  45

Asp Lys Ala Gly Gln Lys Asp Ala Asn Gly Val Glu Leu Pro Ala Asn
    50                  55                  60

Asn Gln Asp His Val Lys Gly Asn Val Gln Asp Ala Trp Asn Gln Gly
65                  70                  75                  80

Tyr Ser Gly Glu His Met Ala Val Ala Val Ile Asp Ser Gly Ile Asp
                85                  90                  95

Val Asp His Lys Asp Phe Gln Thr Met Pro Lys Asp Pro Lys Leu Thr
            100                 105                 110

Ala Asp Glu Met Lys Lys Lys Leu Lys Glu Leu Gly Tyr Gly Arg Tyr
        115                 120                 125

Val Asn Glu Lys Ile Pro Tyr Ala Tyr Asn Tyr Val Asp Asn Glu Asn
    130                 135                 140

Glu His Leu Lys Gly Pro Asp Asp Glu Pro His Gly Gln His Val Ser
145                 150                 155                 160

Gly Thr Ile Ala Ala Asp Gly His Pro Asp Gly Asp Lys Glu Tyr Val
                165                 170                 175

Val Gly Val Ala Pro Gln Ala Gln Leu Leu His Leu Lys Val Phe Gly
            180                 185                 190

Asp Thr Thr Thr Ser Leu Asp Leu Ala Lys Glu Ile Tyr Asp Ala Val
        195                 200                 205

Asn Leu Gly Ala Asp Val Ile Gln Met Ser Leu Gly Gly Gly Val Ser
    210                 215                 220

Ala Ala Asp Leu Asn Asn Ala Asp Gln Arg Ala Val Gln Tyr Ala Ile
225                 230                 235                 240

Asp His Gly Val Ile Val Ser Ile Ser Ala Ser Asn Asn Gly Asn Ser
                245                 250                 255

Ala Ser Val Asp Asn Pro Ser Lys Ile Thr Asp Leu Asp Asp Tyr Glu
            260                 265                 270

Pro Gly Gly Glu Arg Gly Asn Tyr Leu Pro Phe Ser Ser Ser Thr Val
        275                 280                 285

Ala Asn Pro Gly Ala Ala Lys Gly Ala Ile Thr Val Ala Ala Glu Asn
    290                 295                 300

Ser Gly Leu Gly Lys Asp Ser Asp Met Ala Ser Phe Ser Ser Trp Gly
305                 310                 315                 320

Pro Leu Pro Asp Tyr Thr Leu Lys Pro Asp Ile Ser Ala Pro Gly Val
                325                 330                 335

Asp Val Ile Ser Thr Ala Asn Asp Asn Gly Tyr Thr Thr Met Ser Gly
            340                 345                 350

Thr Ser Met Ala Gly Pro Phe Val Ala Gly Ala Ala Thr Leu Val Lys
        355                 360                 365

Gln Arg Leu Leu Lys Thr Asn Pro Glu Leu Lys Gly Ala Ala Leu Val
    370                 375                 380

-continued

Glu Ala Val Lys Ala Leu Leu Met Asn Thr Ala Val Pro Gln Thr Gln
385                 390                 395                 400

Lys Gly Phe Asp Thr Pro Val Ser Pro Arg Gln Gly Ser Gly Gln
            405                 410                 415

Ile Asp Val Gly Ala Ala Thr Lys Ser Pro Val Tyr Ile Thr Ala Asp
            420                 425                 430

Asp Gly Thr Gly Ser Leu Ser Leu Arg Gln Ile Lys Asp Gly Ser Glu
            435                 440                 445

Phe Ala Leu Thr Phe His Asn Leu Ser Asn Gln Val Gln Ala Tyr Asp
450                 455                 460

Phe Asp Asp Met Gly Gly Gly Phe Thr Glu Val Arg Asp Glu Glu Thr
465                 470                 475                 480

Gly Leu Phe His Asp Val Gln Leu Ala Gly Ala Asn Ile Ser Gly Pro
                485                 490                 495

Asn Ser Val Glu Leu Ala Pro Asn Glu Thr Lys Thr Val Asn Phe Val
                500                 505                 510

Leu Asn Leu Ala Gly Leu Lys Asn Asn Gln Leu Val Glu Gly Phe Leu
            515                 520                 525

Asn Phe Lys Ser Ser Lys Gly Ala Asn Asp Leu Ser Val Pro Tyr Leu
530                 535                 540

Gly Tyr Phe Gly Asp Met Thr Ser Glu Asn Val Phe Asp Gln Asn Ala
545                 550                 555                 560

Asn Asp Ala Ala Pro Asp Ile Gln Gly Asn His Leu Ile Asn Glu Asp
                565                 570                 575

Asn Tyr Pro Arg Gly Ile Ala Asp Glu Ser Leu Lys Ala Leu Val
                580                 585                 590

Asn Val Asp Gly Thr Tyr Asn Trp Gln Glu Val Ala Lys Leu Tyr Glu
            595                 600                 605

Ser Gly Lys Val Ala Phe Ser Pro Asn Asn Asn Gln Lys Ser Asp Leu
    610                 615                 620

Leu Lys Pro Val Ala Phe Leu Lys Gln Asn Leu Glu Asp Leu Lys Val
625                 630                 635                 640

Glu Ile Leu Asp Ala Asn Gly Asn Val Val Arg Val Leu Ser Asp Asn
                645                 650                 655

His Gly Pro Glu Lys Ser Tyr His Asp Asp His Asn Gly Met Met Asp
                660                 665                 670

Leu Ser Ser Thr Val Asn Asn Ser Asp Thr Leu Glu Trp Asp Gly Lys
            675                 680                 685

Leu Tyr Asp Lys Thr Thr Gly Lys Met Val Val Ala Pro Asp Gly Gln
            690                 695                 700

Tyr Thr Tyr Arg Phe Val Ala Thr Leu Tyr Asn Asn Gly Glu Asn Lys
705                 710                 715                 720

Val Gln Thr Asn Asp Thr Pro Val Ile Ile Asp Thr Thr Ala Pro Val
                725                 730                 735

Leu Asn Asn Val Lys Tyr Asp Thr Ser Ser Phe Thr Leu Ser Gly Asp
                740                 745                 750

Tyr Ala Asp Ala Gly Ala Gly Phe Thr Asp Tyr Ser Tyr Ala Thr Val
                755                 760                 765

Thr Val Asn Asp His Val Phe Gly Phe Lys Leu Asn Glu Gly Asp Lys
    770                 775                 780

Ser Asn Phe Asp Asn Ala Asn Lys Thr Lys Gly His Phe Val Phe Val
785                 790                 795                 800

```
Leu Thr Pro Glu Glu Gln Ala Ala Leu Thr Ser Ala Ala Asn Lys Val
            805                 810                 815

Thr Val Ala Phe Ser Asp Val Ala Asp Asn Thr Ala Thr Gln Thr Phe
        820                 825                 830

Asn Val Ala Pro Val Ala Gly His Lys Lys Ile Ala Val Trp Asn Ala
        835                 840                 845

Ile Asn Gly Leu Pro Phe Asn Glu Asn Ser Asp Tyr Asn Val Gly
850                 855                 860

Arg Lys Val Phe Met Leu Arg Gly Gly Ala Glu His Asp Phe Tyr Val
865                 870                 875                 880

Asn Gly Lys Trp Val Gln Val Asp Gln Gly Gln Phe Val Leu Pro Val
            885                 890                 895

Ser Val Asp Glu Gln Asn Phe Val Phe Ser Ser Asp Gln Ala Gly Lys
        900                 905                 910

Asn Ile Leu Gly Lys Phe Thr Thr Phe Thr Pro Lys Ala Gln Phe Ala
        915                 920                 925

Trp Gln His Val Asp Gly Glu Glu Arg Ser Phe Gly Val Ser Val Tyr
        930                 935                 940

Ser Val Glu Gly Lys Asp Pro Gln Asp Ile Val Val Gln Ala Ala Val
945                 950                 955                 960

Pro Lys Gly Asp Asn Val Lys Ala Phe Ala Lys Asp Tyr Phe Thr His
                965                 970                 975

Glu Val Tyr Thr Gly Glu Val His Asp Gly Val Ala Thr Phe His Ile
            980                 985                 990

His Thr Ser Val Asn Lys Asp Ala Ala Thr Gly Ile Asn Leu Arg Ala
        995                 1000                1005

Leu Leu Gln Gly Trp Val Glu Ile Asp Gly Pro Thr Phe Asn Ala
        1010                1015                1020

Lys Gln Val Thr Asp Pro Ser Pro Ile Asn Asp Ala Asn Tyr Leu
        1025                1030                1035

Gly Val Tyr Tyr Asn Pro Asn Ala Glu Glu Arg Lys Asn Tyr Asp
        1040                1045                1050

Asn Arg Asp Asp Leu Gly Val Asp Phe Glu Asp Glu Ala Ala Asp
        1055                1060                1065

Thr Asn Thr Phe Gly Pro Gly Asn His Ser Ser Ala Lys Asp Asp
        1070                1075                1080

Ala Lys Ile His Phe Asp Tyr Leu Asn Asn Asn Asp Ile Ser Thr
        1085                1090                1095

Leu Gly Asn Lys Ala Val Glu Lys Gly Tyr Tyr Asn Pro Ala Thr
        1100                1105                1110

His Lys Phe Thr Leu Thr Gly Arg Val Asn Pro Glu Val Ile Ser
        1115                1120                1125

Leu Thr Phe Leu Ala Asp Ser Pro Tyr Glu Val Asp Pro Glu Asn
        1130                1135                1140

Gln Ala Asp Ile His Asp Asn Gly Lys Phe Ser Val Thr Phe Thr
        1145                1150                1155

Ile Asp Asn Pro Ala Thr Arg Gln Leu Ser Tyr Phe Phe Lys Thr
        1160                1165                1170

Asn Asp Gly Lys Thr Thr Arg Gly Ser Leu Thr Leu Ile Leu Asp
        1175                1180                1185

Thr Val Asp Pro Thr Leu Thr Val Asp Gln Leu Gly Asp Lys Asp
        1190                1195                1200

Glu Ala Glu Ile Thr Thr Asn Lys Pro Thr Phe Lys Leu Ser Gly
```

1205                1210                1215

Glu Ala Asn Asp Asn Ile Asp Gly Tyr Asn Val Phe Ile Asn Gly
        1220                1225                1230

Asp Asn Val Phe Gly Gln Phe Gly Asn Ser Gly Tyr Asp Phe Leu
        1235                1240                1245

Pro Gly Ile Tyr Asn Asp Leu Asn Gln Asn Thr Pro Asn Leu Tyr
        1250                1255                1260

Gly Ser Tyr Lys Phe Asp Gln Glu Glu Gln Leu Asp Asp Gln Asn
        1265                1270                1275

Gly Gln Pro Thr Thr His Val Phe Thr Ile Ala Val Glu Asp Gln
        1280                1285                1290

Ala Gly Asn Arg Val Glu Lys Lys Val Thr Val His Tyr Asp Pro
        1295                1300                1305

Asn Tyr Leu Thr Glu Pro Val Asn Thr Gly Lys Lys Asp Asp Gln
        1310                1315                1320

Ala Asp Val Lys Pro Ala Glu Gly Gln Lys Gln Asp Lys Asn Asp
        1325                1330                1335

Asn Gln Thr Val Asn Asn Ser Lys Glu Asp Pro Glu Ser Gly Gln
        1340                1345                1350

Thr Thr Glu Asn Ala Gln Ser Thr Glu Ser Gln Glu Gln Asn Lys
        1355                1360                1365

Thr Asp Val Thr Lys Pro Ala Ala Lys Pro Ser Asn Asp Asp Gln
        1370                1375                1380

Lys Glu Asn His Gly Ala Gly Glu Ser Thr Ile Glu Ser Asn Gln
        1385                1390                1395

Glu Lys Gln Leu Gly Gln Ser Asn Val Gln Ala Gln Asp Thr Lys
        1400                1405                1410

Pro Asp Lys Thr Val Val Gln Gly Asn Val Gln Asn Thr Ala Pro
        1415                1420                1425

Thr Thr Gly His Leu Thr Asn Ser Ser Val Asn Val Gln Gln Phe
        1430                1435                1440

Lys Thr Lys Lys Glu Thr Leu Gln Leu Lys Lys Phe Lys Leu Leu
        1445                1450                1455

Lys Asn Thr Tyr Gly Tyr Thr Leu Asn Gly Lys Ile Ala Lys Lys
        1460                1465                1470

His Gly Lys Lys Leu Leu Phe Asn Lys Gly Lys Thr Val Leu Val
        1475                1480                1485

Trp Asn Asn Arg Lys Val Val Thr Ile Lys Gly Gln Lys Tyr Tyr
        1490                1495                1500

Arg Val Ala Lys Asn Val Phe Val Lys Val Ser Thr Ile Lys Gln
        1505                1510                1515

Val Lys Asp Leu Lys Leu Val Leu Thr Lys Asn Ser Tyr Val Tyr
        1520                1525                1530

Asn Lys Leu Gly Lys Arg Val Lys Tyr Lys Ser Gln Ser Leu Ile
        1535                1540                1545

Lys Glu Gly Lys His Leu Ser Thr His Gln
        1550                1555

<210> SEQ ID NO 43
<211> LENGTH: 1494
<212> TYPE: PRT
<213> ORGANISM: Lactobacillus rhamnosus

<400> SEQUENCE: 43

```
Met Asn Lys Asn Ala Thr Ile Glu Ala Lys Arg His Tyr Lys Met Tyr
1               5                   10                  15

Lys Ala Gly Ser Arg Trp Met Thr Ala Ala Ile Ile Thr Phe Gly Thr
            20                  25                  30

Ser Leu Val Val Leu Gly Gly Thr Ala Thr Gln Ser Val Ser Ala Asp
        35                  40                  45

Thr Lys Thr Pro Thr Ala Asp Lys Thr Thr Gln Pro Val Asn Gln Ala
    50                  55                  60

Gln Thr Gln Thr Ala Thr Ser Thr Ala Ser Ser Gln Ala Thr Thr Ala
65                  70                  75                  80

Asp Ala Lys Asp Lys Thr Ala Glu Thr Gln Pro Thr Thr Thr Thr Thr
                85                  90                  95

Thr Lys Gln Val Thr Ala Gln Ser Gln Ala Ala Pro Ser Thr Ala Thr
        100                 105                 110

Lys Ala Gln Ser Gln Ala Ser Thr Thr Asn Gln Ala Gln Pro Ala Ala
            115                 120                 125

Ala Thr Lys Val Gln Thr Gly Thr Pro Ser Ser Gly Ala Asn Thr Gln
        130                 135                 140

Pro Ala Ala Asn Thr Ala Thr Thr Lys Ser Ala Thr Ser Thr Thr Ser
145                 150                 155                 160

Ser Ala Ala Thr Gln Ser Ala Ala Pro Ala Ser Asn Ala Ala Thr Thr
            165                 170                 175

Asn Ala Ala Lys Thr Gln Ser Thr Ala Ala Thr Thr Asp Pro Gly
            180                 185                 190

Pro Ala Asn Gln Asp Thr Leu Thr Lys Gly Asn Val Lys Gly Leu Trp
195                 200                 205

Asn Glu Gly Tyr Gln Gly Gln Gly Met Val Val Ala Val Ile Asp Ser
    210                 215                 220

Gly Val Gln Ala His Asp Asp Leu Arg Leu Ser Asp Asp Ser Thr Ala
225                 230                 235                 240

Ala Ile Thr Lys Glu Lys Ala Glu Ala Ala Ile Ser Lys Leu Gly Tyr
            245                 250                 255

Gly Ser Tyr Val Asn Ser Lys Ile Pro Phe Ala Tyr Asp Tyr Val Asn
            260                 265                 270

Asn Asp Ser Val Asn Thr Gly Thr Thr Val Ala Gly Ser Thr His Gly
        275                 280                 285

Glu His Val Ala Gly Ile Ile Ala Ala Asn Gly Thr Thr Ala Asp Gly
    290                 295                 300

Ala Thr Gly Asn Glu Lys Ala Thr Thr Tyr Val Lys Gly Val Ala Pro
305                 310                 315                 320

Glu Ala Gln Ile Leu Ala Met Gln Val Ile Asp Glu Phe Ala Asp Glu
            325                 330                 335

Asn Ala Asn Asp Ile Ser Arg Ala Ile Arg Asp Ala Val Thr Leu Gly
            340                 345                 350

Ala Asn Ala Ile Gln Met Ser Leu Gly Ile Gly Val Thr Glu Gln Asp
        355                 360                 365

Leu Thr Asp Glu Glu Gln Ala Ala Val Gln Tyr Ala Thr Asp His Gly
    370                 375                 380

Val Phe Val Ser Ile Ala Gly Asn Asn Asn Ala Gly Ser Ile
385                 390                 395                 400

Ile Gly Ser Lys Thr Ser Asn Asp Ile Ser Thr Ala Tyr Ser Pro Lys
            405                 410                 415

Asn Asp Ser Thr Ile Gly Asp Pro Gly Ala Ala Ala Ser Ala Met Thr
```

```
            420             425             430
    Val Ala Ala Glu Lys Ser Ala Thr Gly Asp Lys Ser Glu Met Asp Gly
                435             440             445
    Phe Ser Ser Trp Gly Pro Met Ala Asp Tyr Thr Leu Lys Pro Asp Ile
        450             455             460
    Ser Ala Pro Gly Asp Asn Val Ile Ser Thr Ala Ile Asp Pro Thr Thr
    465             470             475             480
    Asn Thr Gln Thr Tyr Ala Thr Glu Ser Gly Thr Ser Met Ala Gly Pro
                485             490             495
    Tyr Asn Ala Gly Ala Ala Leu Leu Val Met Gln Lys Ile Lys Ala Thr
                500             505             510
    Arg Pro Asp Leu Gln Gly Ala Asp Leu Val Lys Ala Val Lys Leu Ala
                515             520             525
    Leu Met Asn Ala Ala Asp Pro Met Lys Asp Ile Asn Tyr Pro Asp Thr
                530             535             540
    Tyr Ile Ser Pro Arg Arg Gln Gly Ala Gly Gln Ile Asp Val Ser Lys
    545             550             555             560
    Ala Gly Asp Leu Thr Val Ser Ala Glu Gly Asn Lys Asp Ala Gly Ser
                565             570             575
    Val Ser Leu Gly Lys Ile Gly Gln Thr Thr Ser Phe Thr Val Thr Leu
                580             585             590
    Thr Asn His Gly Lys Thr Ala Gln Asn Tyr Val Val Asp Thr Asn Gly
                595             600             605
    Gly Pro Leu Thr Gln Val Gln Asp Thr Ser Asn Gly Asn Thr Val His
                610             615             620
    Asp Gln Thr Leu Ile Gly Ala Thr Val Asn Thr Asp Thr Ala Asn Phe
    625             630             635             640
    Thr Leu Ala Ala Gly Glu Thr Lys Thr Val Thr Phe Lys Leu Ser Leu
                645             650             655
    Asp Asn Thr Val Ala Ala Asn Gln Leu Val Glu Gly Phe Leu Thr Phe
                660             665             670
    Lys Ala Gly Asp Thr Ser Gln Thr Ile Ser Val Pro Tyr Leu Gly Tyr
                675             680             685
    Tyr Gly Asp Leu Thr Thr Glu Gln Val Val Asp Ala Ser Ala Asn Ser
                690             695             700
    Gly Glu Ser Ile Phe Asn Gly Tyr Leu Val Asp Gly Ala Asn Thr
    705             710             715             720
    Pro Leu Gly Val Thr Asp Ser Ala Ser Leu Ser Ser Leu Val Asn Thr
                725             730             735
    Asp Thr Thr Gly Lys Tyr Thr Trp Thr Leu Val Pro Thr Tyr Val Asp
                740             745             750
    Asn Lys Lys Val Ser Phe Ser Pro Asn Gly Asp Gly Ala Ser Asp Thr
                755             760             765
    Val Tyr Pro Tyr Val Phe Ser Lys Gln Asn Leu Lys Ser Val Thr Ile
                770             775             780
    Gln Ile Leu Asp Ala Gln Gly His Val Val Arg Val Leu Asp Lys Glu
    785             790             795             800
    Asn Asn Thr Thr Lys Ser Tyr Leu Gln Asn Gly Asn Ser Tyr Asn Ser
                805             810             815
    Asp Leu Gly Leu Ser Thr Asp Met Arg Leu Asp Pro Asn Ala Phe Thr
                820             825             830
    Trp Asp Gly Lys Val Tyr Asp Gln Ala Thr Gly Lys Tyr Val Thr Ala
                835             840             845
```

-continued

Pro Asp Gly Lys Tyr Thr Tyr Arg Leu Val Thr Glu Gln Tyr Asn Thr
850                855                860

Gly Ala Gln Gln Asn Gln Asp Phe Asp Leu Pro Val Thr Val Asp Thr
865                870                875                880

Val Ala Pro Thr Leu Thr Gly Leu Ser Tyr Gln Asn Gly Arg Val Thr
                885                890                895

Val Asn Tyr Asn Asp Gln Gly Ala Gly Phe Thr Lys Phe Ser Asp Ile
            900                905                910

Ala Leu Lys Ile Gly Gly Lys Ala Tyr Gly Val Ser Leu Asn Asn Asn
        915                920                925

Gly Gln Asn Asn Asp Gly Thr Leu Ser Phe Asp Leu Thr Ala Ala Gln
    930                935                940

Lys Ala Ala Leu Glu Ser Ser Asp Gly Ser Leu Thr Leu Thr Leu Thr
945                950                955                960

Asp Val Ala Gly Asn Lys Thr Ser Lys Thr Leu Gln Ala Val Thr Gly
                965                970                975

Thr His Gln Ala Thr Thr Pro Thr Ala Thr Ala Asn Val Ala Pro
            980                985                990

Gln Phe Ser Trp Lys Val Gly Asp Gly Pro Tyr Asn His Trp Arg Thr
        995                1000                1005

Asp Gly Phe Val Gln Ala Val Ser Asp Gln Thr Ser Phe Thr Ala
    1010                1015                1020

Tyr Ala Gln Val Pro Ala Gly Val Asp Trp Ile Val Tyr Ala Thr
    1025                1030                1035

Asp Ala Met Thr Gly Lys Val Phe Ser Gly Lys Val Asp Thr Lys
    1040                1045                1050

Thr Gly Asn Val Thr Phe Asn Leu Thr Ala Ser Ala Pro Tyr Gly
    1055                1060                1065

Asp Phe Val Gly Thr Val Leu Ala Pro Thr Ala Asp Phe Gly Thr
    1070                1075                1080

Tyr Glu Gln Ala Gly Arg Ala Asn Gly Asp Glu Met Val Val Phe
    1085                1090                1095

Leu Asp Thr Asp Gly Thr Ala Gly Tyr Gly His Phe Ser Gln Lys
    1100                1105                1110

Asp Pro His Val Ala Val Pro Leu Gln Asp Asn Ala Lys Ala Ala
    1115                1120                1125

Ala Asn Val Lys Thr Thr Ser Gly Ala Pro Val Leu Gly Gly Arg
    1130                1135                1140

Ala Phe Ser Gln Ile Thr Thr His Ala Gln Pro Thr Ala Gly Leu
    1145                1150                1155

Thr Phe Asp Lys Phe Asn Asp Asn Ser Phe Thr Leu Val Gly Ala
    1160                1165                1170

Asp Lys Val Ala Asp Ile Tyr Asn Ala Lys Thr Gly Gln Leu Thr
    1175                1180                1185

Ile Thr Gly His Val Asp Gln Pro Ala Gly Lys Thr Leu Thr Val
    1190                1195                1200

Thr Ser Ala Thr Glu Pro Ala Lys Thr Val Thr Ile Gly Ala Asp
    1205                1210                1215

Gly Lys Phe Ser Phe Thr Val Pro Phe Lys Ala Ala Glu Gln Gln
    1220                1225                1230

Ala Ile Gly Tyr Arg Leu Thr Ser Pro Ala Thr Asp Gly Ser Lys
    1235                1240                1245

```
Ser Thr Gln Thr Ala Tyr Gly Glu Leu Gln Ile Tyr Leu Asp Thr
    1250                1255                1260

Ile Phe Pro Thr Leu Asn Met Pro Gln Ala Asp Thr Leu Gln Val
    1265                1270                1275

Asp Asp Lys Gly Asn Tyr Glu Ile Thr Thr Ser Asp Thr Phe
    1280                1285                1290

Thr Val Ser Gly Thr Val Asn Asp Asn Ile Asn Gly Tyr Arg Leu
    1295                1300                1305

Tyr Thr Asn Gly Asp Asn Ile Val His Gln Lys Asn Leu Ala Gly
    1310                1315                1320

Phe Asn Asn His Leu Asp Pro Leu Ser Thr Thr Ser Asn Pro Tyr
    1325                1330                1335

Gly Ala Ala Ala Phe Thr Gln Thr Tyr Gln Leu Ala Asp Gly Asp
    1340                1345                1350

Asn Tyr Phe Thr Ile Thr Ala Val Asp Met Val Gly Asn Lys Val
    1355                1360                1365

Thr Lys Val Phe His Val Ile Lys Thr Lys Ala Thr Thr Pro Thr
    1370                1375                1380

Thr Pro Glu Thr Pro Lys Thr Pro Thr Pro Thr Pro Lys Pro Gly
    1385                1390                1395

Thr Gly Asp Gln Thr Asp Thr Lys Asn Pro Lys Gly Pro Thr Thr
    1400                1405                1410

Thr Pro Lys Thr Asp Glu Gln Gly Lys Thr Asn Pro Thr Pro Lys
    1415                1420                1425

Phe Val Asp Leu Thr Asn Thr Thr Lys Gly Gln Asp Lys Thr Gly
    1430                1435                1440

Thr Thr Ala Glu Thr Gly Lys Asn Thr Lys Gln Thr Ala Ala Ala
    1445                1450                1455

Lys Thr Met Pro Gln Ala Gly Glu Ala Gln Ser Pro Leu Ala Val
    1460                1465                1470

Leu Gly Leu Ala Ile Leu Ser Met Leu Gly Leu Ala Gly Phe Val
    1475                1480                1485

Ser Arg Lys Lys Arg Val
    1490

<210> SEQ ID NO 44
<211> LENGTH: 1443
<212> TYPE: PRT
<213> ORGANISM: Artificial Sequence
<220> FEATURE:
<223> OTHER INFORMATION: fragment of Lactobacillus rhamnosus ATCC 21052
      protease

<400> SEQUENCE: 44

Pro Thr Ala Asp Lys Thr Thr Gln Pro Val Asn Gln Ala Gln Thr Gln
1               5                   10                  15

Thr Ala Thr Ser Thr Ala Ser Ser Gln Ala Thr Thr Ala Asp Ala Lys
                20                  25                  30

Asp Lys Thr Ala Glu Thr Gln Pro Thr Thr Thr Thr Thr Lys Gln
                35                  40                  45

Val Thr Ala Gln Ser Gln Ala Ala Pro Ser Thr Ala Thr Lys Ala Gln
    50                  55                  60

Ser Gln Ala Ser Thr Thr Asn Gln Ala Gln Pro Ala Ala Ala Thr Lys
65                  70                  75                  80

Val Gln Thr Gly Thr Pro Ser Ser Gly Ala Asn Thr Gln Pro Ala Ala
                85                  90                  95
```

```
Asn Thr Ala Thr Thr Lys Ser Ala Thr Ser Thr Thr Ser Ala Ala
                100                 105                 110

Thr Gln Ser Ala Ala Pro Ala Ser Asn Ala Ala Thr Thr Asn Ala Ala
    115                 120                 125

Lys Thr Gln Ser Thr Ala Ala Thr Thr Thr Asp Pro Gly Pro Ala Asn
130             135                 140

Gln Asp Thr Leu Thr Lys Gly Asn Val Lys Gly Leu Trp Asn Glu Gly
145                 150                 155                 160

Tyr Gln Gly Gln Gly Met Val Val Ala Val Ile Asp Ser Gly Val Gln
                165                 170                 175

Ala His Asp Asp Leu Arg Leu Ser Asp Asp Ser Thr Ala Ala Ile Thr
                180                 185                 190

Lys Glu Lys Ala Glu Ala Ala Ile Ser Lys Leu Gly Tyr Gly Ser Tyr
                195                 200                 205

Val Asn Ser Lys Ile Pro Phe Ala Tyr Asp Tyr Val Asn Asn Asp Ser
    210                 215                 220

Val Asn Thr Gly Thr Thr Val Ala Gly Ser Thr His Gly Glu His Val
225                 230                 235                 240

Ala Gly Ile Ile Ala Ala Asn Gly Thr Thr Ala Asp Gly Ala Thr Gly
                245                 250                 255

Asn Glu Lys Ala Thr Thr Tyr Val Lys Gly Val Ala Pro Glu Ala Gln
                260                 265                 270

Ile Leu Ala Met Gln Val Ile Asp Glu Phe Ala Asp Glu Asn Ala Asn
                275                 280                 285

Asp Ile Ser Arg Ala Ile Arg Asp Ala Val Thr Leu Gly Ala Asn Ala
                290                 295                 300

Ile Gln Met Ser Leu Gly Ile Gly Val Thr Glu Gln Asp Leu Thr Asp
305                 310                 315                 320

Glu Glu Gln Ala Ala Val Gln Tyr Ala Thr Asp His Gly Val Phe Val
                325                 330                 335

Ser Ile Ser Ala Gly Asn Asn Ala Asn Ala Gly Ser Ile Ile Gly Ser
                340                 345                 350

Lys Thr Ser Asn Asp Ile Ser Thr Ala Tyr Ser Pro Lys Asn Asp Ser
                355                 360                 365

Thr Ile Gly Asp Pro Gly Ala Ala Ser Ala Met Thr Val Ala Ala
370                 375                 380

Glu Lys Ser Ala Thr Gly Asp Lys Ser Glu Met Asp Gly Phe Ser Ser
385                 390                 395                 400

Trp Gly Pro Met Ala Asp Tyr Thr Leu Lys Pro Asp Ile Ser Ala Pro
                405                 410                 415

Gly Asp Asn Val Ile Ser Thr Ala Ile Asp Pro Thr Thr Asn Thr Gln
                420                 425                 430

Thr Tyr Ala Thr Glu Ser Gly Thr Ser Met Ala Gly Pro Tyr Asn Ala
                435                 440                 445

Gly Ala Ala Leu Leu Val Met Gln Lys Ile Lys Ala Thr Arg Pro Asp
                450                 455                 460

Leu Gln Gly Ala Asp Leu Val Lys Ala Val Lys Leu Ala Leu Met Asn
465                 470                 475                 480

Ala Ala Asp Pro Met Lys Asp Ile Asn Tyr Pro Asp Thr Tyr Ile Ser
                485                 490                 495

Pro Arg Arg Gln Gly Ala Gly Ile Asp Val Ser Lys Ala Gly Asp
                500                 505                 510
```

```
Leu Thr Val Ser Ala Glu Gly Asn Lys Asp Ala Gly Ser Val Ser Leu
            515                 520                 525

Gly Lys Ile Gly Gln Thr Thr Ser Phe Thr Val Thr Leu Thr Asn His
        530                 535                 540

Gly Lys Thr Ala Gln Asn Tyr Val Val Asp Thr Asn Gly Gly Pro Leu
545                 550                 555                 560

Thr Gln Val Gln Asp Thr Ser Asn Gly Asn Thr Val His Asp Gln Thr
                565                 570                 575

Leu Ile Gly Ala Thr Val Asn Thr Asp Thr Ala Asn Phe Thr Leu Ala
            580                 585                 590

Ala Gly Glu Thr Lys Thr Val Thr Phe Lys Leu Ser Leu Asp Asn Thr
        595                 600                 605

Val Ala Ala Asn Gln Leu Val Glu Gly Phe Leu Thr Phe Lys Ala Gly
    610                 615                 620

Asp Thr Ser Gln Thr Ile Ser Val Pro Tyr Leu Gly Tyr Tyr Gly Asp
625                 630                 635                 640

Leu Thr Thr Glu Gln Val Val Asp Ala Ser Ala Asn Ser Gly Glu Ser
                645                 650                 655

Ile Phe Asn Gly Gly Tyr Leu Val Asp Gly Ala Asn Thr Pro Leu Gly
            660                 665                 670

Val Thr Asp Ser Ala Ser Leu Ser Ser Leu Val Asn Thr Asp Thr Thr
        675                 680                 685

Gly Lys Tyr Thr Trp Thr Leu Val Pro Thr Tyr Val Asp Asn Lys Lys
    690                 695                 700

Val Ser Phe Ser Pro Asn Gly Asp Gly Ala Ser Asp Thr Val Tyr Pro
705                 710                 715                 720

Tyr Val Phe Ser Lys Gln Asn Leu Lys Ser Val Thr Ile Gln Ile Leu
                725                 730                 735

Asp Ala Gln Gly His Val Val Arg Val Leu Asp Lys Glu Asn Asn Thr
            740                 745                 750

Thr Lys Ser Tyr Leu Gln Asn Gly Asn Ser Tyr Asn Ser Asp Leu Gly
        755                 760                 765

Leu Ser Thr Asp Met Arg Leu Asp Pro Asn Ala Phe Thr Trp Asp Gly
    770                 775                 780

Lys Val Tyr Asp Gln Ala Thr Gly Lys Tyr Val Thr Ala Pro Asp Gly
785                 790                 795                 800

Lys Tyr Thr Tyr Arg Leu Val Thr Glu Gln Tyr Asn Thr Gly Ala Gln
                805                 810                 815

Gln Asn Gln Asp Phe Asp Leu Pro Val Thr Val Asp Thr Val Ala Pro
            820                 825                 830

Thr Leu Thr Gly Leu Ser Tyr Gln Asn Gly Arg Val Thr Val Asn Tyr
        835                 840                 845

Asn Asp Gln Gly Ala Gly Phe Thr Lys Phe Ser Asp Ile Ala Leu Lys
    850                 855                 860

Ile Gly Gly Lys Ala Tyr Gly Val Ser Leu Asn Asn Gly Gln Asn
865                 870                 875                 880

Asn Asp Gly Thr Leu Ser Phe Asp Leu Thr Ala Ala Gln Lys Ala Ala
                885                 890                 895

Leu Glu Ser Ser Asp Gly Ser Leu Thr Leu Thr Leu Thr Asp Val Ala
            900                 905                 910

Gly Asn Lys Thr Ser Lys Thr Leu Gln Ala Val Thr Gly Thr His Gln
        915                 920                 925

Ala Thr Thr Pro Thr Ala Thr Thr Ala Asn Val Ala Pro Gln Phe Ser
```

```
            930                935                940
Trp Lys Val Gly Asp Gly Pro Tyr Asn His Trp Arg Thr Asp Gly Phe
945                 950                955                960

Val Gln Ala Val Ser Asp Gln Thr Ser Phe Thr Ala Tyr Ala Gln Val
                965                970                975

Pro Ala Gly Val Asp Trp Ile Val Tyr Ala Thr Asp Ala Met Thr Gly
            980                985                990

Lys Val Phe Ser Gly Lys Val Asp Thr Lys Thr Gly Asn Val Thr Phe
        995                1000               1005

Asn Leu Thr Ala Ser Ala Pro Tyr Gly Asp Phe Val Gly Thr Val
    1010                1015               1020

Leu Ala Pro Thr Ala Asp Phe Gly Thr Tyr Glu Gln Ala Gly Arg
    1025                1030               1035

Ala Asn Gly Asp Glu Met Val Val Phe Leu Asp Thr Asp Gly Thr
    1040                1045               1050

Ala Gly Tyr Gly His Phe Ser Gln Lys Asp Pro His Val Ala Val
    1055                1060               1065

Pro Leu Gln Asp Asn Ala Lys Ala Ala Asn Val Lys Thr Thr
    1070                1075               1080

Ser Gly Ala Pro Val Leu Gly Gly Arg Ala Phe Ser Gln Ile Thr
    1085                1090               1095

Thr His Ala Gln Pro Thr Ala Gly Leu Thr Phe Asp Lys Phe Asn
    1100                1105               1110

Asp Asn Ser Phe Thr Leu Val Gly Ala Asp Lys Val Ala Asp Ile
    1115                1120               1125

Tyr Asn Ala Lys Thr Gly Gln Leu Thr Ile Thr Gly His Val Asp
    1130                1135               1140

Gln Pro Ala Gly Lys Thr Leu Thr Val Thr Ser Ala Thr Glu Pro
    1145                1150               1155

Ala Lys Thr Val Thr Ile Gly Ala Asp Gly Lys Phe Ser Phe Thr
    1160                1165               1170

Val Pro Phe Lys Ala Ala Glu Gln Gln Ala Ile Gly Tyr Arg Leu
    1175                1180               1185

Thr Ser Pro Ala Thr Asp Gly Ser Lys Ser Thr Gln Thr Ala Tyr
    1190                1195               1200

Gly Glu Leu Gln Ile Tyr Leu Asp Thr Ile Phe Pro Thr Leu Asn
    1205                1210               1215

Met Pro Gln Ala Asp Thr Leu Gln Val Asp Asp Lys Gly Asn Tyr
    1220                1225               1230

Glu Ile Thr Thr Thr Ser Asp Thr Phe Thr Val Ser Gly Thr Val
    1235                1240               1245

Asn Asp Asn Ile Asn Gly Tyr Arg Leu Tyr Thr Asn Gly Asp Asn
    1250                1255               1260

Ile Val His Gln Lys Asn Leu Ala Gly Phe Asn Asn His Leu Asp
    1265                1270               1275

Pro Leu Ser Thr Thr Ser Asn Pro Tyr Gly Ala Ala Phe Thr
    1280                1285               1290

Gln Thr Tyr Gln Leu Ala Asp Gly Asp Asn Tyr Phe Thr Ile Thr
    1295                1300               1305

Ala Val Asp Met Val Gly Asn Lys Val Thr Lys Val Phe His Val
    1310                1315               1320

Ile Lys Thr Lys Ala Thr Thr Pro Thr Thr Pro Glu Thr Pro Lys
    1325                1330               1335
```

```
Thr Pro Thr Pro Thr Pro Lys Pro Gly Thr Gly Asp Gln Thr Asp
    1340                1345                1350

Thr Lys Asn Pro Lys Gly Pro Thr Thr Thr Pro Lys Thr Asp Glu
    1355                1360                1365

Gln Gly Lys Thr Asn Pro Thr Pro Lys Phe Val Asp Leu Thr Asn
    1370                1375                1380

Thr Thr Lys Gly Gln Asp Lys Thr Gly Thr Thr Ala Glu Thr Gly
    1385                1390                1395

Lys Asn Thr Lys Gln Thr Ala Ala Ala Lys Thr Met Pro Gln Ala
    1400                1405                1410

Gly Glu Ala Gln Ser Pro Leu Ala Val Leu Gly Leu Ala Ile Leu
    1415                1420                1425

Ser Met Leu Gly Leu Ala Gly Phe Val Ser Arg Lys Lys Arg Val
    1430                1435                1440

<210> SEQ ID NO 45
<211> LENGTH: 1532
<212> TYPE: PRT
<213> ORGANISM: Lactobacillus sp. HMSC068F07

<400> SEQUENCE: 45

Met Asn Lys Asn Ser Thr Thr Glu Met Lys Arg His Tyr Lys Met Tyr
1               5                   10                  15

Lys Ala Gly Ser Lys Trp Met Thr Ala Ala Ile Ile Thr Phe Gly Thr
                20                  25                  30

Ser Leu Ile Val Leu Gly Gly Thr Ala Thr Gln Ser Val Ala Ala Asp
            35                  40                  45

Thr Thr Thr Thr Pro Thr Glu Lys Thr Ser Gln Thr Ala Gln Ser Thr
        50                  55                  60

Ser Ala Gln Ser Gln Pro Ala Ala Gln Thr Thr Thr Ser Gln Ala Thr
65                  70                  75                  80

Ala Ser Asp Ala Thr Ser Ser Ala Thr Gln Thr Ala Ala Ala Asn Ser
                85                  90                  95

Ala Lys Ser Ser Thr Ala Gln Thr Gln Ala Ala Pro Ala Gln Asn Thr
                100                 105                 110

Gln Ser Ser Ala Ser Gln Pro Gln Ala Ala Thr Gln Gln Ala Ser Ser
            115                 120                 125

Ala Thr Ala Lys Thr Thr Ala Pro Ala Ser Gly Ala Thr Thr Gln Thr
        130                 135                 140

Asn Thr Ser Ser Val Ala Ser Gln Ala Thr Thr Ser Thr Ala Thr Thr
145                 150                 155                 160

Ala Thr Ser Gln Ala Ser Ala Ala Thr Ala Thr Ser Thr Ala Thr
                165                 170                 175

Ala Asp Asn Gln Ser Gln Ala Ser Ser Ala Ala Thr Thr Asp Pro Gly
                180                 185                 190

Pro Ala Asn Gln Asp Thr Leu Thr Lys Gly Asn Val Lys Gly Leu Trp
            195                 200                 205

Asp Glu Gly Tyr Gln Gly Gln Gly Met Val Val Ala Val Ile Asp Ser
        210                 215                 220

Gly Val Gln Pro His Ala Asp Leu Arg Leu Ser Asp Asp Ser Thr Ala
225                 230                 235                 240

Thr Leu Thr Lys Glu Lys Ala Glu Ala Ala Ile Ala Lys Leu Gly Tyr
                245                 250                 255

Gly Thr Tyr Val Asn Ser Lys Ile Pro Phe Ala Tyr Asp Tyr Val Asn
```

```
                260                 265                 270
Asn Asp Ser Val Asn Thr Gly Thr Thr Val Ala Gly Ser Thr His Gly
            275                 280                 285

Glu His Val Ala Gly Ile Ile Ala Ala Asn Gly Thr Thr Ala Asp Gly
            290                 295                 300

Ala Thr Gly Lys Glu Lys Ala Ser Thr Tyr Val Lys Gly Val Ala Pro
305                 310                 315                 320

Glu Ala Gln Ile Leu Ala Met Gln Val Ile Asp Glu Phe Pro Asp Glu
                325                 330                 335

Asn Ala Asn Asp Ile Ser Arg Ala Ile Arg Asp Ala Val Ala Leu Gly
            340                 345                 350

Ala Asn Ala Ile Gln Met Ser Leu Gly Ile Gly Val Thr Glu Gln Asp
            355                 360                 365

Leu Thr Asp Glu Glu Gln Ala Ala Val Gln Tyr Ala Thr Glu His Gly
            370                 375                 380

Val Phe Val Ser Ile Ser Ala Gly Asn Asn Ala Ile Ala Gly Ser Ile
385                 390                 395                 400

Ile Gly Ser Lys Thr Pro Asn Asp Ile Ser Thr Ala Tyr Ala Pro Lys
                405                 410                 415

Asn Asp Ser Thr Ile Gly Asp Pro Gly Ala Ala Ser Ala Met Thr
            420                 425                 430

Val Ala Ala Glu Thr Ser Ala Thr Gly Ala Asp Ser Gln Met Asp Gly
            435                 440                 445

Phe Ser Ser Trp Gly Pro Met Ala Asp Tyr Thr Leu Lys Pro Asp Ile
            450                 455                 460

Ser Ala Pro Gly Asp Asn Val Thr Ser Thr Ala Ile Asp Pro Ala Thr
465                 470                 475                 480

Asn Thr Gln Thr Tyr Ala Val Glu Ser Gly Thr Ser Met Ala Gly Pro
                485                 490                 495

Phe Asn Ala Gly Ala Ala Leu Leu Val Met Gln Lys Ile Lys Ala Thr
            500                 505                 510

Gln Pro Asp Leu Thr Gly Ala Asp Leu Val Lys Ala Val Lys Leu Ala
            515                 520                 525

Leu Met Asn Ala Ala Glu Pro Met Lys Asp Ile Asn Tyr Pro Asp Thr
            530                 535                 540

Tyr Ile Ser Pro Arg Arg Gln Gly Ala Gly Gln Ile Asp Val Ala Lys
545                 550                 555                 560

Ala Gly Asp Leu Thr Val Thr Ala Glu Gly Ser Asn Asp Ala Gly Ser
                565                 570                 575

Val Ser Leu Gly Lys Ile Gly Lys Thr Thr Phe Thr Val Thr Leu
            580                 585                 590

Thr Asn His Gly Lys Thr Ala Gln Asn Tyr Thr Val Asp Thr Asn Gly
            595                 600                 605

Gly Pro Leu Thr Gln Val Arg Asp Ala Ser Asn Gly Asn Thr Val His
            610                 615                 620

Asp Glu Thr Leu Val Gly Ala Thr Val Asn Thr Asp Thr Ala Asn Phe
625                 630                 635                 640

Thr Leu Ala Ala Gly Glu Thr Lys Lys Val Thr Phe Lys Leu Ser Leu
                645                 650                 655

Asp Asp Ser Val Ala Ala Asn Gln Leu Val Glu Gly Tyr Leu Thr Phe
            660                 665                 670

Lys Ala Thr Asp Ala Ala Gln Thr Ile Ser Val Pro Tyr Leu Gly Tyr
            675                 680                 685
```

```
Tyr Gly Asp Leu Thr Asp Glu Gln Val Ile Asp Ala Pro Ala Asn Ser
        690                 695                 700

Gly Glu Ser Ile Phe Asn Gly Gly Tyr Leu Val Asp Asn Asn Asn Asn
705                 710                 715                 720

Pro Leu Gly Val Thr Asp Ala Ala Ser Leu Ser Asn Leu Val Asn Thr
                    725                 730                 735

Asp Thr Thr Gly Lys Tyr Thr Trp Thr Leu Val Pro Thr Tyr Val Asp
                740                 745                 750

Asn Lys Lys Val Ser Phe Ser Pro Asn Gly Asp Gly Ala Ser Asp Thr
            755                 760                 765

Val Phe Pro Tyr Val Phe Ser Lys Gln Asn Leu Lys Ser Val Thr Ile
        770                 775                 780

Gln Ile Leu Asp Ala Gln Gly His Val Val Arg Ile Leu Asp Lys Glu
785                 790                 795                 800

Asn Asn Thr Ser Lys Ser Tyr Leu Gln Asn Gly Asn Ser Phe Asn Ser
                805                 810                 815

Asp Leu Gly Leu Ser Thr Asp Met Arg Leu Asp Pro Asn Ala Phe Thr
                820                 825                 830

Trp Asp Gly Lys Val Tyr Asp Gln Ala Thr Gly Lys Tyr Val Thr Ala
                835                 840                 845

Pro Asp Gly Lys Tyr Thr Tyr Arg Leu Val Thr Glu Gln Tyr Asn Thr
850                 855                 860

Gly Ala Gln Gln Asn Gln Asp Tyr Asp Leu Pro Val Thr Val Asp Thr
865                 870                 875                 880

Val Ala Pro Thr Leu Thr Gly Leu Ser Tyr Gln Asp Gly Arg Val Ser
                885                 890                 895

Val His Tyr Asp Asp Gln Gly Ala Gly Phe Thr Lys Phe Ser Asp Leu
                900                 905                 910

Ala Leu Lys Ile Gly Asn Lys Ala Tyr Gly Val Asn Leu Asn Asn Asn
                915                 920                 925

Gly Gln Asn Asn Asp Gly Thr Leu Ser Phe Glu Leu Thr Ala Ala Gln
930                 935                 940

Lys Ala Ala Leu Glu Asn Ser Asp Gly Ser Leu Thr Leu Thr Leu Thr
945                 950                 955                 960

Asp Val Ala Gly Asn Lys Thr Ser Ala Ser Leu Gln Ala Thr Ala Gly
                965                 970                 975

Thr His Gln Thr Asp Thr Thr Thr Pro Thr Ser Asp Val Ala Pro Gln
                980                 985                 990

Phe Thr Trp Lys Val Gly Asp Gly Pro His Asn Phe Trp Arg Ser Glu
                995                 1000                1005

Gly Phe Val Gln Ala Val Ser Asp Gln Thr Ser Phe Thr Ala Tyr
        1010                1015                1020

Ala Gln Val Pro Ala Gly Val Asp Trp Ile Val Tyr Ala Thr Asp
        1025                1030                1035

Ala Gln Thr Gly Lys Val Phe Pro Gly Thr Val Asp Thr Lys Thr
        1040                1045                1050

Gly Thr Val Thr Phe Asn Leu Thr Glu Ser Ala Pro Tyr Gly Asp
        1055                1060                1065

Phe Val Gly Thr Val Leu Ser Pro Thr Ala Asp Phe Gly Thr Tyr
        1070                1075                1080

Glu Glu Ala Gly Arg Ala Asp Gly Asp Glu Met Ile Val Phe Leu
        1085                1090                1095
```

```
Asp Ala Asn Gly Thr Ala Gly Tyr Gly His Phe Ser Gln Lys Asn
    1100                1105                1110

Val His Val Val Val Pro Leu Gln Asp Asn Ala Lys Ala Ala Ala
    1115                1120                1125

Asn Ala Thr Lys Thr Ser Gly Ala Pro Val Leu Gly Gly Arg Ala
    1130                1135                1140

Phe Ser Gln Ile Thr Thr His Ala Gln Pro Thr Ala Gly Leu Lys
    1145                1150                1155

Phe Asp Lys Phe Asn Asp Asn Ser Phe Thr Leu Val Gly Ala Asp
    1160                1165                1170

Gln Val Ala Asp Ile Tyr Asn Ala Gln Thr Gly Gln Leu Thr Ile
    1175                1180                1185

Thr Gly His Val Asp Asn Pro Ala Gly Lys Thr Leu Thr Val Thr
    1190                1195                1200

Asp Ala Thr Glu Pro Ala Lys Thr Val Ala Ile Gly Ala Asp Gly
    1205                1210                1215

Lys Phe Ser Phe Thr Val Pro Phe Lys Ala Ala Glu Gln Gln Ser
    1220                1225                1230

Val Gly Tyr Arg Leu Thr Glu Pro Ala Thr Asp Gly Ser Lys Ser
    1235                1240                1245

Thr Lys Thr Ala Tyr Gly Glu Leu Gln Ile Tyr Leu Asp Thr Ile
    1250                1255                1260

Phe Pro Thr Leu Asp Leu Pro Gln Ala Asp Thr Leu Lys Val Asp
    1265                1270                1275

Asp Gln Gly Asn Tyr Asp Ile Thr Thr Thr Ser Asp Thr Phe Thr
    1280                1285                1290

Val Ser Gly Thr Val Asn Asp Asn Ile Asn Gly Tyr Arg Leu Tyr
    1295                1300                1305

Thr Asn Gly Asp Asn Val Val His Gln Lys Asn Leu Ala Gly Phe
    1310                1315                1320

Asn Asn His Leu Asp Pro Gln Ser Thr Thr Ser Asn Pro Tyr Gly
    1325                1330                1335

Ala Ala Asp Phe Asn Gln Thr Tyr Thr Leu Lys Asp Gly Asp Asn
    1340                1345                1350

Tyr Phe Thr Val Thr Ala Val Asp Met Val Gly Asn Lys Val Thr
    1355                1360                1365

Lys Val Phe His Val Val Lys Val Lys Thr Pro Thr Pro Thr Pro
    1370                1375                1380

Gly Asp Asn Gly Asn Thr Ser Gly Thr Asp Asn Ser Gly Asn Gly
    1385                1390                1395

Asn Pro Asn Gln Gln Gly Thr Gly Gly Asn Ala Gly Asn Gln Gly
    1400                1405                1410

Gly Asn Ala Gly Asn Gln Gly Asn Asn Gly Gly Thr Gln Gly Gly
    1415                1420                1425

Asn Gly Ser Gly Gln Thr Pro Ala Thr Gly Asn Gly Thr Pro Thr
    1430                1435                1440

Thr Pro Thr Thr Gly Thr Gly Thr Asn Gly Gly Asn Gly Asn Asn
    1445                1450                1455

Arg Gln Gln Ser Pro Glu Leu Val Thr Leu Asp Asn Lys Leu Lys
    1460                1465                1470

Asp Gln Thr Lys Thr Pro Ala Ala Lys Asn Gly Thr Thr Ala Asn
    1475                1480                1485

Gly Thr Lys Gln Ala Ala Thr Gly Lys Thr Met Pro Gln Ala Gly
```

```
                    1490               1495               1500

Glu Ser   Gln Ser Pro Leu Ala   Val Ile Gly Leu Ala   Ile Val Ser
          1505              1510              1515

Ile Phe   Ser Phe Met Gly Phe   Ala Ser Arg Lys Lys   Arg Val
1520                 1525                  1530

<210> SEQ ID NO 46
<211> LENGTH: 1481
<212> TYPE: PRT
<213> ORGANISM: Artificial Sequence
<220> FEATURE:
<223> OTHER INFORMATION: fragment of Lactobacillus sp. HMSC068F07
      protease

<400> SEQUENCE: 46

Thr Pro Thr Glu Lys Thr Ser Gln Thr Ala Gln Ser Thr Ser Ala Gln
1               5                   10                  15

Ser Gln Pro Ala Ala Gln Thr Thr Thr Ser Gln Ala Thr Ala Ser Asp
            20                  25                  30

Ala Thr Ser Ser Ala Thr Gln Thr Ala Ala Asn Ser Ala Lys Ser
        35                  40                  45

Ser Thr Ala Gln Thr Gln Ala Ala Pro Ala Gln Asn Thr Gln Ser Ser
    50                  55                  60

Ala Ser Gln Pro Gln Ala Ala Thr Gln Gln Ala Ser Ser Ala Thr Ala
65                  70                  75                  80

Lys Thr Thr Ala Pro Ala Ser Gly Ala Thr Thr Gln Thr Asn Thr Ser
                85                  90                  95

Ser Val Ala Ser Gln Ala Thr Thr Ser Thr Ala Thr Thr Ala Thr Ser
            100                 105                 110

Gln Ala Ser Ala Ala Thr Ala Thr Ser Thr Ala Thr Ala Asp Asn
        115                 120                 125

Gln Ser Gln Ala Ser Ser Ala Ala Thr Asp Pro Gly Pro Ala Asn
130                 135                 140

Gln Asp Thr Leu Thr Lys Gly Asn Val Lys Gly Leu Trp Asp Glu Gly
145                 150                 155                 160

Tyr Gln Gly Gln Gly Met Val Val Ala Val Ile Asp Ser Gly Val Gln
                165                 170                 175

Pro His Ala Asp Leu Arg Leu Ser Asp Asp Ser Thr Ala Thr Leu Thr
            180                 185                 190

Lys Glu Lys Ala Glu Ala Ala Ile Ala Lys Leu Gly Tyr Gly Thr Tyr
        195                 200                 205

Val Asn Ser Lys Ile Pro Phe Ala Tyr Asp Tyr Val Asn Asn Asp Ser
    210                 215                 220

Val Asn Thr Gly Thr Thr Val Ala Gly Ser Thr His Gly Glu His Val
225                 230                 235                 240

Ala Gly Ile Ile Ala Ala Asn Gly Thr Thr Ala Asp Gly Ala Thr Gly
                245                 250                 255

Lys Glu Lys Ala Ser Thr Tyr Val Lys Gly Val Ala Pro Glu Ala Gln
            260                 265                 270

Ile Leu Ala Met Gln Val Ile Asp Glu Phe Pro Asp Glu Asn Ala Asn
        275                 280                 285

Asp Ile Ser Arg Ala Ile Arg Asp Ala Val Ala Leu Gly Ala Asn Ala
    290                 295                 300

Ile Gln Met Ser Leu Gly Ile Gly Val Thr Glu Gln Asp Leu Thr Asp
305                 310                 315                 320
```

```
Glu Glu Gln Ala Ala Val Gln Tyr Ala Thr Glu His Gly Val Phe Val
            325                 330                 335

Ser Ile Ser Ala Gly Asn Asn Ala Ile Ala Gly Ser Ile Ile Gly Ser
            340                 345                 350

Lys Thr Pro Asn Asp Ile Ser Thr Ala Tyr Ala Pro Lys Asn Asp Ser
            355                 360                 365

Thr Ile Gly Asp Pro Gly Ala Ala Ser Ala Met Thr Val Ala Ala
    370                 375                 380

Glu Thr Ser Ala Thr Gly Ala Asp Ser Gln Met Asp Gly Phe Ser Ser
385                 390                 395                 400

Trp Gly Pro Met Ala Asp Tyr Thr Leu Lys Pro Asp Ile Ser Ala Pro
                405                 410                 415

Gly Asp Asn Val Thr Ser Thr Ala Ile Asp Pro Ala Thr Asn Thr Gln
            420                 425                 430

Thr Tyr Ala Val Glu Ser Gly Thr Ser Met Ala Gly Pro Phe Asn Ala
            435                 440                 445

Gly Ala Ala Leu Leu Val Met Gln Lys Ile Lys Ala Thr Gln Pro Asp
    450                 455                 460

Leu Thr Gly Ala Asp Leu Val Lys Ala Val Lys Leu Ala Leu Met Asn
465                 470                 475                 480

Ala Ala Glu Pro Met Lys Asp Ile Asn Tyr Pro Asp Thr Tyr Ile Ser
                485                 490                 495

Pro Arg Arg Gln Gly Ala Gly Gln Ile Asp Val Ala Lys Ala Gly Asp
            500                 505                 510

Leu Thr Val Thr Ala Glu Gly Ser Asn Asp Ala Gly Ser Val Ser Leu
            515                 520                 525

Gly Lys Ile Gly Lys Thr Thr Thr Phe Thr Val Thr Leu Thr Asn His
    530                 535                 540

Gly Lys Thr Ala Gln Asn Tyr Thr Val Asp Thr Asn Gly Gly Pro Leu
545                 550                 555                 560

Thr Gln Val Arg Asp Ala Ser Asn Gly Asn Thr Val His Asp Glu Thr
                565                 570                 575

Leu Val Gly Ala Thr Val Asn Thr Asp Thr Ala Asn Phe Thr Leu Ala
            580                 585                 590

Ala Gly Glu Thr Lys Lys Val Thr Phe Lys Leu Ser Leu Asp Asp Ser
    595                 600                 605

Val Ala Ala Asn Gln Leu Val Glu Gly Tyr Leu Thr Phe Lys Ala Thr
610                 615                 620

Asp Ala Ala Gln Thr Ile Ser Val Pro Tyr Leu Gly Tyr Tyr Gly Asp
625                 630                 635                 640

Leu Thr Asp Glu Gln Val Ile Asp Ala Pro Ala Asn Ser Gly Glu Ser
                645                 650                 655

Ile Phe Asn Gly Gly Tyr Leu Val Asp Asn Asn Asn Pro Leu Gly
            660                 665                 670

Val Thr Asp Ala Ala Ser Leu Ser Asn Leu Val Asn Thr Asp Thr Thr
    675                 680                 685

Gly Lys Tyr Thr Trp Thr Leu Val Pro Thr Tyr Val Asp Asn Lys Lys
690                 695                 700

Val Ser Phe Ser Pro Asn Gly Asp Gly Ala Ser Asp Thr Val Phe Pro
705                 710                 715                 720

Tyr Val Phe Ser Lys Gln Asn Leu Lys Ser Val Thr Ile Gln Ile Leu
                725                 730                 735

Asp Ala Gln Gly His Val Val Arg Ile Leu Asp Lys Glu Asn Asn Thr
```

```
                740                 745                 750
Ser Lys Ser Tyr Leu Gln Asn Gly Asn Ser Phe Asn Ser Asp Leu Gly
            755                 760                 765

Leu Ser Thr Asp Met Arg Leu Asp Pro Asn Ala Phe Thr Trp Asp Gly
        770                 775                 780

Lys Val Tyr Asp Gln Ala Thr Gly Lys Tyr Val Thr Ala Pro Asp Gly
785                 790                 795                 800

Lys Tyr Thr Tyr Arg Leu Val Thr Glu Gln Tyr Asn Thr Gly Ala Gln
                805                 810                 815

Gln Asn Gln Asp Tyr Asp Leu Pro Val Thr Val Asp Thr Val Ala Pro
            820                 825                 830

Thr Leu Thr Gly Leu Ser Tyr Gln Asp Gly Arg Val Ser Val His Tyr
        835                 840                 845

Asp Asp Gln Gly Ala Gly Phe Thr Lys Phe Ser Asp Leu Ala Leu Lys
850                 855                 860

Ile Gly Asn Lys Ala Tyr Gly Val Asn Leu Asn Asn Asn Gly Gln Asn
865                 870                 875                 880

Asn Asp Gly Thr Leu Ser Phe Glu Leu Thr Ala Ala Gln Lys Ala Ala
            885                 890                 895

Leu Glu Asn Ser Asp Gly Ser Leu Thr Leu Thr Leu Thr Asp Val Ala
        900                 905                 910

Gly Asn Lys Thr Ser Ala Ser Leu Gln Ala Thr Ala Gly Thr His Gln
        915                 920                 925

Thr Asp Thr Thr Thr Pro Thr Ser Asp Val Ala Pro Gln Phe Thr Trp
    930                 935                 940

Lys Val Gly Asp Gly Pro His Asn Phe Trp Arg Ser Glu Gly Phe Val
945                 950                 955                 960

Gln Ala Val Ser Asp Gln Thr Ser Phe Thr Ala Tyr Ala Gln Val Pro
                965                 970                 975

Ala Gly Val Asp Trp Ile Val Tyr Ala Thr Asp Ala Gly Thr Gly Lys
            980                 985                 990

Val Phe Pro Gly Thr Val Asp Thr  Lys Thr Gly Thr Val  Thr Phe Asn
        995                 1000                1005

Leu Thr  Glu Ser Ala Pro Tyr  Gly Asp Phe Val Gly  Thr Val Leu
    1010                1015                1020

Ser Pro  Thr Ala Asp Phe Gly  Thr Tyr Glu Glu Ala  Gly Arg Ala
    1025                1030                1035

Asp Gly  Asp Glu Met Ile Val  Phe Leu Asp Ala Asn  Gly Thr Ala
    1040                1045                1050

Gly Tyr  Gly His Phe Ser Gln  Lys Asn Val His Val  Val Val Pro
    1055                1060                1065

Leu Gln  Asp Asn Ala Lys Ala  Ala Ala Asn Ala Thr  Lys Thr Ser
    1070                1075                1080

Gly Ala  Pro Val Leu Gly Gly  Arg Ala Phe Ser Gln  Ile Thr Thr
    1085                1090                1095

His Ala  Gln Pro Thr Ala Gly  Leu Lys Phe Asp Lys  Phe Asn Asp
    1100                1105                1110

Asn Ser  Phe Thr Leu Val Gly  Ala Asp Gln Val Ala  Asp Ile Tyr
    1115                1120                1125

Asn Ala  Gln Thr Gly Gln Leu  Thr Ile Thr Gly His  Val Asp Asn
    1130                1135                1140

Pro Ala  Gly Lys Thr Leu Thr  Val Thr Asp Ala Thr  Glu Pro Ala
    1145                1150                1155
```

| | | | | | | | | | |
|---|---|---|---|---|---|---|---|---|---|
| Lys | Thr | Val | Ala | Ile | Gly | Ala | Asp | Gly | Lys | Phe | Ser | Phe | Thr | Val |
| | 1160 | | | | 1165 | | | | 1170 | | | |

Lys Thr Val Ala Ile Gly Ala Asp Gly Lys Phe Ser Phe Thr Val
    1160                1165                1170

Pro Phe Lys Ala Ala Glu Gln Gln Ser Val Gly Tyr Arg Leu Thr
    1175                1180                1185

Glu Pro Ala Thr Asp Gly Ser Lys Ser Thr Lys Thr Ala Tyr Gly
    1190                1195                1200

Glu Leu Gln Ile Tyr Leu Asp Thr Ile Phe Pro Thr Leu Asp Leu
    1205                1210                1215

Pro Gln Ala Asp Thr Leu Lys Val Asp Asp Gln Gly Asn Tyr Asp
    1220                1225                1230

Ile Thr Thr Thr Ser Asp Thr Phe Thr Val Ser Gly Thr Val Asn
    1235                1240                1245

Asp Asn Ile Asn Gly Tyr Arg Leu Tyr Thr Asn Gly Asp Asn Val
    1250                1255                1260

Val His Gln Lys Asn Leu Ala Gly Phe Asn Asn His Leu Asp Pro
    1265                1270                1275

Gln Ser Thr Thr Ser Asn Pro Tyr Gly Ala Ala Asp Phe Asn Gln
    1280                1285                1290

Thr Tyr Thr Leu Lys Asp Gly Asp Asn Tyr Phe Thr Val Thr Ala
    1295                1300                1305

Val Asp Met Val Gly Asn Lys Val Thr Lys Val Phe His Val Val
    1310                1315                1320

Lys Val Lys Thr Pro Thr Pro Thr Pro Gly Asp Asn Gly Asn Thr
    1325                1330                1335

Ser Gly Thr Asp Asn Ser Gly Asn Gly Asn Pro Asn Gln Gln Gly
    1340                1345                1350

Thr Gly Gly Asn Ala Gly Asn Gln Gly Gly Asn Ala Gly Asn Gln
    1355                1360                1365

Gly Asn Asn Gly Gly Thr Gln Gly Gly Asn Gly Ser Gly Gln Thr
    1370                1375                1380

Pro Ala Thr Gly Asn Gly Thr Pro Thr Thr Pro Thr Thr Gly Thr
    1385                1390                1395

Gly Thr Asn Gly Gly Asn Gly Asn Asn Arg Gln Gln Ser Pro Glu
    1400                1405                1410

Leu Val Thr Leu Asp Asn Lys Leu Lys Asp Gln Thr Lys Thr Pro
    1415                1420                1425

Ala Ala Lys Asn Gly Thr Thr Ala Asn Gly Thr Lys Gln Ala Ala
    1430                1435                1440

Thr Gly Lys Thr Met Pro Gln Ala Gly Glu Ser Gln Ser Pro Leu
    1445                1450                1455

Ala Val Ile Gly Leu Ala Ile Val Ser Ile Phe Ser Phe Met Gly
    1460                1465                1470

Phe Ala Ser Arg Lys Lys Arg Val
    1475                1480

<210> SEQ ID NO 47
<211> LENGTH: 1658
<212> TYPE: PRT
<213> ORGANISM: Enterococcus sp. HMSC069A01

<400> SEQUENCE: 47

Met Arg Arg Asn Ser Met Thr Glu Met Lys Arg His Tyr Lys Leu Tyr
1               5                   10                  15

Lys Ser Gly Ser Lys Gly Val Ala Ala Ala Ile Ile Thr Val Ser Ala

-continued

```
               20                  25                  30
Gly Ala Ile Val Leu Ser Gly Tyr Ala Thr Gln Ser Val Ser Ala Asp
            35                  40                  45
Thr Thr Ala Ala Ala Thr Val Gln Thr Gln Thr Asp Thr Glu Thr Thr
 50                  55                  60
Gly Gln Ser Ser Thr Ala Val Asp Asp Ala Gln Asn Ala Ala Asp Asn
 65                  70                  75                  80
His Thr Gln Ser Ser Thr Ala Thr Glu Glu Gly Thr Thr Pro Ala Thr
                85                  90                  95
Thr Thr Ser Gln Ser Gln Ala Gly Ser Ser Ala Thr Thr Ser Gly Ala
            100                 105                 110
Thr Ala Thr Ala Thr Ser Gly Ala Ser Ala Ser Ser Ser Ser Ala
            115                 120                 125
Ala Thr Thr Leu Ala Ala Thr Val Gln Thr Gln Thr Asp Thr Glu Thr
            130                 135                 140
Thr Gly Gln Ser Ser Thr Ala Val Asp Asp Ala Gln Asn Ala Ala Asp
145                 150                 155                 160
Asn His Thr Gln Ser Ser Thr Ala Thr Glu Glu Gly Thr Thr Pro Ala
                165                 170                 175
Thr Thr Thr Ser Gln Ser Gln Ala Gly Ser Ser Ala Ala Thr Ser Gly
                180                 185                 190
Ala Thr Ala Thr Ser Gly Ala Ser Ala Ser Ser Ser Ala Ala Thr
            195                 200                 205
Thr Leu Ala Ala Thr Val Gln Thr Gln Thr Asp Thr Glu Thr Thr Gly
            210                 215                 220
Gln Ser Ser Thr Ala Val Asp Asp Ala Gln Asn Ala Ala Asp Asn His
225                 230                 235                 240
Thr Gln Ser Ser Thr Ala Thr Glu Glu Gly Thr Thr Pro Ala Gln Ser
                245                 250                 255
Ser Ala Thr Ala Ser Gln Ala Thr Pro Ala Thr Thr Ser Gln Ser
            260                 265                 270
Gln Ala Gly Ser Ser Ala Ala Thr Ser Gly Ala Thr Ala Thr Ser Gly
            275                 280                 285
Ala Ser Ala Ser Ser Ser Ala Ala Thr Thr Thr Pro Ala Ala
            290                 295                 300
Thr Thr Thr Ala Gln Ala Thr Ala Asp Ala Thr Ala Asp Pro Gly Pro
305                 310                 315                 320
Ala Asn Gln Asp Thr Leu Thr Lys Gly Asn Val Glu Gly Leu Trp Asn
                325                 330                 335
Glu Gly Tyr Gln Gly Gln Gly Met Val Val Ala Val Ile Asp Ser Gly
                340                 345                 350
Val Gln Pro His Ala Asp Leu Arg Leu Thr Asp Asp Ser Thr Ala Ala
                355                 360                 365
Ile Ser Lys Asp Ala Ala Glu Ala Ala Ile Ala Lys Leu Gly Tyr Gly
                370                 375                 380
Thr Tyr Val Asn Ser Lys Ile Pro Phe Ala Tyr Asp Tyr Val Asn Asn
385                 390                 395                 400
Asp Ser Val Asn Thr Gly Thr Val Ser Gly Ser Thr His Gly Glu
                405                 410                 415
His Val Ala Gly Ile Ile Ala Ala Asn Gly Thr Val Ala Asp Gly Ala
                420                 425                 430
Thr Gly Thr Ser Lys Ala Ser Val Tyr Val Lys Gly Val Ala Pro Glu
                435                 440                 445
```

```
Ala Gln Ile Leu Ala Met Gln Val Ile Asp Glu Phe Pro Asp Glu Asn
    450                 455                 460

Ala Asn Asp Ile Ser Arg Ala Ile Arg Asp Ala Val Ser Met Gly Ala
465                 470                 475                 480

Asn Ala Ile Gln Met Ser Leu Gly Val Gly Val Ala Glu Gln Asp Leu
                    485                 490                 495

Thr Asp Glu Glu Gln Ala Ala Val Gln Tyr Ala Thr Asp His Gly Val
                500                 505                 510

Phe Val Ser Ile Ser Ala Ser Asn Asn Gly Asn Ala Ala Ser Ile Val
            515                 520                 525

Gly Ser Asp Lys Lys Asn Asp Ile Ser Thr Ala Tyr Val Pro Lys Asn
    530                 535                 540

Asp Ser Thr Ile Ala Asp Pro Gly Ala Ala Ser Ala Met Thr Val
545                 550                 555                 560

Ala Ala Glu Lys Ser Ala Thr Gly Ala Asp Ser Glu Met Asp Gly Phe
                565                 570                 575

Ser Ser Trp Gly Pro Met Ala Asp Tyr Thr Leu Lys Pro Asp Ile Ala
            580                 585                 590

Ala Pro Gly Asp Arg Val Thr Ser Thr Ala Ile Asp Pro Lys Thr Asn
    595                 600                 605

Thr Gln Thr Tyr Ala Val Glu Ser Gly Thr Ser Met Ala Gly Pro Tyr
    610                 615                 620

Asp Ala Gly Ala Ala Leu Leu Val Met Gln Lys Leu Lys Ala Thr Arg
625                 630                 635                 640

Pro Glu Leu Gln Gly Ala Asp Leu Val Lys Ala Val Lys Leu Ala Leu
                645                 650                 655

Met Asn Ala Ala Asp Pro Met Ile Asp Leu Asn Tyr Pro Asp Thr Tyr
                660                 665                 670

Val Ser Pro Arg Arg Gln Gly Ala Gly Gln Ile Asp Val Thr Lys Ala
            675                 680                 685

Gly Asn Leu Asp Val Ala Ala Glu Gly Thr Asn Asn Ala Gly Ser Val
    690                 695                 700

Ser Leu Gly Lys Ile Gly Arg Thr Thr Ser Phe Asn Val Thr Leu Thr
705                 710                 715                 720

Asn Tyr Gly Gln Thr Thr Gln Ser Tyr Thr Val Asp Tyr Asp Gly Gly
                725                 730                 735

Pro Leu Thr Gln Val Arg Asp Thr Ser Lys Gly Asn Ile Val His Asp
                740                 745                 750

Gln Lys Leu Ala Gly Ala Ala Val Asn Ser Ala Thr Pro Thr Phe Thr
            755                 760                 765

Leu Ala Pro Gly Ala Ser Lys Val Val Thr Phe Thr Leu Thr Leu Asp
    770                 775                 780

Asp Ala Val Ala Ala Asn Gln Ile Val Glu Gly Tyr Leu Thr Phe Lys
785                 790                 795                 800

Ala Gly Asp Asp Thr Gln Thr Ile Ser Val Pro Tyr Leu Gly Tyr Phe
                805                 810                 815

Gly Asp Leu Thr Thr Glu Gln Ile Ile Asp Asp Pro Ala Asn Lys Gln
                820                 825                 830

Asp Ser Ile Phe Lys Gly Gly Tyr Leu Val Asp Asn Asn Asn Pro
            835                 840                 845

Leu Gly Val Thr Asp Ala Ala Ser Leu Ser Asn Leu Val Asn Ser Asp
    850                 855                 860
```

```
Val Thr Gly Lys Tyr Thr Trp Gly Gln Val Pro Ala Tyr Ile Glu Asn
865                 870                 875                 880

Gly Lys Val Ser Phe Ser Pro Asn Gly Asp Gly Ala Ser Asp Thr Val
                885                 890                 895

Tyr Pro Tyr Val Phe Ala Lys Gln Asn Leu Lys Ala Val Thr Ile Gln
            900                 905                 910

Ile Leu Asp Ala Asn Gly Asn Leu Val Arg Val Leu Asp Lys Glu Asn
        915                 920                 925

Asn Thr Thr Lys Ser Tyr Leu Gln Asn Gly Phe Ser His Asn Ser Asp
    930                 935                 940

Leu Gly Leu Ser Thr Asp Met Arg Leu Asp Ala Asp Ala Phe Thr Trp
945                 950                 955                 960

Asp Gly Arg Ile Tyr Asp Gln Gln Thr Gly Lys Tyr Ile Thr Ala Pro
                965                 970                 975

Asp Gly Arg Tyr Thr Tyr Arg Ile Val Thr Glu Gln Tyr Asn Asp Gly
            980                 985                 990

Ala Glu Gln Glu Gln Asn Phe Asp Leu Pro Val Ala Val Asp Thr Val
        995                 1000                1005

Ala Pro Thr Leu Thr Gly Leu Thr Tyr Ala Glu Gly Gln Leu Thr
    1010            1015                1020

Ala Ser Tyr Asn Asp Gln Gly Ala Gly Phe Ser Gln Phe Ser Asp
    1025            1030                1035

Ala Val Leu Lys Ile Gly Ala Gln Glu Tyr Gly Val Ser Leu Asp
    1040            1045                1050

Asn Asn Gly Gln Ser Asn Ala Gly Thr Ile Ser Phe Lys Leu Thr
    1055            1060                1065

Ala Ala Gln Met Ala Ala Leu Ala Thr Ser Asp Gly Gln Leu Thr
    1070            1075                1080

Leu Thr Val Thr Asp Val Ala Gly Asn His Thr Ser Ala Ser Val
    1085            1090                1095

Gln Ala Phe Ala Gly Thr Thr Ser Ala Ser Ala Thr Asp Thr Ala
    1100            1105                1110

Ala Asn Val Ala Pro Gln Phe Ser Trp Gln Val Gly Asp Gly Ser
    1115            1120                1125

Asn Asn Tyr Trp Arg Thr Asn Gly Phe Val Gln Ala Val Ser Asp
    1130            1135                1140

Gln Thr Ser Phe Thr Thr Tyr Ala Gln Val Pro Ala Gly Val Asp
    1145            1150                1155

Trp Ile Val Tyr Ala Thr Asp Ala Arg Ala Gly Lys Val Phe Pro
    1160            1165                1170

Gly Lys Val Asp Thr Ala Thr Gly Ile Val Thr Phe Asn Leu Thr
    1175            1180                1185

Glu Gly Ala Pro Tyr Gly Asp Phe Val Gly Thr Val Leu Tyr Pro
    1190            1195                1200

Thr Ala Asn Phe Gly Glu Tyr Lys Arg Ala Gly Arg Ala Asp Gly
    1205            1210                1215

Asp Glu Met Ile Val Phe Leu Asp Ala Asp Gly Thr Ala Gly Tyr
    1220            1225                1230

Gly His Phe Ser Thr Thr Asn Pro His Thr Val Ile Ala Leu Arg
    1235            1240                1245

Asp Asn Ala Asp Ala Ala Asp Ala Thr Val Thr Thr Gly Ala
    1250            1255                1260

Pro Val Leu Ser Gly Arg Ala Phe Ala Asp Ile Thr Thr His Ala
```

```
                 1265                1270                1275
Gln Pro Thr Ala Gly Leu Ser Phe Asp Lys Phe Asn Asp Asn Thr
                 1280                1285                1290
Phe Thr Leu Val Gly Ala Asp Gln Val Ala Asp Val Tyr Asp Pro
                 1295                1300                1305
Gln Thr Gly Glu Leu Thr Ile Thr Gly Lys Val Ala Asp Pro Ala
                 1310                1315                1320
Gly Lys Ala Met Thr Val Thr Asp Ala Thr Glu Pro Thr Lys Ala
                 1325                1330                1335
Val Ala Ile Asn Ala Asp Gly Thr Phe Ser Phe Thr Val Pro Phe
                 1340                1345                1350
Lys Ala Ala Glu Gln Gln Ser Val Gly Tyr Arg Leu Thr Thr Thr
                 1355                1360                1365
Thr Thr Asn Asp Asp Gly Thr Thr Ala Ser Ser Thr Ala Tyr Gly
                 1370                1375                1380
Ala Leu Gln Ile Tyr Leu Asp Thr Val Phe Pro Thr Leu Ser Met
                 1385                1390                1395
Pro Gln Ala Asp Thr Leu Thr Val Asp Ala Asp Gly Asn Tyr Asp
                 1400                1405                1410
Ile Thr Thr Ser Asp Pro Thr Phe Thr Val Thr Gly Thr Val Asn
                 1415                1420                1425
Asp Asn Val Asn Gly Tyr Arg Leu Tyr Thr Asn Gly Asp Asn Val
                 1430                1435                1440
Val His Gln Lys Asn Leu Ala Gly Phe Asn Asn His Val Asp Ala
                 1445                1450                1455
Asp Ala Ala Ser Ser Asn Pro Tyr Gly Ala Ala Asp Phe Ser Gln
                 1460                1465                1470
Thr Tyr Asn Leu Leu Glu Gly Asp Asn Tyr Phe Thr Val Thr Ala
                 1475                1480                1485
Val Asp Met Val Gly Asn Thr Ile Thr Lys Val Phe His Val Val
                 1490                1495                1500
Arg Val Asp Ala Thr Ser Val Thr Pro Lys Ser Gln Gly Ser Lys
                 1505                1510                1515
Gly Thr Ala Ile Thr Ser Pro Val Val Asp Gly Gly Gln Arg Gly
                 1520                1525                1530
Gln Ala Gln Gly Ala Pro Asp Val His Pro Ala Ala Pro Gly Tyr
                 1535                1540                1545
Lys Asn Asp Gly Gln Gly Gly Val Gln Leu Val Pro Ala Ala Ile
                 1550                1555                1560
Thr Ser Pro Gly Val Asp Gly Gly Gln Arg Gly Gln Ala Gln Gly
                 1565                1570                1575
Ala Pro Asp Val His Pro Ala Ala Pro Gly Tyr Lys Asn Asp Gly
                 1580                1585                1590
Gln Gly Gly Val Gln Leu Val Pro Ala Ala Ser Gln Ala Gly Arg
                 1595                1600                1605
Ser Gly Thr Glu Gln Gly Gln Ser Pro Ala Thr Thr Thr Ala Ala
                 1610                1615                1620
Ala Leu Pro Ala Thr Gly Glu Thr His Ser Pro Leu Ala Ala Ile
                 1625                1630                1635
Gly Leu Ala Ile Leu Ser Val Leu Gly Leu Ala Gly Leu Ala Ser
                 1640                1645                1650
Arg Lys Arg Arg Val
                 1655
```

<210> SEQ ID NO 48
<211> LENGTH: 1603
<212> TYPE: PRT
<213> ORGANISM: Artificial Sequence
<220> FEATURE:
<223> OTHER INFORMATION: fragment of Enterococcus sp. HMSC069A01 protease

<400> SEQUENCE: 48

```
Gln Thr Gln Thr Asp Thr Glu Thr Thr Gly Gln Ser Ser Thr Ala Val
1               5                   10                  15

Asp Asp Ala Gln Asn Ala Ala Asp Asn His Thr Gln Ser Ser Thr Ala
            20                  25                  30

Thr Glu Glu Gly Thr Thr Pro Ala Thr Thr Thr Ser Gln Ser Gln Ala
        35                  40                  45

Gly Ser Ser Ala Thr Thr Ser Gly Ala Thr Ala Thr Thr Ala Thr Ser
    50                  55                  60

Gly Ala Ser Ala Ser Ser Ser Ala Ala Thr Thr Leu Ala Ala Thr
65                  70                  75                  80

Val Gln Thr Gln Thr Asp Thr Glu Thr Thr Gly Gln Ser Ser Thr Ala
                85                  90                  95

Val Asp Asp Ala Gln Asn Ala Ala Asp Asn His Thr Gln Ser Ser Thr
            100                 105                 110

Ala Thr Glu Glu Gly Thr Thr Pro Ala Thr Thr Thr Ser Gln Ser Gln
        115                 120                 125

Ala Gly Ser Ser Ala Ala Thr Ser Gly Ala Thr Ala Thr Ser Gly Ala
    130                 135                 140

Ser Ala Ser Ser Ser Ala Ala Thr Thr Leu Ala Ala Thr Val Gln
145                 150                 155                 160

Thr Gln Thr Asp Thr Glu Thr Thr Gly Gln Ser Ser Thr Ala Val Asp
                165                 170                 175

Asp Ala Gln Asn Ala Ala Asp Asn His Thr Gln Ser Ser Thr Ala Thr
            180                 185                 190

Glu Glu Gly Thr Thr Pro Ala Gln Ser Ser Ala Thr Ala Ser Gln Ala
        195                 200                 205

Thr Pro Ala Thr Thr Thr Ser Gln Ser Gln Ala Gly Ser Ser Ala Ala
    210                 215                 220

Thr Ser Gly Ala Thr Ala Thr Ser Gly Ala Ser Ala Ser Ser Ser Ser
225                 230                 235                 240

Ala Ala Thr Thr Thr Pro Ala Ala Thr Thr Thr Ala Gln Ala Thr
                245                 250                 255

Ala Asp Ala Thr Ala Asp Pro Gly Pro Ala Asn Gln Asp Thr Leu Thr
            260                 265                 270

Lys Gly Asn Val Glu Gly Leu Trp Asn Glu Gly Tyr Gln Gly Gln Gly
        275                 280                 285

Met Val Val Ala Val Ile Asp Ser Gly Val Gln Pro His Ala Asp Leu
    290                 295                 300

Arg Leu Thr Asp Asp Ser Thr Ala Ala Ile Ser Lys Asp Ala Ala Glu
305                 310                 315                 320

Ala Ala Ile Ala Lys Leu Gly Tyr Gly Thr Tyr Val Asn Ser Lys Ile
                325                 330                 335

Pro Phe Ala Tyr Asp Tyr Val Asn Asn Asp Ser Val Asn Thr Gly Thr
            340                 345                 350

Thr Val Ser Gly Ser Thr His Gly Glu His Val Ala Gly Ile Ile Ala
```

```
                355                 360                 365
Ala Asn Gly Thr Val Ala Asp Gly Ala Thr Gly Thr Ser Lys Ala Ser
370                 375                 380

Val Tyr Val Lys Gly Val Ala Pro Glu Ala Gln Ile Leu Ala Met Gln
385                 390                 395                 400

Val Ile Asp Glu Phe Pro Asp Glu Asn Ala Asn Asp Ile Ser Arg Ala
                405                 410                 415

Ile Arg Asp Ala Val Ser Met Gly Ala Asn Ala Ile Gln Met Ser Leu
                420                 425                 430

Gly Val Gly Val Ala Glu Gln Asp Leu Thr Asp Glu Glu Gln Ala Ala
                435                 440                 445

Val Gln Tyr Ala Thr Asp His Gly Val Phe Val Ser Ile Ser Ala Ser
                450                 455                 460

Asn Asn Gly Asn Ala Ala Ser Ile Val Gly Ser Asp Lys Lys Asn Asp
465                 470                 475                 480

Ile Ser Thr Ala Tyr Val Pro Lys Asn Asp Ser Thr Ile Ala Asp Pro
                485                 490                 495

Gly Ala Ala Ser Ala Met Thr Val Ala Ala Glu Lys Ser Ala Thr
                500                 505                 510

Gly Ala Asp Ser Glu Met Asp Gly Phe Ser Ser Trp Gly Pro Met Ala
                515                 520                 525

Asp Tyr Thr Leu Lys Pro Asp Ile Ala Ala Pro Gly Asp Arg Val Thr
                530                 535                 540

Ser Thr Ala Ile Asp Pro Lys Thr Asn Thr Gln Thr Tyr Ala Val Glu
545                 550                 555                 560

Ser Gly Thr Ser Met Ala Gly Pro Tyr Asp Ala Gly Ala Ala Leu Leu
                565                 570                 575

Val Met Gln Lys Leu Lys Ala Thr Arg Pro Glu Leu Gln Gly Ala Asp
                580                 585                 590

Leu Val Lys Ala Val Lys Leu Ala Leu Met Asn Ala Ala Asp Pro Met
                595                 600                 605

Ile Asp Leu Asn Tyr Pro Asp Thr Tyr Val Ser Pro Arg Arg Gln Gly
                610                 615                 620

Ala Gly Gln Ile Asp Val Thr Lys Ala Gly Asn Leu Asp Val Ala Ala
625                 630                 635                 640

Glu Gly Thr Asn Asn Ala Gly Ser Val Ser Leu Gly Lys Ile Gly Arg
                645                 650                 655

Thr Thr Ser Phe Asn Val Thr Leu Thr Asn Tyr Gly Gln Thr Thr Gln
                660                 665                 670

Ser Tyr Thr Val Asp Tyr Asp Gly Gly Pro Leu Thr Gln Val Arg Asp
                675                 680                 685

Thr Ser Lys Gly Asn Ile Val His Asp Gln Lys Leu Ala Gly Ala Ala
                690                 695                 700

Val Asn Ser Ala Thr Pro Thr Phe Thr Leu Ala Pro Gly Ala Ser Lys
705                 710                 715                 720

Val Val Thr Phe Thr Leu Thr Leu Asp Ala Val Ala Ala Asn Gln
                725                 730                 735

Ile Val Glu Gly Tyr Leu Thr Phe Lys Ala Gly Asp Asp Thr Gln Thr
                740                 745                 750

Ile Ser Val Pro Tyr Leu Gly Tyr Phe Gly Asp Leu Thr Thr Glu Gln
                755                 760                 765

Ile Ile Asp Asp Pro Ala Asn Lys Gln Asp Ser Ile Phe Lys Gly Gly
                770                 775                 780
```

-continued

```
Tyr Leu Val Asp Asn Asn Asn Pro Leu Gly Val Thr Asp Ala Ala
785                 790                 795                 800

Ser Leu Ser Asn Leu Val Asn Ser Asp Val Thr Gly Lys Tyr Thr Trp
            805                 810                 815

Gly Gln Val Pro Ala Tyr Ile Glu Asn Gly Lys Val Ser Phe Ser Pro
        820                 825                 830

Asn Gly Asp Gly Ala Ser Asp Thr Val Tyr Pro Tyr Val Phe Ala Lys
            835                 840                 845

Gln Asn Leu Lys Ala Val Thr Ile Gln Ile Leu Asp Ala Asn Gly Asn
850                 855                 860

Leu Val Arg Val Leu Asp Lys Glu Asn Asn Thr Thr Lys Ser Tyr Leu
865                 870                 875                 880

Gln Asn Gly Phe Ser His Asn Ser Asp Leu Gly Leu Ser Thr Asp Met
                885                 890                 895

Arg Leu Asp Ala Asp Ala Phe Thr Trp Asp Gly Arg Ile Tyr Asp Gln
            900                 905                 910

Gln Thr Gly Lys Tyr Ile Thr Ala Pro Asp Gly Arg Tyr Thr Tyr Arg
            915                 920                 925

Ile Val Thr Glu Gln Tyr Asn Asp Gly Ala Glu Gln Glu Asn Phe
930                 935                 940

Asp Leu Pro Val Ala Val Asp Thr Val Ala Pro Thr Leu Thr Gly Leu
945                 950                 955                 960

Thr Tyr Ala Glu Gly Gln Leu Thr Ala Ser Tyr Asn Asp Gln Gly Ala
                965                 970                 975

Gly Phe Ser Gln Phe Ser Asp Ala Val Leu Lys Ile Gly Ala Gln Glu
                980                 985                 990

Tyr Gly Val Ser Leu Asp Asn Asn  Gly Gln Ser Asn Ala  Gly Thr Ile
            995                1000                1005

Ser Phe Lys Leu Thr Ala Ala  Gln Met Ala Ala Leu  Ala Thr Ser
       1010               1015               1020

Asp Gly Gln Leu Thr Leu Thr  Val Thr Asp Val Ala  Gly Asn His
       1025               1030               1035

Thr Ser Ala Ser Val Gln Ala  Phe Ala Gly Thr Thr  Ser Ala Ser
       1040               1045               1050

Ala Thr Asp Thr Ala Ala Asn  Val Ala Pro Gln Phe  Ser Trp Gln
       1055               1060               1065

Val Gly Asp Gly Ser Asn Asn  Tyr Trp Arg Thr Asn  Gly Phe Val
       1070               1075               1080

Gln Ala Val Ser Asp Gln Thr  Ser Phe Thr Thr Tyr  Ala Gln Val
       1085               1090               1095

Pro Ala Gly Val Asp Trp Ile  Val Tyr Ala Thr Asp  Ala Arg Ala
       1100               1105               1110

Gly Lys Val Phe Pro Gly Lys  Val Asp Thr Ala Thr  Gly Ile Val
       1115               1120               1125

Thr Phe Asn Leu Thr Glu Gly  Ala Pro Tyr Gly Asp  Phe Val Gly
       1130               1135               1140

Thr Val Leu Tyr Pro Thr Ala  Asn Phe Gly Glu Tyr  Lys Arg Ala
       1145               1150               1155

Gly Arg Ala Asp Gly Asp Glu  Met Ile Val Phe Leu  Asp Ala Asp
       1160               1165               1170

Gly Thr Ala Gly Tyr Gly His  Phe Ser Thr Thr Asn  Pro His Thr
       1175               1180               1185
```

```
Val Ile Ala Leu Arg Asp Asn Ala Asp Ala Ala Ala Asp Ala Thr
    1190                1195                1200

Val Thr Thr Gly Ala Pro Val Leu Ser Gly Arg Ala Phe Ala Asp
    1205                1210                1215

Ile Thr Thr His Ala Gln Pro Thr Ala Gly Leu Ser Phe Asp Lys
    1220                1225                1230

Phe Asn Asp Asn Thr Phe Thr Leu Val Gly Ala Asp Gln Val Ala
    1235                1240                1245

Asp Val Tyr Asp Pro Gln Thr Gly Glu Leu Thr Ile Thr Gly Lys
    1250                1255                1260

Val Ala Asp Pro Ala Gly Lys Ala Met Thr Val Thr Asp Ala Thr
    1265                1270                1275

Glu Pro Thr Lys Ala Val Ala Ile Asn Ala Asp Gly Thr Phe Ser
    1280                1285                1290

Phe Thr Val Pro Phe Lys Ala Ala Glu Gln Gln Ser Val Gly Tyr
    1295                1300                1305

Arg Leu Thr Thr Thr Thr Thr Asn Asp Asp Gly Thr Thr Ala Ser
    1310                1315                1320

Ser Thr Ala Tyr Gly Ala Leu Gln Ile Tyr Leu Asp Thr Val Phe
    1325                1330                1335

Pro Thr Leu Ser Met Pro Gln Ala Asp Thr Leu Thr Val Asp Ala
    1340                1345                1350

Asp Gly Asn Tyr Asp Ile Thr Thr Ser Asp Pro Thr Phe Thr Val
    1355                1360                1365

Thr Gly Thr Val Asn Asp Asn Val Asn Gly Tyr Arg Leu Tyr Thr
    1370                1375                1380

Asn Gly Asp Asn Val Val His Gln Lys Asn Leu Ala Gly Phe Asn
    1385                1390                1395

Asn His Val Asp Ala Asp Ala Ala Ser Ser Asn Pro Tyr Gly Ala
    1400                1405                1410

Ala Asp Phe Ser Gln Thr Tyr Asn Leu Leu Glu Gly Asp Asn Tyr
    1415                1420                1425

Phe Thr Val Thr Ala Val Asp Met Val Gly Asn Thr Ile Thr Lys
    1430                1435                1440

Val Phe His Val Val Arg Val Asp Ala Thr Ser Val Thr Pro Lys
    1445                1450                1455

Ser Gln Gly Ser Lys Gly Thr Ala Ile Thr Ser Pro Val Val Asp
    1460                1465                1470

Gly Gly Gln Arg Gly Gln Ala Gln Gly Ala Pro Asp Val His Pro
    1475                1480                1485

Ala Ala Pro Gly Tyr Lys Asn Asp Gly Gln Gly Val Gln Leu
    1490                1495                1500

Val Pro Ala Ala Ile Thr Ser Pro Gly Val Asp Gly Gly Gln Arg
    1505                1510                1515

Gly Gln Ala Gln Gly Ala Pro Asp Val His Pro Ala Ala Pro Gly
    1520                1525                1530

Tyr Lys Asn Asp Gly Gln Gly Val Gln Leu Val Pro Ala Ala
    1535                1540                1545

Ser Gln Ala Gly Arg Ser Gly Thr Glu Gln Gly Gln Ser Pro Ala
    1550                1555                1560

Thr Thr Thr Ala Ala Ala Leu Pro Ala Thr Gly Glu Thr His Ser
    1565                1570                1575

Pro Leu Ala Ala Ile Gly Leu Ala Ile Leu Ser Val Leu Gly Leu
```

-continued

```
              1580                1585                1590
Ala Gly Leu Ala Ser Arg Lys  Arg Arg Val
        1595                1600

<210> SEQ ID NO 49
<211> LENGTH: 1519
<212> TYPE: PRT
<213> ORGANISM: Actinomyces sp. oral taxon 180 str. F0310

<400> SEQUENCE: 49

Met Lys Arg Ser Arg Leu Ala Val Leu Ser Leu Ala Ala Thr Leu Gly
1               5                   10                  15

Ile Ala Ile Ile Ala Pro Gln Ala Phe Ala Asp Ser Ala Asp Thr Leu
            20                  25                  30

Val Ser Ala Pro Ala Ser Pro Pro Ser Ser Asn Ala Gly Lys Leu Leu
        35                  40                  45

Glu Pro Glu Leu Thr Ser Lys Ser Gln Tyr Asp Ala Gly Gly Ala Thr
    50                  55                  60

Thr Pro Ser Gly Asp Leu Leu Pro Asp Glu Glu Ser Asn His Pro Val
65                  70                  75                  80

Thr Val Ile Val Glu Leu Glu Glu Gly Asp Ala Gly Val Ala Trp Tyr
                85                  90                  95

Arg Arg Ala Val Ser Ala Asp Ala Lys Arg Thr Val Val Lys Glu Arg
            100                 105                 110

Ile Arg Thr Ala Val Glu Ala Ala Pro Gly Gln Val Thr Ser Gly
        115                 120                 125

Gly Gly Pro Val Thr Glu Val Glu Asp Tyr Glu His Val Met Glu Gly
    130                 135                 140

Phe Ala Ile Glu Val Pro Ala Gly Ala Val Glu Ala Val Arg Gly Val
145                 150                 155                 160

Glu Gly Val Lys Arg Ala Phe Val Glu Gln Thr Val Thr Pro Ser Ser
                165                 170                 175

Glu Glu Gly Tyr Ser Gly Pro Gln Asn Gln Tyr Ser Leu Asp Met Thr
            180                 185                 190

Gly Val Asp Arg Ile Ser Gln Lys Gly Asp Gly Thr Thr Ile Ala Ile
        195                 200                 205

Ile Asp Thr Gly Phe Asp Thr Thr His Glu Ala Phe Ser Gly Ala Leu
    210                 215                 220

Asp Glu Ser Arg Ala Ala Tyr Ser Tyr Asp Ser Ile Ser Ser Val Lys
225                 230                 235                 240

Arg Gly Leu Ser Thr Gly Trp Ala Gly Ala Tyr Val Ser Ala Lys Ile
                245                 250                 255

Pro Phe Ala Tyr Asp Tyr Gly Asp Gly Asp Ser Asp Val Ile Pro His
            260                 265                 270

Thr Val His Asn Met Ala His Gly Thr His Val Ala Gly Ile Ala Ala
        275                 280                 285

Ala Asn Gly Gly Ala Ile Leu Gly Ser Ala Pro Gly Ala Gln Leu Leu
    290                 295                 300

Leu Met Lys Ala Gly Ile Asp Ala Thr Gly Gly Leu Ser Asp Ser Ala
305                 310                 315                 320

Ile Phe Ala Ala Leu Asp Asp Cys Ala Val Leu Lys Pro Asp Val Ile
                325                 330                 335

Asn Met Ser Phe Gly Tyr Ala Gly Ala Ser Glu Ala Arg Asn Asp
            340                 345                 350
```

Thr Tyr Gly Ser Val Tyr Tyr Arg Leu Ser Glu Gln Gly Ile Met Leu
        355                 360                 365

Asn Val Ala Gly Gly Asn Phe Gly Ala Ser Ser Gln Gly Asn Ala Ser
        370                 375                 380

Gly Trp Gly Leu Pro Tyr Ala Ser Asp Pro Asp Ser Ser Thr Val Ala
385                 390                 395                 400

Gln Pro Ser Thr Tyr Thr Ala Ser Leu Ser Val Ala Ser Val Asp Asn
                405                 410                 415

Ala Asn Gly Trp Gly Pro Ser Thr Tyr Lys Ala Ser Ser Phe Ser Ser
            420                 425                 430

Trp Gly Val Ala Pro Asn Leu Thr Leu Lys Pro Glu Ile Ala Ala Pro
        435                 440                 445

Gly Gly Tyr Ile Trp Ser Ala Leu Pro Gly Gly Thr Tyr Gly Tyr Ser
        450                 455                 460

Ser Gly Thr Ser Met Ala Thr Pro Tyr Leu Ala Gly Met Ala Ala Asp
465                 470                 475                 480

Ile Lys Gln Arg Val Glu Ser Asp Pro Gly Phe Ala Tyr Met Thr Glu
                485                 490                 495

Ala Gln Lys Thr Gly Val Val Tyr Asn Leu Leu Met Gly Thr Ala Lys
            500                 505                 510

Pro Leu Val Asp Asn Glu Gly Gly Arg Gly Ala Tyr Tyr Ser Pro Arg
        515                 520                 525

Lys Ile Gly Ser Gly Leu Ala Asn Ala Val Ala Ala Ser Ser Ala Thr
        530                 535                 540

Val Phe Pro Thr Val Val Asp Ala Pro Asp Glu Thr Arg Pro Lys Ala
545                 550                 555                 560

Asp Leu Gly Asp Gly Thr Glu Gly Trp Thr Phe Ser Ile Arg Leu Thr
                565                 570                 575

Asn Thr Ala Tyr Glu Ala Arg Thr Tyr Arg Leu Asn Thr Gln Ala Leu
            580                 585                 590

Ser Glu Val Val Ala Ser Gly Val Phe Thr Gln His Ser Ala Asn Trp
        595                 600                 605

Thr Asp Gln Gly Ile Ser Val Ser Tyr Ser Gly Asp Val Ser Gly Ser
        610                 615                 620

Ala Asp Ser Ser Thr Ile Thr Val Pro Gly Arg Gly Val Val Thr Ala
625                 630                 635                 640

Thr Val Thr Ile Thr Pro Gln Ala Ala Phe Ala Ala Tyr Ala Gly Ala
                645                 650                 655

Tyr Ala Pro Asn Gly Thr Phe Val Asp Gly Phe Thr Val Leu Thr Ser
            660                 665                 670

Met Thr Glu Gly Glu Pro Asp Leu Ser Val Pro Phe Leu Gly Phe Tyr
        675                 680                 685

Gly Asp Trp Gly Ala Val Pro Val Phe Asp Ser Leu Ala Ser Asp Gly
        690                 695                 700

Gly Gln Ala His Ala Val Ala Ser Arg Leu Ala Ser Thr Thr Gly
705                 710                 715                 720

Val Ser Leu Gly Val Asn Pro Leu Ala Gly Tyr Thr Ser Ala Ser Ser
                725                 730                 735

Ala Pro Ala Pro Asn Pro Asp Ala Tyr Val Val Ser Ala Ser Thr Trp
            740                 745                 750

Ala Gln Gly Pro Ser Ala Ile Arg Pro Val Thr Gly Leu Leu Arg Ser
        755                 760                 765

Thr Lys Ser Val Thr Tyr Thr Tyr Gln Asp Ser Ala Gly Asn Thr Val

```
                770             775             780
Arg Gln Tyr Ser Tyr Lys Asn Thr Arg Lys Ser Leu Tyr Asp Asp Tyr
785                 790             795                 800

Thr Arg Leu Ile Ala Ser Gly Glu Ser Ser Met Gly Asp Pro Tyr Phe
                805             810              815

Asp Gly Tyr Asp Trp Tyr Gly Arg Arg Leu Pro Glu Gly Arg Tyr Thr
            820             825             830

Leu Arg Ile Asp Ala Val Thr Asp Gly Pro Ser Leu Arg Thr Gln Thr
        835             840             845

Leu Thr Tyr Ser Phe Ala Tyr Asp Leu Thr Gly Pro Lys Ile Ser Gly
    850             855             860

Val His Val Ser Gly Gln Gly Glu Ala Arg Thr Val Ser Phe Asp Val
865             870             875             880

Thr Asp Ser Ser Pro Leu Ala Ser Ile Asp Phe His Asp Pro Ala Asn
                885             890             895

Gly Ser Tyr Tyr Tyr Arg Thr Leu Val Thr Asp Gly Gly Thr Leu Gly
            900             905             910

Ala Asp Gly Gln Arg Thr Tyr His Phe Asp Val Pro Val Ala Asp Leu
        915             920             925

Gln Arg Gly Trp Glu Ser Gln Gly Gly Thr Gly Pro Ala Pro Thr Asn
    930             935             940

Pro Thr Leu Tyr Ala Trp Asp Tyr Gly Val Asn Ala Ser Ala Gly Val
945             950             955             960

Thr Val Ser Val Asp Ala Ser Asp Pro Ile Ser Leu Ser Thr Ser Ser
                965             970             975

Val Val Ile Pro Ser Gly Glu Thr Ser Gln Val Phe Ala Val Leu Ser
            980             985             990

Pro Ser Leu Ser Gly Ser Gln Val Val Trp Ser Leu Ala Asp Ser Ser
        995             1000            1005

Val Ala Ser Leu Ser Thr Ser Ser Asp Thr Leu Thr Ala Thr Ile
        1010            1015            1020

Ala Ala Gly Thr Lys Glu Gly Ala Thr Thr Leu Thr Ala Trp Val
        1025            1030            1035

Arg Gln Gly Asp Gly Thr Trp Ala Ser Ala Ser Ala Glu Val Ser
        1040            1045            1050

Val Arg Ala Ala Ala Ser Ser Asp Phe Val Ile Asp Glu Ala Gly
        1055            1060            1065

Val Leu Arg Ser Tyr Ser Gly Ser Asp Thr Glu Val Ser Val Pro
        1070            1075            1080

Gly Gly Val Thr Ala Leu Ala Asp Arg Val Phe Ala Arg Ser Ser
        1085            1090            1095

Val Ala Ser Val Glu Leu Pro Asp Thr Val Glu Arg Ile Gly Ala
        1100            1105            1110

Ser Ala Phe Glu Gly Ala Ser Leu Ala Ser Val Thr Val Arg
        1115            1120            1125

Asp Ala Arg Gly Gln Val Gly Glu Gly Leu Pro Ser Gly Leu Arg
        1130            1135            1140

Gln Ile Gly Ala Arg Ala Phe Leu Gly Thr Gly Leu Ala Val Ile
        1145            1150            1155

Asn Val Pro Asp Ser Val Ser Asp Ile Gly Pro Gly Ala Phe Ala
        1160            1165            1170

Leu Met Pro Ser Leu Thr Gly Val Asn Ile Gly Ser Gly Val Arg
        1175            1180            1185
```

Glu Gly Gln Leu Val Ser Thr Phe Thr Ala Ser Pro Lys Leu Lys
    1190                1195                1200

Ala Ile Thr Val Lys Ala Asp Asn Ala Ser Tyr Asp Ser Val Asp
    1205                1210                1215

Gly Val Leu Phe Thr Lys Gly Arg Asp Thr Leu Leu Thr Tyr Pro
    1220                1225                1230

Leu Gly Arg Ala Gly Val Ser Tyr Thr Val Pro Asp Gly Thr Arg
    1235                1240                1245

Ala Leu Ala Gln Glu Ser Phe Glu Gly Ala Pro Leu Asp Glu Val
    1250                1255                1260

Thr Leu Pro Asp Ser Leu Arg Arg Ile Asp Arg Tyr Ala Phe Val
    1265                1270                1275

Gly Ser Arg Leu Ser Ser Leu Thr Leu Pro Asp Ser Phe Glu Met
    1280                1285                1290

Ile Gly Ala His Ala Phe Arg Gly Val Thr Ser Leu Thr Trp Val
    1295                1300                1305

Asn Ile Gly Gly Thr Thr Thr Ile Gly Glu Ser Ala Phe Asp Gly
    1310                1315                1320

Asp Arg Asn Leu Thr Ala Ile Asn Phe Arg Ser Asp Leu Ala Arg
    1325                1330                1335

Leu Thr Ser Ile Gly Ala Asn Ala Leu Arg Gly Val Pro Val Thr
    1340                1345                1350

Pro Pro Ala Leu Thr Ser Ala Arg Ala Gln Ala Glu Thr Pro Ala
    1355                1360                1365

Ser Asp Thr Ala Ser Gly Asn Ala Pro Thr Pro Ala Pro Ile Ala
    1370                1375                1380

Ser Pro Glu Ala Thr Gly Ser Asp Ser Ala Ser Asp Asp Arg Ala
    1385                1390                1395

Thr Gly Gly Asp Ala Ala Pro Ala Thr Pro Asn Pro Asn Ala Ser
    1400                1405                1410

Ala Ser Ala Ser Pro Asp Ala Pro Asp Gln Gly Gln Gly Ser Glu
    1415                1420                1425

Ala Pro Gln Ser Ser Ala Ala Pro Ala Ala Ser Thr Arg Ala Pro
    1430                1435                1440

Gly Ala Ala Ala Ser Ser Pro Ala Ala Val Gly Gln Pro Val Ser
    1445                1450                1455

Val Val Gly Arg Thr Ala Leu Ser Leu Gly Asp Ala Ala Asp Tyr
    1460                1465                1470

His Ala Pro His Pro Lys Arg Thr Arg Pro Ser Ser Leu Ala Ala
    1475                1480                1485

Thr Gly Ala Ser Thr Asn Gly Phe Val Gly Ile Leu Thr Ala Ala
    1490                1495                1500

Ala Thr Leu Gly Phe Val Leu Val Val Ala Arg Arg Gln Arg Leu
    1505                1510                1515

Ser

<210> SEQ ID NO 50
<211> LENGTH: 1492
<212> TYPE: PRT
<213> ORGANISM: Artificial Sequence
<220> FEATURE:
<223> OTHER INFORMATION: fragment of Actinomyces sp. oral taxon 180 str.
      F0310 protease

<400> SEQUENCE: 50

-continued

```
Ser Ala Asp Thr Leu Val Ser Ala Pro Ala Ser Pro Pro Ser Ser Asn
1               5                   10                  15
Ala Gly Lys Leu Leu Glu Pro Glu Leu Thr Ser Lys Ser Gln Tyr Asp
            20                  25                  30
Ala Gly Gly Ala Thr Thr Pro Ser Gly Asp Leu Leu Pro Asp Glu Glu
            35                  40                  45
Ser Asn His Pro Val Thr Val Ile Val Glu Leu Glu Glu Gly Asp Ala
        50                  55                  60
Gly Val Ala Trp Tyr Arg Arg Ala Val Ser Ala Asp Ala Lys Arg Thr
65                  70                  75                  80
Val Val Lys Glu Arg Ile Arg Thr Ala Val Glu Ala Ala Pro Gly
            85                  90                  95
Gln Val Thr Ser Gly Gly Pro Val Thr Glu Val Glu Asp Tyr Glu
            100                 105                 110
His Val Met Glu Gly Phe Ala Ile Glu Val Pro Ala Gly Ala Val Glu
        115                 120                 125
Ala Val Arg Gly Val Glu Gly Val Lys Arg Ala Phe Val Glu Gln Thr
        130                 135                 140
Val Thr Pro Ser Ser Glu Glu Gly Tyr Ser Gly Pro Gln Asn Gln Tyr
145                 150                 155                 160
Ser Leu Asp Met Thr Gly Val Asp Arg Ile Ser Gln Lys Gly Asp Gly
            165                 170                 175
Thr Thr Ile Ala Ile Ile Asp Thr Gly Phe Asp Thr Thr His Glu Ala
            180                 185                 190
Phe Ser Gly Ala Leu Asp Glu Ser Arg Ala Ala Tyr Ser Tyr Asp Ser
            195                 200                 205
Ile Ser Ser Val Lys Arg Gly Leu Ser Thr Gly Trp Ala Gly Ala Tyr
        210                 215                 220
Val Ser Ala Lys Ile Pro Phe Ala Tyr Asp Tyr Gly Asp Gly Asp Ser
225                 230                 235                 240
Asp Val Ile Pro His Thr Val His Asn Met Ala His Gly Thr His Val
            245                 250                 255
Ala Gly Ile Ala Ala Ala Asn Gly Gly Ala Ile Leu Gly Ser Ala Pro
            260                 265                 270
Gly Ala Gln Leu Leu Leu Met Lys Ala Gly Ile Asp Ala Thr Gly Gly
            275                 280                 285
Leu Ser Asp Ser Ala Ile Phe Ala Ala Leu Asp Asp Cys Ala Val Leu
        290                 295                 300
Lys Pro Asp Val Ile Asn Met Ser Phe Gly Tyr Ala Gly Gly Ala Ser
305                 310                 315                 320
Glu Ala Arg Asn Asp Thr Tyr Gly Ser Val Tyr Tyr Arg Leu Ser Glu
            325                 330                 335
Gln Gly Ile Met Leu Asn Val Ala Gly Gly Asn Phe Gly Ala Ser Ser
            340                 345                 350
Gln Gly Asn Ala Ser Gly Trp Gly Leu Pro Tyr Ala Ser Asp Pro Asp
            355                 360                 365
Ser Ser Thr Val Ala Gln Pro Ser Thr Tyr Thr Ala Ser Leu Ser Val
        370                 375                 380
Ala Ser Val Asp Asn Ala Asn Gly Trp Gly Pro Ser Thr Tyr Lys Ala
385                 390                 395                 400
Ser Ser Phe Ser Ser Trp Gly Val Ala Pro Asn Leu Thr Leu Lys Pro
            405                 410                 415
```

```
Glu Ile Ala Ala Pro Gly Gly Tyr Ile Trp Ser Ala Leu Pro Gly Gly
                420                 425                 430

Thr Tyr Gly Tyr Ser Ser Gly Thr Ser Met Ala Thr Pro Tyr Leu Ala
            435                 440                 445

Gly Met Ala Ala Asp Ile Lys Gln Arg Val Glu Ser Asp Pro Gly Phe
        450                 455                 460

Ala Tyr Met Thr Glu Ala Gln Lys Thr Gly Val Val Tyr Asn Leu Leu
465                 470                 475                 480

Met Gly Thr Ala Lys Pro Leu Val Asp Asn Glu Gly Gly Arg Gly Ala
                485                 490                 495

Tyr Tyr Ser Pro Arg Lys Ile Gly Ser Gly Leu Ala Asn Ala Val Ala
            500                 505                 510

Ala Ser Ser Ala Thr Val Phe Pro Thr Val Val Asp Ala Pro Asp Glu
        515                 520                 525

Thr Arg Pro Lys Ala Asp Leu Gly Asp Gly Thr Glu Gly Trp Thr Phe
        530                 535                 540

Ser Ile Arg Leu Thr Asn Thr Ala Tyr Glu Ala Arg Thr Tyr Arg Leu
545                 550                 555                 560

Asn Thr Gln Ala Leu Ser Glu Val Val Ala Ser Gly Val Phe Thr Gln
                565                 570                 575

His Ser Ala Asn Trp Thr Asp Gln Gly Ile Ser Val Ser Tyr Ser Gly
            580                 585                 590

Asp Val Ser Gly Ser Ala Asp Ser Ser Thr Ile Thr Val Pro Gly Arg
        595                 600                 605

Gly Val Val Thr Ala Thr Val Thr Ile Thr Pro Gln Ala Ala Phe Ala
        610                 615                 620

Ala Tyr Ala Gly Ala Tyr Ala Pro Asn Gly Thr Phe Val Asp Gly Phe
625                 630                 635                 640

Thr Val Leu Thr Ser Met Thr Glu Gly Glu Pro Asp Leu Ser Val Pro
                645                 650                 655

Phe Leu Gly Phe Tyr Gly Asp Trp Gly Ala Val Pro Val Phe Asp Ser
            660                 665                 670

Leu Ala Ser Asp Gly Gly Gln Ala His Ala Val Ala Ser Arg Leu Ala
        675                 680                 685

Ser Ala Thr Thr Gly Val Ser Leu Gly Val Asn Pro Leu Ala Gly Tyr
        690                 695                 700

Thr Ser Ala Ser Ser Ala Pro Ala Pro Asn Pro Asp Ala Tyr Val Val
705                 710                 715                 720

Ser Ala Ser Thr Trp Ala Gln Gly Pro Ser Ala Ile Arg Pro Val Thr
                725                 730                 735

Gly Leu Leu Arg Ser Thr Lys Ser Val Thr Tyr Thr Gln Asp Ser
            740                 745                 750

Ala Gly Asn Thr Val Arg Gln Tyr Ser Tyr Lys Asn Thr Arg Lys Ser
            755                 760                 765

Leu Tyr Asp Asp Tyr Thr Arg Leu Ile Ala Ser Gly Glu Ser Ser Met
        770                 775                 780

Gly Asp Pro Tyr Phe Asp Gly Tyr Asp Trp Tyr Gly Arg Arg Leu Pro
785                 790                 795                 800

Glu Gly Arg Tyr Thr Leu Arg Ile Asp Ala Val Thr Asp Gly Pro Ser
                805                 810                 815

Leu Arg Thr Gln Thr Leu Thr Tyr Ser Phe Ala Tyr Asp Leu Thr Gly
            820                 825                 830

Pro Lys Ile Ser Gly Val His Val Ser Gly Gln Gly Glu Ala Arg Thr
```

-continued

```
            835                 840                 845
Val Ser Phe Asp Val Thr Asp Ser Ser Pro Leu Ala Ser Ile Asp Phe
            850                 855                 860
His Asp Pro Ala Asn Gly Ser Tyr Tyr Tyr Arg Thr Leu Val Thr Asp
865                 870                 875                 880
Gly Gly Thr Leu Gly Ala Asp Gly Gln Arg Thr Tyr His Phe Asp Val
                    885                 890                 895
Pro Val Ala Asp Leu Gln Arg Gly Trp Glu Ser Gln Gly Thr Gly
            900                 905                 910
Pro Ala Pro Thr Asn Pro Thr Leu Tyr Ala Trp Asp Tyr Gly Val Asn
            915                 920                 925
Ala Ser Ala Gly Val Thr Val Ser Val Asp Ala Ser Asp Pro Ile Ser
            930                 935                 940
Leu Ser Thr Ser Ser Val Val Ile Pro Ser Gly Glu Thr Ser Gln Val
945                 950                 955                 960
Phe Ala Val Leu Ser Pro Ser Leu Ser Gly Ser Gln Val Val Trp Ser
                    965                 970                 975
Leu Ala Asp Ser Ser Val Ala Ser Leu Ser Thr Ser Ser Asp Thr Leu
                    980                 985                 990
Thr Ala Thr Ile Ala Ala Gly Thr Lys Glu Gly Ala Thr Thr Leu Thr
            995                 1000                1005
Ala Trp Val Arg Gln Gly Asp Gly Thr Trp Ala Ser Ala Ser Ala
            1010                1015                1020
Glu Val Ser Val Arg Ala Ala Ser Ser Asp Phe Val Ile Asp
            1025                1030                1035
Glu Ala Gly Val Leu Arg Ser Tyr Ser Gly Ser Asp Thr Glu Val
            1040                1045                1050
Ser Val Pro Gly Gly Val Thr Ala Leu Ala Asp Arg Val Phe Ala
            1055                1060                1065
Arg Ser Ser Val Ala Ser Val Glu Leu Pro Asp Thr Val Glu Arg
            1070                1075                1080
Ile Gly Ala Ser Ala Phe Glu Gly Ala Ala Ser Leu Ala Ser Val
            1085                1090                1095
Thr Val Arg Asp Ala Arg Gly Gln Val Gly Glu Gly Leu Pro Ser
            1100                1105                1110
Gly Leu Arg Gln Ile Gly Ala Arg Ala Phe Leu Gly Thr Gly Leu
            1115                1120                1125
Ala Val Ile Asn Val Pro Asp Ser Val Ser Asp Ile Gly Pro Gly
            1130                1135                1140
Ala Phe Ala Leu Met Pro Ser Leu Thr Gly Val Asn Ile Gly Ser
            1145                1150                1155
Gly Val Arg Glu Gly Gln Leu Val Ser Thr Phe Thr Ala Ser Pro
            1160                1165                1170
Lys Leu Lys Ala Ile Thr Val Lys Ala Asp Asn Ala Ser Tyr Asp
            1175                1180                1185
Ser Val Asp Gly Val Leu Phe Thr Lys Gly Arg Asp Thr Leu Leu
            1190                1195                1200
Thr Tyr Pro Leu Gly Arg Ala Gly Val Ser Tyr Thr Val Pro Asp
            1205                1210                1215
Gly Thr Arg Ala Leu Ala Gln Glu Ser Phe Glu Gly Ala Pro Leu
            1220                1225                1230
Asp Glu Val Thr Leu Pro Asp Ser Leu Arg Arg Ile Asp Arg Tyr
            1235                1240                1245
```

Ala Phe Val Gly Ser Arg Leu Ser Ser Leu Thr Leu Pro Asp Ser
1250 1255 1260

Phe Glu Met Ile Gly Ala His Ala Phe Arg Gly Val Thr Ser Leu
1265 1270 1275

Thr Trp Val Asn Ile Gly Gly Thr Thr Thr Ile Gly Glu Ser Ala
1280 1285 1290

Phe Asp Gly Asp Arg Asn Leu Thr Ala Ile Asn Phe Arg Ser Asp
1295 1300 1305

Leu Ala Arg Leu Thr Ser Ile Gly Ala Asn Ala Leu Arg Gly Val
1310 1315 1320

Pro Val Thr Pro Pro Ala Leu Thr Ser Ala Arg Ala Gln Ala Glu
1325 1330 1335

Thr Pro Ala Ser Asp Thr Ala Ser Gly Asn Ala Pro Thr Pro Ala
1340 1345 1350

Pro Ile Ala Ser Pro Glu Ala Thr Gly Ser Asp Ser Ala Ser Asp
1355 1360 1365

Asp Arg Ala Thr Gly Gly Asp Ala Ala Pro Ala Thr Pro Asn Pro
1370 1375 1380

Asn Ala Ser Ala Ser Ala Ser Pro Asp Ala Pro Asp Gln Gly Gln
1385 1390 1395

Gly Ser Glu Ala Pro Gln Ser Ser Ala Ala Pro Ala Ala Ser Thr
1400 1405 1410

Arg Ala Pro Gly Ala Ala Ala Ser Ser Pro Ala Ala Val Gly Gln
1415 1420 1425

Pro Val Ser Val Val Gly Arg Thr Ala Leu Ser Leu Gly Asp Ala
1430 1435 1440

Ala Asp Tyr His Ala Pro His Pro Lys Arg Thr Arg Pro Ser Ser
1445 1450 1455

Leu Ala Ala Thr Gly Ala Ser Thr Asn Gly Phe Val Gly Ile Leu
1460 1465 1470

Thr Ala Ala Ala Thr Leu Gly Phe Val Leu Val Val Ala Arg Arg
1475 1480 1485

Gln Arg Leu Ser
1490

<210> SEQ ID NO 51
<211> LENGTH: 1532
<212> TYPE: PRT
<213> ORGANISM: Erysipelothrix rhusiopathiae

<400> SEQUENCE: 51

Met Arg Lys Arg Phe Lys Ala Met Met Pro Leu Val Leu Ser Leu Leu
1 5 10 15

Leu Val Ile Thr Thr Gly Thr Asn Ile Arg Ala Asn Asp Glu Gly Thr
20 25 30

Leu Ala Glu Leu Thr Ala Met Asp Asp Val Ser Ile Val Gln Ser Ile
35 40 45

Leu Asp Glu Glu Glu Thr Asn Thr Pro Glu Glu Asp Pro Glu Leu Ser
50 55 60

Val Asp Pro Ser Val Pro Val Asp Ile Ile Val Glu Leu Glu Ala Arg
65 70 75 80

Pro Ile Leu Asp Tyr Glu Asn Glu Ile Lys Gln Val Gly Ser Leu Gly
85 90 95

Asp Phe Ser Glu Thr Lys Gln Ala Gln Asp Leu Glu Ala Asn Leu Ile

```
                100                 105                 110
Lys Ser His Glu Ala Val Val Asp Lys Ile Ser Glu Val Ile Gln Lys
            115                 120                 125

Asp Val Glu Val Asp Ser Asn Phe Thr Arg Val Met Asn Gly Phe Ser
130                 135                 140

Leu Lys Ala Ser Leu Asp Leu Asn Leu Ile Lys Asp Ile Glu Gly
145                 150                 155                 160

Val Lys Ser Ala Phe Val Ser Gln Thr Tyr Asp Ile Pro Glu Pro Gln
                165                 170                 175

Met Val Asp Ser Asn Arg Thr Ile Gly Ser Asp Thr Val Trp Thr Gln
                180                 185                 190

Ser His Tyr Lys Gly Glu Asn Ile Val Val Ala Val Leu Asp Thr Gly
            195                 200                 205

Leu Asp Thr Gly His Pro Ala Phe Ala Val Ala Pro Ser Gln Phe Arg
210                 215                 220

Ile Asn Lys Gln Lys Ile Gln Thr Val Leu Asn Asn Lys Lys Leu Lys
225                 230                 235                 240

Ala Thr Ala Asn Thr Pro Gly Leu Thr Val Asp His Val Tyr Ile Asn
                245                 250                 255

Asp Lys Val Pro Phe Val Tyr Asp Tyr Ala Asp Lys Asp Ala Ile Val
                260                 265                 270

Asp Pro Ser Ala His Asn Tyr Gly Arg Leu Ala His Gly Thr His Val
            275                 280                 285

Ala Gly Thr Val Ala Gly Lys Asp Gln Ala Asp Phe Arg Gly Val Ala
            290                 295                 300

Pro Glu Ala Gln Leu Met Ile Phe Lys Val Phe Ser Asp Lys Gly Gly
305                 310                 315                 320

Gly Ala Ser Asp Ile Ser Leu Val Ser Ala Leu Glu Asp Cys Val Tyr
                325                 330                 335

Leu Gly Val Asp Val Ile Asn Met Ser Leu Gly Ser Asp Ala Gly Phe
                340                 345                 350

Met His Asp Ser Tyr Lys Pro Thr Asn Asp Met Tyr Asn Arg Ile Arg
            355                 360                 365

Asp Asn Gly Ile Val Leu Asp Val Ala Ala Gly Asn Ala Met Ser Ser
370                 375                 380

Ser Glu Lys Asn Leu Tyr Gly Asn Asp Leu Thr Leu Ala Ser Asp Pro
385                 390                 395                 400

Asp His Gly Ile Val Gly Ser Pro Ser Thr Tyr Ala Ser Pro Ile Ser
                405                 410                 415

Val Ala Ser Val Asn Asn Thr Lys Tyr Arg Pro Gly Ser Lys Thr Ile
                420                 425                 430

Asp Pro Thr Gln Val Thr Leu Ser Gly Phe Ser Ser Ile Gly Thr Thr
            435                 440                 445

Pro Asn Ile Ser Ile Lys Pro Glu Ile Ser Ala Pro Gly Ala Trp Ile
            450                 455                 460

Arg Ser Ala Met Pro Arg Leu Asn Gly Gln Asn Tyr Asp Glu Met Ser
465                 470                 475                 480

Gly Thr Ser Met Ala Thr Pro His Val Ala Gly Ala Ser Ala Leu Met
                485                 490                 495

Lys Gln Tyr Leu Asn Asp Lys Phe Gly Asn Leu Thr Asn Ile Gln Lys
                500                 505                 510

Met Glu Leu Thr Asn Asn Leu Leu Met Ser Thr Ala His Pro Ile Val
            515                 520                 525
```

```
Gln Lys Asp Gly Ala Pro Gln Pro Val Arg Lys Gln Gly Ser Gly Met
        530                 535                 540

Met Asp Ile Asn Ala Ala Ile Lys Thr Pro Val Tyr Leu Ser Val Asp
545                 550                 555                 560

Pro Lys Gln Asn His Asp Gly Ser Asn Arg Pro Lys Ile Glu Leu Gly
                565                 570                 575

Asp Asp Gln Asn Lys Thr Gly Asn Tyr Thr Leu Lys Phe Lys Val Thr
                580                 585                 590

Asn Met Gly Thr Gln Thr Glu Thr Tyr Gln Ile Lys Glu Lys Val Ser
            595                 600                 605

Val Pro Val Ile Lys Arg Ser Ile Met Asp Asp His Arg Glu Arg Ala
        610                 615                 620

Phe Met Thr Asp Asp Asn Arg Ser Val Asp Val Thr Arg Ser Gly Val
625                 630                 635                 640

Thr Ser Val Thr Val Lys Ala Lys Glu Thr Lys Asp Val Ser Ile Thr
                645                 650                 655

Val Gln Leu Thr Gln Ala Glu Lys Asn Arg Leu Asn Gln Glu Phe Glu
                660                 665                 670

Asn Gly Thr Tyr Val Glu Gly Phe Val Gln Leu Thr His Ala Ser His
            675                 680                 685

Pro Gln Ile Ser Ile Pro Phe Leu Ala Phe Tyr Gly Asp Trp Glu Lys
        690                 695                 700

Ala Pro Ile Phe Asp His Ala Ala Glu Tyr Glu Met Gly Val Arg Ala
705                 710                 715                 720

Ser Asn Tyr Ala His Arg Tyr Leu Ser Asp Lys Met Pro Met Gly Gly
                725                 730                 735

Asn Ile Phe Asp Arg Arg Met Ile Tyr Thr Asn Pro Ser Arg Phe Val
                740                 745                 750

Ile Ser Pro Asn Gly Asp Gly Leu Tyr Asp Lys Leu Ser Gly Ile Asn
            755                 760                 765

Leu Gly Gln Leu Arg Asn Val Glu Ser Met Thr Met Glu Ile Thr Asn
        770                 775                 780

Lys Lys Thr Lys Gln Val Ile Ile Lys Glu Glu Arg Pro Asn Ile Arg
785                 790                 795                 800

Lys Thr Phe Tyr Asn Asn Ser Tyr Gly Lys Gln Val Pro Asn Ile Leu
                805                 810                 815

Phe Trp Pro Phe Ser Thr Phe Thr Gly Leu Asp Gln Gln Lys Asn Pro
                820                 825                 830

Leu Pro Glu Gly Arg Tyr Asp Leu Lys Ile Ser Ala Asp Leu Gly Tyr
            835                 840                 845

Arg Lys Gly Ile Asp Gln Glu Ile Val His Thr Ile His Val Asp His
        850                 855                 860

Thr Lys Pro Val Ile Pro Gln Asp Lys Ile Lys Phe Thr Glu Lys Asn
865                 870                 875                 880

Gly Thr Val Met Met His Val Glu Ser Asn Asp Asn Thr Phe Leu Thr
                885                 890                 895

Gln Thr Ala Leu Tyr Pro Val Tyr Asn Gly Lys Val Gln Val Asn Arg
            900                 905                 910

Pro Leu Lys Lys Gln Tyr Thr Pro Tyr Asp Leu Val Ser Arg His Ala
        915                 920                 925

Phe Asp Val Asp Val Thr Asn Leu Lys Gly Gln Glu Val Val Ile Ser
930                 935                 940
```

```
Ala Val Asp Ala Gly Met Leu Glu Thr Asn Tyr Lys Thr Val Val Pro
945                 950                 955                 960

Gly Thr Pro Lys Pro His Leu Lys Val Asp Glu Phe Lys Ile Lys Val
            965                 970                 975

Gly Ala Gln Ile Glu Leu Glu Pro Gly Asn Phe Lys Trp Gln Thr Pro
                980                 985                 990

Thr Phe Glu Ser Glu Asp Pro Glu Ile Ala Asp Val Asn Asp Lys Gly
        995                 1000                1005

Leu Val Thr Gly Leu Lys Pro Gly Ala Thr Phe Ile Lys Ile Lys
1010                1015                1020

Asp Lys Asn Gly Ile Asp Leu Val Ala Leu Ile Glu Val Phe Glu
1025                1030                1035

Glu Glu Ser Leu Lys Leu Gln Met Lys Val Gly Glu Lys Arg Lys
1040                1045                1050

Leu Ile Ser Tyr Asn Leu Glu Gly Lys Arg Thr Phe Asp Ser Asp
1055                1060                1065

Ala Pro His Ile Val Ser Ala Arg Asp Thr Gly Glu Ile Glu Ala
1070                1075                1080

His Gln Lys Gly Lys Ala Lys Ile Thr Val Gln Asn Ala Tyr Glu
1085                1090                1095

Lys Leu Glu Tyr Glu Val Glu Val Val Asp Gln Pro Lys Tyr Thr
1100                1105                1110

Pro Ser Leu Ser Phe Asp Lys Lys Val Tyr Glu Ile Asn Ser Gly
1115                1120                1125

Glu Val Val Ala Pro Lys Phe Thr Ile Glu Asn Asp Asp Pro Ser
1130                1135                1140

Asn Pro Gln Val Val Thr Arg Leu Leu Thr Ser Asn Glu Glu His
1145                1150                1155

Val Ser Ile Ala Gly Leu Lys Phe Thr Gly Glu His Ala Gly Glu
1160                1165                1170

Ala Ala Val Ile Ala Glu Leu Lys Asn Gly Thr Arg Ala Val Ala
1175                1180                1185

Lys Val Lys Val Gly Gly Leu Asp Thr Lys Lys Leu Asp Ile Leu
1190                1195                1200

Ile Ser Gln Ala Ser Asn Leu Asn Ala Asp Asp Tyr Thr Lys Thr
1205                1210                1215

Ser Phe Thr Thr Leu Thr Thr Thr Leu Gln Glu Ala Lys Thr Leu
1220                1225                1230

Arg Lys Gln Lys Gly Ile Asp Gln Ser Asn Ile Asp Thr Met Val
1235                1240                1245

Glu Lys Leu Glu Lys Ser Met Asn Gln Leu Val Gln Val Ile Lys
1250                1255                1260

Asn Leu Pro Ser Ala Met Ser Val Glu Val Gly Asn Thr Phe Lys
1265                1270                1275

Leu Ser Pro Lys Pro Ala Gln Gly Lys Trp Ile Trp Asp Ala Glu
1280                1285                1290

Phe Leu Glu Gly Thr Ala Gln Asn Asn Asp Gln Glu Met Met Phe
1295                1300                1305

Lys Gly Leu Lys Glu Gly Gln Thr Asp Val Arg Tyr Arg Thr Lys
1310                1315                1320

Asp Gly Glu Glu Gln Ser Val Ala Val Ala Val Lys Pro Lys Pro
1325                1330                1335

Lys Pro Val Glu Ile Asp Pro Ile Val Pro Thr Asp Pro Val Asp
```

```
    1340                1345                1350

Pro Val  Lys Pro Thr Asp Pro  Val Asp Pro Val Lys  Pro Lys Asp
    1355                1360                1365

Pro Val  Asp Pro Val Lys Pro  Thr Asp Pro Val Asp  Pro Val Lys
    1370                1375                1380

Pro Thr  Asp Pro Val Asp Pro  Val Lys Pro Thr Asp  Pro Val Asp
    1385                1390                1395

Pro Val  Lys Pro Thr Asp Pro  Val Asp Pro Val Lys  Pro Thr Asp
    1400                1405                1410

Pro Val  Asp Pro Val Lys Pro  Thr Asp Pro Val Asp  Pro Val Lys
    1415                1420                1425

Pro Thr  Asp Pro Val Asp Pro  Val Lys Pro Ala Asp  Pro Val Asp
    1430                1435                1440

Pro Val  Lys Pro Thr Asp Pro  Thr Lys Pro Thr Lys  Pro Val Asp
    1445                1450                1455

Ser Gly  Leu Lys Pro Ile Asp  Asn Leu Lys Lys Pro  Ile Val Lys
    1460                1465                1470

Pro Lys  Asp Pro Val Ser Gln  Val Glu Ser Ile Lys  Gln Asp Lys
    1475                1480                1485

Pro Val  Ile His Phe Gly Val  Val Ser Glu Ser Leu  Pro Gln Thr
    1490                1495                1500

Gly Val  Thr Pro Gln Tyr Arg  Gly Tyr Thr Leu Leu  Gly Leu Gly
    1505                1510                1515

Leu Val  Ile Arg Val Ile Asn  Asp Lys Lys Asn Arg  Met Lys
    1520                1525                1530

<210> SEQ ID NO 52
<211> LENGTH: 1504
<212> TYPE: PRT
<213> ORGANISM: Artificial Sequence
<220> FEATURE:
<223> OTHER INFORMATION: fragment of Erysipelothrix rhusiopathiae ATCC
      19414 protease

<400> SEQUENCE: 52

Asp Glu Gly Thr Leu Ala Glu Leu Thr Ala Met Asp Asp Val Ser Ile
1               5                   10                  15

Val Gln Ser Ile Leu Asp Glu Glu Glu Thr Asn Thr Pro Glu Glu Asp
            20                  25                  30

Pro Glu Leu Ser Val Asp Pro Ser Val Pro Val Asp Ile Ile Val Glu
        35                  40                  45

Leu Glu Ala Arg Pro Ile Leu Asp Tyr Glu Asn Glu Ile Lys Gln Val
    50                  55                  60

Gly Ser Leu Gly Asp Phe Ser Glu Thr Lys Gln Ala Gln Asp Leu Glu
65                  70                  75                  80

Ala Asn Leu Ile Lys Ser His Glu Ala Val Val Asp Lys Ile Ser Glu
                85                  90                  95

Val Ile Gln Lys Asp Val Glu Val Asp Ser Asn Phe Thr Arg Val Met
            100                 105                 110

Asn Gly Phe Ser Leu Lys Ala Ser Leu Asp Asp Leu Asn Leu Ile Lys
        115                 120                 125

Asp Ile Glu Gly Val Lys Ser Ala Phe Val Ser Gln Thr Tyr Asp Ile
    130                 135                 140

Pro Glu Pro Gln Met Val Asp Ser Asn Arg Thr Ile Gly Ser Asp Thr
145                 150                 155                 160
```

-continued

```
Val Trp Thr Gln Ser His Tyr Lys Gly Glu Asn Ile Val Val Ala Val
                165                 170                 175
Leu Asp Thr Gly Leu Asp Thr Gly His Pro Ala Phe Ala Val Ala Pro
            180                 185                 190
Ser Gln Phe Arg Ile Asn Lys Gln Lys Ile Gln Thr Val Leu Asn Asn
        195                 200                 205
Lys Lys Leu Lys Ala Thr Ala Asn Thr Pro Gly Leu Thr Val Asp His
    210                 215                 220
Val Tyr Ile Asn Asp Lys Val Pro Phe Val Tyr Asp Tyr Ala Asp Lys
225                 230                 235                 240
Asp Ala Ile Val Asp Pro Ser Ala His Asn Tyr Gly Arg Leu Ala His
                245                 250                 255
Gly Thr His Val Ala Gly Thr Val Ala Gly Lys Asp Gln Ala Asp Phe
            260                 265                 270
Arg Gly Val Ala Pro Glu Ala Gln Leu Met Ile Phe Lys Val Phe Ser
        275                 280                 285
Asp Lys Gly Gly Gly Ala Ser Asp Ile Ser Leu Val Ser Ala Leu Glu
    290                 295                 300
Asp Cys Val Tyr Leu Gly Val Asp Val Ile Asn Met Ser Leu Gly Ser
305                 310                 315                 320
Asp Ala Gly Phe Met His Asp Ser Tyr Lys Pro Thr Asn Asp Met Tyr
                325                 330                 335
Asn Arg Ile Arg Asp Asn Gly Ile Val Leu Asp Val Ala Ala Gly Asn
            340                 345                 350
Ala Met Ser Ser Ser Glu Lys Asn Leu Tyr Gly Asn Asp Leu Thr Leu
        355                 360                 365
Ala Ser Asp Pro Asp His Gly Ile Val Gly Ser Pro Ser Thr Tyr Ala
    370                 375                 380
Ser Pro Ile Ser Val Ala Ser Val Asn Asn Thr Lys Tyr Arg Pro Gly
385                 390                 395                 400
Ser Lys Thr Ile Asp Pro Thr Gln Val Thr Leu Ser Gly Phe Ser Ser
                405                 410                 415
Ile Gly Thr Thr Pro Asn Ile Ser Ile Lys Pro Glu Ile Ser Ala Pro
            420                 425                 430
Gly Ala Trp Ile Arg Ser Ala Met Pro Arg Leu Asn Gly Gln Asn Tyr
        435                 440                 445
Asp Glu Met Ser Gly Thr Ser Met Ala Thr Pro His Val Ala Gly Ala
    450                 455                 460
Ser Ala Leu Met Lys Gln Tyr Leu Asn Asp Lys Phe Gly Asn Leu Thr
465                 470                 475                 480
Asn Ile Gln Lys Met Glu Leu Thr Asn Asn Leu Leu Met Ser Thr Ala
                485                 490                 495
His Pro Ile Val Gln Lys Asp Gly Ala Pro Gln Pro Val Arg Lys Gln
            500                 505                 510
Gly Ser Gly Met Met Asp Ile Asn Ala Ala Ile Lys Thr Pro Val Tyr
        515                 520                 525
Leu Ser Val Asp Pro Lys Gln Asn His Asp Gly Ser Asn Arg Pro Lys
    530                 535                 540
Ile Glu Leu Gly Asp Asp Gln Asn Lys Thr Gly Asn Tyr Thr Leu Lys
545                 550                 555                 560
Phe Lys Val Thr Asn Met Gly Thr Gln Thr Glu Thr Tyr Gln Ile Lys
                565                 570                 575
Glu Lys Val Ser Val Pro Val Ile Lys Arg Ser Ile Met Asp Asp His
```

-continued

```
                580                 585                 590
Arg Glu Arg Ala Phe Met Thr Asp Asp Asn Arg Ser Val Asp Val Thr
            595                 600                 605

Arg Ser Gly Val Thr Ser Val Thr Val Lys Ala Lys Glu Thr Lys Asp
610                 615                 620

Val Ser Ile Thr Val Gln Leu Thr Gln Ala Glu Lys Asn Arg Leu Asn
625                 630                 635                 640

Gln Glu Phe Glu Asn Gly Thr Tyr Val Glu Gly Phe Val Gln Leu Thr
            645                 650                 655

His Ala Ser His Pro Gln Ile Ser Ile Pro Phe Leu Ala Phe Tyr Gly
            660                 665                 670

Asp Trp Glu Lys Ala Pro Ile Phe Asp His Ala Ala Glu Tyr Glu Met
            675                 680                 685

Gly Val Arg Ala Ser Asn Tyr Ala His Arg Tyr Leu Ser Asp Lys Met
            690                 695                 700

Pro Met Gly Gly Asn Ile Phe Asp Arg Arg Met Ile Tyr Thr Asn Pro
705                 710                 715                 720

Ser Arg Phe Val Ile Ser Pro Asn Gly Asp Gly Leu Tyr Asp Lys Leu
                725                 730                 735

Ser Gly Ile Asn Leu Gly Gln Leu Arg Asn Val Glu Ser Met Thr Met
                740                 745                 750

Glu Ile Thr Asn Lys Lys Thr Lys Gln Val Ile Ile Lys Glu Glu Arg
            755                 760                 765

Pro Asn Ile Arg Lys Thr Phe Tyr Asn Asn Ser Tyr Gly Lys Gln Val
770                 775                 780

Pro Asn Ile Leu Phe Trp Pro Phe Ser Thr Phe Thr Gly Leu Asp Gln
785                 790                 795                 800

Gln Lys Asn Pro Leu Pro Glu Gly Arg Tyr Asp Leu Lys Ile Ser Ala
                805                 810                 815

Asp Leu Gly Tyr Arg Lys Gly Ile Asp Gln Glu Ile Val His Thr Ile
                820                 825                 830

His Val Asp His Thr Lys Pro Val Ile Pro Gln Asp Lys Ile Lys Phe
            835                 840                 845

Thr Glu Lys Asn Gly Thr Val Met Met His Val Glu Ser Asn Asp Asn
850                 855                 860

Thr Phe Leu Thr Gln Thr Ala Leu Tyr Pro Val Tyr Asn Gly Lys Val
865                 870                 875                 880

Gln Val Asn Arg Pro Leu Lys Lys Gln Tyr Thr Pro Tyr Asp Leu Val
                885                 890                 895

Ser Arg His Ala Phe Asp Val Asp Val Thr Asn Leu Lys Gly Gln Glu
                900                 905                 910

Val Val Ile Ser Ala Val Asp Ala Gly Met Leu Glu Thr Asn Tyr Lys
            915                 920                 925

Thr Val Pro Gly Thr Pro Lys Pro His Leu Lys Val Asp Glu Phe
            930                 935                 940

Lys Ile Lys Val Gly Ala Gln Ile Glu Leu Glu Pro Gly Asn Phe Lys
945                 950                 955                 960

Trp Gln Thr Pro Thr Phe Glu Ser Glu Asp Pro Glu Ile Ala Asp Val
                965                 970                 975

Asn Asp Lys Gly Leu Val Thr Gly Leu Lys Pro Gly Ala Thr Phe Ile
                980                 985                 990

Lys Ile Lys Asp Lys Asn Gly Ile  Asp Leu Val Ala Leu  Ile Glu Val
            995                 1000                1005
```

-continued

```
Phe Glu Glu Glu Ser Leu Lys Leu Gln Met Lys Val Gly Glu Lys
    1010                1015                1020

Arg Lys Leu Ile Ser Tyr Asn Leu Glu Gly Lys Arg Thr Phe Asp
    1025                1030                1035

Ser Asp Ala Pro His Ile Val Ser Ala Arg Asp Thr Gly Glu Ile
    1040                1045                1050

Glu Ala His Gln Lys Gly Lys Ala Lys Ile Thr Val Gln Asn Ala
    1055                1060                1065

Tyr Glu Lys Leu Glu Tyr Glu Val Glu Val Asp Gln Pro Lys
    1070                1075                1080

Tyr Thr Pro Ser Leu Ser Phe Asp Lys Lys Val Tyr Glu Ile Asn
    1085                1090                1095

Ser Gly Glu Val Val Ala Pro Lys Phe Thr Ile Glu Asn Asp Asp
    1100                1105                1110

Pro Ser Asn Pro Gln Val Val Thr Arg Leu Leu Thr Ser Asn Glu
    1115                1120                1125

Glu His Val Ser Ile Ala Gly Leu Lys Phe Thr Gly Glu His Ala
    1130                1135                1140

Gly Glu Ala Ala Val Ile Ala Glu Leu Lys Asn Gly Thr Arg Ala
    1145                1150                1155

Val Ala Lys Val Lys Val Gly Gly Leu Asp Thr Lys Lys Leu Asp
    1160                1165                1170

Ile Leu Ile Ser Gln Ala Ser Asn Leu Asn Ala Asp Asp Tyr Thr
    1175                1180                1185

Lys Thr Ser Phe Thr Thr Leu Thr Thr Thr Leu Gln Glu Ala Lys
    1190                1195                1200

Thr Leu Arg Lys Gln Lys Gly Ile Asp Gln Ser Asn Ile Asp Thr
    1205                1210                1215

Met Val Glu Lys Leu Glu Lys Ser Met Asn Gln Leu Val Gln Val
    1220                1225                1230

Ile Lys Asn Leu Pro Ser Ala Met Ser Val Glu Val Gly Asn Thr
    1235                1240                1245

Phe Lys Leu Ser Pro Lys Pro Ala Gln Gly Lys Trp Ile Trp Asp
    1250                1255                1260

Ala Glu Phe Leu Glu Gly Thr Ala Gln Asn Asn Asp Gln Glu Met
    1265                1270                1275

Met Phe Lys Gly Leu Lys Glu Gly Gln Thr Asp Val Arg Tyr Arg
    1280                1285                1290

Thr Lys Asp Gly Glu Glu Gln Ser Val Ala Val Ala Val Lys Pro
    1295                1300                1305

Lys Pro Lys Pro Val Glu Ile Asp Pro Ile Val Pro Thr Asp Pro
    1310                1315                1320

Val Asp Pro Val Lys Pro Thr Asp Pro Val Asp Pro Val Lys Pro
    1325                1330                1335

Lys Asp Pro Val Asp Pro Val Lys Pro Thr Asp Pro Val Asp Pro
    1340                1345                1350

Val Lys Pro Thr Asp Pro Val Asp Pro Val Lys Pro Thr Asp Pro
    1355                1360                1365

Val Asp Pro Val Lys Pro Thr Asp Pro Val Asp Pro Val Lys Pro
    1370                1375                1380

Thr Asp Pro Val Asp Pro Val Lys Pro Thr Asp Pro Val Asp Pro
    1385                1390                1395
```

```
Val Lys Pro Thr Asp Pro Val Asp Pro Val Lys Pro Ala Asp Pro
    1400                1405                1410

Val Asp Pro Val Lys Pro Thr Asp Pro Thr Lys Pro Thr Lys Pro
    1415                1420                1425

Val Asp Ser Gly Leu Lys Pro Ile Asp Asn Leu Lys Lys Pro Ile
    1430                1435                1440

Val Lys Pro Lys Asp Pro Val Ser Gln Val Glu Ser Ile Lys Gln
    1445                1450                1455

Asp Lys Pro Val Ile His Phe Gly Val Val Ser Glu Ser Leu Pro
    1460                1465                1470

Gln Thr Gly Val Thr Pro Gln Tyr Arg Gly Tyr Thr Leu Leu Gly
    1475                1480                1485

Leu Gly Leu Val Ile Arg Val Ile Asn Asp Lys Lys Asn Arg Met
    1490                1495                1500

Lys
```

<210> SEQ ID NO 53
<211> LENGTH: 2178
<212> TYPE: PRT
<213> ORGANISM: Lactobacillus paracasei

<400> SEQUENCE: 53

```
Met Asn Arg Val Lys Pro Phe Ser Gln Glu Lys Arg Arg Tyr Lys Met
1               5                   10                  15

Tyr Lys Ser Gly Arg His Trp Val Tyr Ser Ala Ile Val Thr Phe Gly
            20                  25                  30

Ala Ala Ser Phe Leu Met Met Gln Pro Ala Gln Gly Val Ser Ala Asp
        35                  40                  45

Ala Ala Ala Pro Pro Pro Thr Thr Gln Thr Lys Ser Asn Gln Ala Ala
    50                  55                  60

Pro Asp Ala Ala Ser Ala Asp Ser Pro Val Lys Pro Ala Ser Ala
65                  70                  75                  80

Thr Thr Gly Gln Val Thr Ser Ser Ala Asp Thr Pro Thr Thr Thr Ala
                85                  90                  95

Ala Ser Ala Thr Pro Thr Ala Thr Ala Lys Ser Ala Thr Pro Ala Pro
            100                 105                 110

Val Ala Ser Gln Ala Lys Pro Glu Ala Ser Ala Lys Ala Lys Gln Pro
        115                 120                 125

Thr Gln Pro Thr Ser Val Thr Pro Ser Thr Pro Thr Thr Thr Asn Thr
    130                 135                 140

Lys Thr Ala Gln Lys Thr Val Ser Gln Pro Ala Gln Lys Ala Pro Ala
145                 150                 155                 160

Ala Pro Ala Lys Pro Ala Pro Ile Ala Lys Pro Ala Pro Thr Ser Asn
                165                 170                 175

Pro Glu Asn Lys Ala Ser Leu Thr Lys Gly Asn Val Gln Pro Leu Trp
            180                 185                 190

Asp Gln Asn Ile Lys Gly Gln Gly Met Val Ala Ala Val Ile Asp Gln
        195                 200                 205

Gly Val Glu Pro His Gln Asp Phe Arg Leu Ser Asp Ala Lys Thr Ala
    210                 215                 220

Ala Leu Ser Glu Asp Gln Ile Lys Ala Phe Thr Ala Ser His Gly Tyr
225                 230                 235                 240

Gly Asp Tyr Val Asn Glu Lys Ile Pro Phe Tyr Asp Tyr Thr Asn
                245                 250                 255
```

```
Asn Val Asn Glu Asn Leu Lys Phe Asp Thr Ser Asn His Gly Gln His
            260                 265                 270

Leu Ala Gly Ile Ile Ala Ala Asn Gly Gln Pro Ser Asp Ser Lys Lys
            275                 280                 285

Tyr Val Thr Gly Ile Ala Pro Glu Ala Gln Leu Leu Ser Met Lys Ile
            290                 295                 300

Leu Gly Lys Ser Ser Ser Asp Ser Leu Asn Asn Ala Ala Arg Ala Ile
305                 310                 315                 320

Tyr Asp Ala Val Asp Leu Gly Ala Asn Ala Ile Asn Ile Ser Phe Gly
                325                 330                 335

Met Gly Val Asp Ile Asp Asp Pro Thr Ala Glu Gly Gln Ala Ala Ile
            340                 345                 350

Lys Phe Ala Thr Asp His Gly Val Phe Val Thr Val Ala Thr Gly Asn
            355                 360                 365

Asn Gly His Ala Gly Gly Ile Tyr Asp Lys Ser Ala Ser Asn Gly Ile
            370                 375                 380

Thr Thr Ser Tyr Gln Pro Ala Asn Ala Ser Thr Leu Thr Thr Pro Ser
385                 390                 395                 400

Ala Thr Pro Ser Ala Met Ala Val Ala Ala Gly Asn Asp Val Leu Asp
                405                 410                 415

Ala Lys Ala Ala Leu Ile Ser Pro Ser Ser Trp Gly Pro Thr Thr Ser
            420                 425                 430

Tyr Lys Leu Lys Pro Asp Ile Thr Ala Pro Gly Glu Lys Val Ala Ser
            435                 440                 445

Thr Leu Leu Asn Asp Glu Leu Gly Lys Val Ser Gly Thr Ser Gln Ala
450                 455                 460

Asn Ala Tyr Val Thr Gly Ala Ser Leu Leu Val Met Gln Asn Leu Lys
465                 470                 475                 480

Arg Ser Thr Asn Leu Thr Gly Ala Gln Leu Val Lys Ala Val Lys Leu
            485                 490                 495

Ala Leu Met Asn Ala Ala Asn Pro Ile Leu Asp Ile Asn Tyr Pro Gly
            500                 505                 510

Gln Ile Ile Ser Pro Arg Arg Gln Gly Ala Gly Gln Ile Asp Val Ala
            515                 520                 525

Lys Ala Ala Asn Leu Thr Val Ser Ala Glu Gly Thr Asp Asp Ala Gly
530                 535                 540

Ser Val Ser Leu Gln Gln Phe Thr Gly Ser Lys Ser Phe Val Ile Thr
545                 550                 555                 560

Leu Glu Asn Arg Gly Thr Asp Gln Gln Thr Tyr Thr Leu Asp Leu Gly
            565                 570                 575

Gln Pro Ala Thr Glu Val Ile Asp Thr Ala Asn Asn Lys Thr Val His
            580                 585                 590

Asp Arg Thr Leu Pro Gly Ala Thr Leu Thr Ala Thr Pro Thr Phe
            595                 600                 605

Thr Leu Asp Ala Gly Ala Ser Lys Lys Ile Thr Phe Thr Leu Ser Leu
            610                 615                 620

Asp Asp Thr Val Lys Leu Asn Gln Val Val Glu Gly Phe Ile Lys Phe
625                 630                 635                 640

Lys Ala Ala Asp Asp Arg Gln Ser Ile Ser Val Pro Tyr Met Gly Tyr
                645                 650                 655

Tyr Gly Ser Thr Asn Asp Glu Ala Val Phe Asp Lys Pro Ala Asn Glu
            660                 665                 670

Glu Gly Ser Ile Phe Lys Gly Gly Tyr Leu Val Asp Asn Asn His Asn
```

-continued

```
            675                 680                 685
Pro Leu Gly Ile Thr Asp Pro Thr Ser Leu Ser Glu Leu Val Asn Asn
690                 695                 700
Pro Thr Asn Gly Phe Thr Trp Gln Thr Ile Gly Ala Lys Ile Glu Asn
705                 710                 715                 720
Asn Lys Val Ala Phe Ser Pro Asn Gly Asp Gly Ile Ser Asp Thr Ile
                725                 730                 735
Thr Pro Tyr Val Phe Thr Lys Gln Asn Leu Lys Gln Val Ile Ala Gln
                740                 745                 750
Ile Leu Asp Gln Asp Asn Lys Val Met Arg Val Ile Asp Gln Glu Thr
            755                 760                 765
Asp Thr Thr Lys Ser Phe Leu Glu Val Gly Ser Thr Thr Asn Ala Asp
770                 775                 780
Leu Ala Lys Ser Ile Ser Met Phe Leu Asn Pro Asp Lys Leu Lys Trp
785                 790                 795                 800
Asp Gly Gln Val Tyr Asp Gln Thr Thr Gly Gln Met Val Pro Ala Lys
                805                 810                 815
Asp Gly Ile Tyr Thr Tyr Arg Leu Ile Gly Met Thr Tyr Thr Pro Gly
                820                 825                 830
Glu Asn Asn Met Gln Thr Met Ser Leu Pro Val Ala Val Asp Thr Ile
                835                 840                 845
Lys Pro Thr Leu Ser Asn Leu Ala Tyr Ser Asp Gly Lys Leu Thr Ala
850                 855                 860
Asp Tyr Ser Asp Gln Gly Val Gly Phe Thr Ala Tyr Ser Gln Ala Lys
865                 870                 875                 880
Leu Thr Ile Gly Ser Ala Thr Tyr Gly Ile Pro Leu Asn His Asp Asn
                885                 890                 895
Lys Ala Thr Ser Gly Thr Ile Asn Tyr Gln Leu Asn Asp Gln Leu
                900                 905                 910
Ala Asn Leu Lys Thr Gly Glu Gly Lys Val Thr Leu Thr Ile Thr Asp
            915                 920                 925
Ala Ala Gly Asn Ser Asp Gln Gly Ser Ile Lys Ala Val Val Gly Glu
            930                 935                 940
Asn Lys Thr Ile Glu Ser Asn Phe Ile Trp Pro Gln Val Arg Trp Ser
945                 950                 955                 960
Met Pro Asp Thr Lys Gly Asn Leu Thr Arg Ser Asp Gly Arg Tyr Gln
                965                 970                 975
Ala Leu Thr Lys Asp Ser Thr Phe Thr Ala Gln Ala Met Val Pro Lys
                980                 985                 990
Gly Gln Asp Tyr Ile Val Thr Ala Thr Asp Tyr Val Ser Asp Arg Gln
                995                 1000                1005
Tyr Ile Gly Thr Leu Asp Lys Ala Thr Gly Ile Val Thr Phe Asn
            1010                1015                1020
Ile Asp Ala Thr Gly Gln Pro Tyr Ala Asn Leu Thr Ile Ser Ala
            1025                1030                1035
Phe Ala Arg Asp Asp Phe Gly Glu Phe Ile Lys Ser Pro Lys Thr
            1040                1045                1050
Glu Asp Phe Ile Ile Phe Ile Lys Lys Asn Thr Ala Ala Tyr Ser
            1055                1060                1065
Asn Ala Lys Thr Gln Thr Lys Pro Phe Ala Asp Glu Ala Thr Ala
            1070                1075                1080
Ile Lys Gly Ala Lys Phe Phe Ser Gly Ala Ala His Leu Thr Gly
            1085                1090                1095
```

-continued

```
Arg Ser Pro Leu Thr Ser Thr Lys Gly Lys Met Ile Asn Gly Ile
    1100            1105             1110

Ala Phe Leu Asp Leu Asn Asn Lys Arg Thr Leu Val Gly Ile
    1115            1120             1125

Asp Ser Ala Ser Thr Phe Tyr Asp Ala Lys Leu Lys Thr Leu Thr
    1130            1135             1140

Leu Arg Gly Lys Val Ser Asp Pro Lys Asn Ser Lys Leu Arg Ile
    1145            1150             1155

Phe Val Thr Pro Arg Gln Asn Asp Pro Gln Asn Glu Val Thr Phe
    1160            1165             1170

Ala Ala Asp Gly Ser Phe Ser Met Thr Met Pro Cys Asn Pro Thr
    1175            1180             1185

Glu Glu Arg Asn Ile Gly Tyr Val Leu Thr Thr Leu Asp Lys Asp
    1190            1195             1200

Gly Lys Glu Lys Thr Asn Gly Gly Phe Leu Leu Leu Tyr Thr Asp
    1205            1210             1215

Thr Thr Leu Pro Thr Leu Glu Leu Ser Asp Ala Asp Ser Met Lys
    1220            1225             1230

Ile Asp Asp Asp Gly Thr Tyr Leu Val Thr Thr Asp Ala Asp Thr
    1235            1240             1245

Phe Ser Ile Lys Gly Ser Val Thr Asp Asn Ile Gly Gly Tyr Arg
    1250            1255             1260

Leu Tyr Ser Asn Gly Asn Asn Ile Phe Met Gln Gln Asn Leu Ala
    1265            1270             1275

Gly Phe Asn Ala His Gln Ser Ser Ala Ala Pro Asn Gln Leu Thr
    1280            1285             1290

Asn Gly Tyr Asn Pro Tyr Gly Ala Ala Ser Phe Asp Glu Thr Tyr
    1295            1300             1305

Gln Leu Thr Asp Gly Leu Asn Ile Ile Thr Leu Gln Ala Val Asp
    1310            1315             1320

Gln Val Gly Asn Thr Val Thr Lys Thr Phe Asn Val Thr Lys Thr
    1325            1330             1335

Pro Lys Leu Leu Lys Glu Glu Ser Leu Asp Glu Leu Glu Ile Thr
    1340            1345             1350

Pro Glu Gln Gln Asp Gln Thr Pro Lys Asn Asp Ala Gly Glu Ala
    1355            1360             1365

Pro Val Thr Thr Pro Ala Thr Glu Glu Thr Leu Val Thr Pro Ser
    1370            1375             1380

Thr Glu Ser Thr Met Val Asn Pro Glu Asp Ser Lys Val Glu Thr
    1385            1390             1395

Ser Asp Pro Ile Val Glu Thr Ala Pro Ser Lys Glu Ala Gln Ser
    1400            1405             1410

Asp Gly Asn Gly Ala Thr Glu Thr Asn Thr Thr Ala Ser Val Thr
    1415            1420             1425

Thr Gly Val Asp Glu Asn Pro Val Asp Ser Ser Ala Asn Ala Ala
    1430            1435             1440

Thr Pro Met Pro Asn His Val Lys Asp Ala Asn Thr Asp Ala Glu
    1445            1450             1455

Val Thr Glu Val Thr Asn Thr Lys Asp Asn Thr Gln Gly Thr Thr
    1460            1465             1470

Ala Pro Thr Ser Thr Asp Pro Ala Thr Asp Lys Glu Ser Thr Thr
    1475            1480             1485
```

-continued

| | | | | | | | | | | | |
|---|---|---|---|---|---|---|---|---|---|---|---|
| Lys | Ser | Glu | Ile | Asp | Pro | Ala | Ala | Thr | Ser | Pro | Asn |
| | 1490 | | | | 1495 | | | | 1500 | | |

Asp Ser Lys

Val Val Glu Ala Val Thr Lys Glu Ala Ala Val Asn
    1505                1510               1515
Asp Asp Lys

Gly Asn Gln Ala Asp Asp Gly Glu Pro Thr Val Thr
    1520                1525               1530
Asn Leu Ala

Thr Ser Lys Asp Ser Ala Val Gln Pro Glu Val Asp
    1535                1540               1545
Pro Ala Ser

Gly Leu Gln Ser Asp Asp Lys Val Val Glu Thr Ala
    1550                1555               1560
Val Glu Asp

Asp Glu Met Val Glu Lys Glu Gly His Lys Ser Asp
    1565                1570               1575
Asn Ala Lys

Pro Ala Ile Thr Asp Pro Thr Thr Asp Lys Asp Lys
    1580                1585               1590
Ala Val Gln

Ser Glu Val Asn Pro Thr Ala Ser Ser Gln Gly Ala
    1595                1600               1605
Thr Lys Ala

Val Glu Ala Ala Ala Lys Asp Thr Lys Val Glu Asp
    1610                1615               1620
Asp Lys Gly

Asn Lys Thr Ala Ser Val Glu Thr Gly Val Ala Thr
    1625                1630               1635
Pro Ala Met

Asp Asn Asn Ser Ser Val Lys Ser Ala Val Asp Pro
    1640                1645               1650
Thr Ala Thr

Ala Pro Ser Asp Asn Thr Ala Pro Ala Ile Glu Thr
    1655                1660               1665
Ala Ala Glu

Asn Phe Asn Ile Glu Asn Asp Lys Gly Asn Glu Thr
    1670                1675               1680
Asn Ala Val

Glu Thr Val Val Thr Asp Pro Ala Thr Asn Lys Glu
    1685                1690               1695
Gly Thr Val

Lys Ser Glu Ile Glu Pro Val Ala Thr Pro Ser Asn
    1700                1705               1710
Thr Thr

Val Thr Ala Thr Glu Met Thr Lys Glu Asn Thr Pro
    1715                1720               1725
Ala Glu Asp

Glu Lys Asp Asn Gln Val Asn Ala Val Thr Asp Pro
    1730                1735               1740
Lys Thr Thr

Lys Asp Ser Ala Asp Lys Ser Glu Ile Glu Pro Val
    1745                1750               1755
Ala Thr Ala

Ala Thr Asp Lys Asp Arg Thr Val Lys Ser Asp Pro
    1760                1765               1770
Thr Glu Ala

Ala Ser Thr Pro Ser Glu Asp Ser Ile Arg Lys Thr
    1775                1780               1785
Thr Ala Glu

Asp Ala Lys Ala Lys Asp Asp Arg Glu Ala Ala Ala
    1790                1795               1800
Asn Ala Val

Ala Ala Asp Ser Lys Ala Asp Lys Asn Asn Pro Val
    1805                1810               1815
Glu Ser Lys

Ile Asp Ala Thr Ala Ile Thr Pro Ser Asn Ser Gln
    1820                1825               1830
Pro Thr Glu

Thr Asp Thr Glu Asn Ala Ala Val Glu Asn Gly Lys
    1835                1840               1845
Asp Gln Lys

Ser Ala Asp Thr Pro Ser Pro Val Ile Asp Pro Ala
    1850                1855               1860
Val Asp Lys

Asp Arg Ala Val Lys Ser Lys Val Asn Pro Ala Thr
    1865                1870               1875
Thr Ala Pro

Asn Asp Asp Lys Ala Pro Glu Val Thr Thr Glu Ser
                                                  Ser Lys Ile

```
                    1880                1885                1890

Glu Asn Val Lys Ser His Gln Ser Asp Val Val Glu Thr Phe Gly
    1895                1900                1905

Ser Asp Ser Gln Thr Ser Lys Asp Pro Val Ala Glu Ser Lys Arg
    1910                1915                1920

Asn Pro Thr Ala Thr Ser Ser Asp Thr Thr Thr Glu Thr
    1925                1930                1935

Glu Thr Leu Ala Thr Gly Gly Glu Gln Asn Ser Gln Val Asp Thr
    1940                1945                1950

Pro Lys Lys Ala Met Thr Thr Thr Pro Asn Asp Lys Asn Val Ser
    1955                1960                1965

Leu Ala Thr Val Ala Pro Asp Lys Thr Lys Gly Asp Thr Ala Gly
    1970                1975                1980

Ala Arg Thr Val Thr Thr Thr Asp Gly Gln Arg Lys Pro Thr Lys
    1985                1990                1995

Thr Glu Val Gly Ser Ser Asn Val Ala Ser Asn His Pro Ser Thr
    2000                2005                2010

Thr Asp Ser Ser Thr Glu Thr Thr Ser Gln Ser Asp Glu Pro Thr
    2015                2020                2025

Ser Ser Ile Glu Thr Thr Glu Pro Ala Thr Thr Ala Pro Ser Thr
    2030                2035                2040

Glu Asp Lys Pro Val Arg Thr Thr Ala Asp Gln Lys Val Thr Asp
    2045                2050                2055

Gln Lys Ser Asn Lys Asp Asp Gln Ala Asn Pro Thr Ala Ile Lys
    2060                2065                2070

Lys Lys Leu Lys Ser Lys Val Thr Glu Asp Gly Glu Asn Ile Ser
    2075                2080                2085

Gln Thr Asn Gln Lys Asp Pro Lys Thr Lys Thr Ala Lys Gly Glu
    2090                2095                2100

Gln Thr Thr Ser Pro Leu Asp Gln Lys Arg Ser Ala Leu Lys Gln
    2105                2110                2115

Lys Glu Ser Lys Glu Ile Ala Pro Glu Lys Ser Val His Ala Thr
    2120                2125                2130

Lys Thr Ala Ala Lys Thr Leu Pro Pro Met Gly Met Gln Asn Ser
    2135                2140                2145

His Trp Leu Gln Ala Leu Gly Ile Ala Leu Leu Gly Met Ile Leu
    2150                2155                2160

Ala Leu Gly Ile Gly Leu Thr Ser Lys Lys Lys His Glu Lys Ser
    2165                2170                2175

<210> SEQ ID NO 54
<211> LENGTH: 2127
<212> TYPE: PRT
<213> ORGANISM: Artificial Sequence
<220> FEATURE:
<223> OTHER INFORMATION: fragment of Lactobacillus paracasei subsp.
      paracasei 8700:2 protease

<400> SEQUENCE: 54

Pro Pro Pro Thr Thr Gln Thr Lys Ser Asn Gln Ala Ala Pro Asp Ala
1               5                   10                  15

Ala Ser Ala Asp Ser Pro Val Ser Lys Pro Ala Ser Ala Thr Thr Gly
            20                  25                  30

Gln Val Thr Ser Ser Ala Asp Thr Pro Thr Thr Ala Ala Ser Ala
        35                  40                  45
```

```
Thr Pro Thr Ala Thr Ala Lys Ser Ala Thr Pro Ala Pro Val Ala Ser
    50                  55                  60

Gln Ala Lys Pro Glu Ala Ser Ala Lys Ala Lys Gln Pro Thr Gln Pro
65                  70                  75                  80

Thr Ser Val Thr Pro Ser Thr Pro Thr Thr Asn Thr Lys Thr Ala
                85                  90                  95

Gln Lys Thr Val Ser Gln Pro Ala Gln Lys Ala Pro Ala Ala Pro Ala
                100                 105                 110

Lys Pro Ala Pro Ile Ala Lys Pro Ala Pro Thr Ser Asn Pro Glu Asn
                115                 120                 125

Lys Ala Ser Leu Thr Lys Gly Asn Val Gln Pro Leu Trp Asp Gln Asn
130                 135                 140

Ile Lys Gly Gln Gly Met Val Ala Ala Val Ile Asp Gln Gly Val Glu
145                 150                 155                 160

Pro His Gln Asp Phe Arg Leu Ser Asp Ala Lys Thr Ala Ala Leu Ser
                165                 170                 175

Glu Asp Gln Ile Lys Ala Phe Thr Ala Ser His Gly Tyr Gly Asp Tyr
                180                 185                 190

Val Asn Glu Lys Ile Pro Phe Phe Tyr Asp Tyr Thr Asn Asn Val Asn
                195                 200                 205

Glu Asn Leu Lys Phe Asp Thr Ser Asn His Gly Gln His Leu Ala Gly
                210                 215                 220

Ile Ile Ala Ala Asn Gly Gln Pro Ser Asp Ser Lys Lys Tyr Val Thr
225                 230                 235                 240

Gly Ile Ala Pro Glu Ala Gln Leu Leu Ser Met Lys Ile Leu Gly Lys
                245                 250                 255

Ser Ser Ser Asp Ser Leu Asn Asn Ala Ala Arg Ala Ile Tyr Asp Ala
                260                 265                 270

Val Asp Leu Gly Ala Asn Ala Ile Asn Ile Ser Phe Gly Met Gly Val
            275                 280                 285

Asp Ile Asp Asp Pro Thr Ala Glu Gly Gln Ala Ala Ile Lys Phe Ala
            290                 295                 300

Thr Asp His Gly Val Phe Val Thr Val Ala Thr Gly Asn Asn Gly His
305                 310                 315                 320

Ala Gly Gly Ile Tyr Asp Lys Ser Ala Ser Asn Gly Ile Thr Thr Ser
                325                 330                 335

Tyr Gln Pro Ala Asn Ala Ser Thr Leu Thr Thr Pro Ser Ala Thr Pro
                340                 345                 350

Ser Ala Met Ala Val Ala Ala Gly Asn Asp Val Leu Asp Ala Lys Ala
            355                 360                 365

Ala Leu Ile Ser Pro Ser Ser Trp Gly Pro Thr Thr Ser Tyr Lys Leu
370                 375                 380

Lys Pro Asp Ile Thr Ala Pro Gly Glu Lys Val Ala Ser Thr Leu Leu
385                 390                 395                 400

Asn Asp Glu Leu Gly Lys Val Ser Gly Thr Ser Gln Ala Asn Ala Tyr
                405                 410                 415

Val Thr Gly Ala Ser Leu Leu Val Met Gln Asn Leu Lys Arg Ser Thr
                420                 425                 430

Asn Leu Thr Gly Ala Gln Leu Val Lys Ala Val Lys Leu Ala Leu Met
                435                 440                 445

Asn Ala Ala Asn Pro Ile Leu Asp Ile Asn Tyr Pro Gly Gln Ile Ile
450                 455                 460

Ser Pro Arg Arg Gln Gly Ala Gly Gln Ile Asp Val Ala Lys Ala Ala
```

```
            465                 470                 475                 480
        Asn Leu Thr Val Ser Ala Glu Gly Thr Asp Asp Ala Gly Ser Val Ser
                        485                 490                 495
        Leu Gln Gln Phe Thr Gly Ser Lys Ser Phe Val Ile Thr Leu Glu Asn
                        500                 505                 510
        Arg Gly Thr Asp Gln Gln Thr Tyr Thr Leu Asp Leu Gly Gln Pro Ala
                        515                 520                 525
        Thr Glu Val Ile Asp Thr Ala Asn Asn Lys Thr Val His Asp Arg Thr
                    530                 535                 540
        Leu Pro Gly Ala Thr Leu Thr Thr Ala Thr Pro Thr Phe Thr Leu Asp
        545                 550                 555                 560
        Ala Gly Ala Ser Lys Lys Ile Thr Phe Thr Leu Ser Leu Asp Asp Thr
                        565                 570                 575
        Val Lys Leu Asn Gln Val Val Glu Gly Phe Ile Lys Phe Lys Ala Ala
                        580                 585                 590
        Asp Asp Arg Gln Ser Ile Ser Val Pro Tyr Met Gly Tyr Tyr Gly Ser
                        595                 600                 605
        Thr Asn Asp Glu Ala Val Phe Asp Lys Pro Ala Asn Glu Glu Gly Ser
                    610                 615                 620
        Ile Phe Lys Gly Gly Tyr Leu Val Asp Asn Asn His Asn Pro Leu Gly
        625                 630                 635                 640
        Ile Thr Asp Pro Thr Ser Leu Ser Glu Leu Val Asn Asn Pro Thr Asn
                        645                 650                 655
        Gly Phe Thr Trp Gln Thr Ile Gly Ala Lys Ile Glu Asn Asn Lys Val
                        660                 665                 670
        Ala Phe Ser Pro Asn Gly Asp Gly Ile Ser Asp Thr Ile Thr Pro Tyr
                        675                 680                 685
        Val Phe Thr Lys Gln Asn Leu Lys Gln Val Ile Ala Gln Ile Leu Asp
                        690                 695                 700
        Gln Asp Asn Lys Val Met Arg Val Ile Asp Gln Glu Thr Asp Thr Thr
        705                 710                 715                 720
        Lys Ser Phe Leu Glu Val Gly Ser Thr Thr Asn Ala Asp Leu Ala Lys
                        725                 730                 735
        Ser Ile Ser Met Phe Leu Asn Pro Asp Lys Leu Lys Trp Asp Gly Gln
                        740                 745                 750
        Val Tyr Asp Gln Thr Thr Gly Gln Met Val Pro Ala Lys Asp Gly Ile
                        755                 760                 765
        Tyr Thr Tyr Arg Leu Ile Gly Met Thr Tyr Thr Pro Gly Glu Asn Asn
                        770                 775                 780
        Met Gln Thr Met Ser Leu Pro Val Ala Val Asp Thr Ile Lys Pro Thr
        785                 790                 795                 800
        Leu Ser Asn Leu Ala Tyr Ser Asp Gly Lys Leu Thr Ala Asp Tyr Ser
                        805                 810                 815
        Asp Gln Gly Val Gly Phe Thr Ala Tyr Ser Gln Ala Lys Leu Thr Ile
                        820                 825                 830
        Gly Ser Ala Thr Tyr Gly Ile Pro Leu Asn His Asp Asn Lys Ala Thr
                        835                 840                 845
        Ser Gly Thr Ile Asn Tyr Gln Leu Asn Asp Asp Gln Leu Ala Asn Leu
                        850                 855                 860
        Lys Thr Gly Glu Gly Lys Val Thr Leu Thr Ile Thr Asp Ala Ala Gly
        865                 870                 875                 880
        Asn Ser Asp Gln Gly Ser Ile Lys Ala Val Val Gly Glu Asn Lys Thr
                        885                 890                 895
```

-continued

```
Ile Glu Ser Asn Phe Ile Trp Pro Gln Val Arg Trp Ser Met Pro Asp
                900                 905                 910

Thr Lys Gly Asn Leu Thr Arg Ser Asp Gly Arg Tyr Gln Ala Leu Thr
            915                 920                 925

Lys Asp Ser Thr Phe Thr Ala Gln Ala Met Val Pro Lys Gly Gln Asp
        930                 935                 940

Tyr Ile Val Thr Ala Thr Asp Tyr Val Ser Asp Arg Gln Tyr Ile Gly
945                 950                 955                 960

Thr Leu Asp Lys Ala Thr Gly Ile Val Thr Phe Asn Ile Asp Ala Thr
                965                 970                 975

Gly Gln Pro Tyr Ala Asn Leu Thr Ile Ser Ala Phe Ala Arg Asp Asp
            980                 985                 990

Phe Gly Glu Phe Ile Lys Ser Pro  Lys Thr Glu Asp Phe  Ile Ile Phe
        995                 1000                 1005

Ile Lys  Lys Asn Thr Ala Ala  Tyr Ser Asn Ala Lys   Thr Gln Thr
    1010                 1015                 1020

Lys Pro  Phe Ala Asp Glu Ala  Thr Ala Ile Lys Gly  Ala Lys Phe
    1025                 1030                 1035

Phe Ser  Gly Ala Ala His Leu  Thr Gly Arg Ser Pro  Leu Thr Ser
    1040                 1045                 1050

Thr Lys  Gly Lys Met Ile Asn  Gly Ile Ala Phe Leu  Asp Leu Asn
    1055                 1060                 1065

Asn Asn  Lys Arg Thr Leu Val  Gly Ile Asp Ser Ala  Ser Thr Phe
    1070                 1075                 1080

Tyr Asp  Ala Lys Leu Lys Thr  Leu Thr Leu Arg Gly  Lys Val Ser
    1085                 1090                 1095

Asp Pro  Lys Asn Ser Lys Leu  Arg Ile Phe Val Thr  Pro Arg Gln
    1100                 1105                 1110

Asn Asp  Pro Gln Asn Glu Val  Thr Phe Ala Ala Asp  Gly Ser Phe
    1115                 1120                 1125

Ser Met  Thr Met Pro Cys Asn  Pro Thr Glu Glu Arg  Asn Ile Gly
    1130                 1135                 1140

Tyr Val  Leu Thr Thr Leu Asp  Lys Asp Gly Lys Glu  Lys Thr Asn
    1145                 1150                 1155

Gly Gly  Phe Leu Leu Leu Tyr  Thr Asp Thr Thr Leu  Pro Thr Leu
    1160                 1165                 1170

Glu Leu  Ser Asp Ala Asp Ser  Met Lys Ile Asp Asp  Gly Thr
    1175                 1180                 1185

Tyr Leu  Val Thr Thr Asp Ala  Asp Thr Phe Ser Ile  Lys Gly Ser
    1190                 1195                 1200

Val Thr  Asp Asn Ile Gly Gly  Tyr Arg Leu Tyr Ser  Asn Gly Asn
    1205                 1210                 1215

Asn Ile  Phe Met Gln Gln Asn  Leu Ala Gly Phe Asn  Ala His Gln
    1220                 1225                 1230

Ser Ser  Ala Ala Pro Asn Gln  Leu Thr Asn Gly Tyr  Asn Pro Tyr
    1235                 1240                 1245

Gly Ala  Ala Ser Phe Asp Glu  Thr Tyr Gln Leu Thr  Asp Gly Leu
    1250                 1255                 1260

Asn Ile  Ile Thr Leu Gln Ala  Val Asp Gln Val Gly  Asn Thr Val
    1265                 1270                 1275

Thr Lys  Thr Phe Asn Val Thr  Lys Thr Pro Lys Leu  Leu Lys Glu
    1280                 1285                 1290
```

```
Glu Ser Leu Asp Glu Leu Glu Ile Thr Pro Glu Gln Gln Asp Gln
    1295            1300                1305

Thr Pro Lys Asn Asp Ala Gly Glu Ala Pro Val Thr Thr Pro Ala
    1310            1315                1320

Thr Glu Glu Thr Leu Val Thr Pro Ser Thr Glu Ser Thr Met Val
    1325            1330                1335

Asn Pro Glu Asp Ser Lys Val Glu Thr Ser Asp Pro Ile Val Glu
    1340            1345                1350

Thr Ala Pro Ser Lys Glu Ala Gln Ser Asp Gly Asn Gly Ala Thr
    1355            1360                1365

Glu Thr Asn Thr Thr Ala Ser Val Thr Thr Gly Val Asp Glu Asn
    1370            1375                1380

Pro Val Asp Ser Ser Ala Asn Ala Ala Thr Pro Met Pro Asn His
    1385            1390                1395

Val Lys Asp Ala Asn Thr Asp Ala Glu Val Thr Glu Val Thr Asn
    1400            1405                1410

Thr Lys Asp Asn Thr Gln Gly Thr Thr Ala Pro Thr Ser Thr Asp
    1415            1420                1425

Pro Ala Thr Asp Lys Glu Ser Thr Thr Lys Ser Glu Ile Asp Pro
    1430            1435                1440

Ala Ala Thr Ser Pro Asn Asp Ser Lys Val Val Glu Ala Val Thr
    1445            1450                1455

Lys Glu Ala Ala Val Asn Asp Asp Lys Gly Asn Gln Ala Asp Asp
    1460            1465                1470

Gly Glu Pro Thr Val Thr Asn Leu Ala Thr Ser Lys Asp Ser Ala
    1475            1480                1485

Val Gln Pro Glu Val Asp Pro Ala Ser Gly Leu Gln Ser Asp Asp
    1490            1495                1500

Lys Val Val Glu Thr Ala Val Glu Asp Asp Glu Met Val Glu Lys
    1505            1510                1515

Glu Gly His Lys Ser Asp Asn Ala Lys Pro Ala Ile Thr Asp Pro
    1520            1525                1530

Thr Thr Asp Lys Asp Lys Ala Val Gln Ser Glu Val Asn Pro Thr
    1535            1540                1545

Ala Ser Ser Gln Gly Ala Thr Lys Ala Val Glu Ala Ala Ala Lys
    1550            1555                1560

Asp Thr Lys Val Glu Asp Asp Lys Gly Asn Lys Thr Ala Ser Val
    1565            1570                1575

Glu Thr Gly Val Ala Thr Pro Ala Met Asp Asn Asn Ser Ser Val
    1580            1585                1590

Lys Ser Ala Val Asp Pro Thr Ala Thr Ala Pro Ser Asp Asn Thr
    1595            1600                1605

Ala Pro Ala Ile Glu Thr Ala Ala Glu Asn Phe Asn Ile Glu Asn
    1610            1615                1620

Asp Lys Gly Asn Glu Thr Asn Ala Val Glu Thr Val Val Thr Asp
    1625            1630                1635

Pro Ala Thr Asn Lys Glu Gly Thr Val Lys Ser Glu Ile Glu Pro
    1640            1645                1650

Val Ala Thr Thr Pro Ser Asn Thr Thr Val Thr Ala Thr Glu Met
    1655            1660                1665

Thr Lys Glu Asn Thr Pro Ala Glu Asp Glu Lys Asp Asn Gln Val
    1670            1675                1680

Asn Ala Val Thr Asp Pro Lys Thr Thr Lys Asp Ser Ala Asp Lys
```

-continued

```
            1685                1690                1695

Ser Glu Ile Glu Pro Val Ala Thr Ala Ala Thr Asp Lys Asp Arg
    1700                1705                1710

Thr Val Lys Ser Asp Pro Thr Glu Ala Ala Ser Thr Pro Ser Glu
    1715                1720                1725

Asp Ser Ile Arg Lys Thr Thr Ala Glu Asp Ala Lys Ala Lys Asp
    1730                1735                1740

Asp Arg Glu Ala Ala Ala Asn Ala Val Ala Ala Asp Ser Lys Ala
    1745                1750                1755

Asp Lys Asn Asn Pro Val Glu Ser Lys Ile Asp Ala Thr Ala Ile
    1760                1765                1770

Thr Pro Ser Asn Ser Gln Pro Thr Glu Thr Asp Thr Glu Asn Ala
    1775                1780                1785

Ala Val Glu Asn Gly Lys Asp Gln Lys Ser Ala Asp Thr Pro Ser
    1790                1795                1800

Pro Val Ile Asp Pro Ala Val Asp Lys Asp Arg Ala Val Lys Ser
    1805                1810                1815

Lys Val Asn Pro Ala Thr Thr Ala Pro Asn Asp Asp Lys Ala Pro
    1820                1825                1830

Glu Val Thr Thr Glu Ser Ser Lys Ile Glu Asn Val Lys Ser His
    1835                1840                1845

Gln Ser Asp Val Val Glu Thr Phe Gly Ser Asp Ser Gln Thr Ser
    1850                1855                1860

Lys Asp Pro Val Ala Glu Ser Lys Arg Asn Pro Thr Ala Thr Ser
    1865                1870                1875

Ser Ser Asp Asp Thr Thr Thr Glu Thr Glu Thr Leu Ala Thr Gly
    1880                1885                1890

Gly Glu Gln Asn Ser Gln Val Asp Thr Pro Lys Lys Ala Met Thr
    1895                1900                1905

Thr Thr Pro Asn Asp Lys Asn Val Ser Leu Ala Thr Val Ala Pro
    1910                1915                1920

Asp Lys Thr Lys Gly Asp Thr Ala Gly Ala Arg Thr Val Thr Thr
    1925                1930                1935

Thr Asp Gly Gln Arg Lys Pro Thr Lys Thr Glu Val Gly Ser Ser
    1940                1945                1950

Asn Val Ala Ser Asn His Pro Ser Thr Thr Asp Ser Ser Thr Glu
    1955                1960                1965

Thr Thr Ser Gln Ser Asp Glu Pro Thr Ser Ser Ile Glu Thr Thr
    1970                1975                1980

Glu Pro Ala Thr Thr Ala Pro Ser Thr Glu Asp Lys Pro Val Arg
    1985                1990                1995

Thr Thr Ala Asp Gln Lys Val Thr Asp Gln Lys Ser Asn Lys Asp
    2000                2005                2010

Asp Gln Ala Asn Pro Thr Ala Ile Lys Lys Lys Leu Lys Ser Lys
    2015                2020                2025

Val Thr Glu Asp Gly Glu Asn Ile Ser Gln Thr Asn Gln Lys Asp
    2030                2035                2040

Pro Lys Thr Lys Thr Ala Lys Gly Glu Gln Thr Thr Ser Pro Leu
    2045                2050                2055

Asp Gln Lys Arg Ser Ala Leu Lys Gln Lys Glu Ser Lys Glu Ile
    2060                2065                2070

Ala Pro Glu Lys Ser Val His Ala Thr Lys Thr Ala Ala Lys Thr
    2075                2080                2085
```

```
Leu Pro Pro Met Gly Met Gln Asn Ser His Trp Leu Gln Ala Leu
    2090            2095                 2100

Gly Ile Ala Leu Leu Gly Met Ile Leu Ala Leu Gly Ile Gly Leu
    2105                2110                2115

Thr Ser Lys Lys Lys His Glu Lys Ser
    2120                2125

<210> SEQ ID NO 55
<211> LENGTH: 2239
<212> TYPE: PRT
<213> ORGANISM: Lactobacillus sp. HMSC25A02

<400> SEQUENCE: 55

Met Asn Arg Val Lys Pro Phe Ser Gln Glu Lys Arg Tyr Lys Met
1               5                   10                  15

Tyr Lys Ser Gly Arg His Trp Val Tyr Ser Ala Ile Val Thr Phe Gly
            20                  25                  30

Ala Ala Ser Phe Leu Met Met Gln Pro Ala Gln Gly Val Ser Ala Asp
            35                  40                  45

Ala Thr Thr Pro Pro Thr Thr Thr Gln Thr Lys Ser Asn Gln Ala Ala
50                      55                  60

Pro Asp Ala Ala Ser Ala Asp Leu Pro Val Ser Lys Pro Ala Ser Thr
65                  70                  75                  80

Thr Thr Gly Gln Val Thr Ser Ser Ala Asn Thr Pro Thr Thr Thr Ala
                85                  90                  95

Ala Ser Ala Thr Pro Thr Ala Thr Ala Lys Pro Ala Thr Pro Ala Pro
            100                 105                 110

Val Ser Ser Gln Ala Lys Pro Glu Ala Ser Ala Lys Ala Lys Gln Pro
            115                 120                 125

Thr Gln Pro Thr Ser Val Thr Pro Ser Thr Pro Thr Thr Asn Thr
130                 135                 140

Lys Thr Ala Gln Lys Thr Val Ser Gln Pro Ala Gln Lys Ala Pro Ala
145                 150                 155                 160

Ala Pro Ala Lys Pro Ala Pro Ile Ala Lys Pro Ala Pro Thr Phe Asn
                165                 170                 175

Pro Glu Asn Lys Ala Ser Leu Thr Lys Gly Asn Val Gln Pro Leu Trp
            180                 185                 190

Asp Gln Asn Ile Lys Gly Gln Gly Met Val Ala Ala Val Ile Asp Gln
            195                 200                 205

Gly Val Glu Pro His Gln Asp Phe Arg Leu Ser Asp Ala Lys Thr Ala
210                 215                 220

Ala Leu Ser Glu Asp Gln Ile Lys Ala Phe Thr Ala Ser His Gly Tyr
225                 230                 235                 240

Gly Asp Tyr Val Asn Glu Lys Ile Pro Phe Phe Tyr Asp Tyr Thr Asn
                245                 250                 255

Asn Val Asn Glu Asn Leu Lys Phe Asp Thr Ser Asn His Gly Gln His
            260                 265                 270

Leu Ala Gly Ile Ile Ala Ala Asn Gly Gln Pro Ser Asp Ser Lys Lys
            275                 280                 285

Phe Val Thr Gly Ile Ala Pro Glu Ala Gln Leu Leu Ser Met Lys Ile
            290                 295                 300

Leu Gly Lys Ser Ser Ser Asp Ser Leu Asn Asn Ala Ala Arg Ala Ile
305                 310                 315                 320

Tyr Asp Ala Val Asp Leu Gly Ala Asn Ala Ile Asn Ile Ser Phe Gly
```

```
                     325                 330                 335
Met Gly Val Asp Ile Asp Asp Pro Thr Ala Glu Gly Gln Ala Ala Ile
                 340                 345                 350
Lys Phe Ala Thr Asp His Gly Val Phe Val Thr Val Ala Thr Gly Asn
             355                 360                 365
Asn Gly His Ala Gly Gly Ile Tyr Asp Lys Ser Ala Ser Asn Gly Ile
         370                 375                 380
Thr Thr Ser Tyr Gln Pro Ala Asn Ala Ser Thr Leu Thr Thr Pro Ser
385                 390                 395                 400
Ala Thr Pro Ser Ala Met Ala Val Ala Gly Asn Asp Val Leu Asp
                405                 410                 415
Ala Lys Ala Ala Leu Ile Ser Ala Ser Ser Trp Gly Pro Thr Ala Ser
            420                 425                 430
Tyr Lys Leu Lys Pro Asp Ile Thr Ala Pro Gly Glu Lys Val Ala Ser
        435                 440                 445
Thr Leu Leu Asn Asp Gly Leu Gly Lys Val Ser Gly Thr Ser Gln Ala
    450                 455                 460
Asn Ala Tyr Val Thr Gly Ala Ser Leu Leu Val Met Gln Asn Leu Lys
465                 470                 475                 480
Arg Ser Thr Asn Leu Thr Gly Ala Gln Leu Val Lys Ala Val Lys Leu
                485                 490                 495
Ala Leu Met Asn Ala Ala Asn Pro Ile Leu Asp Ile Asn Tyr Pro Gly
            500                 505                 510
Gln Ile Ile Ser Pro Arg Arg Gln Gly Ala Gly Gln Ile Asp Val Ala
        515                 520                 525
Lys Ala Ala Asn Leu Thr Val Ser Ala Glu Gly Thr Asp Asp Ala Gly
    530                 535                 540
Ser Val Ser Leu Gln Gln Phe Thr Gly Ser Lys Ser Phe Val Ile Thr
545                 550                 555                 560
Leu Glu Asn Arg Gly Thr Asp Gln Gln Thr Tyr Thr Leu Asp Leu Gly
                565                 570                 575
Gln Pro Ala Thr Glu Val Ile Asp Thr Ala Asn Asn Lys Thr Val His
            580                 585                 590
Asp Arg Thr Leu Pro Gly Ala Thr Leu Thr Thr Ala Thr Pro Thr Phe
        595                 600                 605
Thr Leu Asp Ala Gly Ala Phe Lys Lys Ile Thr Phe Thr Leu Ser Leu
    610                 615                 620
Asp Asp Thr Val Lys Leu Asn Gln Val Val Glu Gly Phe Ile Lys Phe
625                 630                 635                 640
Lys Ala Ala Asp Asp Arg Gln Ser Ile Ser Val Pro Tyr Met Gly Tyr
                645                 650                 655
Tyr Gly Ser Thr Asn Asp Glu Ala Val Phe Asp Lys Pro Ala Asn Glu
            660                 665                 670
Glu Gly Ser Ile Phe Lys Gly Gly Tyr Leu Val Asp Asn Asn His Asn
        675                 680                 685
Pro Leu Gly Ile Thr Asp Pro Thr Ser Leu Ser Glu Leu Val Asn Asn
    690                 695                 700
Pro Thr Asn Gly Phe Thr Trp Gln Thr Ile Gly Ala Lys Val Gln Asn
705                 710                 715                 720
Asn Lys Val Ala Phe Ser Pro Asn Gly Asp Gly Ile Ser Asp Thr Ile
                725                 730                 735
Thr Pro Tyr Val Phe Thr Lys Gln Asn Leu Lys Gln Val Ile Ala Gln
            740                 745                 750
```

-continued

```
Ile Leu Asp Gln Asp Asp Lys Val Met Arg Val Ile Asp Gln Glu Thr
            755                 760                 765
Asp Thr Thr Lys Ser Phe Leu Glu Val Gly Ser Thr Thr Asn Ala Asp
770                 775                 780
Leu Ala Lys Ser Ile Ser Met Phe Leu Asn Pro Asp Lys Leu Lys Trp
785                 790                 795                 800
Asp Gly Gln Val Tyr Asp Gln Thr Thr Gly Gln Met Val Pro Ala Lys
                805                 810                 815
Asp Gly Ile Tyr Thr Tyr Arg Leu Ile Gly Met Thr Tyr Thr Pro Gly
                820                 825                 830
Glu Asn Asn Met Gln Thr Met Ser Leu Pro Val Ala Val Asp Thr Ile
                835                 840                 845
Lys Pro Thr Leu Ser Asn Leu Ala Tyr Ser Asp Gly Lys Leu Thr Ala
850                 855                 860
Asp Tyr Ser Asp Gln Gly Val Gly Phe Thr Ala Tyr Ser Gln Ala Lys
865                 870                 875                 880
Leu Thr Ile Gly Ser Ala Thr Tyr Gly Ile Pro Leu Asn His Asp Asn
                885                 890                 895
Lys Ala Thr Thr Gly Thr Ile Asn Tyr Gln Leu Asn Asp Asp Gln Leu
                900                 905                 910
Ala Asn Leu Lys Thr Gly Glu Gly Lys Val Thr Leu Thr Ile Thr Asp
                915                 920                 925
Ala Ala Gly Asn Ser Asp Gln Gly Ser Ile Lys Ala Val Val Gly Glu
                930                 935                 940
Asn Lys Thr Ile Glu Ser Asn Phe Ile Trp Pro Gln Val Arg Trp Ser
945                 950                 955                 960
Met Pro Asp Thr Lys Gly Asn Leu Thr Arg Ser Asp Gly Arg Tyr Gln
                965                 970                 975
Ala Leu Thr Lys Asp Ser Thr Phe Thr Ala Gln Ala Met Val Pro Lys
                980                 985                 990
Gly Gln Asp Tyr Ile Val Thr Ala Thr Asp Tyr Val Ser Asp Arg Gln
                995                 1000                1005
Tyr Ile Gly Thr Leu Asp Lys Ala Thr Gly Ile Val Thr Phe Asn
        1010                1015                1020
Ile Asp Ala Thr Gly Gln Pro Tyr Ala Asn Leu Thr Ile Ser Ala
        1025                1030                1035
Ile Ala Arg Asp Ala Phe Gly Glu Phe Ile Lys Ser Pro Lys Thr
        1040                1045                1050
Glu Asp Phe Ile Ile Phe Ile Lys Lys Asn Ala Ala Ala Tyr Ser
        1055                1060                1065
Asn Ala Lys Thr Gln Thr Lys Pro Phe Ala Asp Glu Ala Thr Ala
        1070                1075                1080
Ile Lys Gly Ala Lys Phe Ser Gly Ala Ala His Leu Thr Gly
        1085                1090                1095
Arg Ser Pro Leu Thr Ser Thr Lys Gly Lys Met Ile Asn Gly Ile
        1100                1105                1110
Ala Phe Leu Asp Leu Asn Asn Asn Lys Arg Thr Leu Val Gly Ile
        1115                1120                1125
Asp Ser Ala Ser Thr Phe Tyr Asp Ala Lys Leu Lys Thr Leu Thr
        1130                1135                1140
Leu Arg Gly Lys Val Ser Asp Pro Lys Asn Ser Lys Leu Arg Ile
        1145                1150                1155
```

-continued

Phe Val Thr Pro Arg Gln Asn Asp Pro Gln Asn Glu Val Thr Phe
1160                1165                1170

Ala Ala Asp Gly Ser Phe Ser Met Thr Met Pro Cys Asn Pro Thr
1175                1180                1185

Glu Glu Arg Asn Ile Gly Tyr Val Leu Thr Thr Leu Asp Lys Asp
1190                1195                1200

Gly Lys Glu Lys Thr Asn Gly Gly Phe Leu Leu Leu Tyr Met Asp
1205                1210                1215

Thr Thr Leu Pro Thr Leu Glu Leu Ser Asp Ala Asp Ser Met Lys
1220                1225                1230

Ile Asp Asp Asp Gly Thr Tyr Leu Val Thr Thr Asp Ala Asp Thr
1235                1240                1245

Phe Ser Ile Lys Gly Ser Val Thr Asp Asn Ile Gly Gly Tyr Arg
1250                1255                1260

Leu Tyr Ser Asn Gly Asn Asn Ile Phe Thr Gln Gln Asn Leu Ala
1265                1270                1275

Gly Phe Asn Ala His Gln Ser Ser Ala Ala Pro Asn Gln Leu Thr
1280                1285                1290

Asn Gly Tyr Asn Pro Tyr Gly Ala Ala Ser Phe Asp Glu Thr Tyr
1295                1300                1305

Gln Leu Thr Asp Gly Leu Asn Ile Ile Thr Leu Gln Ala Val Asp
1310                1315                1320

Gln Val Gly Asn Thr Val Thr Lys Thr Phe Asn Val Thr Lys Thr
1325                1330                1335

Pro Lys Leu Leu Lys Glu Glu Ser Leu Asp Glu Leu Glu Ile Thr
1340                1345                1350

Pro Glu Gln Glu Asp Gln Thr Pro Lys Asn Asp Ala Gly Glu Ala
1355                1360                1365

Pro Val Thr Thr Ser Ser Ser Asp Glu Lys Ala Glu Val Thr Pro
1370                1375                1380

Ser Thr Glu Pro Thr Met Val Asn Pro Glu Asp Ser Lys Val Glu
1385                1390                1395

Thr Ser Asn Pro Val Val Glu Ile Asp Thr Ser Lys Glu Ala Gln
1400                1405                1410

Ser Asp Gly Asn Asp Asp Thr Ala Thr Asn Thr Pro Ala Ser Val
1415                1420                1425

Thr Thr Ala Val Asp Glu Asn Pro Val Asp Asn Ser Pro Asn Ala
1430                1435                1440

Thr Thr Thr Met Pro Asn His Ala Lys Gly Val Asp Ser Asp Ala
1445                1450                1455

Glu Ala Thr Glu Ala Thr Asn Thr Lys Asp Asn Thr Pro Gly Thr
1460                1465                1470

Thr Ala Pro Thr Asp Thr Asp Pro Thr Met Asp Lys Glu Ser Pro
1475                1480                1485

Thr Lys Ser Glu Val Asp Pro Thr Ala Thr Ser Leu Pro Asp Ser
1490                1495                1500

Gln Val Val Glu Thr Ala Thr Glu Thr Thr Val Asn Glu Asp Lys
1505                1510                1515

Gly Asn Lys Thr Asp Asp Asp Glu Pro Thr Ala Thr Asn Leu Thr
1520                1525                1530

Thr Ser Lys Asp Ser Ala Ile Gln Pro Lys Ser Asp Pro Ala Ala
1535                1540                1545

Ser Leu Gln Ser Asn Asp Lys Ala Val Glu Ala Ala Ile Glu Asn

-continued

```
              1550              1555              1560
Asp Lys Ile Ala Glu Lys Glu Gly His Gln Ser Ala Asn Thr Gln
    1565              1570              1575
Pro Ala Ile Thr Asp Val Thr Thr Asp Lys Asp Ser Ala Val Lys
    1580              1585              1590
Pro Glu Ile Asp Pro Ala Ala Ser Ser Gln Ser Asn Asp Lys Ala
    1595              1600              1605
Val Glu Ala Ala Met Glu Asp Ser Lys Ala Glu Asn Asp Lys Gly
    1610              1615              1620
Ser Lys Ser Asp Ser Ala Glu Thr Asn Ile Ala Pro Thr Met Ala
    1625              1630              1635
Lys Asn Ser Gly Val Lys Ser Glu Ile Asp Leu Thr Ala Ile Ala
    1640              1645              1650
Pro Arg Asp Asn Thr Ala Thr Ser Ser Gly Thr Ala Lys Glu Asn
    1655              1660              1665
Ala Asp Val Lys Asp Asp Lys Gly Asn Lys Thr Asp Thr Val Glu
    1670              1675              1680
Ser Ala Val Thr Asp Thr Glu Asp Asp Asn Glu Gly Thr Val Lys
    1685              1690              1695
Ser Glu Ile Glu Ser Val Ala Thr Thr Pro Ser Ser Asn Thr Ala
    1700              1705              1710
Thr Ala Thr Glu Ile Thr Lys Glu Asn Thr Pro Thr Glu Asp Glu
    1715              1720              1725
Lys Asp Asn Gln Val Asn Val Val Glu Thr Thr Asp Thr His Pro
    1730              1735              1740
Lys Pro Ile Lys Asp Arg Ala Thr Lys Ser Glu Ile Glu Ser Glu
    1745              1750              1755
Ala Thr Ala Pro Ser Lys Thr Glu Val Gly Glu Thr Val Ala Glu
    1760              1765              1770
Asp Ala Lys Gly Glu His Asp Lys Ser Asn Lys Ser Asp Asp Val
    1775              1780              1785
Glu Pro Thr Val Ser Asp Arg Lys Thr Asp Glu Asp Arg Ala Ile
    1790              1795              1800
Lys Ser Glu Ser Asn Ala Ser Ala Ile Thr Pro Asn Glu Asp Asn
    1805              1810              1815
Ile Asp Glu Thr Thr Val Glu Glu Ala Lys Ala Glu Asp Asn Arg
    1820              1825              1830
Glu Ala Ala Ala Gly Thr Ile Ala Thr Val Ala Ala Asp Pro Lys
    1835              1840              1845
Ala Ser Glu Asp Asn Ser Val Lys Ser Glu Met Asp Ala Thr Thr
    1850              1855              1860
Ile Ala Pro Ile Asp Asn Lys Ala Ile Glu Thr Val Thr Glu Thr
    1865              1870              1875
Thr Gly Val Glu Lys Val Glu Ser His Lys Ser Thr Asp Thr Glu
    1880              1885              1890
Ser Pro Val Thr Asp Pro Ala Ile Asp Lys Asp Arg Ala Val Asn
    1895              1900              1905
Ser Asp Ile Thr Pro Ala Thr Ala Ser Pro Thr Ala Asp Lys Ala
    1910              1915              1920
Pro Glu Ala Thr Thr Glu Ser Val Asp Val Glu Asn Thr Glu Ser
    1925              1930              1935
His His Pro Asp Ile Gly Glu Thr Ser Val Ser Asp Ser Gln Ala
    1940              1945              1950
```

Gly Lys Asp Ser Ala Thr Glu Ser Lys Ile Asp Pro Lys Ala Thr
    1955                1960                1965

Pro Ser Ser Asp Asn Thr Thr Thr Gly Ser Thr Val Glu Ile Leu
    1970                1975                1980

Thr Thr Gly Ser Glu Gln Asn Ser Gln Ile Asp Thr Ser Lys Thr
    1985                1990                1995

Thr Val Thr Pro Ala Thr Asp Lys Lys Val Ser Ser Glu Thr
    2000                2005                2010

Ile Ala Pro Ala Lys Thr Ser Asp Asp Thr Ala Glu Phe Gly Thr
    2015                2020                2025

Ala Thr Thr Thr Ser Gly Gln Asn Thr Leu Thr Lys Thr Glu Val
    2030                2035                2040

Glu Ser Ser Asn His Ala Thr Asn His Pro Asp Thr Thr Asp Ser
    2045                2050                2055

Ser Thr Asp Ala Thr Ser Gln Pro Asp Glu Pro Thr Ile Ser Ile
    2060                2065                2070

Glu Val Thr Lys Pro Val Pro Thr Thr Pro Ser Thr Glu Asp Asn
    2075                2080                2085

Pro Val Gln Pro Asn Val Asp Gln Lys Val Ser Asp Gln Lys Ser
    2090                2095                2100

Asp Lys Asp Asn Gln Asp Asn Pro Thr Ala Ile Glu Lys Asn Pro
    2105                2110                2115

Lys Ser Lys Val Thr Asp Asp Glu Glu Thr Ile Ser Lys Thr Arg
    2120                2125                2130

Gln Lys Asp Pro Lys Ser Asn Ile Val Glu Lys Glu Asp Asp Thr
    2135                2140                2145

Ile Leu Val Val Gln Lys Gly Leu Lys Ala Lys Thr Val Lys Asp
    2150                2155                2160

Ala Glu Pro Thr Ser Ser Leu Asp Gln Lys Thr Ser Ala Leu Lys
    2165                2170                2175

Gln Lys Glu Ser Lys Glu Lys Ala Pro Ala Lys Ser Val His Pro
    2180                2185                2190

Thr Lys Ala Ala Ala Lys Thr Leu Pro Pro Met Gly Met Gln Asn
    2195                2200                2205

Ser His Trp Leu Gln Ala Leu Gly Ile Ala Leu Leu Gly Met Val
    2210                2215                2220

Phe Ala Leu Ser Ile Gly Leu Thr Ser Lys Lys Lys His Glu Lys
    2225                2230                2235

Asn

<210> SEQ ID NO 56
<211> LENGTH: 2188
<212> TYPE: PRT
<213> ORGANISM: Artificial Sequence
<220> FEATURE:
<223> OTHER INFORMATION: fragment of Lactobacillus sp. HMSC25A02
      protease

<400> SEQUENCE: 56

Pro Pro Thr Thr Thr Gln Thr Lys Ser Asn Gln Ala Ala Pro Asp Ala
1               5                   10                  15

Ala Ser Ala Asp Leu Pro Val Ser Lys Pro Ala Ser Thr Thr Thr Gly
            20                  25                  30

Gln Val Thr Ser Ser Ala Asn Thr Pro Thr Thr Thr Ala Ala Ser Ala
        35                  40                  45

```
Thr Pro Thr Ala Thr Ala Lys Pro Ala Thr Pro Ala Pro Val Ser Ser
 50                  55                  60

Gln Ala Lys Pro Glu Ala Ser Ala Lys Ala Lys Gln Pro Thr Gln Pro
 65                  70                  75                  80

Thr Ser Val Thr Pro Ser Thr Pro Thr Thr Asn Thr Lys Thr Ala
                 85                  90                  95

Gln Lys Thr Val Ser Gln Pro Ala Gln Lys Ala Pro Ala Ala Pro Ala
                100                 105                 110

Lys Pro Ala Pro Ile Ala Lys Pro Ala Pro Thr Phe Asn Pro Glu Asn
                115                 120                 125

Lys Ala Ser Leu Thr Lys Gly Asn Val Gln Pro Leu Trp Asp Gln Asn
                130                 135                 140

Ile Lys Gly Gln Gly Met Val Ala Ala Val Ile Asp Gln Gly Val Glu
145                 150                 155                 160

Pro His Gln Asp Phe Arg Leu Ser Asp Ala Lys Thr Ala Ala Leu Ser
                165                 170                 175

Glu Asp Gln Ile Lys Ala Phe Thr Ala Ser His Gly Tyr Gly Asp Tyr
                180                 185                 190

Val Asn Glu Lys Ile Pro Phe Phe Tyr Asp Tyr Thr Asn Asn Val Asn
                195                 200                 205

Glu Asn Leu Lys Phe Asp Thr Ser Asn His Gly Gln His Leu Ala Gly
                210                 215                 220

Ile Ile Ala Ala Asn Gly Gln Pro Ser Asp Ser Lys Lys Phe Val Thr
225                 230                 235                 240

Gly Ile Ala Pro Glu Ala Gln Leu Leu Ser Met Lys Ile Leu Gly Lys
                245                 250                 255

Ser Ser Ser Asp Ser Leu Asn Asn Ala Ala Arg Ala Ile Tyr Asp Ala
                260                 265                 270

Val Asp Leu Gly Ala Asn Ala Ile Asn Ile Ser Phe Gly Met Gly Val
                275                 280                 285

Asp Ile Asp Asp Pro Thr Ala Glu Gly Gln Ala Ala Ile Lys Phe Ala
                290                 295                 300

Thr Asp His Gly Val Phe Val Thr Val Ala Thr Gly Asn Asn Gly His
305                 310                 315                 320

Ala Gly Gly Ile Tyr Asp Lys Ser Ala Ser Asn Gly Ile Thr Thr Ser
                325                 330                 335

Tyr Gln Pro Ala Asn Ala Ser Thr Leu Thr Thr Pro Ser Ala Thr Pro
                340                 345                 350

Ser Ala Met Ala Val Ala Ala Gly Asn Asp Val Leu Asp Ala Lys Ala
                355                 360                 365

Ala Leu Ile Ser Ala Ser Ser Trp Gly Pro Thr Ala Ser Tyr Lys Leu
                370                 375                 380

Lys Pro Asp Ile Thr Ala Pro Gly Glu Lys Val Ala Ser Thr Leu Leu
385                 390                 395                 400

Asn Asp Gly Leu Gly Lys Val Ser Gly Thr Ser Gln Ala Asn Ala Tyr
                405                 410                 415

Val Thr Gly Ala Ser Leu Leu Val Met Gln Asn Leu Lys Arg Ser Thr
                420                 425                 430

Asn Leu Thr Gly Ala Gln Leu Val Lys Ala Val Lys Leu Ala Leu Met
                435                 440                 445

Asn Ala Ala Asn Pro Ile Leu Asp Ile Asn Tyr Pro Gly Gln Ile Ile
450                 455                 460
```

```
Ser Pro Arg Arg Gln Gly Ala Gly Gln Ile Asp Val Ala Lys Ala Ala
465                 470                 475                 480

Asn Leu Thr Val Ser Ala Glu Gly Thr Asp Asp Ala Gly Ser Val Ser
                485                 490                 495

Leu Gln Gln Phe Thr Gly Ser Lys Ser Phe Val Ile Thr Leu Glu Asn
            500                 505                 510

Arg Gly Thr Asp Gln Gln Thr Tyr Thr Leu Asp Leu Gly Gln Pro Ala
        515                 520                 525

Thr Glu Val Ile Asp Thr Ala Asn Asn Lys Thr Val His Asp Arg Thr
    530                 535                 540

Leu Pro Gly Ala Thr Leu Thr Ala Thr Pro Thr Phe Thr Leu Asp
545                 550                 555                 560

Ala Gly Ala Phe Lys Lys Ile Thr Phe Thr Leu Ser Leu Asp Asp Thr
                565                 570                 575

Val Lys Leu Asn Gln Val Val Glu Gly Phe Ile Lys Phe Lys Ala Ala
            580                 585                 590

Asp Asp Arg Gln Ser Ile Ser Val Pro Tyr Met Gly Tyr Tyr Gly Ser
        595                 600                 605

Thr Asn Asp Glu Ala Val Phe Asp Lys Pro Ala Asn Glu Glu Gly Ser
    610                 615                 620

Ile Phe Lys Gly Gly Tyr Leu Val Asp Asn Asn His Asn Pro Leu Gly
625                 630                 635                 640

Ile Thr Asp Pro Thr Ser Leu Ser Glu Leu Val Asn Asn Pro Thr Asn
                645                 650                 655

Gly Phe Thr Trp Gln Thr Ile Gly Ala Lys Val Gln Asn Asn Lys Val
            660                 665                 670

Ala Phe Ser Pro Asn Gly Asp Gly Ile Ser Asp Thr Ile Thr Pro Tyr
        675                 680                 685

Val Phe Thr Lys Gln Asn Leu Lys Gln Val Ile Ala Gln Ile Leu Asp
    690                 695                 700

Gln Asp Asp Lys Val Met Arg Val Ile Asp Gln Glu Thr Asp Thr Thr
705                 710                 715                 720

Lys Ser Phe Leu Glu Val Gly Ser Thr Thr Asn Ala Asp Leu Ala Lys
                725                 730                 735

Ser Ile Ser Met Phe Leu Asn Pro Asp Lys Leu Lys Trp Asp Gly Gln
            740                 745                 750

Val Tyr Asp Gln Thr Thr Gly Gln Met Val Pro Ala Lys Asp Gly Ile
        755                 760                 765

Tyr Thr Tyr Arg Leu Ile Gly Met Thr Tyr Thr Pro Gly Glu Asn Asn
    770                 775                 780

Met Gln Thr Met Ser Leu Pro Val Ala Val Asp Thr Ile Lys Pro Thr
785                 790                 795                 800

Leu Ser Asn Leu Ala Tyr Ser Asp Gly Lys Leu Thr Ala Asp Tyr Ser
                805                 810                 815

Asp Gln Gly Val Gly Phe Thr Ala Tyr Ser Gln Ala Lys Leu Thr Ile
            820                 825                 830

Gly Ser Ala Thr Tyr Gly Ile Pro Leu Asn His Asp Asn Lys Ala Thr
        835                 840                 845

Thr Gly Thr Ile Asn Tyr Gln Leu Asn Asp Asp Gln Leu Ala Asn Leu
    850                 855                 860

Lys Thr Gly Glu Gly Lys Val Thr Leu Thr Ile Thr Asp Ala Ala Gly
865                 870                 875                 880

Asn Ser Asp Gln Gly Ser Ile Lys Ala Val Val Gly Glu Asn Lys Thr
```

|     |     |     |     |     | 885 |     |     |     | 890 |     |     |     |     | 895 |
| --- | --- | --- | --- | --- | --- | --- | --- | --- | --- | --- | --- | --- | --- | --- |

Ile Glu Ser Asn Phe Ile Trp Pro Gln Val Arg Trp Ser Met Pro Asp
                                900                 905                 910

Thr Lys Gly Asn Leu Thr Arg Ser Asp Gly Arg Tyr Gln Ala Leu Thr
            915                 920                 925

Lys Asp Ser Thr Phe Thr Ala Gln Ala Met Val Pro Lys Gly Gln Asp
        930                 935                 940

Tyr Ile Val Thr Ala Thr Asp Tyr Val Ser Asp Arg Gln Tyr Ile Gly
945                 950                 955                 960

Thr Leu Asp Lys Ala Thr Gly Ile Val Thr Phe Asn Ile Asp Ala Thr
                965                 970                 975

Gly Gln Pro Tyr Ala Asn Leu Thr Ile Ser Ala Ile Ala Arg Asp Ala
            980                 985                 990

Phe Gly Glu Phe Ile Lys Ser Pro Lys Thr Glu Asp Phe Ile Ile Phe
        995                 1000                1005

Ile Lys Lys Asn Ala Ala Ala Tyr Ser Asn Ala Lys Thr Gln Thr
    1010                1015                1020

Lys Pro Phe Ala Asp Glu Ala Thr Ala Ile Lys Gly Ala Lys Phe
    1025                1030                1035

Phe Ser Gly Ala Ala His Leu Thr Gly Arg Ser Pro Leu Thr Ser
    1040                1045                1050

Thr Lys Gly Lys Met Ile Asn Gly Ile Ala Phe Leu Asp Leu Asn
    1055                1060                1065

Asn Asn Lys Arg Thr Leu Val Gly Ile Asp Ser Ala Ser Thr Phe
    1070                1075                1080

Tyr Asp Ala Lys Leu Lys Thr Leu Thr Leu Arg Gly Lys Val Ser
    1085                1090                1095

Asp Pro Lys Asn Ser Lys Leu Arg Ile Phe Val Thr Pro Arg Gln
    1100                1105                1110

Asn Asp Pro Gln Asn Glu Val Thr Phe Ala Ala Asp Gly Ser Phe
    1115                1120                1125

Ser Met Thr Met Pro Cys Asn Pro Thr Glu Glu Arg Asn Ile Gly
    1130                1135                1140

Tyr Val Leu Thr Thr Leu Asp Lys Asp Gly Lys Glu Lys Thr Asn
    1145                1150                1155

Gly Gly Phe Leu Leu Leu Tyr Met Asp Thr Thr Leu Pro Thr Leu
    1160                1165                1170

Glu Leu Ser Asp Ala Asp Ser Met Lys Ile Asp Asp Gly Thr
    1175                1180                1185

Tyr Leu Val Thr Thr Asp Ala Asp Thr Phe Ser Ile Lys Gly Ser
    1190                1195                1200

Val Thr Asp Asn Ile Gly Gly Tyr Arg Leu Tyr Ser Asn Gly Asn
    1205                1210                1215

Asn Ile Phe Thr Gln Gln Asn Leu Ala Gly Phe Asn Ala His Gln
    1220                1225                1230

Ser Ser Ala Ala Pro Asn Gln Leu Thr Asn Gly Tyr Asn Pro Tyr
    1235                1240                1245

Gly Ala Ala Ser Phe Asp Glu Thr Tyr Gln Leu Thr Asp Gly Leu
    1250                1255                1260

Asn Ile Ile Thr Leu Gln Ala Val Asp Gln Val Gly Asn Thr Val
    1265                1270                1275

Thr Lys Thr Phe Asn Val Thr Lys Thr Pro Lys Leu Leu Lys Glu
    1280                1285                1290

```
Glu Ser Leu Asp Glu Leu Glu Ile Thr Pro Gln Glu Asp Gln
    1295                1300                1305

Thr Pro Lys Asn Asp Ala Gly Glu Ala Pro Val Thr Thr Ser Ser
    1310                1315                1320

Ser Asp Glu Lys Ala Glu Val Thr Pro Ser Thr Glu Pro Thr Met
    1325                1330                1335

Val Asn Pro Glu Asp Ser Lys Val Glu Thr Ser Asn Pro Val Val
    1340                1345                1350

Glu Ile Asp Thr Ser Lys Glu Ala Gln Ser Asp Gly Asn Asp Asp
    1355                1360                1365

Thr Ala Thr Asn Thr Pro Ala Ser Val Thr Ala Val Asp Glu
    1370                1375                1380

Asn Pro Val Asp Asn Ser Pro Asn Ala Thr Thr Thr Met Pro Asn
    1385                1390                1395

His Ala Lys Gly Val Asp Ser Asp Ala Glu Ala Thr Glu Ala Thr
    1400                1405                1410

Asn Thr Lys Asp Asn Thr Pro Gly Thr Thr Ala Pro Thr Asp Thr
    1415                1420                1425

Asp Pro Thr Met Asp Lys Glu Ser Pro Thr Lys Ser Glu Val Asp
    1430                1435                1440

Pro Thr Ala Thr Ser Leu Pro Asp Ser Gln Val Val Glu Thr Ala
    1445                1450                1455

Thr Glu Thr Thr Val Asn Glu Asp Lys Gly Asn Lys Thr Asp Asp
    1460                1465                1470

Asp Glu Pro Thr Ala Thr Asn Leu Thr Thr Ser Lys Asp Ser Ala
    1475                1480                1485

Ile Gln Pro Lys Ser Asp Pro Ala Ala Ser Leu Gln Ser Asn Asp
    1490                1495                1500

Lys Ala Val Glu Ala Ala Ile Glu Asn Asp Lys Ile Ala Glu Lys
    1505                1510                1515

Glu Gly His Gln Ser Ala Asn Thr Gln Pro Ala Ile Thr Asp Val
    1520                1525                1530

Thr Thr Asp Lys Asp Ser Ala Val Lys Pro Glu Ile Asp Pro Ala
    1535                1540                1545

Ala Ser Ser Gln Ser Asn Asp Lys Ala Val Glu Ala Ala Met Glu
    1550                1555                1560

Asp Ser Lys Ala Glu Asn Asp Lys Gly Ser Lys Ser Asp Ser Ala
    1565                1570                1575

Glu Thr Asn Ile Ala Pro Thr Met Ala Lys Asn Ser Gly Val Lys
    1580                1585                1590

Ser Glu Ile Asp Leu Thr Ala Ile Ala Pro Arg Asp Asn Thr Ala
    1595                1600                1605

Thr Ser Ser Gly Thr Ala Lys Glu Asn Ala Asp Val Lys Asp Asp
    1610                1615                1620

Lys Gly Asn Lys Thr Asp Thr Val Glu Ser Ala Val Thr Asp Thr
    1625                1630                1635

Glu Asp Asp Asn Glu Gly Thr Val Lys Ser Glu Ile Glu Ser Val
    1640                1645                1650

Ala Thr Thr Pro Ser Ser Asn Thr Ala Thr Ala Thr Glu Ile Thr
    1655                1660                1665

Lys Glu Asn Thr Pro Thr Glu Asp Glu Lys Asp Asn Gln Val Asn
    1670                1675                1680
```

| | | | | | | | | | | | |
|---|---|---|---|---|---|---|---|---|---|---|---|
|Val|Val|Glu|Thr|Thr|Asp|Thr|His|Pro|Lys|Pro|Ile|Lys|Asp|Arg|
|1685| | | | |1690| | | |1695| | | | | |

Ala Thr Lys Ser Glu Ile Glu Ser Glu Ala Thr Ala Pro Ser Lys
1700 1705 1710

Thr Glu Val Gly Glu Thr Val Ala Glu Asp Ala Lys Gly Glu His
1715 1720 1725

Asp Lys Ser Asn Lys Ser Asp Asp Val Glu Pro Thr Val Ser Asp
1730 1735 1740

Arg Lys Thr Asp Glu Asp Arg Ala Ile Lys Ser Glu Ser Asn Ala
1745 1750 1755

Ser Ala Ile Thr Pro Asn Glu Asp Asn Ile Asp Glu Thr Thr Val
1760 1765 1770

Glu Glu Ala Lys Ala Glu Asp Asn Arg Glu Ala Ala Ala Gly Thr
1775 1780 1785

Ile Ala Thr Val Ala Ala Asp Pro Lys Ala Ser Glu Asp Asn Ser
1790 1795 1800

Val Lys Ser Glu Met Asp Ala Thr Thr Ile Ala Pro Ile Asp Asn
1805 1810 1815

Lys Ala Ile Glu Thr Val Thr Glu Thr Thr Gly Val Glu Lys Val
1820 1825 1830

Glu Ser His Lys Ser Thr Asp Thr Glu Ser Pro Val Thr Asp Pro
1835 1840 1845

Ala Ile Asp Lys Asp Arg Ala Val Asn Ser Asp Ile Thr Pro Ala
1850 1855 1860

Thr Ala Ser Pro Thr Ala Asp Lys Ala Pro Glu Ala Thr Thr Glu
1865 1870 1875

Ser Val Asp Val Glu Asn Thr Glu Ser His His Pro Asp Ile Gly
1880 1885 1890

Glu Thr Ser Val Ser Asp Ser Gln Ala Gly Lys Asp Ser Ala Thr
1895 1900 1905

Glu Ser Lys Ile Asp Pro Lys Ala Thr Pro Ser Ser Asp Asn Thr
1910 1915 1920

Thr Thr Gly Ser Thr Val Glu Ile Leu Thr Thr Gly Ser Glu Gln
1925 1930 1935

Asn Ser Gln Ile Asp Thr Ser Lys Thr Val Thr Pro Ala Thr
1940 1945 1950

Asp Asp Lys Lys Val Ser Ser Glu Thr Ile Ala Pro Ala Lys Thr
1955 1960 1965

Ser Asp Asp Thr Ala Glu Phe Gly Thr Ala Thr Thr Ser Gly
1970 1975 1980

Gln Asn Thr Leu Thr Lys Thr Glu Val Glu Ser Ser Asn His Ala
1985 1990 1995

Thr Asn His Pro Asp Thr Thr Asp Ser Ser Thr Asp Ala Thr Ser
2000 2005 2010

Gln Pro Asp Glu Pro Thr Ile Ser Ile Glu Val Thr Lys Pro Val
2015 2020 2025

Pro Thr Thr Pro Ser Thr Glu Asp Asn Pro Val Gln Pro Asn Val
2030 2035 2040

Asp Gln Lys Val Ser Asp Gln Lys Ser Asp Lys Asp Asn Gln Asp
2045 2050 2055

Asn Pro Thr Ala Ile Glu Lys Asn Pro Lys Ser Lys Val Thr Asp
2060 2065 2070

Asp Glu Glu Thr Ile Ser Lys Thr Arg Gln Lys Asp Pro Lys Ser

```
                2075                2080                2085
Asn Ile Val Glu Lys Glu Asp Asp Thr Ile Leu Val Val Gln Lys
        2090                2095                2100

Gly Leu Lys Ala Lys Thr Val Lys Asp Ala Glu Pro Thr Ser Ser
        2105                2110                2115

Leu Asp Gln Lys Thr Ser Ala Leu Lys Gln Lys Glu Ser Lys Glu
        2120                2125                2130

Lys Ala Pro Ala Lys Ser Val His Pro Thr Lys Ala Ala Ala Lys
        2135                2140                2145

Thr Leu Pro Pro Met Gly Met Gln Asn Ser His Trp Leu Gln Ala
        2150                2155                2160

Leu Gly Ile Ala Leu Leu Gly Met Val Phe Ala Leu Ser Ile Gly
        2165                2170                2175

Leu Thr Ser Lys Lys Lys His Glu Lys Asn
        2180                2185

<210> SEQ ID NO 57
<211> LENGTH: 819
<212> TYPE: PRT
<213> ORGANISM: Lactobacillus parafarraginis

<400> SEQUENCE: 57

Met Lys His Ile Phe Lys Ser Phe Gly Glu Thr Lys Arg His Pro Phe
1               5                   10                  15

Ile Ile Ala Thr Leu Leu Ala Ile Ser Thr Ile Gly Leu Phe Met Thr
            20                  25                  30

Thr Glu Met Thr Ala Thr Gln Ala Gln Ser Ile Lys Gln Pro Thr Thr
        35                  40                  45

Phe Ser Gln His Lys Pro Ala Lys Lys Pro Thr Lys Thr Asn Gln Thr
    50                  55                  60

Thr Ser Phe Asn Gln Gln Arg Gln Ala Ala Leu Thr Arg Gly Asn Val
65                  70                  75                  80

Pro Thr Leu Trp Ser Gln Gly Tyr Gln Gly Gln Met Val Ile Ala
                85                  90                  95

Val Ile Asp Ser Gly Ile Gln Asn His Pro Asp Leu Gly Leu Ser Asn
            100                 105                 110

Asn Gln Thr Ala Lys Ile Ser Lys Ala Asp Ala Gln Gln Leu Ile Ala
        115                 120                 125

Gln Lys Gly Tyr Gly Lys Tyr Ile Ser Pro Lys Ile Pro Phe Ala Tyr
    130                 135                 140

Asp Tyr Val Asn Asn Asn Asp Asp Thr Ala Ala Asp Ser Thr Ser
145                 150                 155                 160

Gly Phe His Gly Glu Glu Val Gly Gly Val Ala Ala Asn Gly Val
                165                 170                 175

Glu Thr Asn Gln Ala Lys Tyr Met Lys Gly Val Ala Pro Gln Ala Gln
            180                 185                 190

Leu Leu Asn Leu Lys Val Phe Gly Gly Phe Ala Asp Glu Ile Pro Asn
        195                 200                 205

Asp Val Ala Arg Ala Ile His Asp Ala Val Asp Leu Gly Ala Asp Val
    210                 215                 220

Ile Asn Leu Ser Leu Gly Leu Ala Gln Pro His Gln Ser Leu Thr Asp
225                 230                 235                 240

Glu Glu Gln Ala Ala Val Lys Tyr Ala Thr Asp His Gly Val Phe Val
                245                 250                 255
```

Ser Val Ala Gly Ser Asn Tyr Gly His Ala Gly Ser Leu Glu Thr Asn
            260                 265                 270

Ala Asn Asp Leu Ser Asp Ser Thr Thr Thr Tyr Glu Pro Ala Asn
        275                 280                 285

Ser Gly Thr Ile Ala Asp Pro Gly Val Ala Asn Ser Ala Met Thr Val
290                 295                 300

Gly Ser Ala Asn Thr Lys Thr Gly Ser Lys Ser Ala Met Ser Ser Phe
305                 310                 315                 320

Ser Ala Trp Gly Pro Thr Pro Glu Phe Ala Phe Lys Pro Asp Ile Thr
                325                 330                 335

Ala Pro Gly Asp His Ile Ala Thr Ile Asp Glu Asn Lys Thr Tyr Thr
            340                 345                 350

Phe Asp Ser Gly Thr Ser Phe Ala Ser Pro Tyr Ile Ala Gly Ser Ala
            355                 360                 365

Ala Leu Val Leu Gln Arg Val His Lys Asp Gln Pro Asn Leu Lys Gly
            370                 375                 380

Ala Ala Leu Val Asn Ala Ala Lys Val Ala Leu Met Asn Ala Ser Gln
385                 390                 395                 400

Pro Met Asn Asn Ser Gln Phe Pro Gly Glu Ile Val Ser Pro Arg Leu
                405                 410                 415

Gln Gly Ala Gly Val Val Asn Val Ala Asn Ala Ala Asn Leu Asn Ala
            420                 425                 430

Ala Ala Thr Asp Ala Ala Thr Gly Ser Gly Ala Val Ala Leu Arg Gln
            435                 440                 445

Ile Gly Gln Ile Thr Asn Phe Ser Leu Asn Val Thr Asn His Val Ala
450                 455                 460

Ile Pro Gln Thr Tyr Arg Val Asp Thr Thr Gly Pro Asp Thr Glu
465                 470                 475                 480

Thr Arg Lys Ala Asp Lys Asn Gly Ile Gly Val His Asp Val Lys
                485                 490                 495

Ile Asn Gly Ala Ser Leu Thr Ala Ser Leu Pro Thr Ile Thr Val Asp
            500                 505                 510

Pro Gly Lys Thr Val Lys Leu Asp Phe Lys Leu Asp Leu Gly Ser Gln
            515                 520                 525

Ala Ala Arg Asn Lys Ile Ala Glu Gly Tyr Ile Ser Leu Val Asn Ser
            530                 535                 540

Asp Ala Lys Gln Asn Leu Thr Ile Pro Tyr Met Gly Tyr Tyr Gly Asp
545                 550                 555                 560

Ala Thr Thr Glu Gln Ile Ile Asp Gln Pro Ala Asn Gln Thr Gly Ser
                565                 570                 575

Asp Phe Gly Gly Gly Tyr Met Ile Asp Asn His Asn Thr Pro Leu Gly
            580                 585                 590

Val Ser Asp Arg Thr Ser Leu Ala Ser Tyr Ile Asn Ala Gly Ser Pro
            595                 600                 605

Glu Thr Ala Ser Asn Arg Trp Asp Ala Thr Pro Gly Lys Val Asp Asp
            610                 615                 620

Asp Lys Ile Ala Ile Ser Pro Asn Gly Asp Gly Lys Met Asp Val Ala
625                 630                 635                 640

Asn Pro Tyr Val Phe Ala Lys Gln Ser Leu Ala Lys Val Gln Ala Ala
                645                 650                 655

Ile Leu Asn Ser Lys Gly Gln Val Ile Arg Val Ile Asp Gln Glu Thr
            660                 665                 670

Asn Thr Asp Lys Ser Ile His Asp Leu Gly Ser Asp Ala Asn Asn Asp

```
                    675                 680                 685
Leu Ala Leu Ser Val Ser Met Arg Pro Asn Pro Thr Ala Leu Thr Trp
            690                 695                 700

Asn Gly Gln Ala Tyr Asp Arg Ala Thr Gly Lys Met Lys Val Val Pro
705                 710                 715                 720

Asp Gly Arg Tyr Gln Tyr Arg Ile Glu Thr Thr Asn Phe Asn Asp Gly
                725                 730                 735

Ala Asp Lys Val Gln Asp Trp Thr Leu Pro Val Gln Val Asp Thr Lys
            740                 745                 750

Ala Pro Lys Ile Val Lys Ala Thr Tyr His Arg Gly Arg Leu Thr Val
        755                 760                 765

Gly Tyr Arg Asp Ser Gly Val Gly Phe Thr Lys Leu Ser Ala Met Ala
    770                 775                 780

Val Lys Val Gly Lys Lys Val Ala Gly Val Ser Leu Asn Asn Ser Gly
785                 790                 795                 800

Arg Gln Asn Gln Gly Ile Thr His Tyr Thr Leu Ser Lys Lys Leu Ser
                805                 810                 815

Lys Ile Ser

<210> SEQ ID NO 58
<211> LENGTH: 790
<212> TYPE: PRT
<213> ORGANISM: Artificial Sequence
<220> FEATURE:
<223> OTHER INFORMATION: fragment of Lactobacillus parafarraginis
      protease

<400> SEQUENCE: 58

Phe Met Thr Thr Glu Met Thr Ala Thr Gln Ala Gln Ser Ile Lys Gln
1               5                   10                  15

Pro Thr Thr Phe Ser Gln His Lys Pro Ala Lys Lys Pro Thr Lys Thr
            20                  25                  30

Asn Gln Thr Thr Ser Phe Asn Gln Gln Arg Gln Ala Ala Leu Thr Arg
        35                  40                  45

Gly Asn Val Pro Thr Leu Trp Ser Gln Gly Tyr Gln Gly Gln Gly Met
    50                  55                  60

Val Ile Ala Val Ile Asp Ser Gly Ile Gln Asn His Pro Asp Leu Gly
65                  70                  75                  80

Leu Ser Asn Asn Gln Thr Ala Lys Ile Ser Lys Ala Asp Ala Gln Gln
                85                  90                  95

Leu Ile Ala Gln Lys Gly Tyr Gly Lys Tyr Ile Ser Pro Lys Ile Pro
            100                 105                 110

Phe Ala Tyr Asp Tyr Val Asn Asn Asn Asp Asp Thr Ala Ala Asp
        115                 120                 125

Ser Thr Ser Gly Phe His Gly Glu Glu Val Gly Val Ala Ala Ala
    130                 135                 140

Asn Gly Val Glu Thr Asn Gln Ala Lys Tyr Met Lys Gly Val Ala Pro
145                 150                 155                 160

Gln Ala Gln Leu Leu Asn Leu Lys Val Phe Gly Gly Phe Ala Asp Glu
                165                 170                 175

Ile Pro Asn Asp Val Ala Arg Ala Ile His Asp Ala Val Asp Leu Gly
            180                 185                 190

Ala Asp Val Ile Asn Leu Ser Leu Gly Leu Ala Gln Pro His Gln Ser
        195                 200                 205

Leu Thr Asp Glu Glu Gln Ala Ala Val Lys Tyr Ala Thr Asp His Gly
```

```
              210                 215                 220
    Val Phe Val Ser Val Ala Gly Ser Asn Tyr Gly His Ala Gly Ser Leu
    225                 230                 235                 240
    Glu Thr Asn Ala Asn Asp Leu Ser Asp Ser Thr Thr Thr Thr Tyr Glu
                        245                 250                 255
    Pro Ala Asn Ser Gly Thr Ile Ala Asp Pro Gly Val Ala Asn Ser Ala
                        260                 265                 270
    Met Thr Val Gly Ser Ala Asn Thr Lys Thr Gly Ser Lys Ser Ala Met
                275                 280                 285
    Ser Ser Phe Ser Ala Trp Gly Pro Thr Pro Glu Phe Ala Phe Lys Pro
                290                 295                 300
    Asp Ile Thr Ala Pro Gly Asp His Ile Ala Thr Ile Asp Glu Asn Lys
    305                 310                 315                 320
    Thr Tyr Thr Phe Asp Ser Gly Thr Ser Phe Ala Ser Pro Tyr Ile Ala
                        325                 330                 335
    Gly Ser Ala Ala Leu Val Leu Gln Arg Val His Lys Asp Gln Pro Asn
                        340                 345                 350
    Leu Lys Gly Ala Ala Leu Val Asn Ala Ala Lys Val Ala Leu Met Asn
                        355                 360                 365
    Ala Ser Gln Pro Met Asn Asn Ser Gln Phe Pro Gly Glu Ile Val Ser
    370                 375                 380
    Pro Arg Leu Gln Gly Ala Gly Val Val Asn Val Ala Asn Ala Ala Asn
    385                 390                 395                 400
    Leu Asn Ala Ala Ala Thr Asp Ala Ala Thr Gly Ser Gly Ala Val Ala
                        405                 410                 415
    Leu Arg Gln Ile Gly Gln Ile Thr Asn Phe Ser Leu Asn Val Thr Asn
                        420                 425                 430
    His Val Ala Ile Pro Gln Thr Tyr Arg Val Asp Thr Thr Thr Gly Pro
                        435                 440                 445
    Asp Thr Glu Thr Arg Lys Ala Asp Lys Asn Gly Ile Gly Val Val His
                        450                 455                 460
    Asp Val Lys Ile Asn Gly Ala Ser Leu Thr Ala Ser Leu Pro Thr Ile
    465                 470                 475                 480
    Thr Val Asp Pro Gly Lys Thr Val Lys Leu Asp Phe Lys Leu Asp Leu
                        485                 490                 495
    Gly Ser Gln Ala Ala Arg Asn Lys Ile Ala Glu Gly Tyr Ile Ser Leu
                        500                 505                 510
    Val Asn Ser Asp Ala Lys Gln Asn Leu Thr Ile Pro Tyr Met Gly Tyr
                        515                 520                 525
    Tyr Gly Asp Ala Thr Thr Glu Gln Ile Ile Asp Gln Pro Ala Asn Gln
                530                 535                 540
    Thr Gly Ser Asp Phe Gly Gly Gly Tyr Met Ile Asp Asn His Asn Thr
    545                 550                 555                 560
    Pro Leu Gly Val Ser Asp Arg Thr Ser Leu Ala Ser Tyr Ile Asn Ala
                        565                 570                 575
    Gly Ser Pro Glu Thr Ala Ser Asn Arg Trp Asp Ala Thr Pro Gly Lys
                        580                 585                 590
    Val Asp Asp Asp Lys Ile Ala Ile Ser Pro Asn Gly Asp Gly Lys Met
                        595                 600                 605
    Asp Val Ala Asn Pro Tyr Val Phe Ala Lys Gln Ser Leu Ala Lys Val
                        610                 615                 620
    Gln Ala Ala Ile Leu Asn Ser Lys Gly Gln Val Ile Arg Val Ile Asp
    625                 630                 635                 640
```

-continued

```
Gln Glu Thr Asn Thr Asp Lys Ser Ile His Asp Leu Gly Ser Asp Ala
            645                 650                 655

Asn Asn Asp Leu Ala Leu Ser Val Ser Met Arg Pro Asn Pro Thr Ala
            660                 665                 670

Leu Thr Trp Asn Gly Gln Ala Tyr Asp Arg Ala Thr Gly Lys Met Lys
            675                 680                 685

Val Val Pro Asp Gly Arg Tyr Gln Tyr Arg Ile Glu Thr Thr Asn Phe
        690                 695                 700

Asn Asp Gly Ala Asp Lys Val Gln Asp Trp Thr Leu Pro Val Gln Val
705                 710                 715                 720

Asp Thr Lys Ala Pro Lys Ile Val Lys Ala Thr Tyr His Arg Gly Arg
                725                 730                 735

Leu Thr Val Gly Tyr Arg Asp Ser Gly Val Gly Phe Thr Lys Leu Ser
            740                 745                 750

Ala Met Ala Val Lys Val Gly Lys Lys Val Ala Gly Val Ser Leu Asn
            755                 760                 765

Asn Ser Gly Arg Gln Asn Gln Gly Ile Thr His Tyr Thr Leu Ser Lys
    770                 775                 780

Lys Leu Ser Lys Ile Ser
785             790
```

TREATMENT OF IMMUNE DYSREGULATION DISORDERS

This application is the U.S. National Stage of International Application No. PCT/EP2019/078944, filed Oct. 23, 2019, which designates the U.S., published in English, and claims priority under 35 U.S.C. § 119 or 365(c) to European Application No. 18202147.7, filed Oct. 23, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 56691002002 SEQUENCE LISTING.txt; created Apr. 21, 2021, 547 KB in size.

FIELD OF THE INVENTION

The current invention relates to a protease and the use thereof to treat immune dysregulation disorders.

BACKGROUND OF THE INVENTION

Immune dysregulation is increasing recognized as a component of a very broad variety of significant syndromes and disorders including those of the skin, e.g. eczema, the lungs, e.g. asthma, and the gut, e.g. Inflammatory Bowel Disease. The predominant strategies employed to target immune dysregulation and associated disorders are the use of recombinant monoclonal antibodies (MCAb) and the use of antagonists to receptors of pro-inflammatory mediators.

One drawback of a strategy utilising MCAb to tackle immune dysregulation is that production of MCAb is expensive, and large quantities (100's mg or MCAb) have to be administered. Furthermore, both MCAb and receptor antagonists are generally administered intravenously in a healthcare setting. This systemic route leads to significant adverse side effects. For example, targeting TNFα, which is a major target in current treatments of inflammatory diseases, with anti-TNFα results in immuno-suppression leading to increased infections and in some cases, cancer, in patients receiving this treatment. MCAbs by their nature are also very specific having a single mediator target.

Pro-inflammatory mediators or cytokines are substances that are capable of causing inflammation and include vasoactive amines, such as histamine and plasma endopeptidases. Pro-inflammatory mediators are secreted by immune cells and other inflammation-promoting cell types. Excessive chronic production or dysregulation of these mediators is linked to inflammatory disease.

Cell envelope proteases (CEP) are part of a multi-domain protease family and play an important role in lactic acid bacteria growth and pathogenesis. The CEP of *Lactococcus lactis*, PrtP, has been extensively studied and is essential for optimal growth in milk. PrtP of *Lactobacillus casei* has activity against the IP-10. The CEPs from *Streptococcus pyogenes* (ScpA, and ScpC) and *Streptococcus agalactiae* (ScpB) contribute to the bacteria's ability to cause infection. CEPs show homologies but differ in specificity, and domain organisation.

There is a need to provide a treatment strategy targeting immune dysregulation which overcomes the disadvantageous associated with current methods. The current invention serves to solve this problem.

SUMMARY OF THE INVENTION

In a first aspect, the invention provided an isolated protein comprising a protease domain, A-domain, and B-domain, of a Group VII to XIII cell envelope protease (CEP), wherein the protein generally does not have a PA domain (hereafter "isolated protease" of the invention). The absence of a PA domain alters the specificity of the proteases to include larger cytokines, such as TNFα. It allows a broad range of pro inflammatory mediators access the active site of the protease, allowing the isolated protease be used in the treatment of a broad range of immune dysregulation diseases. Moreover, compared to the use of monoclonal antibodies as therapies for immune dysregulation diseases, the use of an enzyme (which can catalyse the destruction of thousands of pro-inflammatory mediators) allows the use of lower quantities of therapeutic (i.e. 0.1-5 mg per dose, as compared to 10-100 mg MAb per dose).

The isolated protease of the invention typically comprises (or consists essentially of) one of the following polypeptide structures:

P-A; P-A-B; P-A-B-W, Pp-P-A-B; Pp-P-A-B-W-An; and P-A-B-W-An, in which P is a protease domain, A is a A-domain, and B is a B-domain, Pp is a propeptide, W is a wall domain, and An is an anchor domain, of a Group VII to XIII cell envelope protease (CEP).

The PA domain (or protease-associated domain) is conserved across many protease superfamilies, including subtilases and Zn-containing metalloproteases. It forms a lid structure that prevents pro- and anti-inflammatory mediators access the active site of the protease. PA domains are described in Luo et al (TRENDS in Biochemical Sciences, Vol. 26, No. 3, March 2001) and Mahon et al (Protein Science 2000, 9:1930-1934). Therefore, the invention relates to CEP's that do not have a PA domain (i.e. Group VII to XIII CEP's) or a functional PA domain, and active fragments of the CEP's, that are isolated, and the use of the proteases and fragments as medicaments in the treatment of immune dysregulation diseases.

In one embodiment, the isolated protease of the invention is selected from a wild-type Group VII to XIII cell envelope protease. Examples include PrtV, a Group VIII cell envelope protease isolated from *Lactobacillus salivarius* JCM1046 (SEQ ID 1), and PrtI, a Group IX cell envelope protease isolated from *Lactobacillus intestinalis* DSM6629 (SEQ ID 5), Nucleic acids sequences encoding PrtV and PrtI are provided in SEQ ID's 2 and 6, respectively. Other proteases of the invention are described in FIG. 5 (groups VII to XIII). Further examples of the proteases include those comprising (or consisting of) SEQ ID NO. 21, 23, 25, 27, 29, 31, 33, 35, 37, 39, 41, 43, 45, 47, 49, 51, 53, 55 and 57.

In one embodiment, the protein is based on a wild-type Group VII to XIII cell envelope protease, but engineered to remove many domains leaving the protease domain, A-domain, and B-domain, and optionally some or all of the propeptide domain. Examples include a fragment of PrtV comprising the propeptide to the B-domain of PrtV (SEQ ID 3), a fragment of PrtI comprising the propeptide to the B-domain of PrtI (SEQ ID 7), and a further fragment of PrtI from residue 36 to the end of the B-domain of Prt1 (SEQID 9). The nucleic acid sequences of the three fragments are provided by SEQ ID 4, 8 and 10. Examples also include fragments comprising (or consisting of) SEQ ID NO. 22, 24, 26, 28, 30, 32, 34, 36, 38, 40, 42, 44, 46, 48, 50, 52, 54, 56 and 58.

In one embodiment, the isolated protein is a recombinant protein. In one embodiment, the isolated protein of the invention is expressed by a *Lactobacillus bacterium*. In one aspect, the isolated protease of the invention is capable of enzymatic destruction of a pro-inflammatory mediator selected from a cytokine and an anaphylotoxin, for example a cytokine selected from IL-3, IL-8, IL-10, IL17, IL-1β, TNF-α, for example an anaphylotoxin selected from C3a, C4a and C5a.

A further aspect of the invention provides a composition comprising the protease of the invention. Typically, the composition is a pharmaceutical composition. Preferably, the composition of the invention comprises a therapeutically effective amount of the protease of the invention.

In an embodiment of the invention, the composition of the invention may include one or more additional components. Preferably, the one or more additional component may be a pharmaceutically active agent. The one or more additional component may be one that benefits the preferred mode of delivery or administration. The one or more additional component may be one that is useful for the treatment of an immune dysregulation disorder or the symptoms thereof. The one or more additional component may be a pharmaceutically acceptable diluents, excipients or carriers.

In an embodiment, the invention provides a conjugate comprising a protease of the invention.

A still further aspect of the invention provides a particle comprising a protease or composition of the invention. The particle may be a sub-micron, micron, or mm sized particle. Preferably, the particle is a microparticle selected from a microcapsule, a microsphere, a nanoparticle and a liposome. In an embodiment, the particle is a microparticle with an average size of between 300 nm to 700 nm. The particles may be disposed on a surface of a membrane, tube or fiber.

A further aspect of the invention provides an isolated peptide comprising (or consisting of) a sequence of SEQUENCE ID NO. 1 or SEQUENCE ID NO. 5.

An aspect of the current invention provides an isolated nucleotide sequence comprising (or consisting of) a sequence of SEQUENCE ID NO. 2 or SEQUENCE ID NO. 6.

In an aspect of the invention there is provided a protease or a composition of the invention for use as a medicament.

In an aspect of the invention there is provided a protease or composition of the invention for use in the treatment of an immune dysregulation disorder or disease.

In an embodiment, the immune dysregulation disorder is selected from the group comprising asthma, eczema, inflammatory bowel disease, cystic fibrosis, bowel cancer, colitis and age-related macular degeneration (AMD). Other examples are provided in the Table 1 below.

TABLE 1

| Family of mediator | Members | Examples of target diseases |
|---|---|---|
| Anaphylotoxin | C3a, C4a, C5a | Sepsis, skin diseases, transplant rejection, Lyme disease, arthritis, cancer, cystic fibrosis, allergic asthma, AMD |
| CXCL cytokine | IL-8, IP10 | Ulcerative Colitis, cancer, gingivitis, psoriasis, inflammatory lung disease, glomerulonephritis |

TABLE 1-continued

| Family of mediator | Members | Examples of target diseases |
|---|---|---|
| Class-2 cytokine | IL-10 | Leishmaniasis |
| IL-17 cytokine | IL-17 | Psoriasis, autoimmune disorders, allergy response, asthma, eczema, :rheumatoid arthritis, multiple sclerosis, and inflammatory bowel diseases |
| IL-1 cytokine | IL-1β | Autoimmune disease, Rheumatoid arthritis |
| TNF cytokine superfamily | TNF-α | Rheumatoid arthritis, ankylosing spondylitis, Alzheimer's, cancer, psoriasis, IBD |
| Common β receptor-signaling cytokines | IL-3 | Allergic inflammation |

The invention also provides a method of treating or preventing an immune dysregulation disorder, said method comprising administering a therapeutically effective amount of the protease or composition of the invention to a patient in need thereof. A therapeutically effective amount may be 0.1 to 100 mg, 1-100 mg, or 10-100 mg.

In one embodiment, the composition of the invention is formulated for oral or parenteral administration. Other methods of administration are described below, and in Fenton et al (Advances in Biomaterials for Drug Delivery, Adv. Mater. 2018, 30, 1705328).

A further aspect of the current invention relates to a man-made treatment composition comprising the composition of the invention or the protease of the invention.

In one aspect, the current invention provides a method for preparing the composition of the invention.

Other aspects and preferred embodiments of the invention are defined and described herein and in the claims set out below.

Definitions

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

The term "protease of the invention" refers to a Group VII to XIII cell envelope protease (CEP), especially proteases expressed by *Lactobacillus bacterium*, that is isolated (i.e. isolated from its natural environment or produced by means of a technical process such as recombinant protein engineering). The term also covers functional fragments of these proteases that include the protease domain, A-domain and B-domain, and sometimes all or part of the propeptide domain. In one embodiment, the engineered variant includes an additional domain. The protease is generally "functional", which means that it exhibits activity against pro-inflammatory mediators described herein and according to the methods as outlined below. The term also includes "variants" of the protease of the invention which are substantially identical to the protease of the invention but include one or more amino acid alternations (for example 1-10 or 1-5 alterations) compared with the reference protease. The alterations may be selected from insertion, addition, deletion, substitution. The variant generally retains the same functionality as the reference protease (i.e. it is a functional variant).

The term "PrtV" when used herein refers to a protease with an amino acid sequence comprising SEQUENCE ID NO. 1 or a functional variant or fragment thereof. The amino acid sequence encoding this enzyme has 1530 amino acids. It has an estimated mass of 163.8 kDa. It originates from *Lactobacillus salivarius* JCM1046. The domain architecture of PrtV is illustrated in FIG. 1.

The term "PrtI" when used herein refers to an enzyme with an amino acid sequence comprising SEQUENCE ID NO. 5 or a functional variant or fragment thereof. The amino acid sequence encoding this enzyme is 1698 amino acids in length. It is a multi-domain cell envelope protease (CEP). It has an estimated mass of 185.8 kDa. It originates from *Lactobacillus intestinalis* DSM6629. The domain architecture of PrtI is illustrated in FIG. 2.

In this specification, the phrase "an amino acid sequence of SEQUENCE ID NO. 1" or "an amino acid sequence of SEQUENCE ID NO. 5", when used refers to a polymer linked via peptide bond linkages that includes the mentioned sequence, or an amino acid sequence consisting essentially of the mentioned sequence. It also should be taken to refer to a polymer that includes (or consists of) a sequence that is substantially identical to the mentioned sequence but altered in respect of one or more amino acid residues. Such sequences are hereafter referred to as "variants" or "fragments". Preferably such alterations involve the insertion, addition, deletion and/or substitution of 500 or fewer amino acids, more preferably of the range 1-10.

Insertion, addition and substitution with natural and modified amino acids is envisaged. The peptide may have conservative amino acid changes, wherein the amino acid being introduced is similar structurally, chemically, or functionally to that being substituted. Generally, the variant will have at least 70% amino acid sequence identity, preferably at least 80% sequence identity, more preferably at least 90% sequence identity, and ideally at least 95%, 96%, 97%, 98% or 99% sequence identity with the parent sequence. Preferably, the variant, or enzyme variant, is a functional variant.

The term "fragment" should be understood to mean a segment of an amino acid sequence of the invention. Typically, the fragment has between 500 and 2000 contiguous amino acids in length. Preferably, the fragment, or enzyme fragment, is a functional fragment.

The term "functional" variant or fragment refers to a variant or fragment as defined herein which is capable of enzymatic destruction of immune regulators as outlined in the methods as described herein and/or capable of treating immune dysregulation disorders.

In this specification, the term "sequence identity" should be understand to comprise both sequence identity and similarity, i.e. a variant (or homolog) that shares 70% sequence identity with a reference sequence is one in which any 70% of aligned residues of the variant (or homolog) are identical to, or conservative substitutions of, the corresponding residues in the reference sequence across the entire length of the sequence. Sequence identity is the amount of characters which match exactly between two different sequences. The measurement is relational to the shorter of the two sequences.

In terms of "sequence homology", the term should be understood to mean that a variant (or homolog) which shares a defined percent similarity or identity with a reference sequence when the percentage of aligned residues of the variant (or homolog) are either identical to, or conservative substitutions of, the corresponding residues in the reference sequence and where the variant (or homolog) shares the same function as the reference sequence.

This alignment and the percent homology or sequence identity can be determined using software programs known in the art, for example, one alignment program is BLAST, using default parameters. Details of these programs can be found at the following Internet address: ncbi.nlm.nih.gov/blast/Blast.cgi.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s). In this case, the term is used synonymously with the term "therapy". Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. In preferred embodiments, the subject is a human.

In this specification, the term "composition" should be understood to mean something made by the hand of man, and not including naturally occurring compositions.

Compositions may be formulated in unit dosage form, i.e., in the form of discrete portions containing a unit dose, or a multiple or sub-unit of a unit dose.

In this specification, the term "pharmaceutical compositions" relates to the enzyme of the invention or the composition of invention, admixed with one or more pharmaceutically acceptable diluents, excipients or carriers. Even though the enzyme and compositions of the present invention can be administered alone, they will generally be administered in admixture with a pharmaceutical carrier, excipient or diluent, particularly for human therapy. The pharmaceutical compositions may be for human or animal usage in human and veterinary medicine. Examples of such suitable excipients for the various different forms of pharmaceutical compositions described herein may be found in the "Handbook of Pharmaceutical Excipients, 8th Edition, Edited by A Wade and PJ Weller. In particular, American Pharmaceutical Review "Opportunities and Challenges in Biologic Drug Discovery (americanpharmaceuticalreview.com/Featured-Articles/345540-Opportunities-and-Challenges-in-Biologic-Drug-Delivery/), formulations for topical delivery are described in Topical drug delivery formulations edited by David Osborne and Antonio Aman, Taylor & Francis, the complete contents of which are incorporated herein by reference. Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of phydroxybenzoic acid. Antioxidants and suspending agents may be also used.

The term "protein" used herein refers to a polymer composed of amino acids, typically linked via peptide bond linkage. Proteins (including fragments and variants thereof) of and for use in the invention may be generated wholly or partly by chemical synthesis or by expression from nucleic acid. For example, the proteases of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Illinois (1984), in M. Bodanzsky and A. Bodanzsky, The Practice of Peptide Synthesis, Springer Verlag, New York (1984). When necessary, any of the peptides employed in the invention can be chemically modified to increase their stability. A chemically modified protein or a protein analog includes any functional chemical equivalent of the protein characterized by its increased stability and/or efficacy in vivo or in vitro in respect of the practice of the invention. The term protein analog also refers to any amino acid derivative of a protein as described herein. A protein analog can be produced by procedures that include, but are not limited to, modifications to side chains, incorporation of unnatural amino acids and/or their derivatives during peptide synthesis and the use of cross-linkers and other methods that impose conformational constraint on the protein or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Protein structure modification includes the generation of retro-inverso protein comprising the reversed sequence encoded by D-amino acids. Changes may be those that reduce susceptibility to proteolysis, reduce susceptibility to oxidation, alter binding affinity of the variant sequence (typically desirably increasing affinity), and/or confer or modify other physicochemical or functional properties on the associated variant/analog protein.

The term "protein analog" also refers to any amino acid derivative of a protein as described herein. A "protein analog" may be used interchangeably with the term "modified protein". A protein analog can be produced by procedures that include, but are not limited to, modifications to side chains, incorporation of unnatural amino acids and/or their derivatives during peptide synthesis and the use of cross-linkers and other methods that impose conformational constraint on the protein or their analogs. Examples of side chain modifications include modification of amino groups, such as by reductive alkylation by reaction with an aldehyde followed by reduction with NaBH$_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with NABH$_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Peptide structure modification includes the generation of retro-inverso peptides comprising the reversed sequence encoded by D-amino acids. Changes may be those that reduce susceptibility to proteolysis, reduce susceptibility to oxidation, alter binding affinity of the variant sequence (typically desirably increasing affinity), and/or confer or modify other physicochemical or functional properties on the associated variant/analog peptide.

The phrase "immune dysregulation disorder" refers to a B cell-related disease, a T-cell related disease, an immune dysregulation disease, an acute or chronic inflammatory disease, a solid cancer, a hematopoietic tumor, a metabolic disease, a neurodegenerative disease or an autoimmune disease.

BRIEF DESCRIPTION OF THE FIGURES

The invention will be more clearly understood from the following description of an embodiment thereof, given by way of example only, with reference to the accompanying drawings, in which.

DETAILS DESCRIPTION OF THE INVENTION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

All publications, patents, patent applications and other references mentioned herein are hereby incorporated by reference in their entireties for all purposes as if each individual publication, patent or patent application were specifically and individually indicated to be incorporated by reference and the content thereof recited in full.

Broadly, the current invention contemplates a protease capable of enzymatic destruction of pro-inflammatory regulators. The protease is a Group VII to XIIII cell envelope protease (CEP), expressed by a bacterium, especially a bacterium of the *Lactobacillus* genus, preferably by the species *Lactobacillus salivarius* or *Lactobacillus intestinalis*, or an engineered fragment of the protein.

The bacterium may be of the following genus: *Leuconostoc, Fructobacillus, Carnobacterium, Enterococcus, Pediococcus, Anaerofustis, Paenisporosarcina, Actinomyces, Erysipelothrix* or *Kefiranofaciens*. The bacterium or species may be any of those listed in Table 3 or as disclosed herein.

The protease of the invention is for intervention in immune dysregulation disorders. In contrast to MCAbs of prior art methods, the protease of the current invention is a catalytic entity having a specific activity against a defined panel of pro-inflammatory mediators but avoids targeting a range of other blood proteins. The catalytic functionality of the protease allows the protease to be re-cycled and effect the destruction of millions of target pro-inflammatory mediators.

Figure 3:
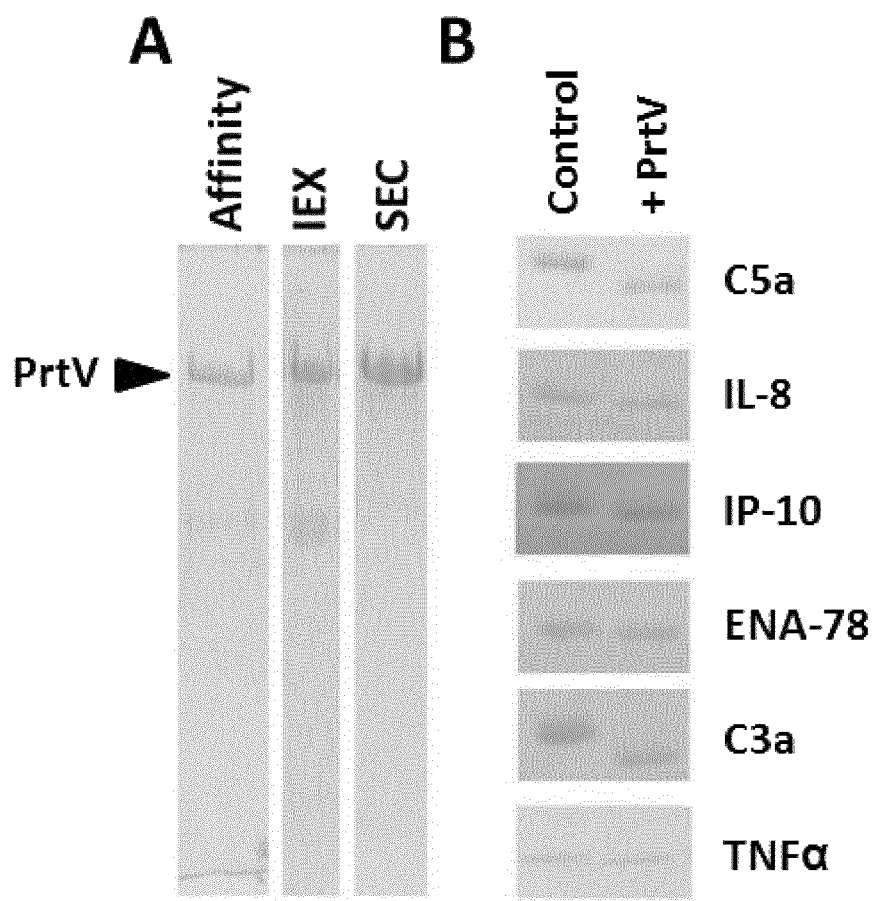
FIG. 3A illustrates purification regime for recombinant PrtV.
FIG. 3B illustrates the activity of PrtV (+) against a panel of mediators.
Figure 4:
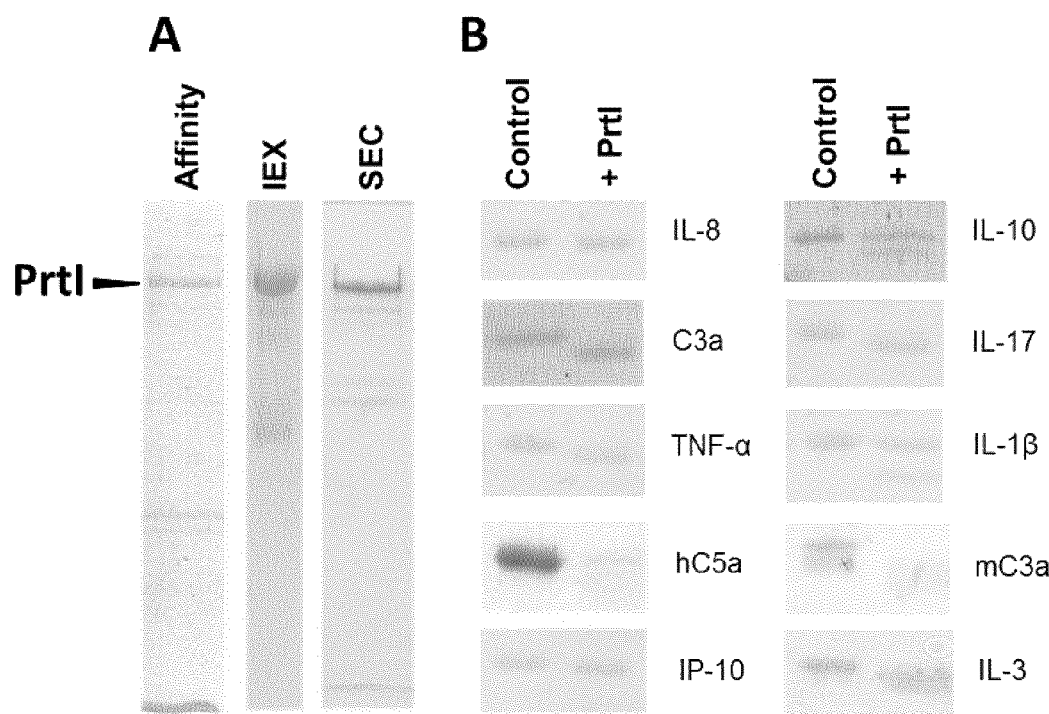
FIG. 4A illustrates purification regime for recombinant PrtI.
FIG. 4B illustrates the activity of PrtI (+) against a panel of mediators.

The absence of the PA domain absence of the PA domain alters the specificity of the proteases to include larger cytokines, such as TNFa (as shown in FIGS. 3 and 4).

The protease of the invention has activity against the pro-inflammatory mediators selected from the group comprising, but not limited to, C5a, IL-8, IP-10, ENA-78, C3a, TNF-α, hC5a, IP-10, IL-10, IL-17, IL-1β, mC3a and IL-3 or a combination thereof. The protease of the invention may have activity against one or more of C5a, IL-8, IP-10, ENA-78, C3a, TNF-α. The protease of the invention may have activity against one or more of IL-8, C3a, TNF-α, hC5a, IP-10, IL-10, IL-17, IL-1β, mC3a and IL-3.

Figure 5:
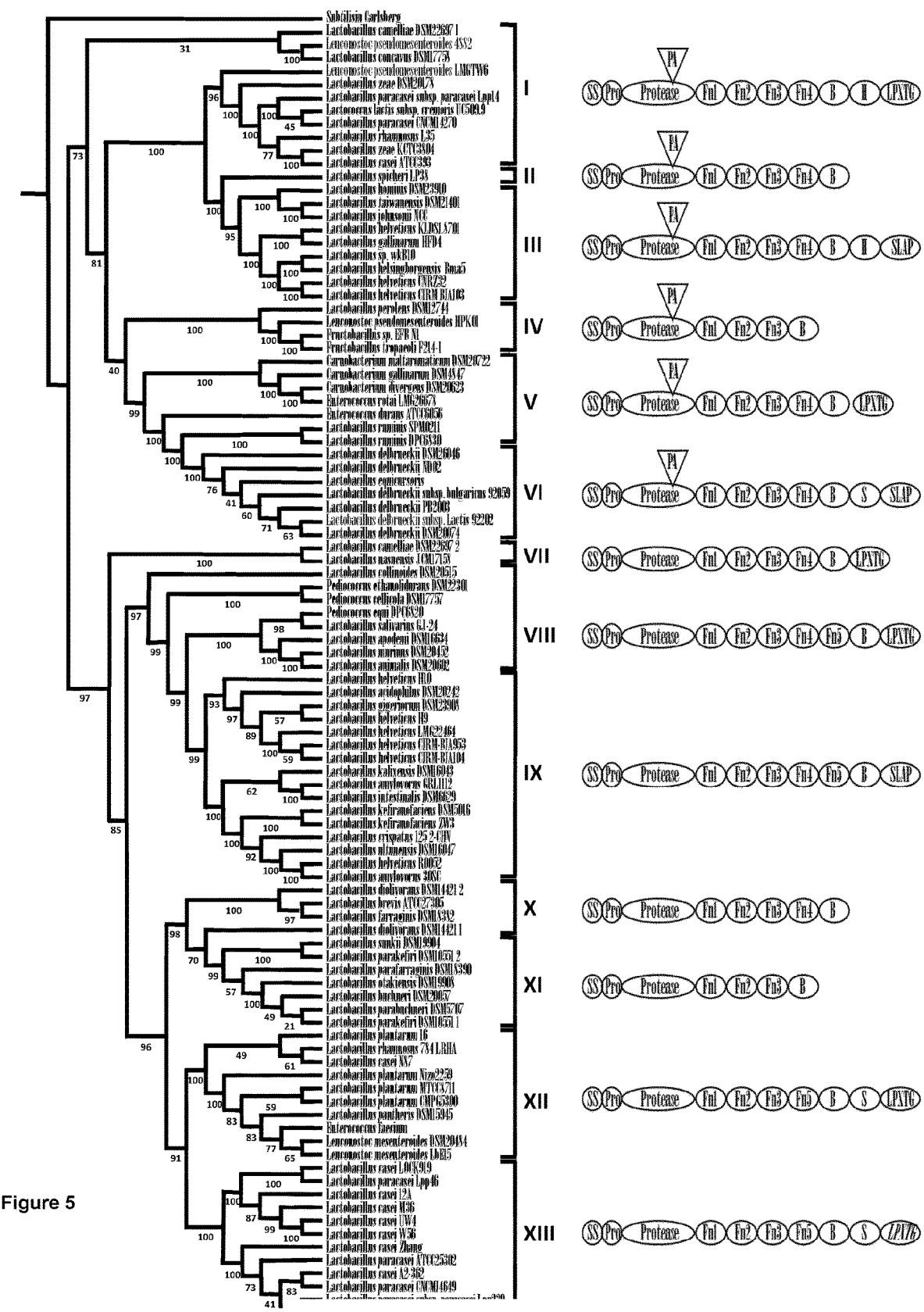
FIG. 5: Phylogenetic tree and domain organization of CEPs from *Lactobacillus* species.
Figure 6:
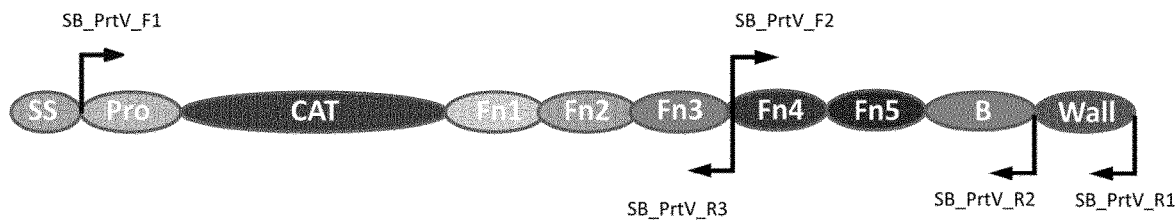
FIG. 6: Cloned fragments of the prtV gene from *Lactobacillus salivarius* incorporate different domains of the CEP. Primer pair SB_PrtV_F1 and SB_PrtV_R1 cloned from the beginning of the pro-peptide to the end of the wall spanning domain. Primer Pair SB_PrtV_F1 and SB_PrtV_R2 cloned from the pro-peptide to the end of the B Domain, while primer pair SB_PrtV_F1 and SB_PrtV_R3 cloned from the pro-peptide to the end of the Fn3 domain.
Figure 7:
FIG. 7: Cloned fragment of the PrtI gene from *Lactobacillus intestinalis*. The primer pair RC_LBin_CEP_f and RC_LBin_CEP_r2 were used to clone the PrtI(ProB) which incorporated the propeptide to the end of the B-domain.
Figure 8:
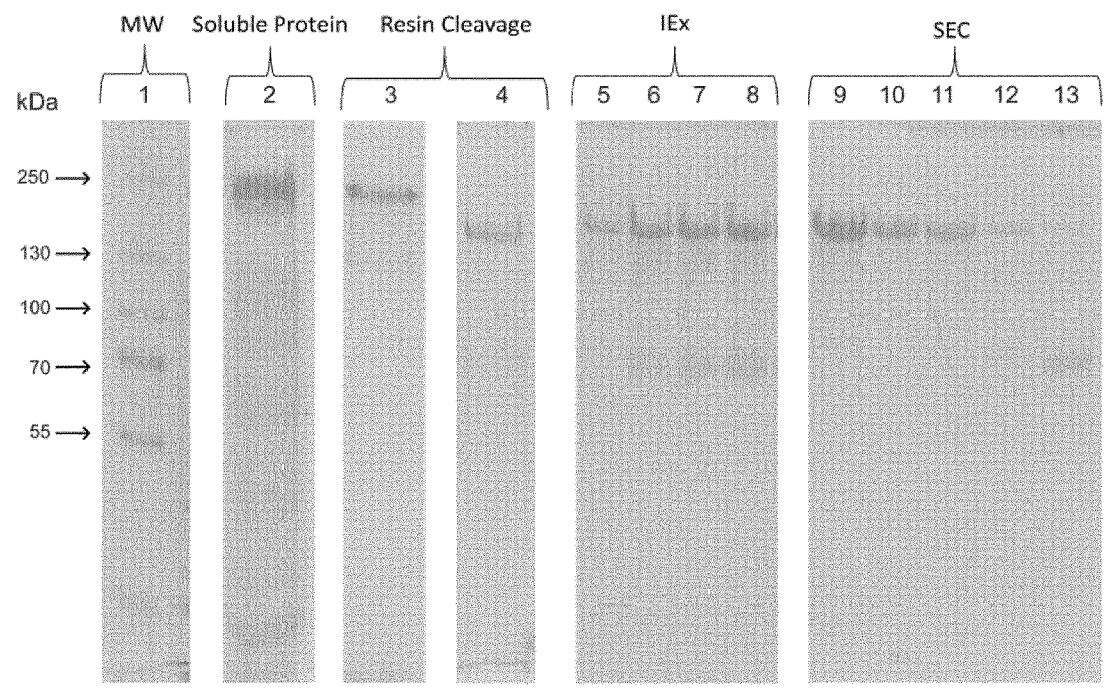
FIG. 8: Analysis of stages of the purification regime of PrtV(Pro-B): Lane 1: Marker; Lane 2: Soluble *E. coli* protein extract containing PrtV(Pro-B); Lane 3: GSH Resin with bound PrtV(Pro-Fn3). Lane 4: supernatant after treatment with PreScission Protease; Lanes 5, to 8: fractions after ion exchange chromatography; Lanes 9 to 13: purified PrtV(Pro-Fn3) after size exclusion chromatography.
Figure 9:
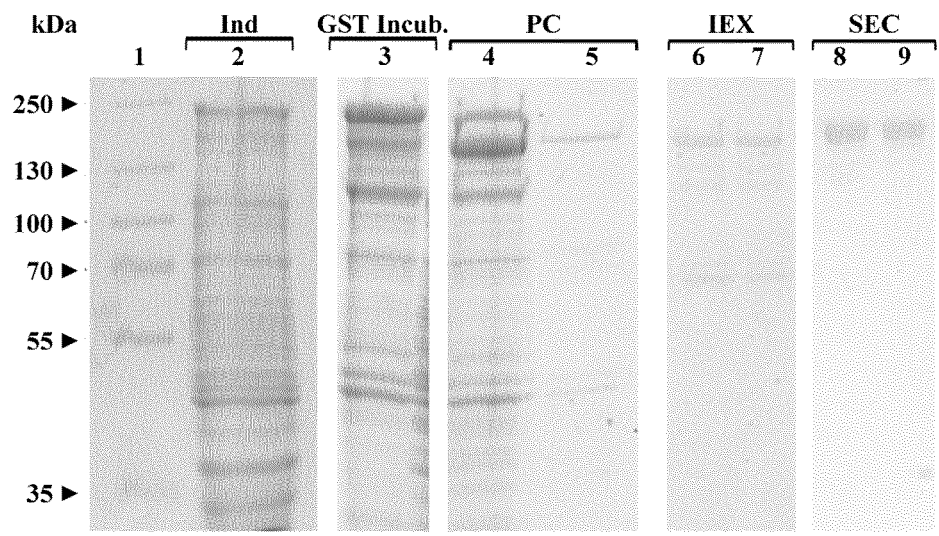
FIG. 9: PrtI(ProB) purification analysed by SDS-PAGE.
Figure 10:
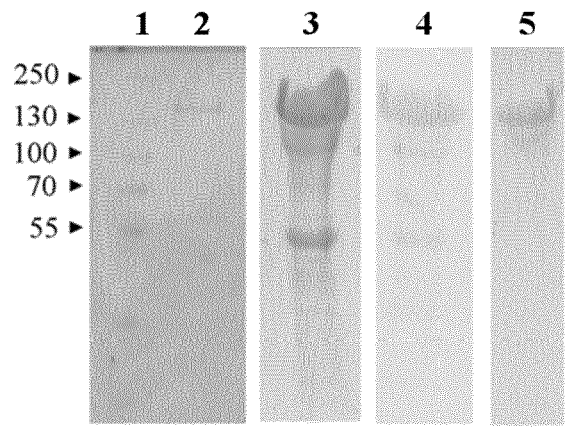
FIG. 10: Analysis of samples from the purification of PrtISS-HT produced from pilot scale fermentation. Lane 1: Protein marker; Lane 2: Culture supernatant; Lane 3: 60% ammonium sulfate precipitation of culture supernatant; Lane 4: nickel affinity chromatography flow-through; Lane 5: 10% ammonium sulfate precipitation. (all 10 µL samples).
Figure 11:
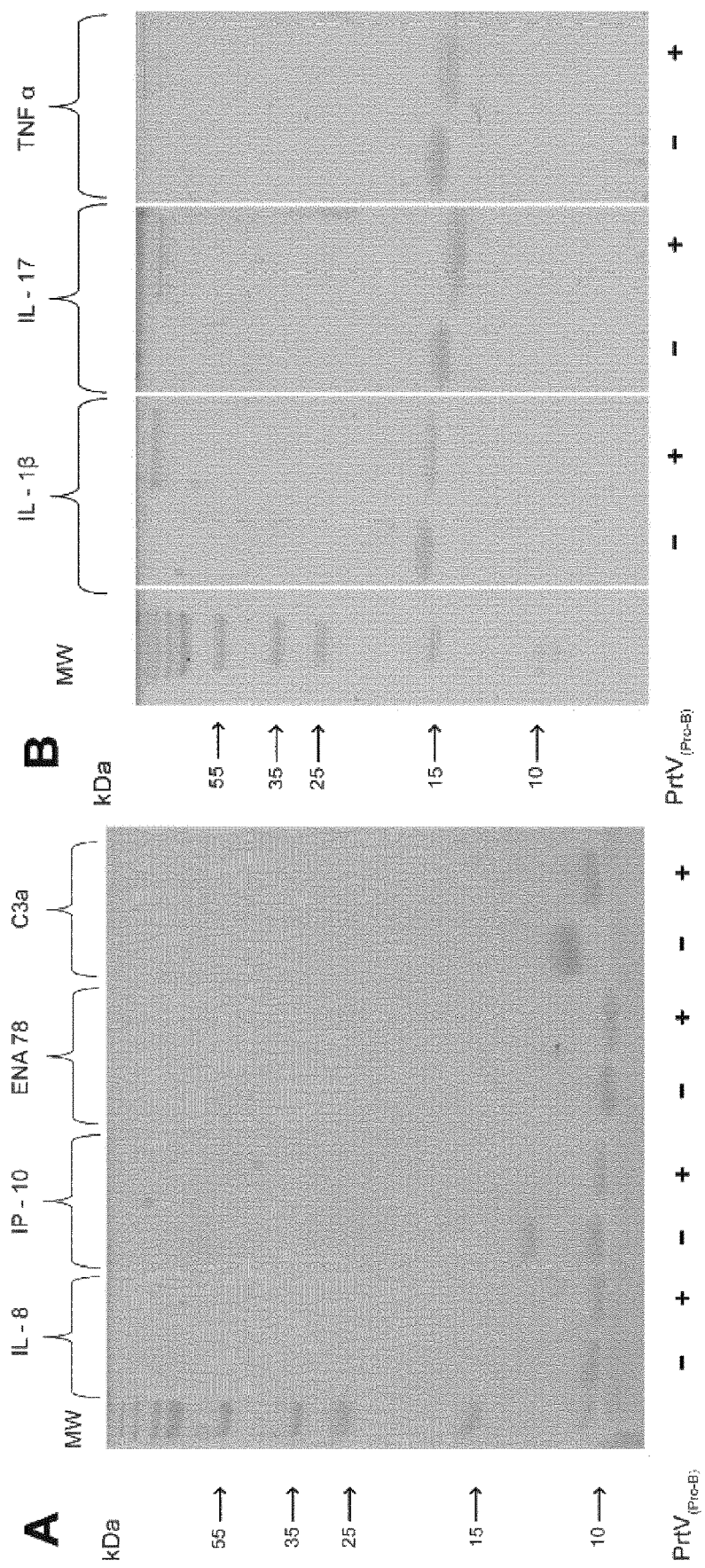
FIG. 11: Activity of recombinant PrtV against mediators (Panels A-C) and other proteins (Panels D and E).
Figure 11:
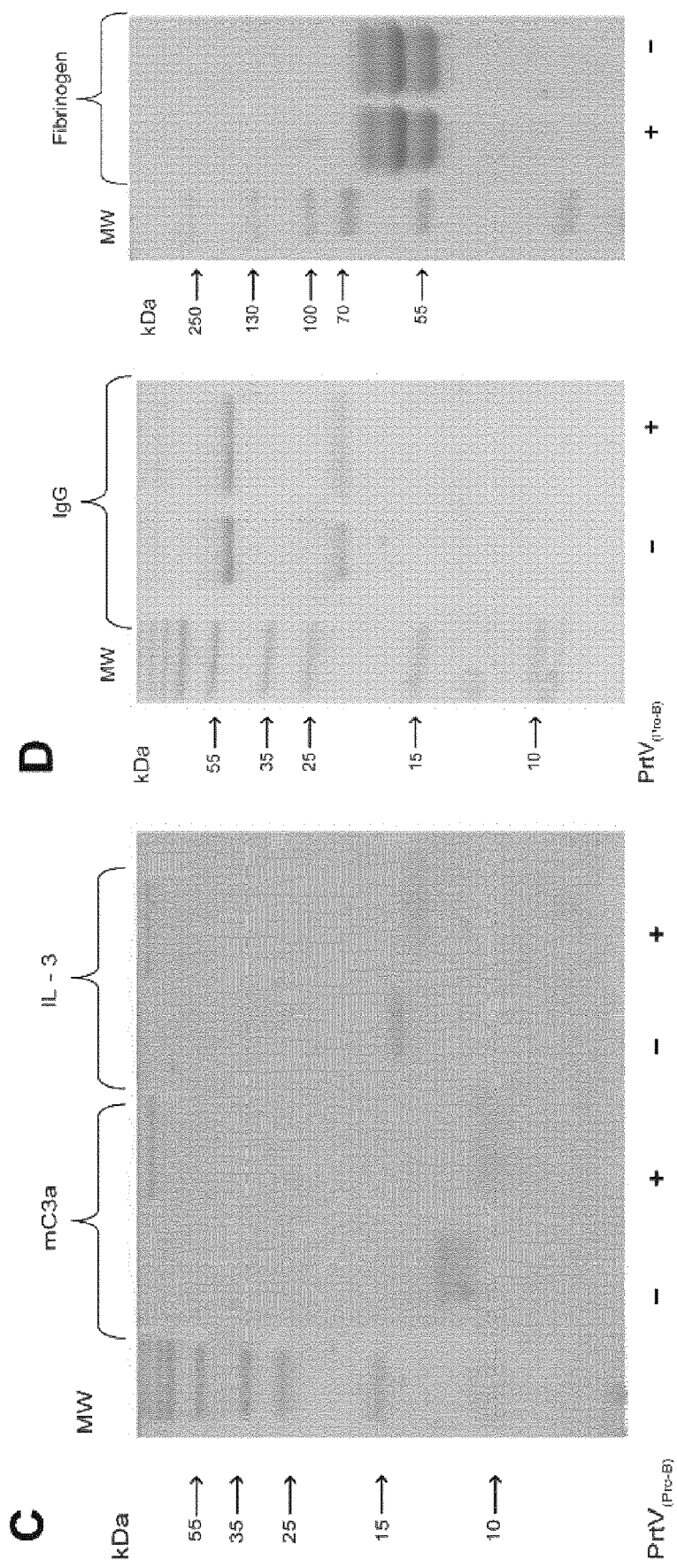
Figure 11:
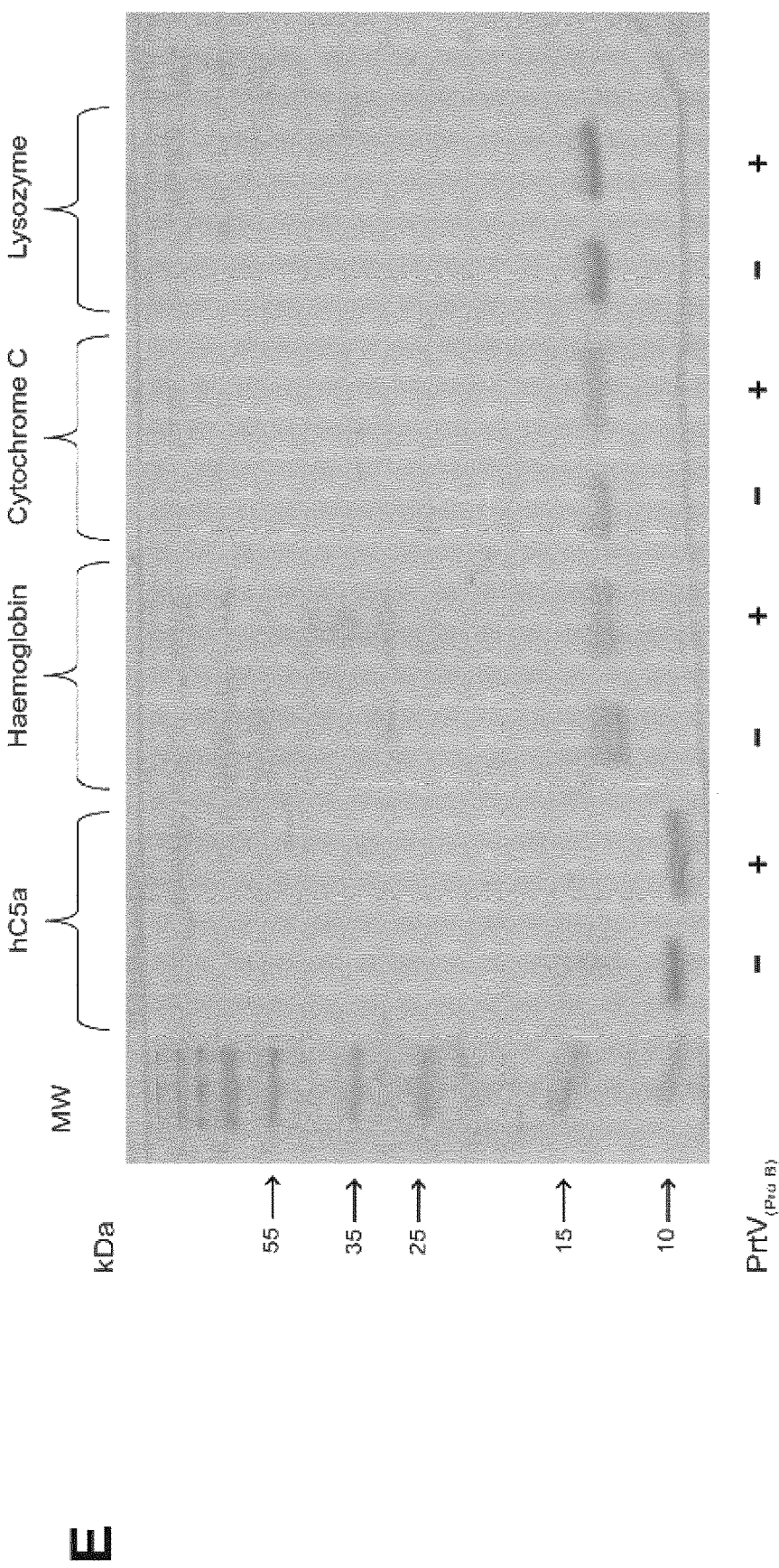
Figure 12:
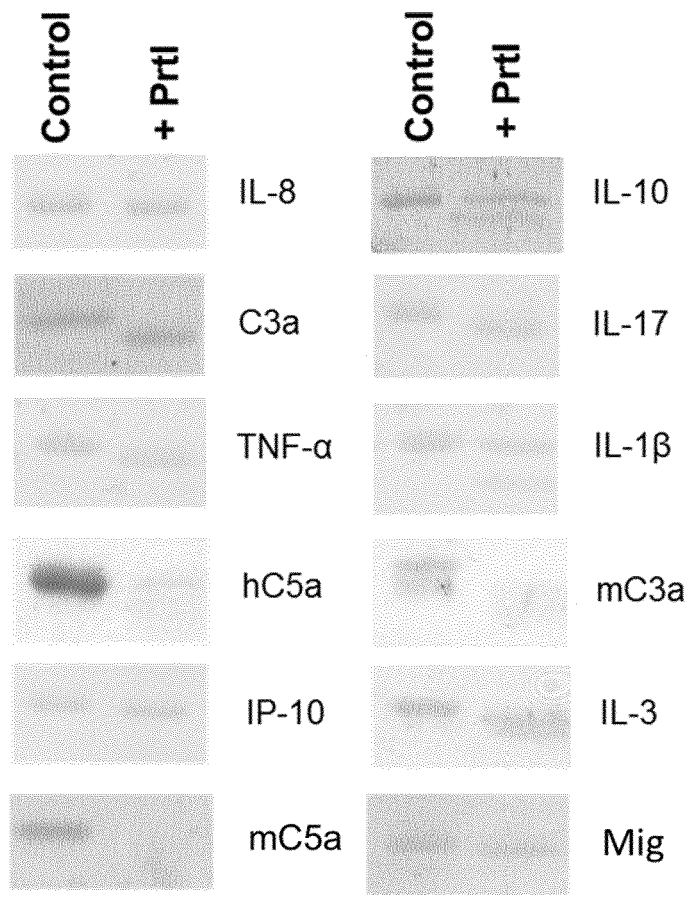
FIG. 12: Immune system mediator cleavage assays with PrtIProB.
Figure 13:
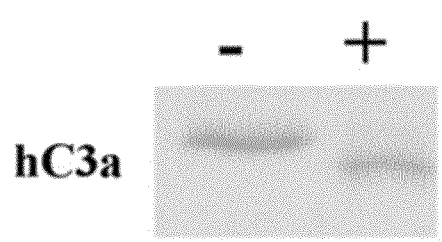
FIG. 13: Analysis of proteolytic degradation assay of PrtISS-HT ¬with hC3a. Samples of hC3a treated with (+) PrtISS-HT and a control hC3a (−) were analyzed by SDS-PAGE.
Figure 14:
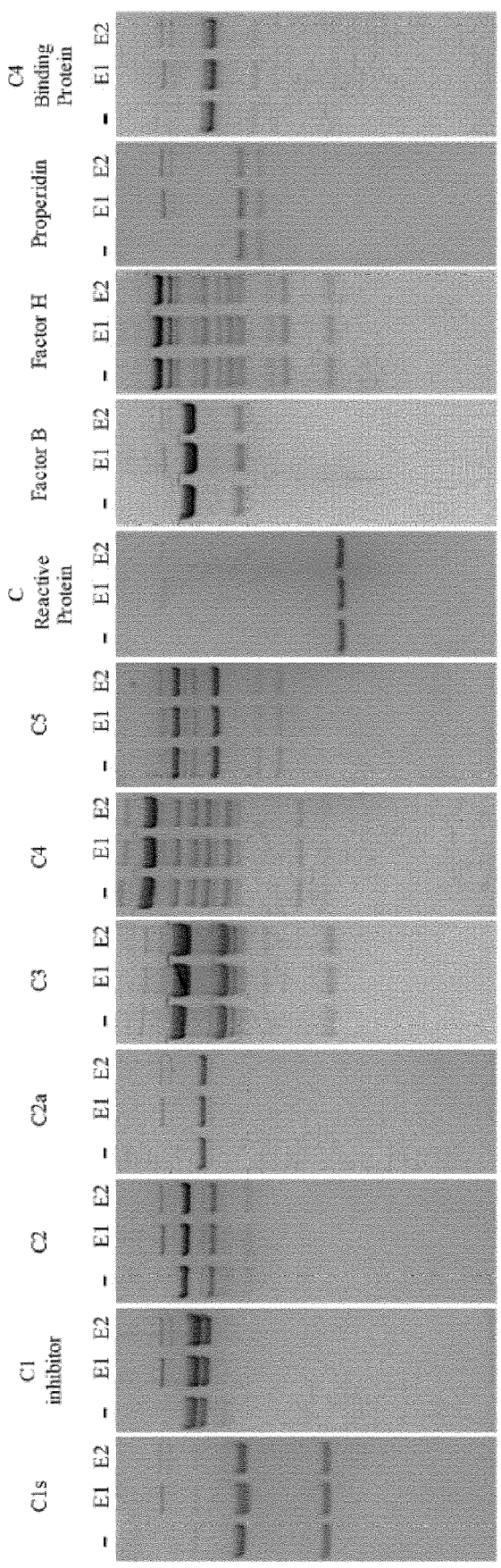
FIG. 14: Proteolytic activity of PrtV and PrtI against 12 human complement proteins.
Figure 15:
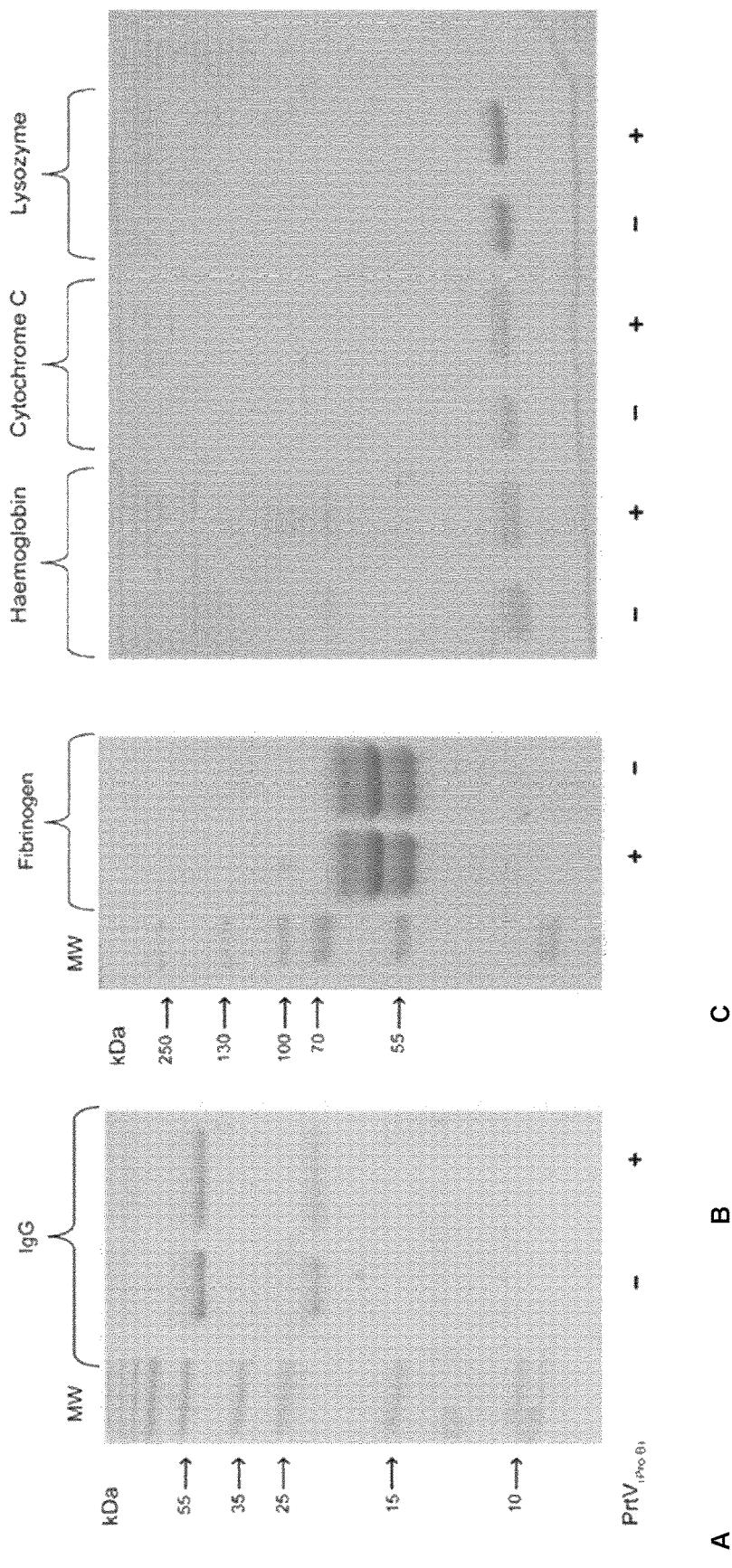
FIG. 15: Activity of PrtV against (A) IgG, (B) fibrinogen and (C) haemoglobin, cytochrome C and lysozyme.
Figure 16:
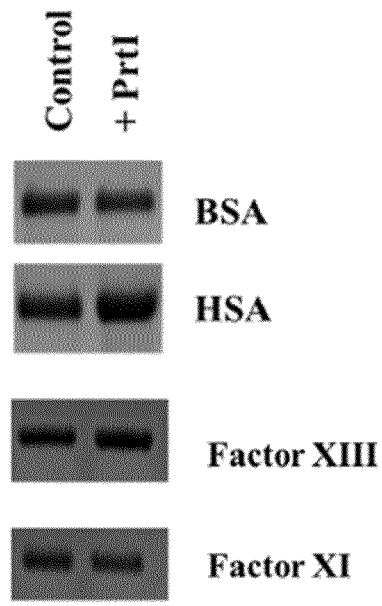
FIG. 16: Activity of PrtI against BSA, HAS, Factor XIII and Factor XI.
Figure 17:
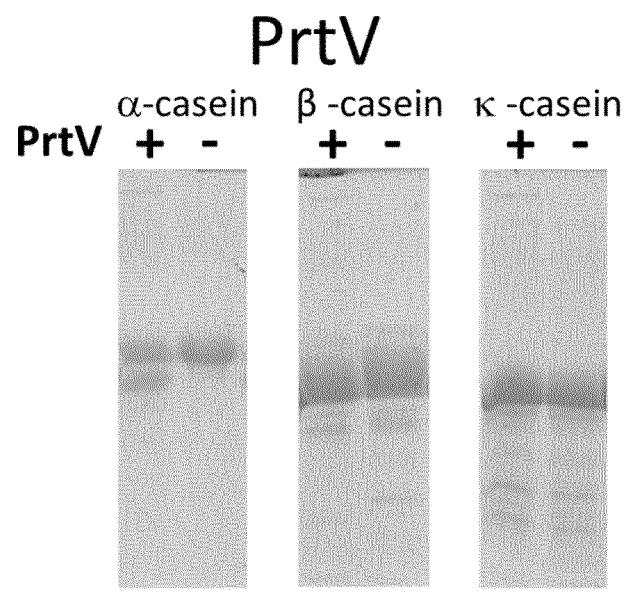
FIG. 17: Activity of PrtV against α-casein, β-casein and κ-caesin.
Figure 18:
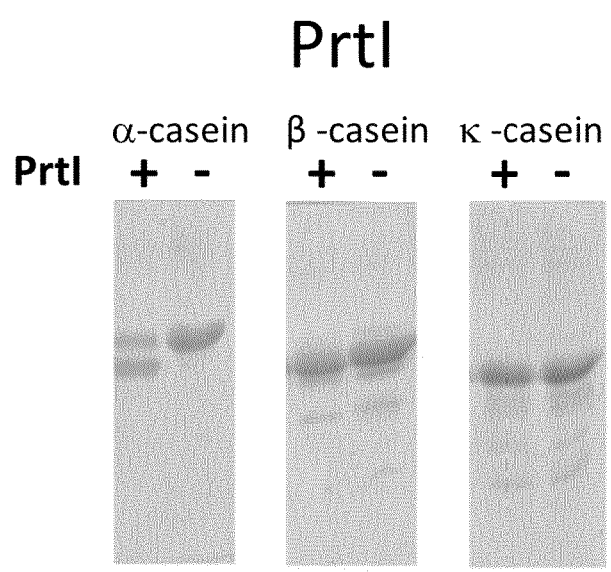
FIG. 18: Activity of PrtI against α-casein, β-casein and κ-caesin.

The enzyme is a multi-domain cell envelope (CEP) protease with polyvalent activity against pro-inflammatory mediators. There are 13 distinct groups of CEPs, see Tables 2 and 3 and FIG. 5. PrtV is a member of Group VIII and PrtI is a member of Group IX

TABLE 3

| Group | Species | Accession Number |
|---|---|---|
| Group I | | |
| | *Lactobacillus camelliae* | WP_056989736.1 |
| | *Leuconostoc pseudomesenteroides* | WP_084013705. |
| | *Leuconostoc pseudomesenteroides* | WP_004915726.1 |
| | *Lactobacillus zeae* | KRK11614.1 |
| | *Lactobacillus paracasei* subsp. *paracasei* | EPC16240 |
| | *Lactococcus lactis* subsp. *cremoris* | AFW92781.1 |
| | *Lactobacillus paracasei* | WP_016369108 |
| | *Lactobacillus rhamnosus* | WP_033572760 |
| | *Lactobacillus zeae* | WP_010492052 |
| | *Lactobacillus casei* 1 | WP_025012709. |
| Group II | | |
| | *Lactobacillus spicheri* | WP_052957116 |
| Group III | | |
| | *Lactobacillus hominis* | WP_008470760.1 |
| | *Lactobacillus johnsonii* | WP_011162614.1 |
| | *Lactobacillus taiwanensis* | WP_057718540.1 |
| | *Lactobacillus gallinarum* | WP_060472098.1 |
| | *Lactobacillus helveticus* | WP_052541115.1 |
| | *Lactobacillus helsingborgensis* | WP_046326482.1 |
| | *Lactobacillus* sp. wkB10 | WP_034978656 |
| | *Lactobacillus helveticus* | WP_023192360.1 |
| | *Lactobacillus helveticus* | AAD50643.1 |
| Group IV | | |
| | *Lactobacillus perolens* | WP_057819010.1 |
| | *Leuconostoc pseudomesenteroides* | WP_080519334.1 |
| | *Fructobacillus* sp. | WP_047974494.1 |
| | *Fructobacillus tropaeoli* | WP_083994293.1 |
| Group V | | |
| | *Carnobacterium maltaromaticum* | WP_057000053 |
| | *Carnobacterium gallinarum* | WP_084679918.1 |
| | *Enterococcus rotai* | ALS36471.1 |
| | *Carnobacterium divergens* | WP_051915581.1 |
| | *Enterococcus durans* | WP_016177430.1 |
| | *Lactobacillus ruminis* | WP_003695905.1 |
| | *Lactobacillus ruminis* | WP_046921068.1 |

TABLE 2

Domain organization of CEPs from *Lactobacillus* species

| Group | Pre/Pro | Cat | PA | Fn1 | Fn2 | Fn3 | Fn4 | Fn5 | B | H/S | Anchor |
|---|---|---|---|---|---|---|---|---|---|---|---|
| I | ✓ | ✓ | ✓ | ✓ | ✓ | ✓ | ✓ | X | ✓ | H | L |
| II | ✓ | ✓ | ✓ | ✓ | ✓ | ✓ | ✓ | X | ✓ | X | T |
| III | ✓ | ✓ | ✓ | ✓ | ✓ | ✓ | ✓ | X | ✓ | H | SL |
| IV | ✓ | ✓ | ✓ | ✓ | ✓ | ✓ | X | X | ✓ | X | T |
| V | ✓ | ✓ | ✓ | ✓ | ✓ | ✓ | ✓ | X | ✓ | X | L |
| VI | ✓ | ✓ | ✓ | ✓ | ✓ | ✓ | ✓ | X | ✓ | S | SL |
| VII | ✓ | ✓ | ✓ | ✓ | ✓ | ✓ | X | ✓ | ✓ | X | L |
| VIII | ✓ | ✓ | X | ✓ | ✓ | ✓ | ✓ | ✓ | ✓ | X | L |
| IX | ✓ | ✓ | X | ✓ | ✓ | ✓ | ✓ | ✓ | ✓ | X | SL |
| X | ✓ | ✓ | X | ✓ | ✓ | ✓ | X | ✓ | ✓ | X | T |
| XI | ✓ | ✓ | X | ✓ | ✓ | ✓ | X | X | ✓ | X | T |
| XII | ✓ | ✓ | X | ✓ | ✓ | ✓ | X | ✓ | ✓ | S | L |
| XIII | ✓ | ✓ | X | ✓ | ✓ | ✓ | X | ✓ | ✓ | S | L |

L—LPxTG
SL—Slayer
T—Truncated
H—Helical
S—Spacer
✓—Present
X—Absent

TABLE 3-continued

| Group | Species | Accession Number |
|---|---|---|
| Group VI | | |
| | Lactobacillus delbrueckii subsp. jakobsenii | EOD02935.1 |
| | Lactobacillus delbrueckii | WP_013439633.1 |
| | Lactobacillus delbrueckii subsp. lactis | CTQ87265.1 |
| | Lactobacillus delbrueckii | WP_052933674 |
| | Lactobacillus delbrueckii | WP_003614221.1 |
| | Lactobacillus delbrueckii subsp. bulgaricus | CTQ87266.1 |
| | Lactobacillus equicursoris | WP_008459526.1 |
| Group VII | | |
| | Lactobacillus camelliae | WP_056989555.1 |
| | Lactobacillus nasuensis | KRK70542 |
| Group VIII | | |
| | Lactobacillus collinoides | WP_056997102.1 |
| | Pediococcus ethanolidurans | KRN83580.1 |
| | Pediococcus cellicola | WP_057752355.1 |
| | Lactobacillus salivarius | WP_003708716.1 |
| | Lactobacillus equi | WP_023860239.1 |
| | Lactobacillus murinus | KRM78109.1 |
| | Lactobacillus animalis | WP_035448767.1 |
| | Lactobacillus apodemi | WP_056957221.1 |
| Group IX | | |
| | Lactobacillus kefiranofaciens | WP_013851245 |
| | Lactobacillus kefiranofaciens subsp. Kefiranofaciens | KRM20081.1 |
| | Lactobacillus ultunensis | WP_007125317.1 |
| | Lactobacillus helveticus | WP_014918309.1 |
| | Lactobacillus acidophilus | WP_013641522.1 |
| | Lactobacillus crispatus | WP_005723347.1 |
| | Lactobacillus kalixensis | WP_057799681.1 |
| | Lactobacillus amylovorus | WP_013437327.1 |
| | Lactobacillus intestinalis | WP_057808721.1 |
| | Lactobacillus acidophilus | WP_003548280.1 |
| | Lactobacillus helveticus | WP_081037619.1 |
| | Lactobacillus helveticus | WP_023061801.1 |
| | Lactobacillus helveticus | WP_023191923.1 |
| | Lactobacillus gigeriorum | WP_008472212.1 |
| | Lactobacillus helveticus | AHI12354.1 |
| | Lactobacillus helveticus | WP_049773663 |
| Group X | | |
| | Lactobacillus dioliverans | KRL63207.1 |
| | Lactobacillus brevis | WP_003553465.1 |
| | Lactobacillus farraginis | WP_056984009 |
| | Lactobacillus dioliverans | WP_083484944.1 |
| Group XI | | |
| | Lactobacillus sunkii | KRK86450.1 |
| | Lactobacillus parakefiri | KRL75314.1 |
| | Lactobacillus parabuchneri | WP_057908990.1 |
| | Lactobacillus buchneri | WP_013728904.1 |
| | Lactobacillus parakefiri | WP_057963287.1 |
| | Lactobacillus otakiensis | WP_039932965 |
| | Lactobacillus parafarraginis | KRM43999.1 |
| Group XII | | |
| | Lactobacillus plantarum | WP_097555516.1 |
| | Lactobacillus plantarum | WP_015639769 |
| | Lactobacillus plantarum | WP_047674582 |
| | Lactobacillus pantheris | WP_056956752 |
| | Leuconostoc mesenteroides | WP_050895316 |
| | Leuconostoc mesenteroides | WP_048593168 |
| | Enterococcus faecium | WP_002330395 |
| | Lactobacillus plantarum | WP_041161890 |
| | Lactobacillus rhamnosus | WP_047675965.1 |
| | Lactobacillus casei | WP_047106937.1 |
| Group XIII | | |
| | Lactobacillus casei | WP_047106937.1 |
| | Lactobacillus paracasei | EPC96395.1 |
| | Lactobacillus casei | ADK17789.1 |
| | Lactobacillus paracasei subsp. paracasei | EEI69179.1 |
| | Lactobacillus paracasei subsp. paracasei | EPC16240 |
| | Lactobacillus paracasei | WP_016387385 |
| | Lactobacillus casei | WP_027111531 |
| | Lactobacillus casei | WP_003586893.1 |
| | Lactobacillus casei | WP_018041452 |
| | Lactobacillus casei | CCK21486.1 |
| | Lactobacillus casei | WP_003563491 |
| | Lactobacillus casei | WP_020751434.1 |

In an embodiment, the protease is a PrtV protease. In an embodiment, the protease is a PrtI enzyme. The protease of the invention have functional domain similarity. The enzymes differ in how they attached or anchor to a cell. PrtV is naturally anchored to the bacterial cell surface through an LPXTG-like motif, while PrtI is naturally anchored to the bacterial cell surface through an S-layer domain.

The proteases of the invention have a sequence identity of greater 47.3% and a sequence similarity of 59.2%.

PrtV versus PrtI (region Pro to end of B) Similarity: 70.9% Identity: 55.9% PrtV versus PrtI (full protein sequence) Similarity: 61.4% Identity: 48.1%

Data generated using BLOSUM50

In an embodiment of the invention, the protease is a PrtV protease. The amino acid sequence encoding this enzyme has 1530 amino acids. It has an estimated mass of 163.8 kDa. It originates from *Lactobacillus salivarius* JCM1046.

Figure 1:
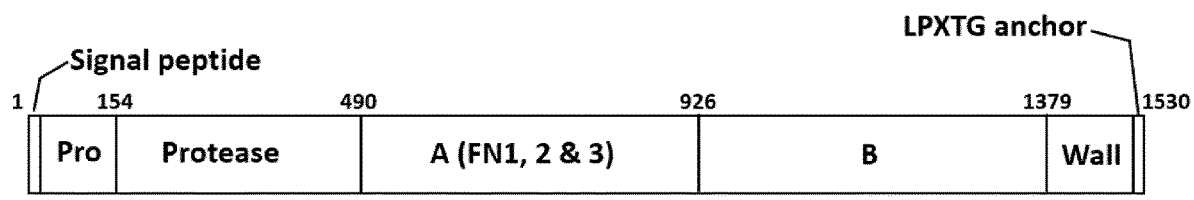
FIG. 1 illustrates the domain architecture of PrtV from *Lactobacillus salivarius* JCM1046. The enzyme comprises standard signal sequence (Signal Peptide) for membrane translocation, a propeptide domain (Pro), catalytic domain (Protease), A domain (A (FN1, 2 & 3)), B domain (B), wall spanning region (Wall) and sequences to anchor the enzyme to the bacterial cell surface (LPXTG anchor).

The domain architecture of PrtV is illustrated in FIG. 1. The protease comprises standard signal sequence (Signal Peptide) domain for membrane translocation, a propeptide domain (Pro), catalytic domain (Protease), A domain (A (FN1, 2 & 3)), B domain (B), wall spanning region (Wall) and sequences to anchor the enzyme to the bacterial cell surface (LPXTG anchor).

PrtV has activity against pro-inflammatory mediators selected from but not limited to the group comprising C3a, C5a, IL-1β, IL-3, IL-8, IP-10, ENA-78, C3a, IL-17, TNF-α, or combinations thereof.

The protease of the invention (PrtV) has a sequence comprising (or consisting of) SEQUENCE ID NO. 1.

SEQUENCE ID NO. 1 has the following sequence.

```
Protein sequence comprising the entire protease
protein
MEKLLGEKRRYKLYKAKSKWVVSAIITISGVTFLVTSPVSNAQADTVNG

SESVKTEATQASGSSVQDNATAKTTVTTNSNSSNNVSNVQTDTVKEAAT

SNVDSVASQNQATTAQQAKTTADTADQTVPPTTYKDHVKGNVQTAWDNG

YKGQGMVVAVIDSGADTNHKDFSKAPESPAISKEDADKKISELGYGKYA

SEKFPFVYNYASRDNNWVKDDGPDASEHGQHVAGIIGADGQPNGNERYA

VGVAPETQLMMMRVFNDQFADENTDDIAQAIYDAVKLGANVIQMSLGQG

VAAANLNDVEQKAVEYATQHGVFVSISASNNGNSASVTGEEVPYKPGGA

DGNFEPFSSSTVANPGASRNAMTVAAENSVVGAGDDMADFSSWGPLQDF

TLKPDVSAPGVSVTSTGNDNRYNTMSGTSMAGPFNAGVAALVMQRLKAT

TNLNGADLVQATKALIMNTAKPMTQQGYDTPVSPRRQGAGEIDAGAATE

SPVYVVAADGTSSVSLRKVGDSTQFALTFKNLSDKDQTYTFDDFGGGLT
```

EVRDADTGTFHDVYLAGAHVYGNKTVTVKAGQSATYNFTLSLTGLKENQ

LVEGWLRFVGNDGQNQLVVPYLAYYGDMTSEDVFDKAANQEGTVYGGNY

FVNEDNYPRGVADEDSLKALVNLEGNYNWQQVAKLYQDGKVAFSPNADG

KSDLLKPYAFVKQNLKDLKVEVLDKSGKVVRVVADEQGLDKSYYESGVN

KDVTLSVSMRNNPNTLAWDGKVYDDKAGEMVNAADGEYTYRYVATLYND

GVNKVQTADYPVVIDTTAPVLSNVKYDAATHTLSFDYKDTGSGFTDYSY

AVVKVNDKTFGYKLNDGKNSKFLDAAKTSGTFKAVLGSDTLAALTAAKN

ALSVAVSDVADNTSTVTLLVNGNNDATTKVSVWNATNGLELDQSSPDYQ

AATSTYNLRGNATSDFYYNGALVQVDNSGNFVVPVSTSDTAVVFTSDAA

GKNVVYKLNTATPKAVFAWQVNNTVKENFGIVLDTVVSNNKDDVVVQAA

VTKGDNVEAYARDYFTGAVYKADVKDGLATFHVKVTNNSGRTVLLGWTE

VVGPTFNDVQRTSANGVYLGVDTDTENPTPAPAFTSADQLGTNVVQEKA

DSATIGNPGDLPGHSLKDLTTRADANPDIHFDYLKDNDYNWVGAQAVKD

GVYNPSTQVFTLTGKVDPNVKSLVVLGDSYNEDDPVNKVNLNSDGTFSF

QFHTAPTSQRPVAYIYTKDDGSTTRGTMELILDTVLPTLSLNNVANLQL

DSNGDYQVYTNNKDFSVSGEATDNLDGYRFFFNGDNDYREFHNSGVNFV

AEAHQDGSTVTNPYPAYKFSKTFNLADATGETTHVYTLSVVDLTGNTVT

RKFYVHYQPASDTVKTVTTDKDGATKVLVDYNNNTLQVKDNTGNWVNAT

AGVEAAKNYRVVNEYGNVVLLLNVLADKEQDNNKVQVNEVTNNKVEQTV

VTKTVSNKSVAKVGKKAAEPVKVLPQTGENNSKSTSVLGAVLASIAGFL

GALGLRRVKKD

The current invention provides a nucleotide sequence comprising (or consisting of) SEQUENCE ID NO. 2.
SEQUENCE ID NO. 2 has the following sequence.

```
DNA sequence comprising the entire protease gene
locus
>gb|CP007647.1|:74529-79118 Lactobacillus
salivarius strain JCM 1046 plasmid pMP1046A, Cell
Envelope Protease
ATGGAAAAGTTGCTAGGTGAAAAACGCCGCTACAAGCTTTATAAAGCTA

AATCTAAGTGGGTGGTGTCAGCGATTATTACTATTTCTGGAGTTACATT

TTTAGTGACAAGTCCAGTTTCTAACGCTCAAGCCGATACCGTTAATGGT

AGTGAAAGTGTAAAAACAGAAGCTACTCAGGCATCAGGTTCGAGTGTGC

AGGATAATGCGACAGCTAAAACAACTGTTACAACCAATAGTAATAGTTC

TAACAATGTTTCTAATGTTCAAACTGATACCGTAAAAGAAGCAGCAACG

AGCAATGTTGATTCAGTAGCTAGTCAAAATCAAGCTACAACAGCTCAAC

AGGCTAAAACTACTGCTGATACTGCTGATCAGACAGTACCACCAACAAC

CTATAAAGATCATGTCAAAGGAAATGTTCAAACTGCATGGGATAATGGC

TATAAAGGACAAGGTATGGTGGTTGCTGTTATTGATTCTGGTGCTGATA

CAAACCATAAAGATTTCTCTAAAGCTCCTGAATCTCCAGCAATTTCTAA

GGAAGATGCTGACAAGAAGATTAGCGAGCTAGGCTACGGGAAATATGCT

TCAGAGAAATTCCCATTCGTATATAATTATGCGAGTCGTGACAACAACT

GGGTTAAAGATGATGGCCCAGATGCATCAGAACACGGTCAACACGTTGC

TGGTATCATTGGTGCTGACGGCCAACCAAATGGCAATGAACGCTATGCA

GTAGGGGTAGCACCTGAAACACAGTTAATGATGATGCGAGTATTTAATG

ATCAATTTGCTGATGAAAATACTGATGATATTGCTCAAGCAATTTATGA

CGCAGTTAAATTAGGTGCTAATGTAATTCAAATGTCCTTAGGTCAAGGC

GTCGCAGCTGCTAATTTGAATGATGTAGAGCAGAAAGCGGTTGAATATG

CAACTCAACATGGTGTGTTCGTCTCCATTTCAGCTTCTAACAATGGTAA

TTCGGCAAGTGTTACTGGTGAAGAAGTTCCTTATAAACCAGGTGGAGCA

GATGGAAACTTTGAACCATTCTCTAGTAGTACGGTAGCTAATCCAGGTG

CATCGCGCAATGCAATGACAGTTGCAGCTGAAAACTCGGTTGTAGGTGC

TGGTGATGACATGGCAGACTTCTCTTCTTGGGGTCCTTTACAAGATTTC

ACTTTGAAACCAGATGTATCAGCTCCTGGGGTTAGTGTAACTTCAACAG

GGAACGATAATCGTTACAATACTATGAGTGGAACTTCTATGGCTGGTCC

ATTTAACGCTGGGGTTGCAGCTTTAGTAATGCAAAGATTAAAAGCTACT

ACTAACTTAAATGGAGCAGATTTAGTTCAAGCTACTAAAGCTTTAATCA

TGAATACAGCTAAACCAATGACGCAACAAGGATATGACACTCCAGTTTC

TCCTAGACGTCAAGGTGCTGGTGAAATTGATGCAGGTGCTGCAACAGAA

TCTCCAGTATATGTTGTGGCAGCAGACGGCACAAGTTCTGTATCTTTGA

GAAAAGTTGGAGATTCAACTCAATTCGCACTAACGTTTAAGAACTTATC

CGATAAAGATCAAACATATACTTTTGATGATTTTGGTGGTGGATTAACT

GAAGTGCGCGATGCCGATACAGGAACTTTCCACGATGTTTATCTGGCAG

GAGCACATGTCTATGGAAATAAGACAGTAACCGTTAAAGCTGGACAAAG

CGCAACTTATAATTTCACATTATCTTTAACAGGTTTGAAAGAAAATCAA

TTAGTTGAAGGTTGGTTGAGATTTGTAGGAAATGATGGTCAAAATCAAT

TAGTAGTTCCATATCTCGCATATTATGGTGATATGACAAGTGAAGATGT

ATTTGACAAAGCTGCTAATCAAGAAGGCACAGTCTATGGTGGTAACTAC

TTTGTTAATGAAGATAACTATCCAAGAGGGGTAGCTGATGAAGATTCCT

TAAAGGCTTTAGTAAATCTTGAAGGTAATTATAATTGGCAACAAGTTGC

TAAATTATACCAAGATGGAAAAGTTGCATTCTCACCAAATGCTGACGGT

AAGAGTGACTTATTAAAACCATATGCCTTTGTTAAACAAAATCTAAAGG

ATCTTAAAGTTGAAGTATTAGATAAGAGTGGAAAAGTTGTTCGTGTAGT

TGCAGATGAACAAGGTCTGGATAAGTCTTACTATGAAAGTGGAGTTAAT

AAAGACGTAACTTTATCAGTTTCAATGCGTAATAATCCAAATACTTTGG

CTTGGGATGGAAAAGTATACGATGATAAGGCCGGTGAAATGGTAAATGC

AGCAGATGGTGAATATACATATCGTTATGTTGCTACTTTGTATAATGAT

GGTGTAAATAAGGTTCAAACAGCTGATTATCCAGTAGTTATCGACACAA

CAGCTCCAGTATTATCAAATGTTAAGTATGATGCTGCAACACATACTTT

AAGCTTTGATTATAAAGATACAGGATCTGGCTTTACAGATTATTCTTAT

GCAGTAGTTAAAGTTAATGATAAGACATTTGGCTATAAGTTAAATGATG

GCAAGAATTCGAAGTTCTTAGATGCAGCTAAAACATCAGGAACATTTAA

AGCCGTATTAGGTAGTGATACTTTAGCAGCACTTACTGCAGCTAAGAAT
```

```
GCTTTATCAGTTGCAGTTAGCGATGTAGCTGATAATACTTCAACAGTAA

CCTTACTGGTAAATGGAAATAATGATGCAACAACTAAAGTATCTGTTTG

GAATGCAACTAATGGATTAGAACTCGATCAAAGTTCCCCAGATTATCAA

GCAGCAACTTCAACTTATAACTTACGTGGGAATGCAACATCTGATTTCT

ATTACAATGGTGCATTAGTTCAAGTTGATAACAGTGGTAATTTTGTGGT

TCCTGTAAGTACAAGTGATACTGCGGTTGTCTTCACATCAGATGCAGCT

GGTAAGAATGTAGTATATAAATTGAATACAGCAACTCCAAAGGCTGTTT

TTGCATGGCAAGTAAATAATACTGTTAAGGAAAACTTTGGTATTGTTTT

AGATACAGTCGTAAGCAACAACAAGGATGATGTAGTCGTACAAGCAGCG

GTTACTAAGGGGGATAATGTTGAAGCTTATGCACGCGACTACTTCACAG

GTGCAGTATATAAAGCAGATGTAAAAGATGGATTAGCAACTTTCCACGT

AAAAGTAACTAATAATAGTGGTAGAACTGTATTATTAGGATGGACAGAA

GTTGTAGGACCAACATTTAATGATGTTCAAAGAACTTCTGCAAATGGTG

TTTATTTGGGTGTTGATACAGATACAGAGAATCCTACGCCAGCACCAGC

CTTTACAAGTGCTGACCAATTAGGAACAAATGTTGTTCAAGAAAAAGCT

GATTCTGCTACAATTGGTAATCCAGGAGATTTGCCAGGACACAGTCTAA

AGGACCTAACAACACGTGCAGATGCTAACCCAGATATCCACTTTGACTA

CTTGAAAGATAATGATTACAACTGGGTAGGAGCGCAAGCTGTTAAAGAT

GGTGTATATAATCCATCAACACAAGTATTTACTTTAACAGGTAAGGTTG

ATCCAAATGTTAAATCATTGGTGGTATTGGGAGATAGTTACAATGAAGA

TGATCCTGTAAATAAGGTTAACTTAAATAGTGATGGAACATTTAGTTTC

CAATTCCATACAGCACCAACTTCACAAAGACCTGTTGCTTACATCTATA

CAAAAGATGATGGTTCAACAACTAGAGGTACAATGGAGTTAATCTTAGA

TACAGTTCTTCCAACACTTAGCTTAAATAATGTGGCTAATTTACAACTG

GATAGTAATGGTGATTACCAAGTCTACACTAATAATAAAGACTTTAGTG

TATCTGGAGAAGCTACTGATAATTTGGACGGATATCGTTTCTTCTTCAA

TGGAGATAATGATTATCGTGAATTCCACAATTCTGGTGTGAACTTTGTT

GCTGAAGCTCATCAAGATGAAGTACAGTGACTAATCCATATCCAGCAT

ACAAGTTTAGTAAGACATTTAACTTAGCTGATGCAACTGGCGAAACAAC

ACATGTATATACATTGAGTGTAGTTGACTTGACAGGTAATACTGTAACT

AGGAAGTTCTATGTTCACTATCAACCAGCTAGTGATACAGTTAAGACTG

TAACAACTGATAAAGATGGTGCAACCAAAGTTCTAGTAGATTACAATAA

CAATACACTACAAGTAAAAGATAATACTGGTAACTGGGTAAATGCTACT

GCTGGAGTTGAAGCTGCTAAGAATTATCGAGTAGTTAATGAATATGGTA

ATGTGGTATTGTTACTAAATGTTCTTGCAGATAAAGAACAAGACAATAA

TAAAGTACAAGTTAATGAAGTTACAAATAATAAAGTAGAACAAACAGTA

GTAACTAAGACTGTTTCAAATAAATCTGTAGCTAAAGTGGGCAAAAAAG

CTGCAGAACCAGTAAAAGTATTACCACAAACTGGTGAAAATAACAGTAA

ATCTACTTCTGTTCTAGGTGCAGTCTTAGCCTCAATCGCAGGATTCTTA

GGTGCATTAGGCTTAAGACGTGTTAAAAAAGAT
```

The invention also provides a fragment of PrtyV protease comprising the propeptide to the end of the B domain of the PrtV protease. This sequence is provided as SEQUENCE ID NO. 3.

SEQUENCE ID NO. 3 has the following sequence.

```
DTVNGSESVKTEATQASGSSVQDNATAKTTVTTNSNSSNNVSNVQTDTV
KEAATSNVDSVASQNQATTAQQAKTTADTADQTVPPTTYKDHVKGNVQT
AWDNGYKGQGMVVAVIDSGADTNHKDFSKAPESPAISKEDADKKISELG
YGKYASEKFPFVYNYASRDNNWVKDDGPDASEHGQHVAGIIGADGQPNG
NERYAVGVAPETQLMMMRVFNDQFADENTDDIAQAIYDAVKLGANVIQM
SLGQGVAAANLNDVEQKAVEYATQHGVFVSISASNNGNSASVTGEEVPY
KPGGADGNFEPFSSSTVANPGASRNAMTVAAENSVVGAGDDMADFSSWG
PLQDFTLKPDVSAPGVSVTSTGNDNRYNTMSGTSMAGPFNAGVAALVMQ
RLKATTNLNGADLVQATKALIMNTAKPMTQQGYDTPVSPRRQGAGEIDA
GAATESPVYVVAADGTSSVSLRKVGDSTQFALTFKNLSDKDQTYTFDDF
GGGLTEVRDADTGTFHDVYLAGAHVYGNKTVTVKAGQSATYNFTLSLTG
LKENQLVEGWLRFVGNDGQNQLVVPYLAYYGDMTSEDVFDKAANQEGTV
YGGNYFVNEDNYPRGVADEDSLKALVNLEGNYNWQQVAKLYQDGKVAFS
PNADGKSDLLKPYAFVKQNLKDLKVEVLDKSGKVVRVVADEQGLDKSYY
ESGVNKDVTLSVSMRNNPNTLAWDGKVYDDKAGEMVNAADGEYTYRYVA
TLYNDGVNKVQTADYPVVIDTTAPVLSNVKYDAATHTLSFDYKDTGSGF
TDYSYAVVKVNDKTFGYKLNDGKNSKFLDAAKTSGTFKAVLGSDTLAAL
TAAKNALSVAVSDVADNTSTVTLLVNGNNDATTKVSVWNATNGLELDQS
SPDYQAATSTYNLRGNATSDFYYNGALVQVDNSGNFVVPVSISDTAVVF
TSDAAGKNVVYKLNTATPKAVFAWQVNNTVKENFGIVLDTVVSNNKDDV
VVQAAVTKGDNVEAYARDYFTGAVYKADVKDGLATFHVKVTNNSGRTVL
LGWTEVVGPTFNDVQRTSANGVYLGVDTDTENPTPAPAFTSADQLGTNV
VQEKADSATIGNPGDLPGHSLKDLTTRADANPDIHFDYLKDNDYNWVGA
QAVKDGVYNPSTQVFTLTGKVDPNVKSLVVLGDSYNEDDPVNKVNLNSD
GTFSFQFHTAPTSQRPVAYIYTKDDGSTTRGTMELILDTVLPTLSLNNV
ANLQLDSNGDYQVYTNNKDFSVSGEATDNLDGYRFFFNGDNDYREFHNS
GVNFVAEAHQDGSTVTNPYPAYKFSKTFNLADATGETTHVYTLSVVDLT
GNTVTRKFYVHY
```

The invention also provides a nucleotide sequence encoding the protease of SEQ ID 3. This nucleotide sequence is provided as SEQUENCE ID NO. 4.

SEQUENCE ID NO. 4 has the following sequence.

```
GATACCGTTAATGGTAGTGAAAGTGTAAAAACAGAAGCTACTCAGGCA
TCAGGTTCGAGTGTGCAGGATAATGCGACAGCTAAAACAACTGTTACAA
CCAATAGTAATAGTTCTAACAATGTTTCTAATGTTCAAACTGATACCGT
AAAAGAAGCAGCAACGAGCAATGTTGATTCAGTAGCTAGTCAAAATCAA
GCTACAACAGCTCAACAGGCTAAAACTACTGCTGATACTGCTGATCAGA
```

```
CAGTACCACCAACAACCTATAAAGATCATGTCAAAGGAAATGTTCAAAC
TGCATGGGATAATGGCTATAAAGGACAAGGTATGGTGGTTGCTGTTATT
GATTCTGGTGCTGATACAAACCATAAAGATTTCTCTAAAGCTCCTGAAT
CTCCAGCAATTTCTAAGGAAGATGCTGACAAGAAGATTAGCGAGCTAGG
CTACGGGAAATATGCTTCAGAGAAATTCCCATTCGTATATAATTATGCG
AGTCGTGACAACAACTGGGTTAAAGATGATGGCCCAGATGCATCAGAAC
ACGGTCAACACGTTGCTGGTATCATTGGTGCTGACGGCCAACCAAATGG
CAATGAACGCTATGCAGTAGGGGTAGCACCTGAAACACAGTTAATGATG
ATGCGAGTATTTAATGATCAATTTGCTGATGAAAATACTGATGATATTG
CTCAAGCAATTTATGACGCAGTTAAATTAGGTGCTAATGTAATTCAAAT
GTCCTTAGGTCAAGGCGTCGCAGCTGCTAATTTGAATGATGTAGAGCAG
AAAGCGGTTGAATATGCAACTCAACATGGTGTGTTCGTCTCCATTTCAG
CTTCTAACAATGGTAATTCGGCAAGTGTTACTGGTGAAGAAGTTCCTTA
TAAACCAGGTGGAGCAGATGGAAACTTTGAACCATTCTCTAGTAGTACG
GTAGCTAATCCAGGTGCATCGCGCAATGCAATGACAGTTGCAGCTGAAA
ACTCGGTTGTAGGTGCTGGTGATGACATGGCAGACTTCTCTTCTTGGGG
TCCTTTACAAGATTTCACTTTGAAACCAGATGTATCAGCTCCTGGGGTT
AGTGTAACTTCAACAGGGAACGATAATCGTTACAATACTATGAGTGGAA
CTTCTATGGCTGGTCCATTTAACGCTGGGGTTGCAGCTTTAGTAATGCA
AAGATTAAAAGCTACTACTAACTTAAATGGAGCAGATTTAGTTCAAGCT
ACTAAAGCTTTAATCATGAATACAGCTAAACCAATGACGCAACAAGGAT
ATGACACTCCAGTTTCTCCTAGACGTCAAGGTGCTGGTGAAATTGATGC
AGGTGCTGCAACAGAATCTCCAGTATATGTTGTGGCAGCAGACGGCACA
AGTTCTGTATCTTTGAGAAAAGTTGGAGATTCAACTCAATTCGCACTAA
CGTTTAAGAACTTATCCGATAAAGATCAAACATATACTTTTGATGATTT
TGGTGGTGGATTAACTGAAGTGCGCGATGCCGATACAGGAACTTTCCAC
GATGTTTATCTGGCAGGAGCACATGTCTATGGAAATAAGACAGTAACCG
TTAAAGCTGGACAAAGCGCAACTTATAATTTCACATTATCTTTAACAGG
TTTGAAAGAAAATCAATTAGTTGAAGGTTGGTTGAGATTTGTAGGAAAT
GATGGTCAAAATCAATTAGTAGTTCCATATCTCGCATATTATGGTGATA
TGACAAGTGAAGATGTATTTGACAAAGCTGCTAATCAAGAAGGCACAGT
CTATGGTGGTAACTACTTTGTTAATGAAGATAACTATCCAAGAGGGGTA
GCTGATGAAGATTCCTTAAAGGCTTTAGTAAATCTTGAAGGTAATTATA
ATTGGCAACAAGTTGCTAAATTATACCAAGATGGAAAAGTTGCATTCTC
ACCAAATGCTGACGGTAAGAGTGACTTATTAAAACCATATGCCTTTGTT
AAACAAAATCTAAAGGATCTTAAAGTTGAAGTATTAGATAAGAGTGGAA
AAGTTGTTCGTGTAGTTGCAGATGAACAAGGTCTGGATAAGTCTTACTA
TGAAAGTGGAGTTAATAAAGACGTAACTTTATCAGTTTCAATGCGTAAT
AATCCAAATACTTTGGCTTGGGATGGAAAAGTATACGATGATAAGGCCG
GTGAAATGGTAAATGCAGCAGATGGTGAATATACATATCGTTATGTTGC
TACTTTGTATAATGATGGTGTAAATAAGGTTCAAACAGCTGATTATCCA
GTAGTTATCGACACAACAGCTCCAGTATTATCAAATGTTAAGTATGATG
CTGCAACACATACTTTAAGCTTTGATTATAAAGATACAGGATCTGGCTT
TACAGATTATTCTTATGCAGTAGTTAAAGTTAATGATAAGACATTTGGC
TATAAGTTAAATGATGGCAAGAATTCGAAGTTCTTAGATGCAGCTAAAA
CATCAGGAACATTTAAAGCCGTATTAGGTAGTGATACTTTAGCAGCACT
TACTGCAGCTAAGAATGCTTTATCAGTTGCAGTTAGCGATGTAGCTGAT
AATACTTCAACAGTAACCTTACTGGTAAATGGAAATAATGATGCAACAA
CTAAAGTATCTGTTTGGAATGCAACTAATGGATTAGAACTCGATCAAAG
TTCCCCAGATTATCAAGCAGCAACTTCAACTTATAACTTACGTGGGAAT
GCAACATCTGATTTCTATTACAATGGTGCATTAGTTCAAGTTGATAACA
GTGGTAATTTTGTGGTTCCTGTAAGTACAAGTGATACTGCGGTTGTCTT
CACATCAGATGCAGCTGGTAAGAATGTAGTATATAAATTGAATACAGCA
ACTCCAAAGGCTGTTTTTGCATGGCAAGTAAATAATACTGTTAAGGAAA
ACTTTGGTATTGTTTTAGATACAGTCGTAAGCAACAACAAGGATGATGT
AGTCGTACAAGCAGCGGTTACTAAGGGGGATAATGTTGAAGCTTATGCA
CGCGACTACTTCACAGGTGCAGTATATAAAGCAGATGTAAAAGATGGAT
TAGCAACTTTCCACGTAAAAGTAACTAATAATAGTGGTAGAACTGTATT
ATTAGGATGGACAGAAGTTGTAGGACCAACATTTAATGATGTTCAAAGA
ACTTCTGCAAATGGTGTTTATTTGGGTGTTGATACAGATACAGAGAATC
CTACGCCAGCACCAGCCTTTACAAGTGCTGACCAATTAGGAACAAATGT
TGTTCAAGAAAAAGCTGATTCTGCTACAATTGGTAATCCAGGAGATTTG
CCAGGACACAGTCTAAAGGACCTAACAACACGTGCAGATGCTAACCCAG
ATATCCACTTTGACTACTTGAAAGATAATGATTACAACTGGGTAGGAGC
GCAAGCTGTTAAAGATGGTGTATATAATCCATCAACACAAGTATTTACT
TTAACAGGTAAGGTTGATCCAAATGTTAAATCATTGGTGGTATTGGGAG
ATAGTTACAATGAAGATGATCCTGTAAATAAGGTTAACTTAAATAGTGA
TGGAACATTTAGTTTCCAATTCCATACAGCACCAACTTCACAAAGACCT
GTTGCTTACATCTATACAAAAGATGATGGTTCAACAACTAGAGGTACAA
TGGAGTTAATCTTAGATACAGTTCTTCCAACACTTAGCTTAAATAATGT
GGCTAATTTACAACTGGATAGTAATGGTGATTACCAAGTCTACACTAAT
AATAAAGACTTTAGTGTATCTGGAGAAGCTACTGATAATTTGGACGGAT
ATCGTTTCTTCTTCAATGGAGATAATGATTATCGTGAATTCCACAATTC
TGGTGTGAACTTTGTTGCTGAAGCTCATCAAGATGGAAGTACAGTGACT
AATCCATATCCAGCATACAAGTTTAGTAAGACATTTAACTTAGCTGATG
CAACTGGCGAAACAACACATGTATATACATTGAGTGTAGTTGACTTGAC
AGGTAATACTGTAACTAGGAAGTTCTATGTTCACTAT
```

In an embodiment, the protease of the invention is the PrtI enzyme. The amino acid sequence encoding this enzyme is 1698 amino acids in length. It is a multi-domain cell envelope protease (CEP). It has an estimated mass of 185.8 kDa. It originates from *Lactobacillus intestinalis* DSM6629.

Figure 2:
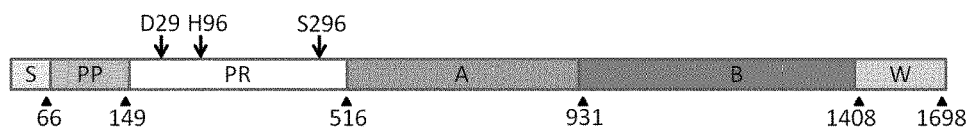
FIG. 2 illustrates the domain architecture of PrtV from *Lactobacillus salivarius* JCM1046.

The domain architecture of PrtI is illustrated in FIG. 2. The protease comprises standard signal sequence (S) for membrane translocation, a propeptide domain (PP), catalytic domain (PR), A domain (A), B domain (B), and wall spanning region (W).

PrtI has activity against pro-inflammatory mediators selected from, but not limited to, the group comprising IL-8, C3a, TNF-α, C5a, IP-10, IL-10, IL-17, IL-1β, C3a and IL-3.

The enzyme of the invention has a sequence comprising (or consisting of) SEQUENCE ID NO. 5.

SEQUENCE ID NO. 5 has the following sequence.

```
Protein sequence comprising the entire protease
protein
>Lactobacillus_intestinalis_788_DSM_6629GL000788
MSDYSWPKSHNKYSYVFKTREGLNKIETQKRAKSVSDMRKKWVATAIIA

LASGSTVFLSQTSSVEAAIGETSVQNVKVSVAKNESDSQKFNNSQNLEQ

KTPQAAAANQNGSQVQNDHTETQLQNQQTTQSQVTQAHTEENNASSIPE

PANQADHVKGNVQSAWDQGYKGQNTVVAVIDSGADTSHKDFQTMPSNPK

LKQEDVQSKIDQQGYGKYVNEKFPYVYNYADRDNDYIKSDDNNQNDSPH

GQHVSGIIAADGHPEGDQQYVVGVAPEAQLMQLRVFGQFSDEKTDDVAR

AIYDATNLGADVIQMSLGQGVADQQLTNIEQKAVQYAIDHGVFVSISAS

NNGNSASVDNPSKVTAKGYGSGSEAGNYEPLNSGTVANPGASKNALTVA

AETSGTGKDSDMASFSSWGPLSDFSLKPDLSAPGYQVVSTVNDNQYQTM

SGTSMAGPFAAGSAALVIQRLKQTNPELKGAELVAATKALLMNSAKVQT

QNGYTTPVSPRRQGAGQIDVGAATANPVYVTAADGTSSLSLRQVDEKTT

FTLTFHNLTDQEQSYSFNDLGGGYTEQRDPDSGVFHEVQLAGAHVNGVG

NFTLAPKEVKDLQYTLDLQGLNKNQPVEGWLHFTNDKDKSTVVVPYLAY

YGDLTSENVFDQNANEEKPDIQGNRFVNENNYPLGVTDQESLKQLVNVD

SDYNWQEVAKLYESGKVAFSPNDDHQSDLIKPYAYLKQNVKDLKVEILD

AKGNVVRVVSDVQGVDKSYDESGVTKDASLSVSMRDNPDAFEWDGKVYD

TKTGQMVTAPDGQYTYRFVATLWNEGPNQKQTADFPVVVDTQAPSLSVK

YDSATHTLSGNYEDKGAGFTDYSYVTVQVNDKVFGYKLNEGESGFDNSE

KTKGHFNFTLSSDALDALSGSLNKVSVTLSDVANNTTVKTVDVPAVKDQ

PAVSVWNATEGVEFNKNSKDYNKENDTYTLYGSAAQDFYLNGALVQVRD

GKYEVPVKTTTQDLVFSTDQAGKNVLKSFTTFTPKAFFNWQNVDGFDGN

FGVNIYSVKTNDPNNAVVQAAVPLGKNVKAYAQDYFTGEVYKGQVENGV

ATFHVHTSINQGEDGIFKRALLTGWSEVDGPAYNDKQVTSKAGVASSNH

LGVYYTTDKVNRKVYTDRADLGVDVQDEAADLSSFGPTAYPGHALADLT

TRTDPNPAIHFDYLNDNDTTRFGQNAVTDGYYDSVTKKFTVTGHVDPEV

KSLTVLGDSSDENAPQNQVKLGKDGKFSFSFTTENVGQRPVAYIYTDQN

GQKVRGTLNVVLDTVAPTLNVDQVNGNELEVKTNNPLFKLSGVVNDNLD

GYRLYVNGNNIYREFLNSGYNKLAGLNTDGTDVNPYGPHNFEESFNLND

DNNQPTTHVFTIYVVDQVGNKVEKKIAVNYDPDYVAEPPKTDQDQNSGQ

TAQPQTNPAVNVDKPTTPDNTSEVPAVDQTKHSDSEQTNQVPKDNPTDQ

LSVQVPVSRETSVTKDNNLNDVVLTAKSFPLLHDAYLYDENGEVVLTSD

PQKKSVLKKGKTISALQNGHVYVIKGVKFYQVGKNQYVKVANTTLQAGK

RLQLKHNAFVYDEKGKLVKKHGKSVLLPKNKWVSALNNADKFKVNGVTY

YKLTDHQYIKVANTVVQPAKKLKLTHNAFVYDQNGKRVKKSKLLKKGTV

LLALNGAEKFKLKNKTYYQVGKNQYVKVANTL
```

The current invention provides a nucleotide sequence comprising (or consisting of) SEQUENCE ID NO. 6.

SEQUENCE ID NO. 6 has the following sequence:

```
DNA sequence comprising the entire protease gene
locus
>Lactobacillus_intestinalis_788_DSM_6629GL000788
ATGAGTGATTATAGCTGGCCAAAGAGCCACAATAAGTATTCTTATGTTTTC

AAAACAAGAGAAGGCTTAAACAAGATTGAAACACAAAAACGTGCGAAGAGC

GTTTCAGATATGCGAAAGAAATGGGTGGCTACAGCTATTATTGCTTTAGCA

TCTGGTTCGACTGTCTTTTTGAGTCAGACATCTTCTGTTGAAGCAGCAATA

GGAGAGACTTCTGTCCAAAATGTTAAAGTTTCTGTGGCTAAAAATGAAAGT

GATTCACAAAAATTTAATAATAGTCAGAACTTGGAACAAAAAACTCCGCAA

GCAGCAGCTGCTAATCAAAATGGGTCACAAGTACAAAATGACCATACTGAA

ACTCAATTACAAAACCAACAAACTACTCAATCTCAGGTAACTCAAGCTCAC

ACAGAAGAAAATAATGCTTCATCAATTCCTGAACCAGCTAATCAGGCCGAT

CATGTAAAAGGAAATGTTCAATCTGCATGGGACCAGGGTTATAAAGGTCAA

AATACGGTTGTAGCCGTAATTGATTCTGGGGCTGATACCAGTCATAAAGAT

TTCCAAACAATGCCATCTAATCCAAAACTTAAGCAAGAAGATGTTCAAAGT

AAGATTGATCAGCAAGGATATGGAAAATATGTTAATGAAAAATTTCCATAT

GTTTATAATTATGCCGATAGGGACAATGATTATATTAAATCGGATGATAAT

AATCAAAATGATAGTCCTCATGGGCAACATGTTTCTGGAATTATTGCGGCA

GATGGGCACCCTGAGGGTGATCAACAATATGTTGTCGGAGTTGCTCCAGAA

GCTCAGCTTATGCAACTTAGAGTATTTGGGCAATTTTCTGATGAAAAAACA

GATGATGTAGCAAGAGCTATCTATGATGCAACTAACTTAGGTGCCGATGTT

ATCCAAATGTCCTTAGGACAGGGTGTGGCAGATCAACAGTTAACTAATATT

GAACAAAAAGCAGTTCAATATGCGATTGACCATGGTGTATTTGTTTCAATT

TCTGCTTCTAATAATGGAAATTCTGCTTCAGTAGATAATCCAAGTAAAGTT

ACCGCAAAAGGTTATGGGTCCGGATCAGAAGCTGGAAATTATGAACCTTTG

AATTCTGGAACGGTCGCCAACCCCGGTGCTTCTAAGAATGCCTTAACTGTT

GCTGCGGAAACTTCTGGAACTGGCAAAGATAGTGACATGGCTTCATTTTCA

TCATGGGGACCATTATCTGATTTTAGTTTAAAGCCAGATCTTTCAGCTCCT

GGTTATCAGGTGGTTTCAACTGTTAATGATAATCAATATCAAACAATGAGT

GGAACTTCAATGGCTGGTCCATTTGCAGCTGGCAGTGCTGCTTTAGTAATC

CAACGGCTAAAGCAAACTAATCCAGAGTTAAAAGGAGCAGAACTTGTTGCT

GCAACTAAAGCATTATTGATGAATAGCGCTAAAGTGCAAACGCAAAATGGA

TACACCACGCCTGTTTCTCCAAGAAGACAAGGTGCAGGTCAAATTGATGTA

GGAGCTGCTACGGCCAATCCAGTTTATGTAACTGCTGCTGATGGAACGAGC

TCCTTATCTTTACGTCAAGTTGATGAAAAAACTACTTTTACTCTTACTTTT

CATAATTTAACAGATCAAGAACAAAGCTACAGCTTTAATGATTTGGGGGGA

GGTTATACTGAACAACGTGATCCCGATAGTGGGGTCTTTCATGAGGTTCAA
```

```
TTAGCAGGAGCTCATGTGAATGGTGTAGGCAATTTTACTCTAGCACCAAAA
GAGGTTAAAGACCTTCAATATACATTAGATTTACAGGGGTTAAATAAAAAT
CAGCCAGTAGAAGGATGGCTTCATTTTACTAATGATAAAGATAAATCGACT
GTGGTAGTGCCATATTTAGCATATTATGGTGATTTGACTAGTGAAAATGTC
TTCGATCAAAATGCAAATGAAGAAAAGCCAGATATTCAAGGTAATCGTTTC
GTTAATGAAAACAATTATCCACTTGGAGTAACTGATCAAGAATCTTTAAAA
CAATTAGTAAATGTTGACAGTGATTACAATTGGCAAGAAGTTGCTAAACTT
TACGAAAGTGGAAAAGTTGCTTTTTCACCAAATGATGATCATCAAAGTGAC
CTTATCAAGCCATATGCTTATTTAAAGCAAAATGTAAAAGACTTAAAGGTT
GAAATTTTAGACGCTAAGGGTAACGTAGTGCGCGTAGTATCTGATGTTCAA
GGGGTTGATAAGTCTTACGATGAAAGTGGAGTAACTAAAGATGCTAGTCTT
TCAGTCTCCATGAGAGACAATCCCGATGCTTTTGAATGGACGGTAAAGTT
TACGATACTAAAACTGGTCAAATGGTAACGGCGCCCGATGGACAATATACT
TATCGCTTTGTTGCTACTCTCTGGAATGAAGGACCAAATCAAAAACAGACT
GCAGATTTTCCAGTTGTAGTAGATACACAAGCTCCTAGTTTAAGCGTTAAA
TATGATTCGGCTACTCATACTTTGTCCGGTAACTATGAAGATAAGGGTGCA
GGTTTTACGGATTATTCTTATGTTACTGTCCAAGTAAATGATAAAGTCTTT
GGTTACAAGTTGAATGAGGGCGAATCAGGTTTTGACAACAGTGAAAAAACA
AAAGGTCATTTCAATTTTACTTTAAGTTCAGATGCTTTGGATGCTTTAAGT
GGTAGTTTGAATAAAGTTTCTGTAACTTTAAGTGATGTAGCTAACAACACG
ACAGTTAAAACTGTTGATGTTCCTGCTGTTAAAGATCAACCAGCAGTTTCT
GTGTGGAATGCAACCGAAGGGGTAGAATTTAATAAAAATTCTAAAGACTAC
AATAAAGAAAATGATACTTACACTTTATATGGTTCAGCGGCCCAAGATTTC
TATTTAAATGGTGCCTTAGTGCAAGTACGAGATGGCAAATACGAGGTTCCA
GTAAAAACGACTACCCAAGATTTGGTATTTTCTACTGATCAAGCAGGTAAA
AATGTTTTAAAGTCTTTCACTACTTTTACCCCTAAGGCATTCTTTAATTGG
CAAAATGTCGATGGCTTTGACGGGAATTTTGGAGTAAATATCTATTCTGTG
AAGACTAATGATCCAAATAATGCAGTTGTGCAAGCAGCAGTTCCTCTAGGT
AAAAATGTCAAAGCCTATGCTCAAGACTATTTCACTGGTGAAGTATATAAA
GGCCAAGTAGAAAATGGAGTAGCTACTTTCCATGTGCATACTTCTATTAAT
CAAGGCGAAGACGGTATATTTAAACGTGCGCTTTTAACAGGGTGGAGTGAA
GTGGACGGTCCGGCATATAATGATAAACAAGTTACCAGTAAAGCTGGTGTA
GCTAGTTCAAATCATTTAGGTGTTTATTACACCACTGATAAGGTTAATCGA
AAGGTTTATACTGATCGCGCTGATTTAGGTGTAGATGTTCAAGATGAAGCA
GCTGACTTAAGTTCATTTGGCCCAACCGCATACCCAGGACATGCTCTAGCA
GATTTAACTACTCGAACGGATCCTAATCCAGCAATTCATTTTGATTATTTG
AATGATAATGACACTACTAGATTTGGACAAAATGCAGTGACTGATGGATAT
TATGATTCCGTAACTAAAAAGTTTACTGTTACAGGACATGTCGATCCAGAA
GTTAAATCGCTTACTGTCTTAGGAGATAGTTCTGATGAAAATGCTCCTCAA
AATCAAGTCAAGTTGGGCAAAGATGGCAAGTTCAGTTTTAGTTTCACTACT
GAAAATGTAGGCCAACGTCCCGTAGCTTATATTTATACTGATCAAAATGGT
CAAAAAGTTCGCGGTACCCTAAATGTTGTCTTAGATACAGTTGCGCCAACC
TTAAATGTAGATCAAGTAAATGGTAACGAACTTGAAGTCAAAACTAACAAT
CCTCTTTTCAAACTTTCAGGAGTAGTTAATGATAATTTAGATGGCTATAGA
CTTTATGTAAATGGCAATAATATTTATCGAGAATTCTTAAATTCTGGCTAC
AATAAATTAGCAGGTTTAAATACTGATGGGACAGATGTAAACCCATATGGT
CCGCATAACTTTGAAGAAAGTTTCAATTTAAATGATGACAACAATCAACCA
ACTACTCATGTCTTTACGATTTACGTAGTTGACCAAGTTGGTAATAAAGTA
GAAAAGAAGATCGCTGTTAATTATGATCCAGACTATGTGGCTGAACCTCCA
AAAACGGATCAAGATCAAAATTCTGGTCAGACTGCACAACCGCAAACAAAT
CCAGCAGTAAATGTTGATAAGCCTACCACTCCAGATAACACATCTGAAGTT
CCAGCTGTTGATCAAACCAAACATTCAGATAGTGAGCAAACTAATCAAGTT
CCAAAGGATAATCCGACAGATCAACTCTCTGTTCAAGTTCCTGTTTCACGT
GAAACTAGTGTTACAAAAGATAATAATCTTAATGATGTAGTTTTAACGGCT
AAATCATTCCCGCTTCTTCATGATGCATATTTATATGATGAAAATGGGGAA
GTCGTTTTAACTAGTGATCCACAGAAGAAATCAGTTTTGAAGAAAGGCAAG
ACAATCAGTGCGCTTCAAAATGGACATGTTTATGTAATTAAAGGTGTAAAA
TTCTACCAAGTTGGTAAGAATCAGTATGTAAAGGTCGCCAACACTACTTTG
CAAGCTGGTAAGAGATTGCAATTAAAGCATAATGCCTTTGTTTATGATGAA
AAAGGAAAGCTGGTTAAGAAGCATGGCAAGAGTGTACTTTTACCAAAAAAT
AAGTGGGTTTCAGCTTTAAATAATGCAGACAAGTTTAAAGTAAATGGTGTA
ACTTATTATAAACTTACGGATCATCAATATATCAAAGTTGCTAATACCGTC
GTTCAACCAGCTAAGAAACTTAAGTTAACTCATAATGCCTTTGTTTATGAT
CAAAATGGCAAACGAGTTAAAAAGAGTAAGCTTTTAAAGAAGGGCACAGTG
CTTTTGGCCTTAAATGGAGCTGAAAAGTTTAAGCTCAAGAATAAGACTTAC
TATCAAGTTGGTAAGAATCAATATGTAAAAGTCGCTAATACTTTA
```

The invention also provides a peptide sequence encoding the propeptide to the end of the B domain of the protein or enzyme of the invention. This sequence comprises (or consists of) SEQUENCE ID NO. 7.

SEQUENCE ID NO. 7 has the following sequence.

Protein sequence comprising the propeptide to the end of the B domain

AIGETSVQNVKVSVAKNESDSQKFNNSQNLEQKTPQAAAANQNGSQVQNDH
TETQLQNQQTTQSQVTQAHTEENNASSIPEPANQADHVKGNVQSAWDQGYK
GQNTVVAVIDSGADTSHKDFQTMPSNPKLKQEDVQSKIDQQGYGKYVNEKF
PYVYNYADRDNDYIKSDDNNQXNDSPHGQHVSGIIAADGHPEGDQQYVVGV
APEAQLMQLRVFGQFSDEKTDDVARAIYDATNLGADVIQMSLGQGVADQQL
TNIEQKAVQYAIDHGVFVSISASNNGNSASVDNPSKVTAKGYGSGSEAGNY
EPLNSGTVANPGASKNALTVAAETSGTGKDSDMASFSSWGPLSDFSLKPDL
SAPGYQVVSTVNDNQYQTMSGTSMAGPFAAGSAALVIQRLKQTNPELKGAE
LVAATKALLMNSAKVQTQNGYTTPVSPRRQGAGQIDVGAATANPVYVTAAD
GTSSLSLRQVDEKTTFTLTFHNLTDQEQSYSFNDLGGGYTEQRDPDSGVFH

-continued

EVQLAGAHVNGVGNFTLAPKEVKDLQYTLDLQGLNKNQPVEGWLHFTNDKD

KSTVVVPYLAYYGDLTSENVFDQNANEEKPDIQGNRFVNENNYPLGVTDQE

SLKQLVNVDSDYNWQEVAKLYESGKVAFSPNDDHQSDLIKPYAYLKQNVKD

LKVEILDAKGNVVRVVSDVQGVDKSYDESGVTKDASLSVSMRDNPDAFEWD

GKVYDTKTGQMVTAPDGQYTYRFVATLWNEGPNQKQTADFPVVVDTQAPSL

SVKYDSATHTLSGNYEDKGAGFTDYSYVTVQVNDKVFGYKLNEGESGFDNS

EKTKGHFNFTLSSDALDALSGSLNKVSVTLSDVANNTTVKTVDVPAVKDQP

AVSVWNATEGVEFNKNSKDYNKENDTYTLYGSAAQDFYLNGALVQVRDGKY

EVPVKTTTQDLVFSTDQAGKNVLKSFTTFTPKAFFNWQNVDGFDGNFGVNI

YSVKTNDPNNAVVQAAVPLGKNVKAYAQDYFTGEVYKGQVENGVATFHVHT

SINQGEDGIFKRALLTGWSEVDGPAYNDKQVTSKAGVASSNHLGVYYTTDK

VNRKVYTDRADLGVDVQDEAADLSSFGPTAYPGHALADLTTRTDPNPAIHF

DYLNDNDTTRFGQNAVTDGYYDSVTKKFTVTGHVDPEVKSLTVLGDSSDEN

APQNQVKLGKDGKFSFSFTTENVGQRPVAYIYTDQNGQKVRGTLNVVLDTV

APTLNVDQVNGNELEVKTNNPLFKLSGVVNDNLDGYRLYVNGNNIYREFLN

SGYNKLAGLNTDGTDVNPYGPHNFEESFNLNDDNNQPTTHVFTIYVVDQVG

NKVEKKIAVNYDPDYVA

The invention also provides a nucleotide sequence encoding the propeptide to the end of the B domain of the protein or enzyme of the invention. This nucleotide sequence comprises (or consists of) SEQUENCE ID NO. 8.

SEQUENCE ID NO. 8 has the following sequence.

GCAATAGGAGAGACTTCTGTCCAAAATGTTAAAGTTTCTGTGGCTAAAAAT

GAAAGTGATTCACAAAAATTTAATAATAGTCAGAACTTGGAACAAAAAACT

CCGCAAGCAGCAGCTGCTAATCAAAATGGGTCACAAGTACAAAATGACCAT

ACTGAAACTCAATTACAAAACCAACAAACTACTCAATCTCAGGTAACTCAA

GCTCACACAGAAGAAATAATGCTTCATCAATTCCTGAACCAGCTAATCAG

GCCGATCATGTAAAAGGAAATGTTCAATCTGCATGGGACCAGGGTTATAAA

GGTCAAAATACGGTTGTAGCCGTAATTGATTCTGGGGCTGATACCAGTCAT

AAAGATTTCCAAACAATGCCATCTAATCCAAAACTTAAGCAAGAAGATGTT

CAAAGTAAGATTGATCAGCAAGGATATGGAAAATATGTTAATGAAAAATTT

CCATATGTTTATAATTATGCCGATAGGGACAATGATTATATTAAATCGGAT

GATAATAATCAAATGATAGTCCTCATGGGCAACATGTTTCTGGAATTATT

GCGGCAGATGGGCACCCTGAGGGTGATCAACAATATGTTGTCGGAGTTGCT

CCAGAAGCTCAGCTTATGCAACTTAGAGTATTTGGGCAATTTTCTGATGAA

AAAACAGATGATGTAGCAAGAGCTATCTATGATGCAACTAACTTAGGTGCC

GATGTTATCCAAATGTCCTTAGGACAGGGTGTGGCAGATCAACAGTTAACT

AATATTGAACAAAAGCAGTTCAATATGCGATTGACCATGGTGTATTTGTT

TCAATTTCTGCTTCTAATAATGGAAATTCTGCTTCAGTAGATAATCCAAGT

AAAGTTACCGCAAAAGGTTATGGGTCCGGATCAGAAGCTGGAAATTATGAA

CCTTTGAATTCTGGAACGGTCGCCAACCCCGGTGCTTCTAAGAATGCCTTA

ACTGTTGCTGCGGAAACTTCTGGAACTGGCAAAGATAGTGACATGGCTTCA

TTTTCATCATGGGGACCATTATCTGATTTTAGTTTAAAGCCAGATCTTTCA

GCTCCTGGTTATCAGGTGGTTTCAACTGTTAATGATAATCAATATCAAACA

ATGAGTGGAACTTCAATGGCTGGTCCATTTGCAGCTGGCAGTGCTGCTTTA

GTAATCCAACGGCTAAAGCAAACTAATCCAGAGTTAAAAGGAGCAGAACTT

GTTGCTGCAACTAAAGCATTATTGATGAATAGCGCTAAAGTGCAAACGCAA

AATGGATACACCACGCCTGTTTCTCCAAGAAGACAAGGTGCAGGTCAAATT

GATGTAGGAGCTGCTACGGCCAATCCAGTTTATGTAACTGCTGCTGATGGA

ACGAGCTCCTTATCTTTACGTCAAGTTGATGAAAAAACTACTTTTACTCTT

ACTTTTCATAATTTAACAGATCAAGAACAAAGCTACAGCTTTAATGATTTG

GGGGGAGGTTATACTGAACAACGTGATCCCGATAGTGGGGTCTTTCATGAG

GTTCAATTAGCAGGAGCTCATGTGAATGGTGTAGGCAATTTTACTCTAGCA

CCAAAAGAGGTTAAAGACCTTCAATATACATTAGATTTACAGGGGTTAAAT

AAAAATCAGCCAGTAGAAGGATGGCTTCATTTTACTAATGATAAAGATAAA

TCGACTGTGGTAGTGCCATATTTAGCATATTATGGTGATTTGACTAGTGAA

AATGTCTTCGATCAAAATGCAAATGAAGAAAAGCCAGATATTCAAGGTAAT

CGTTTCGTTAATGAAAACAATTATCCACTTGGAGTAACTGATCAAGAATCT

TTAAAACAATTAGTAAATGTTGACAGTGATTACAATTGGCAAGAAGTTGCT

AAACTTTACGAAAGTGGAAAAGTTGCTTTTTCACCAAATGATGATCATCAA

AGTGACCTTATCAAGCCATATGCTTATTTAAAGCAAAATGTAAAAGACTTA

AAGGTTGAAATTTTAGACGCTAAGGGTAACGTAGTGCGCGTAGTATCTGAT

GTTCAAGGGGTTGATAAGTCTTACGATGAAAGTGGAGTAACTAAAGATGCT

AGTCTTTCAGTCTCCATGAGAGACAATCCCGATGCTTTTGAATGGGACGGT

AAAGTTTACGATACTAAAACTGGTCAAATGGTAACGGCGCCCGATGGACAA

TATACTTATCGCTTTGTTGCTACTCTCTGGAATGAAGGACCAAATCAAAAA

CAGACTGCAGATTTTCCAGTTGTAGTAGATACAAGCTCCTAGTTTAAGC

GTTAAATATGATTCGGCTACTCATACTTTGTCCGGTAACTATGAAGATAAG

GGTGCAGGTTTTACGGATTATTCTTATGTTACTGTCCAAGTAAATGATAAA

GTCTTTGGTTACAAGTTGAATGAGGGCGAATCAGGTTTTGACAACAGTGAA

AAAACAAAAGGTCATTTCAATTTTACTTTAAGTTCAGATGCTTTGGATGCT

TTAAGTGGTAGTTTGAATAAAGTTTCTGTAACTTTAAGTGATGTAGCTAAC

AACACGACAGTTAAAACTGTTGATGTTCCTGCTGTTAAAGATCAACCAGCA

GTTTCTGTGTGGAATGCAACCGAAGGGGTAGAATTTAATAAAAATTCTAAA

GACTACAATAAAGAAAATGATACTTACACTTTATATGGTTCAGCGGCCCAA

GATTTCTATTTAAATGGTGCCTTAGTGCAAGTACGAGATGGCAAATACGAG

GTTCCAGTAAAAACGACTACCCAAGATTTGGTATTTTCTACTGATCAAGCA

GGTAAAAATGTTTTAAAGTCTTTCACTACTTTTACCCCTAAGGCATTCTTT

AATTGGCAAAATGTCGATGGCTTTGACGGGAATTTTGGAGTAAATATCTAT

TCTGTGAAGACTAATGATCCAAATAATGCAGTTGTGCAAGCAGCAGTTCCT

CTAGGTAAAAATGTCAAAGCCTATGCTCAAGACTATTTCACTGGTGAAGTA

```
TATAAAGGCCAAGTAGAAAATGGAGTAGCTACTTTCCATGTGCATACTTCT
ATTAATCAAGGCGAAGACGGTATATTTAAACGTGCGCTTTTAACAGGGTGG
AGTGAAGTGGACGGTCCGGCATATAATGATAAACAAGTTACCAGTAAAGCT
GGTGTAGCTAGTTCAAATCATTTAGGTGTTTATTACACCACTGATAAGGTT
AATCGAAAGGTTTATACTGATCGCGCTGATTTAGGTGTAGATGTTCAAGAT
GAAGCAGCTGACTTAAGTTCATTTGGCCCAACCGCATACCCAGGACATGCT
CTAGCAGATTTAACTACTCGAACGGATCCTAATCCAGCAATTCATTTTGAT
TATTTGAATGATAATGACACTACTAGATTTGGACAAAATGCAGTGACTGAT
GGATATTATGATTCCGTAACTAAAAAGTTTACTGTTACAGGACATGTCGAT
CCAGAAGTTAAATCGCTTACTGTCTTAGGAGATAGTTCTGATGAAAATGCT
CCTCAAAATCAAGTCAAGTTGGGCAAAGATGGCAAGTTCAGTTTTAGTTTC
ACTACTGAAAATGTAGGCCAACGTCCCGTAGCTTATATTTATACTGATCAA
AATGGTCAAAAAGTTCGCGGTACCCTAAATGTTGTCTTAGATACAGTTGCG
CCAACCTTAAATGTAGATCAAGTAAATGGTAACGAACTTGAAGTCAAAACT
AACAATCCTCTTTTCAAACTTTCAGGAGTAGTTAATGATAATTTAGATGGC
TATAGACTTTATGTAAATGGCAATAATATTTATCGAGAATTCTTAAATTCT
GGCTACAATAAATTAGCAGGTTTAAATACTGATGGGACAGATGTAAACCCA
TATGGTCCGCATAACTTTGAAGAAAGTTTCAATTTAAATGATGACAACAAT
CAACCAACTACTCATGTCTTTACGATTTACGTAGTTGACCAAGTTGGTAAT
AAAGTAGAAAAGAAGATCGCTGTTAATTATGATCCAGACTATGTGGCT
```

The invention also provides a peptide sequence encoding the region starting with residue 38 from SEQUENCE ID NO. 5 to the end of the B domain of the protein or enzyme of the invention. There is a 8 residue extension onto the C-terminus (PrtI$_{SS-HT}$). This sequence comprises (or consists of) SEQUENCE ID NO. 9.

SEQUENCE ID NO. 9 has the following sequence.

```
MRKKWVATAIIALASGSTVFLSQTSSVEAAIGETSVQNVKVSVAKNESDSQ
KFNNSQNLEQKTPQAAAANQNGSQVQNDHTETQLQNQQTTQSQVTQAHTEE
NNASSIPEPANQADHVKGNVQSAWDQGYKGQNTVVAVIDSGADTSHKDFQT
MPSNPKLKQEDVQSKIDQQGYGKYVNEKFPYVYNYADRDNDYIKSDDNNQX
NDSPHGQHVSGIIAADGHPEGDQQYVVGVAPEAQLMQLRVFGQFSDEKTDD
VARAIYDATNLGADVIQMSLGQGVADQQLTNIEQKAVQYAIDHGVFVSISA
SNNGNSASVDNPSKVTAKGYGSGSEAGNYEPLNSGTVANPGASKNALTVAA
ETSGTGKDSDMASFSSWGPLSDFSLKPDLSAPGYQVVSTVNDNQYQTMSGT
SMAGPFAAGSAALVIQRLKQTNPELKGAELVAATKALLMNSAKVQTQNGYT
TPVSPRRQGAGQIDVGAATANPVYVTAADGTSSLSLRQVDEKTTFTLTFHN
LTDQEQSYSFNDLGGGYTEQRDPDSGVFHEVQLAGAHVNGVGNFTLAPKEV
KDLQYTLDLQGLNKNQPVEGWLHFTNDKDKSTVVVPYLAYYGDLTSENVFD
QNANEEKPDIQGNRFVNENNYPLGVTDQESLKQLVNVDSDYNWQEVAKLYE
SGKVAFSPNDDHQSDLIKPYAYLKQNVKDLKVEILDAKGNVVRVVSDVQGV
DKSYDESGVTKDASLSVSMRDNPDAFEWDGKVYDTKTGQMVTAPDGQYTYR
FVATLWNEGPNQKQTADFPVVVDTQAPSLSVKYDSATHTLSGNYEDKGAGF
TDYSYVTVQVNDKVFGYKLNEGESGFDNSEKTKGHFNFTLSSDALDALSGS
LNKVSVTLSDVANNTTVKTVDVPAVKDQPAVSVWNATEGVEFNKNSKDYNK
ENDTYTLYGSAAQDFYLNGALVQVRDGKYEVPVKTTTQDLVFSTDQAGKNV
LKSFTTFTPKAFFNWQNVDGFDGNFGVNIYSVKTNDPNNAVVQAAVPLGKN
VKAYAQDYFTGEVYKGQVENGVATFHVHTSINQGEDGIFKRALLTGWSEVD
GPAYNDKQVTSKAGVASSNHLGVYYTTDKVNRKVYTDRADLGVDVQDEAAD
LSSFGPTAYPGHALADLTTRTDPNPAIHFDYLNDNDTTRFGQNAVTDGYYD
SVTKKFTVTGHVDPEVKSLTVLGDSSDENAPQNQVKLGKDGKFSFSFTTEN
VGQRPVAYIYTDQNGQKVRGTLNVVLDTVAPTLNVDQVNGNELEVKTNNPL
FKLSGVVNDNLDGYRLYVNGNNIYREFLNSGYNKLAGLNTDGTDVNPYGPH
NFEESFNLNDDNNQPTTHVFTIYVVDQVGNKVEKKIAVNYDPDYVAPRHHH
HHH
```

The invention also provides a nucleotide sequence encoding the region starting with residue 38 from SEQUENCE ID NO. 5 to the end of the B domain of the protein or enzyme of the invention. There is a 8 residue extension onto the C-terminus. This nucleotide sequence comprises (or consists of) SEQUENCE ID NO. 10.

SEQUENCE ID NO. 10 has the following sequence.

```
ATGCGAAAGAAATGGGTGGCTACAGCTATTATTGCTTTAGCATCTGGTTCG
ACTGTCTTTTTGAGTCAGACATCTTCTGTTGAAGCAGCAATAGGAGAGACT
TCTGTCCAAAATGTTAAAGTTTCTGTGGCTAAAAATGAAAGTGATTCACAA
AAATTTAATAATAGTCAGAACTTGGAACAAAAAACTCCGCAAGCAGCAGCT
GCTAATCAAATGGGTCACAAGTACAAAATGACCATACTGAAACTCAATTA
CAAAACCAACAAACTACTCAATCTCAGGTAACTCAAGCTCACACAGAAGAA
AATAATGCTTCATCAATTCCTGAACCAGCTAATCAGGCCGATCATGTAAAA
GGAAATGTTCAATCTGCATGGGACCAGGGTTATAAAGGTCAAAATACGGTT
GTAGCCGTAATTGATTCTGGGGCTGATACCAGTCATAAAGATTTCCAAACA
ATGCCATCTAATCCAAAACTTAAGCAAGAAGATGTTCAAAGTAAGATTGAT
CAGCAAGGATATGGAAAATATGTTAATGAAAAATTTCCATATGTTTATAAT
TATGCCGATAGGGACAATGATTATATTAAATCGGATGATAATAATCAAAAT
GATAGTCCTCATGGGCAACATGTTTCTGGAATTATTGCGGCAGATGGGCAC
CCTGAGGGTGATCAACAATATGTTGTCGGAGTTGCTCCAGAAGCTCAGCTT
ATGCAACTTAGAGTATTTGGGCAATTTTCTGATGAAAAAACAGATGATGTA
GCAAGAGCTATCTATGATGCAACTAACTTAGGTGCCGATGTTATCCAAATG
TCCTTAGGACAGGGTGTGGCAGATCAACAGTTAACTAATATTGAACAAAAA
GCAGTTCAATATGCGATTGACCATGGTGTATTTGTTTCAATTTCTGCTTCT
AATAATGGAAATTCTGCTTCAGTAGATAATCCAAGTAAAGTTACCGCAAAA
GGTTATGGGTCCGGATCAGAAGCTGGAAATTATGAACCTTTGAATTCTGGA
ACGGTCGCCAACCCCGGTGCTTCTAAGAATGCCTTAACTGTTGCTGCGGAA
ACTTCTGGAACTGGCAAAGATAGTGACATGGCTTCATTTTCATCATGGGGA
```

```
CCATTATCTGATTTTAGTTTAAAGCCAGATCTTTCAGCTCCTGGTTATCAG
GTGGTTTCAACTGTTAATGATAATCAATATCAAACAATGAGTGGAACTTCA
ATGGCTGGTCCATTTGCAGCTGGCAGTGCTGCTTTAGTAATCCAACGGCTA
AAGCAAACTAATCCAGAGTTAAAAGGAGCAGAACTTGTTGCTGCAACTAAA
GCATTATTGATGAATAGCGCTAAAGTGCAAACGCAAATGGATACACCACG
CCTGTTTCTCCAAGAAGACAAGGTGCAGGTCAAATTGATGTAGGAGCTGCT
ACGGCCAATCCAGTTTATGTAACTGCTGCTGATGGAACGAGCTCCTTATCT
TTACGTCAAGTTGATGAAAAAACTACTTTTACTCTTACTTTTCATAATTTA
ACAGATCAAGAACAAAGCTACAGCTTTAATGATTTGGGGGGAGGTTATACT
GAACAACGTGATCCCGATAGTGGGGTCTTTCATGAGGTTCAATTAGCAGGA
GCTCATGTGAATGGTGTAGGCAATTTTACTCTAGCACCAAAAGAGGTTAAA
GACCTTCAATATACATTAGATTTACAGGGGTTAAATAAAAATCAGCCAGTA
GAAGGATGGCTTCATTTTACTAATGATAAAGATAAATCGACTGTGGTAGTG
CCATATTTAGCATATTATGGTGATTTGACTAGTGAAAATGTCTTCGATCAA
AATGCAAATGAAGAAAAGCCAGATATTCAAGGTAATCGTTTCGTTAATGAA
AACAATTATCCACTTGGAGTAACTGATCAAGAATCTTTAAAACAATTAGTA
AATGTTGACAGTGATTACAATTGGCAAGAAGTTGCTAAACTTTACGAAAGT
GGAAAAGTTGCTTTTTCACCAAATGATGATCATCAAAGTGACCTTATCAAG
CCATATGCTTATTTAAAGCAAAATGTAAAAGACTTAAAGGTTGAAATTTTA
GACGCTAAGGGTAACGTAGTGCGCGTAGTATCTGATGTTCAAGGGGTTGAT
AAGTCTTACGATGAAAGTGGAGTAACTAAAGATGCTAGTCTTTCAGTCTCC
ATGAGAGACAATCCCGATGCTTTTGAATGGGACGGTAAAGTTTACGATACT
AAAACTGGTCAAATGGTAACGGCGCCCGATGGACAATATACTTATCGCTTT
GTTGCTACTCTCTGGAATGAAGGACCAAATCAAAACAGACTGCAGATTTT
CCAGTTGTAGTAGATACACAAGCTCCTAGTTTAAGCGTTAAATATGATTCG
GCTACTCATACTTTGTCCGGTAACTATGAAGATAAGGGTGCAGGTTTTACG
GATTATTCTTATGTTACTGTCCAAGTAAATGATAAAGTCTTTGGTTACAAG
TTGAATGAGGGCGAATCAGGTTTTGACAACAGTGAAAAAACAAAAGGTCAT
TTCAATTTTACTTTAAGTTCAGATGCTTTGGATGCTTTAAGTGGTAGTTTG
AATAAAGTTTCTGTAACTTTAAGTGATGTAGCTAACAACACGACAGTTAAA
ACTGTTGATGTTCCTGCTGTTAAAGATCAACCAGCAGTTTCTGTGTGGAAT
GCAACCGAAGGGGTAGAATTTAATAAAAATTCTAAAGACTACAATAAAGAA
AATGATACTTACACTTTATATGGTTCAGCGGCCCAAGATTTCTATTTAAAT
GGTGCCTTAGTGCAAGTACGAGATGGCAAATACGAGGTTCCAGTAAAAACG
ACTACCCAAGATTTGGTATTTTCTACTGATCAAGCAGGTAAAAATGTTTTA
AAGTCTTTCACTACTTTTACCCCTAAGGCATTCTTTAATTGGCAAAATGTC
GATGGCTTTGACGGGAATTTTGGAGTAAATATCTATTCTGTGAAGACTAAT
GATCCAAATAATGCAGTTGTGCAAGCAGCAGTTCCTCTAGGTAAAAATGTC
AAAGCCTATGCTCAAGACTATTTCACTGGTGAAGTATATAAAGGCCAAGTA
GAAAATGGAGTAGCTACTTTCCATGTGCATACTTCTATTAATCAAGGCGAA
GACGGTATATTTAAACGTGCGCTTTTAACAGGGTGGAGTGAAGTGGACGGT
CCGGCATATAATGATAAACAAGTTACCAGTAAAGCTGGTGTAGCTAGTTCA
AATCATTTAGGTGTTTATTACACCACTGATAAGGTTAATCGAAAGGTTTAT
ACTGATCGCGCTGATTTAGGTGTAGATGTTCAAGATGAAGCAGCTGACTTA
AGTTCATTTGGCCCAACCGCATACCCAGGACATGCTCTAGCAGATTTAACT
ACTCGAACGGATCCTAATCCAGCAATTCATTTTGATTATTTGAATGATAAT
GACACTACTAGATTTGGACAAAATGCAGTGACTGATGGATATTATGATTCC
GTAACTAAAAAGTTTACTGTTACAGGACATGTCGATCCAGAAGTTAAATCG
CTTACTGTCTTAGGAGATAGTTCTGATGAAAATGCTCCTCAAAATCAAGTC
AAGTTGGGCAAAGATGGCAAGTTCAGTTTTAGTTTCACTACTGAAAATGTA
GGCCAACGTCCCGTAGCTTATATTTATACTGATCAAAATGGTCAAAAAGTT
CGCGGTACCCTAAATGTTGTCTTAGATACAGTTGCGCCAACCTTAAATGTA
GATCAAGTAAATGGTAACGAACTTGAAGTCAAAACTAACAATCCTCTTTTC
AAACTTTCAGGAGTAGTTAATGATAATTTAGATGGCTATAGACTTTATGTA
AATGGCAATAATATTTATCGAGAATTCTTAAATTCTGGCTACAATAAATTA
GCAGGTTTAAATACTGATGGGACAGATGTAAACCCATATGGTCCGCATAAC
TTTGAAGAAGTTTCAATTTAAATGATGACAACAATCAACCAACTACTCAT
GTCTTTACGATTTACGTAGTTGACCAAGTTGGTAATAAAGTAGAAAAGAAG
ATCGCTGTTAATTATGATCCAGACTATGTGGCTCCTAGGCATCATCACCAC
CACCAT
```

The protease of the invention (*Lactobacillus crispatus*) may have a sequence comprising (or consisting of) SEQUENCE ID NO. 21.

SEQUENCE ID NO. 21 has the following sequence.

```
Protein sequence comprising the entire protease
protein
MSNLTNPNDHKDLSFLFKSVDRLAALETQKKADTIISVRKKWVAAAMIALA
SGSTVLLTSNTANAATSDVNSEVQVTAQNQNTTENKMQAGDTANSHDTEQN
VTVQANSSQQSNQEANTADQNNTPENDNQVQTPTNQADHVKGNVQSAWDQG
YKGQGTVVAVIDSGADPSHKDFQTMPENPKLSKDDIQKKIEQQGYGKYVNE
KFPYVYNYADRDNDYITSDDTNSNDSPHGQHVSGIIAADGKPDGNKEYVVG
VAPEAQLMQLRVFGQFSDEKTDDVAKAIYDATNLGADVIQMSLGQGVADQQ
LTNIEQKAVQYAIDHGVFVSISASNNGHSGSVDNTSNVTSVESYESGSADG
NYEPLNSSTVANPGASKNALTVAAETSATGKDSDMAGFSSWGPVQDFTLKP
DLAAPGYQVVSTVNNNNYQTMSGTSMAGPFAAASAALVMQRLKKTNPELKG
AQLVAATKALLMNSAKPQTQNGYTTPVSPRRQGAGQIDVGAATSNPVYVIA
DDGTSSVSLHQVKENTPFTLTFHNLTDQEQVYTFDDFGGGYTEQRDSNTGV
YHDVQLAGARVYGENSFSLAPKETKQVTYSLNLNGLNNNQLVEGFLRFTNT
NDKSTVSVPYLAYYGDLTSENVFDQNANEEHPDIQGNRFVNEQSYPRGVAD
QESLKQLVNVEGDYNWQEVAKLYESGKVAFSPNNDNKSDLLKPYTYLKQNV
KDLKAVVLDAQGNVVRVVADVQGVDKSYDENGVTKDTSLSVSMRDNPDAFE
WDGKVYNSKTGQMEVAKDGNYTYRLVATLWNEGPHQVQTADFPVVIDTVAP
TLSNVKYDEATNTLSGEYQDTGAGFTNYSYATVTVNDKVFGYKLSDGQSAF
```

-continued

```
DNAEKTKGHFSFTLDKDAVAALSGAKNKVSVVLSDVADNPVVYSVNVAGKD
IDKPAVSVWNATNGLAFDQSSTSYNKDTKTYTLIGGANQDFYLNGKLVQVQ
NGQYSVPVDVNSTNLVFSTDAAGKNVLKNFSTVTPKAFFNWQVTDTFAGNF
GVSINSVETNRKDDVVVQAAVPKGENIQAFAKDYFTGELYTGEVNDGVATF
HVHTSINGGRRALLTGWTVVNGPSYNDKQETSQRGVASSNHLGVYYEVDAA
DRPVYTNRNQLGVEVKDEAANVDAFGPGAYPGHAPSDLTTRTASNPNIHFD
YMNDNDTTRFGQNAVLKGYYDPTTMKFTVTGNVDDNVTSLTVLSDSSNEND
PANQVKLDQNGKFSFAVTANSTGQRPIAYLYRTKDGQTVRGTLNLILDTVK
PTLEVNQVNGNELELWTNNPKFVLSGKVNDNLDGYRLYVNGNNIYREFLNS
GYNRLEGLNTDTELTNPYGDHEFEQVENLNDNNDQPTTHIFTVNVVDQAGN
TVTKKLTVHFDPNYVVPTDNTDVVVDTSTSDTDGVTETKPIDPLVGKSFKL
LHNAYLYDQNGEVVLTDVENAKSLLKKGQTIVALDNAKVTFINGVKFYRVG
NNTFVKTANTVLQAPKRLKLTHNAYVYDQKGNVVKKHGKKVLLKKNQWISA
LNNADKYVIKGRLYYKLADGQFVKVANTVTKKAKLRKTVVS
```

The invention also provides a fragment of *Lactobacillus crispatus* protease comprising the propeptide to the end of the B domain of the *Lactobacillus crispatus* protease. This sequence comprises (or consists of) SEQUENCE ID NO. 22.

SEQUENCE ID NO. 22 has the following sequence.

```
DVNSEVQVTAQNQNTTENKMQAGDTANSHDTEQNVTVQANSSQQSNQEANT
ADQNNTPENDNQVQTPTNQADHVKGNVQSAWDQGYKGQGTVVAVIDSGADP
SHKDFQTMPENPKLSKDDIQKKIEQQGYGKYVNEKFPYVYNYADRDNDYIT
SDDTNSNDSPHGQHVSGIIAADGKPDGNKEYVVGVAPEAQLMQLRVFGQFS
DEKTDDVAKAIYDATNLGADVIQMSLGQGVADQQLTNIEQKAVQYAIDHGV
FVSISASNNGHSGSVDNTSNVTSVESYESGSADGNYEPLNSSTVANPGASK
NALTVAAETSATGKDSDMAGFSSWGPVQDFTLKPDLAAPGYQVVSTVNNNN
YQTMSGTSMAGPFAAASAALVMQRLKKTNPELKGAQLVAATKALLMNSAKP
QTQNGYTTPVSPRRQGAGQIDVGAATSNPVYVIADDGTSSVSLHQVKENTP
FTLTFHNLTDQEQVYTFDDFGGGYTEQRDSNTGVYHDVQLAGARVYGENSF
SLAPKETKQVTYSLNLNGLNNNQLVEGFLRFTNTNDKSTVSVPYLAYYGDL
TSENVFDQNANEEHPDIQGNRFVNEQSYPRGVADQESLKQLVNVEGDYNWQ
EVAKLYESGKVAFSPNNDNKSDLLKPYTYLKQNVKDLKAVVLDAQGNVVRV
VADVQGVDKSYDENGVTKDTSLSVSMRDNPDAFEWDGKVYNSKTGQMEVAK
DGNYTYRLVATLWNEGPHQVQTADFPVVIDTVAPTLSNVKYDEATNTLSGE
YQDTGAGFTNYSYATVTVNDKVFGYKLSDGQSAFDNAEKTKGHFSFTLDKD
AVAALSGAKNKVSVVLSDVADNPVVYSVNVAGKDIDKPAVSVWNATNGLAF
DQSSTSYNKDTKTYTLIGGANQDFYLNGKLVQVQNGQYSVPVDVNSTNLVF
STDAAGKNVLKNFSTVTPKAFFNWQVTDTFAGNFGVSINSVETNRKDDVVV
QAAVPKGENIQAFAKDYFTGELYTGEVNDGVATFHVHTSINGGRRALLTGW
TVVNGPSYNDKQETSQRGVASSNHLGVYYEVDAADRPVYTNRNQLGVEVKD
EAANVDAFGPGAYPGHAPSDLTTRTASNPNIHFDYMNDNDTTRFGQNAVLK
GYYDPTTMKFTVTGNVDDNVTSLTVLSDSSNENDPANQVKLDQNGKFSFAV
TANSTGQRPIAYLYRTKDGQTVRGTLNLILDTVKPTLEVNQVNGNELELWT
NNPKFVLSGKVNDNLDGYRLYVNGNNIYREFLNSGYNRLEGLNTDTELTNP
YGDHEFEQVENLNDNNDQPTTHIFTVNVVDQAGNTVTKKLTVHFDPNYVVP
TDNTDVVVDTSTSDTDGVTETKPIDPLVGKSFKLLHNAYLYDQNGEVVLTD
VENAKSLLKKGQTIVALDNAKVTFINGVKFYRVGNNTFVKTANTVLQAPKR
LKLTHNAYVYDQKGNVVKKHGKKVLLKKNQWISALNNADKYVIKGRLYYKL
ADGQFVKVANTVTKKAKLRKTVVS
```

The protease of the invention (*Lactobacillus ultunensis*) may have a sequence comprising (or consisting of) SEQUENCE ID NO. 23.

SEQUENCE ID NO. 23 has the following sequence.

```
Protein sequence comprising the entire protease
protein
MSNSTAPNGNRNFSFVFKAKRRLENIETQKRARTIINVRKKWVAAAIIALA
SGSTVFLSQNAVEAATNDPDASDVQVKVVQQDQKQNQNTTANVVVSNSDST
KTQVNTTVQTQNSAVVSGDSTTANPKTSQASNVQNTSTTANSVDPNQEQQP
ANQADHVKGNVQSAWDQGYRGQGTVVAVIDSGADPTHKDFQTMPEDPKLSK
DDMQAKISKQGYGKYVNEKFPYVYNYADRDNDYITSDDTNANDSPHGQHVS
GIIAADGKPDGNKEYVVGVAPEAQLMQLRVFGQFSDEKTDDVARAIYDATN
LGADVIQMSLGQGVADQQLTNIEQKAVQYAIDHGVFVSISASNNGNSASVD
NPSKVQDSGYQSGSQAGNYEPLNSSTVANPGASKNALTVAAETSDTGDLSD
MAYFSSWGPIQDFTLKPDLAAPGYQVVSTVNHDQYQTMSGTSMAGPFAAAS
AALVIQRLKQTNPELKGAQLVTAAKAMLMNTAKPQKQLGYTTPVSPRRQGA
GQIDVGGATATPVYVTTDDGTSSVSLHQVNENTKFTLTFHNLTDQNQTYTF
DDYGGGYTEQRDTTTGVFHDVQLAGARVNGENSFTLAPKEERKVSYSLDLT
GLNKNQLVEGFLRFTNANNVSTVSVPYLAYYGDLTSENVFDQNANEEHPDI
QGNRLVNEQNYPRGIADQESLKELVNVDGNYNWQEVAKLYESGKVAFSPND
NQKSDLLKPYVYLKQNVKDLKVEVLDAQGKVVRVVSDVQGVDKSYDENDVT
KDTSLSVSMRDNPDAFEWDGKVYNSKTGKMETAKDGNYTYRLVATLWNKGP
HQVQTADFPVVVDTVAPTLSNIKYDPASHTLSGEYQDTGAGFTNYSYATVT
VNDKVFGYKLSDDESGFDNTEKTKGHFNFVLGQDALSALTTATNKMTVALS
DVADNTSLATVDVAGDHDSETGVSIWNAVNGLAFDQKSPNYNSVTKTYILF
GGANHDFYLNGKLVQVQNGKYQAPVSVDTTEFVFSTDPEGRHVLNSLSTVT
AKAFFNWQKTDTFDGNFGVTIGSVKTNDPNDTVVQAVVTKGQNVKAYAMDY
FTGEVYTGEVKDGIATFHVHTSVNQDNTTGVYKRALLTGWTEVDGPSFNDK
QETSRGGVASSNHLGVYYFADAADRPIYTDRSALGVEAKDEVAKLDSFGPG
FYPGHAPSDLTTRTDPNPDIHFDYMNDNDTTRFGQNAVTRGYYDPLTQKFM
VTGKVDGNVASLTVLGDNSNENAPENQVKLGNDGKFSFTVTANRTGQRPIA
YIYQTKDGQRVRGTLNLILDTVAPSLEVNQVNGDKLELWTNNPKFILSGKV
NDNLDGYRLFVNGNNIYREFLNSGYNQVAGLNMDTEFTNPYGAHDFEEVEN
```

```
LNDNNDQPTTHVFTVYVVDQVGNKVKKKLTVHFDPNYVAPEEVSNTDTSNN

SNTSGTVENLSSTTIEKSVTDVSTVQPKGETLTGKSFNLLHDAYIYNKDGQ

VVLSTDTNKTSLLKKGQRITALDNGKTVVINGVQYYRVGDNQFVKVANTVL

QAGKRLQLKHNAHLYDKNGKVVKRNGKTILLRNGRWISALNNADKYVIKGK

NFYKLANDQFVKVANTKLQKPKALKLTHNAFVYDKNGKRVKKSKVLKKGQT

ILAENNAEKFHIKGKFYYRVNGQFVKVANTL
```

The invention also provides a fragment of *Lactobacillus ultunensis* protease comprising the propeptide to the end of the B domain of the *Lactobacillus ultunensis* protease. This sequence comprises (or consists of) SEQUENCE ID NO. 24.

SEQUENCE ID NO. 24 has the following sequence.

```
DPDASDVQVKVVQQDQKQNQNTTANVVVSNSDSTKTQVNTTVQTQNSAVVS

GDSTTANPKTSQASNVQNTSTTANSVDPNQEQQPANQADHVKGNVQSAWDQ

GYRGQGTVVAVIDSGADPTHKDFQTMPEDPKLSKDDMQAKISKQGYGKYVN

EKFPVVYNYADRDNDYITSDDTNANDSPHGQHVSGIIAADGKPDGNKEYVV

GVAPEAQLMQLRVFGQFSDEKTDDVARAIYDATNLGADVIQMSLGQGVADQ

QLTNIEQKAVQYAIDHGVFVSISASNNGNSASVDNPSKVQDSGYQSGSQAG

NYEPLNSSTVANPGASKNALTVAAETSDTGDLSDMAYFSSWGPIQDFTLKP

DLAAPGYQVVSTVNHDQYQTMSGTSMAGPFAAASAALVIQRLKQTNPELKG

AQLVTAAKAMLMNTAKPQKQLGYTTPVSPRRQGAGQIDVGGATATPVYVTT

DDGTSSVSLHQVNENTKFTLTFHNLTDQNQTYTFDDYGGGYTEQRDTTTGV

FHDVQLAGARVNGENSFTLAPKEERKVSYSLDLTGLNKNQLVEGFLRFTNA

NNVSTVSVPYLAYYGDLTSENVFDQNANEEHPDIQGNRRLVNEQNYPRGIAD

QESLKELVNVDGNYNWQEVAKLYESGKVAFSPNDNQKSDLLKPYVYLKQNV

KDLKVEVLDAQGKVVRVVSDVQGVDKSYDENDVTKDTSLSVSMRDNPDAFE

WDGKVYNSKTGKMETAKDGNYTYRLVATLWNKGPHQVQTADFPVVVDTVAP

TLSNIKYDPASHTLSGEYQDTGAGFTNYSYATVTVNDKVFGYKLSDDESGF

DNTEKTKGHFNFVLGQDALSALTTATNKMTVALSDVADNTSLATVDVAGDH

DSETGVSIWNAVNGLAFDQKSPNYNSVTKTYILFGGANHDFYLNGKLVQVQ

NGKYQAPVSVDTTEFVFSTDPEGRHVLNSLSTVTAKAFFNWQKTDTFDGNF

GVTIGSVKTNDPNDTVVQAVVTKGQNVKAYAMDYFTGEVYTGEVKDGIATF

HVHTSVNQDNTTGVYKRALLTGWTEVDGPSFNDKQETSRGGVASSNHLGVY

YFADAADRPIYTDRSALGVEAKDEVAKLDSFGPGFYPGHAPSDLTTRTDPN

PDIHFDYMNDNDTTRFGQNAVTRGYYDPLTQKFMVTGKVDGNVASLTVLGD

NSNENAPENQVKLGNDGKFSFTVTANRTGQRPTAYIYQTKDGQRVRGTLNL

ILDTVAPSLEVNQVNGDKLELWTNNPKFILSGKVNDNLDGYRLFVNGNNIY

REFLNSGYNQVAGLNMDTEFTNPYGAHDFEEVENLNDNNDQPTTHVFTVYV

VDQVGNKVKKKLTVHFDPNYVAPEEVSNTDTSNNSNTSGTVENLSSTTIEK

SVTDVSTVQPKGETLTGKSFNLLHDAYIYNKDGQVVLSTDTNKTSLLKKGQ

RITALDNGKTVVINGVQYYRVGDNQFVKVANTVLQAGKRLQLKHNAHLYDK

NGKVVKRNGKTILLRNGRWISALNNADKYVIKGKNFYKLANDQFVKVANTK

LQKPKALKLTHNAFVYDKNGKRVKKSKVLKKGQTILAENNAEKFHIKGKFY

YRVNGQFVKVANTL
```

The protease of the invention (*Anaerofustis stercorihominis*) has a sequence comprising (or consisting of) SEQUENCE ID NO. 25.

SEQUENCE ID NO. 25 has the following sequence.

```
Protein sequence comprising the entire protease
protein
MKNKKIIYTLLSILLILLFTNTVYAQNKADERYDPNSVLVVFKDNISNSKK

SKILSNENLNIEETVDKKENIELVEVPKDSTVEETIRTLNEKNEVLYAQPN

FKYKALATTNDPLLSAQKHLTWTNISGSGTTAWNYSTGENTKIAIFDTGAY

TSNPDLSNIKGTYNASTGSSAKSSVVDYEGHGTHVAGIAAACGNNKSLGAG

VAYNSDLYIAKVADSNGDISSAYLIRAFDWAEEQGCRIINMSLGGYGYEYD

SDGKVNLDLLLKSRIDDAYNKSNNSILTVCAAGNGDDINGYPYYSYPSDFP

NSYSVVALQYDSNGNPTRAKYSDYNEYKDIAAPGSNINSLSNTSTSKLITE

SGTSMAAPFVSGVAGLIMSKVPDLTAKEVVDIINSTANKIGSYSYSKGRNN

YYGYGEINPLKAIKTAIWKKSSMTISKTSDIIGENKKLDITLNMYTEVPMK

VEVYDSNNNLINTLADKTFTAGETKLSWDYSNYKGDKYSIQATMPYKNSKD

KVIQSKTFNLCDLLDITGLSSSYTPLANTSITGNLNLNTDCTVSAGFYDKD

NKLVKTIYNKNTSLTKENKSFSWNYLDDNNKLIPSGTYEFKVSATSGDITK

EYSKNIKITIPEKASISKMSVTSSIKRNDFNKASIKYTLNNQCVTSIKIYN

SSNTLIKSISRNRKGSNTEYWNLKDSKGNLVVAGTYKIIISGYNIAGKFET

TKYIKITNPSKVSISKFKNKSKVIRASGYYTSTKFYLNEDARVKVLLTTTK

NKKLKTLKNVVMKKGTNTVKWNLKSTKGNVYKAGKYKIVVYATNSRNTYQK

SSYVTLVKKKPSIKVSKVKSSYKIRGSKNNPTIKVKTNITAKVTVRVYNRK

NKLIKTITKNKTYKTGTYKFKWNGKSGKNKKVSKTKYYFKVTIKNENGSKT

VKTKQFKYK
```

The invention also provides a fragment of *Anaerofustis stercorihominis* protease comprising the propeptide to the end of the B domain of the *Anaerofustis stercorihominis* protease. This sequence comprises (or consists of) SEQUENCE ID NO. 26.

SEQUENCE ID NO. 26 has the following sequence.

```
NKADERYDPNSVLVVFKDNISNSKKSKILSNENLNIEETVDKKENIELVEV

PKDSTVEETIRTLNEKNEVLYAQPNFKYKALATTNDPLLSAQKHLTWTNIS

GSGTTAWNYSTGENTKIAIFDTGAYTSNPDLSNIKGTYNASTGSSAKSSVV

DYEGHGTHVAGIAAACGNNKSLGAGVAYNSDLYIAKVADSNGDISSAYLIR

AFDWAEEQGCRIINMSLGGYGYEYDSDGKVNLDLLLKSRIDDAYNKSNNSI

LTVCAAGNGDDINGYPYYSYPSDFPNSYSVVALQYDSNGNPTRAKYSDYNE

YKDIAAPGSNINSLSNTSTSKLITESGTSMAAPFVSGVAGLIMSKVPDLTA

KEVVDIINSTANKIGSYSYSKGRNNYYGYGEINPLKAIKTAIWKKSSMTIS

KTSDIIGENKKLDITLNMYTEVPMKVEVYDSNNNLINTLADKTFTAGETKL

SWDYSNYKGDKYSIQATMPYKNSKDKVIQSKTFNLCDLLDITGLSSSYTPL
```

ANTSITGNLNLNTDCTVSAGFYDKDNKLVKTIYNKNTSLTKENKSFSWNYL

DDNNKLIPSGTYEFKVSATSGDITKEYSKNIKITIPEKASISKMSVTSSIK

RNDFNKASIKYTLNNQCVTSIKIYNSSNTLIKSISRNRKGSNTEYWNLKDS

KGNLVVAGTYKIIISGYNIAGKFETTKYIKITNPSKVSISKFKNKSKVIRA

SGYYTSTKFYLNEDARVKVLLTTTKNKKLKTLKNVVMKKGTNTVKWNLKST

KGNVYKAGKYKIVVYATNSRNTYQKSSYVTLVKKKPSIKVSKVKSSYKIRG

SKNNPTIKVKTNIIAKVTVRVYNRKNKLIKTITKNKTYKTGTYKFKWNGKS

GKNKKVSKTKYYFKVTIKNENGSKTVKTKQFKYK

The protease of the invention (*Paenisporosarcina* sp. HGH0030) may have a sequence comprising (or consisting of) SEQUENCE ID NO. 27.

SEQUENCE ID NO. 27 has the following sequence.

```
Protein sequence comprising the entire protease
protein
MNIKKQLKIFLFAYIFFWLPAQFAGAEEEIKVEPKISKFNIEALFDDSKDFY

SNQLIVTFKASPTGSERKQILDSVNAKELSIQVNGKFALVSTPKSSDLSAV

AKELLKHKQVEFVEPNYQLENTFRPKDPSYSKQWHLKKIHASSAWDQTKGR

SGVIVAVIDEGVQTNHPDLKGKFVSPYNAVTGGTSFYSGDHATHVAGIIAA

SFNNSGGAGVAPNIKIMPINVFTGDSASSYDVGEAIIYAADHHADIINLSL

GGSYTYAMDYATQYAKAKDVLIIAAAGNERSYELSYPAALDGVIGVSATDS

NDEITDFSNYGSYIDLAAPGEGIFSSLSGSKYGAMDGTSMAAPVVSGVAAL

VLSKNPLLTSDQLEKILTKSSVDLYHRGWDDFYGYGRVDAYRALQFTTSAI

SNLKLSSTKFTMNGSNKTAFSFEGVKGSKISLYLQNSKGTTIKKIVSYKDW

SGGKFSASWDGRMDNGMYASTGTYKIIAAVSGNGENLHLSATLKVIDKIVP

SINLSGSVNYSPTVTGKLTVPYELNKNAKVTAFIKDKNNKIIKSILNNSSV

SRGQRTVQWDGKDSEGNRVKDGVYSLEMSLVDANKIKGTSRKFSITVDTII

PTAKIALSSELMKLNGSLLNMGKIDVSETVFLTTYIANDNGVKVRKIDTEK

SIKKGAYSLNWDGKNENSEFVAEGNYHLLFELLDSAGNKASLKSTTFAFQD

WNQPVIEGDANYFFTSDGKQTFSYKLSKPGIVTIQLFKNDNLVSTIEQNVP

KSQGNQSFVWDGKDQSGTILPDGQYSYKISIVDAYNLSQTYKGIMNIALTQ

IEIQYPTVVQFIDDDTAEIFYKLSQQANVTIEIYEGNAKIRTIISDKKTDK

GINHFIWDGYDDNGDLVYSDELIYKIKVINTSGNEQTVLGKITNDDLPIWL

VDHKYTFSSSDNYSTYYTHLKLTLVVKAPVKVELFVWDSYNDLIDEKEYNL

KNGINNLVYTKFPVASVNTYGLLYTDSLGNQYFFTIEEAY
```

The invention also provides a fragment of *Paenisporosarcina* sp. HGH0030 protease comprising the propeptide to the end of the B domain of the *Paenisporosarcina* sp. HGH0030 protease. This sequence comprises (or consists of) SEQUENCE ID NO. 28.

SEQUENCE ID NO. 28 has the following sequence.

```
EEIKVEPKISKFNIEALFDDSKDFYSNQLIVTFKASPTGSERKQILDSVNA

KELSIQVNGKFALVSTPKSSDLSAVAKELLKHKQVEFVEPNYQLENTFRPK

DPSYSKQWHLKKIHASSAWDQTKGRSGVIVAVIDEGVQTNHPDLKGKFVSP
```

```
YNAVTGGTSFYSGDHATHVAGIIAASFNNSGGAGVAPNIKIMPINVFTGDS

ASSYDVGEAIIYAADHHADIINLSLGGSYTYAMDYATQYAKAKDVLIIAAA

GNERSYELSYPAALDGVIGVSATDSNDEITDFSNYGSYIDLAAPGEGIFSS

LSGSKYGAMDGTSMAAPVVSGVAALVLSKNPLLTSDQLEKILTKSSVDLYH

RGWDDFYGYGRVDAYRALQFTTSAISNLKLSSTKFTMNGSNKTAFSFEGVK

GSKISLYLQNSKGTTIKKIVSYKDWSGGKFSASWDGRMDNGMYASTGTYKI

IAAVSGNGENLHLSATLKVIDKIVPSINLSGSVNYSPTVTGKLTVPYELNK

NAKVTAFIKDKNNKIIKSILNNSSVSRGQRTVQWDGKDSEGNRVKDGVYSL

EMSLVDANKIKGTSRKFSITVDTIIPTAKIALSSELMKLNGSLLNMGKIDV

SETVFLTTYIANDNGVKVRKIDTEKSIKKGAYSLNWDGKNENSEFVAEGNY

HLLFELLDSAGNKASLKSTTFAFQDWNQPVIEGDANYFFTSDGKQTFSYKL

SKPGIVTIQLFKNDNLVSTIEQNVPKSQGNQSFVWDGKDQSGTILPDGQYS

YKISIVDAYNLSQTYKGIMNIALTQIEIQYPTVVQFIDDDTAEIFYKLSQQ

ANVTIEIYEGNAKIRTIISDKKTDKGINHFIWDGYDDNGDLVYSDELIYKI

KVINTSGNEQTVLGKITNDDLPIWLVDHKYTFSSSDNYSTYYTHLKLTLVV

KAPVKVELFVWDSYNDLIDEKEYNLKNGINNLVYTKFPVASVNTYGLLYTD

SLGNQYFFTIEEAY
```

The protease of the invention (*Actinomyces* sp. ICM47) may have a sequence comprising (or consisting of) SEQUENCE ID NO. 29.

SEQUENCE ID NO. 29 has the following sequence.

```
Protein sequence comprising the entire protease
protein
MTPKKPAKLFAIAGACAVAIALPTSLAMPGSLLHQAGSDADAAQSAQSAAD

EAAASEPAPELPVGDVDNALTSADGESLLDEGDPATTEEDSSTVVDMIVQL

EDGTDTAAALASINSAVAAAYPDASAEVSREYTNAFTGFALSAPIGSMDAI

RGVSGVQSAFLDHETQVSDEGDDTPADAEGTGGADASADSGSAADAESNPM

AAMRAAQHGDVLSAQVMMKADKISQTGAGKVVAIIDTGVDMSHPAFAGGLH

GTPAIDSSKGASLARQVGKSGTYVNQKFPFAYDYADGDNDASPAGSHGTHV

AGITAANGSQITGIAPDAQIIVGKVARSRGGIPDSALLAALDDMAVIKPDV

VNLSLGRTAGMDSAADTLFAGVYEKLQNNGTIVDVAAGNEYSAAYGNKSGK

NLPYASDPDSSTLGEPSTFAPVVSVASIENARNGRGAYKMSDFSSWGVSPD

MRLKPEVTAPGGNIYSSVPGGGYQYMSGTSMATPQITGVSAVVLERVQNDP

LFSSMSARQKADVVQNLIMGTAVPVADPNASSGAYYSPRKQGAGLVNVQAA

TTSSVYPTVNGAADSSRPKAELGDGTKGWHFDVTLHNMSGTAATYDLSAQA

LSENISGGLFTGSSTDWNGKGVSVSFSNNSVTVPAKGEATVGIDVTPGSQF

AQWVSANAPSGTFLDGFVRFTARTNGQSDMTVPYLGFYGSWGTPSIFDQML

SEGDGHAASSAIYNGQNGSLLGYNPLVKGSEREGRPNADRYVISRSTASGA

PTAITPRTGTLRSVHTMTTTYANEAGKSVASFTSTQNWKSVYNSDERRMTW

VEENHESRSINLNDYKYSRLPDGKYTLTISASNDGPSPTKQSLTYNFRVDT

KAPVVERATLSNGGSTLNVEISDESPLAGFTVNDPNSGQYIYRDVIRNDAD

QTYSNGRYHYTATVDMSRVSGGNSSKPYVLAWDYGLNHSKATTIGAATGNG
```

-continued

GGNDGGNTGDQPGNGGGDNGGNTGDQPGNGGGNDGGNTGDQPGNGGGDGGG

IGGNVCSPSMGGRWVTDGYRWAWQCNNGAYLRNGWYLIDGRYYYFDGNGYM

RSGWVRGRGSWYYLGNNGAMQTGWVKIGGRWYYLGSDGAMYSGTRTIDGNS

YEFSESGEWIK

The invention also provides a fragment of *Actinomyces* sp. ICM47 protease comprising the propeptide to the end of the B domain of the *Actinomyces* sp. ICM47 protease. This sequence comprises (or consists of) SEQUENCE ID NO. 30.

SEQUENCE ID NO. 30 has the following sequence.

PGSLLHQAGSDADAAQSAQSAADEAAASEPAPELPVGDVDNALTSADGESL

LDEGDPATTEEDSSTVVDMIVQLEDGTDTAAALASINSAVAAAYPDASAEV

SREYTNAFTGFALSAPIGSMDAIRGVSGVQSAFLDHETQVSDEGDDTPADA

EGTGGADASADSGSAADAESNPMAAMRAAQHGDVLSAQVMMKADKISQTGA

GKVVAIIDTGVDMSHPAFAGGLHGTPAIDSSKGASLARQVGKSGTYVNQKF

PFAYDYADGDNDASPAGSHGTHVAGITAANGSQITGIAPDAQIIVGKVARS

RGGIPDSALLAALDDMAVIKPDVVNLSLGRTAGMDSAADTLFAGVYEKLQN

NGTIVDVAAGNEYSAAYGNKSGKNLPYASDPDSSTLGEPSTFAPVVSVASI

ENARNGRGAYKMSDFSSWGVSPDMRLKPEVTAPGGNIYSSVPGGGYQYMSG

TSMATPQITGVSAVVLERVQNDPLFSSMSARQKADVVQNLIMGTAVPVADP

NASSGAYYSPRKQGAGLVNVQAATTSSVYPTVNGAADSSRPKAELGDGTKG

WHFDVTLHNMSGTAATYDLSAQALSENISGGLFTGSSTDWNGKGVSVSFSN

NSVTVPAKGEATVGIDVTPGSQFAQWVSANAPSGTFLDGFVRFTARTNGQS

DMTVPYLGFYGSWGTPSIFDQMLSEGDGHAASSAIYNGQNGSLLGYNPLVK

GSEREGRPNADRYVISRSTASGAPTAITPRTGTLRSVHTMTTTYANEAGKS

VASFTSTQNWKSVYNSDERRMTWVEENHESRSINLNDYKYSRLPDGKYTLT

ISASNDGPSPTKQSLTYNFRVDTKAPVVERATLSNGGSTLNVEISDESPLA

GFTVNDPNSGQYIYRDVIRNDADQTYSNGRYHYTATVDMSRVSGGNSSKPY

VLAWDYGLNHSKATTIGAATGNGGGNDGGNTGDQPGNGGGDNGGNTGDQPG

NGGGNDGGNTGDQPGNGGGDGGGIGGNVCSPSMGGRWVTDGYRWAWQCNNG

AYLRNGWYLIDGRYYYFDGNGYMRSGWVRGRGSWYYLGNNGAMQTGWVKIG

GRWYYLGSDGAMYSGTRTIDGNSYEFSESGEWIK

The protease of the invention (*Actinomyces georgiae* F0490) may have a sequence comprising (or consisting of) SEQUENCE ID NO. 31.

SEQUENCE ID NO. 31 has the following sequence.

Protein sequence comprising the entire protease protein
MPTRRTNALASLIASSSLLLASAVALPAQAFSPPGEDDQGRGSPATSQAAA

DTALTSKADYENGTGPGPVDDTQSDAAEPDGTGGHAPDEGVRIIVQFEDGV

SESDCDEMVDRIGEAVAASVPSAAAGGPAVTRARDYRNVFIGVAIDAPAAA

LPVIQGVDGMKSAFIEREGHIETDESEQPGGPSGNSSPAHEAGAAGSGSAS

AAGSPSPADAPSPADTPSSGGAASNGDDAPSGAPASGAAPSQDPAADSGNV

EGTAGSLAAEGIDPSNRSAHQMMRMDRVPHKGEGRVIAFLDTGLEVAHPAF

SGAVDASKTALKRADVEQALPRLGEGKDGRYVNDKIPFAYDYADDDADVAP

SSGAGGFHGTHVAGIAAANADRIRGTASGAQIIVAKVARSGNGSLPDSAVL

AALDDMAVLRPDVINLSIGWSAGMDNAADSLYSTVYARLQEAGVTVDAAAG

NAYSAGRGNNSGKNLPYASDPDSSVMDEPATYSSAVAVASVDNAPANGAYK

ASDFSAWGVSPDLRLKPEIASPGGGVVSAVPGGAYDQASGTSMATPQMAGI

SAIVLERVNTDPLFASMSAAERMGVAQSLIMGTAHPLVDADQGTGAFYSPR

KQGAGLVDALAATTSPVYPTVDGAAEPSRPKADLGDGTAGWSFTITVHNLS

DSAKSYALSSQALSEAVEGGFFTLRSKDWRGRGISVSYSGAAVAGSGEGAT

LAVPASGQASVTVSVSPGADFASYAAANAPKGTFIDGFVRLVAQGGSGPDL

SVPYLGFYGSWGAADVFDAKASDAAASPAHIYPSAFVDSRTGRSLGANPFA

PQNTETIPDPGRYVVSRAASSLATRRAEPRTGLLRSVHTLTSTYANEAGTT

VLEYRNYQNYKSVRNANGTVSRAESYHLAPVFDSEDKQVAGLPDGKYTLTI

AATTSGPSPTRHAIAYDFALDTTAPRVTVRGVSGEGAGAKVAFDVTDASPL

AAFDFHDPSNGTWYYRELVNDDGTVNPDGSHTYHFEVSASALQAAWEAQHG

KGAAPSEPYVLAWDWGANPSDKAVVRFPGTTSGAWTHDSHGWWYRLSDGSW

PSSTSMVIDGATYRFDASGYMRTGWVSEAGSWYYHLPSGAMAKGWANVGGT

WYYLSSGTGAMATGWLNQGGTWYYLAASGAMATGWADVGGTWYYFSSSGAM

ATGWKWIDGAWYQFSSSGAWTG

The invention also provides a fragment of *Actinomyces georgiae* F0490 protease comprising the propeptide to the end of the B domain of the *Actinomyces georgiae* F0490 protease. This sequence comprises (or consists of) SEQUENCE ID NO. 32.

SEQUENCE ID NO. 32 has the following sequence.

PPGEDDQGRGSPATSQAAADTALTSKADYENGTGPGPVDDTQSDAAEPDGT

GGHAPDEGVRIIVQFEDGVSESDCDEMVDRIGEAVAASVPSAAAGGPAVTR

ARDYRNVFIGVAIDAPAAALPVIQGVDGMKSAFIEREGHIETDESEQPGGP

SGNSSPAHEAGAAGSGSASAAGSPSPADAPSPADTPSSGGAASNGDDAPSG

APASGAAPSQDPAADSGNVEGTAGSLAAEGIDPSNRSAHQMMRMDRVPHKG

EGRVIAFLDTGLEVAHPAFSGAVDASKTALKRADVEQALPRLGEGKDGRYV

NDKIPFAYDYADDDADVAPSSGAGGFHGTHVAGIAAANADRIRGTASGAQI

IVAKVARSGNGSLPDSAVLAALDDMAVLRPDVINLSIGWSAGMDNAADSLY

STVYARLQEAGVTVDAAAGNAYSAGRGNNSGKNLPYASDPDSSVMDEPATY

SSAVAVASVDNAPANGAYKASDFSAWGVSPDLRLKPEIASPGGGVVSAVPG

GAYDQASGTSMATPQMAGISAIVLERVNTDPLFASMSAAERMGVAQSLIMG

TAHPLVDADQGTGAFYSPRKQGAGLVDALAATTSPVYPTVDGAAEPSRPKA

DLGDGTAGWSFTITVHNLSDSAKSYALSSQALSEAVEGGFFTLRSKDWRGR

GISVSYSGAAVAGSGEGATLAVPASGQASVTVSVSPGADFASYAAANAPKG

TFIDGFVRLVAQGGSGPDLSVPYLGFYGSWGAADVFDAKASDAAASPAHIY

PSAFVDSRTGRSLGANPFAPQNTETIPDPGRYVVSRAASSLATRRAEPRTG

-continued
LLRSVHTLTSTYANEAGTTVLEYRNYQNYKSVRNANGTVSRAESYHLAPVF

DSEDKQVAGLPDGKYTLTIAATTSGPSPTRHAIAYDFALDTTAPRVTVRGV

SGEGAGAKVAFDVTDASPLAAFDFHDPSNGTWYYRELVNDDGTVNPDGSHT

YHFEVSASALQAAWEAQHGKGAAPSEPYVLAWDWGANPSDKAVVRFPGTTS

GAWTHDSHGWWYRLSDGSWPSSTSMVIDGATYRFDASGYMRTGWVSEAGSW

YYHLPSGAMAKGWANVGGTWYYLSSGTGAMATGWLNQGGTWYYLAASGAMA

TGWADVGGTWYYFSSSGAMATGWKWIDGAWYQFSSSGAWTG

The protease of the invention (*Actinomyces* sp. *oral taxon* 877 str. F0543) has a sequence comprising (or consisting of) SEQUENCE ID NO. 33.

SEQUENCE ID NO. 33 has the following sequence.

MPTRRTNALAALLASSSLLLASAVALPAQSFPPPGGDDQGQGSPATSQAAA

DTALTSKADYENGAGPGPADEAHPYGAQSDASQPDAPQSDASQPDGAEGHA

PEEGVRIIVQFADEASESDCDELVDRIGEAVAASVPAAAGGPAITRARDYR

NVFTGVAIDAPAASLPVVQGVDGVKSAFIEREGHIEGDESEQPGGPSGNGG

PAHEAGADGSGSASAAHSPSPAHSPSPAGIPPSGDAASNGDGAPSGAPASG

ASPSPAATPSQDAAAGSGNVEGGADSLAAEGIDPSNRSAHLMMRMDHVSHK

GEGRVIAFLDTGLEVAHPAFSGAVDASKTALKRADVEQVLPRLGEGKDGHY

VNDKIPFVYDYADDDADVAPSSGPGGFHGTHVAGIAAANADRIRGTAPGAQ

IIVAKVARSGNGSLPDSAVLAALDDMAVLRPDVVNLSIGWSAGMDNAADSL

YSTVYASLQGAGVTVNAAAGNSYSAGRGNRSGKNLPYASDPDSSVMDEPAT

YSSAVAVASVDNAPANGAYRASDFSAWGVSPDLRLKPEIASPGGGVVSAVP

GGAYDQASGTSMATPQMAGISAIVLERVSTDPLFAGMSAAERTGVAQSLIM

GTAHPLVDADQGTGAFYSPRKQGAGLVDALAATTSPVYPTVDGAAEPSRPK

ADLGDGTAGWSFTITVHNLSDSAKSYALSSQALSEAVEGGFFTLHSTDWRG

RGVSVSYSGAAVAGSGEGAALTVPASGRASVTVSVAPGAAFASYANANAPK

GTFIDGFVRLAAQNGSGPDLSVPYLGFYGSWGAADVFDAKASDAAVSPAHI

YPSAFVDSRTGRPLGANPLAPRNTETVPDPGRYVVSRAASSLATRRAEPRT

GLLRSVHTLTSTYANEAGATVREYTNYQNYKSVRNANGTVSRAESYHLAPV

FDSEDQVGAGLPDGKYTLTIAATTSGPSPTRHAISYDFALDTTAPRVTVRG

VIGEGAGAKVAFDVTDASPLAAFDFHDPSNGTWYYRELVNDDGTVNPDGSH

TYHFEVSASALQAAWEAQRGKGAAPSQPYVLAWDWGVNPSDKTVVRFPGTT

SGAWTHDSHGWWYRLPDGSWPSSTSMVIDGETYRFDASGYMRTGWVGEAGS

WYYHLPSGAMAKGWAHDSGSWYYLSPGTGAMATGWIEQGGTWYYLSPGTGA

MATGWTNVGGTWYYFSSSGAMATGWLKVGGTWYYLAPSGAMATGWTNIDGT

WYYFSSSGAWTG

The invention also provides a fragment of *Actinomyces* sp. *oral taxon* 877 str. F0543 protease comprising the propeptide to the end of the B domain of the *Actinomyces* sp. *oral taxon* 877 str. F0543 protease. This sequence comprises (or consists of) SEQUENCE ID NO. 34.

SEQUENCE ID NO. 34 has the following sequence.

PPGGDDQGQGSPATSQAAADTALTSKADYENGAGPGPADEAHPYGAQSDAS

QPDAPQSDASQPDGAEGHAPEEGVRIIVQFADEASESDCDELVDRIGEAVA

ASVPAAAGGPAITRARDYRNVFTGVAIDAPAASLPVVQGVDGVKSAFIERE

GHIEGDESEQPGGPSGNGGPAHEAGADGSGSASAAHSPSPAHSPSPAGIPP

SGDAASNGDGAPSGAPASGASPSPAATPSQDAAAGSGNVEGGADSLAAEGI

DPSNRSAHLMMRMDHVSHKGEGRVIAFLDTGLEVAHPAFSGAVDASKTALK

RADVEQVLPRLGEGKDGHYVNDKIPFVYDYADDDADVAPSSGPGGFHGTHV

AGIAAANADRIRGTAPGAQIIVAKVARSGNGSLPDSAVLAALDDMAVLRPD

VVNLSIGWSAGMDNAADSLYSTVYASLQGAGVTVNAAAGNSYSAGRGNRSG

KNLPYASDPDSSVMDEPATYSSAVAVASVDNAPANGAYRASDFSAWGVSPD

LRLKPEIASPGGGVVSAVPGGAYDQASGTSMATPQMAGISAIVLERVSTDP

LFAGMSAAERTGVAQSLIMGTAHPLVDADQGTGAFYSPRKQGAGLVDALAA

TTSPVYPTVDGAAEPSRPKADLGDGTAGWSFTITVHNLSDSAKSYALSSQA

LSEAVEGGFFTLHSTDWRGRGVSVSYSGAAVAGSGEGAALTVPASGRASVT

VSVAPGAAFASYANANAPKGTFIDGFVRLAAQNGSGPDLSVPYLGFYGSWG

AADVFDAKASDAAVSPAHIYPSAFVDSRTGRPLGANPLAPRNTETVPDPGR

YVVSRAASSLATRRAEPRTGLLRSVHTLTSTYANEAGATVREYTNYQNYKS

VRNANGTVSRAESYHLAPVFDSEDQVGAGLPDGKYTLTIAATTSGPSPTRH

AISYDFALDTTAPRVTVRGVIGEGAGAKVAFDVTDASPLAAFDFHDPSNGT

WYYRELVNDDGTVNPDGSHTYHFEVSASALQAAWEAQRGKGAAPSQPYVLA

WDWGVNPSDKTVVRFPGTTSGAWTHDSHGWWYRLPDGSWPSSTSMVIDGET

YRFDASGYMRTGWVGEAGSWYYHLPSGAMAKGWAHDSGSWYYLSPGTGAMA

TGWIEQGGTWYYLSPGTGAMATGWTNVGGTWYYFSSSGAMATGWLKVGGTW

YYLAPSGAMATGWTNIDGTWYYFSSSGAWTG

The protease of the invention (*Actinomyces* sp. ICM47) may have a sequence comprising (or consisting of) SEQUENCE ID NO. 35.

SEQUENCE ID NO. 35 has the following sequence.

MTLKKPAKLTAIAGACAVAVALPTSLALPGSFGPEADSDPEAAQSAAGVVA

QPEPEPELPVGNAENALTSEEGEQVVDGETQASTDDGSSRVVDMIVQLKDG

TDTAAALASINSAVAAAYPDASAEVKREYSNTFTGFALSAPIGSMDAIRGV

SGVQSAFLDRETQVSDDANGDSDDAGSGSATTASRSQHPDNLSAQIMMHAD

KVTQKGEGKVVAIIDTGVEMNHPAFSGALHGTPAIDSSKGASLAQQVGKSG

TYVSEKFPFAYDYADGDNDASPAGAHGTHVAGITAANGDQIMGIAPDAQII

VAKVARSRGGGIPDSALLAALDDMATLHPDAVNMSLGRTAGMDSDADTLFA

GVYEKLQEKGITLDVAGGNEFQAGYGNKSGKNLPYASDPDSSTLGEPGSFA

PVVVTVASIENARNGANGNYKMSDFSSWGVSPDMRLKPEVTAPGGNIYSSVP

GGGYQMMSGTSMATPQMTGASAVVLERVQNDPLFSSLNDRQKVDVVQNLIM

-continued

```
GTAVPVVDPGQGGGAYYSPRKQGAGLANLEGATTSSVYPTVNGAADSSRPK

AELGDGTNGWHFDVTLHNVSDTPATYELSSQALSENTEGGFFTGHSTDWNG

KGVSVSFSGSSVTVPAKGETTVGIDIKPGNEFAQYVSANAPAGTFLDGFVR

FTSRTNGQPDLGVPFLGFYGSWAKPAIFDALVSEGDAHAASSGIYNGDRGG

LLGYNPLLKGRERQGRPNAERYVVSRSTVSGAPTAISPRTGTLRSVHKMTT

TYTNEAGKSVASFTSFQNFKSTIDPEEERMSWVEEGQEPRSIDLKEGKYAS

LPDGNYKLTIAANNDGPSSTEQSITYNFRIDTKAPVVDSAKVNGSTLSVEL

SDESPLAGFTLNDPNSGRYIHLEVARDENSQTYENGRYHYKTSIDLNQVQG

GASNNPYVVAWDYGLNHSEPVTMNGGKPGNGGGQPGVGDDQPGNGGGQPGV

GDDQPGNGGGQPGNGGGQPGDDWGDDQPGNGGGQPGDDWGNGGGQPGDDWG

NGGGQPGNGGGQPGDGWDNGGGQPGGGWDNGGGQPGGNPGNGGNSGYCDFL

NGYWLSDPVGWWQKCVSGKSLPRNQWSNIGGKDYFVGPDGNAQTGWLNQGD

TWYYLDPSNGGSMCTGTRNIDGKTYTFDNSGALVK
```

The invention also provides a fragment of *Actinomyces* sp. ICM47 protease comprising the propeptide to the end of the B domain of the *Actinomyces* sp. ICM47 protease. This sequence comprises (or consists of) SEQUENCE ID NO. 36.

SEQUENCE ID NO. 36 has the following sequence.

```
PGSFGPEADSDPEAAQSAAGVVAQPEPEPELPVGNAENALTSEEGEQVVDG

ETQASTDDGSSRVVDMIVQLKDGTDTAAALASINSAVAAAYPDASAEVKRE

YSNTFTGFALSAPIGSMDAIRGVSGVQSAFLDRETQVSDDANGDSDDAGSG

SATTASRSQHPDNLSAQIMMHADKVTQKGEGKVVAIIDTGVEMNHPAFSGA

LHGTPAIDSSKGASLAQQVGKSGTYVSEKFPFAYDYADGDNDASPAGAHGT

HVAGITAANGDQIMGIAPDAQIIVAKVARSRGGGIPDSALLAALDDMATLH

PDAVNMSLGRTAGMDSDADTLFAGVYEKLQEKGITLDVAGGNEFQAGYGNK

SGKNLPYASDPDSSTLGEPGSFAPVVTVASIENARNGANGNYKMSDFSSWG

VSPDMRLKPEVTAPGGNIYSSVPGGGYQMMSGTSMATPQMTGASAVVLERV

QNDPLFSSLNDRQKVDVVQNLIMGTAVPVVDPGQGGGAYYSPRKQGAGLAN

LEGATTSSVYPTVNGAADSSRPKAELGDGTNGWHFDVTLHNVSDTPATYEL

SSQALSENTEGGFFTGHSTDWNGKGVSVSFSGSSVTVPAKGETTVGIDIKP

GNEFAQYVSANAPAGTFLDGFVRFTSRTNGQPDLGVPFLGFYGSWAKPAIF

DALVSEGDAHAASSGIYNGDRGGLLGYNPLLKGRERQGRPNAERYVVSRST

VSGAPTAISPRTGTLRSVHKMTTTYTNEAGKSVASFTSFQNFKSTIDPEEE

RMSWVEEGQEPRSIDLKEGKYASLPDGNYKLTIAANNDGPSSTEQSITYNF

RIDTKAPVVDSAKVNGSTLSVELSDESPLAGFTLNDPNSGRYIHLEVARDE

NSQTYENGRYHYKTSIDLNQVQGGASNNPYVVAWDYGLNHSEPVTMNGGKP

GNGGGQPGVGDDQPGNGGGQPGVGDDQPGNGGGQPGNGGGQPGDDWGDDQP

GNGGGQPGDDWGNGGGQPGDDWGNGGGQPGNGGGQPGDGWDNGGGQPGGGW

DNGGGQPGGNPGNGGNSGYCDFLNGYWLSDPVGWWQKCVSGKSLPRNQWSN

IGGKDYFVGPDGNAQTGWLNQGDTWYYLDPSNGGSMCTGTRNIDGKTYTFD

NSGALVK
```

The protease of the invention (*Lactobacillus acidophilus* ATCC 4796) may have a sequence comprising (or consisting of) SEQUENCE ID NO. 37.

SEQUENCE ID NO. 37 has the following sequence.

```
MRNKKVGSVTTDYSYLNQSRNHLNLVTGKENDSKLKIWRKNFATAAIIALA

SGTTMLFSAHSVKADEVDDITVQNDKQVNTTIVQNNKDQQSSDTQQNVNEN

RASSQQAIRRPGTGNKLTDQWPDNYQSDQQNNSSQAETTKISTTGYSNQTE

QQSNNTVPSTVASSTVYKESSDDQAGQKDTNGVELPANNQDHIKGNVQDAW

DQGYKGQHTVVAVIDSGVDTSHKDFQTMPENPKLSQAETEALIAKLGYGTY

INSKFPFVYNAVDHENQSMKGPDGEPHGQHVSGIIAADGQPNGDQEYVVGV

APEAQLMHFKVFGDNATSLDLAQEIYDATNLGADVIQMSLGGGVAAADLNV

ADQRAVQYAIDHGVIVSISASNNGNAASIQNPSNVTDLDNYEAGTHVGNYE

PFSSSTVADPGAARGAITGAAETSGLGDKSDMATFTSWGPLPDFTLKPDVS

APGSNVISLANDNGYTTMSGTSMAGPFIAGAAALVRQRLQQTNPELKGADL

VAAVKALLMNTADPQIQQGFTTIVSPRRQGAGQINVGAATKAPVYILANDG

TGSVSLRNIKETTNFELTFHNLTDNTETYTFDDLGGGFTEVRDTDTGLFHD

VQLAGARVTGPNTITVNPKETKKIVFTLNLTGLKQNQLVEGYLNFTNSKDK

LSLSVPYLGYYGDMTSEDVFDKKANEDKPDIKGNRLTNEDNYPRGIADEES

LKELVNIEGNYNWQEVAKLYESGKVAFSPNGDNKSDLIMPYVYLKQNLQDL

KVEILDAKGNVVRVLADAHGVQKSYNEDGTGTVDALISVDSGKFNWDGKVY

NYKTGKMEVAPDGQYTYRFVATLYNDGPHKVQTNDTSVIIDTTAPILKDVE

YDVTTKTITGTYSDAGAGFTDYSYATVTINDRVFGFKLNDNDNSTFDNTDK

TIGHFSFALTPLEQQALTAAHNKVSVCLSDVADNTAVKTLDVASVGDGNKT

ATWNAVNGVPFNSNSQDYSDKNNSYLLRGSATENFYVNGKLVQVAPNGEFV

LPVSLDEQNLVFTSDENGQNVLRQFTTYTPKADFAWQHIDGSERSFGVSVY

SIDAADPNDAIVQAAVPKGNNVKAFAKDYFTGETYVGEVKDGVATFHIHTS

INPDPQTGINRRALLQGWVEIDGPTYNAKQVTDPTAISDRNYIGVYYKPDA

SSHVYSNRDELGVDDFTDEQADVSDFGPSKFLYPGHNAPSDGNANISFDYV

NDNNISTFGQEAVKAGYYDPIAKVFTITGHVDKDVVSLVALQDNPNEDAPE

NRVAIDKDGNFIIKFHMDDPSTRQLTYIYKVKDSSTDKIDTVKGSITLILD

TVLPTLHVDQLNGADNLTITTNNPTFKISGNANDDLDDYSVYINGDNVFTQ

FNGSSFNYIPGMYGDPNQKTPNLYGGYDFEQEVNLDDENGKPTTHIFNIEL

IDQVGNKVFKTLTVNYDPNATNSEDPSNGTGDSGIEVVPTVPRKVQPLSDD

NSTNINDKQTLSTELTITLPRNIFAFDYQGKVARKHGKDIILKKGVVLYNP

KEVNIRKHKYYKVSKNVYIKVTSTRVNKKLKRLILIKNSYVYNLNGKANKV

HNKRVLLKRGLAVDVLHGGKITKVGKYDCYQIGINQYIKVANTALK
```

The invention also provides a fragment of *Lactobacillus acidophilus* ATCC 4796 protease comprising the propeptide to the end of the B domain of the *Lactobacillus acidophilus* ATCC 47967 protease. This sequence comprises (or consists of) SEQUENCE ID NO. 38.

SEQUENCE ID NO. 38 has the following sequence.

DGTDTAAALASINSAVAAAYPDASAEVKREYSNTFTGFALSAPIGSMDAIR
GVSGVQSAFLDRETQVSDDANGDSDDAGSGSATTASRSQHPDNLSAQIMMH
ADKVTQKGEGKVVAIIDTGVEMNHPAFSGALHGTPAIDSSKGASLAQQVGK
GSGTYVSEKFPFAYDYADGDNDASPAGAHGTHVAGITAANGDQIMGIAPDA
QIIVAKVARSRGGIPDSALLAALDDMATLHPDAVNMSLGRTAGMDSDADTL
FAGVYEKLQEKGITLDVAGGNEFQAGYGNKSGKNLPYASDPDSSTLGEPGS
FAPVVTVASIENARNGANGNYKMSDFSSWGVSPDMRLKPEVTAPGGNIYSS
VPGGGYQMMSGTSMATPQMTGASAVVLERVQNDPLFSSLNDRQKVDVVQNL
IMGTAVPVVDPGQGGGAYYSPRKQGAGLANLEGATTSSVYPTVNGAADSSR
PKAELGDGTNGWHFDVTLHNVSDTPATYELSSQALSENTEGGFFTGHSTDW
NGKGVSVSFSGSSVTVPAKGETTVGIDIKPGNEFAQYVSANAPAGTFLDGF
VRFTSRTNGQPDLGVPFLGFYGSWAKPAIFDALVSEGDAHAASSGIYNGDR
GGLLGYNPLLKGRERQGRPNAERYVVSRSTVSGAPTAISPRTGTLRSVHKM
TTTYTNEAGKSVASFTSFQNFKSTIDPEEERMSWVEEGQEPRSIDLKEGKY
ASLPDGNYKLTIAANNDGPSSTEQSITYNFRIDTKAPVVDSAKVNGSTLSV
ELSDESPLAGFTLNDPNSGRYIHLEVARDENSQTYENGRYHYKTSIDLNQV
QGGASNNPYVVAWDYGLNHSEPVTMNGGKPGNGGGQPGVGDDQPGNGGGQP
GVGDDQPGNGGGQPGNGGGQPGDDWGDDQPGNGGGQPGDDWGNGGGQPGDD
WGNGGGQPGNGGGQPGDGWDNGGGQPGGGWDNGGGQPGGNPGNGGNSGYCD
FLNGYWLSDPVGWWQKCVSGKSLPRNQWSNIGGKDYFVGPDGNAQTGWLNQ
GDTWYYLDPSNGGSMCTGTRNIDGKTYTFDNSGALVK

The protease of the invention (*Lactobacillus brevis* subsp. *gravesensis* ATCC 27305) may have a sequence comprising (or consisting of) SEQUENCE ID NO. 39.

SEQUENCE ID NO. 39 has the following sequence.

MKRLCIKKGFIGVFVSAGILLTLGLLIGFSSPVGAGRVSIDLPVYAKGRNE
NQAAIDKGNVPKLWQSGNRGQGMVVAVIDTGIQPHKDFRLTSPGTAKISKA
DAQRMIAQKGYGRYVNSKIPFAYNYASNSNQATEPDDVSGFHGQHVAGIIA
ANGRYTKKQHEYVVGVAPEAQLLDLRVSDMIDDENKNDVARAIHDAVDLGA
NVISISLGISLPNQSFTDEEQAAVQYAINHGVFVSLAGGNYGNSASIFTSN
PLTNTNGINTAYQEANSGTLADPAVSANSMTVAAENSLKGSQNEMASFSSW
GPTPDYTLKPDISVPGMGITSTWQNNTYAMLEGTSMATPFVSGAAALVIQK
LKQSQPDLSGSQLVSQTKNMLMNSATPMKDVNYPGNIVSPRRQGAGQINVT
AAANLKATVQDPATGIGSVSLGQIGGSHSFKVELSNHGSVPINYAVDNDGG
PMTQIRDQKKDGQVHDISLTGASLTSDQSNIVIDPGQRKTLTLSLSISPTV
KPNQVVEGYLHFKADQPGQSLSMPYLAYYGDTTKEQVIDSPAFMPNSAFHG
GYLMDENNTPLGISDRVSLSAYVNNHDNKTNWRKVASYIHPARVAFSPNGD
HHQDSVTPFVFAKQSLANVKAQIVNDQGNVIRVIDQETDTDKSIANDSGNL

DLSTSFSMRQNPKALQWNGRYIDQSTGKSIVVPNGRYHYQLVTTNYNDGAD
QQQLASYPVEVDTRAPQATAVTYNRKTGRLTGQFNDHGAGFTGISRGILST
NGHQFGIKLTKKAALAGQFSDRLTSIVKQMLMKHQANLTLTDIAGNSTKVA
VHRKLSGLVTKKANVSFDRAPQLKWFKYGTGKNASSSYLEISNKKVFTLYA
RVPKGVPALNAYAKDTGTNKVVKGRLNPKTGVVAFTCHFSQTGYETIQGWS
QVPQKKFGAYLKSPSTLIVVSQLPKAPLIAKLKKTTPKLISNAQAQKKTKS
IFGSPIPNGHKTSQLTYRRAPSKGIKFFQLHDNASTFLNAANSATIYDLQT
HQLTINGQISSPNKQRLVILATPDETDPANRVRISKNGTFKFKVPFNPTEQ
RGVGYNLYTKTILRNGQSKVQKQRGILEIYLDVVKPSLAVSENVENNRIRL
TGTVNDNVSGVKLDVNGNNLFSQQKDAGFNRHDQNQPLNPYPDYQINQSYD
LTPGRNTFTVKAIDQVGNVTTKRFVANGHG

The invention also provides a fragment of *Lactobacillus brevis* subsp. *gravesensis* ATCC 27305 protease comprising the propeptide to the end of the B domain of the *Lactobacillus brevis* subsp. *gravesensis* ATCC 27305 protease. This sequence comprises (or consists of) SEQUENCE ID NO. 40.

SEQUENCE ID NO. 40 has the following sequence.

LIGFSSPVGAGRVSIDLPVYAKGRNENQAAIDKGNVPKLWQSGNRGQGMVV
AVIDTGIQPHKDFRLTSPGTAKISKADAQRMIAQKGYGRYVNSKIPFAYNY
ASNSNQATEPDDVSGFHGQHVAGIIAANGRYTKKQHEYVVGVAPEAQLLDL
RVSDMIDDENKNDVARAIHDAVDLGANVISISLGISLPNQSFTDEEQAAVQ
YAINHGVFVSLAGGNYGNSASIFTSNPLTNTNGINTAYQEANSGTLADPAV
SANSMTVAAENSLKGSQNEMASFSSWGPTPDYTLKPDISVPGMGITSTWQN
NTYAMLEGTSMATPFVSGAAALVIQKLKQSQPDLSGSQLVSQTKNMLMNSA
TPMKDVNYPGNIVSPRRQGAGQINVTAAANLKATVQDPATGIGSVSLGQIG
GSHSFKVELSNHGSVPINYAVDNDGGPMTQIRDQKKDGQVHDISLTGASLT
SDQSNIVIDPGQRKTLTLSLSISPTVKPNQVVEGYLHFKADQPGQSLSMPY
LAYYGDTTKEQVIDSPAFMPNSAFHGGYLMDENNTPLGISDRVSLSAYVNN
HDNKTNWRKVASYIHPARVAFSPNGDHHQDSVTPFVFAKQSLANVKAQIVN
DQGNVIRVIDQETDTDKSIANDSGNLDLSTSFSMRQNPKALQWNGRYIDQS
TGKSIVVPNGRYHYQLVTTNYNDGADQQQLASYPVEVDTRAPQATAVTYNR
KTGRLTGQFNDHGAGFTGISRGILSTNGHQFGIKLTKKAALAGQFSDRLTS
IVKQMLMKHQANLTLTDIAGNSTKVAVHRKLSGLVTKKANVSFDRAPQLKW
FKYGTGKNASSSYLEISNKKVFTLYARVPKGVPALNAYAKDTGTNKVVKGR
LNPKTGVVAFTCHFSQTGYETIQGWSQVPQKKFGAYLKSPSTLIVVSQLPK
APLIAKLKKTTPKLISNAQAQKKTKSIFGSPIPNGHKTSQLTYRRAPSKGI
KFFQLHDNASTFLNAANSATIYDLQTHQLTINGQISSPNKQRLVILATPDE
TDPANRVRISKNGTFKFKVPFNPTEQRGVGYNLYTKTILRNGQSKVQKQRG
ILEIYLDVVKPSLAVSENVENNRIRLTGTVNDNVSGVKLDVNGNNLFSQQK
DAGFNRHDQNQPLNPYPDYQINQSYDLTPGRNTFTVKAIDQVGNVTTKRFV
ANGHG

The protease of the invention (*Lactobacillus helveticus* DSM 20075=CGMCC 1.1877) may have a sequence comprising (or consisting of) SEQUENCE ID NO. 41.

SEQUENCE ID NO.41 has the following sequence.

MKELSEHSSEKFVYLNRSKKRLDNLESYTHSKFLKTLRKKWAKAAIVTLAS
GSAILFSANKVKADEVEQNQATEVQQGSQATDQTQNQSDNSENTGQQNSDN
GQADTQVDEVQTADKAGQKDANGVELPANNQDHVKGNVQDAWNQGYSGEHM
AVAVIDSGIDVDHKDFQTMPKDPKLTADEMKKKLKELGYGRYVNEKIPYAY
NYVDNENEHLKGPDDEPHGQHVSGTIAADGHPDGDKEYVVGVAPQAQLLHL
KVFGDTTTSLDLAKEIYDAVNLGADVIQMSLGGGVSAADLNNADQRAVQYA
IDHGVIVSISASNNGNSASVDNPSKITDLDDYEPGGERGNYLPFSSSTVAN
PGAAKGAITVAAENSGLGKDSDMASFSSWGPLPDYTLKPDISAPGVDVIST
ANDNGYTTMSGTSMAGPFVAGAATLVKQRLLKTNPELKGAALVEAVKALLM
NTAVPQTQKGFDTPVSPRRQGSGQIDVGAATKSPVYITADDGTGSLSLRQI
KDGSEFALTFHNLSNQVQAYDFDDMGGGFTEVRDEETGLFHDVQLAGANIS
GPNSVELAPNETKTVNFVLNLAGLKNNQLVEGFLNFKSSKGANDLSVPYLG
YFGDMTSENVFDQNANDAAPDIQGNHLINEDNYPRGIADEESLKALVNVDG
TYNWQEVAKLYESGKVAFSPNNNQKSDLLKPVAFLKQNLEDLKVEILDANG
NVVRVLSDNHGPEKSYHDDHNGMMDLSSTVNNSDTLEWDGKLYDKTTGKMV
VAPDGQYTYRFVATLYNNGENKVQTNDTPVIIDTTAPVLNNVKYDTSSFTL
SGDYADAGAGFTDYSYATVTVNDHVFGFKLNEGDKSNFDNANKTKGHFVFV
LTPEEQAALTSAANKVTVAFSDVADNTATQTFNVAPVAGHKKIAVWNAING
LPFNENSDDYNVGRKVFMLRGGAEHDFYVNGKWVQVDQGQFVLPVSVDEQN
FVFSSDQAGKNILGKFTTFTPKAQFAWQHVDGEERSFGVSVYSVEGKDPQD
IVVQAAVPKGDNVKAFAKDYFTHEVYTGEVHDGVATFHIHTSVNKDAATGI
NLRALLQGWVEIDGPTFNAKQVTDPSPINDANYLGVYYNPNAEERKNYDNR
DDLGVDFEDEAADTNTFGPGNHSSAKDDAKIHFDYLNNNDISTLGNKAVEK
GYYNPATHKFTLTGRVNPEVISLTFLADSPYEVDPENQADIHDNGKFSVTF
TIDNPATRQLSYFFKTNDGKTTRGSLTLILDTVDPTLTVDQLGDKDEAEIT
TNKPTFKLSGEANDNIDGYNVFINGDNVFGQFGNSGYDFLPGIYNDLNQNT
PNLYGSYKFDQEEQLDDQNGQPTTHVFTIAVEDQAGNRVEKKVTVHYDPNY
LTEPVNTGKKDDQADVKPAEGQKQDKNDNQTVNNSKEDPESGQTTENAQST
ESQEQNKTDVTKPAAKPSNDDQKENHGAGESTIESNQEKQLGQSNVQAQDT
KPDKTVVQGNVQNTAPTTGHLTNSSVNVQQFKTKKETLQLKKFKLLKNTYG
YTLNGKIAKKHGKKLLFNKGKTVLVWNNRKVVTIKGQKYYRVAKNVFVKVS
TIKQVKDLKLVLTKNSYVYNKLGKRVKYKSQSLIKEGKHLSTHQ

The invention also provides a fragment of *Lactobacillus helveticus* DSM 20075=CGMCC 1.1877 protease comprising the propeptide to the end of the B domain of the *Lactobacillus helveticus* DSM 20075=CGMCC 1.1877 protease. This sequence comprises (or consists of) SEQUENCE ID NO. 42.

SEQUENCE ID NO. 42 has the following sequence.

EQNQATEVQQGSQATDQTQNQSDNSENTGQQNSDNGQADTQVDEVQTADKA
GQKDANGVELPANNQDHVKGNVQDAWNQGYSGEHMAVAVIDSGIDVDHKDF
QTMPKDPKLTADEMKKKLKELGYGRYVNEKIPYAYNYVDNENEHLKGPDDE
PHGQHVSGTIAADGHPDGDKEYVVGVAPQAQLLHLKVFGDTTTSLDLAKEI
YDAVNLGADVIQMSLGGGVSAADLNNADQRAVQYAIDHGVIVSISASNNGN
SASVDNPSKITDLDDYEPGGERGNYLPFSSSTVANPGAAKGAITVAAENSG
LGKDSDMASFSSWGPLPDYTLKPDISAPGVDVISTANDNGYTTMSGTSMAG
PFVAGAATLVKQRLLKTNPELKGAALVEAVKALLMNTAVPQTQKGFDTPVS
PRRQGSGQIDVGAATKSPVYITADDGTGSLSLRQIKDGSEFALTFHNLSNQ
VQAYDFDDMGGGFTEVRDEETGLFHDVQLAGANISGPNSVELAPNETKTVN
FVLNLAGLKNNQLVEGFLNFKSSKGANDLSVPYLGYFGDMTSENVFDQNAN
DAAPDIQGNHLINEDNYPRGIADEESLKALVNVDGTYNWQEVAKLYESGKV
AFSPNNNQKSDLLKPVAFLKQNLEDLKVEILDANGNVVRVLSDNHGPEKSY
HDDHNGMMDLSSTVNNSDTLEWDGKLYDKTTGKMVVAPDGQYTYRFVATLY
NNGENKVQTNDTPVIIDTTAPVLNNVKYDTSSFTLSGDYADAGAGFTDYSY
ATVTVNDHVFGFKLNEGDKSNFDNANKTKGHFVFVLTPEEQAALTSAANKV
TVAFSDVADNTATQTFNVAPVAGHKKIAVWNAINGLPFNENSDDYNVGRKV
FMLRGGAEHDFYVNGKWVQVDQGQFVLPVSVDEQNFVFSSDQAGKNILGKF
TTFTPKAQFAWQHVDGEERSFGVSVYSVEGKDPQDIVVQAAVPKGDNVKAF
AKDYFTHEVYTGEVHDGVATFHIHTSVNKDAATGINLRALLQGWVEIDGPT
FNAKQVTDPSPINDANYLGVYYNPNAEERKNYDNRDDLGVDFEDEAADTNT
FGPGNHSSAKDDAKIHFDYLNNNDISTLGNKAVEKGYYNPATHKFTLTGRV
NPEVISLTFLADSPYEVDPENQADIHDNGKFSVTFTIDNPATRQLSYFFKT
NDGKTTRGSLTLILDTVDPTLTVDQLGDKDEAEITTNKPTFKLSGEANDNI
DGYNVFINGDNVFGQFGNSGYDFLPGIYNDLNQNTPNLYGSYKFDQEEQLD
DQNGQPTTHVFTIAVEDQAGNRVEKKVTVHYDPNYLTEPVNTGKKDDQADV
KPAEGQKQDKNDNQTVNNSKEDPESGQTTENAQSTESQEQNKTDVTKPAAK
PSNDDQKENHGAGESTIESNQEKQLGQSNVQAQDTKPDKTVVQGNVQNTAP
TTGHLTNSSVNVQQFKTKKETLQLKKFKLLKNTYGYTLNGKIAKKHGKKLL
FNKGKTVLVWNNRKVVTIKGQKYYRVAKNVFVKVSTIKQVKDLKLVLTKNS
YVYNKLGKRVKYKSQSLIKEGKHLSTHQ

The protease of the invention (*Lactobacillus rhamnosus* ATCC 21052) may have a sequence comprising (or consisting of) SEQUENCE ID NO. 43.

SEQUENCE ID NO. 43 has the following sequence.

MNKNATIEAKRHYKMYKAGSRWMTAAIITFGTSLVVLGGTATQSVSADTKT
PTADKTTQPVNQAQTQTATSTASSQATTADAKDKTAETQPTTTTTTKQVTA
QSQAAPSTATKAQSQASTTNQAQPAAATKVQTGTPSSGANTQPAANTATTK

```
SATSTTSSAATQSAAPASNAATTNAAKTQSTAATTTDPGPANQDTLTKGNV
KGLWNEGYQGQGMVVAVIDSGVQAHDDLRLSDDSTAAITKEKAEAAISKLG
YGSYVNSKIPFAYDYVNNDSVNTGTTVAGSTHGEHVAGIIAANGTTADGAT
GNEKATTYVKGVAPEAQILAMQVIDEFADENANDISRAIRDAVTLGANAIQ
MSLGIGVTEQDLTDEEQAAVQYATDHGVFVSISAGNNANAGSIIGSKTSND
ISTAYSPKNDSTIGDPGAAASAMTVAAEKSATGDKSEMDGFSSWGPMADYT
LKPDISAPGDNVISTAIDPTTNTQTYATESGTSMAGPYNAGAALLVMQKIK
ATRPDLQGADLVKAVKLALMNAADPMKDINYPDTYISPRRQGAGQIDVSKA
GDLTVSAEGNKDAGSVSLGKIGQTTSFTVTLTNHGKTAQNYVVDTNGGPLT
QVQDTSNGNTVHDQTLIGATVNTDTANFTLAAGETKTVTFKLSLDNTVAAN
QLVEGFLTFKAGDTSQTISVPYLGYYGDLTTEQVVDASANSGESIFNGGYL
VDGANTPLGVTDSASLSSLVNTDTTGKYTWTLVPTYVDNKKVSFSPNGDGA
SDTVYPYVFSKQNLKSVTIQILDAQGHVVRVLDKENNTTKSYLQNGNSYNS
DLGLSTDMRLDPNAFTWDGKVYDQATGKYVTAPDGKYTYRLVTEQYNTGAQ
QNQDFDLPVTVDTVAPTLTGLSYQNGRVTVNYNDQGAGFTKFSDTALKIGG
SFDLTAAQKAALESSDGSLTLTLTDVAGNKTSKTLQAVTGTHQATTPTATT
ANVAPQFSWKVGDGPYNHWRTKAYGVSLNNNGQNNDGTLDGFVQAVSDQTS
FTAYAQVPAGVDWIVYATDAMTGKVFSGKVDTKTGNVTFNLTASAPYGDFV
GTVLAPTADFGTYEQAGRANGDEMVVFLDTDGTAGYGHFSQKDPHVAVPLQ
DNAKAAANVKTTSGAPVLGGRAFSQITTHAQPTAGLTFDKFNDNSFTLVGA
DKVADIYNAKTGQLTITGHVDQPAGKTLTVTSATEPAKTVTIGADGKFSFT
VPFKAAEQQAIGYRLTSPATDGSKSTQTAYGELQIYLDTIFPTLNMPQADT
LQVDDKGNYEITTTSDTFTVSGTVNDNINGYRLYTNGDNIVHQKNLAGFNN
HLDPLSTTSNPYGAAAFTQTYQLADGDNYFTITAVDMVGNKVTKVFHVIKT
KATTPTTPETPKTPTPTPKPGTGDQTDTKNPKGPTTTPKTDEQGKTNPTPK
FVDLTNTTKGQDKTGTTAETGKNTKQTAAAKTMPQAGEAQSPLAVLGLAIL
SMLGLAGFVSRKKRV
```

The invention also provides a fragment of *Lactobacillus rhamnosus* ATCC 21052 protease comprising the propeptide to the end of the B domain of the *Lactobacillus rhamnosus* ATCC 21052 protease. This sequence comprises (or consists of) SEQUENCE ID NO. 44.

SEQUENCE ID NO. 44 has the following sequence.

```
PTADKTTQPVNQAQTQTATSTASSQATTADAKDKTAETQPTTTTTTKQVTA
QSQAAPSTATKAQSQASTTNQAQPAAATKVQTGTPSSGANTQPAANTATTK
SATSTTSSAATQSAAPASNAATTNAAKTQSTAATTTDPGPANQDTLTKGNV
KGLWNEGYQGQGMVVAVIDSGVQAHDDLRLSDDSTAAITKEKAEAAISKLG
YGSYVNSKIPFAYDYVNNDSVNTGTTVAGSTHGEHVAGIIAANGTTADGAT
GNEKATTYVKGVAPEAQILAMQVIDEFADENANDISRAIRDAVTLGANAIQ
MSLGIGVTEQDLTDEEQAAVQYATDHGVFVSISAGNNANAGSIIGSKTSND
ISTAYSPKNDSTIGDPGAAASAMTVAAEKSATGDKSEMDGFSSWGPMADYT
LKPDISAPGDNVISTAIDPTTNTQTYATESGTSMAGPYNAGAALLVMQKIK
ATRPDLQGADLVKAVKLALMNAADPMKDINYPDTYISPRRQGAGQIDVSKA
GDLTVSAEGNKDAGSVSLGKIGQTTSFTVTLTNHGKTAQNYVVDTNGGPLT
QVQDTSNGNTVHDQTLIGATVNTDTANFTLAAGETKTVTFKLSLDNTVAAN
QLVEGFLTFKAGDTSQTISVPYLGYYGDLTTEQVVDASANSGESIFNGGYL
VDGANTPLGVTDSASLSSLVNTDTTGKYTWTLVPTYVDNKKVSFSPNGDGA
SDTVYPYVFSKQNLKSVTIQILDAQGHVVRVLDKENNTTKSYLQNGNSYNS
DLGLSTDMRLDPNAFTWDGKVYDQATGKYVTAPDGKYTYRLVTEQYNTGAQ
QNQDFDLPVTVDTVAPTLTGLSYQNGRVTVNYNDQGAGFTKFSDIALKIGG
KAYGVSLNNNGQNNDGTLSFDLTAAQKAALESSDGSLTLTLTDVAGNKTSK
TLQAVTGTHQATTPTATTANVAPQFSWKVGDGPYNHWRTDGFVQAVSDQTS
FTAYAQVPAGVDWIVYATDAMTGKVFSGKVDTKTGNVTFNLTASAPYGDFV
GTVLAPTADFGTYEQAGRANGDEMVVFLDTDGTAGYGHFSQKDPHVAVPLQ
DNAKAAANVKTTSGAPVLGGRAFSQITTHAQPTAGLTFDKFNDNSFTLVGA
DKVADIYNAKTGQLTITGHVDQPAGKTLTVTSATEPAKTVTIGADGKFSFT
VPFKAAEQQAIGYRLTSPATDGSKSTQTAYGELQIYLDTIFPTLNMPQADT
LQVDDKGNYEITTTSDTFTVSGTVNDNINGYRLYTNGDNIVHQKNLAGFNN
HLDPLSTTSNPYGAAAFTQTYQLADGDNYFTITAVDMVGNKVTKVFHVIKT
KATTPTTPETPKTPTPTPKPGTGDQTDTKNPKGPTTTPKTDEQGKTNPTPK
FVDLTNTTKGQDKTGTTAETGKNTKQTAAAKTMPQAGEAQSPLAVLGLAIL
SMLGLAGFVSRKKRV
```

The protease of the invention (*Lactobacillus* sp. HMSC068F07) may have a sequence comprising (or consisting of) SEQUENCE ID NO. 45.

SEQUENCE ID NO. 45 has the following sequence.

```
MNKNSTTEMKRHYKMYKAGSKWMTAAIITFGTSLIVLGGTATQSVAADTTT
TPTEKTSQTAQSTSAQSQPAAQTTTSQATASDATSSATQTAAANSAKSSTA
QTQAAPAQNTQSSASQPQAATQQASSATAKTTAPASGATTQTNTSSVASQA
TTSTATTATSQASAAATATSTATADNQSQASSAATTDPGPANQDTLTKGNV
KGLWDEGYQGQGMVVAVIDSGVQPHADLRLSDDSTATLTKEKAEAAIAKLG
YGTYVNSKIPFAYDYVNNDSVNTGTTVAGSTHGEHVAGIIAANGTTADGAT
GKEKASTYVKGVAPEAQILAMQVIDEFPDENANDISRAIRDAVALGANAIQ
MSLGIGVTEQDLTDEEQAAVQYATEHGVFVSISAGNNAIAGSIIGSKTPND
ISTAYAPKNDSTIGDPGAAASAMTVAAETSATGADSQMDGFSSWGPMADYT
LKPDISAPGDNVTSTAIDPATNTQTYAVESGTSMAGPFNAGAALLVMQKIK
ATQPDLTGADLVKAVKLALMNAAEPMKDINYPDTYISPRRQGAGQIDVAKA
GDLTVTAEGSNDAGSVSLGKIGKTTTFTVTLTNHGKTAQNYTVDTNGGPLT
QVRDASNGNTVHDETLVGATVNTDTANFTLAAGETKKVTFKLSLDDSVAAN
QLVEGYLTFKATDAAQTISVPYLGYYGDLTDEQVIDAPANSGESIFNGGYL
VDNNNNPLGVTDAASLSNLVNTDTTGKYTWTLVPTYVDNKKVSFSPNGDGA
SDTVFPYVFSKQNLKSVTIQILDAQGHVVRILDKENNTSKSYLQNGNSFNS
DLGLSTDMRLDPNAFTWDGKVYDQATGKYVTAPDGKYTYRLVTEQYNTGAQ
```

-continued

QNQDYDLPVTVDTVAPTLTGLSYQDGRVSVHYDDQGAGFTKFSDLALKIGN

KAYGVNLNNNGQNNDGTLSFELTAAQKAALENSDGSLTLTLTDVAGNKTSA

SLQATAGTHQTDTTTPTSDVAPQFTWKVGDGPHNFWRSEGFVQAVSDQTSF

TAYAQVPAGVDWIVYATDAQTGKVFPGTVDTKTGTVTFNLTESAPYGDFVG

TVLSPTADFGTYEEAGRADGDEMIVFLDANGTAGYGHFSQKNVHVVVPLQD

NAKAAANATKTSGAPVLGGRAFSQITTHAQPTAGLKFDKFNDNSFTLVGAD

QVADIYNAQTGQLTITGHVDNPAGKTLTVTDATEPAKTVAIGADGKFSFTV

PFKAAEQQSVGYRLTEPATDGSKSTKTAYGELQIYLDTIFPTLDLPQADTL

KVDDQGNYDITTTSDTFTVSGTVNDNINGYRLYTNGDNVVHQKNLAGFNNH

LDPQSTTSNPYGAADFNQTYTLKDGDNYFTVTAVDMVGNKVTKVFHVVKVK

TPTPTPGDNGNTSGTDNSGNGNPNQQGTGGNAGNQGGNAGNQGNNGGTQGG

NGSGQTPATGNGTPTTPTTGTGTNGGNGNNRQQSPELVTLDNKLKDQTKTP

AAKNGTTANGTKQAATGKTMPQAGESQSPLAVIGLAIVSIFSFMGFASRKK

RV

The invention also provides a fragment of *Lactobacillus* sp. HMSC068F07 protease comprising the propeptide to the end of the B domain of the *Lactobacillus* sp. HMSC068F07. This sequence comprises (or consists of) SEQUENCE ID NO. 46.

SEQUENCE ID NO. 46 has the following sequence.

TPTEKTSQTAQSTSAQSQPAAQTTTSQATASDATSSATQTAAANSAKSSTA

QTQAAPAQNTQSSASQPQAATQQASSATAKTTAPASGATTQTNTSSVASQA

TTSTATTATSQASAAATATSTATADNQSQASSAATTDPGPANQDTLTKGNV

KGLWDEGYQGQGMVVAVIDSGVQPHADLRLSDDSTATLTKEKAEAAIAKLG

YGTYVNSKIPFAYDYVNNDSVNTGTTVAGSTHGEHVAGIIAANGTTADGAT

GKEKASTYVKGVAPEAQILAMQVIDEFPDENANDISRAIRDAVALGANAIQ

MSLGIGVTEQDLTDEEQAAVQYATEHGVFVSISAGNNAIAGSIIGSKTPND

ISTAYAPKNDSTIGDPGAAASAMTVAAETSATGADSQMDGFSSWGPMADYT

LKPDISAPGDNVTSTAIDPATNTQTYAVESGTSMAGPFNAGAALLVMQKIK

ATQPDLTGADLVKAVKLALMNAAEPMKDINYPDTYISPRRQGAGQIDVAKA

GDLTVTAEGSNDAGSVSLGKIGKTTTFTVTLTNHGKTAQNYTVDTNGGPLT

QVRDASNGNTVHDETLVGATVNTDTANFTLAAGETKKVTFKLSLDDSVAAN

QLVEGYLTFKATDAAQTISVPYLGYYGDLTDEQVIDAPANSGESIFNGGYL

VDNNNNPLGVTDAASLSNLVNTDTTGKYTWTLVPTYVDNKKVSFSPNGDGA

SDTVFPYVFSKQNLKSVTIQILDAQGHVVRILDKENNTSKSYLQNGNSFNS

DLGLSTDMRLDPNAFTWDGKVYDQATGKYVTAPDGKYTYRLVTEQYNTGAQ

QNQDYDLPVTVDTVAPTLTGLSYQDGRVSVHYDDQGAGFTKFSDLALKIGN

KAYGVNLNNNGQNNDGTLSFELTAAQKAALENSDGSLTLTLTDVAGNKTSA

SLQATAGTHQTDTTTPTSDVAPQFTWKVGDGPHNFWRSEGFVQAVSDQTSF

TAYAQVPAGVDWIVYATDAQTGKVFPGTVDTKTGTVTFNLTESAPYGDFVG

TVLSPTADFGTYEEAGRADGDEMIVFLDANGTAGYGHFSQKNVHVVVPLQD

NAKAAANATKTSGAPVLGGRAFSQITTHAQPTAGLKFDKFNDNSFTLVGAD

QVADIYNAQTGQLTITGHVDNPAGKTLTVTDATEPAKTVAIGADGKFSFTV

PFKAAEQQSVGYRLTEPATDGSKSTKTAYGELQIYLDTIFPTLDLPQADTL

KVDDQGNYDITTTSDTFTVSGTVNDNINGYRLYTNGDNVVHQKNLAGFNNH

LDPQSTTSNPYGAADFNQTYTLKDGDNYFTVTAVDMVGNKVTKVFHVVKVK

TPTPTPGDNGNTSGTDNSGNGNPNQQGTGGNAGNQGGNAGNQGNNGGTQGG

NGSGQTPATGNGTPTTPTTGTGTNGGNGNNRQQSPELVTLDNKLKDQTKTP

AAKNGTTANGTKQAATGKTMPQAGESQSPLAVIGLAIVSIFSFMGFASRKK

RV

The protease of the invention (*Enterococcus* sp. HMSC069A01) may have a sequence comprising (or consisting of) SEQUENCE ID NO. 47.

SEQUENCE ID NO. 47 has the following sequence.

MRRNSMTEMKRHYKLYKSGSKGVAAAIITVSAGAIVLSGYATQSVSADTTA

AATVQTQTDTETTGQSSTAVDDAQNAADNHTQSSTATEEGTTPATTTSQSQ

AGSSATTSGATATTATSGASASSSSAATTLAATVQTQTDTETTGQSSTAVD

DAQNAADNHTQSSTATEEGTTPATTTSQSQAGSSAATSGATATSGASASSS

SAATTLAATVQTQTDTETTGQSSTAVDDAQNAADNHTQSSTATEEGTTPAQ

SSATASQATPATTTSQSQAGSSAATSGATATSGASASSSSAATTTTPAATT

TAQATADATADPGPANQDTLTKGNVEGLWNEGYQGQGMVVAVIDSGVQPHA

DLRLTDDSTAAISKDAAEAAIAKLGYGTYVNSKIPFAYDYVNNDSVNTGTT

VSGSTHGEHVAGIIAANGTVADGATGTSKASVYVKGVAPEAQILAMQVIDE

FPDENANDISRAIRDAVSMGANAIQMSLGVGVAEQDLTDEEQAAVQYATDH

GVFVSISASNNGNAASIVGSDKKNDISTAYVPKNDSTIADPGAAASAMTVA

AEKSATGADSEMDGFSSWGPMADYTLKPDIAAPGDRVTSTAIDPKTNTQTY

AVESGTSMAGPYDAGAALLVMQKLKATRPELQGADLVKAVKLALMNAADPM

IDLNYPDTYVSPRRQGAGQIDVTKAGNLDVAAEGTNNAGSVSLGKIGRTTS

FNVTLTNYGQTTQSYTVDYDGGPLTQVRDTSKGNIVHDQKLAGAAVNSATP

TFTLAPGASKVVTFTLTLDDAVAANQIVEGYLTFKAGDDTQTISVPYLGYF

GDLTTEQIIDDPANKQDSIFKGGYLVDNNNNPLGVTDAASLSNLVNSDVTG

KYTWGQVPAYIENGKVSFSPNGDGASDTVYPYVFAKQNLKAVTIQILDANG

NLVRVLDKENNTTKSYLQNGFSHNSDLGLSTDMRLDADAFTWDGRIYDQQT

GKYITAPDGRYTYRIVTEQYNDGAEQEQNFDLPVAVDTVAPTLTGLTYAEG

QLTASYNDQGAGFSQFSDAVLKIGAQEYGVSLDNNGQSNAGTISFKLTAAQ

MAALATSDGQLTLTVTDVAGNHTSASVQAFAGTTSASATDTAANVAPQFSW

QVGDGSNNYWRTNGFVQAVSDQTSFTTYAQVPAGVDWIVYATDARAGKVFP

GKVDTATGIVTFNLTEGAPYGDFVGTVLYPTANFGEYKRAGRADGDEMIVF

LDADGTAGYGHFSTTNPHTVIALRDNADAAADATVTTGAPVLSGRAFADIT

THAQPTAGLSFDKFNDNTFTLVGADQVADVYDPQTGELTITGKVADPAGKA

MTVTDATEPTKAVAINADGTFSFTVPFKAAEQQSVGYRLTTTTTNDDGTTA

SSTAYGALQIYLDTVFPTLSMPQADTLTVDADGNYDITTSDPTFTVTGTVN

DNVNGYRLYTNGDNVVHQKNLAGFNNHVDADAASSNPYGAADFSQTYNLLE

GDNYFTVTAVDMVGNTITKVFHVVRVDATSVTPKSQGSKGTAITSPVVDGG

QRGQAQGAPDVHPAAPGYKNDGQGGVQLVPAAITSPGVDGGQRGQAQGAPD

VHPAAPGYKNDGQGGVQLVPAASQAGRSGTEQGQSPATTTAAALPATGETH

SPLAAIGLAILSVLGLAGLASRKRRV

The invention also provides a fragment of *Enterococcus* sp. HMSC069A01 protease comprising the propeptide to the end of the B domain of the *Enterococcus* sp. HMSC069A01. This sequence comprises (or consists of) SEQUENCE ID NO. 48.

SEQUENCE ID NO. 48 has the following sequence.

QTQTDTETTGQSSTAVDDAQNAADNHTQSSTATEEGTTPATTTSQSQAGSS

ATTSGATATTATSGASASSSSAATTLAATVQTQTDTETTGQSSTAVDDAQN

AADNHTQSSTATEEGTTPATTTSQSQAGSSAATSGATATSGASASSSSAAT

TLAATVQTQTDTETTGQSSTAVDDAQNAADNHTQSSTATEEGTTPAQSSAT

ASQATPATTTSQSQAGSSAATSGATATSGASASSSSAATTTTPAATTTAQA

TADATADPGPANQDTLTKGNVEGLWNEGYQGQGMVVAVIDSGVQPHADLRL

TDDSTAAISKDAAEAAIAKLGYGTYVNSKIPFAYDYVNNDSVNTGTTVSGS

THGEHVAGIIAANGTVADGATGTSKASVYVKGVAPEAQILAMQVIDEFPDE

NANDISRAIRDAVSMGANAIQMSLGVGVAEQDLTDEEQAAVQYATDHGVFV

SISASNNGNAASIVGSDKKNDISTAYVPKNDSTIADPGAAASAMTVAAEKS

ATGADSEMDGFSSWGPMADYTLKPDIAAPGDRVTSTAIDPKTNTQTYAVES

GTSMAGPYDAGAALLVMQKLKATRPELQGADLVKAVKLALMNAADPMIDLN

YPDTYVSPRRQGAGQIDVTKAGNLDVAAEGTNNAGSVSLGKIGRTTSFNVT

LTNYGQTTQSYTVDYDGGPLTQVRDTSKGNIVHDQKLAGAAVNSATPTFTL

APGASKVVTFTLTLDDAVAANQIVEGYLTFKAGDDTQTISVPYLGYFGDLT

TEQIIDDPANKQDSIFKGGYLVDNNNNPLGVTDAASLSNLVNSDVTGKYTW

GQVPAYIENGKVSFSPNGDGASDTVYPYVFAKQNLKAVTIQILDANGNLVR

VLDKENNTTKSYLQNGFSHNSDLGLSTDMRLDADAFTWDGRIYDQQTGKYI

TAPDGRYTYRIVTEQYNDGAEQEQNFDLPVAVDTVAPTLTGLTYAEGQLTA

SYNDQGAGFSQFSDAVLKIGAQEYGVSLDNNGQSNAGTISFKLTAAQMAAL

ATSDGQLTLTVTDVAGNHTSASVQAFAGTTSASATDTAANVAPQFSWQVGD

GSNNYWRTNGFVQAVSDQTSFTTYAQVPAGVDWIVYATDARAGKVFPGKVD

TATGIVTFNLTEGAPYGDFVGTVLYPTANFGEYKRAGRADGDEMIVFLDAD

GTAGYGHFSTTNPHTVIALRDNADAAADATVTTGAPVLSGRAFADITTHAQ

PTAGLSFDKFNDNTFTLVGADQVADVYDPQTGELTITGKVADPAGKAMTVT

DATEPTKAVAINADGTFSFTVPFKAAEQQSVGYRLTTTTTNDDGTTASSTA

YGALQIYLDTVFPTLSMPQADTLTVDADGNYDITTSDPTFTVTGTVNDNVN

GYRLYTNGDNVVHQKNLAGFNNHVDADAASSNPYGAADFSQTYNLLEGDNY

FTVTAVDMVGNTITKVFHVVRVDATSVTPKSQGSKGTAITSPVVDGGQRGQ

AQGAPDVHPAAPGYKNDGQGGVQLVPAAITSPGVDGGQRGQAQGAPDVHPA

APGYKNDGQGGVQLVPAASQAGRSGTEQGQSPATTTAAALPATGETHSPLA

AIGLAILSVLGLAGLASRKRRV

The protease of the invention (*Actinomyces* sp. *oral taxon* 180 str. F0310) may have a sequence comprising (or consisting of) SEQUENCE ID NO. 49.

SEQUENCE ID NO. 49 has the following sequence.

MKRSRLAVLSLAATLGIAIIAPQAFADSADTLVSAPASPPSSNAGKLLEPE

LTSKSQYDAGGATTPSGDLLPDEESNHPVTVIVELEEGDAGVAWYRRAVSA

DAKRTVVKERIRTAVEAAAPGQVTSGGGPVTEVEDYEHVMEGFAIEVPAGA

VEAVRGVEGVKRAFVEQTVTPSSEEGYSGPQNQYSLDMTGVDRISQKGDGT

TTATIDTGFDTTHEAFSGALDESRAAYSYDSISSVKRGLSTGWAGAYVSAK

IPFAYDYGDGDSDVIPHTVHNMAHGTHVAGIAAANGGAILGSAPGAQLLLM

KAGIDATGGLSDSAIFAALDDCAVLKPDVINMSFGYAGGASEARNDTYGSV

YYRLSEQGIMLNVAGGNFGASSQGNASGWGLPYASDPDSSTVAQPSTYTAS

LSVASVDNANGWGPSTYKASSFSSWGVAPNLTLKPEIAAPGGYIWSALPGG

TYGYSSGTSMATPYLAGMAADIKQRVESDPGFAYMTEAQKTGVVYNLLMGT

AKPLVDNEGGRGAYYSPRKIGSGLANAVAASSATVFPTVVDAPDETRPKAD

LGDGTEGWTFSIRLTNTAYEARTYRLNTQALSEVVASGVFTQHSANWTDQG

ISVSYSGDVSGSADSSTITVPGRGVVTATVTITPQAAFAAYAGAYAPNGTF

VDGFTVLTSMTEGEPDLSVPFLGFYGDWGAVPVFDSLASDGGQAHAVASRL

ASATTGVSLGVNPLAGYTSASSAPAPNPDAYVVSASTWAQGPSAIRPVTGL

LRSTKSVTYTYQDSAGNTVRQYSYKNTRKSLYDDYTRLIASGESSMGDPYF

DGYDWYGRRLPEGRYTLRIDAVTDGPSLRTQTLTYSFAYDLTGPKISGVHV

SGQGEARTVSFDVTDSSPLASIDFHDPANGSYYYRTLVTDGGTLGADGQRT

YHFDVPVADLQRGWESQGGTGPAPTNPTLYAWDYGVNASAGVTVSVDASDP

ISLSTSSVVIPSGETSQVFAVLSPSLSGSQVVWSLADSSVASLSTSSDTLT

ATIAAGTKEGATTLTAWVRQGDGTWASASAEVSVRAAASSDFVIDEAGVLR

SYSGSDTEVSVPGGVTALADRVFARSSVASVELPDTVERIGASAFEGAASL

ASVTVRDARGQVGEGLPSGLRQIGARAFLGTGLAVINVPDSVSDIGPGAFA

LMPSLTGVNIGSGVREGQLVSTFTASPKLKAITVKADNASYDSVDGVLFTK

GRDTLLTYPLGRAGVSYTVPDGTRALAQESFEGAPLDEVTLPDSLRRIDRY

AFVGSRLSSLTLPDSFEMIGAHAFRGVTSLTWVNIGGTTTIGESAFDGDRN

LTAINFRSDLARLTSIGANALRGVPVTPPALTSARAQAETPASDTASGNAP

TPAPIASPEATGSDSASDDRATGGDAAPATPNPNASASASPDAPDQGQGSE

APQSSAAPAASTRAPGAAASSPAAVGQPVSVVGRTALSLGDAADYHAPHPK

RTRPSSLAATGASTNGFVGILTAAATLGFVLVVARRQRLS

The invention also provides a fragment of *Actinomyces* sp. *oral taxon* 180 str. F0310 protease comprising the propeptide to the end of the B domain of the *Actinomyces* sp. *oral taxon* 180 str. F0310. This sequence comprises (or consists of) SEQUENCE ID NO. 50.

SEQUENCE ID NO. 50 has the following sequence.

```
SADTLVSAPASPPSSNAGKLLEPELTSKSQYDAGGATTPSGDLLPDEESNH
PVTVIVELEEGDAGVAWYRRAVSADAKRTVVKERIRTAVEAAAPGQVTSGG
GPVTEVEDYEHVMEGFAIEVPAGAVEAVRGVEGVKRAFVEQTVTPSSEEGY
SGPQNQYSLDMTGVDRISQKGDGTTTATIDTGFDTTHEAFSGALDESRAAY
SYDSISSVKRGLSTGWAGAYVSAKIPFAYDYGDGDSDVIPHTVHNMAHGTH
VAGIAAANGGAILGSAPGAQLLLMKAGIDATGGLSDSAIFAALDDCAVLKP
DVINMSFGYAGGASEARNDTYGSVYYRLSEQGIMLNVAGGNFGASSQGNAS
GWGLPYASDPDSSTVAQPSTYTASLSVASVDNANGWGPSTYKASSFSSWGV
APNLTLKPEIAAPGGYIWSALPGGTYGYSSGTSMATPYLAGMAADIKQRVE
SDPGFAYMTEAQKTGVVYNLLMGTAKPLVDNEGGRGAYYSPRKIGSGLANA
VAASSATVFPTVVDAPDETRPKADLGDGTEGWTFSIRLTNTAYEARTYRLN
TQALSEVVASGVFTQHSANWTDQGISVSYSGDVSGSADSSTITVPGRGVVT
ATVTITPQAAFAAYAGAYAPNGTFVDGFTVLTSMTEGEPDLSVPFLGFYGD
WGAVPVFDSLASDGGQAHAVASRLASATTGVSLGVNPLAGYTSASSAPAPN
PDAYVVSASTWAQGPSAIRPVTGLLRSTKSVTYTYQDSAGNTVRQYSYKNT
RKSLYDDYTRLIASGESSMGDPYFDGYDWYGRRLPEGRYTLRIDAVTDGPS
LRTQTLTYSFAYDLTGPKISGVHVSGQGEARTVSFDVTDSSPLASIDFHDP

ANGSYYYRTLVTDGGTLGADGQRTYHFDVPVADLQRGWESQGGTGPAPTNP

TLYAWDYGVNASAGVTVSVDASDPISLSTSSVVIPSGETSQVFAVLSPSLS

GSQVVWSLADSSVASLSTSSDTLTATIAAGTKEGATTLTAWVRQGDGTWAS

ASAEVSVRAAASSDFVIDEAGVLRSYSGSDTEVSVPGGVTALADRVFARSS
VASVELPDTVERTGASAFEGAASLASVTVRDARGQVGEGLPSGLRQIGARA
FLGTGLAVINVPDSVSDIGPGAFALMPSLTGVNIGSGVREGQLVSTFTASP
KLKAITVKADNASYDSVDGVLFTKGRDTLLTYPLGRAGVSYTVPDGTRALA
QESFEGAPLDEVTLPDSLRRIDRYAFVGSRLSSLTLPDSFEMIGAHAFRGV
TSLTWVNIGGTTTIGESAFDGDRNLTAINFRSDLARLTSIGANALRGVPVT
PPALTSARAQAETPASDTASGNAPTPAPIASPEATGSDSASDDRATGGDAA
PATPNPNASASASPDAPDQGQGSEAPQSSAAPAASTRAPGAAASSPAAVGQ
PVSVVGRTALSLGDAADYHAPHPKRTRPSSLAATGASTNGFVGILTAAATL
GFVLVVARRQRLS
```

The protease of the invention (*Erysipelothrix rhusiopathiae* ATCC 19414) may have a sequence comprising (or consisting of) SEQUENCE ID NO. 51.

SEQUENCE ID NO. 51 has the following sequence.

```
MRKRFKAMMPLVLSLLLVITTGTNIRANDEGTLAELTAMDDVSIVQSILDE

EETNTPEEDPELSVDPSVPVDIIVELEARPILDYENEIKQVGSLGDFSETK

QAQDLEANLIKSHEAVVDKISEVIQKDVEVDSNFTRVMNGFSLKASLDDLN

LIKDIEGVKSAFVSQTYDIPEPQMVDSNRTIGSDTVWTQSHYKGENIVVAV
```

-continued

```
LDTGLDTGHPAFAVAPSQFRINKQKIQTVLNNKKLKATANTPGLTVDHVYI

NDKVPFVYDYADKDAIVDPSAHNYGRLAHGTHVAGTVAGKDQADFRGVAPE

AQLMIFKVFSDKGGGASDISLVSALEDCVYLGVDVINMSLGSDAGFMHDSY

KPTNDMYNRIRDNGIVLDVAAGNAMSSSEKNLYGNDLTLASDPDHGIVGSP

STYASPISVASVNNTKYRPGSKTIDPTQVTLSGFSSIGTTPNISIKPEISA

PGAWIRSAMPRLNGQNYDEMSGTSMATPHVAGASALMKQYLNDKFGNLTNI

QKMELTNNLLMSTAHPIVQKDGAPQPVRKQGSGMMDINAAIKTPVYLSVDP

KQNHDGSNRPKIELGDDQNKTGNYTLKFKVTNMGTQTETYQIKEKVSVPVI

KRSIMDDHRERAFMTDDNRSVDVTRSGVTSVTVKAKETKDVSITVQLTQAE

KNRLNQEFENGTYVEGFVQLTHASHPQISIPFLAFYGDWEKAPIFDHAAEY

EMGVRASNYAHRYLSDKMPMGGNIFDRRMIYTNPSRFVISPNGDGLYDKLS

GINLGQLRNVESMTMEITNKKTKQVIIKEERPNIRKTFYNNSYGKQVPNIL

FWPFSTFTGLDQQKNPLPEGRYDLKISADLGYRKGIDQEIVHTIHVDHTKP

VIPQDKIKFTEKNGTVMMHVESNDNTFLTQTALYPVYNGKVQVNRPLKKQY

TPYDLVSRHAFDVDVTNLKGQEVVISAVDAGMLETNYKTVVPGTPKPHLKV

LDEFKIKVGAQIELEPGNFKWQTPTFESEDPEIADVNDKGVTGLKPGATFI

KIKDKNGIDLVALIEVFEEESLKLQMKVGEKRKLISYNLEGKRTFDSDAPH

IIVSARDTGEEAHQKGKAKITVQNAYEKLEYEVEVVDQPKYTPSLSFDKKV

TYEINSGEVVAPKFTIENDDPSNPQVVTRLLSNEEHVSIAGLKFTGEHAGE

AAVIAELKNGTRAVAKVKVGGLDTKKLDILISQASNLNADDYTKTSFTTLT

TTLQEAKTLRKQKGIDQSNIDTMVEKLEKSMNQLVQVIKNLPSAMSVEVGN

TFKLSPKPAQGKWIWDAEFLEGTAQNNDQEMMFKGLKEGQTDVRYRTKDGE

EQSVAVAVKPKPKPVEIDPIVPTDPVDPVKPTDPVDPVKPKDPVDPVKPTD

PVDPVKPTDPVDPVKPTDPVDPVKPTDPVDPVKPTDPVDPVKPTDPVDPVK

PTDPVDPVKPADPVDPVKPTDPTKPTKPVDSGLKPIDNLKKPIVKPKDPVS

QVESIKQDKPVIHFGVVSESLPQTGVTPQYRGYTLLGLGLVIRVINDKKNR

MK
```

The invention also provides a fragment of *Erysipelothrix rhusiopathiae* ATCC 19414 protease comprising the propeptide to the end of the B domain of the *Erysipelothrix rhusiopathiae* ATCC 19414. This sequence comprises (or consists of) SEQUENCE ID NO. 52.

SEQUENCE ID NO. 52 has the following sequence.

```
DEGTLAELTAMDDVSIVQSILDEEETNTPEEDPELSVDPSVPVDIIVELEA

RPILDYENEIKQVGSLGDFSETKQAQDLEANLIKSHEAVVDKISEVIQKDV

EVDSNFTRVMNGFSLKASLDDLNLIKDIEGVKSAFVSQTYDIPEPQMVDSN

RTIGSDTVWTQSHYKGENIVVAVLDTGLDTGHPAFAVAPSQFRINKQKIQT

VLNNKKLKATANTPGLTVDHVYINDKVPFVYDYADKDAIVDPSAHNYGRLA

HGTHVAGTVAGKDQADFRGVAPEAQLMIFKVFSDKGGGASDISLVSALEDC

VYLGVDVINMSLGSDAGFMHDSYKPTNDMYNRIRDNGIVLDVAAGNAMSSS

EKNLYGNDLTLASDPDHGIVGSPSTYASPISVASVNNTKYRPGSKTIDPTQ

VTLSGFSSIGTTPNISIKPEISAPGAWIRSAMPRLNGQNYDEMSGTSMATP
```

HVAGASALMKQYLNDKFGNLTNIQKMELTNNLLMSTAHPIVQKDGAPQPVR

KQGSGMMDINAAIKTPVYLSVDPKQNHDGSNRPKIELGDDQNKTGNYTLKF

KVTNMGTQTETYQIKEKVSVPVIKRSIMDDHRERAFMTDDNRSVDVTRSGV

TSVTVKAKETKDVSITVQLTQAEKNRLNQEFENGTYVEGFVQLTHASHPQI

SIPFLAFYGDWEKAPIFDHAAEYEMGVRASNYAHRYLSDKMPMGGNIFDRR

MIYTNPSRFVISPNGDGLYDKLSGINLGQLRNVESMTMEITNKKTKQVIIK

EERPNIRKTFYNNSYGKQVPNILFWPFSTFTGLDQQKNPLPEGRYDLKISA

DLGYRKGIDQEIVHTIHVDHTKPVIPQDKIKFTEKNGTVMMHVESNDNTFL

TQTALYPVYNGKVQVNRPLKKQYTPYDLVSRHAFDVDVTNLKGQEVVISAV

DAGMLETNYKTVVPGTPKPHLKVDEFKIKVGAQIELEPGNFKWQTPTFESE

DPEIADVNDKGLVTGLKPGATFIKIKDKNGIDLVALIEVFEEESLKLQMKV

GEKRKLISYNLEGKRTFDSDAPHIVSARDTGEIEAHQKGKAKITVQNAYEK

LEYEVEVVDQPKYTPSLSFDKKVYEINSGEVVAPKFTIENDDPSNPQVVTR

LLTSNEEHVSIAGLKFTGEHAGEAAVIAELKNGTRAVAKVKVGGLDTKKLD

ILISQASNLNADDYTKTSFTTLTTTLQEAKTLRKQKGIDQSNIDTMVEKLE

KSMNQLVQVIKNLPSAMSVEVGNTFKLSPKPAQGKWIWDAEFLEGTAQNND

QEMMFKGLKEGQTDVRYRTKDGEEQSVAVAVKPKPKPVEIDPIVPTDPVDP

VKPTDPVDPVKPKDPVDPVKPTDPVDPVKPTDPVDPVKPTDPVDPVKPTDP

VDPVKPTDPVDPVKPTDPVDPVKPTDPVDPVKPADPVDPVKPTDPTKPTKP

VDSGLKPIDNLKKPIVKPKDPVSQVESIKQDKPVIHFGVVSESLPQTGVTP

QYRGYTLLGLGLVIRVINDKKNRMK

The protease of the invention (*Lactobacillus paracasei* subsp. *paracasei* 8700:2) has a sequence comprising (or consisting of) SEQUENCE ID NO. 53.

SEQUENCE ID NO. 53 has the following sequence.

MNRVKPFSQEKRRYKMYKSGRHWVYSAIVTFGAASFLMMQPAQGVSADAAA

PPPTTQTKSNQAAPDAASADSPVSKPASATTGQVTSSADTPTTTAASATPT

ATAKSATPAPVASQAKPEASAKAKQPTQPTSVTPSTPTTTNTKTAQKTVSQ

PAQKAPAAPAKPAPIAKPAPTSNPENKASLTKGNVQPLWDQNIKGQGMVAA

VIDQGVEPHQDFRLSDAKTAALSEDQIKAFTASHGYGDYVNEKIPFFYDYT

NNVNENLKFDTSNHGQHLAGIIAANGQPSDSKKYVTGIAPEAQLLSMKILG

KSSSDSLNNAARAIYDAVDLGANAINISFGMGVDIDDPTAEGQAAIKFATD

HGVFVTVATGNNGHAGGIYDKSASNGITTSYQPANASTLTTPSATPSAMAV

AAGNDVLDAKAALISPSSWGPTTSYKLKPDITAPGEKVASTLLNDELGKVS

GTSQANAYVTGASLLVMQNLKRSTNLTGAQLVKAVKLALMNAANPILDINY

PGQIISPRRQGAGQIDVAKAANLTVSAEGTDDAGSVSLQQFTGSKSFVITL

ENRGTDQQTYTLDLGQPATEVIDTANNKTVHDRTLPGATLTTATPTFTLDA

GASKKITFTLSLDDTVKLNQVVEGFIKFKAADDRQSISVPYMGYYGSTNDE

AVFDKPANEEGSIFKGGYLVDNNHNPLGITDPTSLSELVNNPTNGFTWQTI

GAKIENNKVAFSPNGDGISDTITPYVFTKQNLKQVIAQILDQDNKVMRVID

QETDTTKSFLEVGSTTNADLAKSISMFLNPDKLKWDGQVYDQTTGQMVPAK

DGIYTYRLIGMTYTPGENNMQTMSLPVAVDTIKPTLSNLAYSDGKLTADYS

DQGVGFTAYSQAKLTIGSATYGIPLNHDNKATSGTINYQLNDDQLANLKTG

EGKVTLTITDAAGNSDQGSIKAVVGENKTIESNFIWPQVRWSMPDTKGNLT

YRSDGRYQALTKDSTFTAQAMVPKGQDYIVTATDYVSDRQIGTLDKATGIV

TFNIDATGQPYANLTISAFARDDFGEFIKSPKTEDFIIFIKKNTAAYSNAK

TQTKPFADEATAIKGAKFFSGAAHLTGRSPLTSTKGKMINGIAFLDLNNNK

RTLVGIDSASTFYDAKLKTLTLRGKVSDPKNSKLRIFVTPRQNDPQNEVTF

AADGSFSMTMPCNPTEERNIGYVLTTLDKDGKEKTNGGFLLLYTDTTLPTL

ELSDADSMKIDDDGTYLVTTDADTFSIKGSVTDNIGGYRLYSNGNNIFMQQ

NLAGFNAHQSSAAPNQLTNGYNPYGAASFDETYQLTDGLNIITLQAVDQVG

NTVTKTFNVTKTPKLLKEESLDELEITPEQQDQTPKNDAGEAPVTTPATEE

TLVTPSTESTMVNPEDSKVETSDPIVETAPSKEAQSDGNGATETNTTASVT

TGVDENPVDSSANAATPMPNHVKDANTDAEVTEVTNTKDNTQGTTAPTSTD

AVPATDKESTTKSEIDPAATSPNDSKVVEAVTKEANDDKGNQADDGEPTVT

NLATSKDSAVQPEVDPASGLQSDDKVVETAVEDDEMVEKEGHKSDNAKPAI

TDPTTDKDKAVQSEVNPTASSQGATKAVEAAAKDTKVEDDKGNKTASVETG

VATPAMDNNSSVKSAVDPTATAPSDNTAPAIETAAENFNIENDKGNETNAV

ETVVTDPATNKEGTVKSEIEPVATTPSNTTVTATEMTKENTPAEDEKDNQV

NAVTDPKTTKDSADKSEIEPVATAATDKDRTVKSDPTEAASTPSEDSIRKT

NTAEDAKAKDDREAAAAVAADSKADKNNPVESKIDATAITPSNSQPTETDT

ENAAVENGKDQKSADTPSPVIDPAVDKDRAVKSKVNPATTAPNDDKAPEVT

TESSKIENVKSHQSDVVETFGSDSQTSKDPVAESKRNPTATSSSDDTTTET

ETLATGEGEQNSQVDTPKKAMTTTPNDKNVSLATVAPDKTKGDTAGARTVTT

TDGQRKPTKTEVGSSNVASNHPSTTDSSTETTSQSDEPTSSIETTEPATTA

PSTEDKPVRTTADQKVTDQKSNKDDQANPTAIKKKLKSKVTEDGENISQTN

QKDPKTKTAKGEQTTSPLDQKRSALKQKESKEIAPEKSVHATKTAAKTLPP

MGMQNSHWLQALGIALLGMILALGIGLTSKKKHEKS

The invention also provides a fragment of *Lactobacillus paracasei* subsp. *paracasei* 8700:2 protease comprising the propeptide to the end of the B domain of the *Lactobacillus paracasei* subsp. *paracasei* 8700:2. This sequence comprises (or consists of) SEQUENCE ID NO. 54.

SEQUENCE ID NO. 54 has the following sequence.

PPPTTQTKSNQAAPDAASADSPVSKPASATTGQVTSSADTPTTTAASATPT

ATAKSATPAPVASQAKPEASAKAKQPTQPTSVTPSTPTTTNTKTAQKTVSQ

PAQKAPAAPAKPAPIAKPAPTSNPENKASLTKGNVQPLWDQNIKGQGMVAA

VIDQGVEPHQDFRLSDAKTAALSEDQIKAFTASHGYGDYVNEKIPFFYDYT

NNVNENLKFDTSNHGQHLAGIIAANGQPSDSKKYVTGIAPEAQLLSMKILG

KSSSDSLNNAARAIYDAVDLGANAINISFGMGVDIDDPTAEGQAAIKFATD

HGVFVTVATGNNGHAGGIYDKSASNGITTSYQPANASTLTTPSATPSAMAV

AAGNDVLDAKAALISPSSWGPTTSYKLKPDITAPGEKVASTLLNDELGKVS

```
GTSQANAYVTGASLLVMQNLKRSTNLTGAQLVKAVKLALMNAANPILDINY
PGQIISPRRQGAGQIDVAKAANLTVSAEGTDDAGSVSLQQFTGSKSFVITL
ENRGTDQQTYTLDLGQPATEVIDTANNKTVHDRTLPGATLTTATPTFTLDA
GASKKITFTLSLDDTVKLNQVVEGFIKFKAADDRQSISVPYMGYYGSTNDE
AVFDKPANEEGSIFKGGYLVDNNHNPLGITDPTSLSELVNNPTNGFTWQTI
GAKIENNNKVAFSPNGDGISDTITPYVFTKQNLKQVIAQILDQDNKVMRVID
QETDTTKSFLEVGSTTNADLAKSISMFLNPDKLKWDGQVYDQTTGQMVPAK
DGIYTYRLIGMTYTPGENNMQTMSLPVAVDTIKPTLSNLAYSDGKLTADYS
DQGVGFTAYSQAKLTIGSATYGIPLNHDNKATSGTINYQLNDDQLANLKTG
EGKVTLTITDAAGNSDQGSIKAVVGENKTIESNFIWPQVRWSMPDTKGNLT
RSDGRYQALTKDSTFTAQAMVPKGQDYIVTATDYVSDRQYIGTLDKATGIV
TFNIDATGQPYANLTISAFARDDFGEFIKSPKTEDFIIFIKKNTAAYSNAK
TQTKPFADEATAIKGAKFFSGAAHLTGRSPLTSTKGKMINGIAFLDLNNNK
RTLVGIDSASTFYDAKLKTLTLRGKVSDPKNSKLRIFVTPRQNDPQNEVTF
AADGSFSMTMPCNPTEERNIGYVLTTLDKDGKEKTNGGFLLLYTDTTLPTL
ELSDADSMKIDDDGTYLVTTDADTFSIKGSVTDNIGGYRLYSNGNNIFMQQ
NLAGFNAHQSSAAPNQLTNGYNPYGAASFDETYQLTDGLNIITLQAVDQVG
DNTVTKTFNVTKTPKLLKEESLELEITPEQQDQTPKNDAGEAPVTTPATEE
TLVTPSTESTMVNPEDSKVETSDPIVETAPSKEAQSDGNGATETNTTASVT
TGVDENPVDSSANAATPMPNHVKDANTDAEVTEVTNTKDNTQGTTAPTSTD
PATDKESTTKSEIDPAATSPNDSKVVEAVTKEAAVNDDKGNQADDGEPTVT
NLATSKDSAVQPEVDPASGLQSDDKVVETAVEDDEMVEKEGHKSDNAKPAI
TDPTTDKDKAVQSEVNPTASSQGATKAVEAAAKDTKVEDDKGNKTASVETG
VATPAMDNNSSVKSAVDPTATAPSDNTAPAIETAAENFNIENDKGNETNAV
ETVVTDPATNKEGTVKSEIEPVATTPSNTTVTATEMTKENTPAEDEKDNQV
NAVTDPKTTKDSADKSEIEPVATAATDKDRTVKSDPTEAASTPSEDSIRKT
TAEDAKAKDDREAAANAVAADSKADKNNPVESKIDATAITPSNSQPTETDT
ENAAVENGKDQKSADTPSPVIDPAVDKDRAVKSKVNPATTAPNDDKAPEVT
TESSKIENVKSHQSDVVETFGSDSQTSKDPVAESKRNPTATSSSDDTTTET
ETLATGGEQNSQVDTPKKAMTTTPNDKNVSLATVAPDKTKGDTAGARTVTT
TDGQRKPTKTEVGSSNVASNHPSTTDSSTETTSQSDEPTSSIETTEPATTA
PSTEDKPVRTTADQKVTDQKSNKDDQANPTAIKKKLKSKVTEDGENISQTN
QKDPKTKTAKGEQTTSPLDQKRSALKQKESKEIAPEKSVHATKTAAKTLPP
MGMQNSHWLQALGIALLGMILALGIGLTSKKKHEKS
```

The protease of the invention (*Lactobacillus* sp. HMSC25A02) may have a sequence comprising (or consisting of) SEQUENCE ID NO. 55.

SEQUENCE ID NO. 55 has the following sequence.

```
MNRVKPFSQEKRRYKMYKSGRHWVYSAIVTFGAASFLMMQPAQGVSADATT
PPTTTQTKSNQAAPDAASADLPVSKPASTTTGQVTSSANTPTTTAASATPT
ATAKPATPAPVSSQAKPEASAKAKQPTQPTSVTPSTPTTTNTKTAQKTVSQ
PAQKAPAAPAKPAPIAKPAPTFNPENKASLTKGNVQPLWDQNIKGQGMVAA
VIDQGVEPHQDFRLSDAKTAALSEDQIKAFTASHGYGDYVNEKIPPFFYDYT
FNNVNENLKFDTSNHGQHLAGIIAANGQPSDSKKVTGIAPEAQLLSMKILG
KSSSDSLNNAARAIYDAVDLGANAINISFGMGVDIDDPTAEGQAAIKFATD
HGVFVTVATGNNGHAGGIYDKSASNGITTSYQPANASTLTTPSATPSAMAV
AAGNDVLDAKAALISASSWGPTASYKLKPDITAPGEKVASTLLNDGLGKVS
GTSQANAYVTGASLLVMQNLKRSTNLTGAQLVKAVKLALMNAANPILDINY
PGQIISPRRQGAGQIDVAKAANLTVSAEGTDDAGSVSLQQFTGSKSFVITL
ENRGTDQQTYTLDLGQPATEVIDTANNKTVHDRTLPGATLTTATPTFTLDA
ISGAFKKITFTLSLDDTVKLNQVVEGFIKFKAADDRQSVPYMGYYGSTNDE
AVFDKPANEEGSIFKGGYLVDNNHNPLGITDPTSLSELVNNPTNGFTWQTI
GAKVQNNKVAFSPNGDGISDTITPYVFTKQNLKQVIAQILDQDDKVMRVID
QETDTTKSFLEVGSTTNADLAKSISMFLNPDKLKWDGQVYDQTTGQMVPAK
DDGIYTYRLIGMTYTPGENNMQTMSLPVAVDTIKPTLSNLAYSDGKLTAYS
DQGVGFTAYSQAKLTIGSATYGIPLNHDNKATTGTINYQLNDDQLANLKTG
EGKVTLTITDAAGNSDQGSIKAVVGENKTIESNFIWPQVRWSMPDTKGNLT
RSDGRYQALTKDSTFTAQAMVPKGQDYIVTATDYVSDRQYIGTLDKATGIV
TFNIDATGQPYANLTISAIARDAFGEFIKSPKTEDFIIFIKKNAAAYSNAK
TQTKPFADEATAIKGAKFFSGAAHLTGRSPLTSTKGKMINGIAFLDLNNNK
RTLVGIDSASTFYDAKLKTLTLRGKVSDPKNSKLRIFVTPRQNDPQNEVTF
AADGSFSMTMPCNPTEERNIGYVLTTLDKDGKEKTNGGFLLLYMDTTLPTL
ELSDADSMKIDDDGTYLVTTDADTFSIKGSVTDNIGGYRLYSNGNNIFTQQ
NLAGFNAHQSSAAPNQLTNGYNPYGAASFDETYQLTDGLNIITLQAVDQVG
NTVTKTFNVTKTPKLLKEESDELEITPEQEDQTPKNDAGEAPVTTSSSDE
KAEVTPSTEPTMVNPEDSKVETSNPVVEIDTSKEAQSDGNDDTATNTPASV
TTAVDENPVDNSPNATTTMPNHAKGVDSDAEATEATNTKDNTPGTTAPTDT
DPTMDKESPTKSEVDPTATSLPDSQVVETATETTVNEDKGNKTDDDEPTAT
NLTTSKDSAIQPKSDPAASLQSNDKAVEAAIENDKIAEKEGHQSANTQPAI
TDVTTDKDSAVKPEIDPAASSQSNDKAVEAAMEDSKAENDKGSKSDSAETN
NTIAPTMAKNSGVKSEIDLTAIAPRDATSSGTAKENADVKDDKGNKTDTVE
SAVTDTEDDNEGTVKSEIESVATTPSSNTATATEITKENTPTEDEKDNQVN
VVETTDTHPKPIKDRATKSEIESEATAPSKTEVGETVAEDAKGEHDKSNKS
DDVEPTVSDRKTDEDRAIKSESNASAITPNEDNIDETTVEEAKAEDNREAA
AGTIATVAADPKASEDNSVKSEMDATTIAPIDNKAIETVTETTGVEKVESH
KSTDTESPVTDPAIDKDRAVNSDITPATASPTADKAPEATTESVDVENTES
HHPDIGETSVSDSQAGKDSATESKIDPKATPSSDNTTTGSTVEILTTGSEQ
NSQIDTSKTTVTPATDDKKVSSETIAPAKTSDDTAEFGTATTTSGQNTLTK
TEVESSNHATNHPDTTDSSTDATSQPDEPTISIEVTKPVPTTPSTEDNPVQ
PNVDQKVSDQKSDKDNQDNPTAIEKNPKSKVTDDEETISKTRQKDPKSNIV
EKEDDTILVVQKGLKAKTVKDAEPTSSLDQKTSALKQKESKEKAPAKSVHP
TKAAAKTLPPMGMQNSHWLQALGIALLGMVFALSIGLTSKKKHEKN
```

The invention also provides a fragment of *Lactobacillus* sp. HMSC25A02 protease comprising the propeptide to the end of the B domain of the *Lactobacillus* sp. HMSC25A02. This sequence comprises (or consists of) SEQUENCE ID NO. 56.

SEQUENCE ID NO. 56 has the following sequence.

```
PPTTTQTKSNQAAPDAASADLPVSKPASTTTGQVTSSANTPTTTAASATPT
ATAKPATPAPVSSQAKPEASAKAKQPTQPTSVTPSTPTTTNTKTAQKTVSQ
PAQKAPAAPAKPAPIAKPAPTFNPENKASLTKGNVQPLWDQNIKGQGMVAA
VIDQGVEPHQDFRLSDAKTAALSEDQIKAFTASHGYGDYVNEKIPFFYDYT
NNVNENLKFDTSNHGQHLAGIIAANGQPSDSKKFVTGIAPEAQLLSMKILG
KSSSDSLNNAARAIYDAVDLGANAINISFGMGVDIDDPTAEGQAAIKFATD
HGVFVTVATGNNGHAGGIYDKSASNGITTSYQPANASTLTTPSATPSAMAV
AAGNDVLDAKAALISASSWGPTASYKLKPDITAPGEKVASTLLNDGLGKVS
GTSQANAYVTGASLLVMQNLKRSTNLTGAQLVKAVKLALMNAANPILDINY
PGQIISPRRQGAGQIDVAKAANLTVSAEGTDDAGSVSLQQFTGSKSFVITL
ENRGTDQQTYTLDLGQPATEVIDTANNKTVHDRTLPGATLTTATPTFTLDA
GAFKKITFTLSLDDTVKLNQVVEGFIKFKAADDRQSISVPYMGYYGSTNDE
EAVFDKPANEEGSIFKGGYLVDNNHNPLGITDPTSLSLVNNPTNGFTWQTI
GAKVQNNKVAFSPNGDGISDTITPYVFTKQNLKQVIAQILDQDDKVMRVID
QETDTTKSFLEVGSTTNADLAKSISMFLNPDKLKWDGQVYDQTTGQMVPAK
DGIYTYRLIGMTYTPGENNMQTMSLPVAVDTIKPTLSNLAYSDGKLTADYS
DQGVGFTAYSQAKLTIGSATYGIPLNHDNKATTGTINYQLNDDQLANLKTG
EGKVTLTITDAAGNSDQGSIKAVVGENKTIESNFIWPQVRWSMPDTKGNLT
RSDGRYQALTKDSTFTAQAMVPKGQDYIVTATDYVSDRQYIGTLDKATGIV
ITFNIDATGQPYANLTISAIARDAFGEFIKSPKTEDFIIFKKNAAAYSNAK
TQTKPFADEATAIKGAKFFSGAAHLTGRSPLTSTKGKMINGIAFLDLNNNK
RTLVGIDSASTFYDAKLKTLTLRGKVSDPKNSKLRIFVTPRQNDPQNEVTF
AADGSFSMTMPCNPTEERNIGYVLTTLDKDGKEKTNGGFLLLYMDTTLPTL
ELSDADSMKIDDDGTYLVTTDADTFSIKGSVTDNIGGYRLYSNGNNIFTQQ
NLAGFNAHQSSAAPNQLTNGYNPYGAASFDETYQLTDGLNIITLQAVDQVG
NTVTKTFNVTKTPKLLKEESLDELEITPEQEDQTPKNDAGEAPVTTSSSDE
TKAEVTPSTEPTMVNPEDSKVETSNPVVEIDTSKEAQSDGNDDATNTPASV
TTAVDENPVDNSPNATTTMPNHAKGVDSDAEATEATNTKDNTPGTTAPTDT
DPTMDKESPTKSEVDPTATSLPDSQVVETATETTVNEDKGNKTDDDEPTAT
NLTTSKDSAIQPKSDPAASLQSNDKAVEAAIENDKIAEKEGHQSANTQPAI
TDVTTDKDSAVKPEIDPAASSQSNDKAVEAAMEDSKAENDKGSKSDSAETN
IAPTMAKNSGVKSEIDLTAIAPRDNTATSSGTAKENADVKDDKGNKTDTVE
SAVTDTEDDNEGTVKSEIESVATTPSSNTATATEITKENTPTEDEKDNQVN
VVETTDTHPKPIKDRATKSEIESEATAPSKTEVGETVAEDAKGEHDKSNKS
DDVEPTVSDRKTDEDRATKSESNASAITPNEDNIDETTVEEAKAEDNREAA
AGTIATVAADPKASEDNSVKSEMDATTIAPIDNKAIETVTETTGVEKVESH
KSTDTESPVTDPAIDKDRAVNSDITPATASPTADKAPEATTESVDVENTES
HHPDIGETSVSDSQAGKDSATESKIDPKATPSSDNTTTGSTVEILTTGSEQ
NSQIDTSKTTVTPATDDKKVSSETIAPAKTSDDTAEFGTATTTSGQNTLTK
TEVESSNHATNHPDTTDSSTDATSQPDEPTISIEVTKPVPTTPSTEDNPVQ
PNVDQKVSDQKSDKDNQDNPTAIEKNPKSKVTDDEETISKTRQKDPKSNIV
EKEDDTILVVQKGLKAKTVKDAEPTSSLDQKTSALKQKESKEKAPAKSVHP
TKAAAKTLPPMGMQNSHWLQALGIALLGMVFALSIGLTSKKKHEKN
```

The protease of the invention (*Lactobacillus parafarraginis*) may have a sequence comprising (or consisting of) SEQUENCE ID NO. 57.

SEQUENCE ID NO. 57 has the following sequence.

```
Protein sequence comprising the entire protease
protein
MKHIFKSFGETKRHPFIIATLLAISTIGLFMTTEMTATQAQSIKQPTTFSQ
HKPAKKPTKTNQTTSFNQQRQAALTRGNVPTLWSQGYQGQGMVIAVIDSGI
QNHPDLGLSNNQTAKISKADAQQLIAQKGYGKYISPKIPFAYDYVNNNNDD
TAADSTSGFHGEEVGGVAAANGVETNQAKYMKGVAPQAQLLNLKVFGGFAD
EIPNDVARAIHDAVDLGADVINLSLGLAQPHQSLTDEEQAAVKYATDHGVF
VSVAGSNYGHAGSLETNANDLSDSTTTTYEPANSGTIADPGVANSAMTVGS
ANTKTGSKSAMSSFSAWGPTPEFAFKPDITAPGDHIATIDENKTYTFDSGT
SFASPYIAGSAALVLQRVHKDQPNLKGAALVNAAKVALMNASQPMNNSQFP
GEIVSPRLQGAGVVNVANAANLNAAATDAATGSGAVALRQIGQITNFSLNV
TNHVAIPQTYRVDTTTGPDTETRKADKNGIGVVHDVKINGASLTASLPTIT
VDPGKTVKLDFKLDLGSQAARNKIAEGYISLVNSDAKQNLTIPYMGYYGDA
TTEQIIDQPANQTGSDFGGGYMIDNHNTPLGVSDRTSLASYINAGSPETAS
NRWDATPGKVDDDKTATSPNGDGKMDVANPYVFAKQSLAKVQAAILNSKGQ
VIRVIDQETNTDKSIHDLGSDANNDLALSVSMRPNPTALTWNGQAYDRATG
KMKVVPDGRYQYRIETTNFNDGADKVQDWTLPVQVDTKAPKIVKATYHRGR
GLTVGYRDSGVGFTKLSAMAVKVGKKVAVSLNNSGRQNQGITHYTLSKKLS
KIS
```

The invention also provides a fragment of *Lactobacillus parafarraginis* protease comprising the propeptide to the end of the B domain of the *Lactobacillus parafarraginis* protease. This sequence comprises (or consists of) SEQUENCE ID NO. 58.

SEQUENCE ID NO. 58 has the following sequence.

```
FMTTEMTATQAQSIKQPTTFSQHKPAKKPTKTNQTTSFNQQRQAALTRGNV
PTLWSQGYQGQGMVIAVIDSGIQNHPDLGLSNNQTAKISKADAQQLIAQKG
YGKYISPKIPFAYDYVNNNNDDTAADSTSGFHGEEVGGVAAANGVETNQAK
YMKGVAPQAQLLNLKVFGGFADEIPNDVARAIHDAVDLGADVINLSLGLAQ
PHQSLTDEEQAAVKYATDHGVFVSVAGSNYGHAGSLETNANDLSDSTTTTY
EPANSGTIADPGVANSAMTVGSANTKTGSKSAMSSFSAWGPTPEFAFKPDI
TAPGDHIATIDENKTYTFDSGTSFASPYIAGSAALVLQRVHKDQPNLKGAA
```

-continued

```
LVNAAKVALMNASQPMNNSQFPGEIVSPRLQGAGVVNVANAANLNAAATDA

ATGSGAVALRQIGQITNFSLNVTNHVAIPQTYRVDTTTGPDTETRKADKNG

IGVVHDVKINGASLTASLPTITVDPGKTVKLDFKLDLGSQAARNKIAEGYI

SLVNSDAKQNLTIPYMGYYGDATTEQIIDQPANQTGSDFGGGYMIDNHNTP

LGVSDRTSLASYINAGSPETASNRWDATPGKVDDDKTATSPNGDGKMDVAN

PYVFAKQSLAKVQAAILNSKGQVIRVIDQETNTDKSIHDLGSDANNDLALS

VSMRPNPTALTWNGQAYDRATGKMKVVPDGRYQYRIETTNFNDGADKVQDW

TLPVQVDTKAPKIVKATYHRGRLTVGYRDSGVGFTKLSAMAVKVGKKVAGV

SLNNSGRQNQGITHYTLSKKLSKIS
```

The inventors have surprisingly found that the protease of the invention causes enzymatic destruction of pro-inflammatory mediators. In this manner, the protease of the invention is for use as a medicament, particularly for the treatment of disease or disorders associated with immune dysregulation.

In an aspect of the invention, the protease of the invention is for use in the treatment of immune dysregulation disorders. Preferably, the disorder is selected from the group comprising, but not limited to, an immune dysregulation disorder disorder(s) of the blood, skin, lung and gut. Typically, the disorder is selected from eczema, asthma, cystic fibrosis, bowel cancer, colitis and inflammatory bowel disease. The disorder may be one in which complement split factors, e.g. C3a, C4a, C5a, are implicated, including but not limited to Irritable Bowel Disease, cystic fibrosis, age related macular degeneration, lupus (SLE). The disorder may be one in which mediators, e.g. IL-1, IL-3, IL-8 and/or IL-17, are implicated, including but not limited to treatment of bowel and colitis associated cancers.

The protease the invention can be produced readily in recombinant expression systems, e.g. *E. coli* and produced as an extracellular protease by *Lactococcus lactis*. Methods such as these are known in the art and it is to be understood that any such method may be used. This reduces the cost of production and hence the cost of therapy significantly.

The catalytic nature of the enzyme(s) of the invention means that very small doses of the enzyme are required compared to the stoichiometric requirements for MCAb to be efficacious. This reduces the cost involved.

Administration

The preferred route of administration is parenteral delivery. However, it will be appreciated that any suitable route or mode of delivery may be used, for example, oral delivery, aerosol delivery, intraocular injection, parenteral injection, or topical delivery.

The composition or protease of the invention may be presented, prepared and/or administered in a variety of suitable forms. Such forms include, for example, but are not limited to, liquid, semi-solid and solid dosage forms, such as liquid solutions (e.g., injectable and infusible solutions), dispersions or suspensions, emulsions, microemulsions, tablets, pills, powders, liposomes, dendrimers and other nanoparticles, microparticles, and suppositories. It will be appreciated that the form may depend on the intended mode of administration, the nature of the composition or combination, and therapeutic application or other intended use.

In an embodiment of the invention, the protease is in vehicle molecule such as a particle or bead which encapsulates the protease. Vehicle molecules include micelle, liposome (e.g., cationic liposome), nanoparticle, microsphere, or biodegradable polymer. The enzyme encapsulated within the vehicle can be associated with lipophilic molecules, which can aid in the delivery of the imaging molecule/drug to the interior of the vehicle. The vehicle may comprise poly (lactic-co-glycolic acid) (PLGA).

The protease may be immobilised on a solid support, such as a particle or bead as described herein. The therapy of the invention may be performed by withdrawing blood from a patient, treating the blood with a protease of the invention (which may optionally be immobilised on a solid support), and then returning the treated blood to the patient. Methods of performing such extracorporeal treatment of blood, and methods of immobilising enzymes to a support, are described in U.S. Pat. No. 9,422,541.

The protease may be expressed on the surface of a non-native host organism, for example, *Lactobacillus lactis*.

In preferred embodiments, repeated use of the composition is provided.

In some embodiments of the current invention, the composition may be delivered via any one of liposomes, mixed liposomes, oleosomes, niosomes, ethosomes, millicapsules, capsules, macrocapsules, nanocapsules, nanostructured lipid carriers, sponges, cyclodextrins, vesicles, micelles, mixed micelles of surfactants, surfactant-phospholipid mixed micelles, millispheres, spheres, liposheres, particles, nanospheres, nanoparticles, milliparticles, solid nanopartciles as well as microemulsions including water-in-oil microemulsions with an internal structure of reverse micelle and nanoemulsions microspheres, microparticles.

The compound of the invention may be administered by oral administration. The compound (and other ingredients, if desired) may also be enclosed in a hard, or soft, shell gelatin capsule, compressed into tablets, an edible carrier or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. The capsule may be a hard, or soft, shell gelatin capsule. The compound may be coated, or co-administer the compound with, a material to prevent its inactivation.

In an embodiment, the composition of the invention may be administered by parenteral administration (e.g., intravenous, subcutaneous, intraperitoneal, and/or intramuscular administration). For example, it may be administered by intravenous infusion or injection or by intramuscular or subcutaneous injection.

The composition of the invention may be for human or animal usage in human and veterinary medicine.

Compositions may be formulated in unit dosage form, i.e., in the form of discrete portions containing a unit dose, or a multiple or sub-unit of a unit dose.

The preparation of pharmaceutical compositions that contain protease as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified.

A protease of the invention can be formulated into a pharmaceutical composition as neutralized physiologically acceptable salt forms. Suitable salts include the acid addition salts (i.e., formed with the free amino groups of the peptide molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In the case of combination compositions (discussed further herein), a protease of the invention can be co-formulated with and/or coadministered with one or more additional therapeutic agents (e.g., an anti-diabetic agent such as an insulin, an insulin analogue, metformin or other anti-diabetic biguanide, a glucagon receptor antagonist, sulfonylurea, a thiazolidinedione, an alpha-glucosidase inhibitor, a meglitinide, a glucagon-like peptide-1 (GLP-1), a GLP-1 analog, etc.). Such combination therapies may require lower dosages of the protease of the invention and/or the co-administered agents, so as to avoid possible toxicities or complications associated with the various monotherapies.

In another aspect, a composition or protease of the invention is administered by intramuscular or subcutaneous injection. Intratumor administration also may be useful in certain therapeutic regimens.

Thus, protease of the invention may be formulated in, for example, solid formulations (including, e.g., granules, powders, projectile particles, or suppositories), semisolid forms (gels, creams, etc.), or in liquid forms (e.g., solutions, suspension, or emulsions), or by means of microneedles In practicing the invention, the amount or dosage range of the protease of the invention employed typically is one that effectively induces, promotes, or enhances a physiological response associated with protease of the invention binding of a cognate IR. In one aspect, the dosage range is selected such that the protease of the invention employed induces, promotes, or enhances a medially significant effect in a patient suffering from or being at substantial risk of developing a condition associated that is at least in part modulated by IR activity, which effect is associated with the activation, signaling, and/or biological modification (e.g., phosphorylation) of the cognate IR.

Modification

When necessary, any of proteases or compositions described herein can be modified, e.g. chemically modified, to increase their stability or to add in their delivery. Such modifications are known in the art and any such modification may be used.

The composition of the invention may comprise one or more additional components. Such additional components may be those of benefit to include in a composition, or of benefit depending on the intended use of the composition. The additional ingredient may be active or functional or both. The component may be administered in addition to the protease of the invention (also known as the active of the composition). In addition, or alternatively, the composition may be administered in combination with one or more other additional components. The compounds of the invention may be administered consecutively, simultaneously or sequentially with the one or more other additional components.

The additional component may be an active ingredient. Typical said additional active agent is present in trace amounts only. In some embodiments, there may be no additional active agent present in the composition. The amount of additional active agent included will depend on numerous factors, including the type of additional active agent used, the nature of the additional active agent, the component(s) of the composition, the amount of active or protease in the composition and/or the intended use of the composition. The nature and amount of any additional active agent should not unacceptably alter the benefits of the protease of this invention.

The active ingredient may be one suitable for the treatment of an immune dysregulation disorder as defined herein. The active ingredient may be one that adds or enhances delivery of the protease or the composition of the invention.

The active therapeutic ingredient is often mixed with excipients that are pharmaceutically (i.e., physiologically) acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH-buffering agents, which enhance the effectiveness of the active ingredient.

The additional component may be a pharmaceutical excipient, diluent or carrier.

In an embodiment of the invention, the composition may further comprise at least one pharmaceutically acceptable excipient. Pharmaceutically acceptable excipient are well known in the art and any known excipient, may be used provided that it is suitable for administration to a human and/or animal.

Preferably any excipient included is present in trace amounts. The amount of excipient included will depend on numerous factors, including the type of excipient used, the nature of the excipient, the component(s) of the composition, the amount of active or protease in the composition and/or the intended use of the composition. The nature and amount of any excipient should not unacceptably alter the benefits of the enzyme of this invention.

In an embodiment of the invention the excipient may be a suitable diluent, carrier, binder, lubricant, suspending agent, coating agent, preservative, stabilisers, dyes, vehicle, solubilising agent, base, emollient, emulsifying agent, fragrance, humectant, and/or surfactants.

The carrier may be any suitable carried known in the art. In some embodiments, the carrier may include, but is not limited to, a liquid, such as water, oils or surfactants, including those of petroleum, animal, plant or synthetic origin, polymer, oil, such as peanut oil, mineral oil, castor oil, soybean oil, alcohol, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, or digitonin.

A protease of the invention (including variants and modified protease) can be combined with one or more carriers (diluents, excipients, and the like) appropriate for one or more intended routes of administration to provide compositions that are pharmaceutically acceptable in the context of preparing a pharmaceutically acceptable composition comprising one or moreprotease of the invention A composition or protease of the invention may be applied in a variety of solutions. Suitable solutions for use in accordance with the invention typically are sterile, dissolve sufficient amounts of the protease of the invention and other components of the composition, stable under conditions for manufacture and storage, and not harmful to the subject for the proposed application. A protease of the invention may be subjected to conventional pharmaceutical operations such as sterilization and/or may contain conventional adjuvants, such as preservatives, stabilizers, wetting agents, emulsifiers, buffers etc. A composition also can be formulated as a solution, microemulsion, dispersion, powder, macroemulsion, liposome, or other ordered structure suitable to high drug concentration. Desirable fluidity properties of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. These and other components of a pharmaceutically acceptable composition of the invention can impart advantageous properties such as improved transfer, delivery, tolerance, and the like.

A composition for pharmaceutical use can include various diluents, fillers, salts, buffers, detergents (e.g., a nonionic detergent, such as Tween-80), stabilizers (e.g., sugars or protein-free amino acids), preservatives, tissue fixatives, solubilizers, and/or other materials suitable for inclusion in a composition for pharmaceutical use. Proteases or compositions of the invention can be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid, and combinations of any thereof, so as to provide such a composition. Methods for the preparation of such compositions are known. See, e.g., Sustained and Controlled Release Drug Delivery Systems, J. R. Robinson, ed., Marcel Dekker, Inc., New York, 1978

It is to be understood that an ingredient that is considered to be an "active" ingredient in one product may be a "functional" or "excipient" ingredient in another and vice versa. It will also be appreciated that some ingredients play a dual role as both an active ingredient and as a functional or excipient ingredient.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Production of Recombinant Enzyme PrtV, PrtI$_{ProB}$ and PrtI$_{SS-HT}$
Materials and Methods
Cloning of the CEP PrtV from Lactobacillus salivarius JCM 1046

Three constructs of the CEP gene (prtV) from L. salivarius JCM1046 were generated using the primers in Table 4. Primers were used at a final concentration of 0.2 µM. Primer pair SB_PrtV_F1 and SB_PrtV_R1 cloned from the beginning of the pro-peptide to the end of the wall spanning domain (PrtV$_{(Pro-W)}$); Primer Pair SB_PrtV_F1 and SB_PrtV_R2 cloned from the pro-peptide to the end of the B Domain (PrtV$_{(Pro-B)}$), while primer pair SB_PrtV_F1 and SB_PrtV_R3 cloned from the pro-peptide to the end of the Fn3 domain (PrtV$_{(Pro-Fn3)}$) (Figure SB1). The Primer pair of SB_PrtV_F2 and SB_PrtV_R2 were used to clone PrtV$_{(Fn4-B)}$.

TABLE 4

Primer sequences used for PCR of the PrtV encoding gene from Lactobacillus salivarius JCM1046. Restriction sites are shown in Italics and stop codons are in Bold.

| Primer Name | Sequence | Comments |
|---|---|---|
| SB_PrtV_F1 | CAGCAG *GGATCC*GATACC GTTAATGGTAGTGAAAGT (SEQ ID 11) | Forward primer for PrtV containing BamHI site. Starting at the propeptide. |
| SB_PrtV_R1 | CAGCAG*CTCGAG*CTATACT TTTACTGGTTCTGCAGCTT TTTT GCCC (SEQ ID 12) | Reverse primer for PrtV containing XhoI restriction site. Clone to the end of the wall domain. |
| SB_PrtV_R2 | CAGCAG*CTCGAG*CTAATAG TGAACATAGAACTTCCTAG TTAC (SEQ ID 13) | Reverse primer for PrtV containing XhoI restriction site. Clone to the end of the B domain. |
| SB_PrtV_R3 | CAGCAG*CTCGAG*CTAATTA TTTACTTGCCATGCAAAAA GCA (SEQ ID 14) | Reverse primer for PrtV containing XhoI restriction site. Clones to the end of the Fn3 domain. |
| SB_PrtV_F2 | CAGCAG*GGATCC*ACTGTTA AGGAAAACTTTGGTATTG (SEQ ID 15) | Forward primer for PrtV containing BamHI site. Starting at the Fn4 domain. |

Reactions were carried out with approximately 50 ng of genomic DNA from L. salivarius JCM 1046. Phusion DNA Polymerase was used in cloning. The PCR cycle for all primer pairs used was 95° C. for 90 s, 95° C. for 30 s, 55° C. for 30 s and 72° C. for 4.5 min with a final extension step at 72° C. for 4 min. PCR amplicons were purified using QIAquick PCR purification kit (Qiagen) following the manufacturers protocol and analysed using 0.8% agarose gel electrophoresis. Purified DNA was quantified using the nanodrop.
Purification of Recombinant PrtV Cell pellets containing either recombinant PrtV were removed from the freezer and subjected to three rounds of freeze-thaw action. The pellet was then resuspended in 10 mL of PBS with the addition of 0.2 mg DNase and allowed to sit on ice for once hour. Cell debris was subsequently removed by centrifuging at 12000 g for 30 mins at 4° C. The cleared lysate containing the recombinant protein was removed and protein harvest from it immediately. Recombinant PrtV was produced as a fusion protein tagged with glutathione S-transferase (GST) using the pGEx-6P-3 plasmid. Recombinant protein was extracted from the cleared lysate using affinity chromatography onto Gluthathione Sepharose 4 Fast Flow (GE Healthcare). PrtV was immobilised onto GSH resin by batch purification where GSH resin, equilibrated in PBS, was added to the cleared lysate and allowed to incubate at 4° C. for 4 h on a tube roller. The resin was centrifuged at 800×g for 2 minutes and allowed to settle. The supernatant was removed and the resin was washed three times with 15 mL of PBS. The resin was subsequently washed three times with 10 mL of PreScission cleavage buffer (50 mM Tris-HCl pH 7.0, 150 mM NaCl, 1 mM CaCl$_2$ and 1 mM DTT) in preparation for GST tag removal. The resin was incubated with 25 units of PreScission protease (GE Healthcare) in PreScission cleavage buffer on a tube roller at 4° C. for 24 hours. The resin was centrifuged at 800×g for 2 min and allowed to settle. The supernatant containing PrtV without GST-tag was removed and analysed by SDS-PAGE (Laemmli 1970).

PrtV) with the affinity tag removed was dialysed against 5 mM Tris-HCl buffer, pH 8.0 containing 10 mM NaCl and then subjected to ion exchange chromatography which was performed on the ÄKTAprime plus (GE Healthcare) using Fast Flow Q Sepharose (GE Healthcare). The resin packed in a Tricorn 5/50 column (GE Healthcare) was equilibrated with 5 mM Tris-HCl buffer pH 8.0 containing 10 mM NaCl and 1 mM CaCl$_2$. The sample was loaded at 0.5 mL/min flow rate using a Bio-Rad Econo system (Bio Rad, USA). The protein was eluted in 200 mL over 200 min by applying a linear gradient from 10 mM to 1 M NaCl Tris-HCl buffer pH 8.0 containing 1 mM CaCl$_2$. The purity of the collected fractions was verified by SDS-PAGE(Laemmli 1970).

Size exclusion chromatography was carried out using ÄKTAprime plus system (GE Healthcare) and Superdex 200 column (GE Healthcare). The column was equilibrated with 50 mM HEPES-KOH pH 7.0 containing 150 mM NaCl and 1 mM CaCl$_2$. The column was developed using an isocratic gradient of the buffer at a flow rate of 0.3 mL/min. Collected protein fractions were additionally analysed by SDS-PAGE (Laemmli 1970). The fractions containing the purified protein were pooled and stored at −80° C. until required.

Production of Recombinant PrtI Enzyme

Constructs include: PrtI$_{(PrtB)}$, PrtI$_{(Prt-Fn3)}$, PrtI$_{(PrtP-An)}$, PrtI$_{(Pro-TEV-PrtT)}$, PrtI$_{(Pro-TEV-S445A)}$, PrtI$_{(His6)}$

TABLE 5

Table of primers used to clone fragments of PrtI gene.

| Primer name | Sequence | Comment |
|---|---|---|
| RC_Lbin_CEP_f | Cagcaggaattccg ctgaataggagaga cttctc (SEQ ID 16) | Forward: start of propeptide (PrtI$_{(PrtB)}$) |
| RC_Lbin_CEP_r2 | Cagcagctcgagtt aagccacatagtct ggatcataattaac (SEQ ID 17) | Reverse: end of B-domain (PrtI$_{(PrtB)}$) |
| RC_PrtI_TEVF | Cttcatcaattcct gaaccagaaaacct gtattttcagggcg ctaatcaggccgat catg (SEQ ID 18) | Forward: TEV site insertion. (PrtI$_{(Pro-TEV-S445A)}$), (PrtI$_{(Pro-TEV-PrtT)}$) |
| RC_LbinHT_F | Cagcaggcatgcta actaaggaggtcat gatatgcgaaagaa atgggtggctacag c (SEQ ID 19) | Forward: start of signal peptide (PrtI$_{(PrtP-An)}$) (PrtI$_{(His6)}$) |
| RC_LbinHT_R | cagcagctcgagtc tagattaatggtgg tggtgatgatgcct aggagccacatagt ctggatcataatta acagcg (SEQ ID 20) | Reverse: end of B-domain plus C-term His$_6$ addition. (PrtI$_{(His6)}$) |

The following purification scheme describes the production of PrtI$_{(PrtB)}$ in E. coli:

Cloning of PrtI$_{(ProB)}$

Production of PrtI$_{(ProB)}$ used Glutathione S-transferase (GST) gene fusion system (GE Healthcare). The pGEX-6P-3 expression vector was used to produce a protein with an N-terminus GST-tag and Precision cleavage site for tag removal. The expressed protein was intended for expression into E. coli cytoplasm.

A 5 mL overnight of Lb. intestinalis was grown statically and anaerobically overnight, at 37° C. Genomic DNA was isolated using the GenElute Bacterial Genomic DNA kit (Sigma-Aldrich). Protocol was followed as per manufacturer's instructions. Amplification of the PrtI gene was achieved using the primer pair RC_Lbin_F and RC_Lbin_R (Table 4) as forward and reverse primers respectively, and as indicated in Fig RC2. A total of 50 ng of Lb. intestinalis genomic DNA was added to the PCR reaction with primers at a final concentration of 0.2 μM. PCR reaction was completed with an initial denaturation step at 94° C. for 2 minutes, followed by 30 cycles of denaturation at 94° C. for 30 s, annealing at 58° C. for 30 seconds and elongation at 72° C. for 260 s. PCR reaction was then completed with a final denaturation cycle at 72° C. for 5 minutes.

The expression vector and PrtI amplicon were digested with restriction endonucleases XhoI and EcoRI (Roche) to generate complementary 5' and 3' overhangs. These were then ligated at a 1:1 ratio using T4 DNA ligase (Roche) and T4 DNA ligase buffer (Roche). Transformation following 4 hour incubation at room temperature was completed into E. coli DH5α chemically competent cells. The plasmid constructed will be referred to as pGEX-6P-3$_{PrtI(ProB)}$ herein and the recombinant E. coli strain as EC$_{PrtI(ProB)}$.

Purification of PrtI$_{(ProB)}$

For PrtI$_{(ProB)}$ protein expression, 16 hour cultures of the respective EC$_{PrtI(ProB)}$ stocks were inoculated into LB-broth supplemented with 100 mg/mL ampicillin, at ¹/₁₀₀ and grown at 37° C., 250 rpm. When the cultures reached an OD$_{600}$ of 0.6, expression was induced using the lactose homolog, IPTG (Sigma) at a final concentration of 0.1 mM and incubated at 30° C. for 2 hours. Following this, lysozyme was added to achieve a final concentration of 0.25 mg/mL and incubated for a further hour to commence cell lysis. Subsequently, the cells were harvested by centrifugation at 6000×g, 4° C. The cell pellet was then washed and stored in GST-PBS, pH 7.4 at −80° C. Upon thawing, the cell pellet was treated with DNase on ice for 1 hour followed by centrifugation at 11,000×g to harvest the cell lysate.

Initial purification of the desired protein was completed utilizing the N-terminal GST-tag fused to the protein. For this, the cleared lysate was incubated for 4 hours with Glutathione sepharose (GE Healthcare) pre-equilibrated in GST-PBS, pH 7.4 at 4° C. with gentle mixing. Following initial binding, the sepharose was then washed 3 times in GST-PBS pH7.4 by centrifugation (500 rpm, 4° C.) and resuspension. The glutathione-sepharose was then buffer exchanged into Precision cleavage buffer (PCB) (50 mM Tris-HCL, 150 mM NaCl, 1 mM EDTA, 1 mM DTT, pH 7). This mixture was then incubated with Precision protease (GE Healthcare) and incubated at 4° C. to remove the PrtI$_{(ProB)}$ off the resin. Following this, the supernatants with PrtI$_{(ProB)}$ were stored at −80° C.

To prepare PrtI$_{(ProB)}$ for IEX, protein supernatants were dialyzed extensively into IEX Buffer A (5 mM Tris-HCl, 10 mM NaCl, pH 8). Subsequently PrtI$_{(ProB)}$ was subjected to IEX using a linear gradient of NaCl (0.005-1.0 M) for elution. Fractions containing the desired protein were visualized using SDS-PAGE and pooled (Laemmli 1970). These fractions were then ultrafiltered (Millipore) to a final volume of 1 mL. The concentrated $PrtI_{(ProB)}$ was then buffer exchanged into Storage Buffer (100 mM HEPES, 100 mM NaCl, pH 7.5) by SEC and visualized using SDS-PAGE (Laemmli 1970).

Cloning of $PrtI_{SS-HT}$

Bacterial Strains and Growth Conditions

The plasmids and bacterial strains used in this work are listed in Table 5. *E. coli* strains were grown in Luria-Bertani (LB)-Broth, at 37° C. with vigorous agitation. *E. coli* strains harboring the pNZ8048 vector and its derivatives were cultured in LB-broth supplemented with 5 mg/mL chloramphenicol (Sigma Aldrich) ($LB_{CM10}$). *Lactococcus lactis* strains were cultured in M17 media (Sigma Aldrich) supplemented with 0.5% (w/v) glucose (GM17) at 30° C. The degree of agitation varied depending on the volume being cultured and will be specified accordingly. The cultures of *L. lactis* strains which harbored the pNZ8048 plasmid or its derivatives, were supplemented with 10 ml/mL chloramphenicol ($GM17_{CM5}$).

TABLE 6

Plasmids and bacterial strains

| | Relevant features | Reference |
|---|---|---|
| Plasmid | | |
| pNZ8048 | $CM^r$, pNZ8048 (*E. coli* - *L. lactis* high-copy-number shuttle vector, nisin-inducible PnisA promoter) | (Kuipers et al. 1998) |
| pNZ8048:PrtI | $CM^r$, pNZ8048; gene expressed encodes $PrtI_{SS-HT}$ | This work |
| Strain | | |
| *E. coli* Top10 | recA1 for reduced occurrence of non-specific recombination | Invitrogen |
| *L. lactis* NZ9000 | MG1363 (wild type), nisRK genes into chromosome, plasmid free | (Kuipers et al. 1998) |
| *L. lactis* $LAC8048_{PrtI}$ | *L. lactis* NZ9000, pNZ8048:PrtI | This work |

Amplification of $PrtI_{SS-HT}$ Gene

*Lb. intestinalis* DSM6629 (Fujisawa et al. 1990) was cultured overnight in MRS media at 37° C. and the total genomic DNA was extracted using the GenElute bacterial genomic DNA kit (Sigma-Aldrich). Protocol was followed as per manufacturer's instructions. PrtI was amplified using the primer pair RC_LbinHT_F and RC_LbinHT_R (Table 5). These primers were designed to amplify the PrtI gene spanning the region encoding from the end of the B-domain (nucleotides 111-4224). HT-PrtI-F was engineered to introduce a SphI restriction site and ribosome binding site (RBS) proceeding the native PrtI signal sequence. HT-PrtI-R was designed to introduce an C-terminal $His_6$ tag, a stop codon and an XbaI restriction site on the 3' end of the PrtI amplicon. This amplicon and expressed protein will be referred to at $PrtI_{SS-HT}$ and $PrtI_{SS-HT}$, respectively, herein. PCR was performed using 2× MasterMix (Thermo-Scientific). PCR cycles included a denaturation step at 94° C. for 30 sec, an annealing step of 60° C. for 30 sec and elongation of step of 72° for 4 min 30 sec. This was repeated 30 times, with in initial denaturation for 2 min and final elongation step for 5 min. When the reaction was complete, the amplicon was purified using the QIAquick PCR purification kit (Qiagen, UK) and quantified using the NanoDrop 1000 (Thermo Fisher).

Restriction Digestion of Amplicon and Vector

*Lactococcus lactis* derived pNZ8048 and $PrtI_{SS-HT}$ amplicon were digested with SphI (Thermo Scientific) and XbaI (Roche). The reaction was performed using 2× Tango Buffer (Thermo Scientific) in a final volume of 100 µL which had 4.5 µg of DNA and 5 units of each restriction enzyme added. The reaction mixture was incubated at 37° C. for 90 minutes. After restriction digestion, the products were purified and quantified.

Ligation of pNZ8048 and $PrtI_{SS-HT}$

Ligation to generate pNZ8048: PrtI plasmid was completed at a 3:1 insert to vector molar ratio. Three reactions of 20 µL were set up, each with 0.1 µL of T4 DNA ligase (Roche) and 2 µL of T4 DNA ligase buffer (Roche). Reactions were incubated at room temperature for 16 hours.

Ethanol Precipitation of pNZ8048: PrtI Ligation Reactions

The ligation reactions were pooled and ethanol precipitated to remove salts for downstream electroporation (Maniatis et al. 1982). Briefly, a 1/10 volume of 3 M sodium acetate, pH 5.2, was added to the ligation reaction, onto which, 2.5 volumes of ice cold ethanol was carefully added. This was then incubated at −20° C. for 30 min followed by centrifugation at 11,000×g, at 4° C. for 30 minutes. The supernatant was removed, and 1 mL of ice cold ethanol carefully added to the DNA pellet. Centrifugation was repeated as above, the ethanol decanted and the pellet air dried. The pellet was resuspended in 5 µL of sterile MilliQ water, 2.5 µL of this was used for electroporation.

Preparation of Electrocompetent *E. coli* Top 10 Cells

A 3 mL *E. coli* Top 10 culture was incubated at 30° C. at 200 rpm for 16 hours. The culture was then centrifuged at 6000×g for 10 minutes and resuspended in ice-cold wash buffer (1 mM MOPS, 20% glycerol). This process was repeated, and the final pellet resuspended in 200 µL of wash buffer.

Electroporation of pNZ8048: PrtI into *E. coli* Top 10 Electrocompetent Cells 2.5 µL of the ethanol precipitated DNA was incubated with 50 µL of the freshly prepared electrocompetent *E. coli* Top10 cells for 5 minutes on ice. This suspension was then placed into an ice-cold electroporation cuvette (VWR) and using the Easyject Prime electroporator (EquiBio, UK), electroporation was performed at 25 µF, 200 ohms, 1.8 kV. Immediately following this, the contents of the cuvette were mixed with 950 µL of LB-broth and incubated at 37° C., at 250 rpm for 1 hour. After incubation, 100 µL of the culture was spread onto $LB_{CM10}$ agar for selection of potential clones and incubated at 37° C. for 48 hours.

Screening for *E. coli* TOP10 Clones Harboring the pNZ8048: PrtI Plasmid

Single transformant colonies were used to inoculate 2 mL of $LB_{CM10}$ and were cultured overnight. Following this, the cells were harvested by centrifugation at 11,000×g for 60 sec and the plasmids isolated using the QIAprep Spin Miniprep kit (Qiagen, UK). Protocol was followed according to the manufacturer's instructions. To confirm the presence and correct size of insert, plasma DNA from potential clones were restriction digested using SphI (Thermo Scientific) and XbaI (Roche) restriction endonucleases.

Preparation of *L. lactis* NZ9000 Electrocompetent Cells

To generate the electrocompetent *L. lactis* cells, a single *L. lactis* NZ9000 colony was inoculated into 10 mL of GM17 broth and incubated for 24 hours at 30° C. without agitation. This was used as for inoculation of 40 mL of fresh GM17 at a 1 in 400 dilution. This culture was incubated for 16 hours at 30° C. This 40 mL culture was then used to inoculate 400 mL of filter sterilized SGM17 broth (GM17 broth, 2% glycine (VWR), 0.5 M sucrose (Sigma Aldrich)).

The culture was incubated for 5 hours at 30° C. without shaking. The cells were harvested by centrifugation at 6,000×g for 10 minutes at 4° C. Following this, cells were washed twice with an ice cold 0.5 M sucrose, 10% glycerol solution and finally suspended in 4 mL of this solution. Electrocompetent cells were then aliquoted for storage at −80° C. (Holo and Nes 1989).

Electroporation of L. lactis Electrocompetent Cells 40 ng of plasmid DNA was added to 50 µL of freshly thawed on ice electrocompetent L. lactis NZ9000 cells. This suspension was then placed into an ice-cold electroporation cuvette (VWR) and using the Easyject Prime electroporator (EquiBio, UK), electroporation was performed at 25 µF, 200 ohms, 1.8 kV. Immediately following this, the contents of the cuvette was mixed with 950 µL of GM17 broth with subsequent static incubation for 2 hours at 30° C. After incubation, 50 µL of the culture was spread onto GM17$_{CM5}$ agar for selection of potential clones and incubated at 30° C. for 24 hours.

Screening for Lactococcus lactis Clones Harbouring the pNZ8048: PrtI Plasmid.

As this was L. lactis plasmid isolation, there was an initial incubation step of the cells in buffer P1 supplemented with 100 mg/mL lysozyme (Sigma Aldrich) for 1 hour at 37° C. To confirm the presence and correct size of insert, appropriate restriction digests followed by DNA agarose gel electrophoresis were performed. The DNA sequence of possible clones was confirmed by Sanger sequencing (GATC Biotech). The construction was called pNZ8048: PrtI.

Production of PrtI$_{SS-HT}$

PrtI$_{SS-HT}$ Fermentation

Fermentation was completed using the New Brunswick BioFlo® 415 Benchtop SIP Fermenter. L. lactis LAC8048$_{PrtI}$ was cultured in GM17$_{CM5}$ overnight and inoculated into 5 L of LOM$_{CM5}$ at a 1/1000 dilution. The culture was incubated at 30° C. with gentle agitation (propeller speed of 60 rpm) and the pH was maintained at pH 7.0 by injection of 5 M Na$_4$OH. The culture was induced with 15 ng/mL nicin when an OD$_{600}$ of 2.0 was reached, followed by incubation for a further 4 hrs. When the fermentation run was complete, the cells were separated from the culture media by centrifugation at 6000×g for 30 minutes. The supernatant was then treated with 0.0001% sodium azide.

Purification of PrtI$_{SS-HT}$

The culture supernatant was subjected to ammonium sulfate precipitation in the same manner. Following dialysis, the protein was applied to chelating sepharose (GE Healthcare) charged with 0.2 M NiSO$_4$·6H$_2$O to separate out some of the media peptides from the PrtI$_{SS-HT}$ main fraction. This material was dialyzed extensively against 5 mM Tris-HCl, pH 8.0, 10 mM NaCl. This sample was then incubated with Q sepharose (GE healthcare), a strong anion exchanger, to remove negatively charged nucleic acids from the PrtI$_{SS-HT}$. Finally, the Q sepharose treated PrtI$_{SS-HT}$ was subjected to 10% ammonium sulfate precipitation, resuspended and extensively dialyzed into 5 mM Tris-HCL, pH 8.0, 10 mM NaCl. Samples were taken throughout for SDS-PAGE analysis (Laemmli 1970) and quantified using the NanoDrop 1000. Purified protein was stored at −80° C.

A recombinant enzyme (PrtV) with well-defined properties was produced (Fig. SB3A). A recombinant enzyme (PrtI$_{ProB}$ and PrtI$_{SS-HT}$) with well-defined properties was produced (Fig. RC3B and RC3C).

Example 2

Activity of PrtV, PrtI$_{ProB}$ and PrtI$_{SS-HT}$

Activity Assays

The activity and specificity of PrtV$_{(Pro-B)}$ was assessed by protein cleavage assays. Activity of PrtV$_{(Pro-B)}$ was assessed against IL-8, C3a, TNFα, C5a, IP-10, IL-10, IL-17, IL-1β, IL-3, Mig, Haemoglobin, Cytochrome C, Lysozyme, Fibrinogen, Human IgG (FIG. 4a). Assays were performed in PBS in a final volume of 10 µL. 1 µg of substrate was incubated with PrtV$_{(Pro-B)}$ at a final concentration of 40 nM for 1 h at 37° C. The reaction was stopped by the addition of 10 µL of SDS-PAGE loading buffer and heating at 95° C. for 5 min. Cleavage was assessed by SDS-PAGE (Laemmli 1970).

The enzyme PrtV has activities against the following pro-inflammatory mediators: C3a, C5a, IL-1β, IL-3, IL-8, IP-10, ENA-78, C3a, IL-17, TNF-α. The results are illustrated in Figure SB4A-C.

Example 3

Activity of PrtI

PrtI$_{(ProB)}$ Activity

The activity and specificity of PrtI$_{(ProB)}$ was assessed by protein cleavage assays. These assays included immune system cytokines and complement factors IL-8, C3a, TNFα, C5a, IP-10, IL-10, IL-17, IL-1β, IL-3 and Mig (Fig. RC4A). Assays were performed in PBS, the reaction was completed with 100 nM PrtI$_{(ProB)}$ and 1.5 µM substrate for 90 minutes at 37° C. The reaction was stopped by the addition of SDS-PAGE loading buffer and visualised by SDS-PAGE (Laemmli 1970) with appropriate controls.

Results

The enzyme PrtI$_{ProB}$ has activities against the following pro-inflammatory mediators (Fig. RC5A): IL-8, C3a, TNF-α, human C5a (hC5a), IP-10, IL-10, IL-17, IL-1β, mouse C3a (mC3a) and IL-3.

C3a was used as a sample substrate to test and confirm the activity of the variant of PrtI, PrtI$_{SS-HT}$. This variant displayed activity against hC3a (Fig. RC4B).

Example 4

Activity of PrtV and PrtI Against Blood Proteins

This study investigated the ability of PrtV and PrtI to cleave 12 human complement proteins when tested in vitro.

PrtV was also tested for its ability to digest IgG, fibrinogen, haemoglobin, cytochrome C and lysozyme.

PrtI was also tested for its ability to digest BSA, HSA, Factor XIII, and Factor XI.

Proteolytic activity of PrtV (E1) and PrtI (E2) was tested against 12 human complement proteins (C1s, C1 inhibitor, C2, C2a, C3, C4, C5, C-Reactive protein, Factor B, Factor H, Properidin, C4-Binding protein).

For PrtI, assays were performed in 1×PBS, pH 7.4. The reactions were completed with 100 nM PrtI and 13 µM substrate for 90 min at 37° C.

For PrtV, assays were performed in 1×PBS, pH 7.4 in a final volume of 10 µL. 1 µg of substrate was incubated with 40 nM PrtV for 1 h at 37° C.

Control experiments without PrtV or PrtI are indicated with '-'. Stock samples of both PrtV and PrtI were shown to be active against C3a prior to tests with human complement proteins.

Results

None of the complement proteins tested show evidence of breakdown after a 1-hour treatment with these enzymes. Thus, neither PrtV nor PrtI have obvious activity against any of the proteins tested.

PrtV did not digest IgG, fibrinogen, haemoglobin, cytochrome C and lysozyme when tested and PrtI did not digest BSA, HSA, Factor XIII, and Factor XI, when tested Example 5

Activity of PrtV and PrtI Against Casein

To support that PrtV and PrtI are distinct from typical CEPs and lactocepins the following tests on casein were performed.

The activity assay of PrtV with α-, β-, κ-casein was performed in 0.1 M NaPhosphate pH 7.0. The assay was performed for 2 hours at 37° C. with 40 nM PrtV and 6 µg casein species. The reactions were terminated by boiling in loading dye and analysed using SDS-PAGE.

The activity assay of PrtI with α-, β-, κ-casein was performed in 1×PBS, pH 7.4. The assay was performed for 6 hours at 37° C. with 100 nM PrtI and 13 µg casein species. The reactions were terminated by boiling in loading dye and analysed using SDS-PAGE.

Results

PrtV has restricted activity against casein, cleaving only α-casein in a limited manner. This is in contrast to the extensive hydrolysis of casein species by classical cell envelope proteins, e.g. Lactocepins.

PrtV has restricted activity against casein, cleaving only a-casein in a limited manner. This is in contrast to the extensive hydrolysis of casein species by classical cell envelope proteins.

These results indicate that PrtV and PrtI form a group distinct from lactocepins and have a limited range of target substrates.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of treating an immune dysregulation disorder, said method comprising administering a therapeutically effective amount of an isolated protease comprising a polypeptide having the structure:

P-A-B wherein P is a protease domain, A is an A-domain, and B is a B-domain, of a Group VII to XIII cell envelope protease (CEP), wherein the protease does not have a PA domain, and wherein the immune dysregulation disorder is selected from the group consisting of;
(i) a disorder associated with dysregulation of C5a, selected from the group consisting of sepsis, skin disease, transplant rejection, lyme disease, arthritis, cancer, cystic fibrosis, allergic asthma and age-related macular degeneration (AMD);
(ii) a disorder associated with dysregulation of C3a selected from the group consisting of kidney disease, and age-related macular degeneration (AMD);
(iii) a disorder associated with dysregulation of IL-8 and selected from the group consisting of ulcerative colitis, cancer, gingivitis, psoriasis, inflammatory lung disease and glomerulonephritis;
(iv) a disorder associated with dysregulation of IL-17 selected from the group consisting of psoriasis, allergy response, autoimmune disorder, asthma, eczema, multiple sclerosis, arthritis, and inflammatory bowel disease;
(v) a disorder associated with dysregulation of IL-1β selected from the group consisting of rheumatoid arthritis, and diabetes;
(vi) a disorder associated with dysregulation of TNF-α selected from the group consisting of rheumatoid arthritis, ankylosing spondylitis, Alzheimer's disease, cancer, psoriasis, and inflammatory bowel disease;
(vii) a disorder associated with dysregulation of IL-6 selected from the group consisting of rheumatoid arthritis, transplant rejection and cancer; and
(viii) a disorder associated with dysregulation of IL-3 selected from the group consisting of allergic inflammation, leukemia, and rheumatoid arthritis.

2. The method of claim 1, wherein the cancer is bowel cancer.

3. The method of claim 1, wherein the isolated protease is administered in combination with a suitable pharmaceutical excipient to a patient in need thereof.

4. The method of claim 1, wherein the isolated protease is selected from a wild-type Group VIII or IX cell envelope protease.

5. The method of claim 1, wherein the isolated protease is selected from a wild-type Group VIII or IX cell envelope protease and comprises SEQ ID NO: 1 or SEQ ID NO: 5.

6. The method of claim 1, wherein the isolated protease is selected from a wild-type Group VIII or IX cell envelope protease and comprises SEQ ID NO: 21, 23, 25, 27, 29, 31, 33, 35, 37, 39, 41, 43, 45, 47, 49, 51, 53, 55 or 57.

7. The method of claim 1, wherein the isolated protease is engineered to remove the signal peptide, wall domain, and anchor domain.

8. The method of claim 7, wherein the isolated protease consists essentially of a propeptide domain, protease domain, A-domain, and B-domain.

9. The method of claim 1, wherein the isolated protease consists essentially of a propeptide domain, protease domain, A-domain, and B-domain and is selected from SEQ ID NOs: 3, 7, 9, 22, 24, 26, 28, 30, 32, 34, 36, 38, 40, 42, 44, 46, 48, 50, 52, 54, 56 and 58.

10. The method of claim 1, wherein the isolated protease is modified by PEGylation.

* * * * *